United States Patent
Gray et al.

(10) Patent No.: US 12,187,701 B2
(45) Date of Patent: Jan. 7, 2025

(54) TAIRE FAMILY KINASE INHIBITORS AND USES THEREOF

(71) Applicant: Dana-Farber Cancer Institute, Inc., Boston, MA (US)

(72) Inventors: Nathanael S. Gray, Boston, MA (US); Fleur M. Ferguson, Boston, MA (US); Zainab M. Doctor, Brookline, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 807 days.

(21) Appl. No.: 17/255,647

(22) PCT Filed: Jun. 24, 2019

(86) PCT No.: PCT/US2019/038677
§ 371 (c)(1),
(2) Date: Dec. 23, 2020

(87) PCT Pub. No.: WO2020/005807
PCT Pub. Date: Jan. 2, 2020

(65) Prior Publication Data
US 2021/0292299 A1   Sep. 23, 2021
US 2022/0169631 A9   Jun. 2, 2022

Related U.S. Application Data

(60) Provisional application No. 62/689,551, filed on Jun. 25, 2018.

(51) Int. Cl.
*C07D 401/12* (2006.01)
*A61K 45/06* (2006.01)
*C07D 231/40* (2006.01)
*C07D 403/12* (2006.01)
*C07D 417/12* (2006.01)
*C07D 495/04* (2006.01)

(52) U.S. Cl.
CPC ............ *C07D 401/12* (2013.01); *A61K 45/06* (2013.01); *C07D 231/40* (2013.01); *C07D 403/12* (2013.01); *C07D 417/12* (2013.01); *C07D 495/04* (2013.01)

(58) Field of Classification Search
CPC .. C07D 401/12; C07D 231/40; C07D 403/12; C07D 417/12; C07D 495/04; C07D 417/14; A61K 45/06; A61K 31/415; A61K 31/4155; A61K 31/454
See application file for complete search history.

(56) References Cited

U.S. PATENT DOCUMENTS

| | | |
|---|---|---|
| 4,231,938 A | 11/1980 | Monaghan et al. |
| 4,270,537 A | 6/1981 | Romaine et al. |
| 4,596,556 A | 6/1986 | Morrow et al. |
| 4,782,084 A | 11/1988 | Vyas et al. |
| 4,790,824 A | 12/1988 | Morrow et al. |
| 4,885,314 A | 12/1989 | Vyas et al. |
| 4,886,499 A | 12/1989 | Cirelli et al. |
| 4,940,460 A | 7/1990 | Casey et al. |

(Continued)

FOREIGN PATENT DOCUMENTS

| | | |
|---|---|---|
| CA | 2486101 A1 | 11/2003 |
| CA | 2503646 A1 | 5/2004 |

(Continued)

OTHER PUBLICATIONS

Malumbres, M. et al, CDK inhibitors in cancer therapy: what is next?, Trends in Pharmacological Sciences. vol. 29, Issue 1, p. 16-21, 2008. (Year: 2008).*
Barf, T.; Kaptein, A., Irreversible Protein Kinase Inhibitors: Balancing the Benefits and Risks., J. Med. Chem. 2012, 55, 6243-6262 (Year: 2012).*
Healy et al, Pharmaceutical solvates, hydrates and amorphous forms: A special emphasis on cocrystals. Advanced Drug Delivery Reviews 117 (2017) 25-46. (Year: 2017).*
Mikhail, S., et al., The American Journal of Pathology, vol. 185, No. 5, May 2015. (Year: 2015).*
International Search Report and Written Opinion for PCT/US2013/065708, mailed Feb. 4, 2014.

(Continued)

*Primary Examiner* — Eric Olson
*Assistant Examiner* — Samuel L Galster
(74) *Attorney, Agent, or Firm* — Nielsen IP Law LLC

(57) ABSTRACT

Provided herein are compounds of Formula (I') or (I), and pharmaceutically acceptable salts, solvates, hydrates, polymorphs, co-crystals, tautomers, stereoisomers, isotopically labeled derivatives, prodrugs, and compositions thereof. Also provided are methods and kits involving the inventive compounds or compositions for treating and/or preventing diseases (e.g., proliferative diseases (e.g., cancers (e.g., carcinoma); lung cancer, breast cancer, liver cancer, pancreatic cancer, gastric cancer, ovarian cancer, colon cancer, colorectal cancer)), metabolic disorders (e.g., diabetes), autoimmune diseases, and neurological diseases (e.g., Alzheimer's disease, gliosis, spinal cord injury)) in a subject, as well as for male contraception (e.g., reducing or inhibiting spermatogenesis, or reducing the rate of male fertility in a healthy fertile male subject). Provided are methods of inhibiting a CDK (e.g., CDK14, CDK15, CDK16, CDK17, CDK18) in a subject.

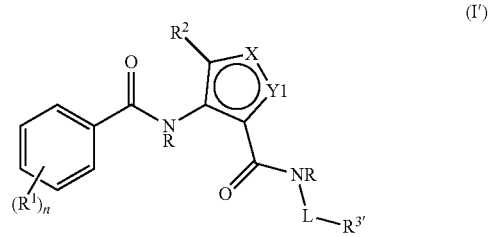

53 Claims, 8 Drawing Sheets

(56) References Cited

U.S. PATENT DOCUMENTS

| | | |
|---|---|---|
| 4,941,880 A | 7/1990 | Burns et al. |
| 5,015,235 A | 5/1991 | Crossman et al. |
| 5,064,413 A | 11/1991 | McKinnon et al. |
| 5,141,496 A | 8/1992 | Dalto et al. |
| 5,190,521 A | 3/1993 | Hubbard et al. |
| 5,312,335 A | 5/1994 | McKinnon et al. |
| 5,328,483 A | 7/1994 | Jacoby et al. |
| 5,334,144 A | 8/1994 | Alchas et al. |
| 5,339,163 A | 8/1994 | Homma et al. |
| 5,383,851 A | 1/1995 | McKinnon et al. |
| 5,417,662 A | 5/1995 | Hjertman et al. |
| 5,420,245 A | 5/1995 | Brown et al. |
| 5,466,220 A | 11/1995 | Brenneman et al. |
| 5,480,381 A | 1/1996 | Weston et al. |
| 5,484,596 A | 1/1996 | Hanna et al. |
| 5,503,627 A | 4/1996 | McKinnon et al. |
| 5,510,510 A | 4/1996 | Patel et al. |
| 5,520,639 A | 5/1996 | Peterson et al. |
| 5,523,430 A | 6/1996 | Patel et al. |
| 5,527,288 A | 6/1996 | Gross et al. |
| 5,532,359 A | 7/1996 | Marsters et al. |
| 5,569,189 A | 10/1996 | Parsons et al. |
| 5,571,792 A | 11/1996 | Bolton et al. |
| 5,589,485 A | 12/1996 | Hocolowski et al. |
| 5,599,302 A | 2/1997 | Lilley et al. |
| 5,602,098 A | 2/1997 | Sebti et al. |
| 5,643,958 A | 7/1997 | Iwasawa et al. |
| 5,649,912 A | 7/1997 | Peterson et al. |
| 5,661,152 A | 8/1997 | Bishop et al. |
| 5,704,911 A | 1/1998 | Parsons et al. |
| 5,750,567 A | 5/1998 | Baudoin et al. |
| 5,856,439 A | 1/1999 | Clerc et al. |
| 5,889,053 A | 3/1999 | Baudoin et al. |
| 5,893,397 A | 4/1999 | Peterson et al. |
| 5,925,641 A | 7/1999 | Kanda et al. |
| 5,936,097 A | 8/1999 | Commercon et al. |
| 5,993,412 A | 11/1999 | Deily et al. |
| 6,069,134 A | 5/2000 | Roth et al. |
| 6,214,852 B1 | 4/2001 | Kim et al. |
| 6,921,763 B2 | 7/2005 | Hirst et al. |
| 6,939,874 B2 | 9/2005 | Harmange et al. |
| 7,115,617 B2 | 10/2006 | Buchanan et al. |
| 7,312,225 B2 | 12/2007 | Luecking et al. |
| 7,728,131 B2 | 6/2010 | Asaki et al. |
| 7,884,117 B2 | 2/2011 | Zhang et al. |
| 7,928,140 B2 | 4/2011 | Booker et al. |
| 8,273,765 B2 | 9/2012 | Fancelli et al. |
| 8,394,818 B2 | 3/2013 | Gray et al. |
| 8,765,747 B2 | 7/2014 | Choi et al. |
| 8,877,761 B2 | 11/2014 | Li |
| 8,889,706 B2 | 11/2014 | Gray et al. |
| 8,987,275 B2 | 3/2015 | Gray et al. |
| 9,180,127 B2 | 11/2015 | Gray et al. |
| 9,358,231 B2 | 6/2016 | Gray et al. |
| 9,382,239 B2 | 7/2016 | Gray et al. |
| 9,505,784 B2 | 11/2016 | Choi et al. |
| 9,670,165 B2 | 6/2017 | Cohen et al. |
| 9,758,522 B2 | 9/2017 | Gray et al. |
| 9,814,709 B2 | 11/2017 | Liu et al. |
| 9,862,688 B2 | 1/2018 | Gray et al. |
| 9,879,003 B2 | 1/2018 | Gray et al. |
| 10,000,483 B2 | 6/2018 | Gray et al. |
| 10,017,477 B2 | 7/2018 | Gray et al. |
| 10,047,070 B2 | 8/2018 | Gray et al. |
| 10,112,927 B2 | 10/2018 | Gray et al. |
| 10,144,730 B2 | 12/2018 | Gray et al. |
| 10,336,760 B2 | 7/2019 | Marineau et al. |
| 10,342,798 B2 | 7/2019 | Gray et al. |
| 10,550,121 B2 | 2/2020 | Gray et al. |
| 10,695,346 B2 | 6/2020 | Gray et al. |
| 10,702,527 B2 | 7/2020 | Hammerman et al. |
| RE48,175 E | 8/2020 | Gray et al. |
| 10,787,436 B2 | 9/2020 | Gray et al. |
| 10,870,651 B2 | 12/2020 | Gray et al. |
| 10,969,394 B2 | 4/2021 | Marto et al. |
| 11,142,507 B2 | 10/2021 | Gray et al. |
| 11,306,070 B2 | 4/2022 | Gray et al. |
| 11,325,910 B2 | 5/2022 | Gray et al. |
| 11,932,625 B2 | 3/2024 | Gray et al. |
| 2003/0139416 A1 | 7/2003 | Buchanan et al. |
| 2004/0106634 A1 | 6/2004 | Satoh et al. |
| 2004/0126359 A1 | 7/2004 | Lamb et al. |
| 2004/0138245 A1 | 7/2004 | Coulomb et al. |
| 2004/0209878 A1 | 10/2004 | Guzi et al. |
| 2005/0026914 A1 | 2/2005 | Buchanan et al. |
| 2005/0197338 A1 | 9/2005 | Huang et al. |
| 2005/0228031 A1 | 10/2005 | Bilodeau et al. |
| 2005/0250837 A1 | 11/2005 | D'Mello et al. |
| 2006/0106083 A1 | 5/2006 | Martina et al. |
| 2006/0189627 A1 | 8/2006 | Laird et al. |
| 2006/0252748 A1* | 11/2006 | Lindenthal ............ A61K 31/454 514/218 |
| 2007/0004705 A1 | 1/2007 | Brasca et al. |
| 2007/0060546 A1 | 3/2007 | Ruat et al. |
| 2007/0093537 A1 | 4/2007 | Hynes et al. |
| 2007/0155746 A1 | 7/2007 | Lang et al. |
| 2007/0185171 A1 | 8/2007 | Germain et al. |
| 2007/0225286 A1 | 9/2007 | Ren et al. |
| 2007/0275963 A1 | 11/2007 | Guzi et al. |
| 2007/0281907 A1 | 12/2007 | Watkins |
| 2008/0039629 A1 | 2/2008 | Ramesh et al. |
| 2008/0090849 A1 | 4/2008 | Bordon-Pallier et al. |
| 2008/0103167 A1 | 5/2008 | Bebernitz et al. |
| 2008/0214501 A1 | 9/2008 | Pan et al. |
| 2008/0249079 A1 | 10/2008 | Chen et al. |
| 2008/0300267 A1 | 12/2008 | Okram et al. |
| 2009/0054392 A1 | 2/2009 | Pelletier et al. |
| 2009/0054405 A1 | 2/2009 | Booker et al. |
| 2009/0082346 A1 | 3/2009 | Brasca et al. |
| 2009/0221632 A1 | 3/2009 | Fancelli et al. |
| 2009/0105250 A1 | 4/2009 | Sim et al. |
| 2009/0156582 A1 | 6/2009 | Tsukamoto et al. |
| 2010/0029638 A1 | 2/2010 | Melvin, Jr. et al. |
| 2010/0056524 A1 | 3/2010 | Mciver et al. |
| 2010/0197688 A1 | 8/2010 | Nantermet et al. |
| 2010/0254905 A1 | 10/2010 | Honigberg et al. |
| 2011/0039873 A1 | 2/2011 | Gaeta et al. |
| 2011/0086858 A1 | 4/2011 | Wang et al. |
| 2011/0098280 A1 | 4/2011 | Garcia-Echeverria et al. |
| 2011/0178070 A1 | 7/2011 | Gong et al. |
| 2011/0207711 A1 | 8/2011 | Katz et al. |
| 2011/0212053 A1 | 9/2011 | Qian et al. |
| 2012/0088766 A1 | 4/2012 | Choi et al. |
| 2012/0094999 A1 | 4/2012 | Gray et al. |
| 2012/0165309 A1 | 6/2012 | Takahashi et al. |
| 2012/0196865 A1 | 8/2012 | Ruat et al. |
| 2012/0202809 A1 | 8/2012 | Li et al. |
| 2012/0277248 A1 | 11/2012 | Caruso et al. |
| 2012/0329771 A1 | 12/2012 | Treu et al. |
| 2013/0040949 A1 | 2/2013 | Gray et al. |
| 2013/0184264 A1 | 7/2013 | Bradner et al. |
| 2013/0184287 A1 | 7/2013 | Gray et al. |
| 2014/0187772 A1 | 7/2014 | Bebbington et al. |
| 2014/0303112 A1 | 10/2014 | Chen et al. |
| 2014/0309249 A1 | 10/2014 | Gray et al. |
| 2015/0094315 A1 | 4/2015 | Choi et al. |
| 2015/0157629 A1 | 6/2015 | Gray et al. |
| 2015/0166532 A1 | 6/2015 | Gray et al. |
| 2015/0203502 A1 | 7/2015 | Cheng et al. |
| 2015/0246913 A1 | 9/2015 | Gray et al. |
| 2015/0274728 A1 | 10/2015 | Gray et al. |
| 2015/0291593 A1 | 10/2015 | Bembenek et al. |
| 2015/0322528 A1 | 11/2015 | Caponigro et al. |
| 2016/0046636 A1 | 2/2016 | Gray et al. |
| 2016/0122323 A1 | 5/2016 | Gray et al. |
| 2016/0264551 A1 | 9/2016 | Ciblat et al. |
| 2016/0264554 A1 | 9/2016 | Gray et al. |
| 2016/0368910 A1 | 12/2016 | Gray et al. |
| 2017/0044111 A1 | 2/2017 | Gray et al. |
| 2017/0044112 A1 | 2/2017 | Gray et al. |
| 2017/0204096 A1 | 7/2017 | Gelin et al. |
| 2018/0093990 A1 | 4/2018 | Gray et al. |
| 2018/0169097 A1 | 6/2018 | Hammerman et al. |
| 2018/0319801 A1 | 11/2018 | Gray et al. |

(56) References Cited

U.S. PATENT DOCUMENTS

| | | |
|---|---|---|
| 2018/0344733 A9 | 12/2018 | Gray et al. |
| 2018/0362483 A1 | 12/2018 | Gray et al. |
| 2018/0369243 A9 | 12/2018 | Gray et al. |
| 2019/0015411 A9 | 1/2019 | Hammerman et al. |
| 2019/0031642 A1 | 1/2019 | Gray et al. |
| 2019/0055248 A1 | 2/2019 | Gray et al. |
| 2019/0241541 A1 | 8/2019 | Ciblat et al. |
| 2019/0248778 A1 | 8/2019 | Gray et al. |
| 2019/0315747 A9 | 10/2019 | Gray et al. |
| 2020/0017475 A9 | 1/2020 | Gray et al. |
| 2020/0024271 A9 | 1/2020 | Gray et al. |
| 2020/0277292 A1 | 9/2020 | Gray et al. |
| 2021/0115051 A1 | 4/2021 | Gray et al. |
| 2021/0315894 A9 | 10/2021 | Gray et al. |
| 2021/0317105 A9 | 10/2021 | Gray et al. |
| 2022/0024929 A9 | 1/2022 | Gray et al. |
| 2022/0055998 A1 | 2/2022 | Gray et al. |
| 2022/0089611 A1 | 3/2022 | Gray et al. |
| 2022/0169631 A9 | 6/2022 | Gray et al. |
| 2022/0213067 A1 | 7/2022 | Gray et al. |
| 2022/0242865 A1 | 8/2022 | Gray et al. |
| 2022/0281874 A1 | 9/2022 | Zhang et al. |
| 2023/0114207 A1 | 4/2023 | Gray et al. |

FOREIGN PATENT DOCUMENTS

| | | |
|---|---|---|
| CA | 2526430 A1 | 12/2004 |
| CA | 2550128 A1 | 6/2005 |
| CA | 2563212 A1 | 10/2005 |
| CA | 2805827 A1 | 2/2012 |
| CA | 2940488 A1 | 9/2015 |
| CA | 2954298 A1 | 1/2016 |
| CA | 2988461 A1 | 12/2019 |
| CA | 2895239 C | 10/2020 |
| CA | 3134221 A1 | 11/2020 |
| CA | 2927917 C | 8/2022 |
| CN | 1701073 | 11/2005 |
| CN | 1726217 A | 1/2006 |
| CN | 1735614 | 2/2006 |
| CN | 100482665 | 5/2006 |
| CN | 1784410 | 6/2006 |
| CN | 102406644 A | 4/2012 |
| CN | 102406646 A | 4/2012 |
| CN | 102408408 A | 4/2012 |
| CN | 103242341 A | 8/2013 |
| CN | 104177363 A | 12/2014 |
| CN | 104487594 A | 4/2015 |
| CN | 107235906 A | 10/2017 |
| CN | 107427521 A | 12/2017 |
| CN | 107686477 A | 2/2018 |
| EP | 0604181 A1 | 12/1993 |
| EP | 0618221 A2 | 3/1994 |
| EP | 0675112 A1 | 3/1995 |
| EP | 0696593 A2 | 8/1995 |
| EP | 1847531 A1 | 10/2007 |
| EP | 1 935 890 A1 | 6/2008 |
| EP | 2 311 842 A2 | 4/2011 |
| EP | 3214086 A1 | 5/2014 |
| EP | 3273966 A2 | 1/2018 |
| GB | 796524 A | 6/1958 |
| JP | H11-514336 | 12/1999 |
| JP | 2000-515550 | 11/2000 |
| JP | 2001-522842 | 11/2001 |
| JP | 2002-537300 | 11/2002 |
| JP | 2003-503351 A | 1/2003 |
| JP | 2003-503481 A | 1/2003 |
| JP | 2003-509342 | 3/2003 |
| JP | 2003-516981 | 5/2003 |
| JP | 2003-516987 | 5/2003 |
| JP | 2004-505977 | 2/2004 |
| JP | 2004-516326 | 6/2004 |
| JP | 2004-517075 | 6/2004 |
| JP | 2004-529140 A | 9/2004 |
| JP | 2005-501860 A | 1/2005 |
| JP | 2005-505535 A | 2/2005 |
| JP | 2005-506950 | 3/2005 |
| JP | 2005-530711 A | 10/2005 |
| JP | 2005-533808 | 11/2005 |
| JP | 2005-534635 A | 11/2005 |
| JP | 2005-538100 A | 12/2005 |
| JP | 2006-502163 | 1/2006 |
| JP | 2006-502184 | 1/2006 |
| JP | 2006-514026 | 4/2006 |
| JP | 2006-518368 | 8/2006 |
| JP | 2006-521394 A | 9/2006 |
| JP | 2006-528163 A | 12/2006 |
| JP | 2007-500226 A | 1/2007 |
| JP | 2007-500725 A | 1/2007 |
| JP | 2007-509130 | 4/2007 |
| JP | 2007-516201 A | 6/2007 |
| JP | 2007-522220 | 8/2007 |
| JP | 2008-500320 A | 1/2008 |
| JP | 2008-501669 A | 1/2008 |
| JP | 2008-502610 A | 1/2008 |
| JP | 2008-528465 A | 7/2008 |
| JP | 2008-528467 A | 7/2008 |
| JP | 2008-538749 | 11/2008 |
| JP | 2009-510110 A | 3/2009 |
| JP | 2009-511483 | 3/2009 |
| JP | 2009-520805 | 5/2009 |
| JP | 2009-538304 | 11/2009 |
| JP | 2010-505905 | 2/2010 |
| JP | 2010-511655 A | 4/2010 |
| JP | 2010-514686 | 5/2010 |
| JP | 2010-518069 | 5/2010 |
| JP | 2010-521487 A | 6/2010 |
| JP | 2010-523643 | 7/2010 |
| JP | 2010-529140 | 8/2010 |
| JP | 2010-536869 A | 12/2010 |
| JP | 2011-515371 A | 5/2011 |
| JP | 2011-516533 A | 5/2011 |
| JP | 2011-526594 A | 10/2011 |
| JP | 2012-511021 A | 5/2012 |
| JP | 2012-529519 | 11/2012 |
| JP | 2012-530071 A | 11/2012 |
| JP | 2014-526549 A | 10/2014 |
| JP | 2015-503625 A | 2/2015 |
| JP | 2016-512534 A | 4/2016 |
| JP | 2016-533379 A | 10/2016 |
| JP | 2017-504651 A | 2/2017 |
| JP | 2018-506531 A | 3/2018 |
| KR | 10-2009-0053593 A | 5/2009 |
| MX | 2016-009974 A | 10/2016 |
| MX | 2016-009975 A | 10/2016 |
| MX | 2016-009976 A | 11/2016 |
| WO | WO 84/02131 A1 | 6/1984 |
| WO | WO 94/19357 A1 | 9/1994 |
| WO | WO 95/08542 A1 | 3/1995 |
| WO | WO 95/10514 A1 | 4/1995 |
| WO | WO 95/10515 A1 | 4/1995 |
| WO | WO 95/10516 A1 | 4/1995 |
| WO | WO 95/11917 A1 | 5/1995 |
| WO | WO 95/12572 A1 | 5/1995 |
| WO | WO 95/12612 A1 | 5/1995 |
| WO | WO 95/25086 A1 | 9/1995 |
| WO | WO 95/26412 A1 | 10/1995 |
| WO | WO 95/32987 A1 | 12/1995 |
| WO | WO 95/34535 A1 | 12/1995 |
| WO | WO 96/00736 A1 | 1/1996 |
| WO | WO 96/05168 A1 | 2/1996 |
| WO | WO 96/05169 A1 | 2/1996 |
| WO | WO 96/17861 A1 | 6/1996 |
| WO | WO 96/21456 A1 | 7/1996 |
| WO | WO 96/22278 A1 | 7/1996 |
| WO | WO 96/24611 A1 | 8/1996 |
| WO | WO 96/30017 A1 | 10/1996 |
| WO | WO 96/30018 A1 | 10/1996 |
| WO | WO 96/30343 A1 | 10/1996 |
| WO | WO 96/30362 A1 | 10/1996 |
| WO | WO 96/30363 A1 | 10/1996 |
| WO | WO 96/31111 A1 | 10/1996 |
| WO | WO 96/31477 A1 | 10/1996 |
| WO | WO 96/31478 A1 | 10/1996 |
| WO | WO 96/31501 A1 | 10/1996 |

(56) References Cited

FOREIGN PATENT DOCUMENTS

| | | |
|---|---|---|
| WO | WO 96/33159 A1 | 10/1996 |
| WO | WO 96/34850 A1 | 11/1996 |
| WO | WO 96/34851 A1 | 11/1996 |
| WO | WO 97/00252 A1 | 1/1997 |
| WO | WO 97/03047 A1 | 1/1997 |
| WO | WO 97/03050 A1 | 1/1997 |
| WO | WO 97/04785 A1 | 2/1997 |
| WO | WO 97/17070 A1 | 5/1997 |
| WO | WO 97/18813 A1 | 5/1997 |
| WO | WO 97/21701 A1 | 6/1997 |
| WO | WO 97/23478 A1 | 7/1997 |
| WO | WO 97/26246 A1 | 7/1997 |
| WO | WO 97/30053 A1 | 8/1997 |
| WO | WO 97/38665 A2 | 10/1997 |
| WO | WO 97/44350 A1 | 11/1997 |
| WO | WO 98/02436 A1 | 1/1998 |
| WO | WO 98/28980 A1 | 7/1998 |
| WO | WO 98/29119 A1 | 7/1998 |
| WO | WO 00/44777 A1 | 8/2000 |
| WO | WO 00/50032 A1 | 8/2000 |
| WO | WO 00/61186 A1 | 10/2000 |
| WO | WO 01/02369 A2 | 1/2001 |
| WO | WO 01/019829 A2 | 3/2001 |
| WO | WO 01/053267 A1 | 7/2001 |
| WO | WO 02/12242 A2 | 2/2002 |
| WO | WO 02/076986 A1 | 10/2002 |
| WO | WO 02/079197 A1 | 10/2002 |
| WO | WO 02/080926 A1 | 10/2002 |
| WO | WO 02/083653 A1 | 10/2002 |
| WO | WO 02/096905 A1 | 12/2002 |
| WO | WO 02/102800 A1 | 12/2002 |
| WO | WO 2003/018021 A1 | 3/2003 |
| WO | WO 2003/018022 A1 | 3/2003 |
| WO | WO 2003/026664 A1 | 4/2003 |
| WO | WO 2003/051847 A1 | 6/2003 |
| WO | WO 2003/078403 A2 | 9/2003 |
| WO | WO 2003/097610 A1 | 11/2003 |
| WO | WO 2004/000214 A2 | 12/2003 |
| WO | WO 2004/002948 A1 | 1/2004 |
| WO | WO 2004/005283 A1 | 1/2004 |
| WO | WO 2004/009601 A1 | 1/2004 |
| WO | WO 2004/010995 A1 | 2/2004 |
| WO | WO 2004/022561 A1 | 3/2004 |
| WO | WO 2004/026229 A2 | 4/2004 |
| WO | WO 2004/039796 A1 | 5/2004 |
| WO | WO 2004/046118 A2 | 6/2004 |
| WO | WO 2004/074283 A1 | 9/2004 |
| WO | WO 2004/076458 A1 | 9/2004 |
| WO | WO 2004/078757 A2 | 9/2004 |
| WO | WO 2004/081013 A1 | 9/2004 |
| WO | WO 2004/087699 A2 | 10/2004 |
| WO | WO 2004/087707 A1 | 10/2004 |
| WO | WO 2004/100868 A2 | 11/2004 |
| WO | WO 2004/113303 A1 | 12/2004 |
| WO | WO 2004/113304 A1 | 12/2004 |
| WO | WO 2005/002576 A3 | 1/2005 |
| WO | WO 2005/011597 A2 | 2/2005 |
| WO | WO 2005/012256 A1 | 2/2005 |
| WO | WO 2005/058891 A1 | 6/2005 |
| WO | WO 2005/063709 A1 | 7/2005 |
| WO | WO 2005/097790 A1 | 10/2005 |
| WO | WO 2005/108397 A1 | 11/2005 |
| WO | WO 2005/116025 A2 | 12/2005 |
| WO | WO 2006/003276 A1 | 1/2006 |
| WO | WO 2006/024834 A1 | 3/2006 |
| WO | WO 2006/031806 A2 | 3/2006 |
| WO | WO 2006/034341 A2 | 3/2006 |
| WO | WO 2006/040568 A1 | 4/2006 |
| WO | WO 2006/072831 A1 | 7/2006 |
| WO | WO-2006077414 A1 * | 7/2006 ................ A61P 1/04 |
| WO | WO 2006/085685 A1 | 8/2006 |
| WO | WO 2006/093247 A1 | 9/2006 |
| WO | WO 2006/124731 A2 | 11/2006 |
| WO | WO 2007/002325 A1 | 1/2007 |
| WO | WO 2007/002433 A1 | 1/2007 |
| WO | WO 2007/024680 A1 | 3/2007 |
| WO | WO 2007/035428 A1 | 3/2007 |
| WO | WO 2007/042786 A2 | 4/2007 |
| WO | WO 2007/044420 A1 | 4/2007 |
| WO | WO 2007/048070 A2 | 4/2007 |
| WO | WO 2007/056023 A2 | 5/2007 |
| WO | WO 2007/072153 A2 | 6/2007 |
| WO | WO 2007/075869 A2 | 7/2007 |
| WO | WO 2007/076161 A2 | 7/2007 |
| WO | WO 2007/086584 A1 | 8/2007 |
| WO | WO 2007/129195 A2 | 11/2007 |
| WO | WO 2007/138277 A1 | 12/2007 |
| WO | WO-2008009954 A1 * | 1/2008 ........... A61K 31/415 |
| WO | WO 2008/049856 A1 | 5/2008 |
| WO | WO 2008/063888 A2 | 5/2008 |
| WO | WO 2008/068171 A1 | 6/2008 |
| WO | WO 2008/074749 A1 | 6/2008 |
| WO | WO 2008/079460 A2 | 7/2008 |
| WO | WO 2008/080015 A2 | 7/2008 |
| WO | WO 2008/112913 A1 | 9/2008 |
| WO | WO 2008/124393 A1 | 10/2008 |
| WO | WO 2008/144253 A1 | 11/2008 |
| WO | WO 2008/151183 A1 | 12/2008 |
| WO | WO 2008/151304 A1 | 12/2008 |
| WO | WO 2009/017822 A2 | 2/2009 |
| WO | WO 2009/028655 A1 | 3/2009 |
| WO | WO 2009/032694 A1 | 3/2009 |
| WO | WO 2009/036016 A1 | 3/2009 |
| WO | WO 2009/115572 A2 | 9/2009 |
| WO | WO 2009/145360 A1 | 12/2009 |
| WO | WO 2009/152027 A1 | 12/2009 |
| WO | WO 2009/155017 A2 | 12/2009 |
| WO | WO 2010/001166 A1 | 1/2010 |
| WO | WO 2010/008847 A2 | 1/2010 |
| WO | WO 2010/044885 A2 | 4/2010 |
| WO | WO 2010/051781 A1 | 5/2010 |
| WO | WO 2010/065893 A1 | 6/2010 |
| WO | WO 2010/075542 A1 | 7/2010 |
| WO | WO 2010/092962 A1 | 8/2010 |
| WO | WO 2010/125799 A1 | 11/2010 |
| WO | WO 2010/144909 A1 | 12/2010 |
| WO | WO 2011/079231 A1 | 6/2011 |
| WO | WO 2011/115725 A2 | 9/2011 |
| WO | WO 2012/066061 A1 | 5/2012 |
| WO | WO 2012/090219 A1 | 7/2012 |
| WO | WO 2013/014162 A1 | 1/2013 |
| WO | WO 2013/040436 A2 | 3/2013 |
| WO | WO 2013/049279 A2 | 4/2013 |
| WO | WO 2013/074986 A1 | 5/2013 |
| WO | WO 2013/154778 A1 | 10/2013 |
| WO | WO 2014/063061 A1 | 4/2014 |
| WO | WO 2014/063068 A1 | 4/2014 |
| WO | WO 2014/147021 A2 | 9/2014 |
| WO | WO 2014/149164 A1 | 9/2014 |
| WO | WO 2014/165065 A1 | 10/2014 |
| WO | WO 2015/006754 A2 | 1/2015 |
| WO | WO 2015/013635 A2 | 1/2015 |
| WO | WO 2015/025197 A1 | 2/2015 |
| WO | WO 2015/058126 A1 | 4/2015 |
| WO | WO 2015/058140 A1 | 4/2015 |
| WO | WO 2015/089479 A1 | 6/2015 |
| WO | WO 2015/117087 A1 | 8/2015 |
| WO | WO 2015/154022 A1 | 10/2015 |
| WO | WO 2015/154038 A1 | 10/2015 |
| WO | WO 2015/164604 A1 | 10/2015 |
| WO | WO 2015/164614 A1 | 10/2015 |
| WO | WO 2016/014542 A1 | 1/2016 |
| WO | WO 2016/014551 A1 | 1/2016 |
| WO | WO 2016/058544 A1 | 4/2016 |
| WO | WO 2016/068287 A1 | 5/2016 |
| WO | WO 2016/105528 A2 | 6/2016 |
| WO | WO 2016/142855 A2 | 9/2016 |
| WO | WO 2016/160617 A2 | 10/2016 |
| WO | WO 2016/193939 A1 | 12/2016 |
| WO | WO 2016/201370 A1 | 12/2016 |
| WO | WO 2017/037576 A1 | 3/2017 |
| WO | WO 2017/160717 A2 | 9/2017 |
| WO | WO 2020/100944 A1 | 5/2020 |
| WO | WO 2020/140098 A1 | 7/2020 |

(56) References Cited

FOREIGN PATENT DOCUMENTS

| WO | WO 2021/016388 A1 | 1/2021 |
|---|---|---|
| WO | WO 2021/026109 A1 | 2/2021 |
| WO | WO 2021/133601 A1 | 7/2021 |

OTHER PUBLICATIONS

International Preliminary Report on Patentability for PCT/US2013/065708, mailed Apr. 30, 2015.
International Search Report and Written Opinion for PCT/US2014/061232, mailed Dec. 23, 2014.
Extended European Search Report for EP 15873803.9 mailed on Apr. 12, 2018.
Partial Supplementary Search Report for EP 16808476.2, mailed on Mar. 7, 2019.
Extended European Search Report for EP 16808476.2, mailed on Jun. 14, 2019.
International Search Report and Written Opinion for PCT/US2016/037086, mailed Sep. 2, 2016.
International Preliminary Report on Patentability for PCT/US/2016/037086, mailed Dec. 21, 2017.
Partial European Search Report for EP 16773870.7, dated Jul. 12, 2018.
Extended European Search Report for EP 15773870.7, mailed on Oct. 17, 2018.
Invitation to Pay Additional Fees for PCT/US2016/024345, mailed Aug. 9, 2016.
International Search Report and Written Opinion for PCT/US2016/024345, mailed Oct. 6, 2016.
International Preliminary Report on Patentability for PCT/US2016/024345, mailed Oct. 12, 2017.
International Search Report and Written Opinion for PCT/US16/39302, mailed Sep. 27, 2016.
Extended European Search Report for EP 16845194.6, mailed Mar. 1, 2019.
Extended European Search Report for EP 21193645.5, mailed on May 11, 2022.
Invitation to Pay Additional Fees for PCT/US2016/051118, mailed Dec. 1, 2016.
International Search Report and Written Opinion for PCT/US2016/051118, mailed Mar. 13, 2017.
International Preliminary Report on Patentability for PCT/US2016/051118, mailed Mar. 22, 2018.
Extended European Search Report for EP 19826764.3 mailed on May 23, 2022.
Extended European Search Report for EP 19903185.7 mailed on Aug. 5, 2022.
International Preliminary Report on Patentability for PCT/US2019/068835, mailed Jul. 8, 2021.
International Preliminary Report on Patentability for PCT/US2020/043132, mailed Feb. 3, 2022.
International Search Report and Written Opinion for PCT/US2020/065267, mailed Mar. 26, 2021.
International Preliminary Report on Patentability for PCT/US2020/065267, mailed Jul. 7, 2022.
CAS Registry No. 1998741-43-7, STN Entry Date 2016.
Brasca et al., Optimization of 6,6-dimethyl pyrrolo[3,4-c]pyrazoles: Identification of PHA-793887, a potent CDK inhibitor suitable for intravenous dosing. Bioorg Med Chem. Mar. 1, 2010;18(5):1844-53. doi: 10.1016/j.bmc.2010.01.042. Epub Jan. 25, 2010. PMID: 20153204.
Choong et al., A diaminocyclohexyl analog of SNS-032 with improved permeability and bioavailability properties. Bioorg Med Chem Lett. Nov. 1, 2008;18(21):5763-5. doi: 10.1016/j.bmcl.2008.09.073. Epub Sep. 24, 2008. PMID: 18842409.
Ferguson et al., Synthesis and structure activity relationships of a series of 4-amino-1H-pyrazoles as covalent inhibitors of CDK14. Bioorg Med Chem Lett. Aug. 1, 2019;29(15):1985-1993. doi: 10.1016/j.bmcl.2019.05.024. Epub May 23, 2019.

Hazlitt et al., Development of Second-Generation CDK2 Inhibitors for the Prevention of Cisplatin-Induced Hearing Loss. J Med Chem. Sep. 13, 2018;61(17):7700-7709. doi: 10.1021/acs.jmedchem.8b00669. Epub Aug. 24, 2018. PMID: 30091915; PMCID: PMC6443376.
Olson et al. Development of a Selective CDK7 Covalent Inhibitor Reveals Predominant Cell-Cycle Phenotype. Cell Chem Biol. Jun. 20, 2019;26(6):792-803.e10. doi: 10.1016/j.chembiol.2019.02.012. Epub Mar. 21, 2019. PMID: 30905681.
International Search Report and Written Opinion for PCT/US2015/000297, mailed Mar. 4, 2016.
International Preliminary Report on Patentability PCT/US2015/000297, mailed Jul. 6, 2017.
International Search Report and Written Opinion for PCT/US2019/038677, mailed Oct. 2, 2019.
International Preliminary Report on Patentability PCT/US2019/038677, mailed Jan. 7, 2021.
Invitation to Pay Additional Fees for PCT/US2019/038677, mailed Aug. 13, 2019.
Akhtar et al., TFIIH kinase places bivalent marks on the carboxy-terminal domain of RNA polymerase II. Mol Cell. May 15, 2009;34(3):387-93. doi: 10.1016/j.molcel.2009.04.016, Author Manuscript, 15 pages.
Bai et al., Design, synthesis and anticancer activity of 1-acyl-3-amino-1,4,5,6-tetrahydropyrrolo[3,4-c]pyrazole derivatives. Bioorg Med Chem Lett. Nov. 15, 2012;22(22):6947-51. Suppl. Info, 46 pages. doi: 10.1016/j.bmcl.2012.08.117. Epub Sep. 8, 2012.
Bajrami et al., Genome-wide profiling of genetic synthetic lethality identifies CDK12 as a novel determinant of PARP1/2 inhibitor sensitivity. Cancer Res. Jan. 1, 2014;74(1):287-97. doi: 10.1158/0008-5472.CAN-13-2541. Epub Nov. 15, 2013.
Bartkowiak et al., CDK12 is a transcription elongation-associated CTD kinase, the metazoan ortholog of yeast Ctk1. Genes Dev. Oct. 15, 2010;24(20):2303-16. doi: 10.1101/gad.1968210.
Beeler et al., Role of the JNK-interacting protein 1/islet brain 1 in cell degeneration in Alzheimer disease and diabetes. Brain Res Bull. Oct. 28, 2009;80(4-5):274-81. doi: 10.1016/j.brainresbull.2009.07.006. Epub Jul. 16, 2009.
Bell et al., Integrated genomic analyses of ovarian carcinoma. Nature. Jun. 29, 2011;474(7353):609-15. doi: 10.1038/nature10166.
Ben-Av et al., Induction of vascular endothelial growth factor expression in synovial fibroblasts by prostaglandin E and interleukin-1: a potential mechanism for inflammatory angiogenesis. FEBS Letters 1995;372:83-7.
Benezra et al., In vivo angiogenic activity of interleukins. Archives of Opthamology 1990; 108:573.
Blachly et al., Emerging drug profile: cyclin-dependent kinase inhibitors. Leuk Lymphoma. Oct. 2013;54(10):2133-43. doi: 10.3109/10428194.2013.783911. Epub Jul. 29, 2013. Author manuscript, 22 pages.
Blazek et al., The Cyclin K/Cdk12 complex maintains genomic stability via regulation of expression of DNA damage response genes. Genes Dev. Oct. 15, 2011;25(20):2158-72. doi: 10.1101/gad.16962311.
Blazek et al., The cyclin K/Cdk12 complex: an emerging new player in the maintenance of genome stability. Cell Cycle. Mar. 15, 2012;11(6):1049-50. doi: 10.4161/cc.11.6.19678. Epub Mar. 15, 2012.
Bloom et al., The requirement for Phr1 in CNS axon tract formation reveals the corticostriatal boundary as a choice point for cortical axons. Genes Dev. Oct. 15, 2007;21(20):2593-606. Epub Sep. 27, 2007.
Bogoyevitch et al., c-Jun N-terminal kinase (JNK) signaling: recent advances and challenges. Biochim Biophys Acta. Mar. 2010; 1804(3):463-75. doi: 10.1016/j.bbapap.2009.11.002. Epub Nov. 10, 2009.
Bosken et al., The structure and substrate specificity of human Cdk12/Cyclin K. Nat Commun. Mar. 24, 2014;5:3505. doi: 10.1038/ncomms4505.
Brasca et al., 6-Substituted pyrrolo[3,4-c]pyrazoles: an improved class of CDK2 inhibitors. ChemMedChem. Jun. 2007;2(6):841-52.
Brower et al., Tumor Angiogenesis: New drugs on the block. Nature Biotechnology 1999;17:963-8.

(56) References Cited

OTHER PUBLICATIONS

Brunton et al., eds., Chemotherapy of Neoplastic Diseases. In Goodman & Gilman's The Pharmacological Basis of Therapeutics. 2008; 11th edition:853-908.

Cai et al., Discovery of orally active pyrrolopyridine- and aminopyridine-based Met kinase inhibitors. Bioorg Med Chem Lett. Jun. 1, 2008;18(11):3224-9. doi: 10.1016/j.bmcl.2008.04.047. Epub Apr. 25, 2008.

Cappuzzo et al., Increased MET gene copy number negatively affects survival of surgically resected non-small-cell lung cancer patients. J Clin Oncol. Apr. 1, 2009;27(10):1667-74. doi: 10.1200/JCO.2008.19.1635. Epub Mar. 2, 2009.

Carvajal et al., KIT as a therapeutic target in metastatic melanoma. JAMA. Jun. 8, 2011;305(22):2327-34. doi: 10.1001/jama.2011.746.

CAS Registry No. 1334419-59-8, STN Entry Date Dec. 30, 2013.
CAS Registry No. 769961-59-3, STN Entry Date Oct. 27, 2004.
CAS Registry No. 916173-61-0, STN Entry Date Dec. 21, 2006.
CAS Registry No. 769961-42-4, STN Entry Date Oct. 27, 2004.

Castillo et al., suzuki reaction on pyridinium N-haloheteroarylaminides: regioselective synthesis of 3,5-disubstituted 2-aminopyrazines. Available Online Nov. 22, 2007; 2008; 64(7);1351-1370.

Chakraborty et al., Developmental expression of the cyclo-oxygenase-1 and cyclo-oxygenase-2 genes in the peri-implantation mouse uterus and their differential regulation by the blastocyst and ovarian steroids. Journal of Molecular Endocrinology 1996;16:107-122.

Chen et al., Antiapoptotic and trophic effects of dominant-negative forms of dual leucine zipper kinase in dopamine neurons of the substantia nigra in vivo. J Neurosci. Jan. 16, 2008;28(3):672-80. doi: 10.1523/JNEUROSCI.2132-07.2008.

Chen et al., Cdk12 and Cdk13 regulate axonal elongation through a common signaling pathway that modulates Cdk5 expression. Exp Neurol. Nov. 2014;261:10-21. doi: 10.1016/j.expneurol.2014.06.024. Epub Jul. 3, 2014.

Chène, Challenges in design of biochemical assays for the identification of small molecules to target multiple conformations of protein kinases. Drug Discov Today. Jun. 2008;13(11-12):522-9. doi: 10.1016/j.drudis.2008.03.023. Epub May 5, 2008.

Chiarugi et al., Cox-2, iNOS and p53 as play-makers of tumor angiogenesis. International Journal of Molecular Medicine 1998;2:715-9.

Choi et al., Development of 'DFG-out' inhibitors of gatekeeper mutant kinases. Bioorg Med Chem Lett. Aug. 15, 2012;22(16):5297-302. doi: 10.1016/j.bmcl.2012.06.036. Epub Jun. 23, 2012, Author Manuscript, 15 pages.

Choi et al., Discovery and structural analysis of Eph receptor tyrosine kinase inhibitors. Bioorg Med Chem Lett. Aug. 1, 2009;19(15):4467-70. doi: 10.1016/j.bmcl.2009.05.029. Epub May 13, 2009. Supplementary Materials.

Chong et al., Positive and negative regulation of Raf kinase activity and function by phosphorylation EMBO J. Jul. 1, 20016;20(14):3716-27.

Christensen et al., Cytoreductive antitumor activity of PF-2341066, a novel inhibitor of anaplastic lymphoma kinase and c-Met, in experimental models of anaplastic large-cell lymphoma. Mol Cancer Ther. Dec. 2007;6(12 Pt 1):3314-22.

Christensen et al., Targeting transcriptional addictions in small cell lung cancer with a covalent CDK7 inhibitor. Cancer Cell. Dec. 8, 2014;26(6):909-22.

Christian et al., Flavopiridol in chronic lymphocytic leukemia: a concise review. Clin Lymphoma Myeloma. 2009;9 Suppl 3:S179-85. doi: 10.3816/CLM.2009.s.009.

Database Registry [Online] Retrieved from STN, 2011年12月4日,, search date :Oct. 7, 2019; RN 1350102-23-6, 1349782-05-3, 1349471-31-3, 1349357-86-3, 1349106-33-7, 1348397-56-7, 1348192-23-3, 1348088-42-5.

Davies et al., Mutations of the BRAF gene in human cancer Nature. Jun. 27, 2002;417(6892):949-54. Epub Jun. 9, 2002.

Davis et al., Comprehensive analysis of kinase inhibitor selectivity. Nat Biotechnol. Oct. 30, 2011;29(11):1046-51. doi: 10.1038/nbt.1990.

Dent et al.Synergistic combinations of signaling pathway inhibitors: mechanisms for improved cancer therapy. Drug Resist Updat. Jun. 2009;12(3):65-73. doi: 10.1016/j.drup.2009.03.001.

Desai et al., Effects of phosphorylation by CAK on cyclin binding by CDC2 and CDK2. Mol Cell Biol. Jan. 1995;15(1):345-50.

Diaz-Flores et al., Intense vascular sprouting from rat femoral vein induced by prostaglandins E1 and E2. Anatomical Record 1994;238:68-76.

Downward, Targeting RAS signalling pathways in cancer therapy Nat Rev Cancer. Jan. 2003;3(1):11-22.

Dranchak et al. Profile of the GSK published protein kinase inhibitor set across ATP-dependent and-independent luciferases: implications for reporter-gene assays. PLoS One. 2013;8(3):e57888. doi: 10.1371/journal.pone.0057888.

Drapkin et al., Human cyclin-dependent kinase-activating kinase exists in three distinct complexes. Proc Natl Acad Sci U S A. Jun. 25, 1996;93(13):6488-93.

Ercan et al., Reactivation of ERK signaling causes resistance to EGFR kinase inhibitors. Cancer Discov. Oct. 2012;2(10):934-47.

Even et al., CDC2L5, a Cdk-like kinase with RS domain, interacts with the ASF/SF2-associated protein p32 and affects splicing in vivo. J Cell Biochem. Oct. 15, 2006;99(3):890-904.

Fan et al., Dual leucine zipper-bearing kinase (DLK) activates p46SAPK and p38mapk but not ERK2. J Biol Chem. Oct. 4, 1996;271(40):24788-93.

Fancelli et al., Potent and selective Aurora inhibitors identified by the expansion of a novel scaffold for protein kinase inhibition. J Med Chem. Apr. 21, 2005;48(8):3080-4.

Fernandes et al., JNK2 and JNK3 are major regulators of axonal injury-induced retinal ganglion cell death. Neurobiol Dis. May 2012;46(2):393-401. doi: 10.1016/j.nbd.2012.02.003. Epub Feb. 14, 2012.

Fernandez et al., Neovascularization produced by angiotensin I.Journal of Laboratory and Clinical Medicine 1985;105(2):141-5.

Filippakopoulos et al., Selective inhibition of BET bromodomains. Nature. Dec. 23, 2010;468(7327):1067-73.

Finn et al., Dasatinib, an orally active small molecule inhibitor of both the src and abl kinases, selectively inhibits growth of basal-type/"triple-negative" breast cancer cell lines growing in vitro. Breast Cancer Res Treat. Nov. 2007;105(3):319-26. Epub Feb. 1, 2007.

Fiskus et al., BET protein antagonist JQ1 is synergistically lethal with FLT3 tyrosine kinase inhibitor (TKI) and overcomes resistance to FLT3-TKI in AML cells expressing FLT-ITD. Mol Cancer Ther. Oct. 2014; 13(10): 2315-2327. Published online Jul. 22, 2014. doi: 10.1158/1535-7163.MCT-14-0258, Author Manuscript, 30 pages.

Fizazi, The role of Src in prostate cancer. Ann Oncol. Nov. 2007;18(11):1765-73. Epub Apr. 10, 2007.

Fleisher et al., Improved oral drug delivery: solubility limitations overcome by the use of prodrugs. Advanced Drug Delivery Reviews 1996;19:115-30.

Fleming et al., Synergistic inhibition of ErbB signaling by combined treatment with seliciclib and ErbB-targeting agents. Clin Cancer Res. Jul. 1, 2008;14(13):4326-35. doi: 10.1158/1078-0432.CCR-07-4633.

Fraser et al., Dasatinib inhibits the secretion of TNF-alpha following TLR stimulation in vitro and in vivo. Exp Hematol. Dec. 2009;37(12):1435-44. doi: 10.1016/j.exphem.2009.09.007. Epub Sep. 26, 2009.

Fry et al., Specific inhibition of cyclin-dependent kinase 4/6 by PD 0332991 and associated antitumor activity in human tumor xenografts. Mol Cancer Ther. Nov. 2004;3(11):1427-38.

Garnett et al., Guilty as charged: B-RAF is a human oncogene Cancer Cell. Oct. 2004;6(4):313-9.

GenBank Accession No. M80629. Lapidot-Lifson et al., Dec. 31, 1994. 2 pages.

GenBank Accession No. NP_001790. Yang et al., Oct. 6, 2016. 4 pages.

Girotti et al., No longer an untreatable disease: How targeted and immunotherapies have changed the management of melanoma

(56) References Cited

OTHER PUBLICATIONS patients. Mol Oncol. Sep. 2014; 8(6): 1140-1158. Published online Aug. 15, 2014. doi: 10.1016/j.molonc.2014.07.027.
Glover-Cutter et al., TFIIH-associated Cdk7 kinase functions in phosphorylation of C-terminal domain Ser7 residues, promoter-proximal pausing, and termination by RNA polymerase II. Mol Cell Biol. Oct. 2009;29(20):5455-64. doi: 10.1128/MCB.00637-09. Epub Aug. 10, 2009.
Gojo et al., The cyclin-dependent kinase inhibitor flavopiridol induces apoptosis in multiple myeloma cells through transcriptional repression and down-regulation of Mcl-1. Clin Cancer Res. Nov. 2002;8(11):3527-38.
Gu et al., Effect of novel CAAX peptidomimetic farnesyltransferase inhibitor on angiogenesis in vitro and in vivo. European Journal of Cancer 1999;35(9):1394-1401.
Harada et al., Expression and regulation of vascular endothelial growth factor in osteoblasts. Clinical Orthopedics 1995;313:76-80.
Hart et al., SB1518, a novel macrocyclic pyrimidine-based JAK2 inhibitor for the treatment of myeloid and lymphoid malignancies. Leukemia. Nov. 2011;25(11):1751-9. doi: 10.1038/leu.2011.148. Epub Jun. 21, 2011.
Hirai et al., The c-Jun N-terminal kinase activator dual leucine zipper kinase regulates axon growth and neuronal migration in the developing cerebral cortex. J Neurosci. Nov. 15, 2006;26(46):11992-2002.
Hla et al., Human cyclooxygenase-2 cDNA. Proceedings of the National Academy of Sciences 1992;89(16):7384-8.
Hur et al., Clinical stage EGFR inhibitors irreversibly alkylate Bmx kinase. Bioorg Med Chem Lett. Nov. 15, 2008;18(22):5916-9. doi: 10.1016/j.bmcl.2008.07.062. Epub Jul. 18, 2008.
Iorns et al., CRK7 modifies the MAPK pathway and influences the response to endocrine therapy. Carcinogenesis. Oct. 2009;30(10):1696-701. doi: 10.1093/carcin/bgp187. Epub Aug. 3, 2009.
Itoh et al., Impaired regenerative response of primary sensory neurons in ZPK/DLK gene-trap mice. Biochem Biophys Res Commun. May 29, 2009;383(2):258-62. doi: 10.1016/j.bbrc.2009.04.009. Epub Apr. 7, 2009.
Janne et al., Factors underlying sensitivity of cancers to small-molecule kinase inhibitors. Nat Rev Drug Discov. Sep. 2009;8(9):709-23. doi: 10.1038/nrd2871. Epub Jul. 24, 2009.
Joh et al., Ginsenoside Rb1 and its metabolite compound K inhibit IRAK-1 activation—the key step of inflammation. Biochem Pharmacol. Aug. 1, 2011;82(3):278-86. doi: 10.1016/j.bcp.2011.05.003. Epub May 12, 2011.
Joshi et al., Ovarian cancer-associated mutations disable catalytic activity of CDK12, a kinase that promotes homologous recombination repair and resistance to cisplatin and poly(ADP-ribose) polymerase inhibitors. J Biol Chem. Mar. 28, 2014;289(13):9247-53. doi: 10.1074/jbc.M114.551143. Epub Feb. 19, 2014.
Jouve et al., Oxidative cyclization of n-methyl- and n-benzoylpyridylthioureas. Preparation of new thiazolo[4,5-b] and [5,4-b] pyridine derivatives. J Heterocyclic Chemistry. 2003;40(2):261-68.
Kaldis et al., Analysis of CAK activities from human cells. Eur J Biochem. Jul. 2000;267(13):4213-21.
Kanakaraj et al., Interleukin (IL)-1 receptor-associated kinase (IRAK) requirement for optimal induction of multiple IL-1 signaling pathways and IL-6 production. J Exp Med. Jun. 15, 1998;187(12):2073-9.
Kantarjian et al., Dasatinib versus imatinib in newly diagnosed chronic-phase chronic myeloid leukemia. N Engl J Med. Jun. 17, 2010;362(24):2260-70.
Katt et al., Dissemination from a Solid Tumor: Examining the Multiple Parallel Pathways. Trends Cancer. Jan. 2018;4(1):20-37. doi: 10.1016/j.trecan.2017.12.002. Epub Jan. 10, 2018. Author manuscript, 26 pages.
Kauraniemi et al., New amplified and highly expressed genes discovered in the ERBB2 amplicon in breast cancer by cDNA microarrays. Cancer Res. Nov. 15, 2001;61(22):8235-40.

Kim et al., Discovery of pyrrolopyridine-pyridone based inhibitors of Met kinase: synthesis, X-ray crystallographic analysis, and biological activities. J Med Chem. Sep. 11, 2008;51(17):5330-41. doi: 10.1021/jm800476q. Epub Aug. 9, 2008.
Kim et al., Inhibition of vascular endothelial growth factor-induced angiogenesis suppresses tumour growth in vivo. Nature 1993;362:841.
King et al., Demonstration of a genetic therapeutic index for tumors expressing oncogenic BRAF by the kinase inhibitor SB-590885. Cancer Res. Dec. 1, 2006;66(23):11100-5.
Ko et al., CrkRS: a novel conserved Cdc2-related protein kinase that colocalises with SC35 speckles. J Cell Sci. Jul. 2001;114(Pt 14):2591-603.
Koivunen et al., EML4-ALK fusion gene and efficacy of an ALK kinase inhibitor in lung cancer. Clin Cancer Res. Jul. 1, 2008;14(13):4275-83. doi: 10.1158/1078-0432.CCR-08-0168.
Konig et al., The novel cyclin-dependent kinase inhibitor flavopiridol downregulates Bcl-2 and induces growth arrest and apoptosis in chronic B-cell leukemia lines. Blood. Dec. 1, 1997;90(11):4307-12.
Kooistra et al., Kinase-Centric Computational Drug Development, In 50 Annual Reports in Medicinal Chemistry. 2017;197-236.
Kwiatkowski et al., Targeting transcription regulation in cancer with a covalent CDK7 inhibitor. Nature. Jul. 31, 2014;511(7511):616-20.
Kwong et al., Targeted therapy for melanoma: rational combinatorial approaches. Oncogene. Jan. 2, 2014;33(1):1-9. doi: 10.1038/onc.2013.34. Epub Feb. 18, 2013.
Larochelle et al., Requirements for Cdk7 in the assembly of Cdk1/cyclin B and activation of Cdk2 revealed by chemical genetics in human cells. Mol Cell. Mar. 23, 2007;25(6):839-50.
Lavis et al., Bright ideas for chemical biology. ACS Chem Biol. Mar. 20, 2008;3(3):142-55. doi: 10.1021/cb700248m.
Lee et al., BRAF mutations in non-Hodgkin's lymphoma. Br J Cancer. Nov. 17, 2003;89(10):1958-60.
Li et al., Identification of novel pyrrolopyrazoles as protein kinase C β II inhibitors. Bioorg Med Chem Lett. Jan. 1, 2011;21(1):584-7. doi: 10.1016/j.bmcl.2010.10.032. Epub Oct. 13, 2010.
Lin et al., Phase II study of flavopiridol in relapsed chronic lymphocytic leukemia demonstrating high response rates in genetically high-risk disease. J Clin Oncol. Dec. 10, 2009;27(35):6012-8.
Liu et al., Discovery and optimization of potent and selective benzonaphthyridinone analogs as small molecule mTOR inhibitors with improved mouse microsome stability. Bioorg Med Chem Lett. Jul. 1, 2011;21(13):4036-40. doi: 10.1016/j.bmcl.2011.04.129. Epub May 7, 2011.
Liu et al., Discovery of 1-(4-(4-propionylpiperazin-1-yl)-3-(trifluoromethyl)phenyl)-9-(quinolin-3-yl)benzo[h][1,6]naphthyridin-2(1H)-one as a highly potent, selective mammalian target of rapamycin (mTOR) inhibitor for the treatment of cancer. J Med Chem. Oct. 14, 2010;53(19):7146-55. doi: 10.1021/jm101144f.
Liu et al., Salt-inducible kinase is involved in the regulation of corticotropin-releasing hormone transcription in hypothalamic neurons in rats. Endocrinology. Jan. 2012;153(1):223-33. doi: 10.1210/en.2011-1404. Epub Nov. 22, 2011.
Liu et al., Two cyclin-dependent kinases promote RNA polymerase II transcription and formation of the scaffold complex. Mol Cell Biol. Feb. 2004;24(4):1721-35.
Llambi et al., Apoptosis and oncogenesis: give and take in the BCL-2 family. Curr Opin Genet Dev. Feb. 2011;21(1):12-20. doi: 10.1016/j.gde.2010.12.001. Epub Jan. 13, 2011.
Lorenzo et al., Expression of proto-oncogene c-kit in high risk prostate cancer. Eur J Surg Oncol. Nov. 2004;30(9):987-92.
Lyne et al., Identification of amidoheteroaryls as potent inhibitors of mutant (V600E) B-Raf kinase with in vivo activity. Bioorg Med Chem Lett. Feb. 1, 2009;19(3):1026-9. doi: 10.1016/j.bmcl.2008.10.053. Epub Oct. 15, 2008.
Majima et al., Significant Roles of Inducible Cyclooxygenase (COX)-2 in Angiogenesis in Rat Sponge Implants. Japanese Journal of Pharmacology 1997;75;105-14.
Mallinson et al., Macrocycles in new drug discovery. Future Med Chem. Jul. 2012;4(11):1409-38. doi: 10.4155/fmc.12.93.
March, Advanced Organic Chemistry Reactions, Mechanisms and Structure. 4th ed. 1992:383-386.
Marelli et al., Tumor targeting via integrin ligands. Front. Oncol., Aug. 30, 2013. https://doi.org/10.3389/fonc.2013.00222.

(56) References Cited

OTHER PUBLICATIONS

Marques et al., A new subfamily of high molecular mass CDC2-related kinases with PITAI/VRE motifs. Biochem Biophys Res Commun. Dec. 29, 2000;279(3):832-7.

Matsuyama et al., Activation of Discoidin Domain Receptor 1 Isoform b with Collagen Up-Regulates Chemokine Production in Human Macrophages: Role of p38 Mitogen-Activated Protein Kinase and Nf-κb. J Immunol Feb. 15, 2004, 172 (4) 2332-2340; DOI: https://doi.org/10.4049/jimmunol.172.4.2332.

McAuley et al., CARMA3 Is a Critical Mediator of G Protein-Coupled Receptor and Receptor Tyrosine Kinase-Driven Solid Tumor Pathogenesis. Front Immunol. Aug. 15, 2018;9:1887. doi: 10.3389/fimmu.2018.01887. eCollection 2018.

Mukaiyama et al., The unexpected and the unpredictable in organic synthesis. Tetrahedron Jul. 1999;55(29):8609-70.

Neklesa et al., Small-molecule hydrophobic tagging-induced degradation of HaloTag fusion proteins. Nat Chem Biol. Jul. 3, 2011;7(8):538-43. doi: 10.1038/nchembio.597.

Obenauf et al., Therapy-induced tumour secretomes promote resistance and tumour progression. Nature. Apr. 16, 2015;520(7547):368-72. doi: 10.1038/nature14336. Epub Mar. 25, 2015.

Ochiana et al., The human Aurora kinase inhibitor danusertib is a lead compound for anti-trypanosomal drug discovery via target repurposing. Eur J Med Chem. Apr. 2013;62:777-84. doi: 10.1016/j.ejmech.2012.07.038. Epub Jul. 31, 2012, Author Manuscript, 22 pages.

Odingo et al., Synthesis and evaluation of the 2,4-diaminoquinazoline series as anti-tubercular agents. Bioorg Med Chem. Dec. 15, 2014;22(24):6965-79. doi: 10.1016/j.bmc.2014.10.007. Epub Oct. 22, 2014.

Orzaez et al., Intrinsic caspase-8 activation mediates sensitization of erlotinib-resistant tumor cells to erlotinib/cell-cycle inhibitors combination treatment. Cell Death Dis. Oct. 25, 2012;3:e415. doi: 10.1038/cddis.2012.155.

Ou et al., Activity of crizotinib (PF02341066), a dual mesenchymal-epithelial transition (MET) and anaplastic lymphoma kinase (ALK) inhibitor, in a non-small cell lung cancer patient with de novo MET amplification. J Thorac Oncol. May 2011;6(5):942-6. doi: 10.1097/JTO.0b013e31821528d3.

Patani et al., Bioisosterism: A Rational Approach in Drug Design. Chem Rev. 1996;96:3147-3176.

Patel et al., Discovery of dual leucine zipper kinase (DLK, MAP3K12) inhibitors with activity in neurodegeneration models. J Med Chem. Jan. 8, 2015;58(1):401-18. doi: 10.1021/jm5013984. Epub Oct. 23, 2014.

Peifer et al., Small-molecule inhibitors of PDK1. ChemMedChem. Dec. 2008;3(12):1810-38. doi: 10.1002/cmdc.200800195.

Pevarello et al., 3-Amino-1,4,5,6-tetrahydropyrrolo[3,4-c]pyrazoles: A new class of CDK2 inhibitors. Bioorg Med Chem Lett. Feb. 15, 2006;16(4):1084-90.

Powell et al., Regulation of immune responses by mTOR. Annu Rev Immunol. 2012;30:39-68. doi: 10.1146/annurev-immunol-020711-075024. Epub Nov. 29, 2011, Author Manuscript, 34 pages.

Powers et al., Discovery and initial SAR of inhibitors of interleukin-1 receptor-associated kinase-4. Bioorg Med Chem Lett. Jun. 1, 2006;16(11):2842-5. Epub Mar. 24, 2006.

PubChem-CID-68365059. Available at https://pubchem.ncbi.nlm.nih.gov/compound/68365059. Accessed Jun. 17, 2016.

Roberts et al., Antiangiogenic and antitumor activity of a selective PDGFR tyrosine kinase inhibitor, CP-673,451. Cancer Res. Feb. 1, 2005;65(3):957-66.

Robinson et al., Discovery of the hemifumarate and (alpha-L-alanyloxy)methyl ether as prod rugs of an anti rheumatic oxindole: prod rugs for the enolic OH group. J. Med. Chem. 1996;39:10-8.

Rubin et al., KIT activation is a ubiquitous feature of gastrointestinal stromal tumors. Cancer Res. Nov. 15, 2001;61(22):8118-21.

Sánchez-Martínez et al., Cyclin dependent kinase (CDK) inhibitors as anticancer drugs. Bioorg Med Chem Lett. Sep. 1, 2015;25(17):3420-35. doi: 10.1016/j.bmcl.2015.05.100. Epub Jun. 6, 2015.

Schroeder et al., Discovery of N-(4-(2-amino-3-chloropyridin-4-yloxy)-3-fluorophenyl)-4-ethoxy-1-(4-fluorophenyl)-2-oxo-1,2-dihydropyridine-3-carboxamide (BMS-777607), a selective and orally efficacious inhibitor of the Met kinase superfamily. J Med Chem. Mar. 12, 2009;52(5):1251-4. doi: 10.1021/jm801586s.

Seed et al., The Inhibition of colon-26 Adenocarcinoma Development and Angiogenesis by Topical Diclofenac in 2.5% Hyaluronan. Cancer Research 1997;57:1625-9.

Sengupta et al., DLK induces developmental neuronal degeneration via selective regulation of proapoptotic JNK activity. Journal of Cell Biology 2011;194(5):751-764. DOI https://doi.org/10.1083/jcb.201103153.

Serizawa et al., Association of Cdk-activating kinase subunits with transcription factor TFIIH. Nature. Mar. 16, 1995;374(6519):280-2.

Sharma et al., A chromatin-mediated reversible drug-tolerant state in cancer cell subpopulations. Cell. Apr. 2, 2010;141(1):69-80.

Shiekhattar et al., Cdk-activating kinase complex is a component of human transcription factor TFIIH. Nature. Mar. 16, 1995;374(6519):283-7.

Shin et al., Dual leucine zipper kinase is required for retrograde injury signaling and axonal regeneration. Neuron. Jun. 21, 2012;74(6):1015-22. doi: 10.1016/j.neuron.2012.04.028.

Sidow et al., Concepts in solid tumor evolution. Trends Genet. Apr. 2015;31(4):208-14. doi: 10.1016/j.tig.2015.02.001. Epub Feb. 27, 2015, Author Manuscript, 14 pages.

Smith et al., Recent advances in the research and development of RAF kinase inhibitors. Curr. Top Med. Chem. 2006; 6(11):1071-89.

Smith et al., The effect of the nature of the amine leaving group on the nature of the E2 transition state for the reaction of 1-phenylethylammonium ions sodium ethoxide in ethanol. Can J Chem. Mar. 28, 1989;67:1457-67.

Srivastava et al., Augmentation of therapeutic responses in melanoma by inhibition of IRAK-1,-4. Cancer Res. Dec. 1, 2012;72(23):6209-16. doi: 10.1158/0008-5472.CAN-12-0337. Epub Oct. 4, 2012.

Stanovnik et al., The Tautomerism of Heterocycles: Substituent Tautomerism of Six-Membered Ring Heterocycles. Advances in Heterocyclic Chemistry. 2006;91:1-134.

Stuhlmiller et al., Inhibition of Lapatinib-Induced Kinome Reprogramming in ERBB2-Positive Breast Cancer by Targeting BET Family Bromodomains. Cell Rep. Apr. 21, 2015;11(3):390-404.

Sun et al.Inhibition of the transcriptional kinase CDK7 overcomes therapeutic resistance in HER2-positive breast cancers. Oncogene. 2020;39(1):50-63. doi:10.1038/s41388-019-0953-9.

Takemori et al., Inactivation of HDAC5 by SIK1 in AICAR-treated C2C12 myoblasts. Endocr J. 2009;56(1):121-30. Epub Oct. 22, 2008.

Terai et al., Activation of the FGF2-FGFR1 autocrine pathway: a novel mechanism of acquired resistance to gefitinib in NSCLC. Mol Cancer Res. Jul. 2013;11(7):759-67.

Tian et al., mTOR Signaling in Cancer and mTOR Inhibitors in Solid Tumor Targeting Therapy. Int J Mol Sci. Feb. 11, 2019;20(3). pii: E755. doi: 10.3390/ijms20030755.

Tsai et al., Discovery of a selective inhibitor of oncogenic B-Raf kinase with potent antimelanoma activity. Proc Natl Acad Sci U S A. Feb. 26, 2008;105(8):3041-6. doi: 10.1073/pnas.0711741105. Epub Feb. 19, 2008.

Tsujii et al., Cyclooxygenase regulates angiogenesis induced by colon cancer cells. Cell. May 29, 1998;93(5):705-16.

Uniprot No. Q9NYV4. Last modified Mar. 15, 2017. 14 pages.

Vora et al., CDK 4/6 inhibitors sensitize PIK3CA Mutant Breast Cancer to PI3K inhibitors. Cancer Cell. Jul. 14, 2014;26(1):136-149. Published online Jul. 4, 2014. doi: 10.1016/j.ccr.2014.05.020.

Wang et al., IRAK-4 inhibitors for inflammation. Curr Top Med Chem. 2009;9(8):724-37.

Wang et al., Ligand-associated ERBB2/3 activation confers acquired resistance to FGFR inhibition in FGFR3-dependent cancer cells. Oncogene. Apr. 23, 2015;34(17):2167-77. doi: 10.1038/onc.2014.161. Epub Jun. 9, 2014.

Wang et al., Pharmacophore and structure-activity relationships of integrase inhibition within a dual inhibitor scaffold of HIV reverse

(56) References Cited

OTHER PUBLICATIONS transcriptase and integrase. Bioorg Med Chem. Jun. 15, 2010;18(12):4202-11. doi: 10.1016/j.bmc.2010.05.004. Epub May 7, 2010.
Wellbrock et al., The RAF proteins take centre stage Nat Rev Mol Cell Biol. Nov. 2004;5(11):875-85.
Wietek et al., IRAK-4: a new drug target in inflammation, sepsis, and autoimmunity. Mol Interv. Jul. 2002;2(4):212-8.
Williamson et al., Structure-guided design of pyrazolo[1,5-a]pyrimidines as inhibitors of human cyclin-dependent kinase 2. Bioorg Med Chem Lett. Feb. 15, 2005;15(4):863-7.
Wu et al., FDA-approved small-molecule kinase inhibitors. Trends Pharmacol Sci. Jul. 2015;36(7):422-39. doi: 10.1016/j.tips.2015.04.005. Epub May 12, 2015.
Xin et al., Peroxisome proliferator-activated receptor gamma ligands are potent inhibitors of angiogenesis in vitro and in vivo. Journal of Biological Chemistry 1996;274(13):9116-21.
Yalpani, Cholesterol Lowering Drugs. Chemistry and Industry Feb. 1996;3:85-89.
Yasuda et al., The stem cell factor/c-kit receptor pathway enhances proliferation and invasion of pancreatic cancer cells. Mol Cancer. Oct. 18, 2006;5:46.
Zambon et al., Small molecule inhibitors of BRAF in clinical trials. Bioorg Med Chem Lett. Jan. 15, 2012;22(2):789-92. doi: 10.1016/j.bmcl.2011.11.060. Epub Dec. 3, 2011.
Zang et al., Genetic and structural variation in the gastric cancer kinome revealed through targeted deep sequencing. Cancer Res. Jan. 1, 2011;71(1):29-39. doi: 10.1158/0008-5472.CAN-10-1749. Epub Nov. 19, 2010.
Zarei et al.Tumors with TSC mutations are sensitive to CDK7 inhibition through NRF2 and glutathione depletion. J Exp Med. 2019;216(11):2635-2652. doi:10.1084/jem.20190251.
Zebisch et al., Back to the roots: the remarkable RAF oncogene story Cell Mol Life Sci. Jun. 2006;63(11):1314-30.
Zeng et al.Targeting MYC dependency in ovarian cancer through inhibition of CDK7 and CDK12/13. Elife. 2018;7:e39030. Published Nov. 13, 2018. doi:10.7554/eLife.39030.
Zhang et al.CDK7 Inhibition Potentiates Genome Instability Triggering Anti-tumor Immunity in Small Cell Lung Cancer. Cancer Cell. 2020;37(1):37-54.e9. doi: 10.1016/j.ccell.2019.11.003.
Zhang et al., Discovery of potent and selective covalent inhibitors of JNK. Chem Biol. Jan. 27, 2012;19(1):140-54. doi: 10.1016/j.chembiol.2011.11.010, Author Manuscript, 28 pages.
Zhang et al., Etk/Bmx transactivates vascular endothelial growth factor 2 and recruits phosphatidylinositol 3-kinase to mediate the tumor necrosis factor-induced angiogenic pathway. J Biol Chem. Dec. 19, 2003;278(51):51267-76. Epub Oct. 7, 2003.
Zhou et al., Novel mutant-selective EGFR kinase inhibitors against EGFR T790M. Nature. Dec. 24, 2009;462(7276):1070-4.
Ziche et al., Role of prostaglandin E1 and copper in angiogenesis. Journal of the National Cancer Institute 1982;69(2):475-82.
Zompi et al., Animal models of dengue virus infection. Viruses. Jan. 2012;4(1):62-82. doi: 10.3390/v4010062. Epub Jan. 9, 2012.
U.S. Appl. No. 17/034,822, filed Sep. 28, 2020, Gray et al.
PCT/US2019/038677, Oct. 2, 2019, International Search Report and Written Opinion.
PCT/US2019/038677, Jan. 7, 2021, International Preliminary Report on Patentability.
PCT/US2019/038677, Aug. 13, 2019, Invitation to Pay Additional Fees.
PCT/US2015/000297, Mar. 4, 2016, International Search Report and Written Opinion.
PCT/US2015/000297, Jul. 6, 2017, International Preliminary Report on Patentability.
[No Author Listed], CAS Registry No. 1347879-84-8. Entered STN: Dec. 4, 2011. 1 page.
[No Author Listed], CAS Registry No. 1349030-04-1. Entered STN: Dec. 5, 2011. 1 page.
Urich et al., The design and synthesis of potent and selective inhibitors of Trypanosoma brucei glycogen synthase kinase 3 for the treatment of human african trypanosomiasis. J Med Chem. Sep. 25, 2014;57(18):7536-49. doi: 10.1021/jm500239b. Epub Sep. 8, 2014. Supplemental information included. 18 total pages.
U.S. Appl. No. 18/181,463, filed Mar. 9, 2023, Gray et al.
U.S. Appl. No. 17/715,874, filed Apr. 7, 2022, Gray et al.
U.S. Appl. No. 17/688,822, filed Mar. 7, 2022, Gray et al.
U.S. Appl. No. 17/418,353, filed Jun. 25, 2021, Gray et al.
U.S. Appl. No. 17/628,794, filed Jan. 20, 2022, Zhang et al.
U.S. Appl. No. 17/789,047, filed Jun. 24, 2022, Gray et al.
EP 16815401.1, Jan. 17, 2019, Extended European Search Report.
PCT/US2016/39312, Sep. 27, 2016, International Search Report and Written Opinion.
PCT/US2016/39312, Jan. 4, 2018, International Preliminary Report on Patentability.
EP 16815397.1, Nov. 22, 2018, Extended European Search Report.
PCT/US2016/39302, Jan. 4, 2018, International Preliminary Report on Patentability.
Extended European Search Report for EP 16815401.1, mailed on Jan. 17, 2019.
International Search Report and Written Opinion for PCT/US2016/39312, mailed Sep. 27, 2016.
International Preliminary Report on Patentability for PCT/US2016/39312, mailed Jan. 4, 2018.
Extended European Search Report for EP 16815397.1, mailed on Nov. 22, 2018.
International Preliminary Report on Patentability for PCT/US2016/39302, mailed Jan. 4, 2018.
[No Author Listed], GenBank: M80629.1. Human cdc2-related protein kinase (CHED) mRNA, complete cds. Entered Dec. 13, 1994.
[No Author Listed], NCBI Reference Sequence: NP_001790.1. cyclin-dependent kinase 7 isoform 1 [*Homo sapiens*]. Entered Apr. 1, 2018.
[No Author Listed], Uniprot Number Q9NYV4. Cyclin-dependent kinase 12. Gene CDK12. *Homo sapiens* (Human). Entered Dec. 1, 2000.
Camilli et al., Phosphoinositides as regulators in membrane traffic. Science. Mar. 15, 1996;271(5255):1533-9.
CAS Registry No. 1025964-63-9 Entered STN: Jun. 6, 2008.
CAS Registry No. 1026531-51-0 Entered STN: Jun. 8, 2008.
CAS Registry No. 1026878-26-1 Entered STN: Jun. 10, 2008.
CAS Registry No. 1026975-11-0 Entered STN: Jun. 10, 2008.
CAS Registry No. 1027155-85-6 Entered STN: Jun. 11, 2008.
CAS Registry No. 1028288-20-1 Entered STN: Jun. 15, 2008.
CAS Registry No. 1347533-63-4 Entered STN: Dec. 2, 2011.
CAS Registry No. 1347548-09-7 Entered STN: Dec. 2, 2011.
CAS Registry No. 1609787-73-6 Entered STN: Jun. 6, 2014.
CAS Registry No. 1702381-29-0 Entered STN: May 13, 2015.
CAS Registry No. 1702381-42-7 Entered STN: May 13, 2015.
CAS Registry No. 1702381-64-3 Entered STN: May 13, 2015.
CAS Registry No. 1702381-71-2 Entered STN: May 13, 2015.
CAS Registry No. 1702381-78-9 Entered STN: May 13, 2015.
CAS Registry No. 1702809-46-8 Entered STN: May 13, 2015.
CAS Registry No. 1703051-55-1 Entered STN: May 13, 2015.
CAS Registry No. 1703051-60-8 Entered STN: May 13, 2015.
CAS Registry No. 1703051-61-9 Entered STN: May 13, 2015.
CAS Registry No. 1703051-63-1 Entered STN: May 13, 2015.
CAS Registry No. 1998741-41-5 Entered STN: Sep. 23, 2016.
CAS Registry No. 956025-12-0 Entered STN: Nov. 27, 2007.
Database Registry Chemical Abstracts Service, Columbus, Ohio. Accession No. RN 1025874-73-0. Entered STN on Jun. 5, 2008.
Database Registry Chemical Abstracts Service, Columbus, Ohio. Accession No. RN 1205276-48-7, 1205371-13-6. Entered STN on Feb. 10, 2010.
Devegowda et al., Novel 6-N-arylcarboxamidopyrazolo[4,3-d]pyrimidin-7-one derivatives as potential anti-cancer agents. Bioorg Med Chem Lett. Mar. 1, 2010;20(5):1630-3. doi: 10.1016/j.bmcl.2010.01.029. Epub Jan. 20, 2010.
Emerling et al., Depletion of a putatively druggable class of phosphatidylinositol kinases inhibits growth of p53-null tumors. Cell. Nov. 7, 2013;155(4):844-57. doi: 10.1016/j.cell.2013.09.057.
Fruman et al., Phosphoinositide Kinases. Annual Review of Biochemistry 1998;67(1):481-507.

(56) References Cited

OTHER PUBLICATIONS

Hellvard et al., Inhibition of CDK9 as a therapeutic strategy for inflammatory arthritis. Sci Rep. Aug. 11, 2016;6:31441. doi: 10.1038/srep31441.

Liu et al., Targeting the phosphoinositide 3-kinase pathway in cancer. Nat Rev Drug Discov. Aug. 2009;8(8):627-44. doi: 10.1038/nrd2926.

Martin, Phosphoinositide lipids as signaling molecules: common themes for signal transduction, cytoskeletal regulation, and membrane trafficking. Annu Rev Cell Dev Biol. 1998;14:231-64.

Rameh et al., A new pathway for synthesis of phosphatidylinositol-4,5-bisphosphate. Nature. Nov. 13, 1997;390(6656):192-6.

Schramp et al., Phosphoinositides I: Enzymes of Synthesis and Degradation, 2012, Chapter 2, PIP Kinases from the Cell Membrane to the Nucleus, p. 25.

Taneera et al., Expression profiling of cell cycle genes in human pancreatic islets with and without type 2 diabetes. Mol Cell Endocrinol. Aug. 15, 2013;375(1-2):35-42. doi: 10.1016/j.mce.2013.05.003. Epub May 22, 2013.

Voss et al., Discovery and pharmacological characterization of a novel small molecule inhibitor of phosphatidylinositol-5-phosphate 4-kinase, type II, beta. Biochem Biophys Res Commun. Jul. 4, 2014;449(3):327-31. doi: 10.1016/j.bbrc.2014.05.024.

Extended European Search Report for EP 20843441.5 mailed on Dec. 12, 2023.

Extended European Search Report for EP 20908219.7 mailed on Dec. 12, 2023.

Carmi et al., Novel irreversible epidermal growth factor receptor inhibitors by chemical modulation of the cysteine-trap portion. J Med Chem. Mar. 11, 2010;53(5):2038-50. doi: 10.1021/jm901558p.

Dorée et al., The cyclin-dependent protein kinases and the control of cell division. FASEB J. Nov. 1994;8(14):1114-21. doi: 10.1096/fasebj.8.14.7958616.

Gu et al., Upregulated PFTK1 promotes tumor cell proliferation, migration, and invasion in breast cancer. Med Oncol. Jul. 2015;32(7):195. doi: 10.1007/s12032-015-0641-8. Epub Jun. 2, 2015.

Leung et al., A novel interplay between oncogenic PFTK1 protein kinase and tumor suppressor TAGLN2 in the control of liver cancer cell motility. Oncogene. Nov. 3, 2011;30(44):4464-75. doi: 10.1038/onc.2011.161. Epub May 16, 2011.

Liu et al., Cyclin Y regulates the proliferation, migration, and invasion of ovarian cancer cells via Wnt signaling pathway. Tumour Biol. Aug. 2016;37(8):10161-75. doi: 10.1007/s13277-016-4818-3. Epub Jan. 29, 2016.

Ou-Yang et al., Cyclin-Dependent Kinase 14 Promotes Cell Proliferation, Migration and Invasion in Ovarian Cancer by Inhibiting Wnt Signaling Pathway. Gynecol Obstet Invest. 2017;82(3):230-239. doi: 10.1159/000447632. Epub Aug. 10, 2016.

Pang et al., Identification of PFTAIRE protein kinase 1, a novel cell division cycle-2 related gene, in the motile phenotype of hepatocellular carcinoma cells. Hepatology. Aug. 2007;46(2):436-45. doi: 10.1002/hep.21691.

Patricelli et al., Functional interrogation of the kinome using nucleotide acyl phosphates. Biochemistry. Jan. 16, 2007;46(2):350-8. doi: 10.1021/bi062142x.

Sun et al., PFTK1 interacts with cyclin Y to activate non-canonical Wnt signaling in hepatocellular carcinoma. Biochem Biophys Res Commun. Jun. 20, 2014;449(1):163-8. doi: 10.1016/j.bbrc.2014.05.002. Epub May 10, 2014.

Zhang et al., PFTK1 regulates cell proliferation, migration and invasion in epithelial ovarian cancer. Int J Biol Macromol. Apr. 2016;85:405-16. doi: 10.1016/j.ijbiomac.2016.01.009. Epub Jan. 6, 2016.

McMahon, VEGF receptor signaling in tumor angiogenesis. Oncologist. 2000;5 Suppl 1:3-10. doi: 10.1634/theoncologist.5-suppl_1-3.

Pinedo et al., Introduction: translational research: the role of VEGF in tumor angiogenesis. The Oncologist. Apr. 1, 2000;5(S1):1-2.

* cited by examiner

| Kinase | FMF-4-107-2 1uM | FMF-4-107-2 0.25uM | FMF-4-107-2 0.25uM washout |
|---|---|---|---|
| CDK17 | >95 | 91.5 | 89.9 |
| CDK12 | >92 | 60.3 | 6.5 |
| CDK17, CDK18 | >90 | >90 | 79.7 |
| CDK16 | >80 | >80 | 82.5 |
| CDK2 | 98.9 | 94 | 53.7 |
| CDK16, CDK18 | 95.7 | 89.7 | 78.8 |
| CDK2 | 94.8 | 89 | 52.5 |
| CDK5 | 94.7 | 76.9 | 32.1 |
| GSK3B | 94.1 | 75.6 | 19.2 |
| GSK3A | 94 | 75.6 | 26.3 |
| CDK5 | 93.4 | 72.5 | 29.1 |
| CDK1 | 88.9 | 59.1 | 36.4 |
| CDK14 | 82.2 | 74 | 82.3 |
| CDK20 | 81 | -2.8 | 11.1 |
| Erk5 | 79.6 | 31.3 | 20.1 |
| CDK9 | 77.7 | 52.7 | 1.6 |
| CaMKK2 | 74.9 | 59 | 0.9 |
| CCRK | 71.8 | 19.1 | -24.3 |
| CaMKK2 | 69.1 | -3.5 | 17.2 |
| CDK11B | 66.6 | 45.1 | 21.2 |
| MAP3K1 | 60.2 | -13.5 | -15.4 |
| CDK7 | 59.2 | 25.2 | 16 |
| CDK4 | 51.9 | -9.6 | 3.2 |
| CDK7 | 45.9 | 4 | 6.3 |

| Kinase | FMF-04-159-2 1μM |
|---|---|
| CDK16 | >95 |
| CDK14 | 96.6 |
| CDK2 | 96.5 |
| CDK2 | 95.1 |
| CDK17 | 94.2 |
| CDK14 | 94.0 |
| CDK17, CDK18 | 81.3 |
| CDK16, CDK18 | 80.1 |
| CDK10 | 76.5 |
| CDC2 | 54.4 |
| CDK5 | 44.9 |
| Erk5 | 44.3 |
| CDK5 | 41.3 |
| AurA | 30.7 |

Figure 3B

TAIRE FAMILY KINASE INHIBITORS AND USES THEREOF

RELATED APPLICATIONS

This application is a national stage filing under 35 U.S.C. § 371 of International PCT Application PCT/US2019/038677, filed Jun. 24, 2019, which claims priority under 35 U.S.C. § 119(e) to U.S. Provisional Application, U.S. Ser. No. 62/689,551, filed Jun. 25, 2018, each of which is incorporated herein by reference.

BACKGROUND OF THE INVENTION

The members of the cyclin-dependent kinase (CDK) family play critical regulatory roles in proliferation. There are currently 20 known mammalian CDKs. Evidence shows that certain TAIRE family kinases including CDK14 (also known as PFTAIRE1 or PFTK1), as well as CDK15, CDK16, CDK17 and CDK18 play a role in cancer progression. Targeting TAIRE family kinases is therefore a promising therapeutic strategy in cancer. CDK14 has been implicated in promoting cell motility in cancer. For example, CDK14 has been implicated in promoting metastasis in various cancers, including, but not limited to, pancreatic cancer (Zheng, L., Zhou, Z. & He, Z. Knockdown of PFTK1 inhibits tumor cell proliferation, invasion and epithelial-to-mesenchymal transition in pancreatic cancer. *Int. J. Clin. Exp. Pathol.*, 8, 14005-12 (2015); hepatocellular carcinoma (Sun, T. et al., PFTK1 interacts with cyclin Y to activate non-canonical Wnt signaling in hepatocellular carcinoma. *Biochem. Biophys. Res. Commun.* 449, 163-8 (2014); and gastric cancer (Yang, L. et al. PFTK1 Promotes Gastric Cancer Progression by Regulating Proliferation, Migration and Invasion. *PLoS ONE,* 10, e0140451 (2015)). CDK14 has also been identified as contributing to neurological conditions or diseases, including gliosis (Duan C, et al., *J. Mol Neurosci.* 2015). Additional evidence suggests that certain TAIRE family kinases play a role in other cancers, and other diseases, including, but not limited to, metabolic disorders, and neurological diseases, and in male reproduction. CDK18 is implicated in diabetes, and CDK17 and CDK18 have been implicated in Alzheimer's disease, for which targeting these TAIRE kinases may be a promising therapeutic strategy (Potential role of PCTAIRE-2, PCTAIRE-3 and P-Histone H4 in amyloid precursor protein-dependent Alzheimer pathology. *Oncotarget.* 2016). CDK16 is implicated in several cancers, and is also implicated in spermatogenesis (Zi Z. et al., *pLoS Genet.* 2015). CDK15 is implicated in cancer apopotosis (ALS2CR7 (CDK15) attenuates TRAIL induced apoptosis by inducing phosphorylation of survivin Thr34. *Biochemical and Biophysical Research Communications.* 2014). The TAIRE family of cyclin-dependent kinases is comprised of CDK14, CDK15, CDK16, CDK17 and CDK18, all of which bind to Cyclin Y. (Mikolcevic, P. et al., *Cell Cycle,* 2012, 11 (20), 3758-68). Cyclin Y activates these kinases and is capable of targeting them to the plasma membrane. See id. These kinases are highly conserved but poorly characterized. Nonetheless the TAIRE family kinases are frequently overexpressed in a wide variety of cancers and associated with invasion, migration, and proliferation phenotypes. These oncogenic cell traits can be reduced by RNAi-induced knockdown of one or more of the TAIRE kinases, or Cyclin Y. (Yang, L. et al., *PloS One* 2015, 10 (10), e0140451; Liu, M. H.; et al., Knockdown of PFTK1 Expression by RNAi Inhibits the Proliferation and Invasion of Human Non-Small Lung Adenocarcinoma Cells. *Oncology Research* 2016, 24 (3), 181-7; Zhu, J.; et al., Knockdown of PFTAIRE Protein Kinase 1 (PFTK1) Inhibits Proliferation, Invasion, and EMT in Colon Cancer Cells. *Oncology Research* 2016, 24 (3), 137-44; Zheng, L.; et al., Knockdown of PFTK1 inhibits tumor cell proliferation, invasion and epithelial-to-mesenchymal transition in pancreatic cancer. *Int'l J. Clinical and Experimental Pathology* 2015, 8 (11), 14005-12; Zhang, W. et al., PFTK1 regulates cell proliferation, migration and invasion in epithelial ovarian cancer. *Int'l J. Biological Macromolecules* 2016, 85, 405-16; Zi, Z. et al., CCNYL1, but Not CCNY, Cooperates with CDK16 to Regulate Spermatogenesis in Mouse. *PLoS Genetics* 2015, 11 (8), e1005485).

CDK14 has been shown to regulate Wnt signaling during mitosis and is overexpressed in many Wnt-dependent cancers, such as colorectal and ovarian cancers. (Davidson, G. et al., Cell cycle control of wnt receptor activation. *Developmental Cell* 2009, 17 (6), 788-99; Zhou, Y. et al., Spontaneous genomic alterations in a chimeric model of colorectal cancer enable metastasis and guide effective combinatorial therapy. *PloS One* 2014, 9 (8), e105886. Ou-Yang, J. et al., Cyclin-Dependent Kinase 14 Promotes Cell Proliferation, Migration and Invasion in Ovarian Cancer by Inhibiting Wnt Signaling Pathway. *Gynecologic and Obstetric Investigation* 2017, 82 (3), 230-239). CDK16 is essential for spermatogenesis, and therefore, inhibitors of CDK16 may be developed as a form of male contraception. Mikolcevic, P.; et al., Cyclin-dependent kinase 16/PCTAIRE kinase 1 is activated by cyclin Y and is essential for spermatogenesis. *Molecular and Cellular Biology* 2012, 32 (4), 868-79; Zi, Z. et al., CCNYL1, but Not CCNY, Cooperates with CDK16 to Regulate Spermatogenesis in Mouse. *PLoS Genetics* 2015, 11 (8), e1005485). Due to the important regulatory functions of kinases, such as CDK's, including CDK14, CDK15, CDK16, CDK17, and CDK18, in cell cycle control, cell proliferation, differentiation, and apoptosis, it is important to develop modulators of the activities of these kinases, including selective modulators (e.g., selective inhibitors), for use as research tools as well as therapeutic agents in the treatment of various diseases and as agents for male contraception.

SUMMARY OF THE INVENTION

Described herein are compounds of Formula (I') or (I), and salts, solvates, hydrates, polymorphs, co-crystals, tautomers, stereoisomers, isotopically labeled derivatives, and prodrugs thereof, and mixtures thereof. The compounds of Formula (I') or (I), and pharmaceutically acceptable salts, solvates, hydrates, polymorphs, co-crystals, tautomers, stereoisomers, isotopically labeled derivatives, prodrugs, and compositions thereof, may inhibit the activity of a kinase (e.g., a CDK) in a biological sample or subject. In certain embodiments, the kinase is a cyclin-dependent kinase (CDK). In certain embodiments, the CDK is CDK14. In certain embodiments, the CDK is CDK15, CDK16, CDK17, or CDK18. In certain embodiments, the compounds of Formula (I') and (I) are selective for CDK14 compared to other kinases. Described herein are methods of using the inventive compounds, and pharmaceutically acceptable salts, solvates, hydrates, polymorphs, co-crystals, tautomers, stereoisomers, isotopically labeled derivatives, prodrugs, and compositions thereof, to study the inhibition of a kinase (e.g., CDK14, CDK15, CDK16, CDK17, CDK18) or as therapeutics for the prevention and/or treatment of diseases associated with the overexpression and/or aberrant (e.g., increased or unwanted) activity of a kinase (e.g., CDK14, CDK15, CDK16, CDK17, CDK18). The compounds described herein may be useful in treating and/or preventing a disease or condition, e.g., in treating and/or preventing a disease (e.g., proliferative disease (e.g., cancers), metabolic disorder (e.g., diabetes), autoimmune disease, or neurological disease (e.g., Alzheimer's disease, gliosis, spinal cord injury)), in a subject in need thereof. The compounds described herein may be useful in male contraception (e.g., reducing or inhibiting spermatogenesis, or reducing the rate of male fertility) in a healthy fertile male subject. Also provided are uses, pharmaceutical compositions and kits including a compound described herein.

In one aspect, the present disclosure provides compounds of Formula (I'):

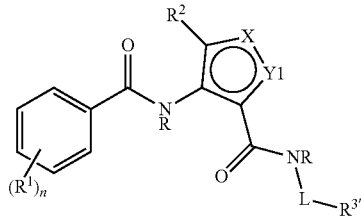

and pharmaceutically acceptable salts, solvates, hydrates, polymorphs, co-crystals, tautomers, stereoisomers, isotopically labeled derivatives, and prodrugs thereof, wherein $R^1$, $R^2$, $R^{3'}$, R, n, L, X, and Y1 are as defined herein. $R^{3'}$ is a warhead which covalently or non-covalently binds a CDK (e.g., CDK14, CDK15, CDK16, CDK17, CDK18). In certain embodiments, the warhead non-covalently binds to a CDK, e.g., CDK15, CDK16, CDK17, CDK18. In certain embodiments, the warhead covalently binds to a CDK, e.g., CDK14. In certain embodiments, $R^{3'}$ is $R^3$. In certain embodiments, a compound of Formula (I') is of Formula (I).

In one aspect, the present disclosure provides compounds of Formula (I):

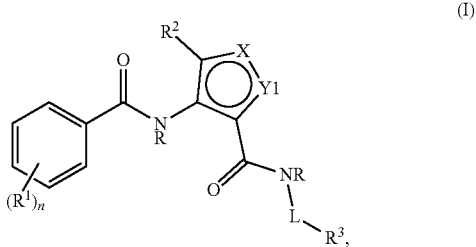

and pharmaceutically acceptable salts, solvates, hydrates, polymorphs, co-crystals, tautomers, stereoisomers, isotopically labeled derivatives, and prodrugs thereof, wherein $R^1$, $R^2$, $R^3$, R, n, L, X, and Y1 are as defined herein. $R^3$ is a warhead which covalently or non-covalently binds a CDK (e.g., CDK14, CDK15, CDK16, CDK17, CDK18). In certain embodiments, the warhead non-covalently binds to a CDK, e.g., CDK15, CDK16, CDK17, CDK18. In certain embodiments, the warhead covalently binds to a CDK, e.g., CDK14.

Exemplary compounds of Formulae (I) and (I') include, but are not limited to:

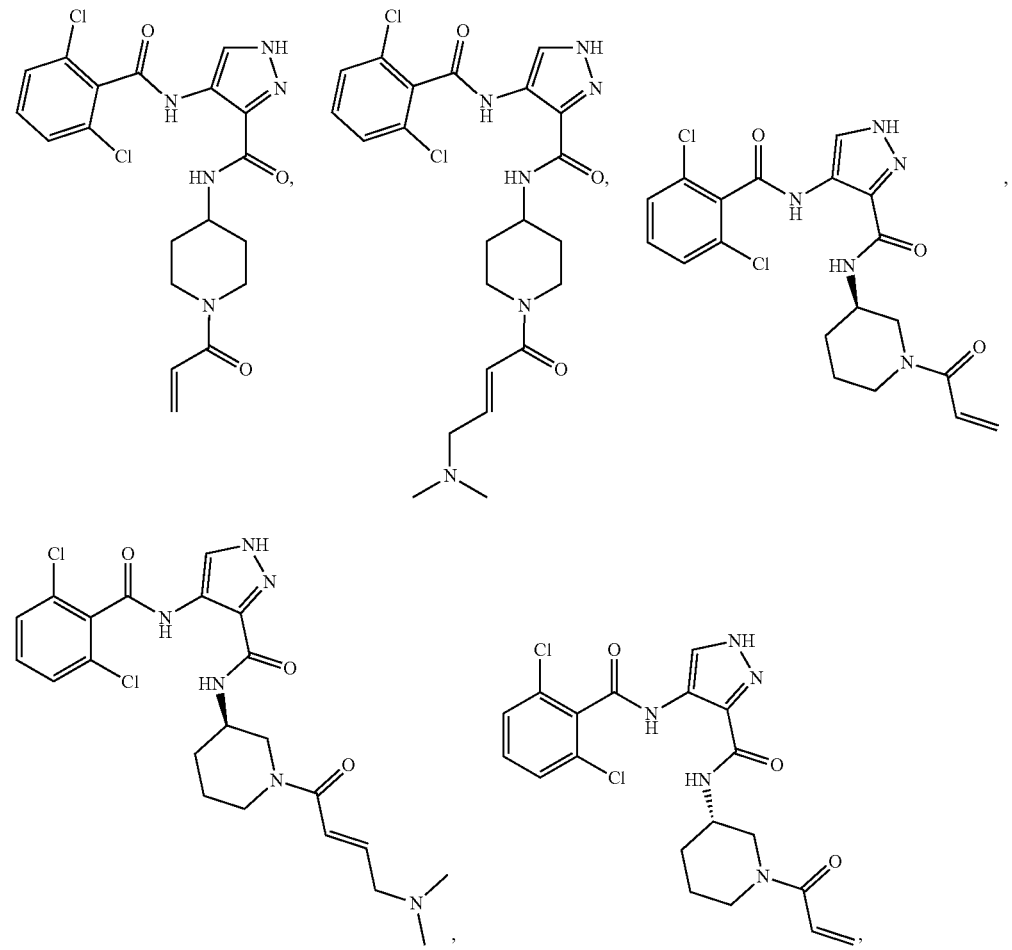

-continued
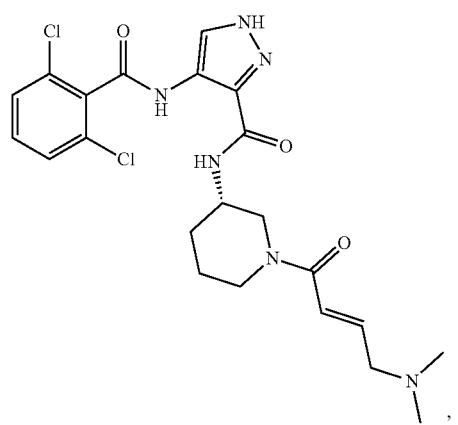 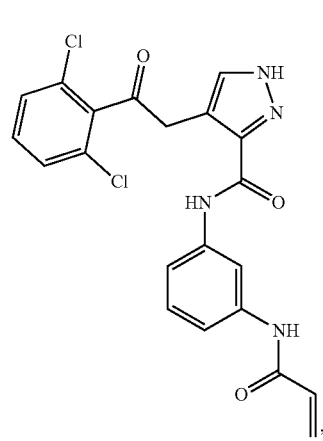 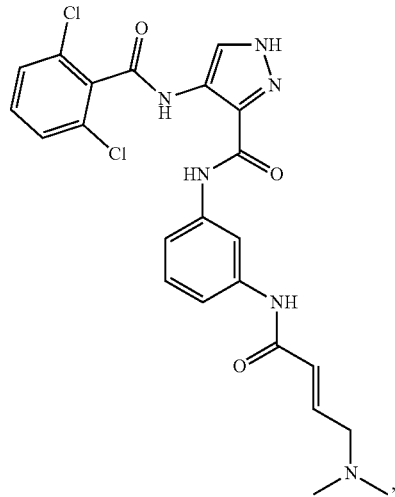
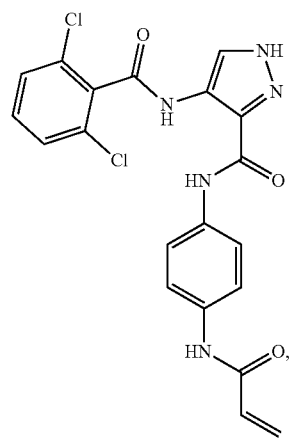 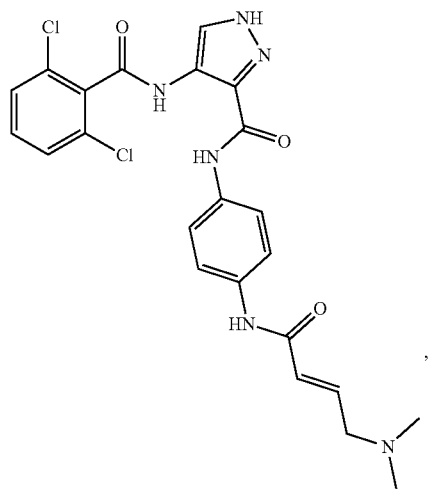
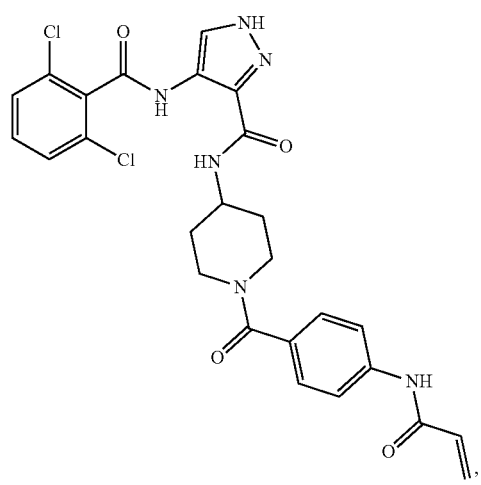 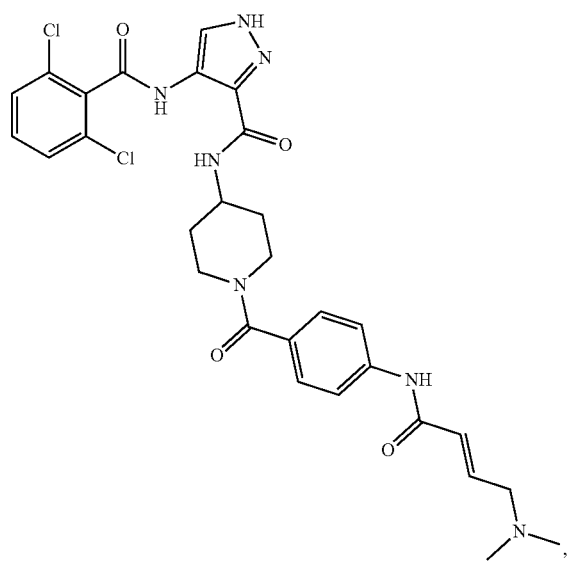

7
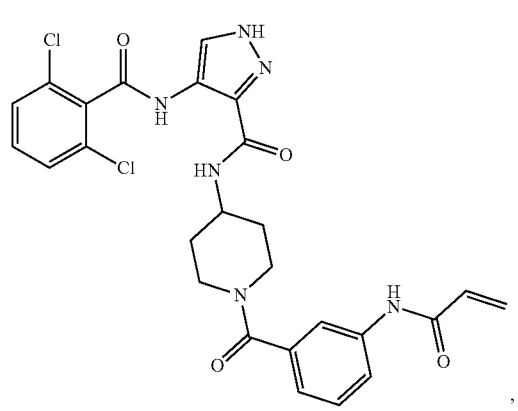
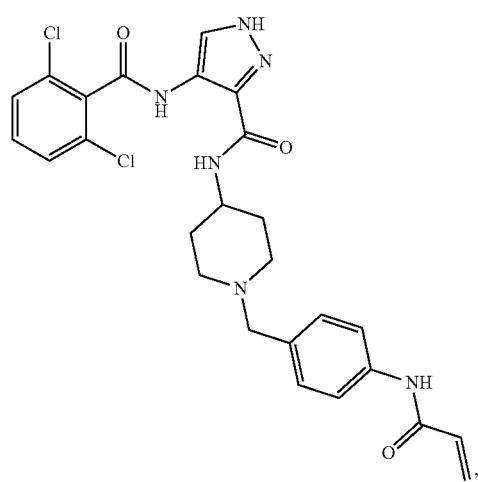
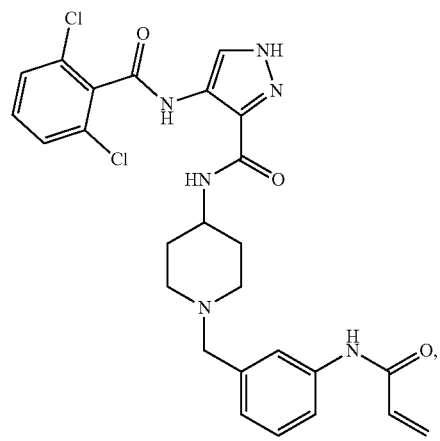
8
-continued
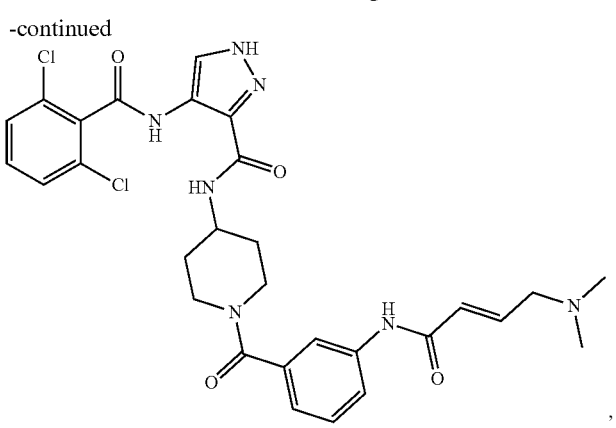
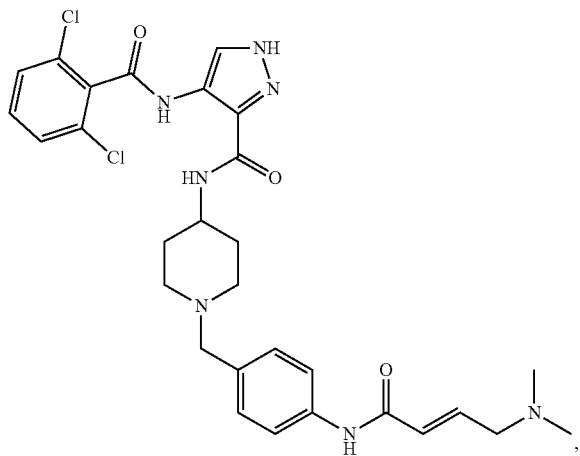
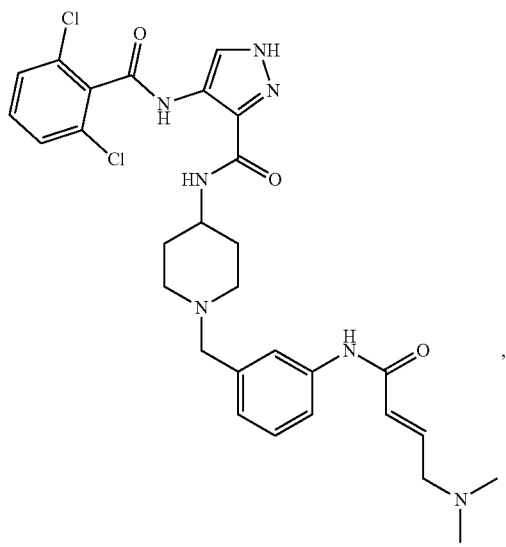

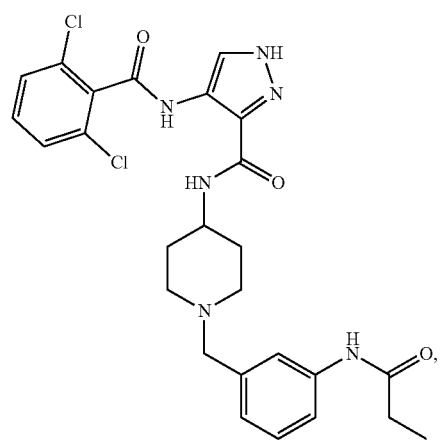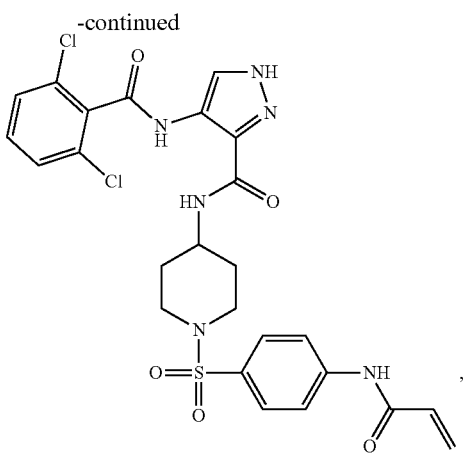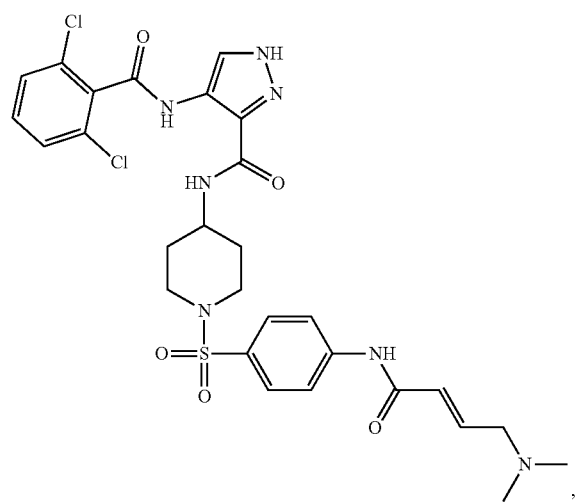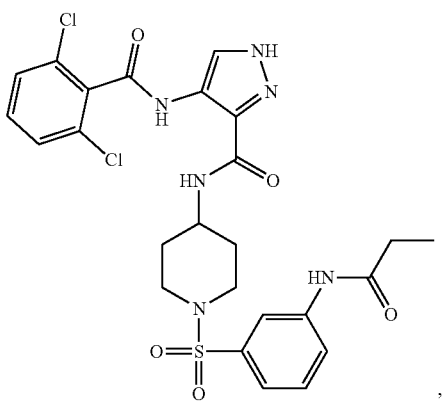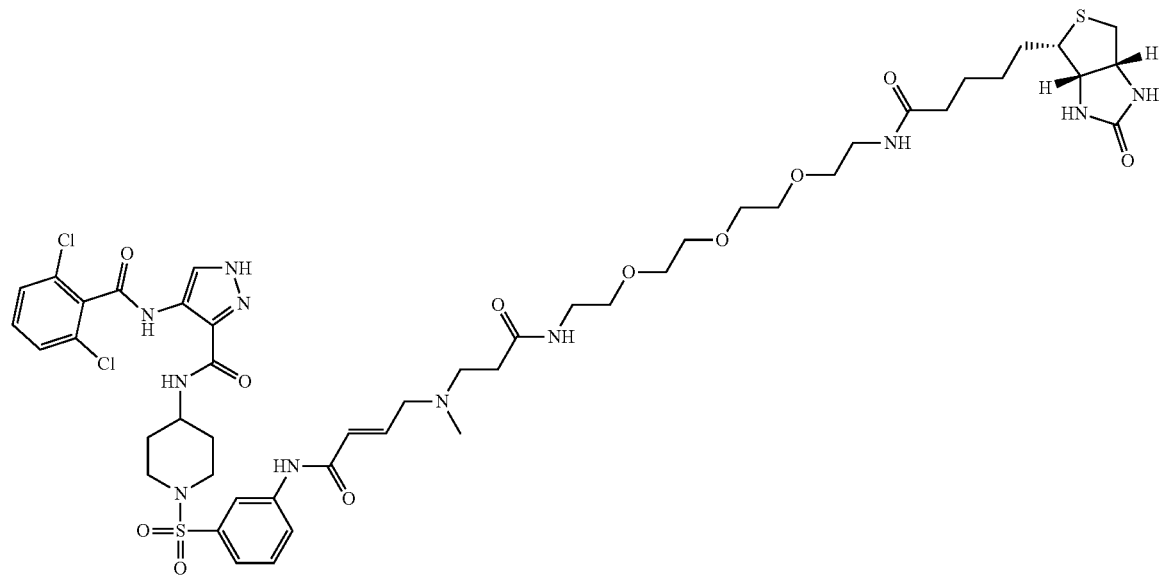

-continued
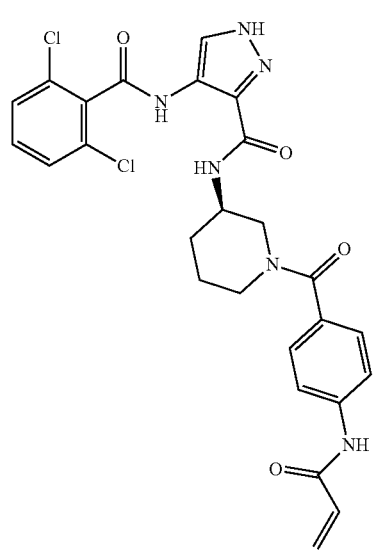
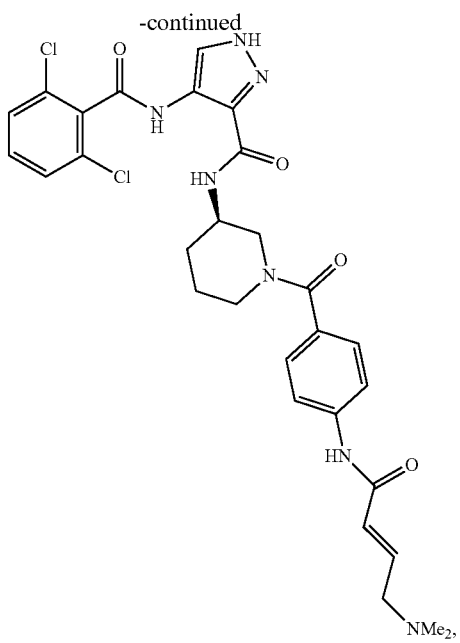
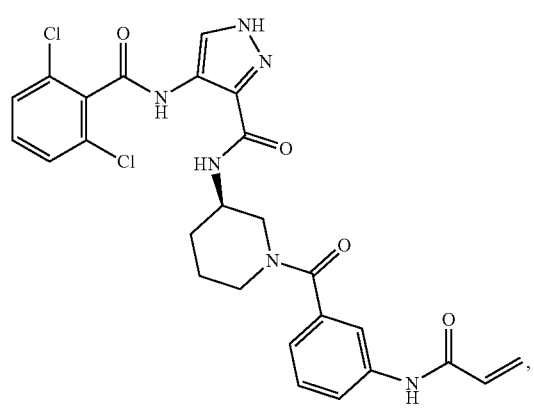
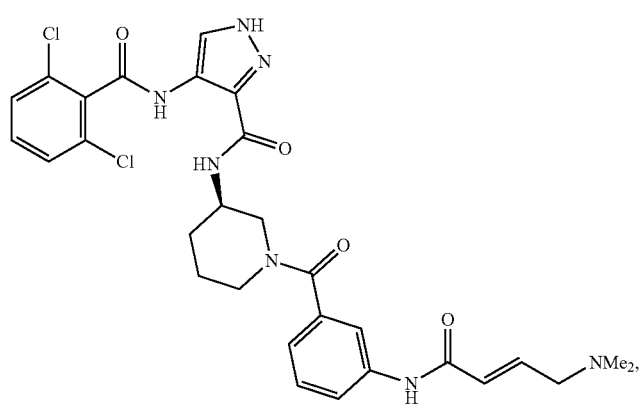
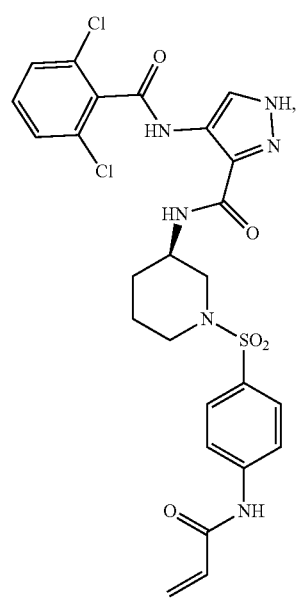
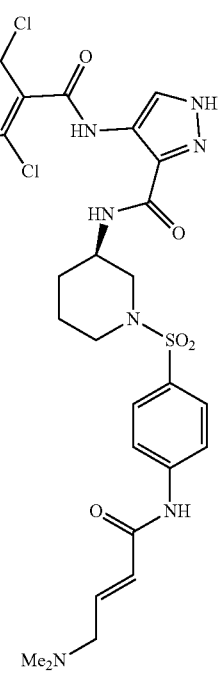
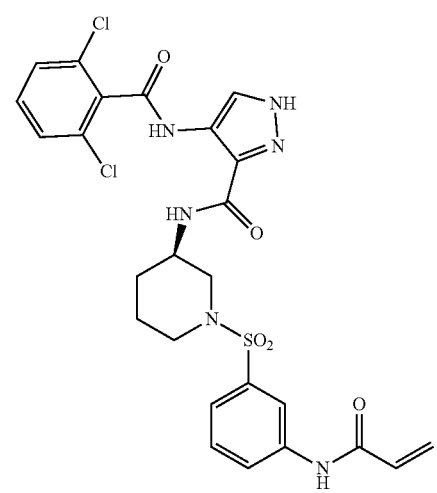

13
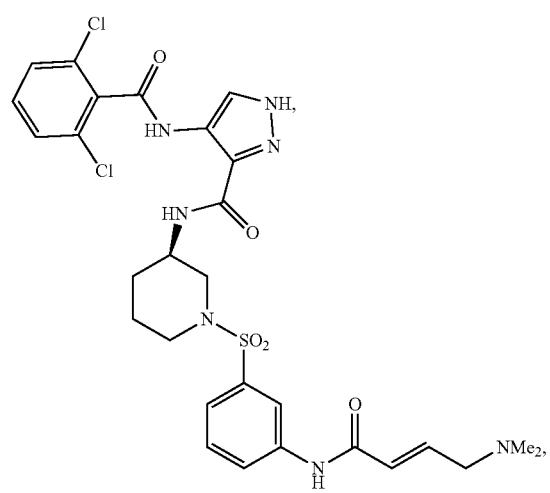
-continued
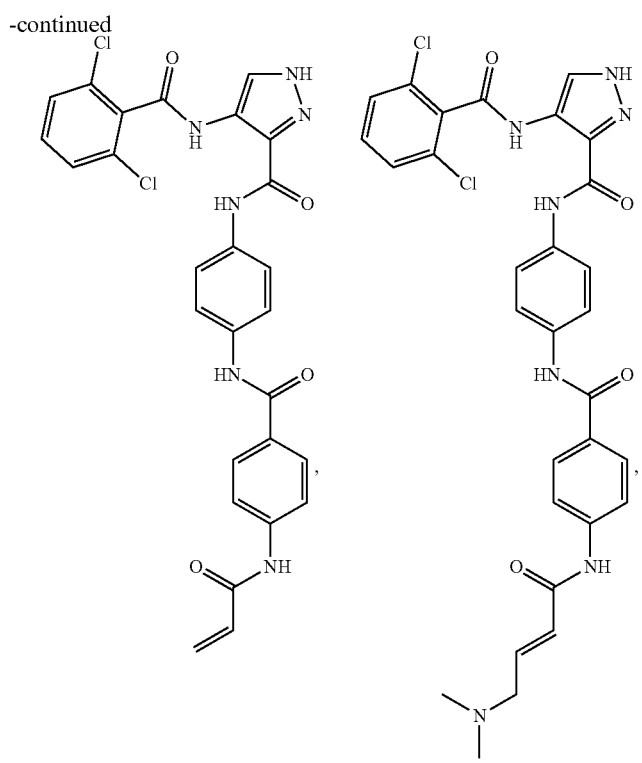
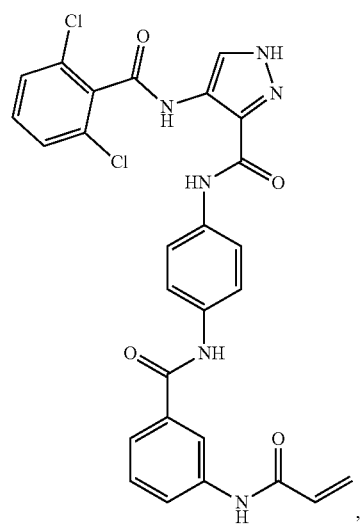
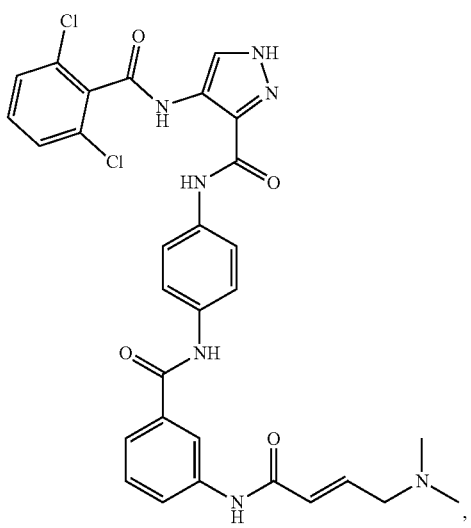

-continued
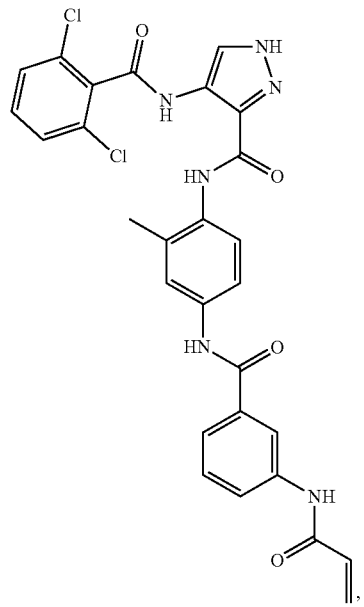
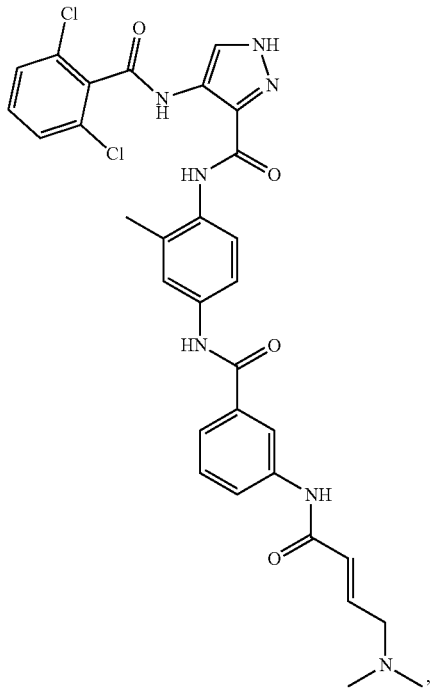
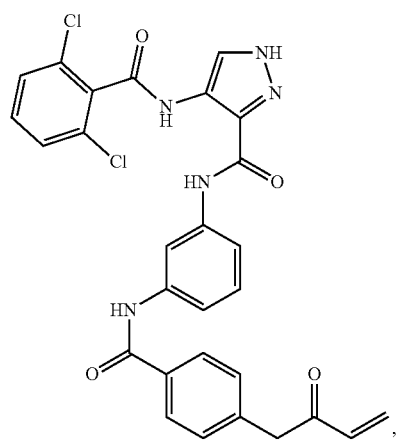
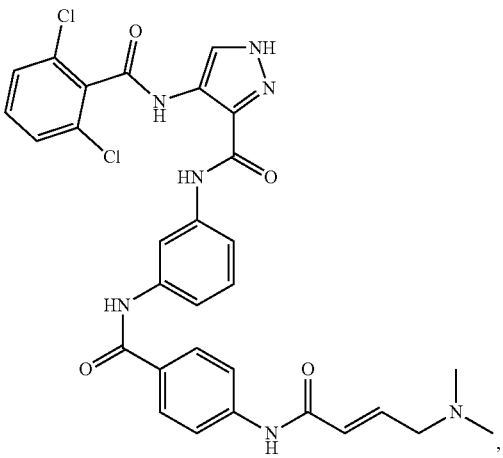
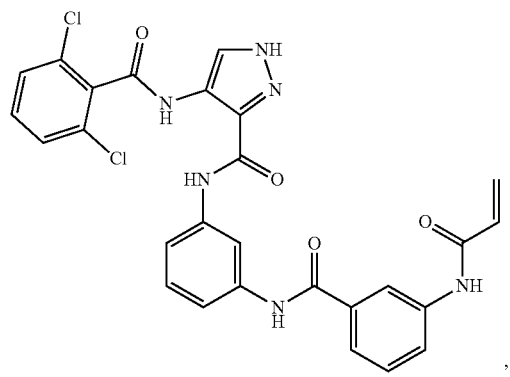
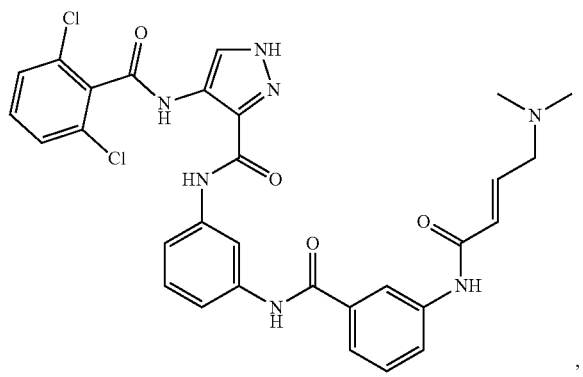

17
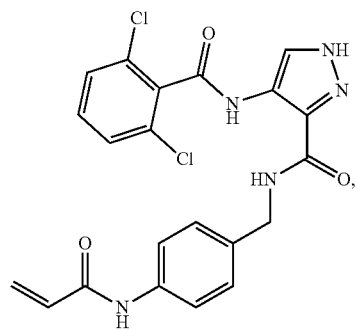
-continued
18
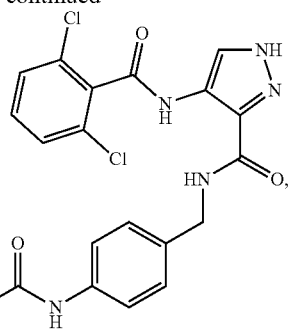
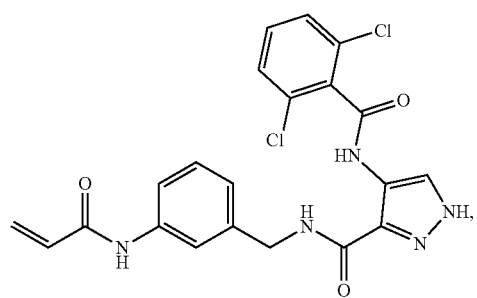
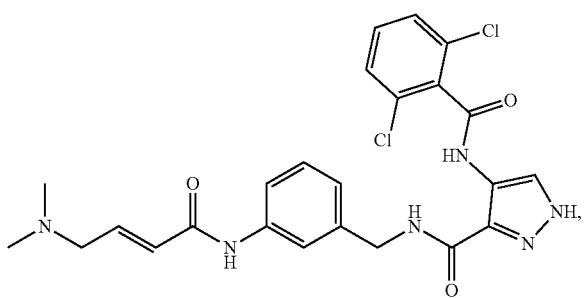
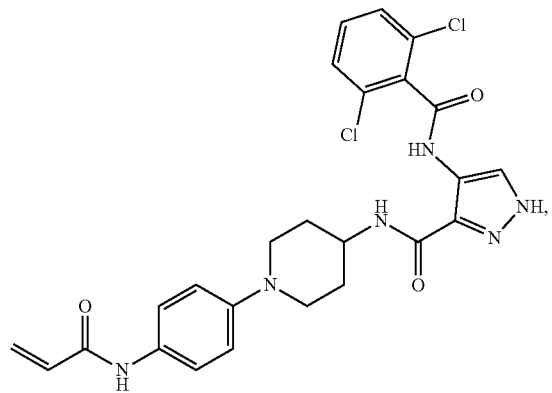
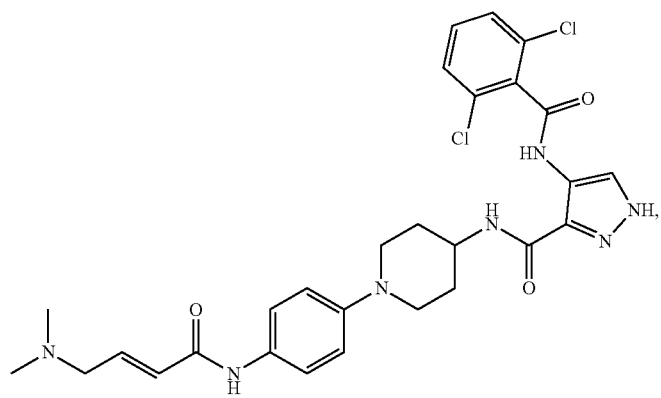

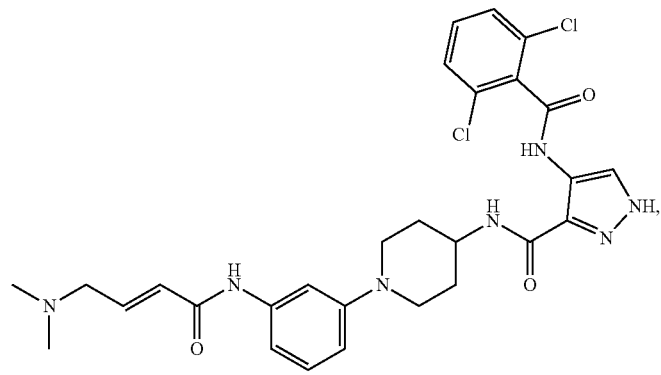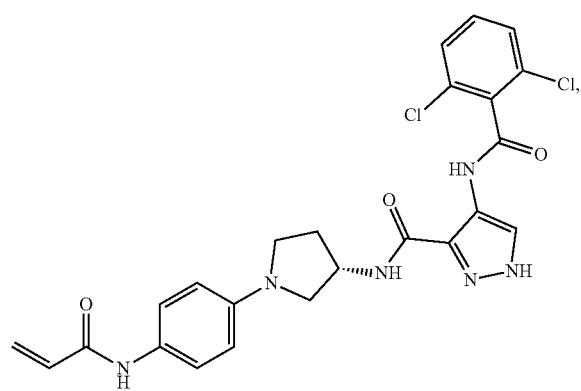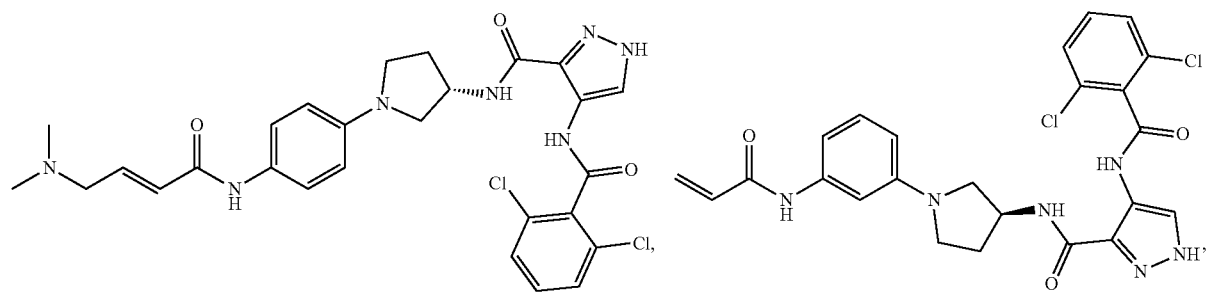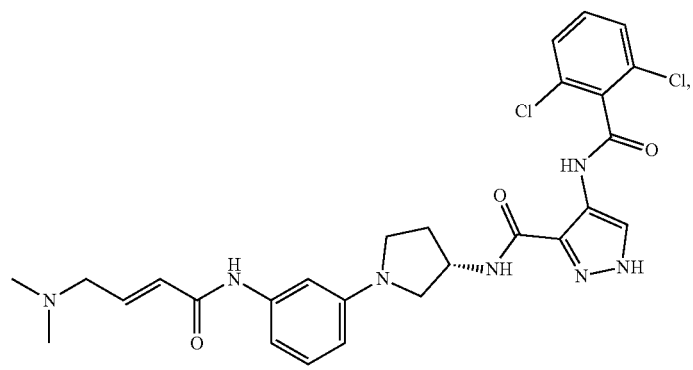

-continued
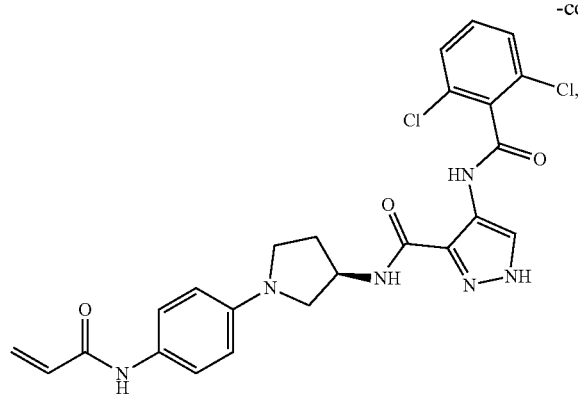
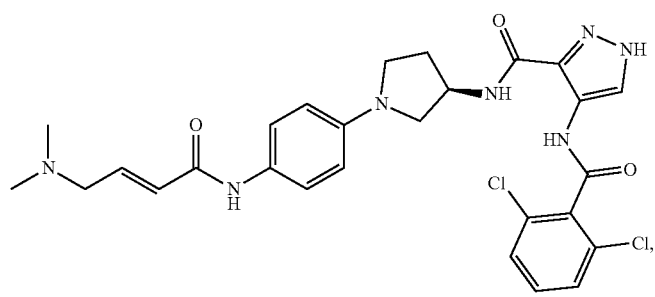
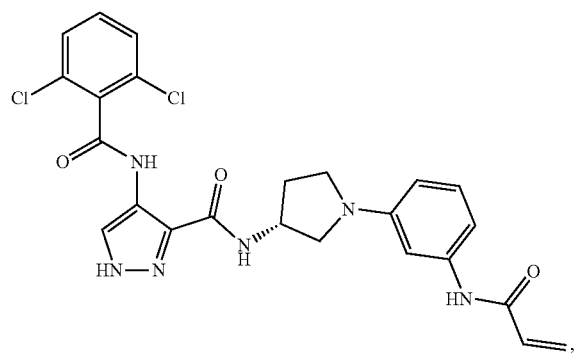
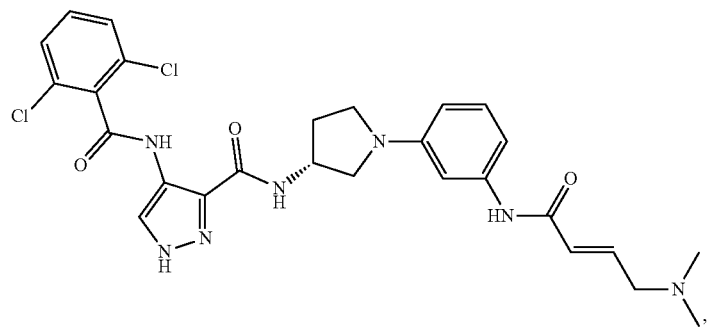

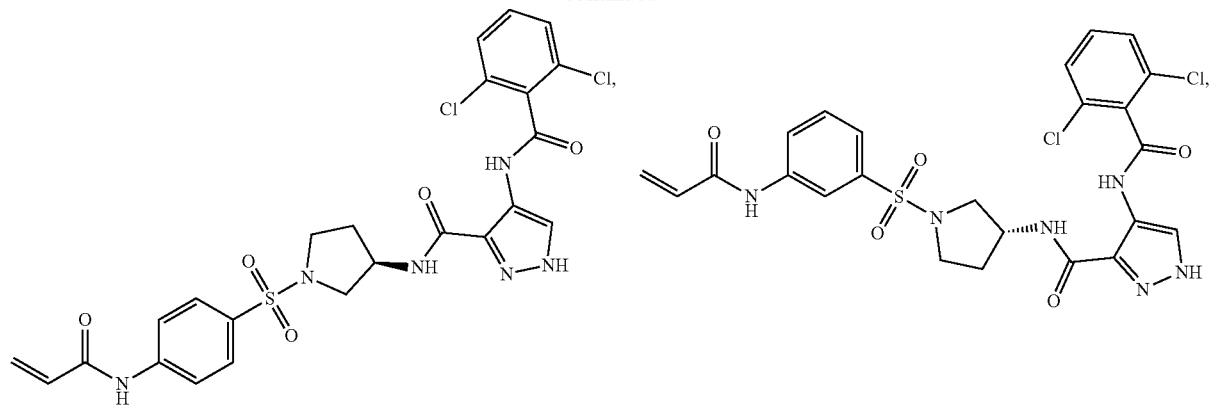
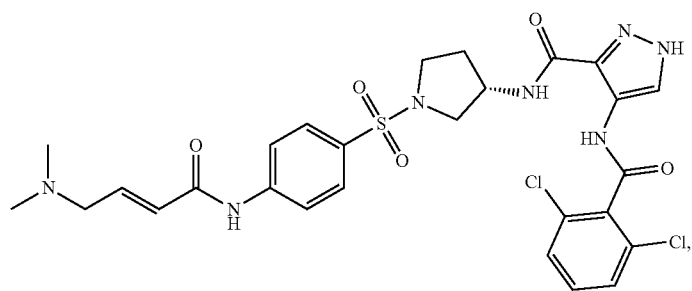
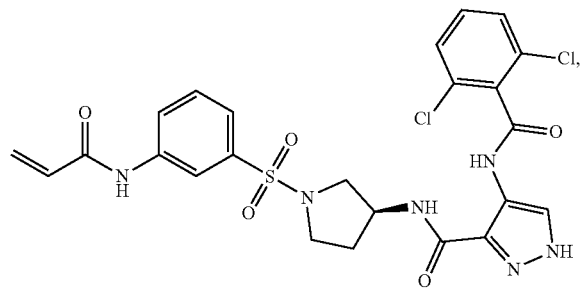
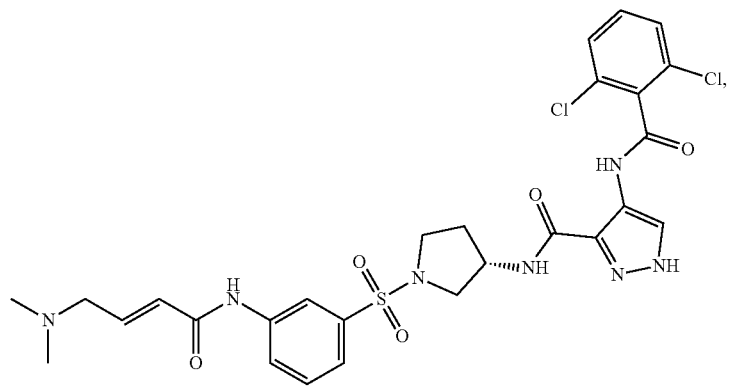

-continued
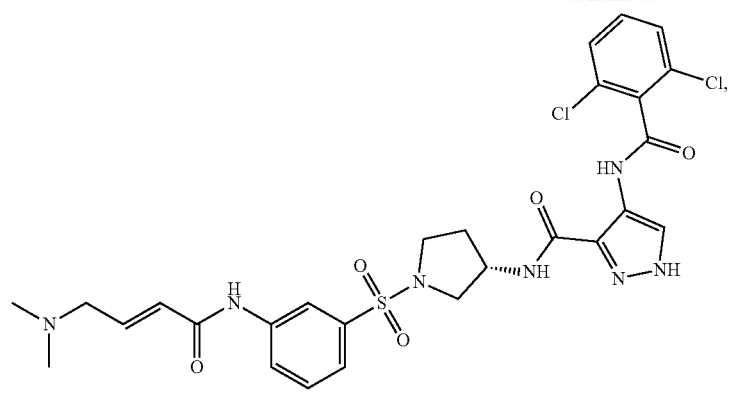
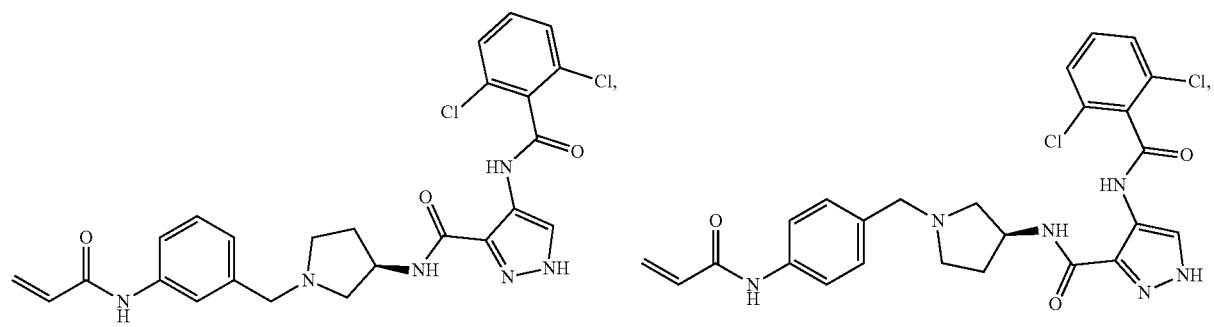
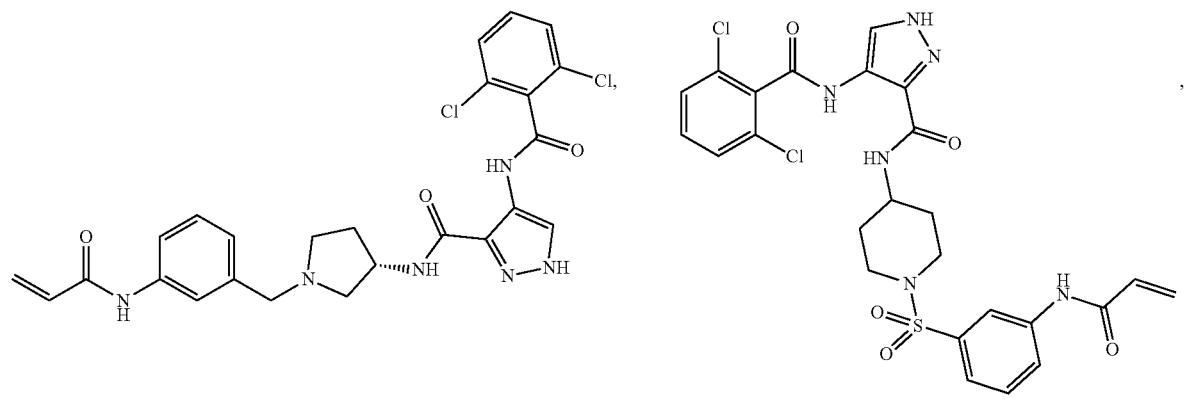
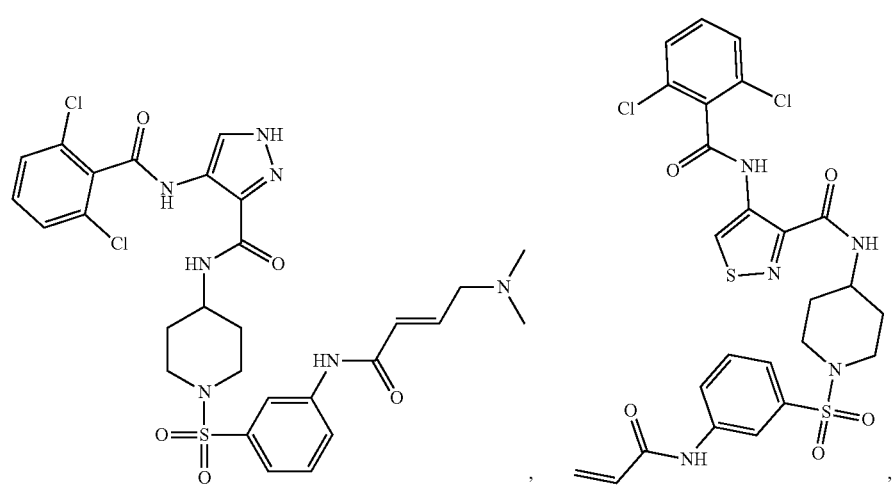

27
-continued
28
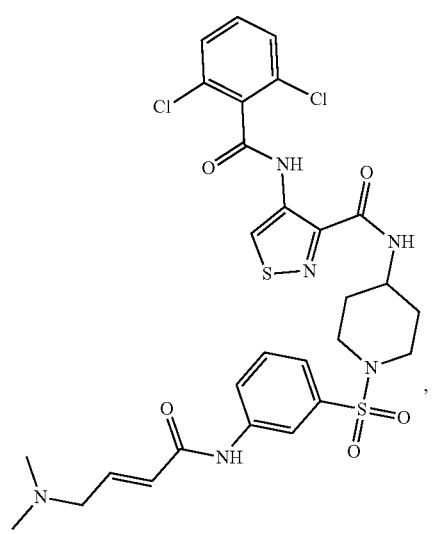
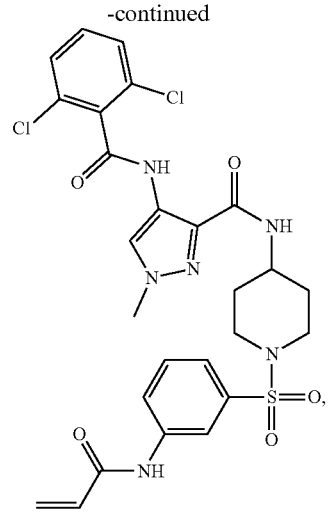
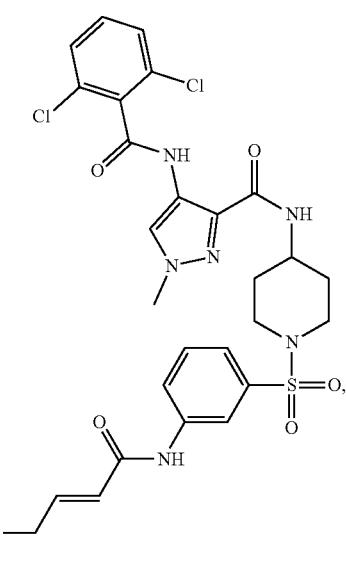
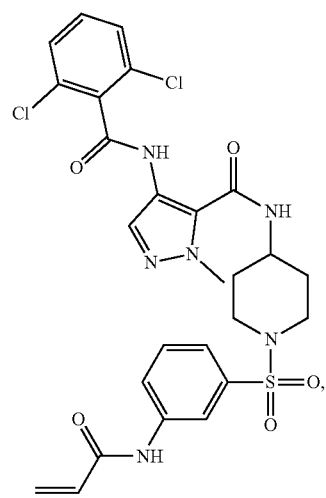
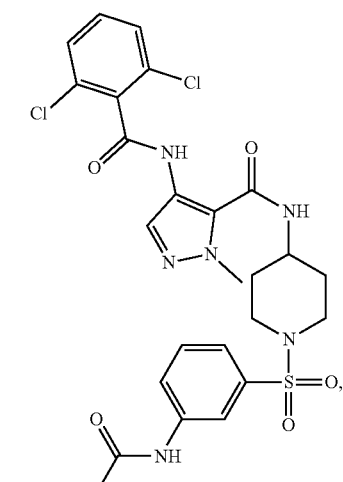
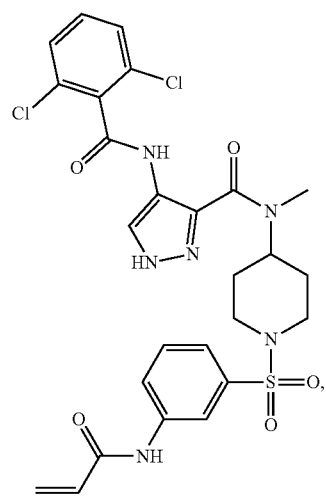
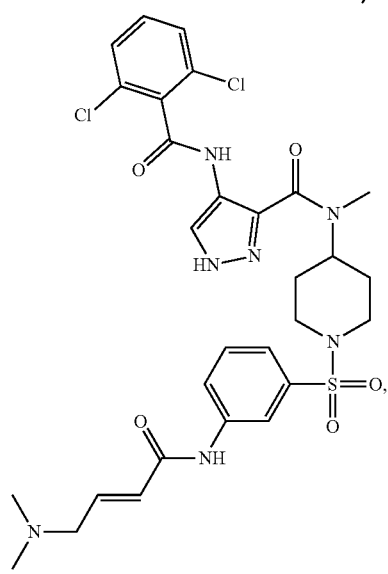
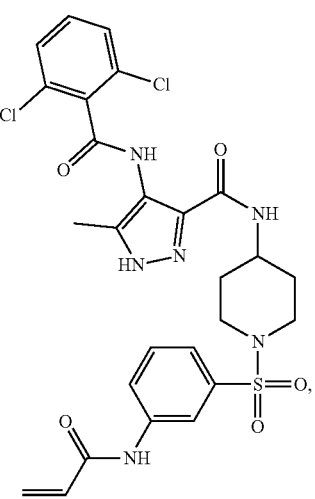
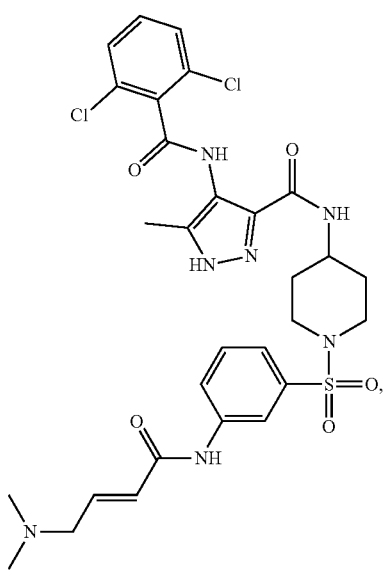

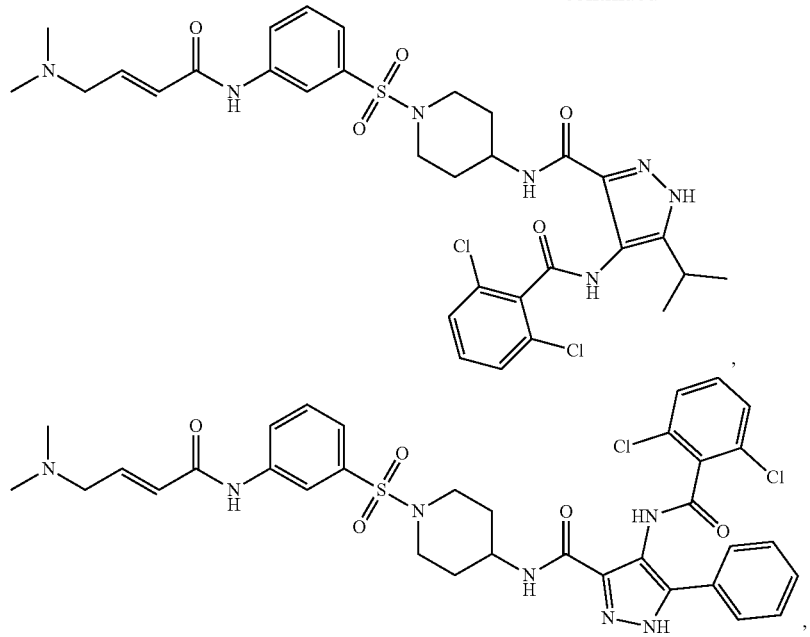

and pharmaceutically acceptable salts, solvates, hydrates, polymorphs, co-crystals, tautomers, stereoisomers, isotopically labeled derivatives, and prodrugs thereof.

In another aspect, the present disclosure provides pharmaceutical compositions including a compound described herein, and optionally a pharmaceutically acceptable excipient. In certain embodiments, the pharmaceutical compositions described herein include a therapeutically or prophylactically effective amount of a compound described herein. The pharmaceutical composition may be useful for treating and/or preventing a disease (e.g., a proliferative disease, metabolic disorder, autoimmune disease, or neurological disease) in a subject in need thereof, or inhibiting the activity of a protein kinase (e.g., CDK14, CDK15, CDK16, CDK17, CDK18) in a subject, biological sample, tissue, or cell. In certain embodiments, the proliferative disease is cancer (e.g., lung cancer, breast cancer, liver cancer, pancreatic cancer, gastric cancer, ovarian cancer, colon cancer, colorectal cancer). In certain embodiments, the cancer is a carcinoma.

In another aspect, the present disclosure provides pharmaceutical compositions including a compound described herein, and optionally a pharmaceutically acceptable excipient. In certain embodiments, the pharmaceutical compositions described herein include a therapeutically or prophylactically effective amount of a compound described herein. The pharmaceutical composition may be useful for treating a disease (e.g., a proliferative disease, metabolic disorder, autoimmune disease, or neurological disease) in a subject in need thereof in a subject in need thereof, or inhibiting the activity of a protein kinase (e.g., CDK) in a subject, biological sample, tissue, or cell. In certain embodiments, the disease is a proliferative disease (e.g., cancer (e.g., lung cancer, breast cancer, liver cancer, pancreatic cancer, gastric cancer, ovarian cancer, colon cancer, colorectal cancer)). In certain embodiments, the cancer is a carcinoma. In certain embodiments, the disease is a metabolic disorder (e.g., diabetes). In certain embodiments, the disease is an autoimmune disease (e.g., systemic lupus erythematosis, rheumatoid arthritis). In certain embodiments, the disease is a neurological disease (e.g., Alzheimer's disease, gliosis, spinal cord injury).

In another aspect, described herein are methods for treating and/or preventing a disease (e.g., a proliferative disease, metabolic disorder, autoimmune disease, or neurological disease). Exemplary proliferative diseases which may be treated include diseases associated with the overexpression or increased activity of a CDK, e.g., cancer. In certain embodiments, the cancer is a carcinoma. In certain embodiments, the cancer is selected from the group consisting of lung cancer, breast cancer, liver cancer, pancreatic cancer, gastric cancer, ovarian cancer, colon cancer, and colorectal cancer. In certain embodiments, the disease is a metabolic disorder (e.g., diabetes). In certain embodiments, the disease is a neurological disease (e.g., Alzheimer's disease, gliosis, spinal cord injury).

Another aspect relates to methods of inhibiting the activity of a kinase (e.g., CDK (e.g., CDK14, CDK15, CDK16, CDK17, CDK18)) using a compound described herein in a biological sample (e.g., cell, tissue). In another aspect, described herein are methods of inhibiting the activity of a kinase (e.g., CDK (e.g., CDK14, CDK15, CDK16, CDK17, CDK18)) using a compound described herein in a subject. In certain embodiments, the method involves the inhibition of CDK14.

Described herein are methods for administering to a subject in need thereof an effective amount of a compound, or pharmaceutical composition thereof, as described herein. Also described are methods for contacting a cell with an effective amount of a compound, or pharmaceutical composition thereof, as described herein. In certain embodiments, a method described herein further includes administering to the subject an additional pharmaceutical agent. In certain embodiments, a method described herein further includes contacting the cell with an additional pharmaceutical agent (e.g., an anti-proliferative agent). In certain embodiments, the additional pharmaceutical agent is a kinase inhibitor (e.g., an inhibitor of a CDK).

In yet another aspect, the present disclosure provides compounds of Formula (I') or (I), and pharmaceutically acceptable salts, solvates, hydrates, polymorphs, co-crystals, tautomers, stereoisomers, isotopically labeled derivatives, prodrugs, and compositions thereof, for use in the treatment of a disease (e.g., a proliferative disease, metabolic disorder, autoimmune disease, or neurological disease) in a subject.

Another aspect of the present disclosure relates to kits comprising a container with a compound, or pharmaceutical composition thereof, as described herein. The kits described herein may include a single dose or multiple doses of the compound or pharmaceutical composition. The kits may be useful in a method of the disclosure. In certain embodiments, the kit further includes instructions for using the compound or pharmaceutical composition. A kit described herein may also include information (e.g. prescribing information) as required by a regulatory agency, such as the U.S. Food and Drug Administration (FDA).

The details of one or more embodiments of the invention are set forth herein. Other features, objects, and advantages of the invention will be apparent from the Detailed Description, Examples, Figures, and Claims.

Definitions

Definitions of specific functional groups and chemical terms are described in more detail below. The chemical elements are identified in accordance with the Periodic Table of the Elements, CAS version, *Handbook of Chemistry and Physics*, 75th Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5th Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3rd Edition, Cambridge University Press, Cambridge, 1987. The disclosure is not intended to be limited in any manner by the exemplary listing of substituents described herein.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, NY, 1962); and Wilen, *Tables of Resolving Agents and Optical Resolutions* p. 268 (E. L. Eliel, Ed., Univ. of Notre Dame Press, Notre Dame, IN 1972). The invention additionally encompasses compounds described herein as individual isomers substantially free of other isomers, and alternatively, as mixtures of various isomers.

When a range of values is listed, it is intended to encompass each value and sub-range within the range. For example, "$C_{1-6}$" is intended to encompass $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

"Hydrocarbon chain" refers to a substituted or unsubstituted divalent alkyl, alkenyl, or alkynyl group. A hydrocarbon chain includes at least one chain, each node ("carbon unit") of which including at least one carbon atom, between the two radicals of the hydrocarbon chain. For example, hydrocarbon chain —$C^A H(C^B H_2 C^C H_3)$— includes only one carbon unit $C^A$. The term "$C_x$ hydrocarbon chain," wherein x is a positive integer, refers to a hydrocarbon chain that includes x number of carbon unit(s) between the two radicals of the hydrocarbon chain. If there is more than one possible value of x, the smallest possible value of x is used for the definition of the hydrocarbon chain. For example, —$CH(C_2 H_5)$— is a $C_1$ hydrocarbon chain, and

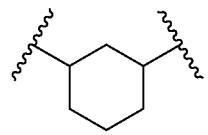 [SMILES: *C1CCCC(*)C1]

is a $C_3$ hydrocarbon chain. When a range of values is used, e.g., a $C_{1-6}$ hydrocarbon chain, the meaning of the range is as described herein. A hydrocarbon chain may be saturated (e.g., —$(CH_2)_4$—). A hydrocarbon chain may also be unsaturated and include one or more C=C and/or C≡C bonds anywhere in the hydrocarbon chain. For instance, —CH=CH—$(CH_2)_2$—, —$CH_2$—C≡C—$CH_2$—, and —C≡C—CH=CH— are all examples of a unsubstituted and unsaturated hydrocarbon chain. In certain embodiments, the hydrocarbon chain is unsubstituted (e.g., —$(CH_2)_4$—). In certain embodiments, the hydrocarbon chain is substituted (e.g., —$CH(C_2 H_5)$— and —$CF_2$—). Any two substituents on the hydrocarbon chain may be joined to form an optionally substituted carbocyclyl, optionally substituted heterocyclyl, optionally substituted aryl, or optionally substituted heteroaryl ring. For instance

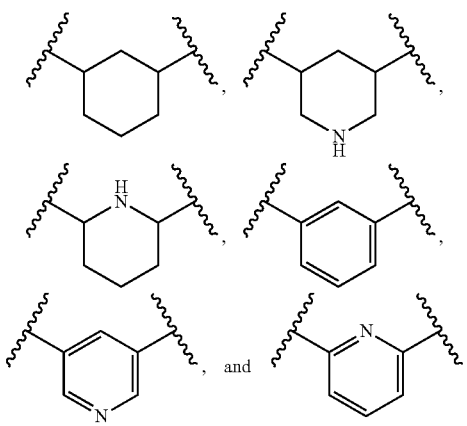

are all examples of a hydrocarbon chain. In contrast, in certain embodiments

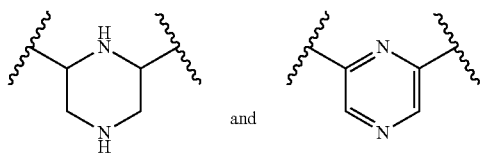 [SMILES: *C1CNCC(*)N1 ; *c1cncc(*)n1]

are not within the scope of the hydrocarbon chains described herein.

"Alkyl" refers to a radical of a straight-chain or branched saturated hydrocarbon group having from 1 to 20 carbon atoms ("$C_{1-20}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently optionally substituted, i.e., unsubstituted (an "unsubstituted alkyl") or substituted (a "substituted alkyl") with one or more substituents. In certain embodiments, the alkyl group is unsubstituted $C_{1-10}$ alkyl (e.g., —$CH_3$). In certain embodiments, the alkyl group is substituted $C_{1-10}$ alkyl.

"Alkenyl" refers to a radical of a straight-chain or branched hydrocarbon group having from 2 to 20 carbon atoms, one or more carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl.

"Alkynyl" refers to a radical of a straight-chain or branched hydrocarbon group having from 2 to 20 carbon atoms, one or more carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-5}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

"Carbocyclyl" or "carbocyclic" refers to a radical of a non-aromatic cyclic hydrocarbon group having from 3 to 10 ring carbon atoms ("$C_{3-10}$ carbocyclyl") and $_{ww}$ero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl"

also includes ring systems wherein the carbocyclic ring, as defined above, is fused with one or more aryl or heteroaryl groups wherein the point of attachment is on the carbocyclic ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is a substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from the group consisting of nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclic ring, as defined above, is fused with one or more carbocyclyl groups wherein the point of attachment is either on the carbocyclyl or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from the group consisting of nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from the group consisting of nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from the group consisting of nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, and thiiranyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, and dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14 pi electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Aralkyl" is a subset of alkyl and aryl and refers to an optionally substituted alkyl group substituted by an optionally substituted aryl group. In certain embodiments, the aralkyl is optionally substituted benzyl. In certain embodiments, the aralkyl is benzyl. In certain embodiments, the aralkyl is optionally substituted phenethyl. In certain embodiments, the aralkyl is phenethyl.

"Heteroaryl" refers to a radical of a 5-10 membered monocyclic or bicyclic 4n+2 aromatic ring system (e.g., having 6 or 10 pi electrons shared in a cyclic array) having ring carbon atoms and 1-4 ring heteroatoms provided in the aromatic ring system, wherein each heteroatom is independently selected from the group consisting of nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from the group consisting of nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from the group consisting of nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from the group consisting of nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

"Heteroaralkyl" is a subset of alkyl and heteroaryl and refers to an optionally substituted alkyl group substituted by an optionally substituted heteroaryl group.

"Partially unsaturated" refers to a group that includes at least one double or triple bond. A "partially unsaturated" ring system is further intended to encompass rings having multiple sites of unsaturation but is not intended to include aromatic groups (e.g., aryl or heteroaryl groups) as defined herein. Likewise, "saturated" refers to a group that does not contain a double or triple bond, i.e., contains all single bonds.

Alkyl, alkenyl, alkynyl, carbocyclyl, heterocyclyl, aryl, and heteroaryl groups, which are divalent bridging groups are further referred to using the suffix-ene, e.g., alkylene, alkenylene, alkynylene, carbocyclylene, heterocyclylene, arylene, and heteroarylene.

The term "optionally substituted" refers to substituted or unsubstituted.

Alkyl, alkenyl, alkynyl, carbocyclyl, heterocyclyl, aryl, and heteroaryl groups are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR—, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR—, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R—, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)(R$^{aa}$)$_2$, —P(=O)(OR$^{cc}$)$_2$, —OP(=O)(R$^{aa}$)$_2$, —OP(=O)(OR$^{cc}$)$_2$, —P(=O)(N(R$^{bb}$)$_2$)$_2$, —OP(=O)(N(R$^{bb}$)$_2$)$_2$, —NR$^{bb}$P(=O)(R$^{aa}$)$_2$, —NR$^{bb}$P(=O)(OR$^{cc}$)$_2$, —NR$^{bb}$P(=O)(N(R$^{bb}$)$_2$)$_2$, —P(R$^{cc}$)$_2$, —P(OR$^{cc}$)$_2$, —P(R$^{aa}$)$_3$$^+$X$^-$, —P(OR$^{aa}$)$_3$$^+$X$^-$, —P(R$^{cc}$)$_4$, —P(OR$^{cc}$)$_4$, —OP(R$^{cc}$)$_2$, —OP(R$^{aa}$)$_3$$^+$X$^-$, —OP(OR$^{cc}$)$_2$, —OP(OR$^{aa}$)$_3$$^+$X$^-$, —OP(R$^{cc}$)$_4$, —OP(OR$^{cc}$)$_4$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

or two geminal hydrogens on a carbon atom are replaced with the group =O, =S, =NN(R$^{bb}$)$_2$, =NNR$^{bb}$C(=O)R—, =NNR$^{bb}$C(=O)OR$^{aa}$, =NNR$^{bb}$S(=O)$_2$R$^{aa}$, =NR$^{bb}$, or =NOR$^{aa}$;

each instance of R$^{cc}$ is, independently, selected from C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(R$^{aa}$)$_2$, —P(=O)(OR$^{cc}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —N$_{O2}$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{aa}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)(OR$^{ee}$)$_2$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S; wherein X$^-$ is a counterion;

each instance of R$^{ee}$ is, independently, selected from C$_{1-6}$ alkyl, C$_{1-6}$ perhaloalkyl, C$_{2-6}$ alkenyl, C$_{2-6}$ alkynyl, heteroC$_{1-6}$ alkyl, heteroC$_{2-6}$alkenyl, heteroC$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl and 5-10 membered heteroaryl, or two R$^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups; and each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3^+$X$^-$, —NH(C$_{1-6}$ alkyl)$_2^+$X$^-$, —NH$_2$(C$_{1-6}$ alkyl)$^+$X$^-$, —NH$_3^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$—C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)(OC$_{1-6}$ alkyl)$_2$, —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_2$-6 alkenyl, heteroC$_{2-6}$alkynyl, C$_{3-10}$ carbocyclyl, C$_{6-10}$ aryl, 3-10 membered heterocyclyl, 5-10 membered heteroaryl; or two geminal $R^{gg}$ substituents can be joined to form O or =S; wherein X$^-$ is a counterion.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., F$^-$, Cl$^-$, Br$^-$, I$^-$), NO$_3^-$, ClO$_4^-$, OH$^-$, H$_2$PO$_4^-$, HCO$_3^-$, HSO$_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), BF$_4^-$, PF$_4^-$, PF$_6^-$, AsF$_6^-$, SbF$_6^-$, B[3,5-(CF$_3$)$_2$C$_6$H$_3$]$_4$]$^-$, B(C$_6$F$_5$)$_4^-$, BPh$_4^-$, Al(OC(CF$_3$)$_3$)$_4^-$, and carborane anions (e.g., CB$_{11}$H$_{12}^-$ or (HCB$_{11}$Me$_5$Br$_6$)$^-$). Exemplary counterions which may be multivalent include CO$_3^{2-}$, HPO$_4^{2-}$, PO$_4^{3-}$, B$_4$O$_7^{2-}$, SO$_4^{2-}$, S$_2$O$_3^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

"Halo" or "halogen" refers to fluorine (fluoro, —F), chlorine (chloro, —Cl), bromine (bromo, —Br), or iodine (iodo, —I).

The term "acyl" refers to a group having the general formula —C(=O)R$^{X1}$, —C(=O)OR$^{X1}$, —C(=O)—O—C(=O)R$^{X1}$, —C(=O)SR$^{X1}$, —C(=O)N(R$^{X1}$)$_2$, —C(=S)R$^{X1}$, —C(=S)N(R$^{X1}$)$_2$, and —C(=S)S(R$^{X1}$), —C(=NR$^{X1}$)R$^{X1}$, —C(=NR$^{X1}$)OR$^{X1}$, —C(=NR$^{X1}$)SR$^{X1}$, and —C(=NR$^{X1}$)N(R$^{X1}$)$_2$, wherein R$^{X1}$ is hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two R$^{X1}$ groups taken together form a 5- to 6-membered heterocyclic ring. Exemplary acyl groups include aldehydes (—CHO), carboxylic acids (—CO$_2$H), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

"Alkoxy" or "alkoxyl" refers to a radical of the formula: —O-alkyl.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R—, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(OR$^{cc}$)$_2$, —P(=O)(R$^{aa}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

In certain embodiments, the substituent present on a nitrogen atom is a nitrogen protecting group (also referred to as an amino protecting group). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, and o-(benzoyloxymethyl)benzamide.

Nitrogen protecting groups such as carbamate groups (e.g., —C(=O)OR$^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl) ethyl carbamate (Pyoc), 2-(N,N-dicyclohexylcarboxamido) ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium) benzyl carbamate, and 2,4,6-trimethylbenzyl carbamate.

Nitrogen protecting groups such as sulfonamide groups (e.g., —S(=O)$_2$Ra$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), (β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N-(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to herein as an "hydroxyl protecting group"). Oxygen protecting groups include, but are not limited to, —R$^{aa}$, —N(R$^{bb}$)$_2$, —C(=O)SR$^{aa}$, —C(=O)R$^{aa}$, —CO$_2$R$^{aa}$, —C(=O)N (R$^{bb}$)$_2$, —C(=NR$^{bb}$)R—, —C(=NR$^{bb}$)OR—, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$$^+$X$^-$, —P(OR$^{cc}$)$_2$, —P(OR$^{cc}$)$_3$$^+$X$^-$, —P(=O)(R$^{aa}$)$_2$, —P(=O)(OR$^{cc}$)$_2$, and —P(=O)(N(R$^{bb}$)$_2$)$_2$, wherein X$^-$, R$^{aa}$, R$^{bb}$, and R$^{cc}$ are as defined herein. Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4''-tris(4,5-dichlorophthalimidophenyl)methyl, 4,4',4''-tris(levulinoyloxyphenyl)methyl, 4,4',4''-tris(benzoyloxyphenyl)methyl, 3-(imidazol-1-yl)bis(4',4''-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on a sulfur atom is a sulfur protecting group (also referred to as a "thiol protecting group"). Sulfur protecting groups include, but are not limited to, —R$^{aa}$, —N(R$^{bb}$)$_2$, —C(=O)SR$^{aa}$, —C(=O)R—, —CO$_2$R$^{aa}$, —C(=O)N(R$^{bb}$)$_2$, —C(=NR$^{bb}$)R$^{aa}$, —C(=NR$^{bb}$)OR—, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R)$_3$$^+$X$^-$, —P(OR$^{cc}$)$_2$, —P(OR)$_3$$^+$X$^-$, —P(=O)(R$^{aa}$)$_2$, —P(=O)(OR$^{cc}$)$_2$, and —P(=O)(N(R$^{bb}$)$_2$)$_2$, wherein R$^{aa}$, R$^{bb}$, and R$^{cc}$ are as defined herein. Sulfur protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

As used herein, a "leaving group" (LG) is an art-understood term referring to a molecular fragment that departs with a pair of electrons in a heterolytic bond cleavage, wherein the molecular fragment is an anion or neutral molecule. As used herein, a leaving group can be an atom or a group capable of being displaced by a nucleophile. See, for example, Smith, *March Advanced Organic Chemistry* 6th ed. (501-502). Exemplary leaving groups include, but are not limited to, halo (e.g., chloro, bromo, iodo) and activated substituted hydroxyl groups (e.g., —OC(=O)SR$^{aa}$, —OC(=O)R$^{aa}$, —OCO$_2$R$^{aa}$, —OC(=O)N(R$^{bb}$)$_2$, —OC(=NR$^{bb}$)R—, —OC(=NR$^{bb}$)OR—, —OC(=NR$^{bb}$)N(R$^{bb}$)$_2$, —OS(=O)R$^{aa}$, —OSO$_2$R$^{aa}$, —OP(R$^{cc}$)$_2$, —OP(R$^{aa}$)$_3$, —OP(=O)$_2$R$^{aa}$, —OP(=O)(R$^{aa}$)$_2$, —OP(=O)(OR$^{cc}$)$_2$, —OP(=O)$_2$N(R$^{bb}$)$_2$, and —OP(=O)(NR$^{bb}$)$_2$, wherein R$^{aa}$, R$^{bb}$, and R$^{cc}$ are as defined herein). Examples of suitable leaving groups include, but are not limited to, halogen (such as F, Cl, Br, or I (iodine)), alkoxycarbonyloxy, aryloxycarbonyloxy, alkanesulfonyloxy, arenesulfonyloxy, alkyl-carbonyloxy (e.g., acetoxy), arylcarbonyloxy, aryloxy, methoxy, N,O-dimethylhydroxylamino, pixyl, and haloformates. In some cases, the leaving group is a sulfonic acid ester, such as toluenesulfonate (tosylate, —OTs), methanesulfonate (mesylate, —OMs), p-bromobenzenesulfonyloxy (brosylate, —OBs), or trifluoromethanesulfonate (triflate, —OTf). In some cases, the leaving group is a brosylate, such as p-bromobenzenesulfonyloxy. In some cases, the leaving group is a nosylate, such as 2-nitrobenzenesulfonyloxy. In some embodiments, the leaving group is a sulfonate-containing group. In some embodiments, the leaving group is a tosylate group. The leaving group may also be a phosphineoxide (e.g., formed during a Mitsunobu reaction) or an internal leaving group such as an epoxide or cyclic sulfate. Other non-limiting examples of leaving groups are water, amines, ammonia, alcohols, ether moieties, sulfur-containing moieties, thioether moieties, zinc halides, magnesium moieties, diazonium salts, and copper moieties.

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}\ alkyl)_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound that are associated with a solvent, usually by a solvolysis reaction. This physical association may include hydrogen bonding. Conventional solvents include water, methanol, ethanol, acetic acid, DMSO, THF, diethyl ether, and the like. The compounds of Formula (I') or (I) may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolable solvates. Representative solvates include hydrates, ethanolates, and methanolates.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula $R·x\ H_2O$, wherein R is the compound and wherein x is a number greater than 0. A given compound may form more than one type of hydrates, including, e.g., monohydrates (x is 1), lower hydrates (x is a number greater than 0 and smaller than 1, e.g., hemihydrates ($R·0.5\ H_2O$)), and polyhydrates (x is a number greater than 1, e.g., dihydrates ($R·2H_2O$) and hexahydrates ($R·6H_2O$)).

The term "tautomers" refer to compounds that are interchangeable forms of a particular compound structure, and that vary in the displacement of hydrogen atoms and electrons. Thus, two structures may be in equilibrium through the movement of J electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base.

Tautomeric forms may be relevant to the attainment of the optimal chemical reactivity and biological activity of a compound of interest.

It is also to be understood that compounds that have the same molecular formula but differ in the nature or sequence of bonding of their atoms or the arrangement of their atoms in space are termed "isomers." Isomers that differ in the arrangement of their atoms in space are termed "stereoisomers."

Stereoisomers that are not mirror images of one another are termed "diastereomers" and those that are non-superimposable mirror images of each other are termed "enantiomers." When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture."

The term "polymorphs" refers to a crystalline form of a compound (or a salt, hydrate, or solvate thereof) in a particular crystal packing arrangement. All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "prodrugs" refer to compounds, including derivatives of the compounds of Formula (I') or (I), which have cleavable groups and become by solvolysis or under physiological conditions the compounds of Formula (I') or (I) which are pharmaceutically active in vivo. Such examples include, but are not limited to, ester derivatives and the like. Other derivatives of the compounds of this invention have activity in both their acid and acid derivative forms, but in the acid sensitive form often offers advantages of solubility, tissue compatibility, or delayed release in the mammalian organism (see, Bundgard, H., *Design of Prodrugs*, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds of this invention are particular prodrugs. In some cases it is desirable to prepare double ester type prodrugs such as (acyloxy)alkyl esters or ((alkoxycarbonyl)oxy)alkylesters. $C_1$-$C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds of Formula (I') or (I) may be preferred.

A "subject" to which administration is contemplated includes, but is not limited to, humans (i.e., a male or female of any age group, e.g., a pediatric subject (e.g., infant, child, adolescent) or adult subject (e.g., young adult, middle-aged adult, or senior adult)) and/or other non-human animals, for example, mammals (e.g., primates (e.g., cynomolgus monkeys, rhesus monkeys); commercially relevant mammals such as cattle, pigs, horses, sheep, goats, cats, and/or dogs) and birds (e.g., commercially relevant birds such as chickens, ducks, geese, and/or turkeys). In certain embodiments, the animal is a mammal. The animal may be a male or female and at any stage of development. A non-human animal may be a transgenic animal.

The terms "administer," "administering," or "administration," refers to implanting, absorbing, ingesting, injecting, inhaling, or otherwise introducing an inventive compound, or a pharmaceutical composition thereof.

The terms "treatment," "treat," and "treating" refer to reversing, alleviating, delaying the onset of, or inhibiting the progress of a "pathological condition" (e.g., a disease, disorder, or condition, or one or more signs or symptoms thereof) described herein. In some embodiments, treatment may be administered after one or more signs or symptoms have developed or have been observed. In other embodiments, treatment may be administered in the absence of signs or symptoms of the disease or condition. For example, treatment may be administered to a susceptible individual prior to the onset of symptoms (e.g., in light of a history of symptoms and/or in light of genetic or other susceptibility factors). Treatment may also be continued after symptoms have resolved, for example, to delay or prevent recurrence.

The terms "condition," "disease," and "disorder" are used interchangeably.

An "effective amount" of a compound of Formula (I') or (I) refers to an amount sufficient to elicit the desired biological response, i.e., treating the condition. As will be appreciated by those of ordinary skill in this art, the effective amount of a compound of Formula (I') or (I) may vary depending on such factors as the desired biological endpoint, the pharmacokinetics of the compound, the condition being treated, the mode of administration, and the age and health of the subject. An effective amount encompasses therapeutic and prophylactic treatment. For example, in treating cancer, an effective amount of an inventive compound may reduce the tumor burden or stop the growth or spread of a tumor.

A "therapeutically effective amount" of a compound of Formula (I') or (I) is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces, or avoids symptoms or causes of the condition, or enhances the therapeutic efficacy of another therapeutic agent.

A "prophylactically effective amount" of a compound of Formula (I') or (I) is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

A "proliferative disease" refers to a disease that occurs due to abnormal growth or extension by the multiplication of cells (Walker, *Cambridge Dictionary of Biology*; Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as the matrix metalloproteinases (e.g., collagenases, gelatinases, and elastases); or 4) the pathological angiogenesis as in proliferative retinopathy and tumor metastasis. Exemplary proliferative diseases include cancers (i.e., "malignant neoplasms"), benign neoplasms, angiogenesis, inflammatory diseases, autoinflammatory diseases, and autoimmune diseases.

The terms "neoplasm" and "tumor" are used interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An exemplary pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites.

The term "metastasis," "metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located. For example, a prostate cancer that has migrated to bone is said to be metastasized prostate cancer and includes cancerous prostate cancer cells growing in bone tissue.

The term "cancer" refers to a malignant neoplasm (*Stedman's Medical Dictionary*, 25th ed.; Hensyl ed.; Williams & Wilkins: Philadelphia, 1990). Exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kdposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; eye cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenstram's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; and multiple myeloma (MM)), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendocrinetumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

The term "angiogenesis" refers to the formation and the growth of new blood vessels. Normal angiogenesis occurs in the healthy body of a subject for healing wounds and for restoring blood flow to tissues after injury. The healthy body controls angiogenesis through a number of means, e.g., angiogenesis-stimulating growth factors and angiogenesis inhibitors. Many disease states, such as cancer, diabetic blindness, age-related macular degeneration, rheumatoid arthritis, and psoriasis, are characterized by abnormal (i.e., increased or excessive) angiogenesis. Abnormal or pathological angiogenesis refers to angiogenesis greater than that in a normal body, especially angiogenesis in an adult not related to normal angiogenesis (e.g., menstruation or wound healing). Abnormal angiogenesis can provide new blood vessels that feed diseased tissues and/or destroy normal tissues, and in the case of cancer, the new vessels can allow tumor cells to escape into the circulation and lodge in other organs (tumor metastases). In certain embodiments, the angiogenesis is pathological angiogenesis.

An "autoimmune disease" refers to a disease arising from an inappropriate immune response of the body of a subject against substances and tissues normally present in the body. In other words, the immune system mistakes some part of the body as a pathogen and attacks its own cells. This may be restricted to certain organs (e.g., in autoimmune thyroiditis) or involve a particular tissue in different places (e.g., Goodpasture's disease which may affect the basement membrane in both the lung and kidney). The treatment of autoimmune diseases is typically with immunosuppression, e.g., medications which decrease the immune response. Exemplary autoimmune diseases include, but are not limited to, glomerulonephritis, Goodpasture's syndrome, necrotizing vasculitis, lymphadenitis, peri-arteritis nodosa, systemic lupus erythematosis, rheumatoid arthritis, psoriatic arthritis, systemic lupus erythematosis, psoriasis, ulcerative colitis, systemic sclerosis, dermatomyositis/polymyositis, antiphospholipid antibody syndrome, scleroderma, pemphigus vulgaris, ANCA-associated vasculitis (e.g., Wegener's granulomatosis, microscopic polyangiitis), uveitis, Sjogren's syndrome, Crohn's disease, Reiter's syndrome, ankylosing spondylitis, Lyme disease, Guillain-Barré syndrome, Hashimoto's thyroiditis, and cardiomyopathy.

The term "neurological disease" refers to any disease of the nervous system, including diseases that involve the central nervous system (brain, brainstem and cerebellum), the peripheral nervous system (including cranial nerves), and the autonomic nervous system (parts of which are located in both central and peripheral nervous system). Neurodegenerative diseases refer to a type of neurological disease marked by the loss of nerve cells, including, but not limited to, Alzheimer's disease, Parkinson's disease, amyotrophic lateral sclerosis, tauopathies (including frontotemporal dementia), and Huntington's disease. Examples of neurological diseases include, but are not limited to, headache, stupor and coma, dementia, seizure, sleep disorders, trauma, infections, neoplasms, neuro-ophthalmology, movement disorders, demyelinating diseases, spinal cord disorders, and disorders of peripheral nerves, muscle and neuromuscular junctions. Addiction and mental illness, include, but are not limited to, bipolar disorder and schizophrenia, are also included in the definition of neurological diseases. Further examples of neurological diseases include acquired epileptiform aphasia; acute disseminated encephalomyelitis; adrenoleukodystrophy; agenesis of the corpus callosum; agnosia; Aicardi syndrome; Alexander disease; Alpers' disease; alternating hemiplegia; Alzheimer's disease; amyotrophic lateral sclerosis; anencephaly; Angelman syndrome; angiomatosis; anoxia; aphasia; apraxia; arachnoid cysts; arachnoiditis; Arnold-Chiari malformation; arteriovenous malformation; Asperger syndrome; ataxia telangiectasia; attention deficit hyperactivity disorder; autism; autonomic dysfunction; back pain; Batten disease; Behcet's disease; Bell's palsy; benign essential blepharospasm; benign focal; amyotrophy; benign intracranial hypertension; Binswanger's disease; blepharospasm; Bloch Sulzberger syndrome; brachial plexus injury; brain abscess; bbrain injury; brain tumors (including glioblastoma multiforme); spinal tumor; Brown-Sequard syndrome; Canavan disease; carpal tunnel syndrome (CTS); causalgia; central pain syndrome; central pontine myelinolysis; cephalic disorder; cerebral aneurysm; cerebral arteriosclerosis; cerebral atrophy; cerebral gigantism; cerebral palsy; Charcot-Marie-Tooth disease; chemotherapy-induced neuropathy and neuropathic pain; Chiari malformation; chorea; chronic inflammatory demyelinating polyneuropathy (CIDP); chronic pain; chronic regional pain syndrome; Coffin Lowry syndrome; coma, including persistent vegetative state; congenital facial diplegia; corticobasal degeneration; cranial arteritis; craniosynostosis; Creutzfeldt-Jakob disease; cumulative trauma disorders; Cushing's syndrome; cytomegalic inclusion body disease (CIBD); cytomegalovirus infection; dancing eyes-dancing feet syndrome; Dandy-Walker syndrome; Dawson disease; De Morsier's syndrome; Dejerine-Klumpke palsy; dementia; dermatomyositis; diabetic neuropathy; diffuse sclerosis; dysautonomia; dysgraphia; dyslexia; dystonias; early infantile epileptic encephalopathy; empty sella syndrome; encephalitis; encephaloceles; encephalotrigeminal angiomatosis; epilepsy; Erb's palsy; essential tremor; Fabry's disease; Fahr's syndrome; fainting; familial spastic paralysis; febrile seizures; Fisher syndrome; Friedreich's ataxia; frontotemporal dementia and other "tauopathies"; Gaucher's disease; Gerstmann's syndrome; giant cell arteritis; giant cell inclusion disease; globoid cell leukodystrophy; Guillain-Barre syndrome; HTLV-1 associated myelopathy; Hallervorden-Spatz disease; head injury; headache; hemifacial spasm; hereditary spastic paraplegia; heredopathia atactica polyneuritiformis; herpes zoster oticus; herpes zoster; Hirayama syndrome; HIV-associated dementia and neuropathy (see also neurological manifestations of AIDS); holoprosencephaly; Huntington's disease and other polyglutamine repeat diseases; hydranencephaly; hydrocephalus; hypercortisolism; hypoxia; immune-mediated encephalomyelitis; inclusion body myositis; incontinentia pigmenti; infantile; phytanic acid storage disease; Infantile Refsum disease; infantile spasms; inflammatory myopathy; intracranial cyst; intracranial hypertension; Joubert syndrome; Kearns-Sayre syndrome; Kennedy disease; Kinsbourne syndrome; Klippel Feil syndrome; Krabbe disease; Kugelberg-Welander disease; kuru; Lafora disease; Lambert-Eaton myasthenic syndrome; Landau-Kleffner syndrome; lateral medullary (Wallenberg) syndrome; learning disabilities; Leigh's disease; Lennox-Gastaut syndrome; Lesch-Nyhan syndrome; leukodystrophy; Lewy body dementia; lissencephaly; locked-in syndrome; Lou Gehrig's disease (aka motor neuron disease or amyotrophic lateral sclerosis); lumbar disc disease; lyme disease-neurological sequelae; Machado-Joseph disease; macrencephaly; megalencephaly; Melkersson-Rosenthal syndrome; Menieres disease; meningitis; Menkes disease; metachromatic leukodystrophy; microcephaly; migraine; Miller Fisher syndrome; mini-strokes; mitochondrial myopathies; Mobius syndrome; monomelic amyotrophy; motor neurone disease; moyamoya disease; mucopolysaccharidoses; multi-infarct dementia; multifocal motor neuropathy; multiple sclerosis and other demyelinating disorders; multiple system atrophy with postural hypotension; muscular dystrophy; myasthenia gravis; myelinoclastic diffuse sclerosis; myoclonic encephalopathy of infants; myoclonus; myopathy; myotonia congenital; narcolepsy; neurofibromatosis; neuroleptic malignant syndrome; neurological manifestations of AIDS; neurological sequelae of lupus; neuromyotonia; neuronal ceroid lipofuscinosis; neuronal migration disorders; Niemann-Pick disease; O'Sullivan-McLeod syndrome; occipital neuralgia; occult spinal dysraphism sequence; Ohtahara syndrome; olivopontocerebellar atrophy; opsoclonus myoclonus; optic neuritis; orthostatic hypotension; overuse syndrome; paresthesia; Parkinson's disease; paramyotonia congenita; paraneoplastic diseases; paroxysmal attacks; Parry Romberg syndrome; Pelizaeus-Merzbacher disease; periodic paralyses; peripheral neuropathy; painful neuropathy and neuropathic pain; persistent vegetative state; pervasive developmental disorders; photic sneeze reflex; phytanic acid storage disease; Pick's disease; pinched nerve; pituitary tumors; polymyositis; porencephaly; Post-Polio syndrome; postherpetic neuralgia (PHN); postinfectious encephalomyelitis; postural hypotension; Prader-Willi syndrome; primary lateral sclerosis; prion diseases; progressive; hemifacial atrophy; progressive multifocal leukoencephalopathy; progressive sclerosing poliodystrophy; progressive supranuclear palsy; pseudotumor cerebri; Ramsay-Hunt syndrome (Type I and Type II); Rasmussen's Encephalitis; reflex sympathetic dystrophy syndrome; Refsum disease; repetitive motion disorders; repetitive stress injuries; restless legs syndrome; retrovirus-associated myelopathy; Rett syndrome; Reye's syndrome; Saint Vitus Dance; Sandhoff disease; Schilder's disease; schizencephaly; septo-optic dysplasia; shaken baby syndrome; shingles; Shy-Drager syndrome; Sjogren's syndrome; sleep apnea; Soto's syndrome; spasticity; spina bifida; spinal cord injury; spinal cord tumors; spinal muscular atrophy; stiff-person syndrome; stroke; Sturge-Weber syndrome; subacute sclerosing panencephalitis; subarachnoid hemorrhage; subcortical arteriosclerotic encephalopathy; sydenham chorea; syncope; syringomyelia; tardive dyskinesia; Tay-Sachs disease; temporal arteritis; tethered spinal cord syndrome; Thomsen disease; thoracic outlet syndrome; tic douloureux; Todd's paralysis; Tourette syndrome; transient ischemic attack; transmissible spongiform encephalopathies; transverse myelitis; traumatic brain injury; gliosis; tremor; trigeminal neuralgia; tropical spastic paraparesis; tuberous sclerosis; vascular dementia (multi-infarct dementia); vasculitis including temporal arteritis; Von Hippel-Lindau Disease (VHL); Wallenberg's syndrome; Werdnig-Hoffman disease; West syndrome; whiplash; Williams syndrome; Wilson's disease; and Zellweger syndrome.

The term "metabolic disorder" refers to any disorder that involves an alteration in the normal metabolism of carbohydrates, lipids, proteins, nucleic acids, or a combination thereof. A metabolic disorder is associated with either a deficiency or excess in a metabolic pathway resulting in an imbalance in metabolism of nucleic acids, proteins, lipids, and/or carbohydrates. Factors affecting metabolism include, and are not limited to, the endocrine (hormonal) control system (e.g., the insulin pathway, the enteroendocrine hormones including GLP-1, PYY or the like), the neural control system (e.g., GLP-1 in the brain), or the like. Examples of metabolic disorders include, but are not limited to, diabetes (e.g., Type I diabetes, Type II diabetes, gestational diabetes), hyperglycemia, hyperinsulinemia, insulin resistance, and obesity.

The term "male contraception" refers to methods involving inducing a contraceptive effect to reduce male fertility. Examples of methods of reducing male fertility include, but are not limited to, inducing azoospermia, oligozoospermia, or asthenozoospermia; or reducing sperm number, or reducing sperm motility.

The term "biological sample" refers to any sample including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments or organelles (such as obtained by lysing cells and separating the components thereof by centrifugation or otherwise). Other examples of biological samples include blood, serum, urine, semen, fecal matter, cerebrospinal fluid, interstitial fluid, mucus, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample. Biological samples also include those biological samples that are transgenic, such as a transgenic oocyte, sperm cell, blastocyst, embryo, fetus, donor cell, or cell nucleus.

The term "kinase" refers to any enzyme that catalyzes the addition of phosphate groups to an amino acid residue of a protein. For example, a serine kinase catalyzes the addition of a phosphate group to serine residue in a protein. In certain embodiments, the kinase is a protein kinase. Examples of kinases include, but are not limited to, a cyclin-dependent kinase (CDK, e.g., CDK1, CDK2, CDK2, CDK4, CDK5, CDK7, CDK8, CDK9, CDK10, CDK11, CDK12, CDK13, CDK14, CDK16, CDK20)), a mitogen-activated protein kinase (MAPK, e.g., MAPK1, MAPK3, MAPK4, MAPK6, MAPK7, MAPK8, MAPK9, MAPK10, MAPK11, MAPK12, MAPK13, MAPK14, MAPK15), a glycogen synthase kinase 3 (GSK3, e.g., GSK3α, GSK3β), a CDK-like kinase (CLK, e.g., CLK1, CLK2, CLK3, CLK4)), an AGC kinase (e.g., protein kinase A (PKA), protein kinase C (PKC), protein kinase G (PKG)), a $Ca^{2+}$/calmodulin-dependent protein kinase (CaM kinase, e.g., a specialized CaM kinase, a multifunctional CaM kinase), a casein kinase 1 (CK1, e.g., CK1alpha, CK1beta 1, CK1gamma 1, CK1gamma 2, CK1gamma 3, CK1delta, CK1epsilon), a STE kinase (e.g., a homolog of yeast Sterile 7, Sterile 11, or Sterile 20 kinase), a tyrosine kinase (TK, e.g., a receptor tyrosine kinase (RTK), a non-receptor tyrosine kinase (nRTK)), and a tyrosine-kinase-like kinase (TKL, e.g., a mixed lineage kinase (MLK), RAF, a serine threonine kinase receptor (STKR), a leucine rich repeat kinase (LRRK), a LIM domain kinase (LIMK), a testis expressed serine kinase (TESK), an IL1 receptor associated kinase (IRAK), a receptor interacting protein kinase (RIPK)).

The term "CDK" refers to a cyclin-dependent kinase. The term "TAIRE family" kinase refers to a subfamily of CDK kinases.

CDKs are a family of protein serine or threonine kinases, where the activity of these kinases is based on association with a non-catalytic regulatory subunit called a cyclin. CDKs are involved in the control of the cell cycle. Examples of CDKs include, but are not limited to, CDK14, CDK15, CDK16, CDK17, or CDK18. The process of eukaryotic cell division may be broadly divided into a series of sequential phases termed G1, S, G2, and M. Correct progression through the various phases of the cell cycle has been shown to be critically dependent upon the spatial and temporal regulation of a family of proteins known as cyclin dependent kinases (CDKs) and a diverse set of their cognate protein partners termed cyclins. CDKs are CDC2 (also known as CDK1) homologous serine-threonine kinase proteins that are able to utilize ATP as a substrate in the phosphorylation of diverse polypeptides in a sequence-dependent context. Cyclins are a family of proteins characterized by a homology region, containing approximately 100 amino acids, termed the "cyclin box" which is used in binding to, and defining selectivity for, specific CDK partner proteins. Modulation of the expression levels, degradation rates, protein levels, and activity levels of various CDKs and cyclins throughout the cell cycle leads to the cyclical formation of a series of CDK/cyclin complexes, in which the CDKs are enzymatically active. The formation of these complexes controls passage through discrete cell cycle checkpoints and thereby enables the process of cell division to continue. Failure to satisfy the prerequisite biochemical criteria at a given cell cycle checkpoint, e.g., failure to form a required CDK/cyclin complex, can lead to cell cycle arrest and/or cellular apoptosis. Aberrant cellular proliferation can often be attributed to loss of correct cell cycle control. Inhibition of CDK enzymatic activity therefore provides a means by which abnormally dividing cells can have their division arrested and/or be killed. The diversity of CDKs, CDK complexes, and their critical roles in mediating the cell cycle, provides a broad spectrum of potential therapeutic targets selected on the basis of a defined biochemical rationale.

BRIEF DESCRIPTION OF THE DRAWINGS

FIGS. 3A to 3C show the chemical structure of exemplary CDK inhibitor FMF-04-159-2 (FIG. 3A), Kinativ profiling (FIG. 3B), and cellular pull-down assay +/− washout (FIG. 3C).

FIG. 4A shows the procedure and FIG. 4B shows the results.

DETAILED DESCRIPTION OF CERTAIN EMBODIMENTS OF THE INVENTION

Figure 1:
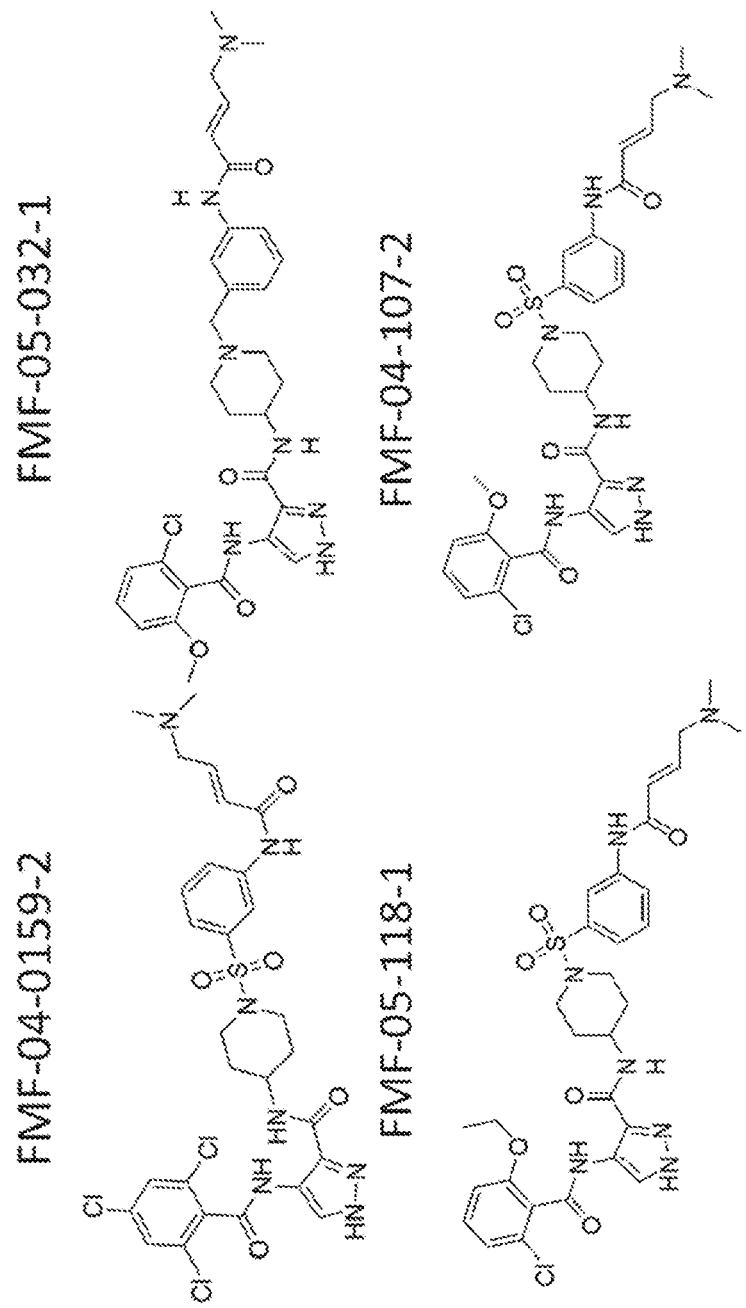
FIG. 1 shows a summary of select exemplary compounds.

The present disclosure provides selective inhibitors of CDKs (e.g., CDK14, CDK15, CDK16, CDK17, CDK18). In certain embodiments, the inventive compounds inhibit the activity of cyclin-dependent kinase 14 (CDK14). The present disclosure further provides methods of using the compounds described herein, e.g., as biological probes to study the inhibition of the activity of a kinase (e.g., CDK (e.g., CDK14, CDK15, CDK16, CDK17, CDK18)), and as therapeutics, e.g., in the treatment and/or prevention of diseases associated with the overexpression and/or aberrant activity of the kinase (e.g., CDK (e.g., CDK14, CDK15, CDK16, CDK17, CDK18)). In certain embodiments, the compounds covalently inhibit CDKs (e.g., CDK14). In certain embodiments, the diseases treated and/or prevented include, but are not limited to, proliferative diseases, metabolic disorders, autoimmune diseases, and neurological diseases. The proliferative diseases include, but are not limited to, cancer (e.g., lung cancer, breast cancer, liver cancer, pancreatic cancer, gastric cancer, ovarian cancer, colon cancer, colorectal cancer). In certain embodiments, the cancer is a carcinoma. The metabolic disorders include, but are not limited to, diabetes. The autoimmune diseases include, but are not limited to, systemic lupus erythematosis, rheumatoid arthritis, psoriatic arthritis, systemic lupus erythematosis, psoriasis, ulcerative colitis, and systemic sclerosis. The neurological diseases include, but are not limited to, Alzheimer's disease, gliosis, and spinal cord injury. In certain embodiments, the cancer is associated with the overexpression and/or aberrant activity of a kinase (e.g., CDK (e.g., CDK14, CDK15, CDK16, CDK17, CDK18)). In certain embodiments, the compounds described herein are used for male contraception (e.g., reducing or inhibiting spermatogenesis, or reducing the rate of male fertility) in a healthy fertile male subject. Also provided by the present disclosure are pharmaceutical compositions, kits, methods, and uses of a compound of Formula (I') or (I) as described herein.

Compounds

Certain aspects of the present disclosure relate to the compounds described herein. The compounds described herein may be useful in treating and/or preventing diseases (e.g., proliferative diseases (e.g., cancers), metabolic disorders (e.g., diabetes), autoimmune diseases, or neurological diseases (e.g., Alzheimer's disease, gliosis, spinal cord injury)) or diseases associated with the activity of a protein kinase (e.g., CDK) in a subject, or inhibiting the activity of a protein kinase (e.g., CDK) in a subject or biological sample. In certain embodiments, a compound described herein is a compound of Formula (I') or (I), or a pharmaceutically acceptable salt, solvate, hydrate, polymorph, co-crystal, tautomer, stereoisomer, isotopically labeled derivative, or prodrug thereof. In certain embodiments, a compound described herein is a compound of Formula (I') or (I), or a pharmaceutically acceptable salt thereof.

In certain embodiments, a compound described herein is of Formula (I'):

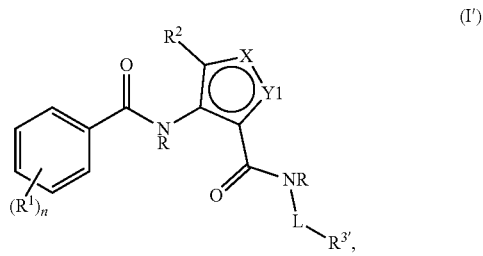

or a pharmaceutically acceptable salt, solvate, hydrate, tautomer, or stereoisomer thereof, wherein:

each instance of $R^1$ is independently selected from the group consisting of is halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, $-OR^{D1}$, $-N(R^{D1a})_2$ and $-SR^{D1}$, wherein $R^{D1}$ is independently selected from hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, and a sulfur protecting group when attached to a sulfur atom;

wherein each occurrence of $R^{D1a}$ is independently selected from the group consisting of hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, and a nitrogen protecting group; or optionally two instances of $R^{D1a}$ are taken together with their intervening atoms to form a substituted or unsubstituted heterocyclic or substituted or unsubstituted heteroaryl ring;

$R^2$ is hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, or optionally substituted heteroaryl;

each instance of R is independently selected from the group consisting of hydrogen, optionally substituted alkyl, and a nitrogen protecting group;

$R^x$ is selected from the group consisting of hydrogen, optionally substituted alkyl, and a nitrogen protecting group;

n is 0, 1, 2, 3, 4, or 5;

X is N, $-NR^x-$, S, or O, as valency permits;

Y1 is N, $-NR^x-$, S, or O, as valency permits;

L is an optionally substituted $C_{1-6}$ hydrocarbon chain, optionally wherein one or more carbon units of the hydrocarbon chain are independently replaced with $-C=O-$, $-O-$, $-S-$, $-S(=O)O-$, $-NR(C=O)-$, $-NR-$, optionally substituted carbocyclylene, optionally substituted heterocyclylene, optionally substituted arylene, or optionally substituted heteroarylene;

R³' is a warhead of formula:
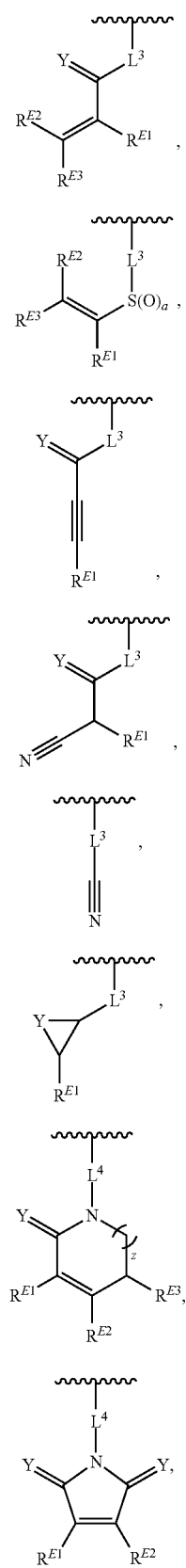
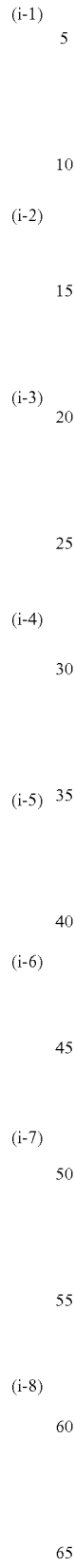
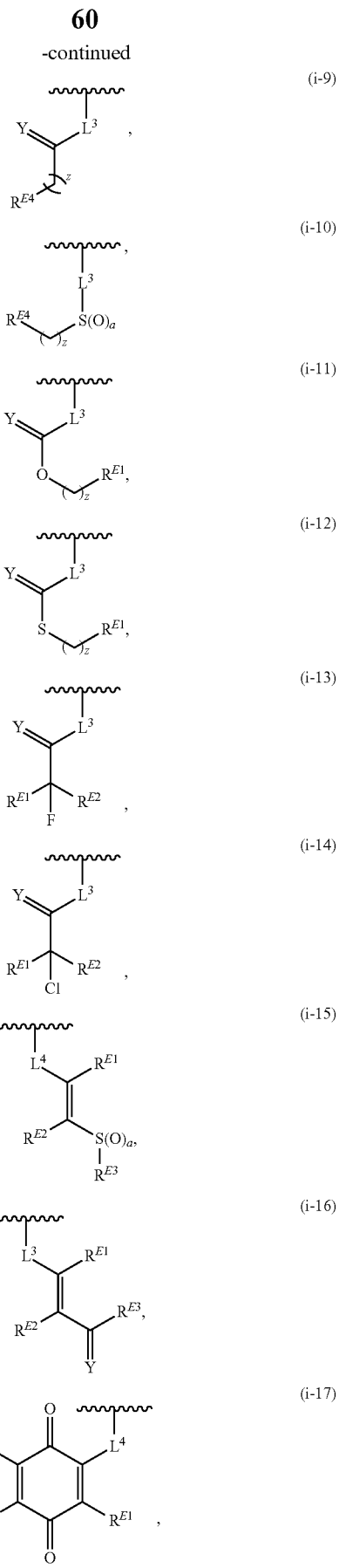

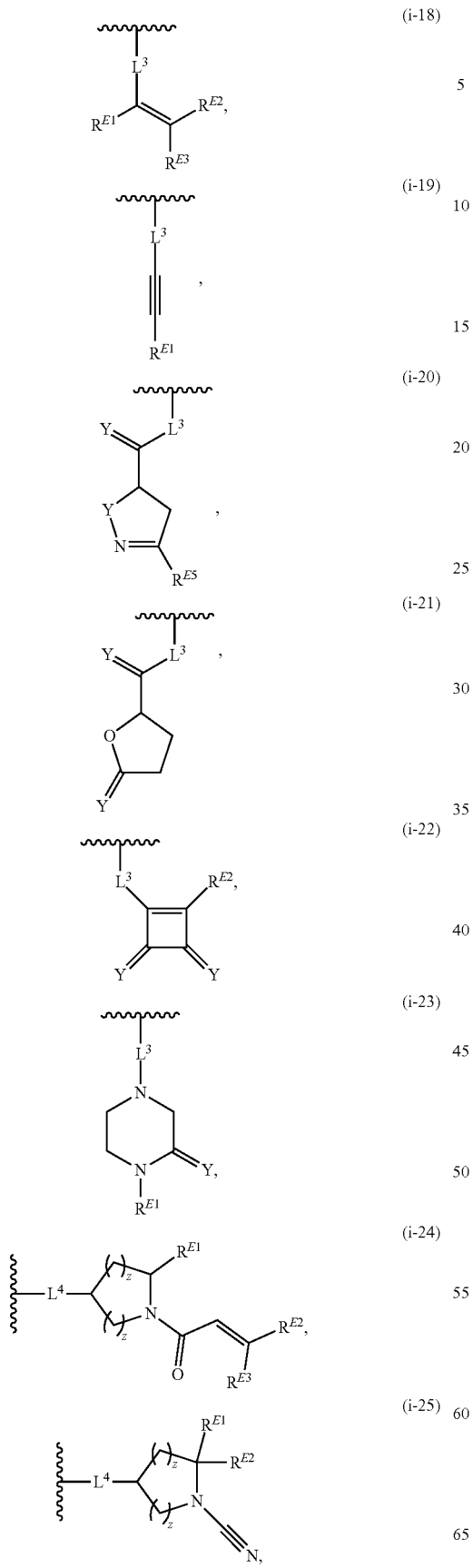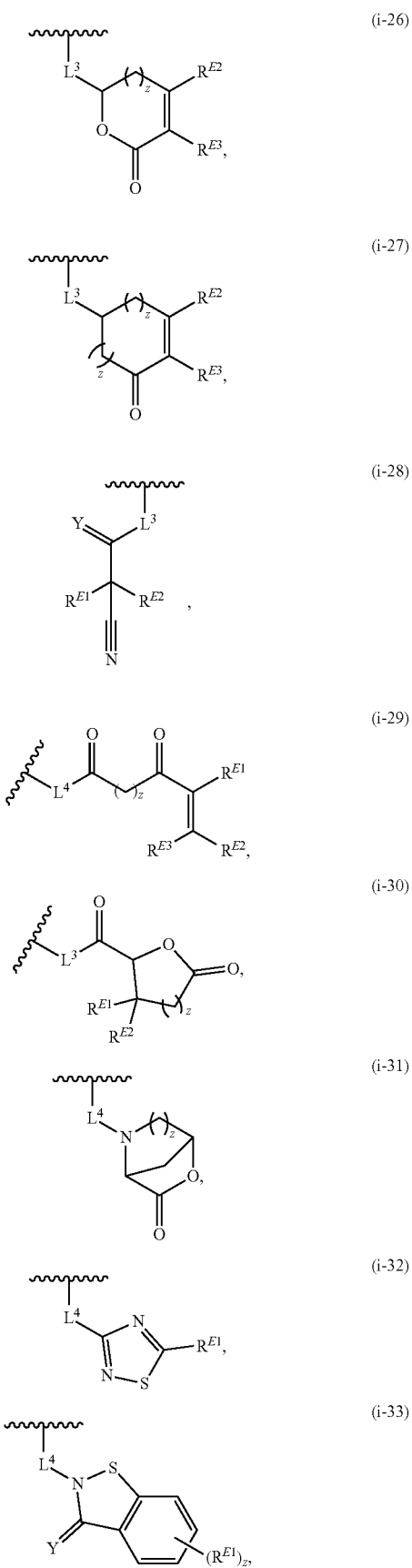

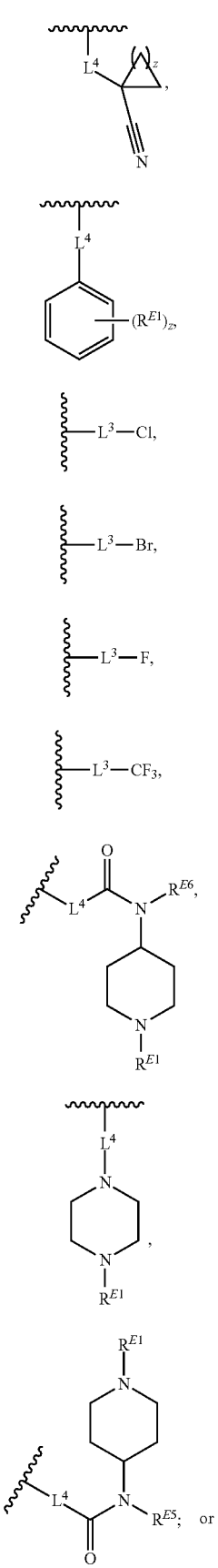
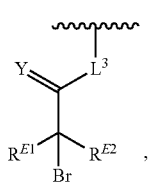

wherein:

L³ is a bond or an optionally substituted $C_{1-4}$ hydrocarbon chain, optionally wherein one or more carbon units of the hydrocarbon chain are independently replaced with —C(=O)—, —O—, —S—, —NR$^{L3a}$—, —NR$^{L3a}$C(=O)—, —C(=O)NR$^{L3a}$—, —SC(=O)—, —C(=O)S—, —OC(=O)—, —C(=O)O—, —NR$^{L3a}$C(=S)—, —C(=S)NR$^{L3a}$—, trans-CR$^{L3b}$=CR$^{L3b}$—, cis-CR$^{L3b}$=CR$^{L3b}$—, —C≡C—, —S(=O)—, —S(=O)O—, —OS(=O)—, —S(=O)NR$^{L3a}$—, —NR$^{L3a}$S(=O)—, —S(=O)$_2$—, —S(=O)$_2$O—, —OS(=O)$_2$—, —S(=O)$_2$NR$^{L3a}$—, or —NR$^{L3a}$S(=O)$_2$—, wherein R$^{L3a}$ is hydrogen, substituted or unsubstituted $C_{1-6}$ alkyl, or a nitrogen protecting group, and wherein each occurrence of R$^{L3b}$ is independently hydrogen, halogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two R$^{L3b}$ groups are joined to form an optionally substituted carbocyclic or optionally substituted heterocyclic ring;

L⁴ is a bond or an optionally substituted, branched or unbranched $C_{1-6}$ hydrocarbon chain;

each of R$^{E1}$, R$^{E2}$, and R$^{E3}$ is independently hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —CH$_2$OR$^{EE}$, —CH$_2$N(R$^{EE}$)$_2$, —CH$_2$SR$^{EE}$, —OR$^{EE}$, —N(R$^{EE}$)$_2$, —Si(R$^{EE}$)$_3$, or —SR$^{EE}$, wherein each instance of R$^{EE}$ is independently hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, or optionally substituted heteroaryl, or two R$^{EE}$ groups are joined to form an optionally substituted heterocyclic ring; or R$^{E1}$ and R$^{E3}$, or R$^{E2}$ and R$^{E3}$, or R$^{E1}$ and R$^{E2}$ are joined to form an optionally substituted carbocyclic or optionally substituted heterocyclic ring;

R$^{E4}$ is a leaving group;

R$^{E5}$ is halogen;

R$^{E6}$ is hydrogen, substituted or unsubstituted $C_{1-6}$ alkyl, or a nitrogen protecting group;

each instance of Y is independently O, S, or NR$^{E7}$, wherein R$^{E7}$ is hydrogen, substituted or unsubstituted $C_{1-6}$ alkyl, or a nitrogen protecting group;

a is 1 or 2; and each instance of z is independently 0, 1, 2, 3, 4, 5, or 6, as valency permits.

In certain embodiments, the compound of Formula (I') is of Formula (I).

In certain embodiments, a compound described herein is of Formula (I):

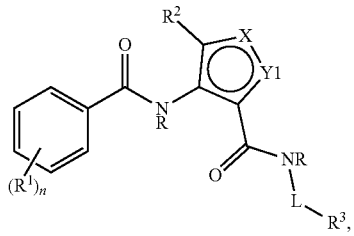

(I)

or a pharmaceutically acceptable salt, solvate, hydrate, tautomer, or stereoisomer thereof, wherein:
- each instance of each instance of $R^1$ is independently selected from the group consisting of halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, $-OR^{D1}$, $-N(R^{D1a})_2$ and $-SR^{D1}$, wherein $R^{D1}$ is independently selected from hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, and a sulfur protecting group when attached to a sulfur atom;
- wherein each occurrence of $R^{D1a}$ is independently selected from the group consisting of hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, and a nitrogen protecting group; or optionally two instances of $R^{D1a}$ are taken together with their intervening atoms to form a substituted or unsubstituted heterocyclic or substituted or unsubstituted heteroaryl ring;
- $R^2$ is hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, or optionally substituted heteroaryl;
- each instance of R is independently selected from the group consisting of hydrogen, optionally substituted alkyl, and a nitrogen protecting group;
- $R^x$ is selected from the group consisting of hydrogen, optionally substituted alkyl, and a nitrogen protecting group;
- n is 0, 1, 2, 3, 4, or 5;
- X is N, $-NR^x-$, S, or O, as valency permits;
- Y1 is N, $-NR^x-$, S, or O, as valency permits;
- L is an optionally substituted $C_{1-6}$ hydrocarbon chain, optionally wherein one or more carbon units of the hydrocarbon chain are independently replaced with $-C=O-$, $-O-$, $-S-$, $-S(=O)O-$, $-NR(C=O)-$, $-NR-$, optionally substituted carbocyclylene, optionally substituted heterocyclylene, optionally substituted arylene, or optionally substituted heteroarylene;

$R^3$ is a warhead of formula:

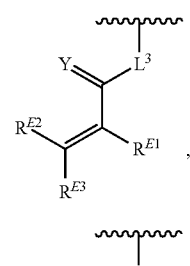

(i-1)

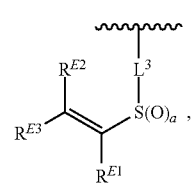

(i-2)

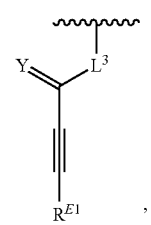

(i-3)

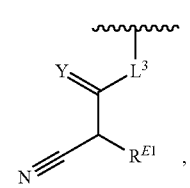

(i-4)

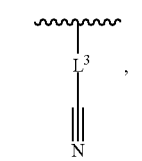

(i-5)

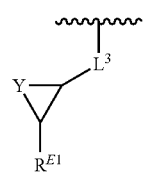

(i-6)

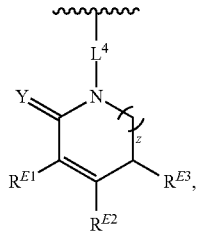

(i-7)

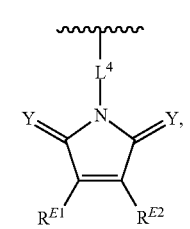

(i-8)

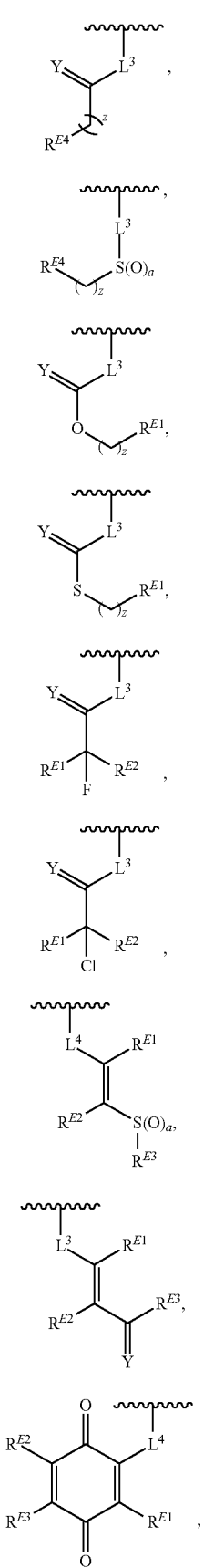
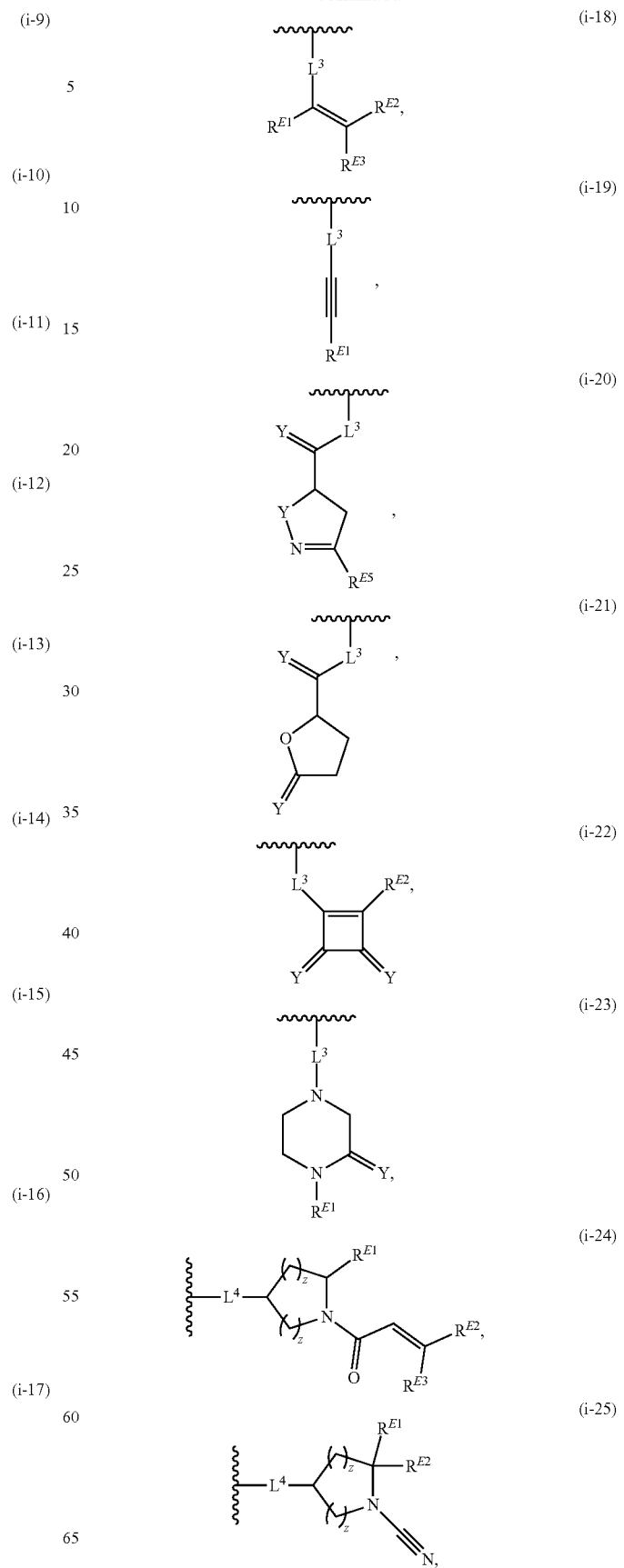

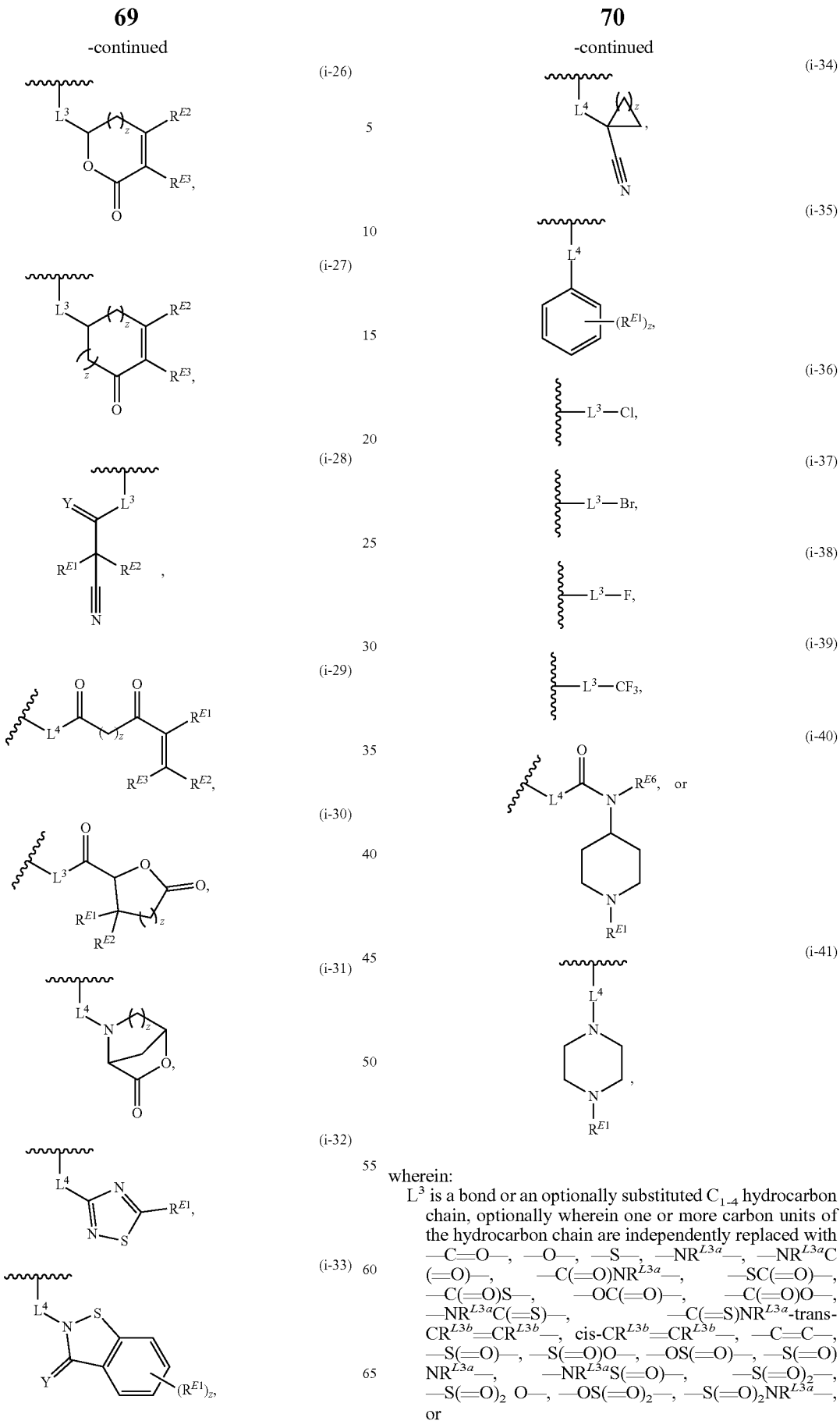

wherein:
L³ is a bond or an optionally substituted $C_{1-4}$ hydrocarbon chain, optionally wherein one or more carbon units of the hydrocarbon chain are independently replaced with —C=O—, —O—, —S—, —NR$^{L3a}$—, —NR$^{L3a}$C(=O)—, —C(=O)NR$^{L3a}$—, —SC(=O)—, —C(=O)S—, —OC(=O)—, —C(=O)O—, —NR$^{L3a}$C(=S)—, —C(=S)NR$^{L3a}$-trans-CR$^{L3b}$=CR$^{L3b}$—, cis-CR$^{L3b}$=CR$^{L3b}$—, —C≡C—, —S(=O)—, —S(=O)O—, —OS(=O)—, —S(=O)NR$^{L3a}$—, —NR$^{L3a}$S(=O)—, —S(=O)$_2$—, —S(=O)$_2$O—, —OS(=O)$_2$—, —S(=O)$_2$NR$^{L3a}$—, or —NR$^{L3a}$S(=O)$_2$—, wherein R$^{L3a}$ is hydrogen, substituted or unsubstituted C$_{1-6}$ alkyl, or a nitrogen protecting group, and wherein each occurrence of R$^{L3b}$ is independently hydrogen, halogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two R$^{L3b}$ groups are joined to form an optionally substituted carbocyclic or optionally substituted heterocyclic ring;

L$^4$ is a bond or an optionally substituted, branched or unbranched C$_{1-6}$ hydrocarbon chain;

each of R$^{E1}$, R$^{E2}$, and R$^{E3}$ is independently hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —CH$_2$OR$^{EE}$, —CH$_2$N(R$^{EE}$)$_2$, —CH$_2$SR$^{EE}$, —OR$^{EE}$, —N(R$^E$E)$_2$, —Si(R$^E$E)$_3$, or —SR$^{EE}$, wherein each instance of R$^{EE}$ is independently hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, or optionally substituted heteroaryl, or two R$^{EE}$ groups are joined to form an optionally substituted heterocyclic ring; or R$^{E1}$ and R$^{E3}$, or R$^{E2}$ and R$^{E3}$, or R$^{E1}$ and R$^{E2}$ are joined to form an optionally substituted carbocyclic or optionally substituted heterocyclic ring;

R$^{E4}$ is a leaving group;

R$^{E5}$ is halogen;

R$^{E6}$ is hydrogen, substituted or unsubstituted C$_{1-6}$ alkyl, or a nitrogen protecting group;

each instance of Y is independently O, S, or NR$^{E7}$, wherein R$^{E7}$ is hydrogen, substituted or unsubstituted C$_{1-6}$ alkyl, or a nitrogen protecting group;

a is 1 or 2; and each instance of z is independently 0, 1, 2, 3, 4, 5, or 6, as valency permits.

In certain embodiments, Formula (I') includes no instances of substituent R$^1$. In certain embodiments, Formula (I') includes one or more instances of substituent R$^1$. In certain embodiments, Formula (I) includes no instances of substituent R$^1$. In certain embodiments, Formula (I) includes one or more instances of substituent R$^1$. In certain embodiments, n is 0. In certain embodiments, n is 1. In certain embodiments, n is 2. In certain embodiments, n is 3. In certain embodiments, n is 4. In certain embodiments, n is 5. In certain embodiments, at least one instance of R$^1$ is halogen (e.g., F, Cl, Br, or I). In certain embodiments, at least one instance of R$^1$ is optionally substituted acyl (e.g., —C(=O)Me). In certain embodiments, at least one instance of R$^1$ is optionally substituted alkyl (e.g., substituted or unsubstituted C$_{1-6}$ alkyl). In certain embodiments, at least one instance of R$^1$ is substituted or unsubstituted methyl. In certain embodiments, at least one instance of R$^1$ is substituted or unsubstituted ethyl. In certain embodiments, at least one instance of R$^1$ is substituted or unsubstituted propyl. In certain embodiments, at least one instance of R$^1$ is optionally substituted alkenyl (e.g., substituted or unsubstituted C$_{2-6}$ alkenyl). In certain embodiments, at least one instance of R$^1$ is optionally substituted alkynyl (e.g., substituted or unsubstituted C$_{2-6}$ alkynyl). In certain embodiments, at least one instance of R$^1$ is optionally substituted carbocyclyl (e.g., substituted or unsubstituted, 3- to 7-membered, monocyclic carbocyclyl comprising zero, one, or two double bonds in the carbocyclic ring system). In certain embodiments, at least one instance of R$^1$ is optionally substituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, at least one instance of R$^1$ is optionally substituted aryl (e.g., substituted or unsubstituted, 6- to 10-membered aryl). In certain embodiments, at least one instance of R$^1$ is benzyl. In certain embodiments, at least one instance of R$^1$ is substituted or unsubstituted phenyl. In certain embodiments, at least one instance of R$^1$ is optionally substituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, at least one instance of R$^1$ is —OR$^{D1}$ (e.g., —OH or —OMe). In certain embodiments, at least one instance of R$^1$ is —N(R$^{D1a}$)$_2$ (e.g., —NMe$_2$). In certain embodiments, at least one instance of R$^1$ is —SR$^{D1}$ (e.g., —SMe). In certain embodiments, at least one instance of R$^1$ is halogen or —OR$^{D1}$; and R$^{D1}$ is independently selected from hydrogen or optionally substituted alkyl. In certain embodiments, at least one instance of R$^1$ is —Cl or —F. In certain embodiments, at least one instance of R$^1$ is —OMe or —OEt. In certain embodiments, at least one instance of R$^1$ is —C$_1$ or —F; and at least one instance of R$^1$ is —OMe or —OEt. In certain embodiments, n is 2; and both instances of R$^1$ are —Cl. In certain embodiments, n is 2; and both instances of R$^1$ are —F.

In certain embodiments, at least one instance of R$^1$ is —OR$^{D1}$, —N(R$^{D1a}$)$_2$ or —SR$^{D1}$, and R$^{D1}$ is as defined herein. In certain embodiments, R$^{D1}$ is hydrogen. In certain embodiments, R$^{D1}$ is substituted or unsubstituted acyl (e.g., —C(=O)Me). In certain embodiments, R$^{D1}$ is substituted or unsubstituted alkyl (e.g., substituted or unsubstituted C$_{1-6}$ alkyl). In certain embodiments, R$^{D1}$ is substituted or unsubstituted methyl. In certain embodiments, R$^{D1}$ is substituted or unsubstituted ethyl. In certain embodiments, R$^{D1}$ is substituted or unsubstituted propyl. In certain embodiments, R$^{D1}$ is substituted or unsubstituted alkenyl (e.g., substituted or unsubstituted C$_{2-6}$ alkenyl). In certain embodiments, R$^{D1}$ is substituted or unsubstituted alkynyl (e.g., substituted or unsubstituted C$_{2-6}$ alkynyl). In certain embodiments, R$^{D1}$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, R$^{D1}$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, R$^{D1}$ is substituted or unsubstituted aryl (e.g., substituted or unsubstituted, 6- to 10-membered aryl). In certain embodiments, R$^{D1}$ is benzyl. In certain embodiments, R$^{D1}$ is substituted or unsubstituted phenyl. In certain embodiments, R$^{D1}$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, R$^{D1}$ is an oxygen protecting group when attached to an oxygen atom.

In certain embodiments, $R^{D1}$ is a sulfur protecting group when attached to a sulfur atom.

In certain embodiments, at least one instance of $R^{D1a}$ is hydrogen. In certain embodiments, at least one instance of $R^{D1a}$ is substituted or unsubstituted acyl (e.g., —C(=O)Me). In certain embodiments, at least one $R^{D1a}$ is substituted or unsubstituted alkyl (e.g., substituted or unsubstituted $C_{1-6}$ alkyl). In certain embodiments, at least one instance of $R^{D1a}$ is substituted or unsubstituted methyl. In certain embodiments, at least one instance of $R^{D1a}$ is substituted or unsubstituted ethyl. In certain embodiments, at least one instance of $R^{D1a}$ is substituted or unsubstituted propyl. In certain embodiments, at least one instance of $R^{D1}$a is substituted or unsubstituted alkenyl (e.g., substituted or unsubstituted $C_{2-6}$ alkenyl). In certain embodiments, at least one instance of $R^{D1}$a is substituted or unsubstituted alkynyl (e.g., substituted or unsubstituted $C_{2-6}$ alkynyl). In certain embodiments, at least one instance of $R^{D1}$a is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, at least one instance of $R^{D1a}$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, at least one instance of $R^{D}$a is substituted or unsubstituted aryl (e.g., substituted or unsubstituted, 6- to 10-membered aryl). In certain embodiments, at least one instance of $R^{D1a}$ is benzyl. In certain embodiments, at least one instance of $R^{D1a}$ is substituted or unsubstituted phenyl. In certain embodiments, at least one instance of $R^{D1a}$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, at least one instance of $R^{D1a}$ is a nitrogen protecting group (e.g., benzyl (Bn), t-butyl carbonate (BOC or Boc), benzyl carbamate (Cbz), 9-fluorenylmethyl carbonate (Fmoc), trifluoroacetyl, triphenylmethyl, acetyl, or p-toluenesulfonamide (Ts)). In certain embodiments, two instances of $R^{D1a}$ are taken together with their intervening atoms to form a substituted or unsubstituted heterocyclic ring (e.g., substituted or unsubstituted, 5- to 10-membered monocyclic or bicyclic heterocyclic ring, wherein one or two atoms in the heterocyclic ring are independently nitrogen, oxygen, or sulfur) or substituted or unsubstituted heteroaryl ring (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9-to 10-membered, bicyclic heteroaryl, wherein one, two, three, or four atoms in the heteroaryl ring system are independently nitrogen, oxygen, or sulfur).

In certain embodiments, the moiety

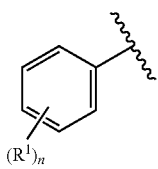

is of the formula:

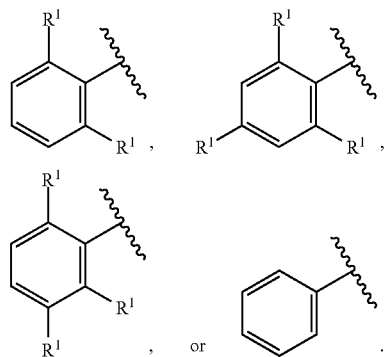

In certain embodiments, the moiety

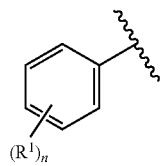

is of the formula:

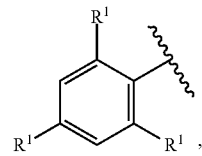

wherein $R^1$ is optionally substituted alkyl, halogen, or —$OR^{D1}$ wherein $R^{D1}$ is optionally substituted alkyl. In certain embodiments, the moiety

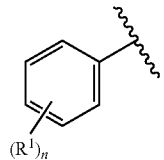

is of the formula:

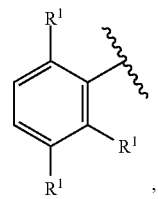

wherein $R^1$ is optionally substituted alkyl, halogen, or —ORD1 wherein $R^{D1}$ is optionally substituted alkyl.

In certain embodiments, the moiety

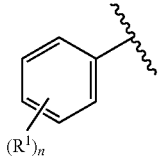

is of the formula:

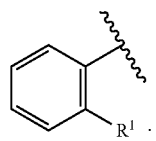

In certain embodiments, the moiety

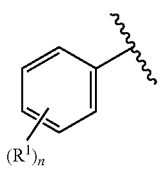

is of the formula:

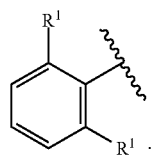

In certain embodiments, the moiety

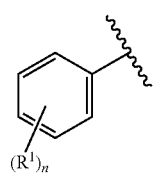

is of the formula:

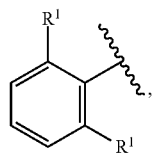

wherein $R^1$ is optionally substituted alkyl, halogen, or —$OR^{D1}$, wherein $R^{D1}$ is optionally substituted alkyl. In certain embodiments, the moiety

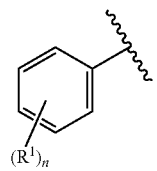

is of the formula:

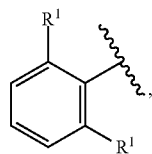

wherein both instances of $R^1$ are halogen. In certain embodiments, the moiety

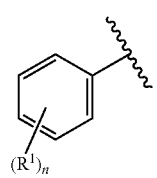

is of the formula:

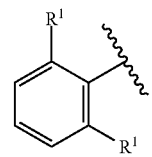

wherein one instance of $R^1$ is halogen and the other instance of $R^1$ is —$OR^{D1}$, wherein $R^{D1}$ is optionally substituted alkyl.

In certain embodiments, the moiety

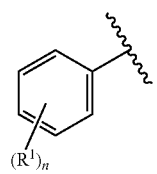

is of the formula:

-continued

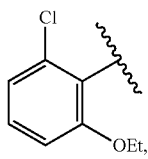 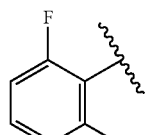 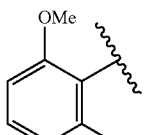

In certain embodiments, the moiety

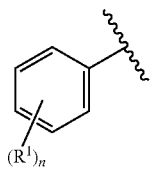

is of the formula:

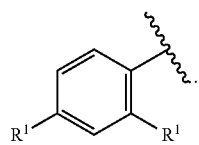

In certain embodiments, the moiety

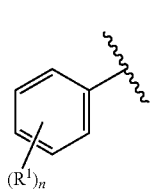

is of the formula:

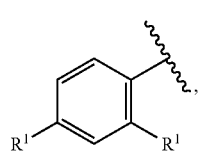

wherein $R^1$ is optionally substituted alkyl, halogen, or $-OR^{D1}$, wherein $R^{D1}$ is optionally substituted alkyl. In certain embodiments, the moiety

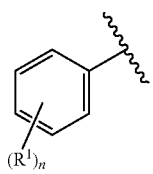

is of the formula:

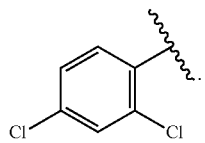 [SMILES: *c1ccc(Cl)cc1Cl]

In certain embodiments, the moiety

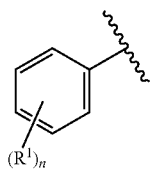

is of the formula:

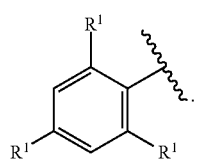

In certain embodiments, the moiety

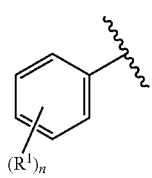

is of the formula:

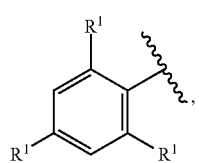

wherein $R^1$ is optionally substituted alkyl, halogen, or $-OR^{D1}$, wherein $R^{D1}$ is optionally substituted alkyl. In certain embodiments, the moiety

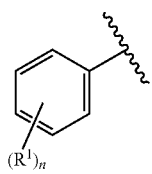

is of the formula:

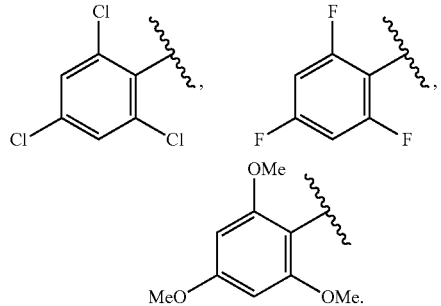

In certain embodiments, the moiety

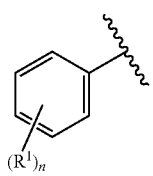

is of the formula:

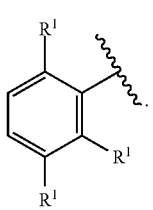

In certain embodiments, the moiety

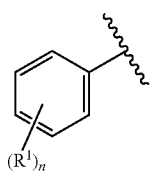

is of the formula:

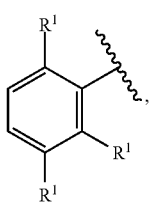

wherein $R^1$ is optionally substituted alkyl, halogen, or —$OR^{D1}$, wherein $R^{D1}$ is optionally substituted alkyl. In certain embodiments, the moiety

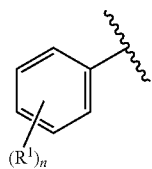

is of the formula:

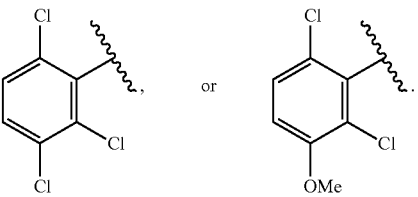 [SMILES: *c1c(Cl)ccc(Cl)c1Cl ; *c1c(Cl)ccc(OC)c1Cl]

In certain embodiments, the moiety

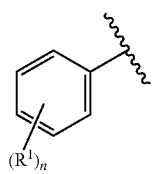

is of the formula:

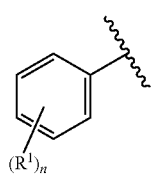

In certain embodiments, the moiety is of the formula:

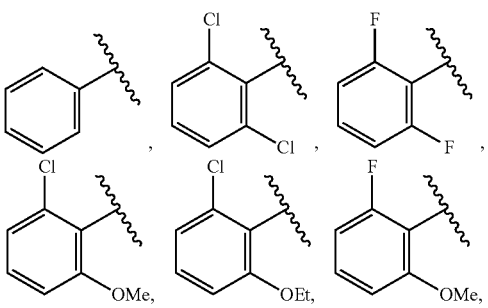

-continued

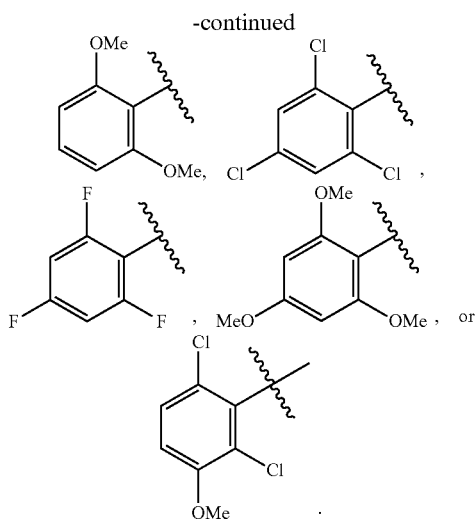

Formula (I') includes substituent $R^2$. Formula (I) includes substituent $R^2$. In certain embodiments, $R^2$ is hydrogen. In certain embodiments, $R^2$ is halogen (e.g., F, Cl, Br, or I). In certain embodiments, $R^2$ is optionally substituted acyl (e.g., —C(═O)Me). In certain embodiments, $R^2$ is optionally substituted alkyl (e.g., substituted or unsubstituted $C_{1-6}$ alkyl). In certain embodiments, $R^2$ is substituted or unsubstituted methyl. In certain embodiments, $R^2$ is substituted or unsubstituted ethyl. In certain embodiments, $R^2$ is unsubstituted ethyl. In certain embodiments, $R^2$ is substituted or unsubstituted propyl. In certain embodiments, $R^2$ is unsubstituted n-propyl. In certain embodiments, $R^2$ is unsubstituted methyl or isopropyl. In certain embodiments, $R^2$ is optionally substituted alkenyl (e.g., substituted or unsubstituted $C_{2-6}$ alkenyl). In certain embodiments, $R^2$ is optionally substituted alkynyl (e.g., substituted or unsubstituted $C_{2-6}$ alkynyl). In certain embodiments, $R^2$ is optionally substituted carbocyclyl (e.g., substituted or unsubstituted, 3- to 7-membered, monocyclic carbocyclyl comprising zero, one, or two double bonds in the carbocyclic ring system). In certain embodiments, $R^2$ is optionally substituted heterocyclyl (e.g., substituted or unsubstituted, 5-to 10-membered monocyclic or bicyclic heterocyclic ring, wherein one or two atoms in the heterocyclic ring are independently nitrogen, oxygen, or sulfur). In certain embodiments, $R^2$ is optionally substituted aryl (e.g., substituted or unsubstituted, 6- to 10-membered aryl). In certain embodiments, $R^2$ is benzyl. In certain embodiments, $R^2$ is substituted or unsubstituted phenyl. In certain embodiments, $R^2$ is unsubstituted phenyl. In certain embodiments, $R^2$ is optionally substituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, $R^2$ is optionally substituted $C_{1-6}$ alkyl or optionally substituted aryl.

Formula (I') includes two instances of substituent R. Formula (I) includes two instances of substituent R. In certain embodiments, both instances of R are the same. In certain embodiments, each instance of R is different. In certain embodiments, at least one instance of R is hydrogen. In certain embodiments, both instances of R are hydrogen. In certain embodiments, at least one instance of R is optionally substituted alkyl. In certain embodiments, at least one instance of R is substituted or unsubstituted alkyl (e.g., substituted or unsubstituted $C_{1-6}$ alkyl). In certain embodiments, at least one instance of R is substituted or unsubstituted methyl. In certain embodiments, at least one instance of R is substituted or unsubstituted ethyl. In certain embodiments, at least one instance of R is substituted or unsubstituted propyl. In certain embodiments, at least one instance of R is a nitrogen protecting group (e.g., benzyl (Bn), t-butyl carbonate (BOC or Boc), benzyl carbamate (Cbz), 9-fluorenylmethyl carbonate (Fmoc), trifluoroacetyl, triphenylmethyl, acetyl, or p-toluenesulfonamide (Ts)). In certain embodiments, n is 2, and both instances of R are hydrogen. In certain embodiments, one instance of R is hydrogen; and the other instance of R is substituted or unsubstituted alkyl (e.g., substituted or unsubstituted $C_{1-6}$alkyl). In certain embodiments, the moiety:

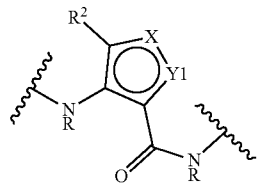

is of the formula:

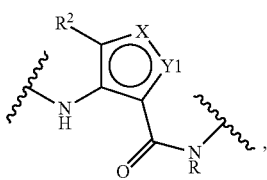

wherein R is substituted or unsubstituted alkyl. In certain embodiments, the moiety:

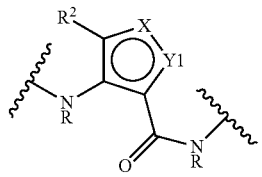

is of the formula:

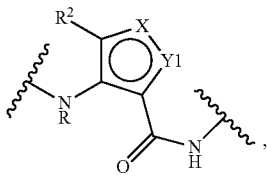

wherein R is substituted or unsubstituted alkyl.

Formula (I') includes substituent X. Formula (I) includes substituent X. In certain embodiments, X is N, —NR$^x$, S, or O, as valency permits; wherein R$^x$ is selected from the group consisting of hydrogen, optionally substituted alkyl, and a nitrogen protecting group. In certain embodiments, R$^x$ is hydrogen. In certain embodiments, R<sup>x</sup> is optionally substituted alkyl. In certain embodiments, R<sup>x</sup> is substituted or unsubstituted alkyl (e.g., substituted or unsubstituted $C_{1-6}$ alkyl). In certain embodiments, R<sup>x</sup> is substituted or unsubstituted methyl. In certain embodiments, R<sup>x</sup> is substituted or unsubstituted ethyl. In certain embodiments, R<sup>x</sup> is substituted or unsubstituted propyl. In certain embodiments, R<sup>x</sup> is a nitrogen protecting group (e.g., benzyl (Bn), t-butyl carbonate (BOC or Boc), benzyl carbamate (Cbz), 9-fluorenylmethyl carbonate (Fmoc), trifluoroacetyl, triphenylmethyl, acetyl, or p-toluenesulfonamide (Ts)). In certain embodiments, X is —N—. In certain embodiments, X is —NR<sup>x</sup>—. In certain embodiments, X is —NH—. In certain embodiments, X is —N(substituted or unsubstituted alkyl)-(e.g., —N(substituted or unsubstituted $C_{1-6}$ alkyl)-). In certain embodiments, X is —N(nitrogen protecting group)-. In certain embodiments, X is S. In certain embodiments, X is O.

Formula (I') includes substituent Y1. Formula (I) includes substituent Y1. In certain embodiments, Y1 is N, —NR<sup>x</sup>, S, or O, as valency permits; wherein R<sup>x</sup> is selected from the group consisting of hydrogen, optionally substituted alkyl, and a nitrogen protecting group. In certain embodiments, Y1 is —N—. In certain embodiments, Y1 is —NR<sup>x</sup>. In certain embodiments, Y1 is —NH—. In certain embodiments, Y1 is —N(substituted or unsubstituted alkyl)-(e.g., —N(substituted or unsubstituted $C_{1-6}$ alkyl)-). In certain embodiments, Y1 is —N(nitrogen protecting group)-. In certain embodiments, Y1 is S. In certain embodiments, Y1 is O. In certain embodiments, one of X and Y1 is N, and the other one is —NR<sup>x</sup>— (e.g., —NH— or —N(substituted or unsubstituted alkyl)-(e.g., —N(substituted or unsubstituted $C_{1-6}$ alkyl-). In certain embodiments, one of X and Y1 is S, and the other one is —N—.

In certain embodiments,

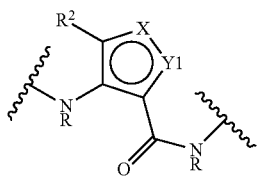

is of the formula:

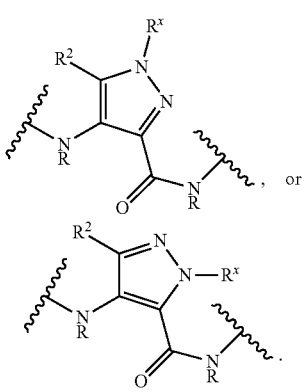

In certain embodiments,

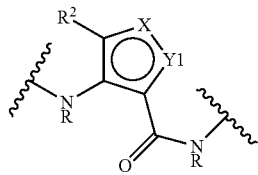

is of the formula:

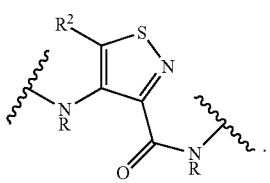

In certain embodiments,

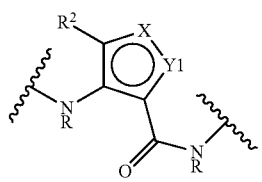

is of the formula:

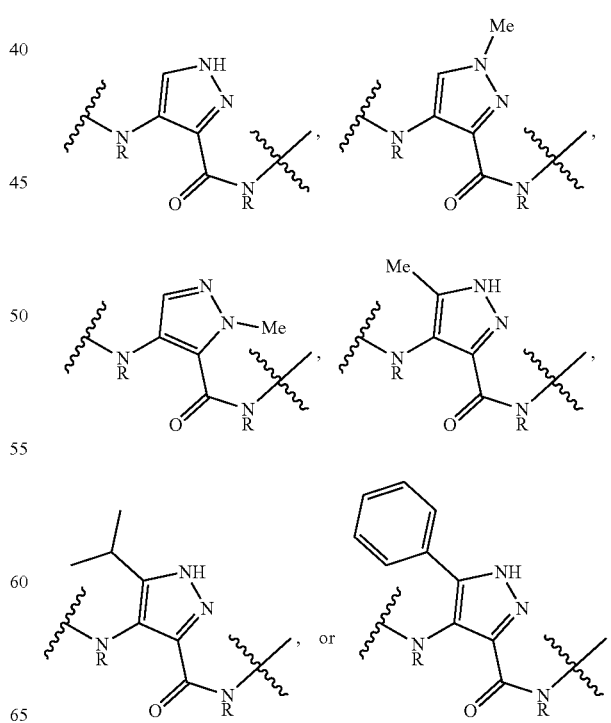

In certain embodiments,

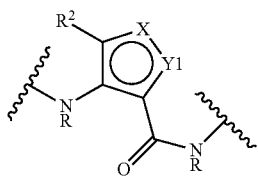

is of the formula:

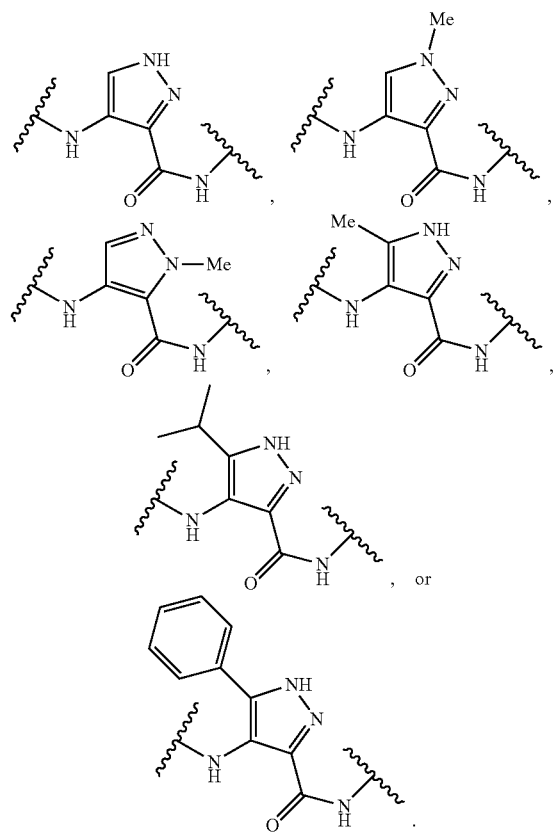

In certain embodiments,

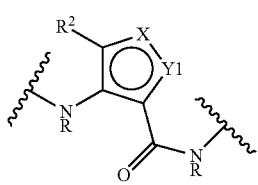

is of the formula:

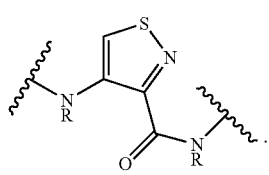

In certain embodiments,

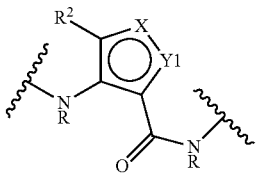

is of the formula:

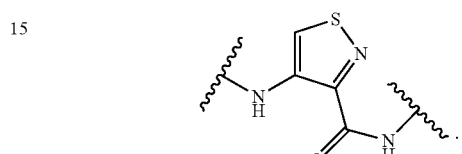

Formula (I') includes linker L. Formula (I) includes linker L. In certain embodiments, L is an optionally substituted $C_{1-6}$ hydrocarbon chain, optionally wherein one or more carbon units of the hydrocarbon chain are independently replaced with —C=O—, —O—, —S—, —S(=O)O—, —NR(C=O)—, —NR—, optionally substituted carbocyclylene, optionally substituted heterocyclylene, optionally substituted arylene, or optionally substituted heteroarylene, and wherein each instance of R is independently selected from the group consisting of hydrogen, optionally substituted alkyl, and nitrogen protecting groups.

In certain embodiments, L comprises up to 20 atoms, excluding hydrogen atoms and substituents. In certain embodiments, L comprises up to 14 atoms, excluding hydrogen atoms and substituents. In certain embodiments, L comprises up to 15 atoms, excluding hydrogen atoms and substituents. In certain embodiments, L comprises up to 12 atoms, excluding hydrogen atoms and substituents. In certain embodiments, L comprises up to 10 atoms, excluding hydrogen atoms and substituents. In certain embodiments, L comprises up to 9 atoms excluding hydrogen atoms and substituents. In certain embodiments, L comprises up to 6 atoms excluding hydrogen atoms and substituents. In certain embodiments, L comprises up to 5 atoms excluding hydrogen atoms and substituents. In certain embodiments, L comprises up to 3 atoms excluding hydrogen atoms and substituents.

In certain embodiments, any of the atoms in L can be substituted. In certain embodiments, none of the atoms in the linker L are substituted. In certain embodiments, none of the carbon atoms in the linker are substituted.

In certain embodiments, one or more carbon units of the hydrocarbon chain are independently replaced with at least one instance of —C=O—. In certain embodiments, one or more carbon units of the hydrocarbon chain are independently replaced with at least one instance of —O—. In certain embodiments, one or more carbon units of the hydrocarbon chain are independently replaced with at least one instance of —S—. In certain embodiments, one or more carbon units of the hydrocarbon chain are independently replaced with at least one instance of —S(=O)O—. In certain embodiments, one or more carbon units of the hydrocarbon chain are independently replaced with at least one instance of —NR(C=O)—, wherein R is hydrogen, optionally substituted alkyl, or a nitrogen protecting group. In certain embodiments, one or more carbon units of the hydrocarbon chain are independently replaced with at least one instance of —NR(C═O)—, wherein R is hydrogen or optionally substituted alkyl. In certain embodiments, one or more carbon units of the hydrocarbon chain are independently replaced with at least one instance of —NR—, wherein R is hydrogen, optionally substituted alkyl, or a nitrogen protecting group. In certain embodiments, one or more carbon units of the hydrocarbon chain are independently replaced with at least one instance of —NR—, wherein R is hydrogen or optionally substituted alkyl. In certain embodiments, one or more carbon units of the hydrocarbon chain are independently replaced with at least one instance of optionally substituted carbocyclylene. In certain embodiments, one or more carbon units of the hydrocarbon chain are independently replaced with at least one instance of optionally substituted heterocyclylene. In certain embodiments, one or more carbon units of the hydrocarbon chain are independently replaced with at least one instance of optionally substituted arylene. In certain embodiments, one or more carbon units of the hydrocarbon chain are independently replaced with at least one instance of optionally substituted heteroarylene.

In certain embodiments, L is optionally substituted carbocyclylene, optionally substituted heterocyclylene, optionally substituted arylene, or optionally substituted heteroarylene. In certain embodiments, L is optionally substituted carbocyclylene (e.g., substituted or unsubstituted, 3- to 7-membered, monocyclic carbocyclylene comprising zero, one, or two double bonds in the carbocyclic ring system). In certain embodiments, L is optionally substituted heterocyclylene (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, L is optionally substituted piperidinylene. In certain embodiments, L is optionally substituted piperazinylene. In certain embodiments, L is optionally substituted morpholinylene. In certain embodiments, L is optionally substituted arylene (e.g., substituted or unsubstituted, 6- to 10-membered aryl). In certain embodiments, L is optionally substituted benzylene. In certain embodiments, L is substituted benzylene. In certain embodiments, L is unsubstituted benzylene. In certain embodiments, L is substituted or unsubstituted phenylene. In certain embodiments, L is unsubstituted phenylene. In certain embodiments, L is optionally substituted heteroarylene (e.g., substituted or unsubstituted, 5- to 6-membered, monocyclic heteroarylene, wherein one, two, three, or four atoms in the heteroaryl ring system are independently nitrogen, oxygen, or sulfur; or substituted or unsubstituted, 9- to 10-membered, bicyclic heteroarylene, wherein one, two, three, or four atoms in the heteroaryl ring system are independently nitrogen, oxygen, or sulfur). In certain embodiments, L is optionally substituted 6-membered heterocyclylene or optionally substituted arylene. In certain embodiments, L is optionally substituted piperidinylene or optionally substituted phenylene.

In certain embodiments, L is of the formula:

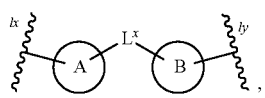

wherein:
Ring A is optionally substituted heterocyclyl, optionally substituted aryl, or optionally substituted heteroaryl;

Ring B is optionally substituted heterocyclyl, or optionally substituted aryl;
LX is a bond, —CH$_2$—, —C(═O)—, —S(═O)$_2$, or —NH(C═O)—; and
1× indicates the point of attachment to —NR— and ly indicates the point of attachment to R$^3$.

In certain embodiments, Ring A is optionally substituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, Ring A is optionally substituted aryl (e.g., substituted or unsubstituted, 6- to 10-membered aryl). In certain embodiments, Ring A is optionally substituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur).

In certain embodiments, Ring B is optionally substituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, Ring B is optionally substituted aryl (e.g., substituted or unsubstituted, 6- to 10-membered aryl). In certain embodiments, LX is a bond. In certain embodiments, LX is —CH$_2$—. In certain embodiments, LX is —C(═O)—. In certain embodiments, LX is —S(═O)$_2$. In certain embodiments, LX is —NH(C═O)—. In certain embodiments, one of Ring A and Ring B is optionally substituted heterocyclyl and the other one is optionally substituted aryl. In certain embodiments, one of Ring A and Ring B is optionally substituted heterocyclyl containing one nitrogen atom and the other one is optionally substituted phenyl. In certain embodiments, one of Ring A and Ring B is optionally substituted piperidinyl containing one nitrogen atom and the other one is optionally substituted phenyl. In certain embodiments, one of Ring A and Ring B is optionally substituted pyrrolidinyl containing one nitrogen atom and the other one is optionally substituted phenyl. In certain embodiments, L is of the formula:

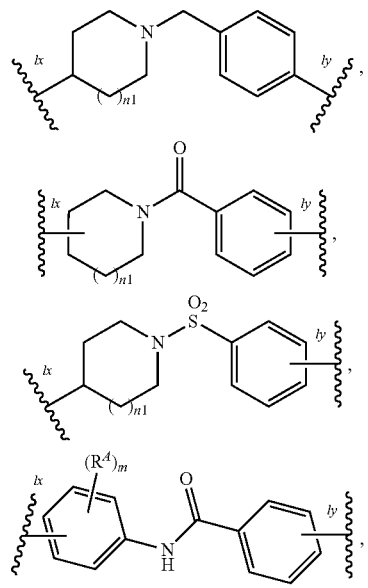

-continued

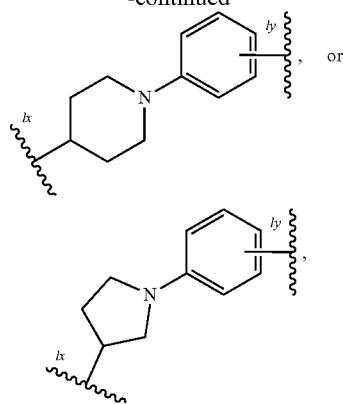

wherein R$^A$ is halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^{D1}$, —N(R$^{D1a}$)$_2$, or —SR$^{D1}$; n1 is 0 or 1; and m is 0, 1, 2, 3, or 4. lx indicates the point of attachment to —NR— and ly indicates the point of attachment to R$^3$.

In certain embodiments, at least one instance of R$^A$ is halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^D$, —N(R$^{D1a}$)$_2$ or —SR$^{D1}$. In certain embodiments, n1 is 0. In certain embodiments, n1 is 1. In certain embodiments, m is 0. In certain embodiments, m is 1. In certain embodiments, m is 2. In certain embodiments, m is 3. In certain embodiments, m is 4. In certain embodiments, L is of the formula:

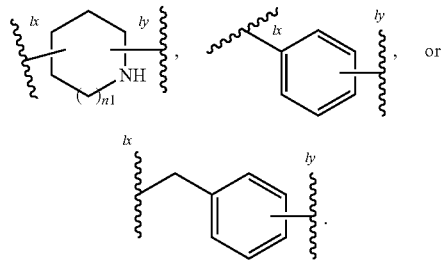

In certain embodiments, L is of the formula:

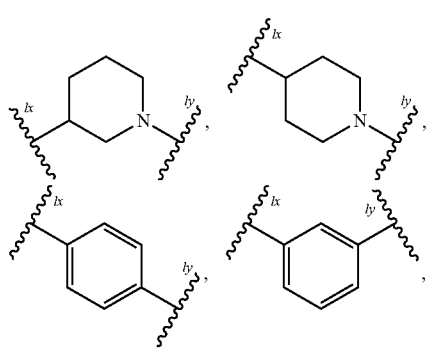

-continued

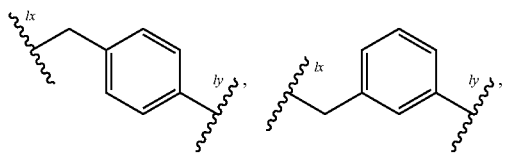

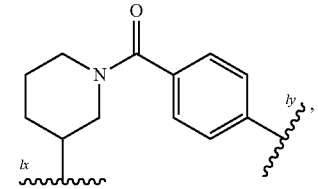

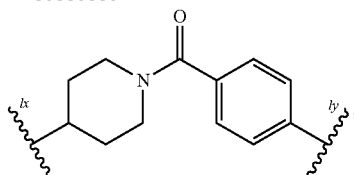

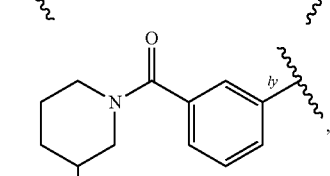

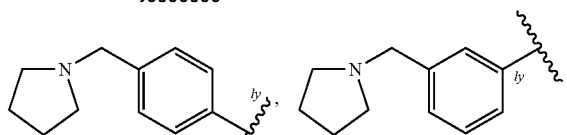

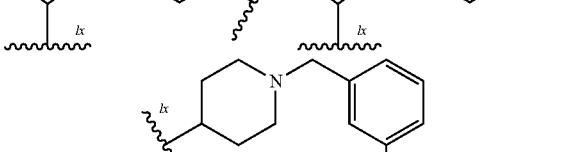

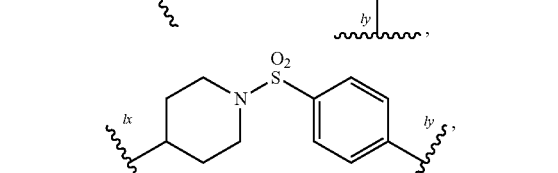

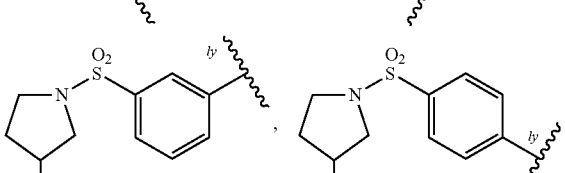

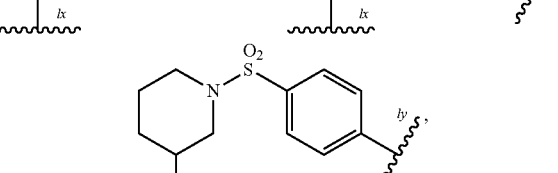

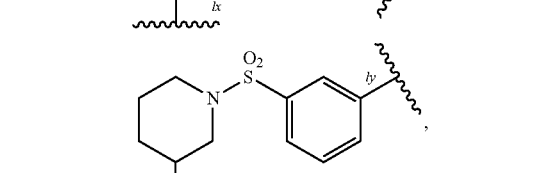

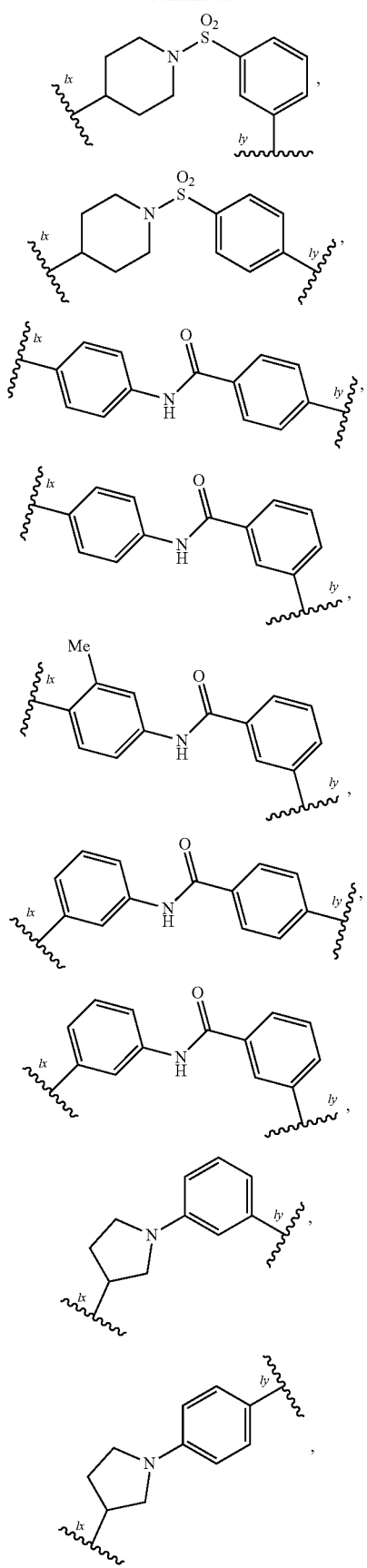
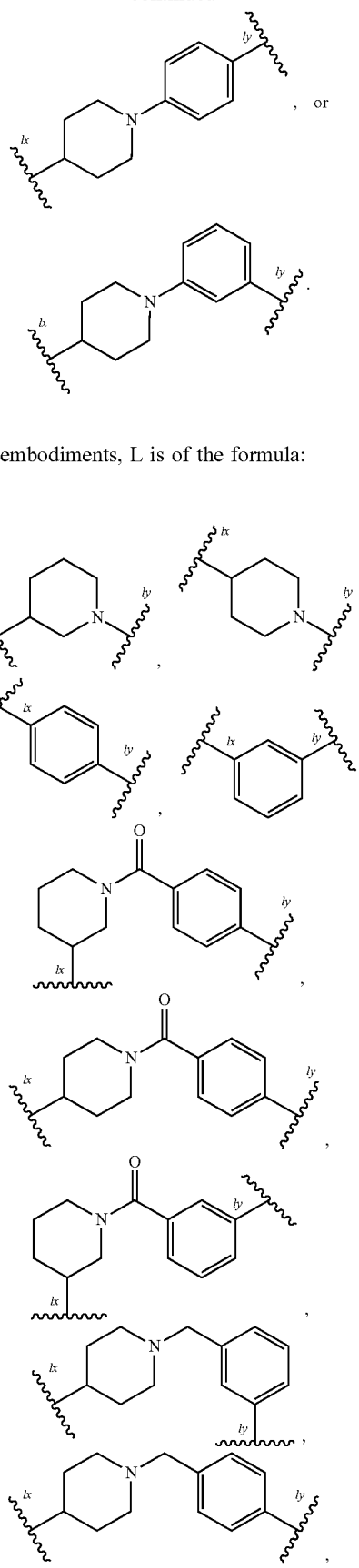
In certain embodiments, L is of the formula:

-continued
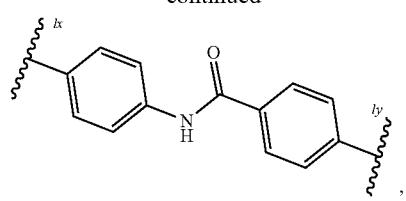,
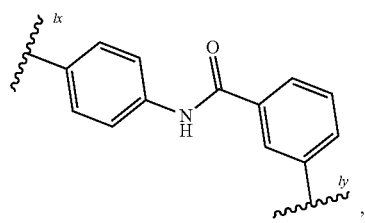,
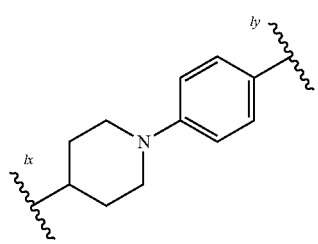, or
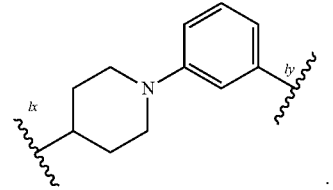.
In certain embodiments, L is of the formula:
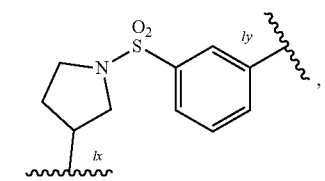,
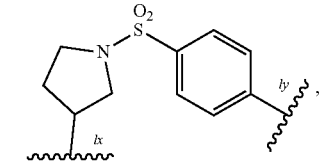,
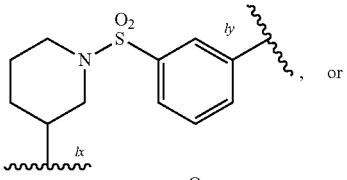, or
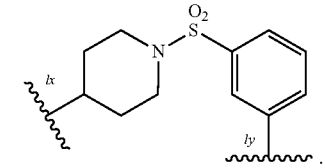.
As generally defined herein, Formula (I') includes substituent $R^{3'}$, wherein $R^{3'}$ is a warhead of formula:
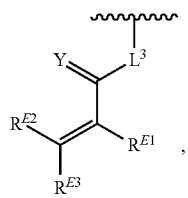 (i-1)
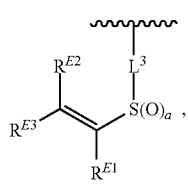 (i-2)
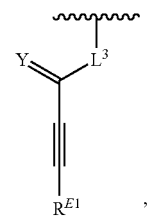 (i-3)
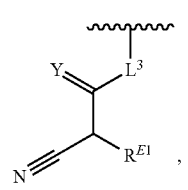 (i-4)
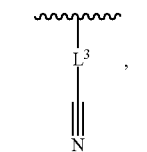 (i-5)
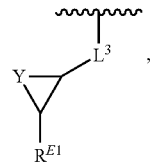 (i-6)
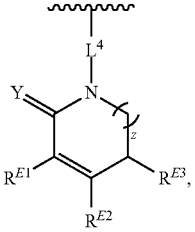 (i-7)
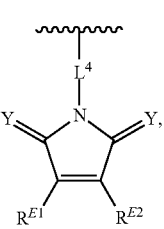 (i-8)

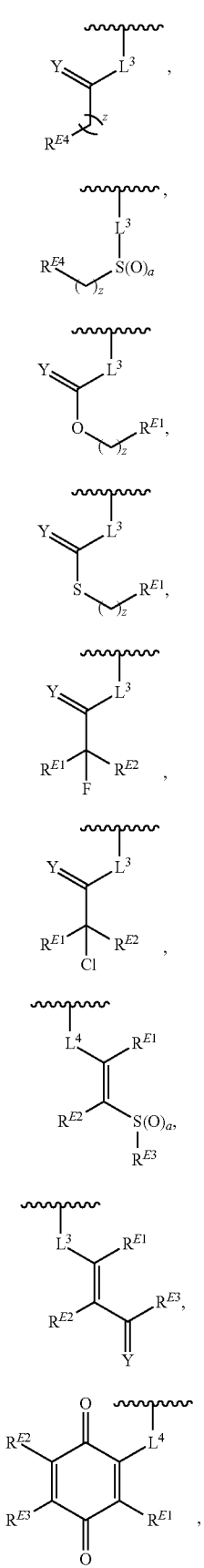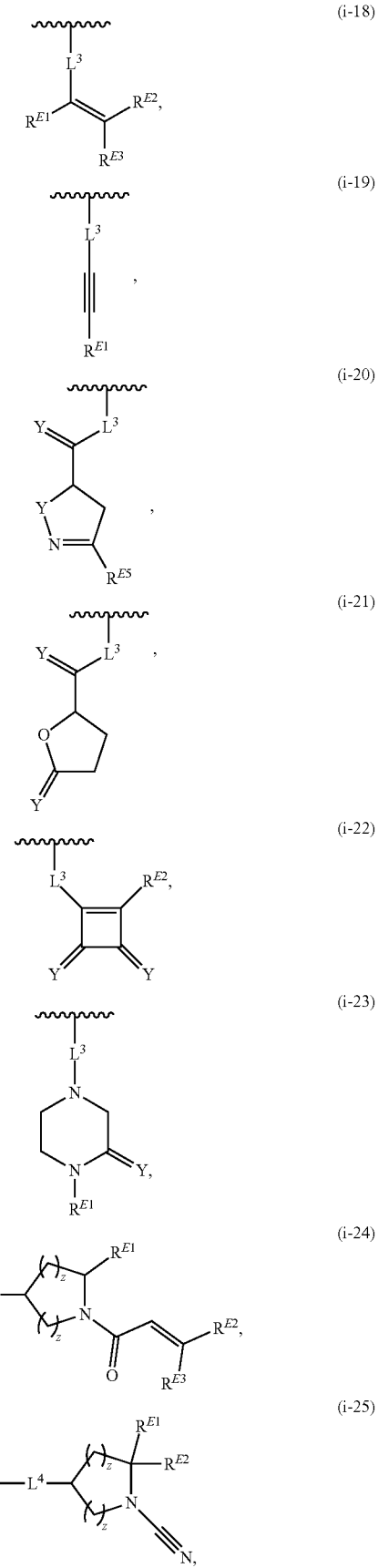

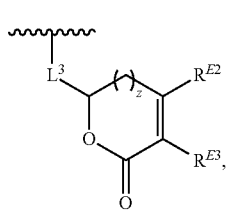 (i-26)
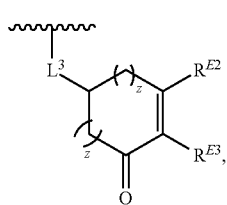 (i-27)
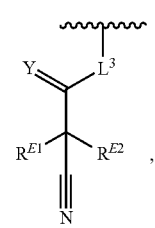 (i-28)
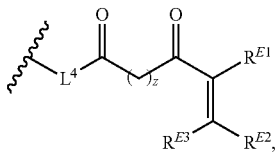 (i-29)
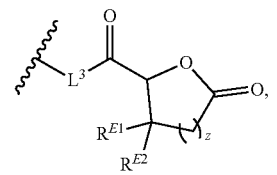 (i-30)
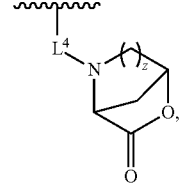 (i-31)
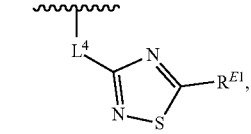 (i-32)
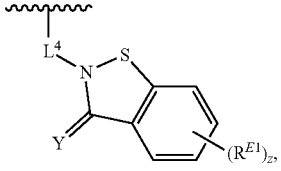 (i-33)
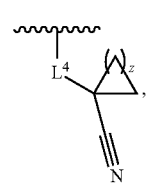 (i-34)
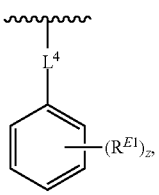 (i-35)
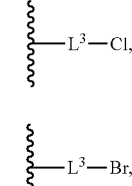 (i-36)
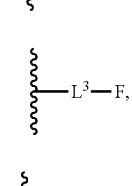 (i-37)
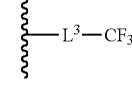 (i-38)
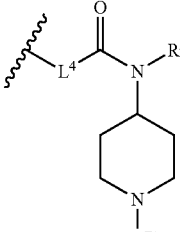 (i-39)
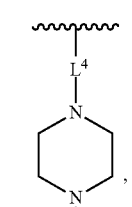 (i-40)
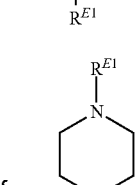 (i-41)
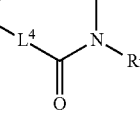 (i-42)

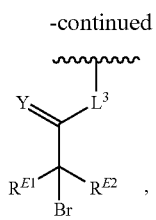
(i-43)

wherein:
- L³ is a bond or an optionally substituted C₁₋₄ hydrocarbon chain, optionally wherein one or more carbon units of the hydrocarbon chain are independently replaced with —C=O—, —O—, —S—, —NR$^{L3a}$—, —NR$^{L3a}$C(=O)—, —C(=O)NR$^{L3a}$—, —SC(=O)—, —C(=O)S—, —OC(=O)—, —C(=O)O—, —NR$^{L3a}$C(=S)—, —C(=S)NR$^{L3a}$—, trans-CR$^{L3b}$=CR$^{L3b}$—, cis-CR$^{L3b}$=CR$^{L3b}$—, —C≡C—, —S(=O)—, —S(=O)O—, —OS(=O)—, —S(=O)NR$^{L3a}$, —NR$^{L3a}$S(=O)—, —S(=O)₂—, —S(=O)₂O—, —OS(=O)₂—, —S(=O)₂NR$^{L3a}$—, or —NR$^{L3a}$S(=O)₂—, wherein R$^{L3a}$ is hydrogen, substituted or unsubstituted C₁₋₆ alkyl, or a nitrogen protecting group, and wherein each occurrence of R$^{L3b}$ is independently hydrogen, halogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two R$^{L3b}$ groups are joined to form an optionally substituted carbocyclic or optionally substituted heterocyclic ring;
- L⁴ is a bond or an optionally substituted, branched or unbranched C₁₋₆ hydrocarbon chain;
- each of R$^{E1}$, R$^{E2}$, and R$^{E3}$ is independently hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —CH₂OR$^{EE}$, —CH₂N(R$^{EE}$)₂, —CH₂SR$^{EE}$, —OR$^{EE}$, —N(R$^{EE}$)₂, —Si(R$^{EE}$)₃, or —SR$^{EE}$, wherein each instance of R$^{EE}$ is independently hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, or optionally substituted heteroaryl, or two R$^{EE}$ groups are joined to form an optionally substituted heterocyclic ring; or
- R$^{E1}$ and R$^{E3}$, or R$^{E2}$ and R$^{E3}$, or R$^{E1}$ and R$^{E2}$ are joined to form an optionally substituted carbocyclic or optionally substituted heterocyclic ring;
- R$^{E4}$ is a leaving group;
- R$^{E5}$ is halogen;
- R$^{E6}$ is hydrogen, substituted or unsubstituted C₁₋₆ alkyl, or a nitrogen protecting group;
- each instance of Y is independently O, S, or NR$^{E7}$, wherein R$^{E7}$ is hydrogen, substituted or unsubstituted C₁₋₆ alkyl, or a nitrogen protecting group;
- a is 1 or 2; and
- each instance of z is independently 0, 1, 2, 3, 4, 5, or 6, as valency permits.

In certain embodiments, R$^{3'}$ is R³.

As generally defined herein, Formula (I) includes substituent R³, wherein R³ is a warhead of formula:

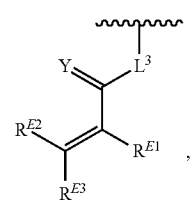
(i-1)

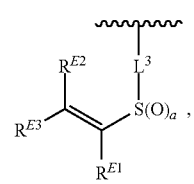
(i-2)

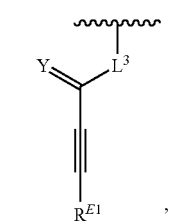
(i-3)

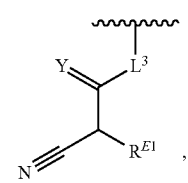
(i-4)

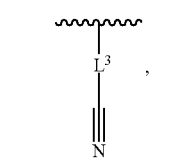
(i-5)

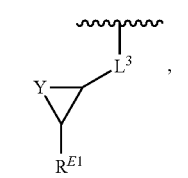
(i-6)

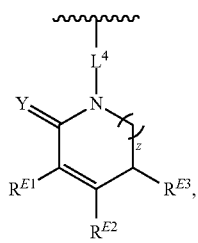
(i-7)

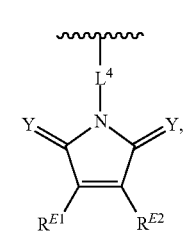
(i-8)

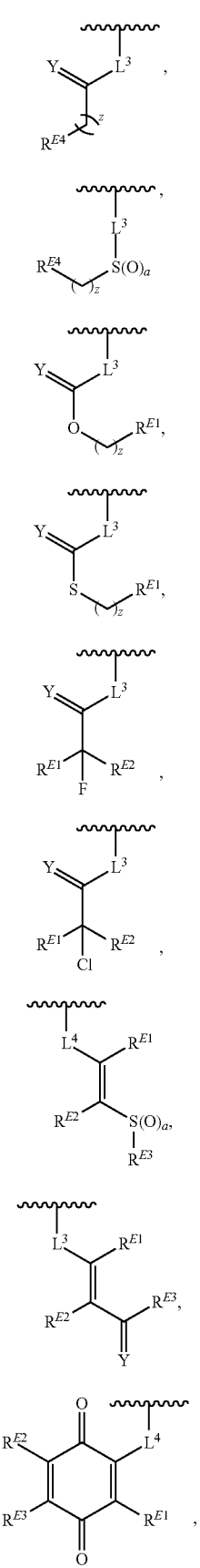
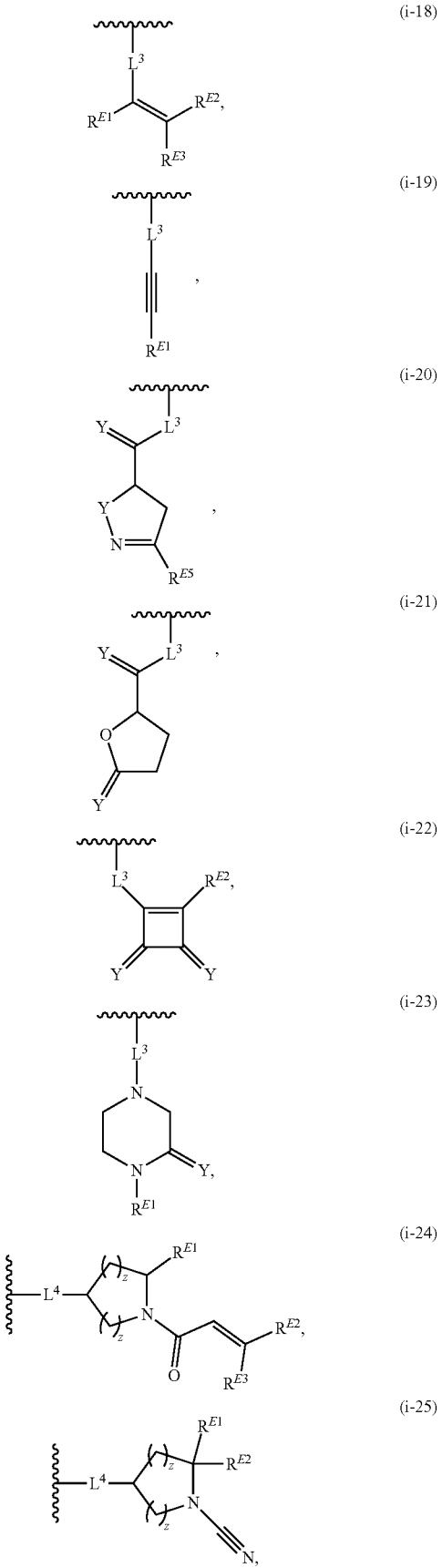

-continued (i-26)
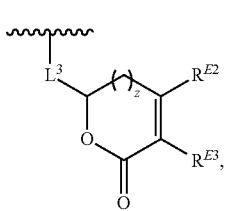

(i-27)
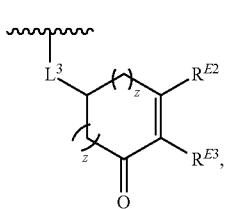

(i-28)
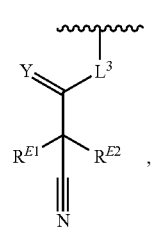

(i-29)
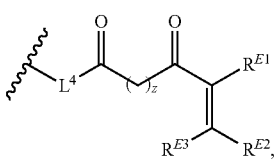

(i-30)
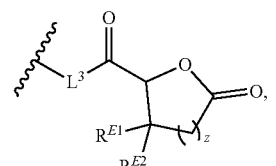

(i-31)
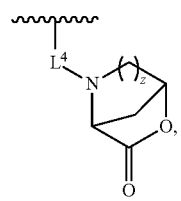

(i-32)
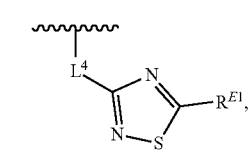

(i-33)
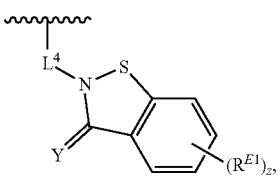

-continued (i-34)
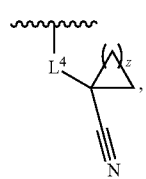

(i-35)
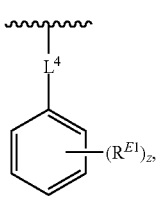

(i-36)
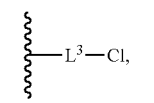

(i-37)
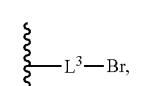

(i-38)
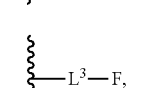

(i-39)
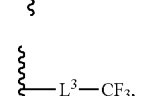

(i-40)
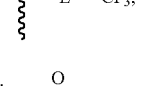

(i-41)
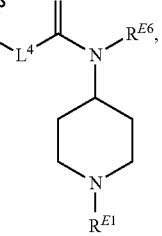

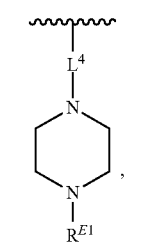

wherein:
$L^3$ is a bond or an optionally substituted $C_{1-4}$ hydrocarbon chain, optionally wherein one or more carbon units of the hydrocarbon chain are independently replaced with —C(=O)—, —O—, —S—, —NR$^{L3a}$—, —NR$^{L3a}$C(=O)—, —C(=O)NR$^{L3a}$—, —SC(=O)—, —C(=O)S—, —OC(=O)—, —C(=O)O—, —NR$^{L3a}$C(=S)—, —C(=S)NR$^{L3a}$—, trans-CR$^{L3b}$=CR$^{L3b}$—, cis-CR$^{L3b}$=CR$^{L3b}$—, —C≡C—, —S(=O)—, —S(=O)O—, —OS(=O)—, —S(=O)NR$^{L3a}$, —NR$^{L3a}$S(=O)—, —S(=O)$_2$—, —S(=O)$_2$O—, —OS(=O)$_2$—, —S(=O)$_2$NR$^{L3a}$—, or —NR$^{L3a}$S(=O)$_2$—, wherein R$^{L3a}$ is hydrogen, substituted or unsubstituted C$_{1-6}$ alkyl, or a nitrogen protecting group, and wherein each occurrence of R$^{L3b}$ is independently hydrogen, halogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two R$^{L3b}$ groups are joined to form an optionally substituted carbocyclic or optionally substituted heterocyclic ring;

L$^4$ is a bond or an optionally substituted, branched or unbranched C$_{1-6}$ hydrocarbon chain;

each of R$^{E1}$, R$^{E2}$, and R$^{E3}$ is independently hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —CH$_2$OR$^{EE}$, —CH$_2$N(R$^{EE}$)$_2$, —CH$_2$SR$^{EE}$, —OR$^{EE}$, —N(R$^{EE}$)$_2$, —Si(R$^{EE}$)$_3$, or —SR$^{EE}$, wherein each instance of R$^{EE}$ is independently hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, or optionally substituted heteroaryl, or two R$^{EE}$ groups are joined to form an optionally substituted heterocyclic ring; or R$^{E1}$ and R$^{E3}$, or R$^{E2}$ and R$^{E3}$, or R$^{E1}$ and R$^{E2}$ are joined to form an optionally substituted carbocyclic or optionally substituted heterocyclic ring;

R$^E$4 is a leaving group;
R$^{E5}$ is halogen;
R$^{E6}$ is hydrogen, substituted or unsubstituted C$_{1-6}$ alkyl, or a nitrogen protecting group;
each instance of Y is independently O, S, or NR$^{E7}$, wherein R$^{E7}$ is hydrogen, substituted or unsubstituted C$_{1-6}$ alkyl, or a nitrogen protecting group;
a is 1 or 2; and
each instance of z is independently 0, 1, 2, 3, 4, 5, or 6, as valency permits.

In certain embodiments, R$^{3'}$ is a warhead of formula (i-1) through (i-43). In certain embodiments, the warhead is of formula

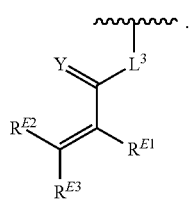

(i-1)

In certain embodiments, R$^{3'}$ is a warhead of formula

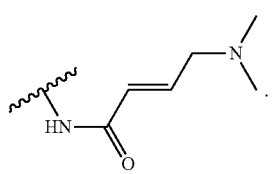 [SMILES: *NC(=O)/C=C/CN(C)C]

In certain embodiments, R$^{3'}$ is a warhead of formula

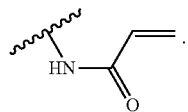 [SMILES: *NC(=O)C=C]

In certain embodiments, R$^{3'}$ is a warhead of formula

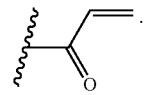

In certain embodiments, R$^{3'}$ is of formula:

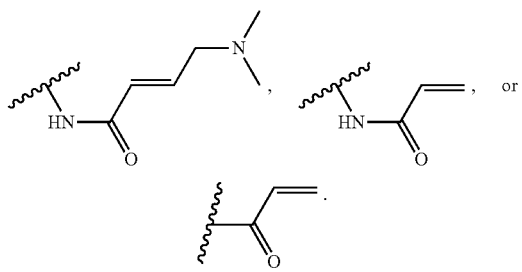

In certain embodiments, R$^{3'}$ is of formula:

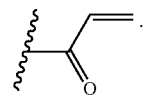

In certain embodiments, R$^{3'}$ is of formula:

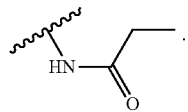 [SMILES: *NC(=O)CC]

In certain embodiments, R$^{3'}$ is of formula:

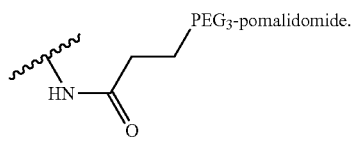

In certain embodiments, R$^{3'}$ is of formula:

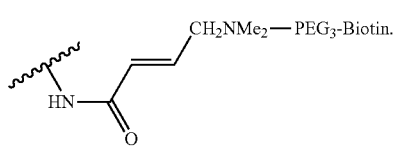

In certain embodiments, L3 is a bond. In certain embodiments, L3 is —NH—. In certain embodiments, R$^{E1}$ and R$^{E2}$ are hydrogen. In certain embodiments, R$^{E1}$, R$^{E2}$, and R$^{E3}$ are all hydrogen. In certain embodiments, R$^{E3}$ is —CH$_2$NMe$_2$. In certain embodiments, the warhead is of formula

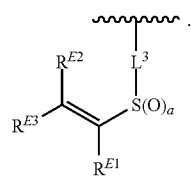

(i-2)

In certain embodiments, the warhead is of formula

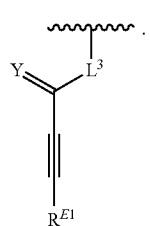

(i-3)

In certain embodiments, the warhead is of formula

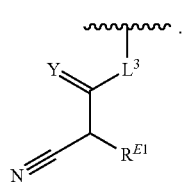

(i-4)

In certain embodiments, the warhead is of formula

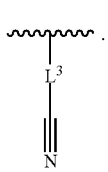

(i-5)

In certain embodiments, the warhead is of formula

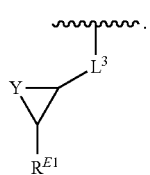

(i-6)

In certain embodiments, the warhead is of formula

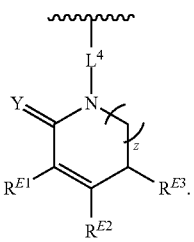

(i-7)

In certain embodiments, the warhead is of formula

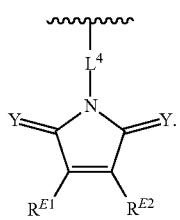

(i-8)

In certain embodiments, the warhead is of formula

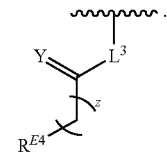

(i-9)

In certain embodiments, the warhead is of formula

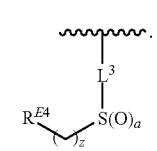

(i-10)

In certain embodiments, the warhead is

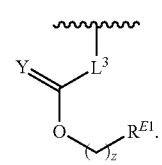

(i-11)

In certain embodiments, the warhead is of formula

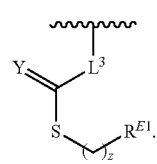
(i-12)

In certain embodiments, the warhead is of formula

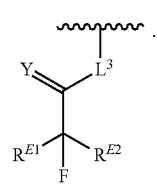
(i-13)

In certain embodiments, the warhead is of formula

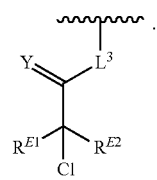
(i-14)

In certain embodiments, the warhead is of formula

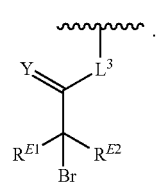
(i-43)

In certain embodiments, the warhead is of formula

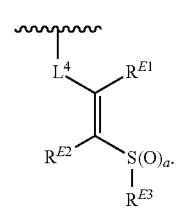
(i-15)

In certain embodiments, the warhead is of formula

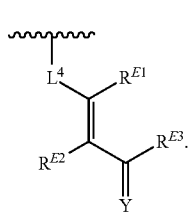
(i-16)

In certain embodiments, the warhead is of formula

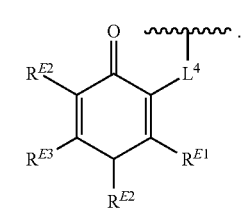
(i-17)

In certain embodiments, the warhead is of formula

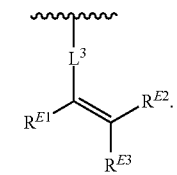
(i-18)

In Certain embodiments, the warhead is of formula

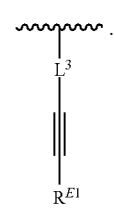
(i-19)

In Certain embodiments, the warhead is of formula

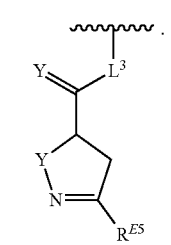
(i-20)

In certain embodiments, the warhead is

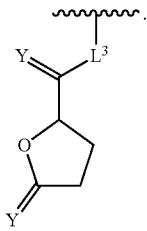
(i-21)

In certain embodiments, the warhead is of formula

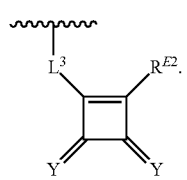
(i-22)

In certain embodiments, the warhead is of formula

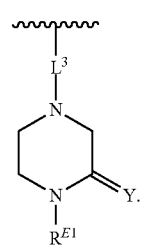
(i-23)

In certain embodiments, the warhead is of formula

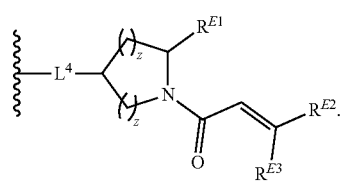
(i-24)

In certain embodiments, the warhead is of formula

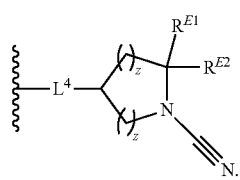
(i-25)

In certain embodiments, the warhead is of formula

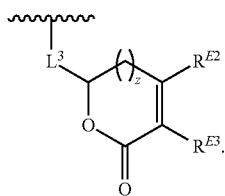
(i-26)

In certain embodiments, the warhead is of formula

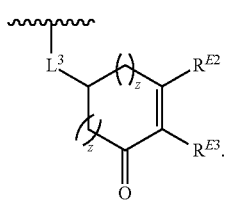
(i-27)

In certain embodiments, the warhead is of formula

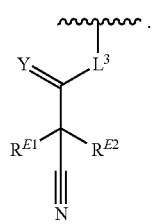
(i-28)

In certain embodiments, the warhead is of formula

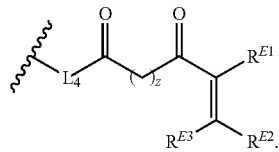
(i-29)

In certain embodiments, the warhead is of formula

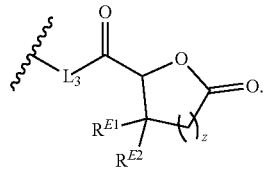
(i-30)

In certain embodiments, the warhead is of formula

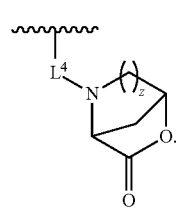

(i-31)

In certain embodiments, the warhead is of formula

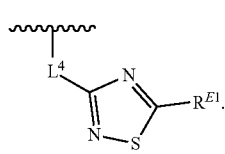

(i-32)

In certain embodiments, the warhead is of formula

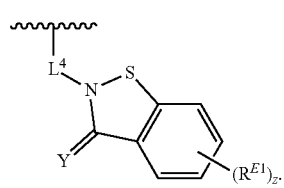

(i-33)

In certain embodiments, the warhead is of formula

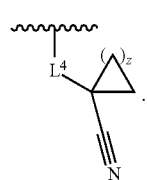

(i-34)

In certain embodiments, the warhead is of formula

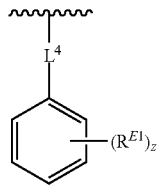

In certain embodiments, the warhead is of formula

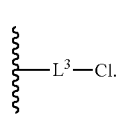

(i-36)

In certain embodiments, the warhead is of formula

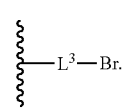

(i-37)

In certain embodiments, the warhead is of formula

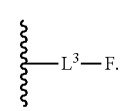

(i-38)

In certain embodiments, the warhead is of formula

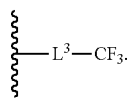

(i-39)

In certain embodiments, the warhead is of formula (i-40)

In certain embodiments, the warhead is of formula

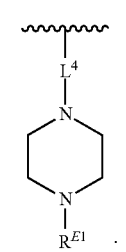

(i-41)

In certain embodiments, the warhead is of formula

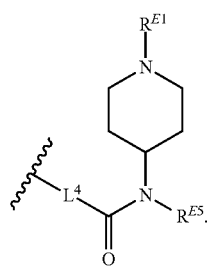

(i-42)

In certain embodiments, $R^{3\prime}$ is a warhead of formula

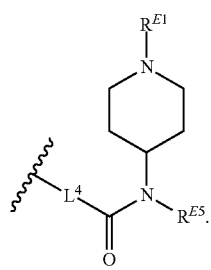

(i-42)

In certain embodiments, $R^{3\prime}$ is a warhead of formula

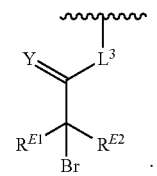

(i-43)

In certain embodiments, $R^3$ is a warhead of formula (i-1) through (i-41). In certain embodiments, the warhead is of formula

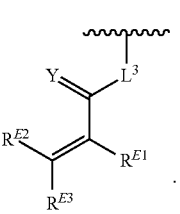

(i-1)

In certain embodiments, $R^3$ is a warhead of formula

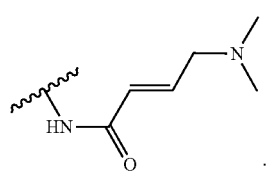 [SMILES: *NC(=O)/C=C/CN(C)C]

In certain embodiments, $R^3$ is a warhead of formula

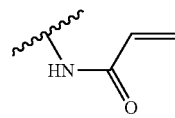

In certain embodiments, $R^3$ is a warhead of formula

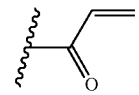

In certain embodiments, $R^3$ is of formula:

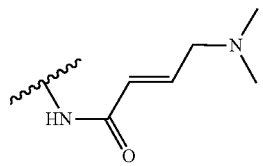

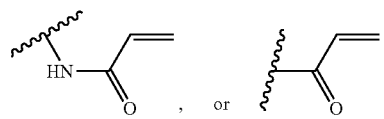

In certain embodiments, $R^3$ is of formula:

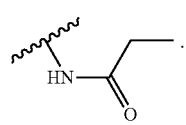 [SMILES: *NC(=O)CC]

In certain embodiments, $R^3$ is of formula:

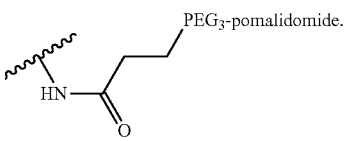

In certain embodiments, $R^3$ is of formula:

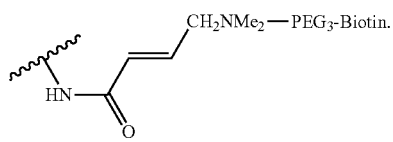

In certain embodiments, $L^3$ is a bond. In certain embodiments, $L^3$ is —NH—. In certain embodiments, $R^{E1}$ and $R^{E2}$ are hydrogen. In certain embodiments, $R^{E1}$, $R^{E2}$, and $R^{E3}$ are all hydrogen. In certain embodiments, $R^{E3}$ is —CH$_2$NMe$_2$.

In certain embodiments, the warhead is of formula

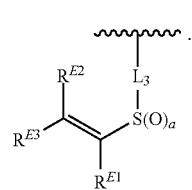
(i-2)

In certain embodiments, the warhead is of formula

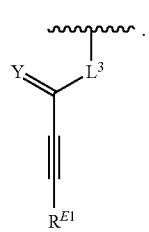
(i-3)

In certain embodiments, the warhead is of formula

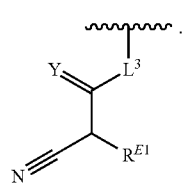
(i-4)

In certain embodiments, the warhead is of formula

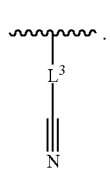
(i-5)

In certain embodiments, the warhead is of formula

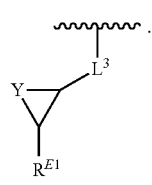
(i-6)

In certain embodiments, the warhead is of formula

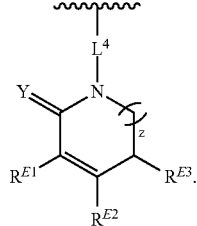
(i-7)

In certain embodiments, the warhead is of formula

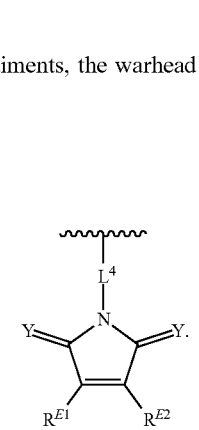
(i-8)

In certain embodiments, the warhead is of formula

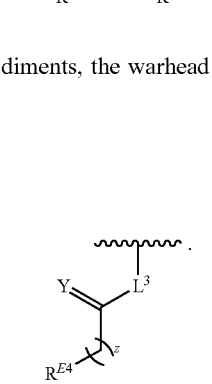
(i-9)

In certain embodiments, the warhead is of formula

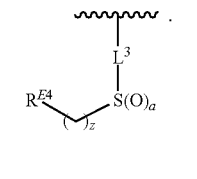
(i-10)

In certain embodiments, the warhead is

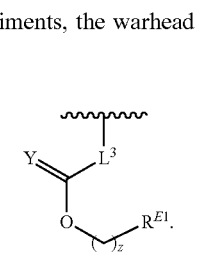
(i-11)

In certain embodiments, the warhead is of formula

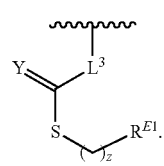

(i-12)

In certain embodiments, the warhead is of formula

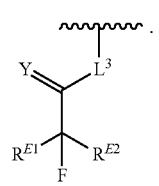

(i-13)

In certain embodiments, the warhead is of formula

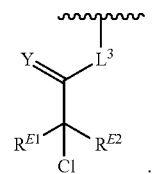

(i-14)

In certain embodiments, the warhead is of formula

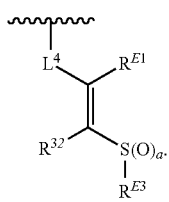

(i-15)

In certain embodiments, the warhead is of formula

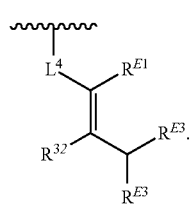

(i-16)

In certain embodiments, the warhead is of formula

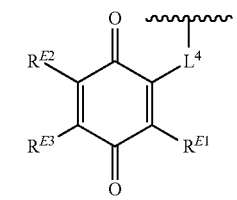

(i-17)

In certain embodiments, the warhead is of formula

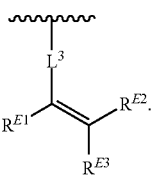

(i-18)

In certain embodiments, the warhead is of formula

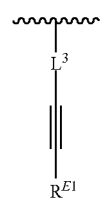

(i-19)

In certain embodiments, the warhead is of formula

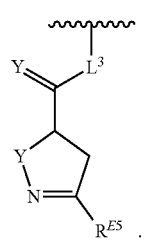

(i-20)

In certain embodiments, the warhead is

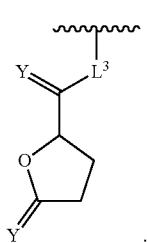

(i-21)

In certain embodiments, the warhead is of formula

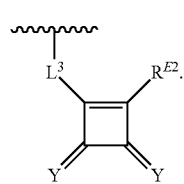

(i-22)

In certain embodiments, the warhead is of formula

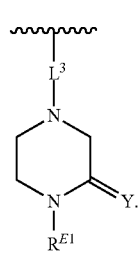

(i-23)

In certain embodiments, the warhead is of formula

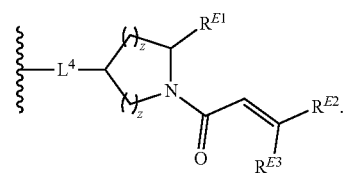

(i-24)

In certain embodiments, the warhead is of formula

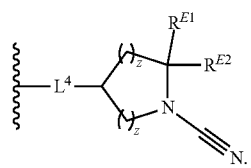

(i-25)

In certain embodiments, the warhead is of formula

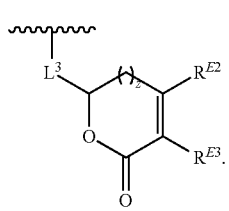

(i-26)

In certain embodiments, the warhead is of formula

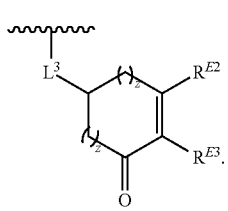

(i-27)

In certain embodiments, the warhead is of formula

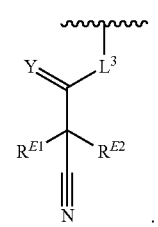

(i-28)

In certain embodiments, the warhead is of formula

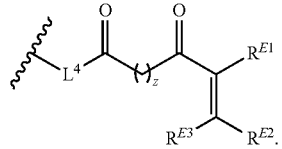

(i-29)

In certain embodiments, the warhead is of formula

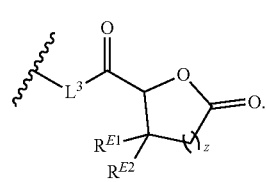

(i-30)

In certain embodiments, the warhead is of formula

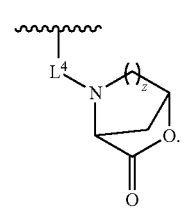

(i-31)

In certain embodiments, the warhead is of formula

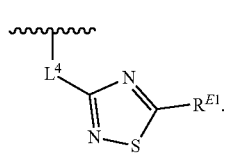
(i-32)

In certain embodiments, the warhead is of formula

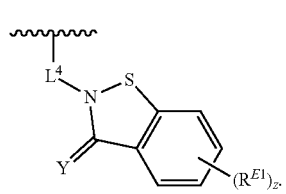
(i-33)

In certain embodiments, the warhead is of formula

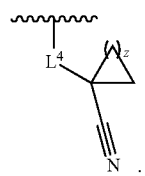
(i-34)

In certain embodiments, the warhead is of formula

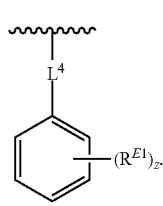
(i-35)

In certain embodiments, the warhead is of formula

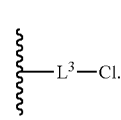
(i-36)

In certain embodiments, the warhead is of formula

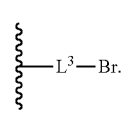
(i-37)

In certain embodiments, the warhead is of formula

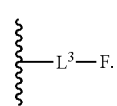
(i-38)

In certain embodiments, the warhead is of formula

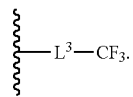
(i-39)

In certain embodiments, the warhead is of formula

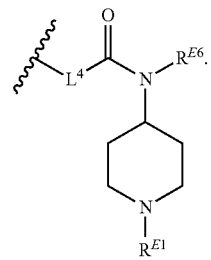
(i-40)

In certain embodiments, the warhead is of formula

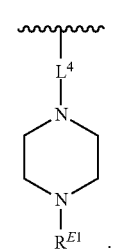
(i-41)

In certain embodiments, the warhead is of formula

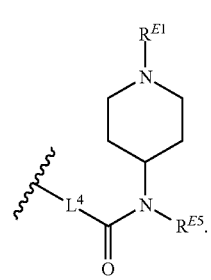
(i-42)

In certain embodiments, the warhead is of formula

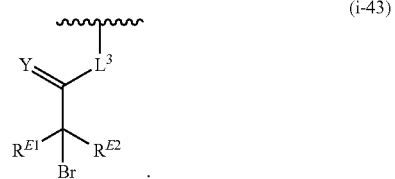

(i-43)

In certain embodiments, L³ is a bond (e.g., a single bond, a double bond, or a triple bond). In certain embodiments, L³ is a single bond. In certain embodiments, L³ is a double bond. In certain embodiments, L³ is a triple bond. In certain embodiments, L³ is an optionally substituted $C_{1-4}$ hydrocarbon chain, optionally wherein one or more carbon units of the hydrocarbon chain are independently replaced with —C=O—, —O—, —S—, —NR$^{L3a}$—, —NR$^{L3a}$C(=O)—, —C(=O)NR$^{L3a}$—, —SC(=O)—, —C(=O)S—, —OC(=O)—, —C(=O)O—, —NR$^{L3a}$C(S—, —C(=S)NR$^{L3a}$—, trans-CR$^{L3b}$=CR$^{L3b}$—, cis-CR$^{L3b}$=CR$^{L3b}$—C=C—, —S(=O)—, —S(=O)O—, —OS(=O)—, —S(=O)NR$^{L3a}$—, —NR$^{L3a}$S(=O)—, —S(=O)$_2$—, —S(=O)$_2$O—, —OS(=O)$_2$—, —S(=O)$_2$NR$^{L3a}$—, or —NR$^{L3a}$S(=O)$_2$—, wherein R$^{L3a}$ is hydrogen, substituted or unsubstituted $C_{1-6}$ alkyl, or a nitrogen protecting group, and wherein each occurrence of R$^{L3b}$ is independently hydrogen, halogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two R$^{L3b}$ groups are joined to form an optionally substituted carbocyclic or optionally substituted heterocyclic ring. In certain embodiments, L⁴ is a bond (e.g., a single bond, a double bond, or a triple bond). In certain embodiments, L⁴ is an optionally substituted branched $C_{1-6}$ hydrocarbon chain (e.g., i-Pr). In certain embodiments, L⁴ is an optionally substituted unbranched $C_{1-6}$ hydrocarbon chain (e.g., n-Pr, or n-Bu). In certain embodiments, at least one instance of R$^{E1}$ is H. In certain embodiments, at least one instance of R$^{E1}$ is halogen (e.g., F, Cl, Br, or I). In certain embodiments, at least one instance of R$^{E1}$ is optionally substituted alkyl (e.g., Me, or Et). In certain embodiments, at least one instance of R$^{E1}$ is optionally substituted alkenyl (e.g., optionally substituted vinyl). In certain embodiments, at least one instance of R$^{E1}$ is optionally substituted alkynyl. In certain embodiments, at least one instance of R$^{E1}$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, at least one instance of R$^{E1}$ is substituted or unsubstituted heterocyclyl (e.g., substituted or unsubstituted, 3- to 7-membered, monocyclic heterocyclyl comprising zero, one, or two double bonds in the heterocyclic ring system, wherein one, two, or three atoms in the heterocyclic ring system are independently nitrogen, oxygen, or sulfur). In certain embodiments, at least one instance of R$^{E1}$ is substituted or unsubstituted aryl (e.g., substituted or unsubstituted, 6- to 10-membered aryl). In certain embodiments, at least one instance of R$^{E1}$ is substituted or unsubstituted phenyl. In certain embodiments, at least one instance of R$^{E1}$ is substituted or unsubstituted heteroaryl (e.g., substituted or unsubstituted, 5-to 6-membered, monocyclic heteroaryl, wherein one, two, three, or four atoms in the heteroaryl ring system are independently nitrogen, oxygen, or sulfur). In certain embodiments, at least one instance of R$^{E1}$ is —CN. In certain embodiments, at least one instance of R$^{E1}$ is —CH$_2$OR$^{EE}$, wherein each instance of R$^{EE}$ is independently hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, or optionally substituted heteroaryl. In certain embodiments, at least one instance of R$^{E1}$ is —CH$_2$N(R$^{EF}$)$_2$ or —N(R$^{EF}$)$_2$, wherein each instance of R$^{EF}$ is independently hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, or optionally substituted heteroaryl, optionally wherein two R$^{EF}$ groups are joined to form an optionally substituted heterocyclic ring. In certain embodiments, at least one instance of R$^{E1}$ is —CH$_2$SR$^{EE}$ or —SR$^{EE}$ (e.g., —CH$_2$SMe or —SMe). In certain embodiments, at least one instance of R$^{E1}$ is —OR$^{EE}$ (e.g., —OMe). In certain embodiments, at least one instance of R$^{E1}$ is —Si(R$^{EG}$)$_3$, wherein each instance of R$^{EG}$ is independently hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, or optionally substituted heteroaryl (e.g., —Si(Me)$_3$).

In certain embodiments, at least one instance of R$^{E2}$ is H. In certain embodiments, at least one instance of R$^{E2}$ is halogen (e.g., F, Cl, Br, or I). In certain embodiments, at least one instance of R$^{E2}$ is optionally substituted alkyl (e.g., Me, or Et). In certain embodiments, at least one instance of R$^{E2}$ is optionally substituted alkenyl (e.g., optionally substituted vinyl). In certain embodiments, at least one instance of R$^{E2}$ is optionally substituted alkynyl. In certain embodiments, at least one instance of R$^{E2}$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, at least one instance of R$^{E2}$ is substituted or unsubstituted heterocyclyl (e.g., substituted or unsubstituted, 3- to 7-membered, monocyclic heterocyclyl comprising zero, one, or two double bonds in the heterocyclic ring system, wherein one, two, or three atoms in the heterocyclic ring system are independently nitrogen, oxygen, or sulfur). In certain embodiments, at least one instance of R$^{E2}$ is substituted or unsubstituted aryl (e.g., substituted or unsubstituted, 6- to 10-membered aryl). In certain embodiments, at least one instance of R$^{E2}$ is substituted or unsubstituted phenyl. In certain embodiments, at least one instance of R$^{E2}$ is substituted or unsubstituted heteroaryl (e.g., substituted or unsubstituted, 5-to 6-membered, monocyclic heteroaryl, wherein one, two, three, or four atoms in the heteroaryl ring system are independently nitrogen, oxygen, or sulfur). In certain embodiments, at least one instance of R$^{E2}$ is —CN. In certain embodiments, at least one instance of R$^{E2}$ is —CH$_2$OR$^{EE}$, wherein each instance of R$^{EE}$ is independently hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, or optionally substituted heteroaryl. In certain embodiments, at least one instance of R$^{E2}$ is —CH$_2$N(R$^{EF}$)$_2$ or N(R$^{EF}$)$_2$, wherein each instance of R$^{EF}$ is independently hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, or optionally substituted heteroaryl, optionally wherein two R$^{EF}$ groups are joined to form an optionally substituted heterocyclic ring. In certain embodiments, at least one instance of R$^{E2}$ is —CH$_2$SR$^{EE}$ or —SR$^{EE}$ (e.g., —CH$_2$SMe or —SMe). In certain embodiments, at least one instance of R$^{E2}$ is —OR$^{EE}$ (e.g., —OMe). In certain embodiments, at least one instance of R$^{E2}$ is —Si(R$^{EG}$)$_3$, wherein each instance of R$^{EG}$ is independently hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, or optionally substituted heteroaryl (e.g., —Si(Me)$_3$). In certain embodiments, at least one instance of R$^{E3}$ is H. In certain embodiments, at least one instance of R$^{E3}$ is halogen (e.g., F, Cl, Br, or I). In certain embodiments, at least one instance of R$^{E3}$ is optionally substituted alkyl (e.g., Me, or Et). In certain embodiments, at least one instance of R$^{E3}$ is optionally substituted alkenyl (e.g., optionally substituted vinyl). In certain embodiments, at least one instance of R$^{E3}$ is optionally substituted alkynyl. In certain embodiments, at least one instance of R$^{E3}$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, at least one instance of R$^{E3}$ is substituted or unsubstituted heterocyclyl (e.g., substituted or unsubstituted, 3- to 7-membered, monocyclic heterocyclyl comprising zero, one, or two double bonds in the heterocyclic ring system, wherein one, two, or three atoms in the heterocyclic ring system are independently nitrogen, oxygen, or sulfur). In certain embodiments, at least one instance of R$^{E3}$ is substituted or unsubstituted aryl (e.g., substituted or unsubstituted, 6- to 10-membered aryl). In certain embodiments, at least one instance of R$^{E3}$ is substituted or unsubstituted phenyl. In certain embodiments, at least one instance of R$^{E3}$ is substituted or unsubstituted heteroaryl (e.g., substituted or unsubstituted, 5-to 6-membered, monocyclic heteroaryl, wherein one, two, three, or four atoms in the heteroaryl ring system are independently nitrogen, oxygen, or sulfur). In certain embodiments, at least one instance of R$^{E3}$ is —CN. In certain embodiments, at least one instance of R$^{E3}$ is —CH$_2$OR$^{EE}$, wherein each instance of R$^{EE}$ is independently hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, or optionally substituted heteroaryl. In certain embodiments, at least one instance of R$^{E3}$ is —CH$_2$N(R$^{EF}$)$_2$ or —N(R$^{EF}$)$_2$, wherein each instance of R$^{EF}$ is independently hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, or optionally substituted heteroaryl, optionally wherein two R$^{EF}$ groups are joined to form an optionally substituted heterocyclic ring. In certain embodiments, at least one instance of R$^{E3}$ is —CH$_2$SR$^{EE}$ or —SR$^{EE}$ (e.g., —CH$_2$SMe or —SMe). In certain embodiments, at least one instance of R$^{E3}$ is —OR$^{EE}$ (e.g., —OMe). In certain embodiments, at least one instance of R$^{E3}$ is —Si(R$^{EG}$)$_3$, wherein each instance of R$^{EG}$ is independently hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, or optionally substituted heteroaryl (e.g., —Si(Me)$_3$). In certain embodiments, R$^{E1}$ and R$^{E3}$ are joined to form an optionally substituted carbocyclic ring (e.g., substituted or unsubstituted, 3- to 7-membered, monocyclic carbocyclyl comprising zero, one, or two double bonds in the carbocyclic ring system). In certain embodiments, R$^{E1}$ and R$^{E3}$ are joined to form an optionally substituted heterocyclic ring (e.g., substituted or unsubstituted, 3- to 7-membered, monocyclic heterocyclyl comprising zero, one, or two double bonds in the heterocyclic ring system, wherein one, two, or three atoms in the heterocyclic ring system are independently nitrogen, oxygen, or sulfur). In certain embodiments, R$^{E2}$ and R$^{E3}$ are joined to form an optionally substituted carbocyclic ring (e.g., substituted or unsubstituted, 3- to 7-membered, monocyclic carbocyclyl comprising zero, one, or two double bonds in the carbocyclic ring system). In certain embodiments, R$^{E2}$ and R$^{E3}$ are joined to form an optionally substituted heterocyclic ring (e.g., substituted or unsubstituted, 3- to 7-membered, monocyclic heterocyclyl comprising zero, one, or two double bonds in the heterocyclic ring system, wherein one, two, or three atoms in the heterocyclic ring system are independently nitrogen, oxygen, or sulfur). In certain embodiments, R$^{E1}$ and R$^{E2}$ are joined to form an optionally substituted carbocyclic ring (e.g., substituted or unsubstituted, 3- to 7-membered, monocyclic carbocyclyl comprising zero, one, or two double bonds in the carbocyclic ring system). In certain embodiments, R$^{E1}$ and R$^{E2}$ are joined to form an optionally substituted heterocyclic ring (e.g., substituted or unsubstituted, 3- to 7-membered, monocyclic heterocyclyl comprising zero, one, or two double bonds in the heterocyclic ring system, wherein one, two, or three atoms in the heterocyclic ring system are independently nitrogen, oxygen, or sulfur). In certain embodiments, R$^{E4}$ is a leaving group (e.g., halogen, or a sulfonic acid ester, e.g., —O(tosylate) or —O(mesylate)). In certain embodiments, R$^{E5}$ is halogen (e.g., F, Cl, Br, or I). In certain embodiments, R$^{E6}$ is H. In certain embodiments, R$^{E6}$ is substituted or unsubstituted C$_{1-6}$ alkyl (e.g., Me, is —CF$_3$, Bn, Et, perfluoroethyl, Pr, perfluoropropyl, Bu, or perfluorobutyl). In certain embodiments, R$^{E6}$ is a nitrogen protecting group (e.g., Bn, Boc, Cbz, Fmoc, trifluoroacetyl, triphenylmethyl, acetyl, or Ts). In certain embodiments, at least one instance of Y is O. In certain embodiments, at least one instance of Y is S. In certain embodiments, at least one instance of Y is NR$^{E7}$, wherein R$^{E7}$ is hydrogen, substituted or unsubstituted C$_{1-6}$ alkyl, or a nitrogen protecting group (e.g., NMe). In certain embodiments, a is 1. In certain embodiments, a is 2. In certain embodiments, at least one instance of z is 0. In certain embodiments, at least one instance of z is 1. In certain embodiments, at least one instance of z is 2. In certain embodiments, at least one instance of z is 3. In certain embodiments, at least one instance of z is 4. In certain embodiments, at least one instance of z is 5. In certain embodiments, at least one instance of z is 6.

In certain embodiments, the compound of Formula (I) is of the formula:

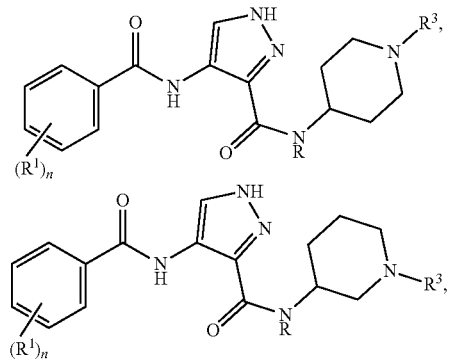

-continued
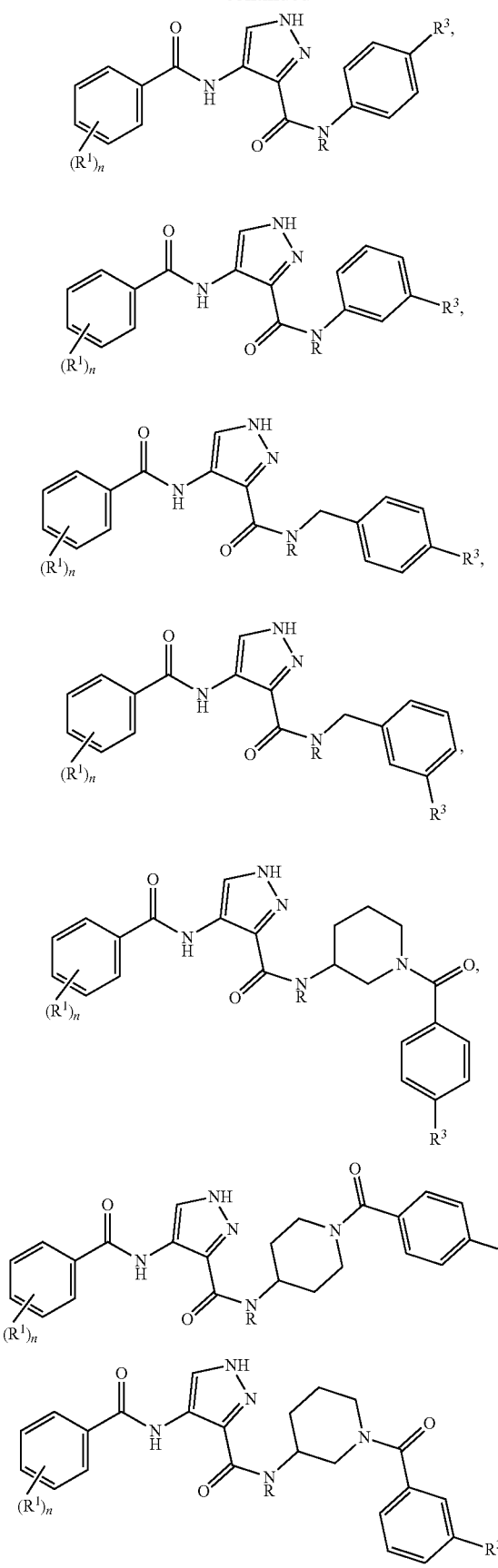
-continued
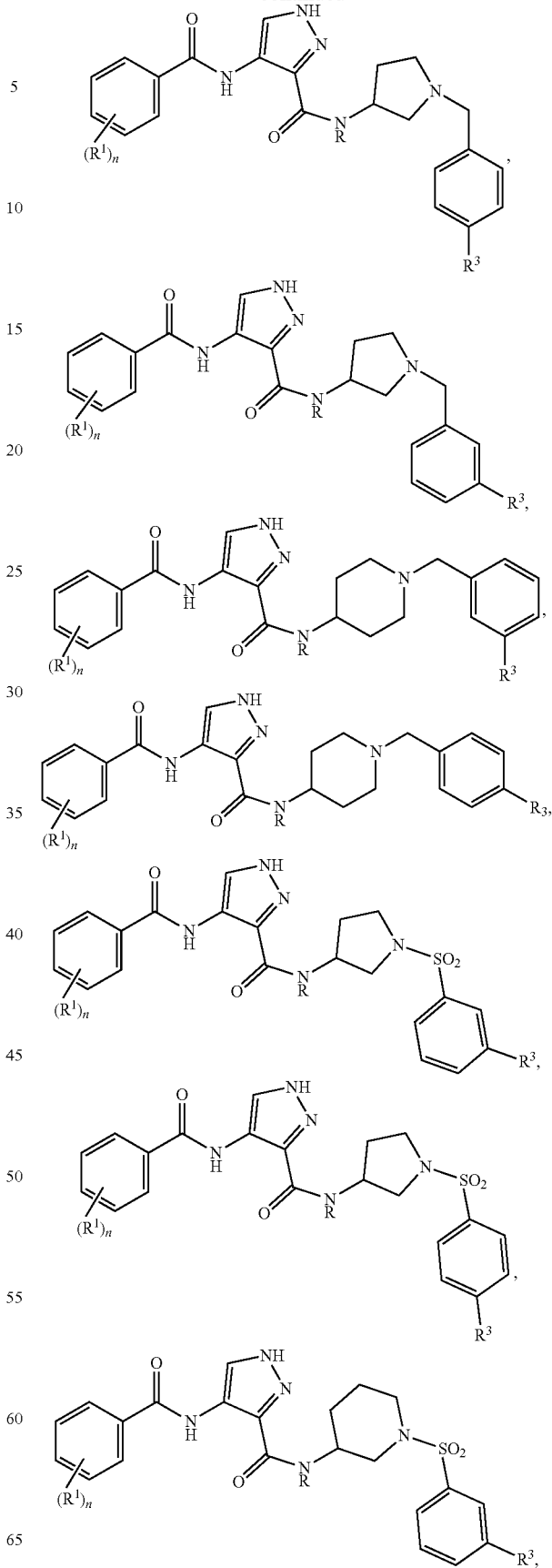

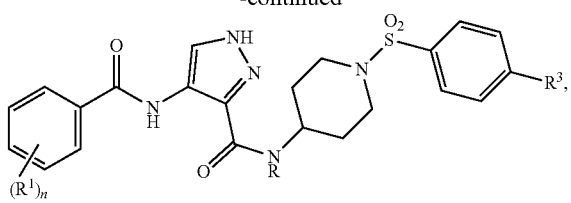
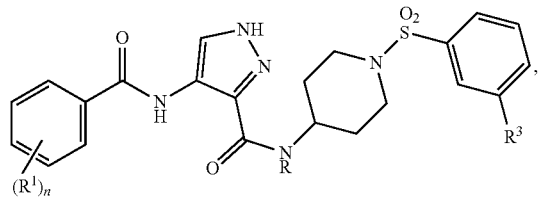
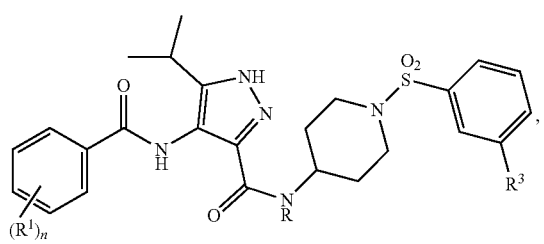
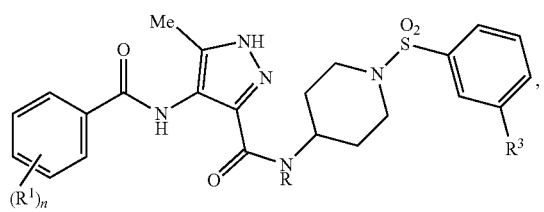
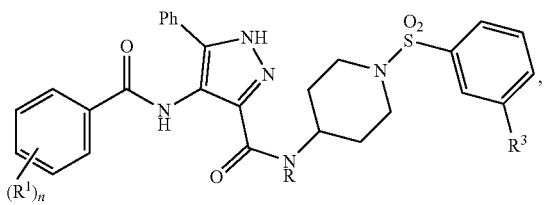
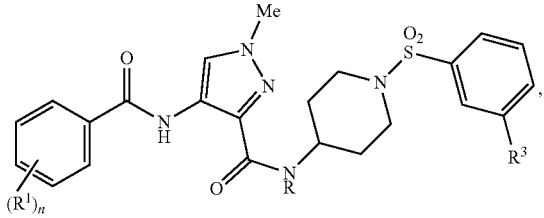
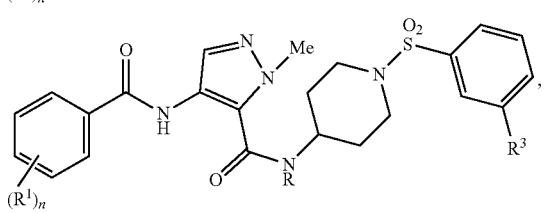
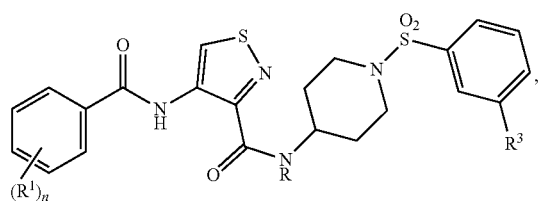
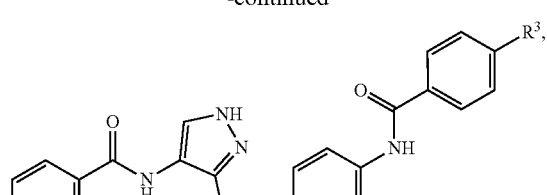

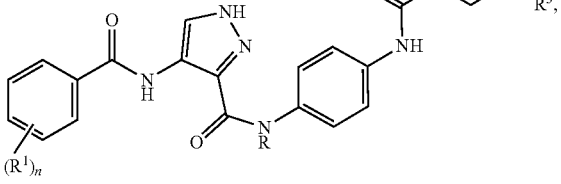
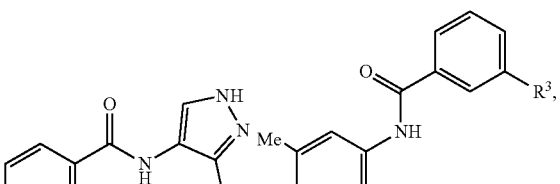
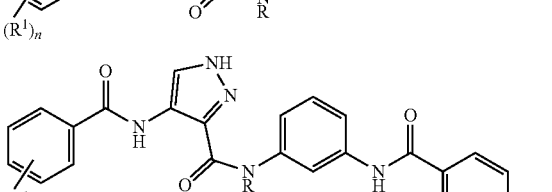
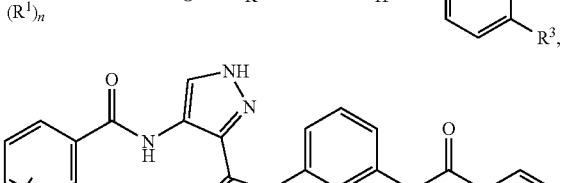
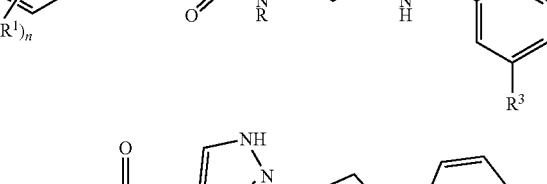
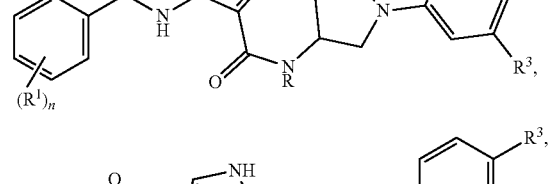
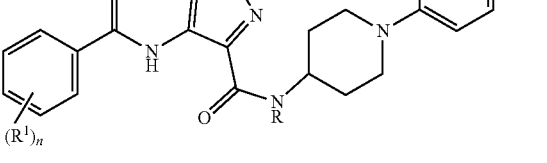

-continued
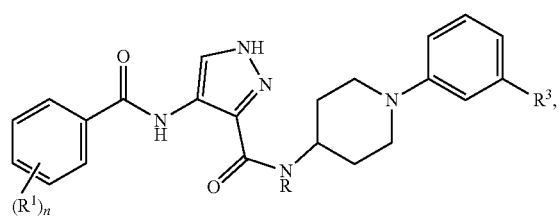
or a pharmaceutically acceptable salt, solvate, hydrate, tautomer, or stereoisomer thereof.
In certain embodiments, the compound of Formula (I) is of the formula:
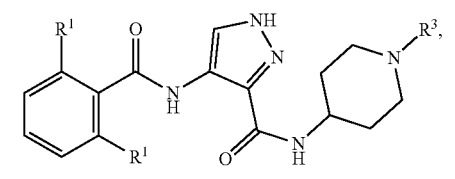
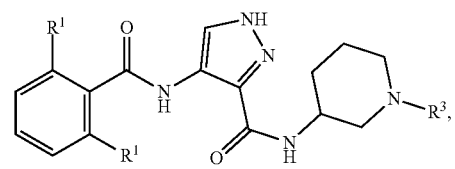
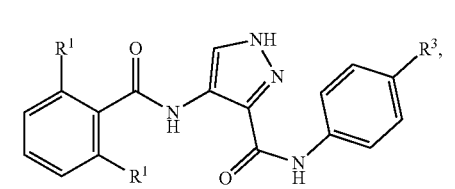
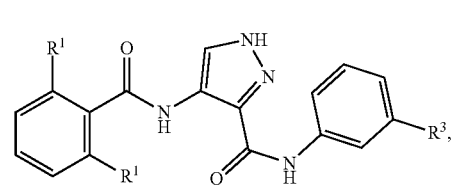
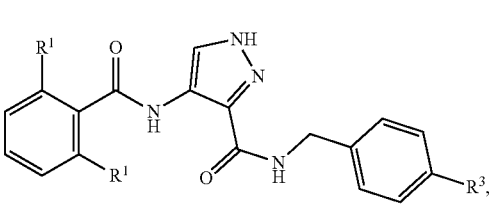
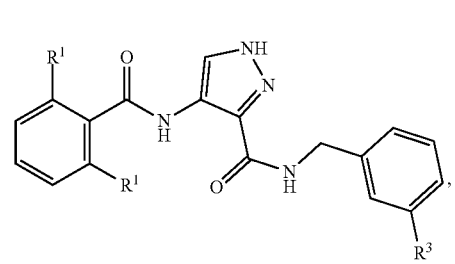
-continued
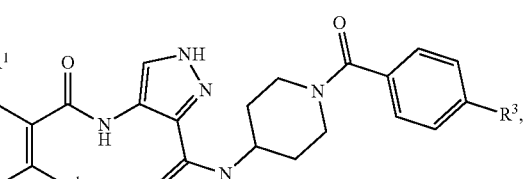
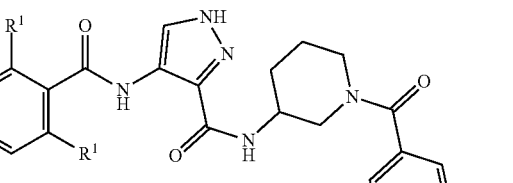
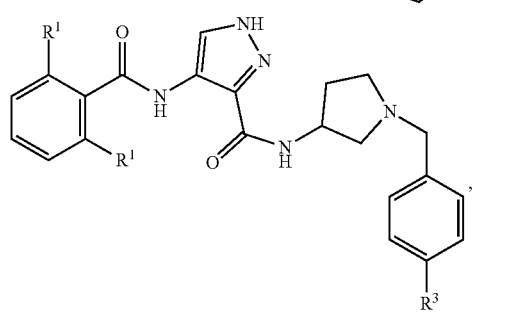
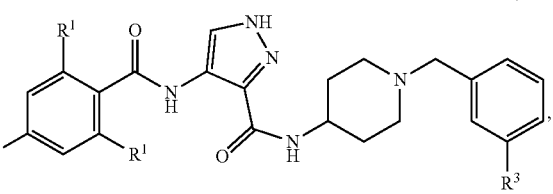
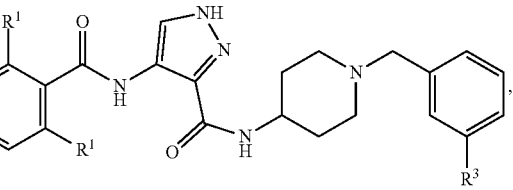

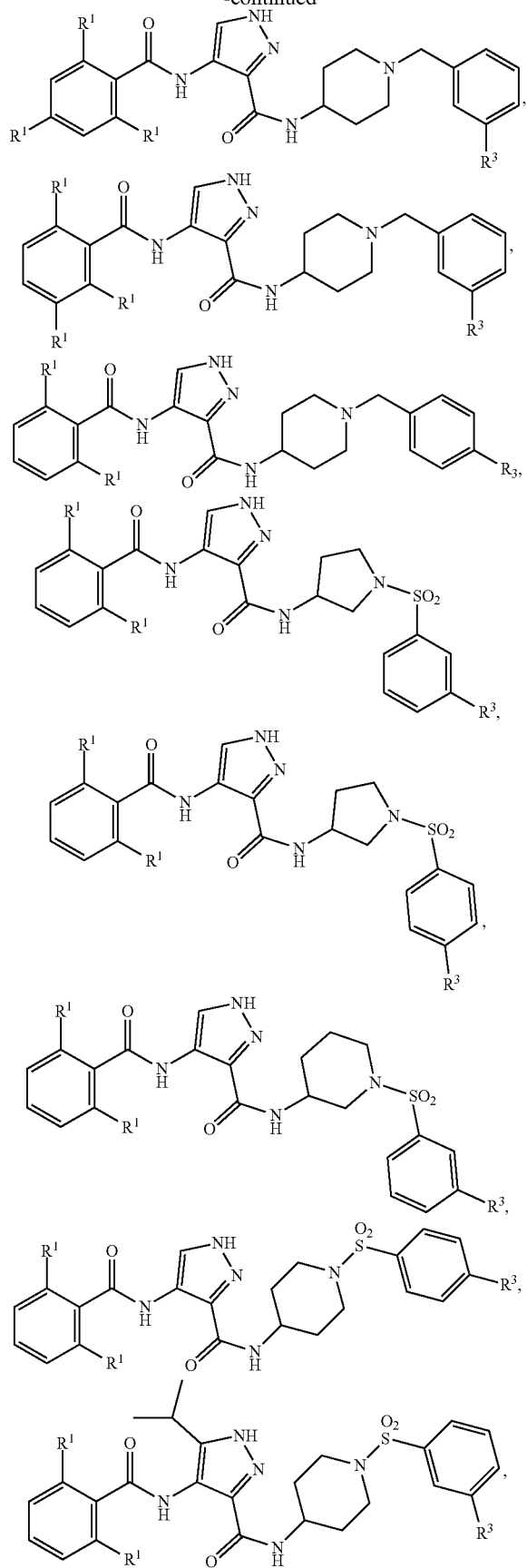
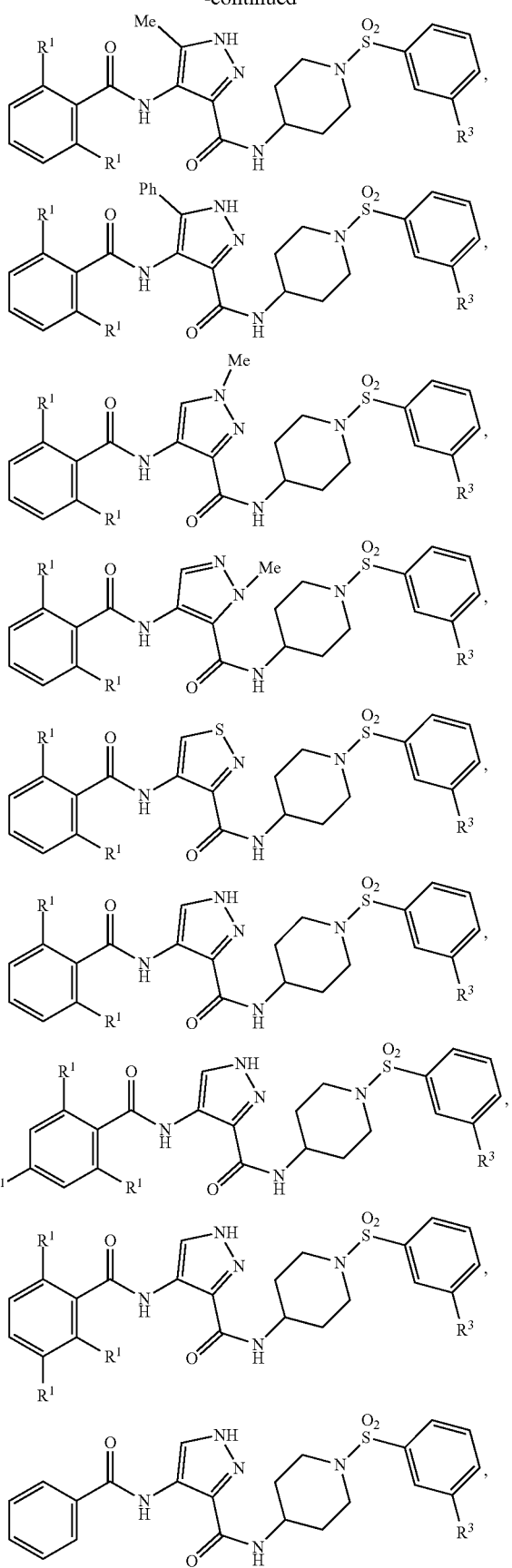

137
-continued
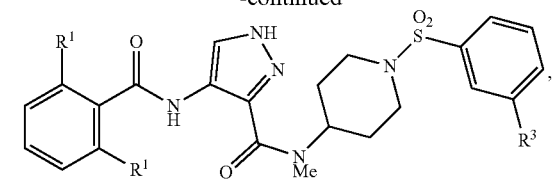
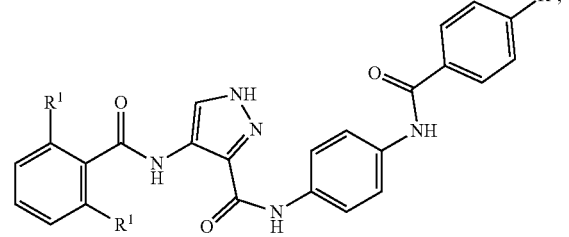
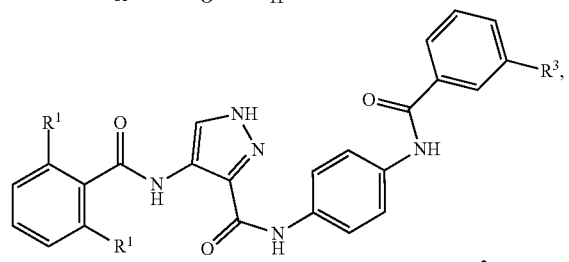
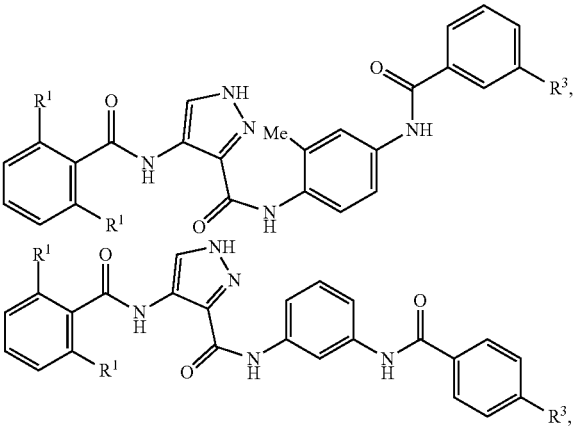
138
-continued
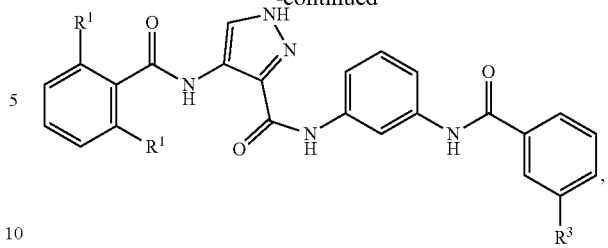
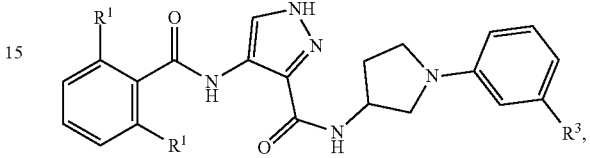
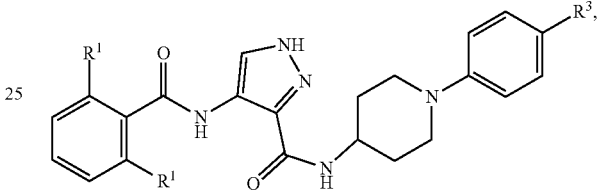
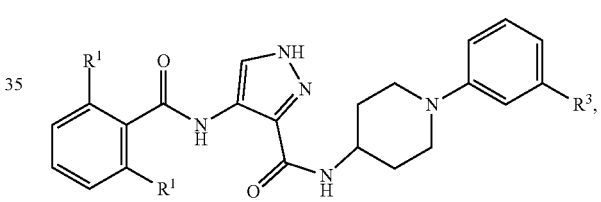
or a pharmaceutically acceptable salt, solvate, hydrate, tautomer, or stereoisomer thereof.
In certain embodiments, the compound of Formula (I) is of the formula:
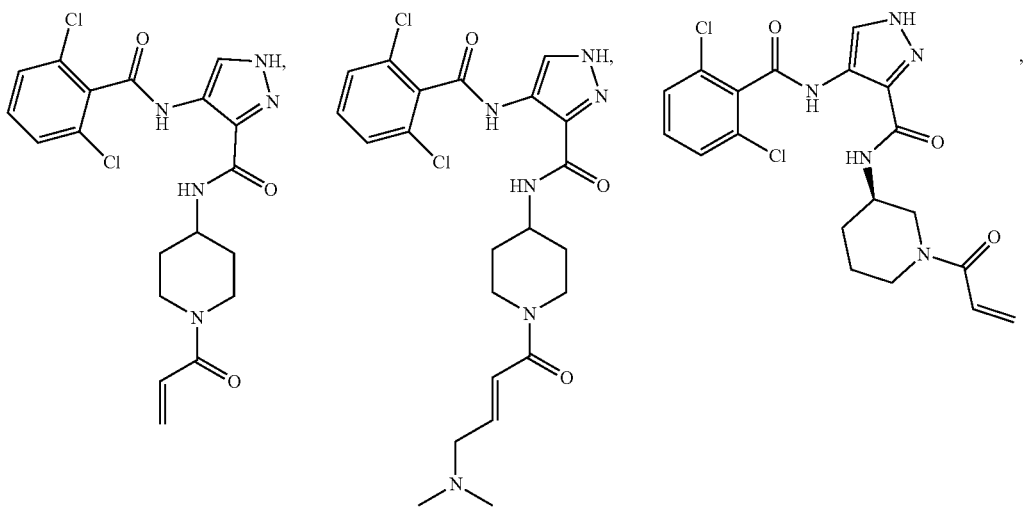

-continued
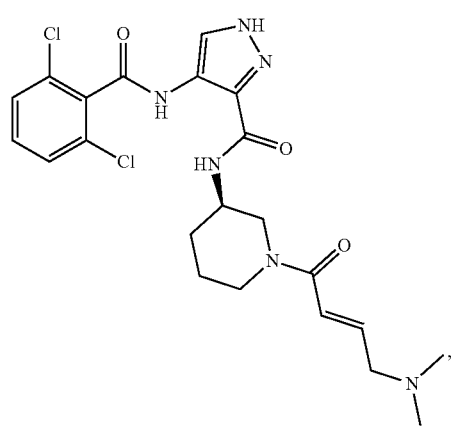
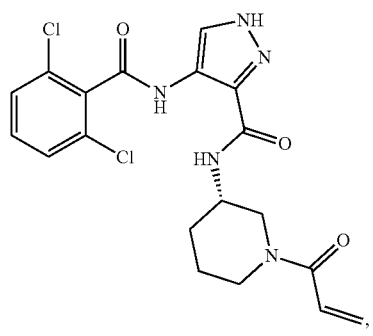
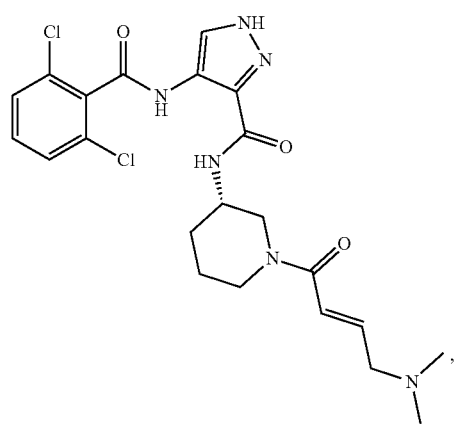
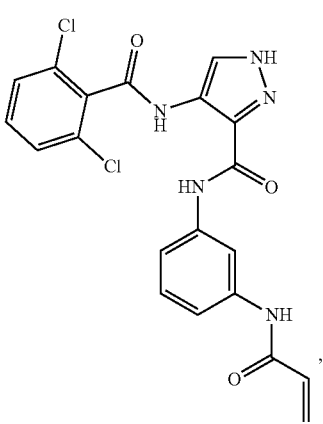
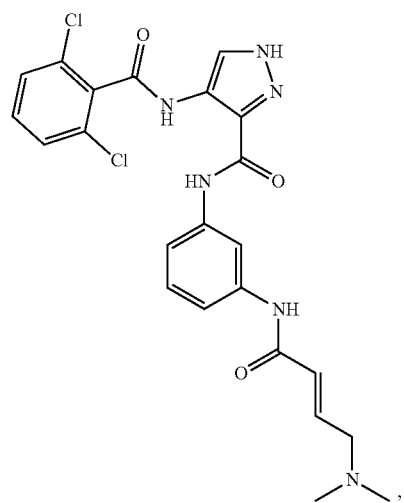
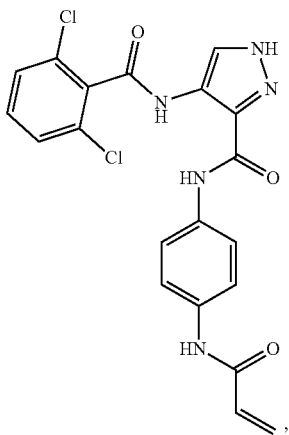
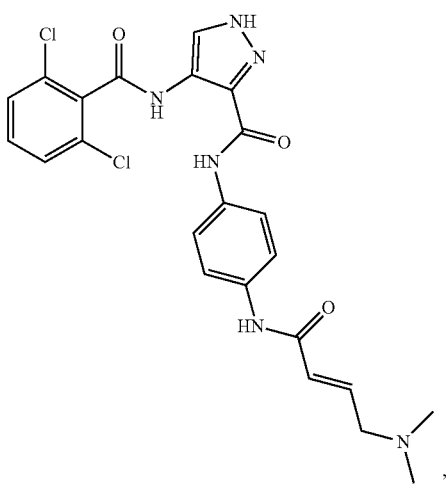

141
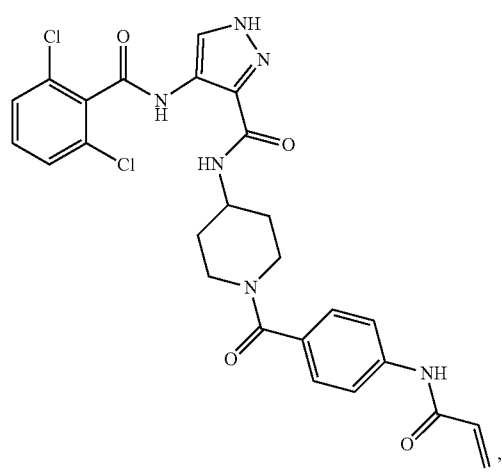
-continued
142
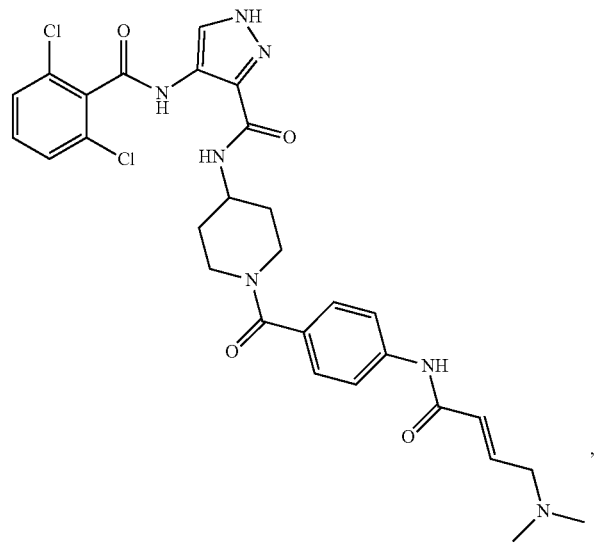
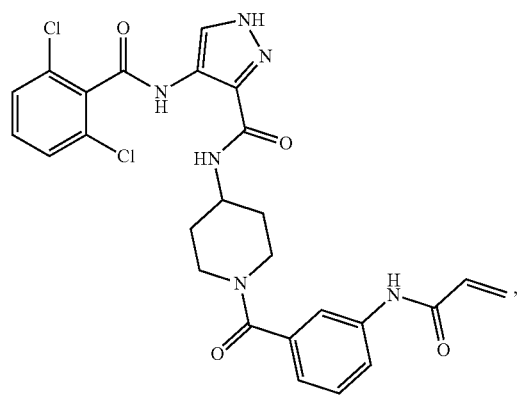
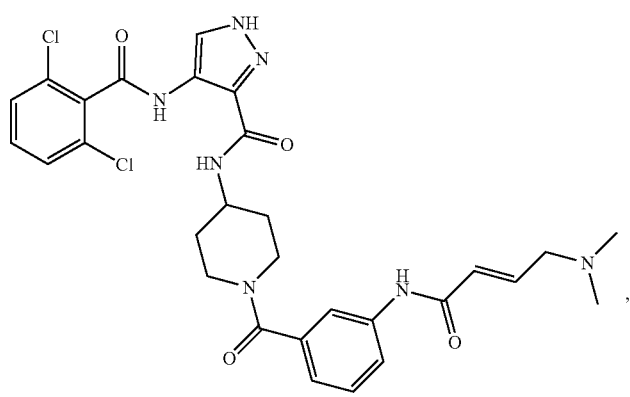
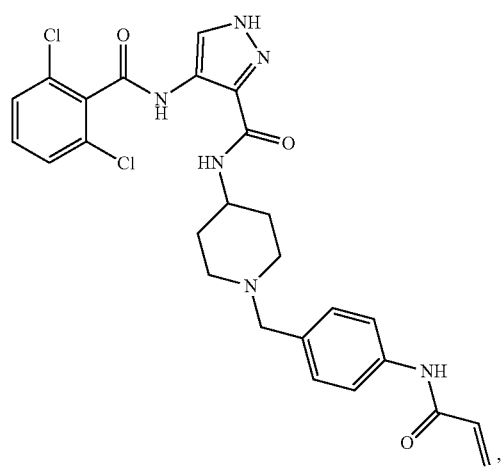
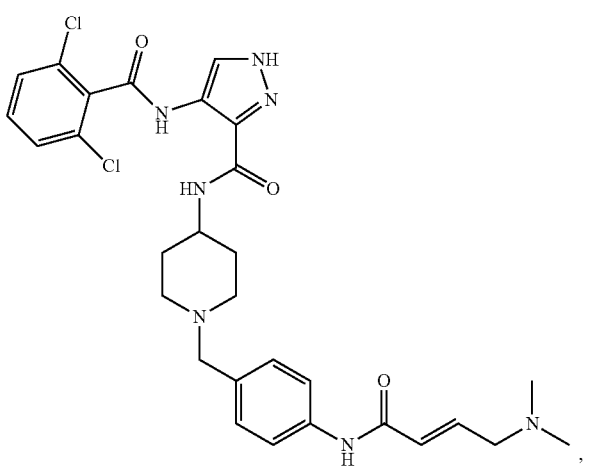

143
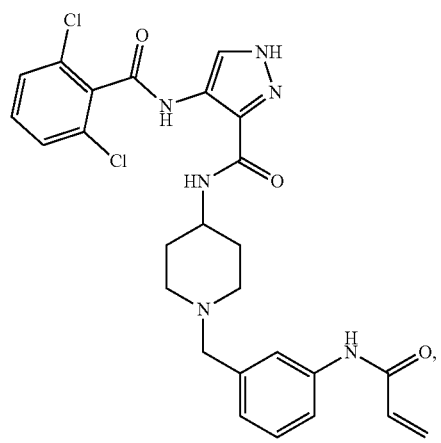
-continued
144
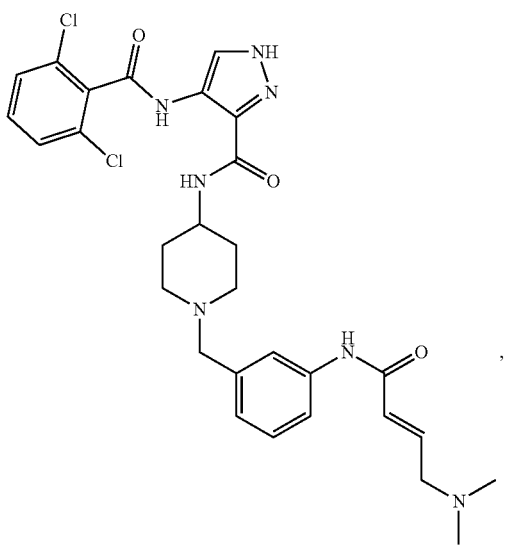
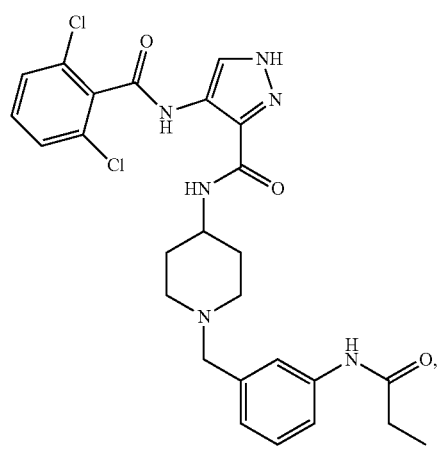
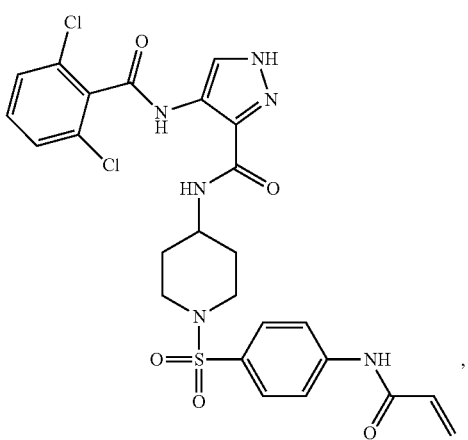
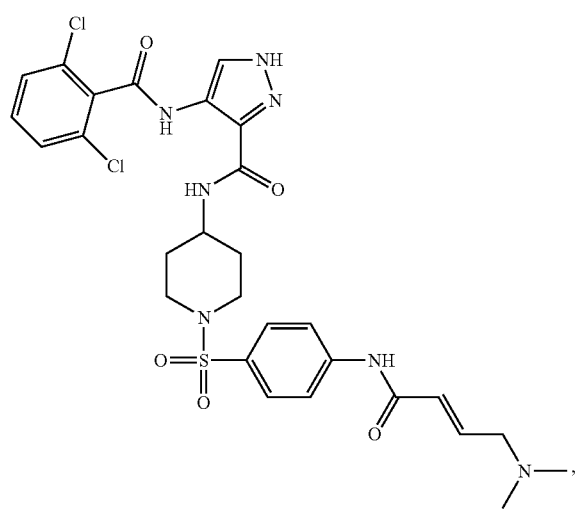
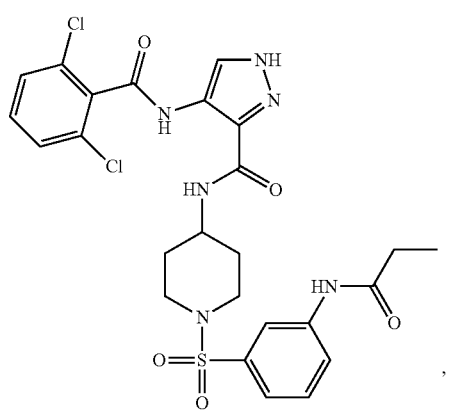

145
146
-continued
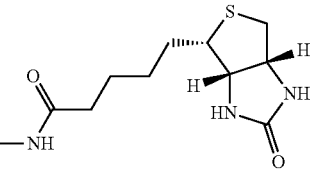
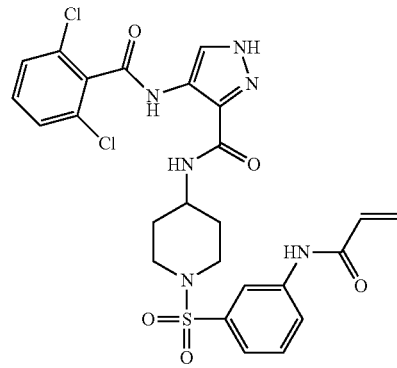
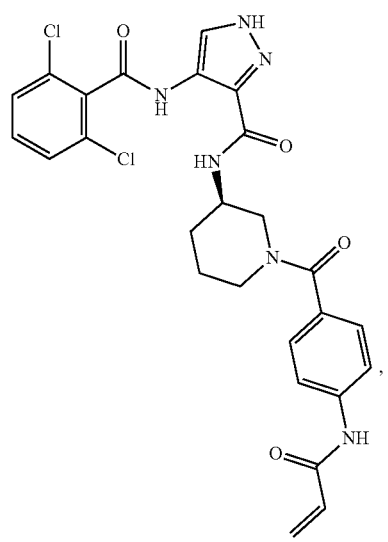
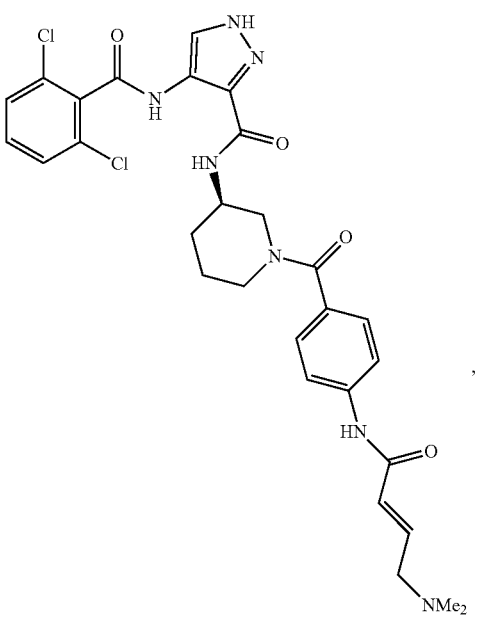
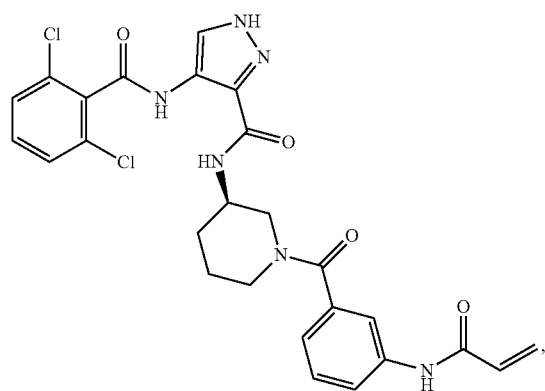
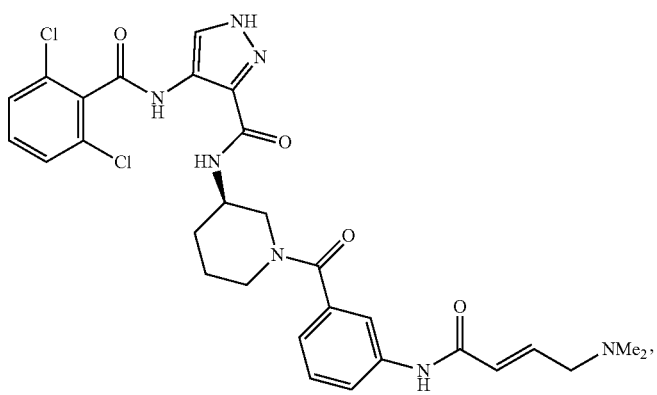

147
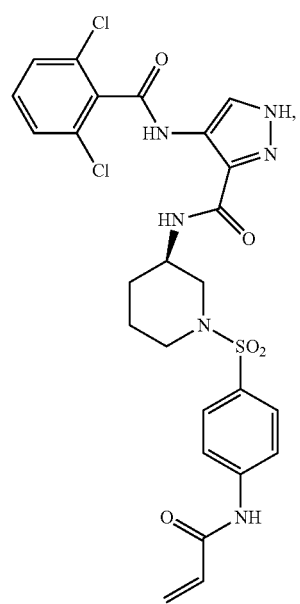
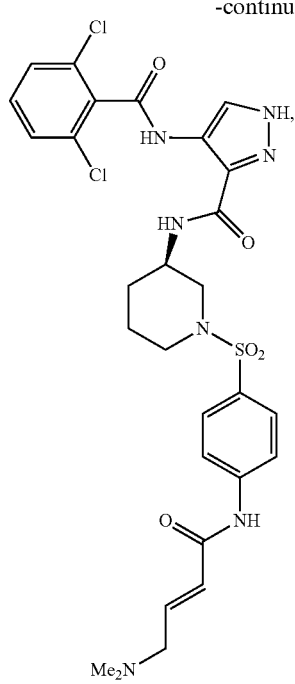
148
-continued
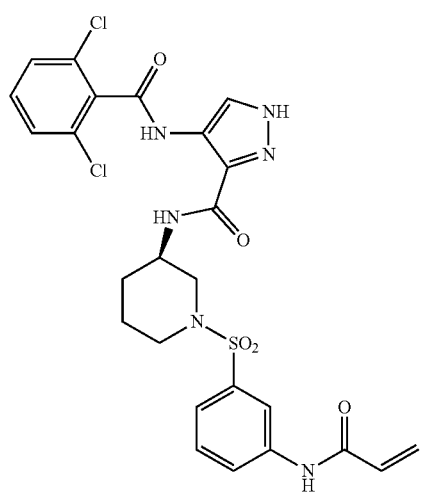
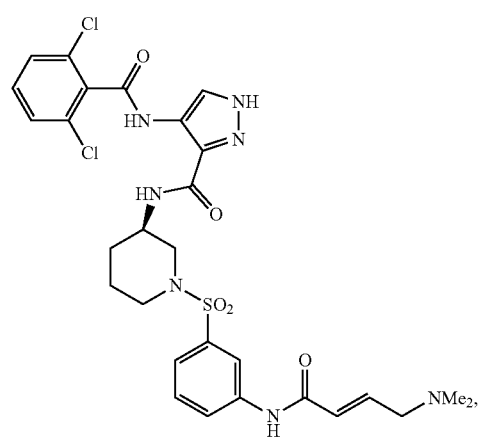
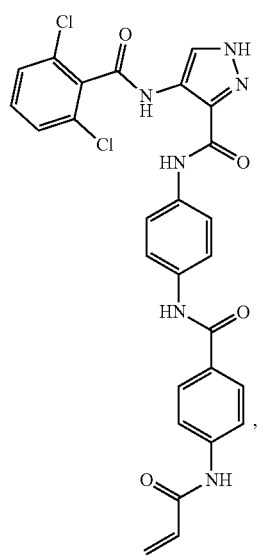
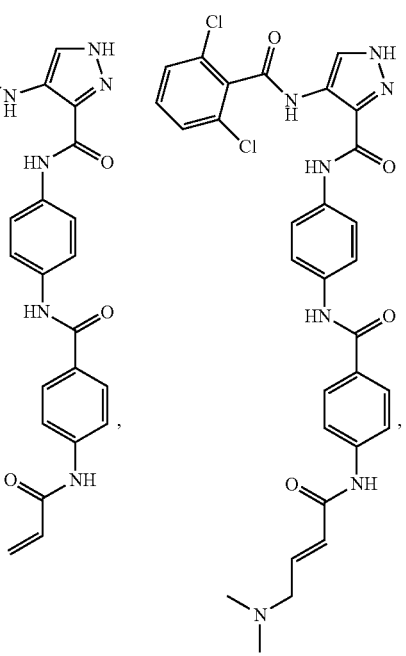

149
-continued
150
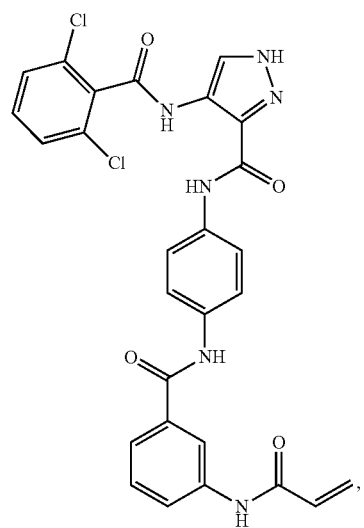 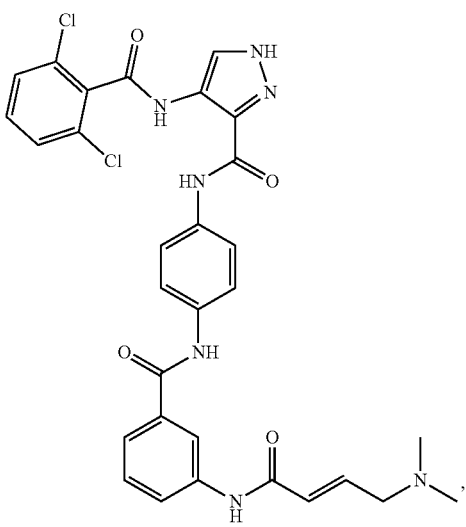 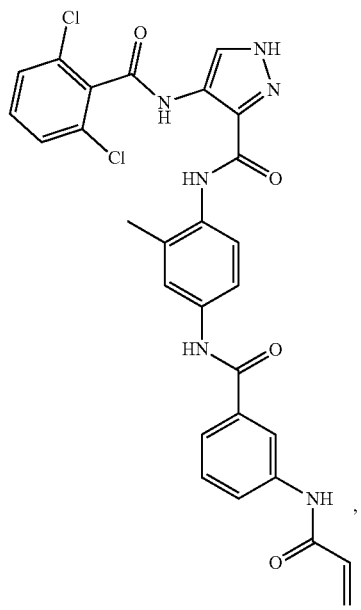
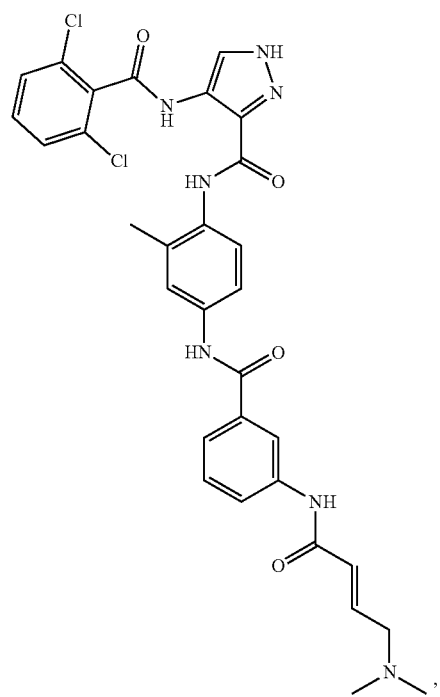 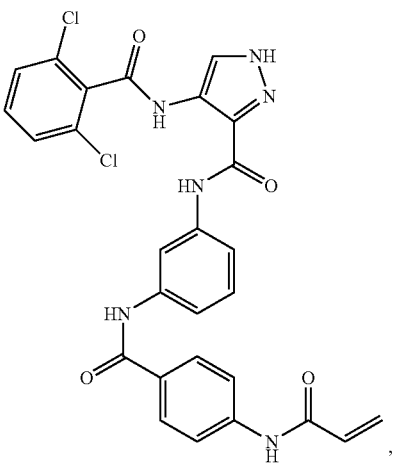

-continued
151
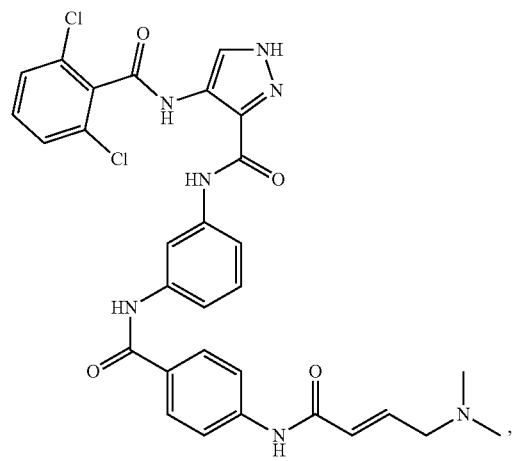
152
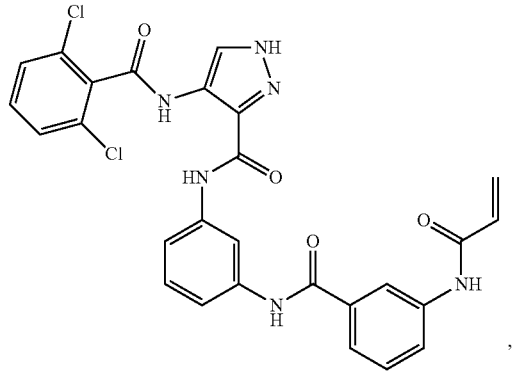
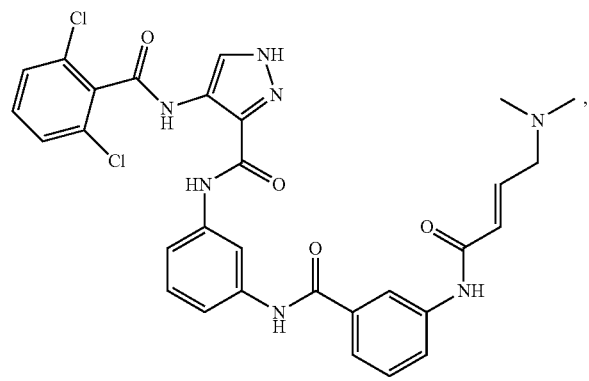
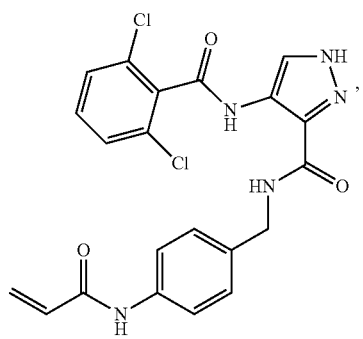
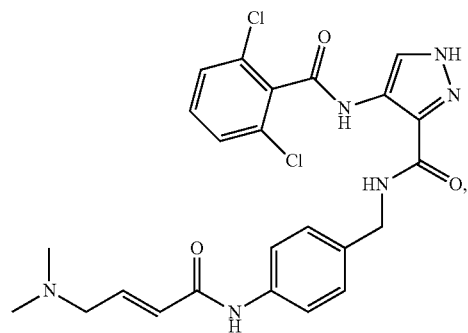
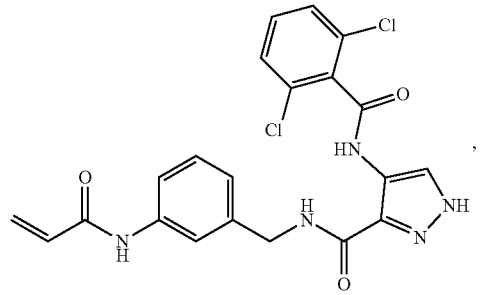
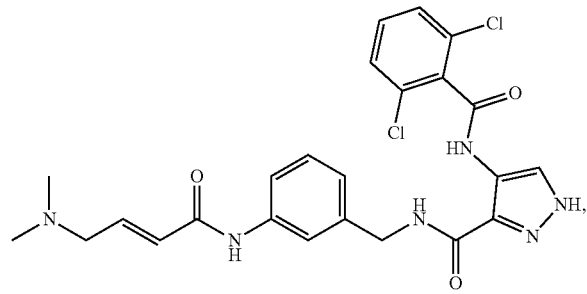
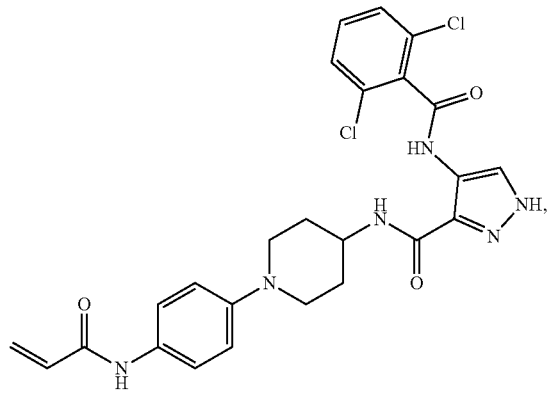

153
-continued
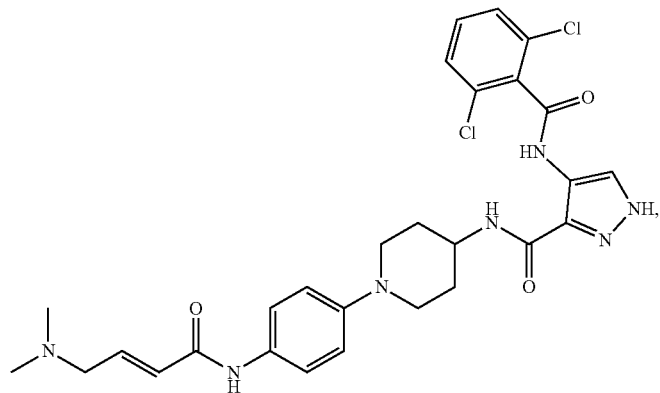
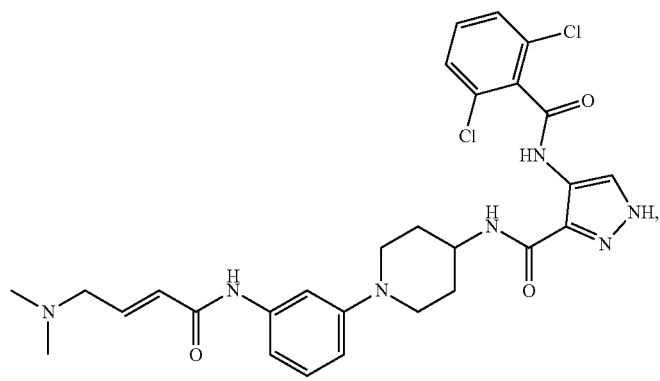
154
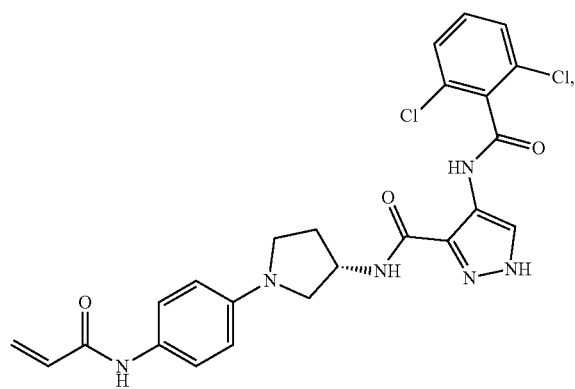
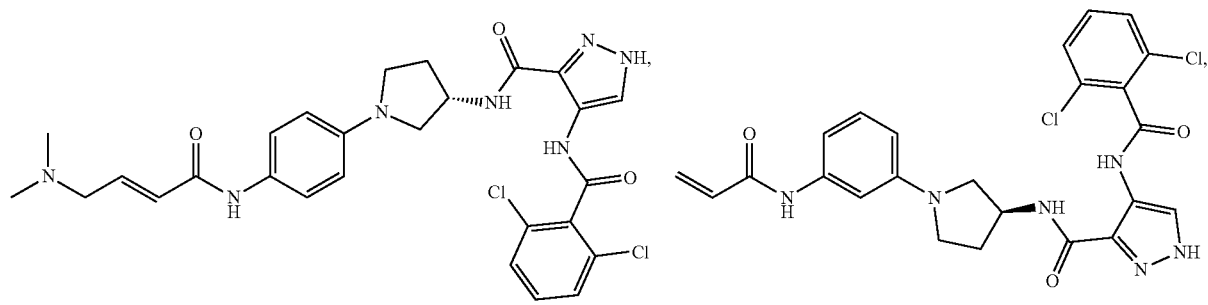

-continued
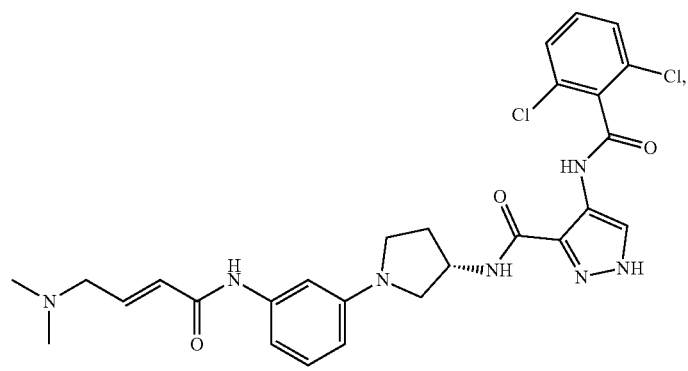
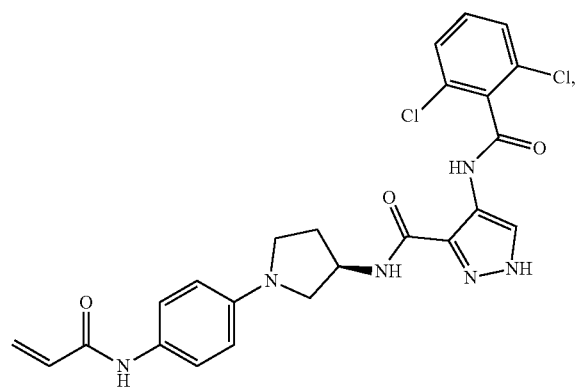
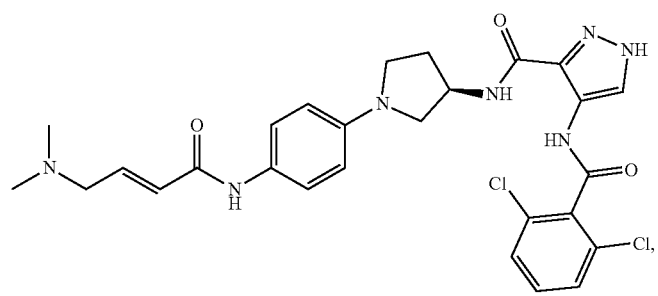
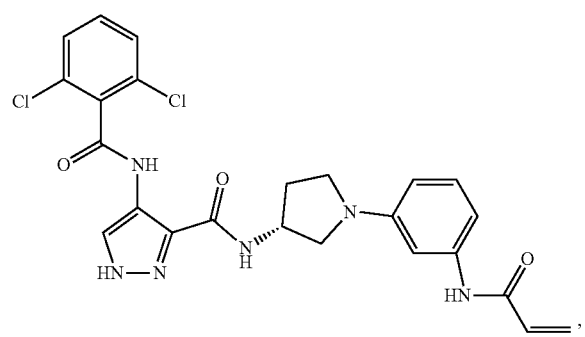
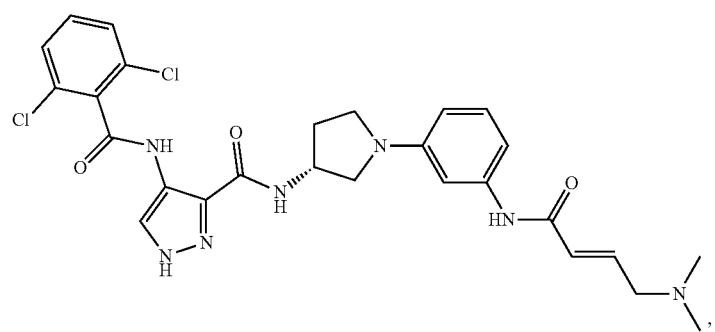

-continued
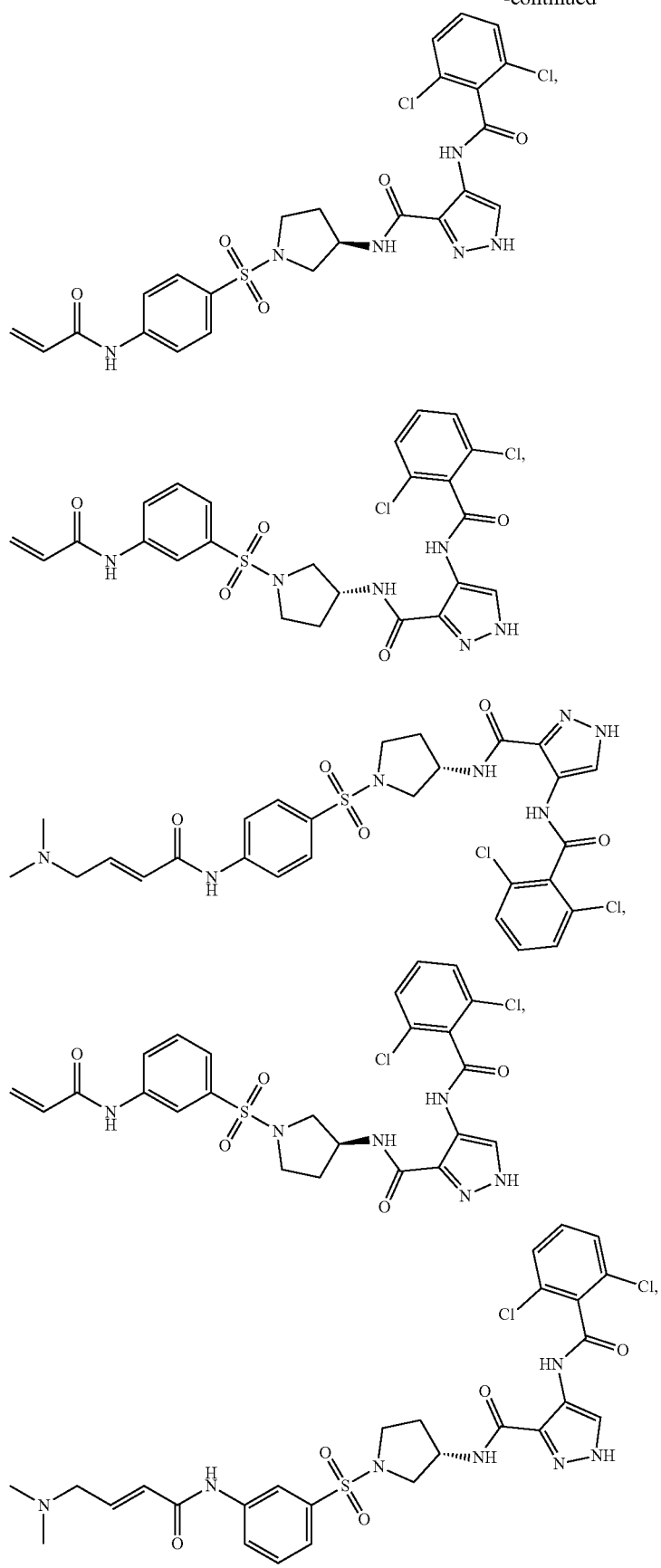

-continued
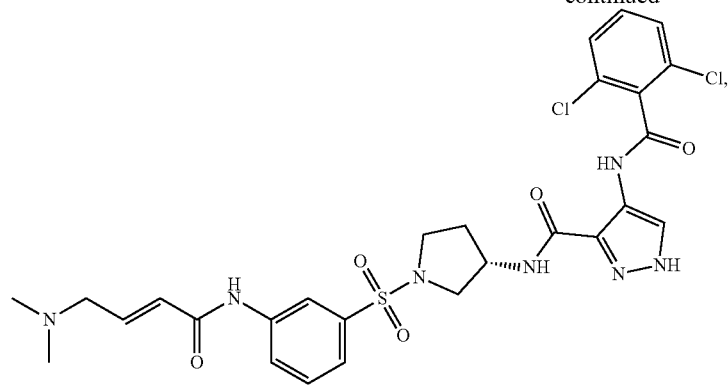
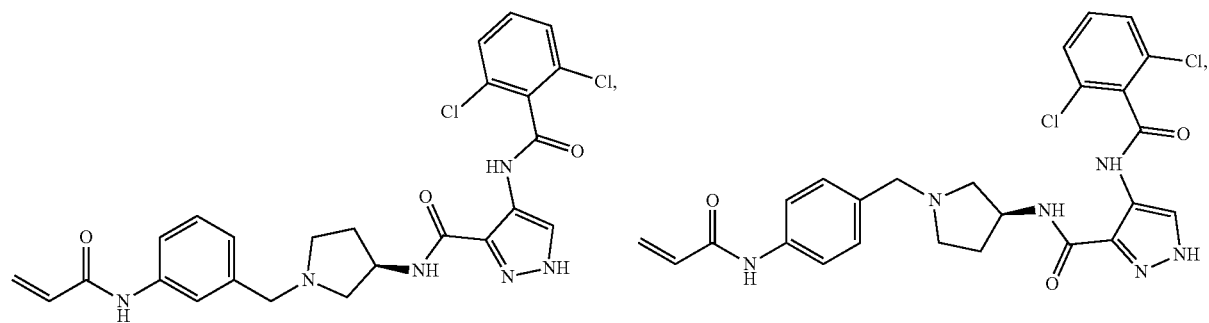
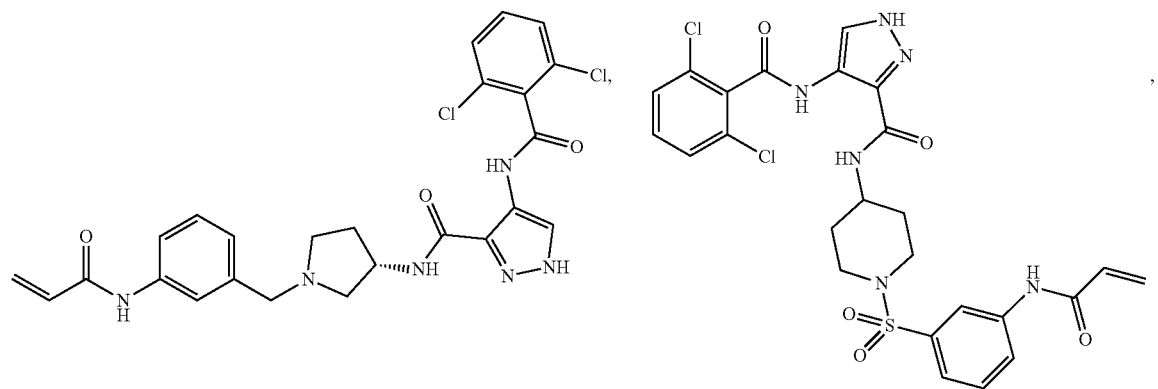
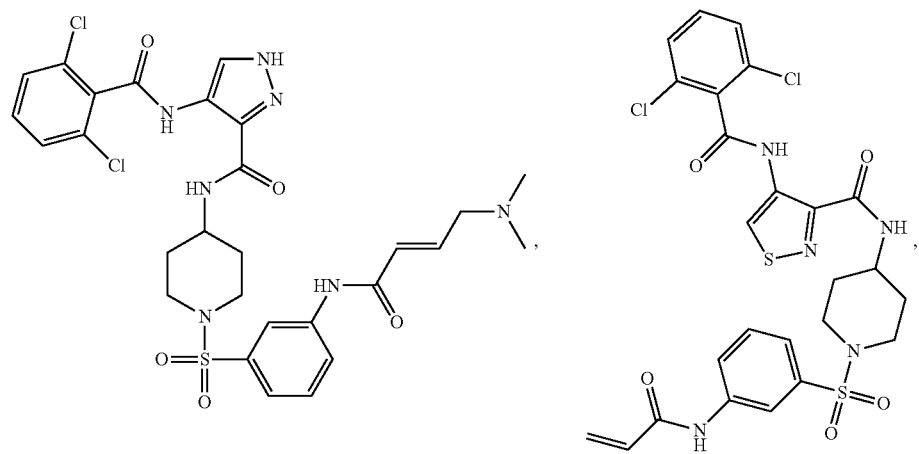

161 162
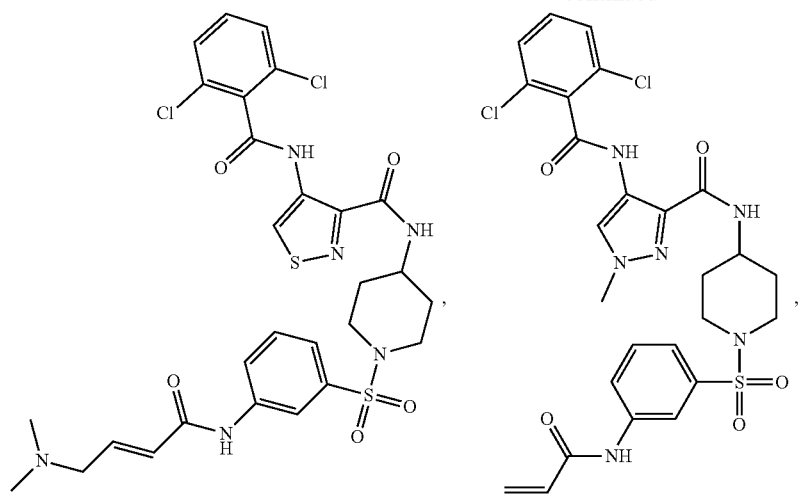
-continued
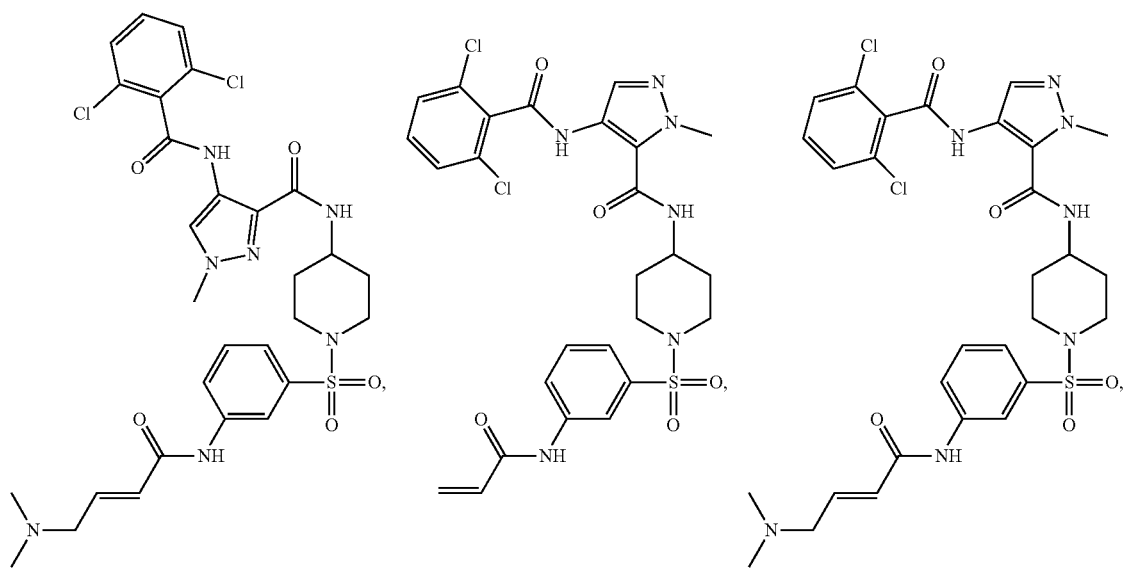
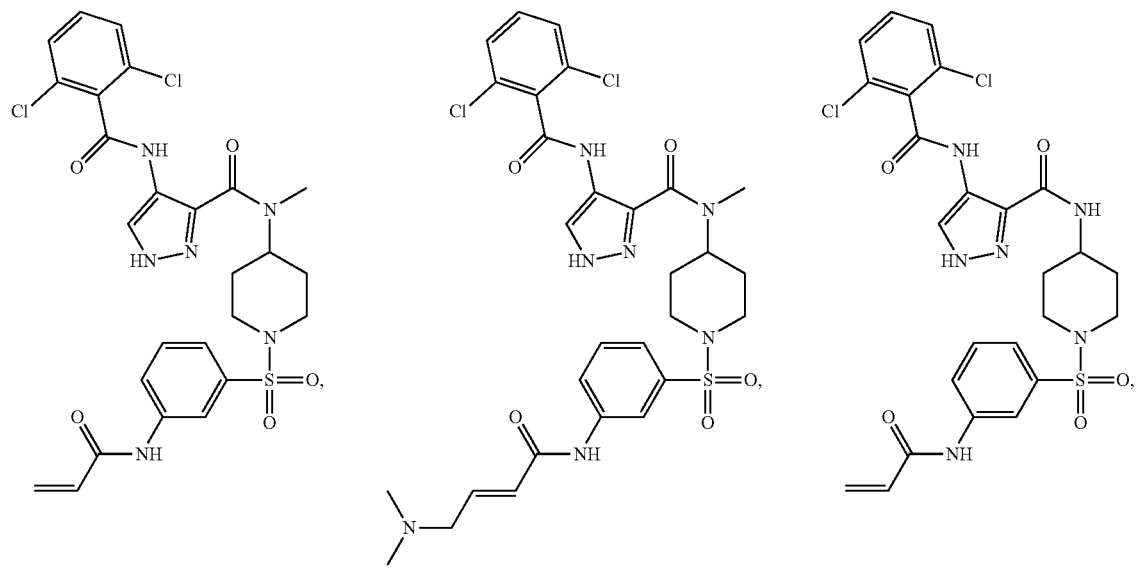

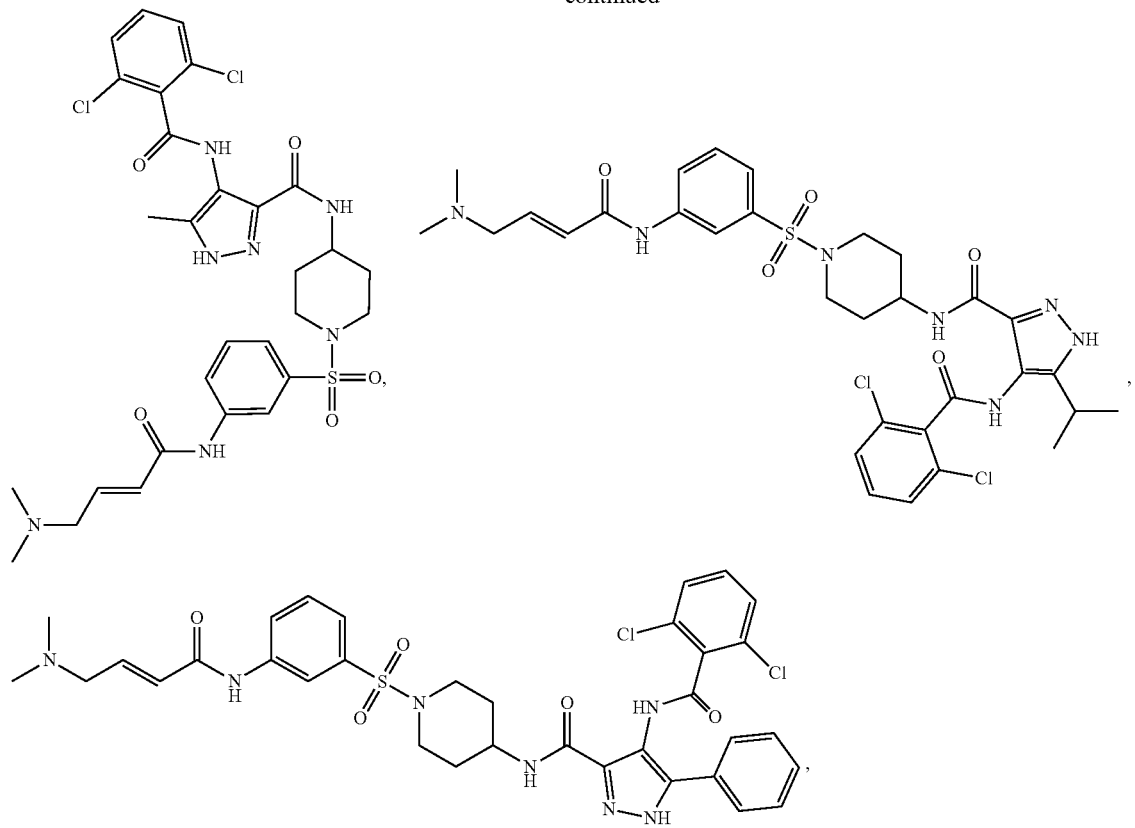

or a pharmaceutically acceptable salt, solvate, hydrate, tautomer, or stereoisomer thereof.

In certain embodiments, the compound of Formula (I') or (I) is a compound provided in any one of the Examples below. In certain embodiments, the compound of Formula (I') or (I) is a compound provided in Example 2 below.

In certain embodiments, the compound of Formula (I) is a compound provided in any one of the Examples below. In certain embodiments, the compound of Formula (I) is a compound provided in Example 2 below.

In certain embodiments, a compound described herein is a compound of Formula (I') or (I), or a pharmaceutically acceptable salt, solvate, hydrate, polymorph, co-crystal, tautomer, stereoisomer, isotopically labeled derivative, or prodrug thereof. In certain embodiments, a compound described herein is a compound of Formula (I') or (I), or a pharmaceutically acceptable salt thereof.

Certain compounds described herein bind, covalently modify, and/or inhibit a protein kinase. In certain embodiments, the compounds described herein irreversibly inhibit a protein kinase. In certain embodiments, the compounds described herein reversibly inhibit a protein kinase. In certain embodiments, the protein kinase is a CDK. In certain embodiments, the protein kinase is a TAIRE family kinase. In certain embodiments, the protein kinase is CDK14. In certain embodiments, the protein kinase is CDK15. In certain embodiments, the protein kinase is CDK16. In certain embodiments, the protein kinase is CDK17. In certain embodiments, the protein kinase is CDK18. In certain embodiments, the compounds described herein covalently bind to the protein kinase (e.g., CDK (e.g., CDK14)). In certain embodiments, the compounds described herein reversibly bind to the protein kinase (e.g., CDK (e.g., CDK14, CDK15, CDK16, CDK17, CDK18)). In certain embodiments, the compounds described herein non-reversibly bind to the protein kinase (e.g., CDK (e.g., CDK14, CDK15, CDK16, CDK17, CDK18)). In certain embodiments, the compounds described herein modulate the activity of a protein kinase (e.g., CDK (e.g., CDK14, CDK15, CDK16, CDK17, CDK18)). In certain embodiments, the compounds described herein inhibit the activity of a protein kinase (e.g., TAIRE family kinase (e.g., CDK (e.g., CDK14, CDK15, CDK16, CDK17, CDK18)). In certain embodiments, the compounds described herein reversibly inhibit the activity of a protein kinase (e.g., CDK (e.g., CDK14, CDK15, CDK16, CDK17, CDK18)).

The binding affinity of a compound described herein to a protein kinase (e.g., CDK (e.g., CDK14, CDK15, CDK16, CDK17, CDK18)) may be measured by the dissociation constant ($K_d$) value of an adduct of the compound and the protein kinase (e.g., CDK (e.g., CDK14, CDK15, CDK16, CDK17, CDK18)) using methods known in the art (e.g., isothermal titration calorimetry (ITC)). In certain embodiments, the $K_d$ value of the adduct is not more than about 100 μM, not more than about 10 μM, not more than about 1 uM, not more than about 100 nM, not more than about 10 nM, or not more than about 1 nM.

In certain embodiments, the activity of a protein kinase (e.g., CDK (e.g., CDK14, CDK15, CDK16, CDK17, CDK18)) is inhibited by a compound described herein. The inhibition of the activity of a protein kinase (e.g., TAIRE family kinase (e.g., CDK (e.g., CDK14, CDK15, CDK16, CDK17, CDK18)) by a compound described herein may be measured by determining the half maximal inhibitory concentration (IC$_{50}$) of the compound when the compound, or a pharmaceutical composition thereof, is contacted with the protein kinase (e.g., CDK (e.g., CDK14, CDK15, CDK16, CDK17, CDK18)). The IC$_{50}$ values may be obtained using methods known in the art (e.g., by a competition binding assay). In certain embodiments, the IC$_{50}$ value of a compound described herein is not more than about 1 mM, not more than about 100 μM, not more than about 10 μM, not more than about 1 μM, not more than about 100 nM, not more than about 10 nM, or not more than about 1 nM.

The compounds described herein may selectively modulate the activity of a protein kinase (e.g., CDK (e.g., CDK14, CDK15, CDK16, CDK17, CDK18)). In certain embodiments, the compounds selectively increase the activity of a protein kinase (e.g., CDK (e.g., CDK14, CDK15, CDK16, CDK17, CDK18)). In certain embodiments, the compounds selectively inhibit the activity of a protein kinase (e.g., CDK (e.g., CDK14, CDK15, CDK16, CDK17, CDK18)). In certain embodiments, the compounds inhibit the activity of two or more protein kinases (e.g., CDK (e.g., CDK14, CDK15, CDK16, CDK17, CDK18)) to the same extent. In certain embodiments, the compounds increase the activity of two or more protein kinases (e.g., CDK (e.g., CDK14, CDK15, CDK16, CDK17, CDK18)) to the same extent.

The selectivity of a compound described herein in inhibiting the activity of a first protein kinase (e.g., CDK) over a second protein kinase may be measured by the quotient of the IC$_{50}$ value of the compound in inhibiting the activity of the second protein kinase (e.g., CDK) over the IC$_{50}$ value of the compound in inhibiting the activity of the first protein kinase (e.g., CDK). The selectivity of a compound described herein in modulating the activity of a first protein kinase (e.g., CDK) over a second protein kinase may also be measured by the quotient of the K$_d$ value of an adduct of the compound and the second protein kinase over the K$_d$ value of an adduct of the compound and the first protein kinase (e.g., CDK). In certain embodiments, the selectivity is at least about 1-fold, at least about 3-fold, at least about 10-fold, at least about 30-fold, at least about 100-fold, at least about 300-fold, at least about 1,000-fold, at least about 3,000-fold, at least about 10,000-fold, at least about 30,000-fold, or at least about 100,000-fold.

It is expected that the compounds described herein may be useful in treating and/or preventing diseases associated with aberrant activity (e.g., increased activity, undesired activity, abnormal activity) of a protein kinase (e.g., CDK (e.g., CDK14, CDK15, CDK16, CDK17, CDK18)). It is known in the art that protein kinases are implicated in a wide range of diseases and conditions, such as proliferative diseases, metabolic disorders, autoimmune diseases, neurological diseases, and male reproduction. Therefore, the compounds described herein are expected to be useful in treating and/or preventing diseases (e.g., proliferative diseases, metabolic disorders, autoimmune diseases, and neurological diseases). The compounds described herein are also expected to be useful in male contraception in a subject (e.g., a human male) in need thereof.

Pharmaceutical Compositions, Kits, and Administration

The present disclosure also provides pharmaceutical compositions comprising a compound described herein and optionally a pharmaceutically acceptable excipient. In certain embodiments, a compound described herein is a compound of Formula (I') or (I), or a pharmaceutically acceptable salt thereof, and a pharmaceutically acceptable excipient.

In certain embodiments, the compound described herein is provided in an effective amount in the pharmaceutical composition. In certain embodiments, the effective amount is a therapeutically effective amount. In certain embodiments, the effective amount is a prophylactically effective amount. In certain embodiments, a therapeutically effective amount is an amount effective for inhibiting the aberrant activity of a protein kinase (e.g., CDK (e.g., CDK14, CDK15, CDK16, CDK17, CDK18)). In certain embodiments, a therapeutically effective amount is an amount effective for treating a disease (e.g., a disease associated with aberrant activity of a CDK (e.g., proliferative disease, a metabolic disorder, autoimmune disease, or neurological disease)). In certain embodiments, a therapeutically effective amount is an amount effective for inhibiting the aberrant activity of a CDK (e.g., CDK14, CDK15, CDK16, CDK17, CDK18)) and treating a disease (e.g., a disease associated with aberrant activity of a protein kinase (e.g., CDK (e.g., CDK14, CDK15, CDK16, CDK17, CDK18)) (e.g., proliferative disease, a metabolic disorder, autoimmune disease, or neurological disease))). In certain embodiments, a therapeutically effective amount is an amount effective for inducing apoptosis of a cell (e.g., cell in vivo or in vitro). In certain embodiments, a prophylactically effective amount is an amount effective for inhibiting the aberrant activity of a protein kinase (e.g., CDK (e.g., CDK14, CDK15, CDK16, CDK17, CDK18)). In certain embodiments, a prophylactically effective amount is an amount effective for preventing or keeping a subject in need thereof in remission of a disease (e.g., a disease associated with aberrant activity of a CDK (e.g., proliferative disease, a metabolic disorder, autoimmune disease, or neurological disease)). In certain embodiments, a prophylactically effective amount is an amount effective for inhibiting the aberrant activity of a CDK, and preventing or keeping a subject in need thereof in remission of a disease (e.g., a disease associated with aberrant activity of a CDK (e.g., proliferative disease, a metabolic disorder, autoimmune disease, or neurological disease)).

In certain embodiments, the effective amount is an amount effective for inhibiting the activity of a protein kinase (e.g., CDK (e.g., CDK14, CDK15, CDK16, CDK17, CDK18)) by at least 10%, at least 20%, at least 30%, at least 40%, at least 50%, at least 60%, at least 70%, at least 80%, at least 90%, at least 95%, or at least 98%. In certain embodiments, the effective amount is an amount effective for inhibiting the activity of a CDK (e.g., CDK14, CDK15, CDK16, CDK17, CDK18)) by not more than 10%, not more than 20%, not more than 30%, not more than 40%, not more than 50%, not more than 60%, not more than 70%, not more than 80%, not more than 90%, not more than 95%, or not more than 98%.

In certain embodiments, the subject is an animal. The animal may be of either sex and may be at any stage of development. In certain embodiments, the subject described herein is a human. In certain embodiments, the subject is a non-human animal. In certain embodiments, the subject is a mammal. In certain embodiments, the subject is a non-human mammal. In certain embodiments, the subject is a domesticated animal, such as a dog, cat, cow, pig, horse, sheep, or goat. In certain embodiments, the subject is a companion animal, such as a dog or cat. In certain embodiments, the subject is a livestock animal, such as a cow, pig, horse, sheep, or goat. In certain embodiments, the subject is a zoo animal. In another embodiment, the subject is a research animal, such as a rodent (e.g., mouse, rat), dog, pig, or non-human primate. In certain embodiments, the animal is a genetically engineered animal. In certain embodiments, the animal is a transgenic animal (e.g., transgenic mice and transgenic pigs). In certain embodiments, the subject is a fish or reptile.

In certain embodiments, the cell being contacted with a compound or composition described herein is in vitro. In certain embodiments, the cell being contacted with a compound or composition described herein is in vivo.

Pharmaceutical compositions described herein can be prepared by any method known in the art of pharmacology. In general, such preparatory methods include bringing the compound described herein (i.e., the "active ingredient") into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as one-half or one-third of such a dosage.

Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween® 20), polyoxyethylene sorbitan (Tween® 60), polyoxyethylene sorbitan monooleate (Tween® 80), sorbitan monopalmitate (Span® 40), sorbitan monostearate (Span® 60), sorbitan tristearate (Span® 65), glyceryl monooleate, sorbitan monooleate (Span® 80), polyoxyethylene esters (e.g., polyoxyethylene monostearate (Myrj® 45), polyoxyethylene hydrogenated castor oil, polyethoxylated castor oil, polyoxymethylene stearate, and Solutol*), sucrose fatty acid esters, polyethylene glycol fatty acid esters (e.g., Cremophor®), polyoxyethylene ethers, (e.g., polyoxyethylene lauryl ether (Brij® 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic® F-68, poloxamer P-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant® Plus, Phenonip®, methylparaben, Germall® 115, Germaben® II, Neolone®, Kdthon®, and Euxyl®.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates described herein are mixed with solubilizing agents such as Cremophor®, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

Compositions for rectal or vaginal administration are typically suppositories which can be prepared by mixing the conjugates described herein with suitable non-irritating excipients or carriers such as cocoa butter, polyethylene glycol, or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating agents which can be used include polymeric substances and waxes.

Dosage forms for topical and/or transdermal administration of a compound described herein may include ointments, pastes, creams, lotions, gels, powders, solutions, sprays, inhalants, and/or patches. Generally, the active ingredient is admixed under sterile conditions with a pharmaceutically acceptable carrier or excipient and/or any needed preservatives and/or buffers as can be required. Additionally, the present disclosure contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices. Intradermal compositions can be administered by devices which limit the effective penetration length of a needle into the skin. Alternatively or additionally, conventional syringes can be used in the classical mantoux method of intradermal administration. Jet injection devices which deliver liquid formulations to the dermis via a liquid jet injector and/or via a needle which pierces the stratum corneum and produces a jet which reaches the dermis are suitable. Ballistic powder/particle delivery devices which use compressed gas to accelerate the compound in powder form through the outer layers of the skin to the dermis are suitable.

Formulations suitable for topical administration include, but are not limited to, liquid and/or semi-liquid preparations such as liniments, lotions, oil-in-water and/or water-in-oil emulsions such as creams, ointments, and/or pastes, and/or solutions and/or suspensions. Topically administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition described herein can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers, or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions described herein formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition described herein. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient, and may comprise one or more of the additional ingredients described herein. A pharmaceutical composition described herein can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition described herein can be prepared, packaged, and/or sold in a formulation for ophthalmic administration. Such formulations may, for example, be in the form of eye drops including, for example, a 0.1-1.0% (w/w) solution and/or suspension of the active ingredient in an aqueous or oily liquid carrier or excipient. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are also contemplated as being within the scope of this disclosure.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form for ease of administration and uniformity of dosage. It will be understood, however, that the total daily usage of the compositions described herein will be decided by a physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, the compound or pharmaceutical composition described herein is suitable for topical administration to the eye of a subject.

The exact amount of a compound required to achieve an effective amount will vary from subject to subject, depending, for example, on species, age, and general condition of a subject, severity of the side effects or disorder, identity of the particular compound, mode of administration, and the like. An effective amount may be included in a single dose (e.g., single oral dose) or multiple doses (e.g., multiple oral doses). In certain embodiments, when multiple doses are administered to a subject or applied to a biological sample, tissue, or cell, any two doses of the multiple doses include different or substantially the same amounts of a compound described herein. In certain embodiments, when multiple doses are administered to a subject or applied to a biological sample, tissue, or cell, the frequency of administering the multiple doses to the subject or applying the multiple doses to the biological sample, tissue, or cell is three doses a day, two doses a day, one dose a day, one dose every other day, one dose every third day, one dose every week, one dose every two weeks, one dose every three weeks, or one dose every four weeks. In certain embodiments, the frequency of administering the multiple doses to the subject or applying the multiple doses to the biological sample, tissue, or cell is one dose per day. In certain embodiments, the frequency of administering the multiple doses to the subject or applying the multiple doses to the biological sample, tissue, or cell is two doses per day. In certain embodiments, the frequency of administering the multiple doses to the subject or applying the multiple doses to the biological sample, tissue, or cell is three doses per day. In certain embodiments, when multiple doses are administered to a subject or applied to a biological sample, tissue, or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, tissue, or cell. In certain embodiments, the duration between the first dose and last dose of the multiple doses is three months, six months, or one year. In certain embodiments, the duration between the first dose and last dose of the multiple doses is the lifetime of the subject, tissue, or cell. In certain embodiments, a dose (e.g., a single dose, or any dose of multiple doses) described herein includes independently between 0.1 µg and 1 µg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of a compound described herein. In certain embodiments, a dose described herein includes independently between 1 mg and 3 mg, inclusive, of a compound described herein. In certain embodiments, a dose described herein includes independently between 3 mg and 10 mg, inclusive, of a compound described herein. In certain embodiments, a dose described herein includes independently between 10 mg and 30 mg, inclusive, of a compound described herein. In certain embodiments, a dose described herein includes independently between 30 mg and 100 mg, inclusive, of a compound described herein.

Dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

A compound or composition, as described herein, can be administered in combination with one or more additional pharmaceutical agents (e.g., therapeutically and/or prophylactically active agents). The compounds or compositions can be administered in combination with additional pharmaceutical agents that improve their activity (e.g., activity (e.g., potency and/or efficacy) in treating a disease in a subject in need thereof, in preventing a disease in a subject in need thereof, in inhibiting the activity of a protein kinase (e.g., CDK (e.g., CDK14, CDK15, CDK16, CDK17, CDK18)) in a subject, biological sample, tissue, or cell), improve bioavailability, improve safety, reduce drug resistance, reduce and/or modify metabolism, inhibit excretion, and/or modify distribution in a subject, biological sample, tissue, or cell. It will also be appreciated that the therapy employed may achieve a desired effect for the same disorder, and/or it may achieve different effects. In certain embodiments, a pharmaceutical composition described herein including a compound described herein and an additional pharmaceutical agent shows a synergistic effect that is absent in a pharmaceutical composition including one of the compound and the additional pharmaceutical agent, but not both.

The compound or composition can be administered concurrently with, prior to, or subsequent to one or more additional pharmaceutical agents, which may be useful as, e.g., combination therapies. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful for treating and/or preventing a disease (e.g., proliferative disease, metabolic disorder, autoimmune disease, or neurological disease). Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the compound described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

The additional pharmaceutical agents include, but are not limited to, anti-proliferative agents, anti-cancer agents, anti-angiogenesis agents, anti-inflammatory agents, immunosuppressants, anti-bacterial agents, anti-viral agents, cardiovascular agents, cholesterol-lowering agents, anti-diabetic agents, anti-allergic agents, contraceptive agents, pain-relieving agents, and a combination thereof. In certain embodiments, the additional pharmaceutical agent is an anti-proliferative agent (e.g., anti-cancer agent). In certain embodiments, the additional pharmaceutical agent is an anti-leukemia agent. In certain embodiments, the additional pharmaceutical agent is ABITREXATE (methotrexate), ADE, Adriamycin RDF (doxorubicin hydrochloride), Ambochlorin (chlorambucil), ARRANON (nelarabine), ARZERRA (ofatumumab), BOSULIF (bosutinib), BUSULFEX (busulfan), CAMPATH (alemtuzumab), CERUBIDINE (daunorubicin hydrochloride), CLAFEN (cyclophosphamide), CLOFAREX (clofarabine), CLOLAR (clofarabine), CVP, CYTOSAR-U (cytarabine), CYTOXAN (cyclophosphamide), ERWINAZE (Asparaginase Erwinia Chrysanthemi), FLUDARA (fludarabine phosphate), FOLEX (methotrexate), FOLEX PFS (methotrexate), GAZYVA (obinutuzumab), GLEEVEC (imatinib mesylate), Hyper-CVAD, ICLUSIG (ponatinib hydrochloride), IMBRUVICA (ibrutinib), LEUKERAN (chlorambucil), LINFOLIZIN (chlorambucil), MARQIBO (vincristine sulfate liposome), METHOTREXATE LPF (methorexate), MEXATE (methotrexate), MEXATE-AQ (methotrexate), mitoxantrone hydrochloride, MUSTARGEN (mechlorethamine hydrochloride), MYLERAN (busulfan), NEOSAR (cyclophosphamide), ONCASPAR (Pegaspargase), PURINETHOL (mercaptopurine), PURIXAN (mercaptopurine), Rubidomycin (daunorubicin hydrochloride), SPRYCEL (dasatinib), SYNRIBO (omacetaxine mepesuccinate), TARABINE PFS (cytarabine), TASIGNA (nilotinib), TREANDA (bendamustine hydrochloride), TRISENOX (arsenic trioxide), VINCASAR PFS (vincristine sulfate), ZYDELIG (idelalisib), or a combination thereof. In certain embodiments, the additional pharmaceutical agent is an anti-lymphoma agent. In certain embodiments, the additional pharmaceutical agent is ABITREXATE (methotrexate), ABVD, ABVE, ABVE-PC, ADCETRIS (brentuximab vedotin), ADRIAMYCIN PFS (doxorubicin hydrochloride), ADRIAMYCIN RDF (doxorubicin hydrochloride), AMBOCHLORIN (chlorambucil), AMBOCLORIN (chlorambucil), ARRANON (nelarabine), BEACOPP, BECENUM (carmustine), BELEODAQ (belinostat), BEXXAR (tositumomab and iodine I 131 tositumomab), BICNU (carmustine), BLENOXANE (bleomycin), CARMUBRIS (carmustine), CHOP, CLAFEN (cyclophosphamide), COPP, COPP-ABV, CVP, CYTOXAN (cyclophosphamide), DEPOCYT (liposomal cytarabine), DTIC-DOME (dacarbazine), EPOCH, FOLEX (methotrexate), FOLEX PFS (methotrexate), FOLOTYN (pralatrexate), HYPER-CVAD, ICE, IMBRUVICA (ibrutinib), INTRON A (recombinant interferon alfa-2b), ISTODAX (romidepsin), LEUKERAN (chlorambucil), LINFOLIZIN (chlorambucil), Lomustine, MATULANE (procarbazine hydrochloride), METHOTREXATE LPF (methotrexate), MEXATE (methotrexate), MEXATE-AQ (methotrexate), MOPP, MOZOBIL (plerixafor), MUSTARGEN (mechlorethamine hydrochloride), NEOSAR (cyclophosphamide), OEPA, ONTAK (denileukin diftitox), OPPA, R-CHOP, REVLIMID (lenalidomide), RITUXAN (rituximab), STANFORD V, TREANDA (bendamustine hydrochloride), VAMP, VELBAN (vinblastine sulfate), VELCADE (bortezomib), VELSAR (vinblastine sulfate), VINCASAR PFS (vincristine sulfate), ZEVALIN (ibritumomab tiuxetan), ZOLINZA (vorinostat), ZYDELIG (idelalisib), or a combination thereof. In certain embodiments, the additional pharmaceutical agent is REVLIMID (lenalidomide), DACOGEN (decitabine), VIDAZA (azacitidine), CYTOSAR-U (cytarabine), IDAMYCIN (idarubicin), CERUBIDINE (daunorubicin), LEUKERAN (chlorambucil), NEOSAR (cyclophosphamide), FLUDARA (fludarabine), LEUSTATIN (cladribine), or a combination thereof. In certain embodiments, the additional pharmaceutical agent is ABITREXATE (methotrexate), ABRAXANE (paclitaxel albumin-stabilized nanoparticle formulation), AC, AC-T, ADE, ADRIAMYCIN PFS (doxorubicin hydrochloride), ADRUCIL (fluorouracil), AFINITOR (everolimus), AFINITOR DISPERZ (everolimus), ALDARA (imiquimod), ALIMTA (pemetrexed disodium), AREDIA (pamidronate disodium), ARIMIDEX (anastrozole), AROMASIN (exemestane), AVASTIN (bevacizumab), BECENUM (carmustine), BEP, BICNU (carmustine), BLENOXANE (bleomycin), CAF, CAMPTOSAR (irinotecan hydrochloride), CAPOX, CAPRELSA (vandetanib), CARBOPLATIN-TAXOL, CARMUBRIS (carmustine), CASODEX (bicalutamide), CEENU (lomustine), CERUBIDINE (daunorubicin hydrochloride), CERVARIX (recombinant HPV bivalent vaccine), CLAFEN (cyclophosphamide), CMF, COMETRIQ (cabozantinib-s-malate), COSMEGEN (dactinomycin), CYFOS (ifosfamide), CYRAMZA (ramucirumab), CYTOSAR-U (cytarabine), CYTOXAN (cyclophosphamide), DACOGEN (decitabine), DEGARELIX, DOXIL (doxorubicin hydrochloride liposome), DOXORUBICIN HYDROCHLORIDE, DOX-SL (doxorubicin hydrochloride liposome), DTIC-DOME (dacarbazine), EFUDEX (fluorouracil), ELLENCE (epirubicin hydrochloride), ELOXATIN (oxaliplatin), ERBITUX (cetuximab), ERIVEDGE (vismodegib), ETOPOPHOS (etoposide phosphate), EVACET (doxorubicin hydrochloride liposome), FARESTON (toremifene), FASLODEX (fulvestrant), FEC, FEMARA (letrozole), FLUOROPLEX (fluorouracil), FOLEX (methotrexate), FOLEX PFS (methotrexate), FOLFIRI, FOLFIRI-BEVACIZUMAB, FOLFIRI-CETUXIMAB, FOLFIRINOX, FOLFOX, FU-LV, GARDASIL (recombinant human papillomavirus (HPV) quadrivalent vaccine), GEMCITABINE-CISPLATIN, GEMCITABINE-OXALIPLATIN, GEMZAR (gemcitabine hydrochloride), GILOTRIF (afatinib dimaleate), GLEEVEC (imatinib mesylate), GLIADEL (carmustine implant), GLIADEL WAFER (carmustine implant), HERCEPTIN (trastuzumab), HYCAMTIN (topotecan hydrochloride), IFEX (ifosfamide), IFOSFAMIDUM (ifosfamide), INLYTA (axitinib), INTRON A (recombinant interferon alfa-2b), IRESSA (gefitinib), IXEMPRA (ixabepilone), JAKAFI (ruxolitinib phosphate), JEVTANA (cabazitaxel), KADCYLA (ado-trastuzumab emtansine), KEYTRUDA (pembrolizumab), KYPROLIS (carfilzomib), LIPODOX (doxorubicin hydrochloride liposome), LUPRON (leuprolide acetate), LUPRON DEPOT (leuprolide acetate), LUPRON DEPOT-3 MONTH (leuprolide acetate), LUPRON DEPOT-4 MONTH (leuprolide acetate), LUPRON DEPOT-PED (leuprolide acetate), MEGACE (megestrol acetate), MEKINIST (trametinib), METHAZOLASTONE (temozolomide), METHOTREXATE LPF (methotrexate), MEXATE (methotrexate), MEXATE-AQ (methotrexate), MITOXANTRONE HYDROCHLORIDE, MITOZYTREX (mitomycin c), MOZOBIL (plerixafor), MUSTARGEN (mechlorethamine hydrochloride), MUTAMYCIN (mitomycin c), MYLOSAR (azacitidine), NAVELBINE (vinorelbine tartrate), NEOSAR (cyclophosphamide), NEXAVAR (sorafenib tosylate), NOLVADEX (tamoxifen citrate), NOVALDEX (tamoxifen citrate), OFF, PAD, PARAPLAT (carboplatin), PARAPLATIN (carboplatin), PEG-INTRON (peginterferon alfa-2b), PEMETREXED DISODIUM, PERJETA (pertuzumab), PLATINOL (cisplatin), PLATINOL-AQ (cisplatin), POMALYST (pomalidomide), prednisone, PROLEUKIN (aldesleukin), PROLIA (denosumab), PROVENGE (sipuleucel-t), REVLIMID (lenalidomide), RUBIDOMYCIN (daunorubicin hydrochloride), SPRYCEL (dasatinib), STIVARGA (regorafenib), SUTENT (sunitinib malate), SYLATRON (peginterferon alfa-2b), SYLVANT (siltuximab), SYNOVIR (thalidomide), TAC, TAFINLAR (dabrafenib), TARABINE PFS (cytarabine), TARCEVA (erlotinib hydrochloride), TASIGNA (nilotinib), TAXOL (paclitaxel), TAXOTERE (docetaxel), TEMODAR (temozolomide), THALOMID (thalidomide), TOPOSAR (etoposide), TORISEL (temsirolimus), TPF, TRISENOX (arsenic trioxide), TYKERB (lapatinib ditosylate), VECTIBIX (panitumumab), VEIP, VELBAN (vinblastine sulfate), VELCADE (bortezomib), VELSAR (vinblastine sulfate), VEPESID (etoposide), VIADUR (leuprolide acetate), VIDAZA (azacitidine), VINCASAR PFS (vincristine sulfate), VOTRIENT (pazopanib hydrochloride), WELLCOVORIN (leucovorin calcium), XALKORI (crizotinib), XELODA (capecitabine), XELOX, XGEVA (denosumab), XOFIGO (radium 223 dichloride), XTANDI (enzalutamide), YERVOY (ipilimumab), ZALTRAP (ziv-aflibercept), ZELBORAF (vemurafenib), ZOLADEX (goserelin acetate), ZOMETA (zoledronic acid), ZYKADIA (ceritinib), ZYTIGA (abiraterone acetate), ENMD-2076, PCI-32765, AC220, dovitinib lactate (TK1258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (Velcade)), mTOR inhibitors (e.g., rapamycin, temsirolimus (CCI-779), everolimus (RAD-001), ridaforolimus, AP23573 (Ariad), AZD8055 (AstraZeneca), BEZ235 (Novartis), BGT226 (Norvartis), XL765 (Sanofi Aventis), PF-4691502 (Pfizer), GDC0980 (Genetech), SF1126 (Semafoe) and OSI-027 (OSI)), oblimersen, gemcitabine, carminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, carminomycin, aminopterin, and hexamethyl melamine, or a combination thereof. In certain embodiments, the additional pharmaceutical agent is ibrutinib. In certain embodiments, the additional pharmaceutical agent is a protein kinase inhibitor (e.g., tyrosine protein kinase inhibitor). In certain embodiments, the additional pharmaceutical agent is a binder or inhibitor of a CDK (e.g., CDK14, CDK15, CDK16, CDK17, CDK18)). In certain embodiments, the additional pharmaceutical agent is a binder or inhibitor of a CDK. In certain embodiments, the additional pharmaceutical agent is a binder or inhibitor of CDK14. In certain embodiments, the additional pharmaceutical agent is a binder or inhibitor of CDK15. In certain embodiments, the additional pharmaceutical agent is a binder or inhibitor of CDK16. In certain embodiments, the additional pharmaceutical agent is a binder or inhibitor of CDK17. In certain embodiments, the additional pharmaceutical agent is a binder or inhibitor of CDK18. In certain embodiments, the additional pharmaceutical agent is a binder or inhibitor of PFTAIRE1. In certain embodiments, the additional pharmaceutical agent is a binder or inhibitor of Bruton's tyrosine kinase (BTK). In certain embodiments, the additional pharmaceutical agent is selected from the group consisting of epigenetic or transcriptional modulators (e.g., DNA methyltransferase inhibitors, histone deacetylase inhibitors (HDAC inhibitors), lysine methyltransferase inhibitors), antimitotic drugs (e.g., taxanes and vinca alkaloids), hormone receptor modulators (e.g., estrogen receptor modulators and androgen receptor modulators), cell signaling pathway inhibitors (e.g., tyrosine protein kinase inhibitors), modulators of protein stability (e.g., proteasome inhibitors), Hsp90 inhibitors, glucocorticoids, all-trans retinoic acids, and other agents that promote differentiation. In certain embodiments, the compounds described herein or pharmaceutical compositions can be administered in combination with an anti-cancer therapy including, but not limited to, surgery, radiation therapy, transplantation (e.g., stem cell transplantation, bone marrow transplantation), immunotherapy, and chemotherapy.

Also encompassed by the disclosure are kits (e.g., pharmaceutical packs). The kits provided may comprise a pharmaceutical composition or compound described herein and a container (e.g., a vial, ampule, bottle, syringe, and/or dispenser package, or other suitable container). In some embodiments, provided kits may optionally further include a second container comprising a pharmaceutical excipient for dilution or suspension of a pharmaceutical composition or compound described herein. In some embodiments, the pharmaceutical composition or compound described herein provided in the first container and the second container are combined to form one unit dosage form.

Thus, in one aspect, provided are kits including a first container comprising a compound or pharmaceutical composition described herein. In certain embodiments, the kits are useful for treating a disease (e.g., proliferative disease, metabolic disorder, autoimmune disease, or neurological disease) in a subject in need thereof. In certain embodiments, the kits are useful for preventing a disease (e.g., proliferative disease, metabolic disorder, autoimmune disease, or neurological disease) in a subject in need thereof. In certain embodiments, the kits are useful for inhibiting the activity (e.g., aberrant or unwanted activity, such as increased activity) of a protein kinase (e.g., CDK) in a subject, biological sample, tissue, or cell. In certain embodiments, the kits are useful for inducing apoptosis of a cell (e.g., cell in vivo or in vitro).

In certain embodiments, a kit described herein further includes instructions for using the compound or pharmaceutical composition included in the kit. A kit described herein may also include information as required by a regulatory agency such as the U.S. Food and Drug Administration (FDA). In certain embodiments, the information included in the kits is prescribing information. In certain embodiments, the kits and instructions provide for treating a disease (e.g., proliferative disease, metabolic disorder, autoimmune disease, or neurological disease) in a subject in need thereof. In certain embodiments, the kits and instructions provide for preventing a disease (e.g., proliferative disease, metabolic disorder, autoimmune disease, or neurological disease) in a subject in need thereof. In certain embodiments, the kits and instructions provide for modulating (e.g., inhibiting) the activity (e.g., aberrant activity, such as increased activity) of a protein kinase (e.g., CDK) in a subject, biological sample, tissue, or cell. In certain embodiments, the kits and instructions provide for inducing apoptosis of a cell. A kit described herein may include one or more additional pharmaceutical agents described herein as a separate composition.

Methods of Treatment and Uses

The present disclosure provides methods of modulating (e.g., inhibiting or increasing) the activity (e.g., aberrant activity, such as increased or decreased activity) of a protein kinase (e.g., CDK (e.g., CDK14, CDK15, CDK16, CDK17, CDK18)). The present disclosure provides methods of modulating (e.g., inhibiting or increasing) the activity (e.g., aberrant activity, such as increased or decreased activity) of a CDK (e.g., CDK14, CDK15, CDK16, CDK17, CDK18) in a subject, biological sample, or cell. The present disclosure also provides methods for the treatment of a wide range of diseases, such as diseases associated with the aberrant activity (e.g., increased activity) of a protein kinase, e.g., proliferative diseases, metabolic disorders, autoimmune diseases, and neurological diseases in a subject in need thereof. The present disclosure provides methods for the treatment and/or prevention of a proliferative disease (e.g., cancers (e.g., carcinoma); lung cancer, breast cancer, liver cancer, pancreatic cancer, gastric cancer, ovarian cancer, colon cancer, colorectal cancer)), metabolic disorder (e.g., diabetes), autoimmune disease, or neurological disease (e.g., Alzheimer's disease, gliosis, spinal cord injury). The present disclosure provides methods for male contraception (e.g., reducing or inhibiting spermatogenesis in a healthy fertile male subject, inducing azoospermia, oligozoospermia, and/or asthenozoospermia; reducing the rate of male fertility in a healthy fertile male subject).

The present disclosure also provides a compound of Formula (I') or (I), or a pharmaceutically acceptable salt, co-crystal, tautomer, stereoisomer, solvate, hydrate, polymorph, isotopically enriched derivative, or prodrug, or composition thereof, for use in the treatment of diseases, such as proliferative diseases, metabolic disorders, autoimmune diseases, or neurological diseases, in a subject in need thereof.

The present disclosure also provides uses of a compound of Formula (I') or (I), or a pharmaceutically acceptable salt, co-crystal, tautomer, stereoisomer, solvate, hydrate, polymorph, isotopically enriched derivative, or prodrug, or composition thereof, in the manufacture of a medicament for the treatment of diseases, such as proliferative diseases, metabolic disorders, autoimmune diseases, or neurological diseases, in a subject in need thereof.

In another aspect, the present disclosure provides methods of modulating the activity of a protein kinase (e.g., CDK (e.g., CDK14, CDK15, CDK16, CDK17, CDK18)) in a subject, biological sample, or cell. In certain embodiments, provided are methods of inhibiting the activity of a protein kinase in a subject. In certain embodiments, provided are methods of inhibiting the activity of a protein kinase in a cell. In certain embodiments, provided are methods of increasing the activity of a protein kinase (e.g., CDK (e.g., CDK14, CDK15, CDK16, CDK17, CDK18)) in a subject. The compounds described herein may exhibit kinase inhibitory activity; the ability to inhibit a TAIRE family kinase; the ability to inhibit CDK; the ability to inhibit CDK14, without inhibiting another kinase (e.g., CDK); the ability to inhibit CDK15, without inhibiting another kinase (e.g., CDK); the ability to inhibit CDK16, without inhibiting another kinase (e.g., CDK); the ability to inhibit CDK17, without inhibiting another kinase (e.g., CDK); the ability to inhibit CDK18, without inhibiting another kinase (e.g., CDK); the ability to inhibit PFTAIRE1, without inhibiting another kinase (e.g., another CDK); a therapeutic effect and/or preventative effect in the treatment of cancers; a therapeutic effect and/or preventative effect in the treatment of proliferative diseases, metabolic disorders, autoimmune diseases, or neurological diseases; and/or a therapeutic profile (e.g., optimum safety and curative effect) that is superior to existing chemotherapeutic agents, or agents for treating metabolic disorders, autoimmune diseases, or neurological diseases.

In certain embodiments, provided are methods of decreasing the activity of a protein kinase (e.g., CDK (e.g., CDK14, CDK15, CDK16, CDK17, CDK18)) in a subject or biological sample (e.g., cell, tissue) by a method described herein by at least about 1%, at least about 3%, at least about 10%, at least about 20%, at least about 30%, at least about 40%, at least about 50%, at least about 60%, at least about 70%, at least about 80%, or at least about 90%. In certain embodiments, the activity of a protein kinase (e.g., CDK (e.g., CDK14, CDK15, CDK16, CDK17, CDK18)) in a subject or cell is decreased by a method described herein by at least about 1%, at least about 3%, at least about 10%, at least about 20%, at least about 30%, at least about 40%, at least about 50%, at least about 60%, at least about 70%, at least about 80%, or at least about 90%. In some embodiments, the activity of a protein kinase (e.g., CDK (e.g., CDK14, CDK15, CDK16, CDK17, CDK18)) in a subject or cell is selectively inhibited by the method. In some embodiments, the activity of a protein kinase (e.g., CDK (e.g., CDK14, CDK15, CDK16, CDK17, CDK18)) in a subject or cell is selectively decreased by the method.

Without wishing to be bound by any particular theory, the compounds described herein are able to bind (e.g., covalently modify) the protein kinase being inhibited. In certain embodiments, a compound described herein is able to bind (e.g., covalently modify) the protein kinase. In certain embodiments, the compound described herein is able to covalently bind a cysteine residue of the protein kinase. In certain embodiments, the compound is capable of covalently binding C218 of CDK14. In certain embodiments, the compound is capable of covalently binding CDK14. In certain embodiments, the compound is capable of covalently modifying CDK14 (e.g., C218 of CDK14). In certain embodiments, the compound is capable of covalently modifying C218 of CDK14. In certain embodiments, the compound is capable of covalently modifying CDK14. In certain embodiments, the compound is capable of non-covalently modifying CDK15. In certain embodiments, the compound is capable of non-covalently modifying CDK16. In certain embodiments, the compound is capable of non-covalently modifying CDK17. In certain embodiments, the compound is capable of non-covalently modifying CDK18. In certain embodiments, the compound is capable of non-covalently inhibiting CDK15. In certain embodiments, the compound is capable of non-covalently inhibiting CDK16. In certain embodiments, the compound is capable of non-covalently inhibiting CDK17. In certain embodiments, the compound is capable of non-covalently inhibiting CDK18.

In another aspect, the present disclosure provides methods of inhibiting the activity of a protein kinase in a subject, the methods comprising administering to the subject an effective amount (e.g., therapeutically effective amount) of a compound, or pharmaceutical composition thereof, as described herein. In another aspect, the present disclosure provides methods of inhibiting the activity of a protein kinase (e.g., CDK (e.g., CDK14, CDK15, CDK16, CDK17, CDK18)) in a biological sample, the methods comprising contacting the biological sample with an effective amount of a compound, or pharmaceutical composition thereof, as described herein. In another aspect, the present disclosure provides methods of inhibiting the activity of a protein kinase in a tissue or cell, the methods comprising contacting the tissue or cell with an effective amount of a compound, or pharmaceutical composition thereof, as described herein.

In another aspect, the present disclosure provides methods of inhibiting the activity of a protein kinase (e.g., CDK (e.g., CDK14, CDK15, CDK16, CDK17, CDK18)) in a cell, the methods comprising contacting the cell with an effective amount of a compound, or pharmaceutical composition thereof, as described herein.

In certain embodiments, the subject being treated is a mammal. In certain embodiments, the subject is a human. In certain embodiments, the subject is a human male. In certain embodiments, the subject is a fertile human male. In certain embodiments, the subject is a domesticated animal, such as a dog, cat, cow, pig, horse, sheep, or goat. In certain embodiments, the subject is a companion animal, such as a dog or cat. In certain embodiments, the subject is a livestock animal, such as a cow, pig, horse, sheep, or goat. In certain embodiments, the subject is a zoo animal. In another embodiment, the subject is a research animal such as a rodent, dog, or non-human primate. In certain embodiments, the subject is a non-human transgenic animal such as a transgenic mouse or transgenic pig.

In certain embodiments, the biological sample being contacted with the compound or composition is breast tissue, bone marrow, lymph node, lymph tissue, spleen, or blood. In certain embodiments, the biological sample being contacted with the compound or composition is a tumor or cancerous tissue. In certain embodiments, the biological sample being contacted with the compound or composition is serum, cerebrospinal fluid, interstitial fluid, mucous, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample.

In certain embodiments, the cell or tissue being contacted with the compound or composition is present in vitro. In certain embodiments, the cell or tissue being contacted with the compound or composition is present in vivo. In certain embodiments, the cell or tissue being contacted with the compound or composition is present ex vivo. In certain embodiments, the cell or tissue being contacted with the compound or composition is a malignant cell (e.g., malignant blood cell). In certain embodiments, the cell being contacted with the compound or composition is a malignant hematopoietic stem cell (e.g., malignant myeloid cell or malignant lymphoid cell). In certain embodiments, the cell being contacted with the compound or composition is a malignant lymphocyte (e.g., malignant T-cell or malignant B-cell). In certain embodiments, the cell being contacted with the compound or composition is a malignant white blood cell. In certain embodiments, the cell being contacted with the compound or composition is a malignant neutrophil, malignant macrophage, or malignant plasma cell. In certain embodiments, the cell being contacted with the compound or composition is a carcinoma cell. In certain embodiments, the cell being contacted with the compound or composition is a breast carcinoma cell. In certain embodiments, the cell being contacted with the compound or composition is a sarcoma cell. In certain embodiments, the cell being contacted with the compound or composition is a sarcoma cell from breast tissue.

The disease (e.g., proliferative disease) to be treated or prevented using the compounds described herein may be associated with increased activity of a kinase, such as a CDK (e.g., CDK14, CDK15, CDK16, CDK17, CDK18). The disease (e.g., proliferative disease) to be treated or prevented using the compounds described herein may be associated with the overexpression of a kinase, such as a CDK (e.g., CDK14, CDK15, CDK16, CDK17, CDK18).

In certain embodiments, the disease (e.g., proliferative disease, metabolic disorder, autoimmune disease, or neurological disease) to be treated or prevented using the compounds described herein may be associated with the overexpression of a CDK (e.g., CDK14, CDK15, CDK16, CDK17, CDK18). A disease (e.g., proliferative disease, metabolic disorder, autoimmune disease, or neurological disease) may be associated with aberrant activity of a CDK (e.g., CDK14, CDK15, CDK16, CDK17, CDK18). Aberrant activity of a CDK (e.g., CDK14, CDK15, CDK16, CDK17, CDK18) may be elevated and/or inappropriate or undesired activity of the CDK. The compounds described herein, and pharmaceutically acceptable salts, solvates, hydrates, polymorphs, co-crystals, tautomers, stereoisomers, isotopically labeled derivatives, prodrugs, and compositions thereof, may inhibit the activity of a CDK (e.g., CDK14, CDK15, CDK16, CDK17, CDK18) and be useful in treating and/or preventing diseases (e.g., proliferative diseases, metabolic disorders, autoimmune diseases, or neurological diseases). The compounds described herein, and pharmaceutically acceptable salts, solvates, hydrates, polymorphs, co-crystals, tautomers, stereoisomers, isotopically labeled derivatives, prodrugs, and compositions thereof, may inhibit the activity of a CDK and be useful in treating and/or preventing diseases (e.g., proliferative diseases, metabolic disorders, autoimmune diseases, or neurological diseases). The compounds described herein, and pharmaceutically acceptable salts, solvates, hydrates, polymorphs, co-crystals, tautomers, stereoisomers, isotopically labeled derivatives, prodrugs, and compositions thereof, may inhibit the activity of a CDK and be useful in treating and/or preventing diseases (e.g., proliferative diseases, metabolic disorders, autoimmune diseases, or neurological diseases).

All types of biological samples described herein or known in the art are contemplated as being within the scope of the invention. In certain embodiments, the disease (e.g., proliferative disease, metabolic disorder, autoimmune disease, or neurological disease) to be treated or prevented using the compounds described herein is cancer. All types of cancers disclosed herein or known in the art are contemplated as being within the scope of the invention. In certain embodiments, the proliferative disease is a hematological malignancy. In certain embodiments, the proliferative disease is a blood cancer. In certain embodiments, the proliferative disease is a hematological malignancy. In certain embodiments, the proliferative disease is leukemia. In certain embodiments, the proliferative disease is chronic lymphocytic leukemia (CLL). In certain embodiments, the proliferative disease is acute lymphoblastic leukemia (ALL). In certain embodiments, the proliferative disease is T-cell acute lymphoblastic leukemia (T-ALL). In certain embodiments, the proliferative disease is chronic myelogenous leukemia (CML). In certain embodiments, the proliferative disease is acute myeloid leukemia (AML). In certain embodiments, the proliferative disease is acute monocytic leukemia (AMoL). In certain embodiments, the proliferative disease is Waldenström's macroglobulinemia. In certain embodiments, the proliferative disease is Waldenström's macroglobulinemia associated with the MYD88 L265P somatic mutation. In certain embodiments, the proliferative disease is myelodysplastic syndrome (MDS). In certain embodiments, the proliferative disease is a carcinoma. In certain embodiments, the proliferative disease is lymphoma. In certain embodiments, the proliferative disease is T-cell lymphoma. In some embodiments, the proliferative disease is Burkitt's lymphoma. In certain embodiments, the proliferative disease is a Hodgkin's lymphoma. In certain embodiments, the proliferative disease is a non-Hodgkin's lymphoma. In certain embodiments, the proliferative disease is multiple myeloma. In certain embodiments, the proliferative disease is melanoma. In certain embodiments, the proliferative disease is colorectal cancer. In certain embodiments, the proliferative disease is colon cancer. In certain embodiments, the proliferative disease is breast cancer. In certain embodiments, the proliferative disease is recurring breast cancer. In certain embodiments, the proliferative disease is mutant breast cancer. In certain embodiments, the proliferative disease is HER2+ breast cancer. In certain embodiments, the proliferative disease is HER2− breast cancer. In certain embodiments, the proliferative disease is triple-negative breast cancer (TNBC). In certain embodiments, the proliferative disease is a bone cancer. In certain embodiments, the proliferative disease is osteosarcoma. In certain embodiments, the proliferative disease is Ewing's sarcoma. In some embodiments, the proliferative disease is a brain cancer. In some embodiments, the proliferative disease is neuroblastoma. In some embodiments, the proliferative disease is a lung cancer. In some embodiments, the proliferative disease is small cell lung cancer (SCLC). In some embodiments, the proliferative disease is non-small cell lung cancer. In some embodiments, the proliferative disease is liver cancer. In some embodiments, the proliferative disease is pancreatic cancer. In some embodiments, the proliferative disease is gastric cancer. In some embodiments, the proliferative disease is ovarian cancer. In some embodiments, the proliferative disease is ovarian cancer. In some embodiments, the proliferative disease is a benign neoplasm. All types of benign neoplasms disclosed herein or known in the art are contemplated as being within the scope of the invention. In some embodiments, the proliferative disease is associated with angiogenesis. All types of angiogenesis disclosed herein or known in the art are contemplated as being within the scope of the invention.

In certain embodiments, the metabolic disorder to be treated or prevented using the compounds described herein is diabetes (e.g., Type I diabetes, Type II diabetes, gestational diabetes). In some embodiments, the metabolic disorder is hyperglycemia. In some embodiments, the metabolic disorder is hyperinsulinemia. In some embodiments, the metabolic disorder is insulin resistance. In some embodiments, the metabolic disorder is obesity. In certain embodiments, the neurological disease to be treated or prevented using the compounds described herein is Alzheimer's disease. In certain embodiments, the neurological disease is gliosis. In certain embodiments, the neurological disease is spinal cord injury. In certain embodiments, the neurological disease is Parkinson's disease. In certain embodiments, the neurological disease is amyotrophic lateral sclerosis.

Another aspect of the disclosure relates to methods of male contraception in a subject in need thereof (e.g., a fertile male human) using compounds described herein. In certain embodiments, the method comprises administering the compound or a salt thereof in an amount sufficient to reduce sperm number and/or reduce sperm motility. In certain embodiments, method comprises administering the compound or a salt thereof in an amount sufficient to induce azoospermia, oligozoospermia, and/or asthenozoospermia. One aspect of the disclosure relates to methods of reducing the rate of male fertility in a healthy fertile male subject in a subject in need thereof, the method comprising administering to the subject a therapeutically effective amount of compounds described herein. One aspect of the disclosure relates to methods of inducing apoptosis in a cell in a biological sample or subject, the method comprising administering to the biological sample or subject a therapeutically effective amount of compounds described herein.

Another aspect of the disclosure relates to methods of inhibiting the activity of a kinase in a biological sample, tissue, cell, or subject. In certain embodiments, the kinase is a CDK. In certain embodiments, the CDK is a TAIRE family kinase. In certain embodiments, the kinase is CDK14. In certain embodiments, the kinase is CDKCDK15. In certain embodiments, the kinase is CDK16. In certain embodiments, the kinase is CDK17. In certain embodiments, the kinase is CDK18. In certain embodiments, the kinase is PFTAIRE1. In certain embodiments, the activity of the kinase is aberrant activity of the kinase. In certain embodiments, the activity of the kinase is increased activity of the kinase. In certain embodiments, the inhibition of the activity of the kinase is irreversible. In other embodiments, the inhibition of the activity of the kinase is reversible. In certain embodiments, the methods of inhibiting the activity of the kinase include attaching a compound described herein to the kinase. In certain embodiments, the methods comprise covalently inhibiting a CDK (e.g., CDK14,). In certain embodiments, the methods comprise reversibly inhibiting a CDK (e.g., CDK14, CDK15, CDK16, CDK17, CDK18). The present invention provides methods of inhibiting cell growth in a biological sample, tissue, cell, or subject.

In certain embodiments, the methods described herein include administering to a subject or contacting a biological sample with an effective amount of a compound described herein, or a pharmaceutically acceptable salt, solvate, hydrate, polymorph, co-crystal, tautomer, stereoisomer, isotopically labeled derivative, or prodrug thereof, or a pharmaceutical composition thereof. In certain embodiments, the methods described herein include administering to a subject or contacting a biological sample with an effective amount of a compound described herein, or a pharmaceutically acceptable salt thereof, or a pharmaceutical composition thereof. In certain embodiments, the compound is contacted with a biological sample. In certain embodiments, the compound is administered to a subject. In certain embodiments, the compound is administered in combination with one or more additional pharmaceutical agents described herein. The additional pharmaceutical agent may be an anti-proliferative agent. In certain embodiments, the additional pharmaceutical agent is an anti-cancer agent. The additional pharmaceutical agent may also be a kinase inhibitor. In certain embodiments, the additional pharmaceutical agent is an inhibitor of CDK. In certain embodiments, the additional pharmaceutical agent is an inhibitor of a TAIRE family kinase. In certain embodiments, the additional pharmaceutical agent is an inhibitor of CDK14. In certain embodiments, the additional pharmaceutical agent is an inhibitor of CDK15. In certain embodiments, the additional pharmaceutical agent is an inhibitor of CDK16. In certain embodiments, the additional pharmaceutical agent is an inhibitor of CDK17. In certain embodiments, the additional pharmaceutical agent is an inhibitor of CDK18. In certain embodiments, the additional pharmaceutical agent is a selective inhibitor of CDK14. In certain embodiments, the additional pharmaceutical agent is a selective inhibitor of CDK15. In certain embodiments, the additional pharmaceutical agent is a selective inhibitor of CDK16. In certain embodiments, the additional pharmaceutical agent is a selective inhibitor of CDK17. In certain embodiments, the additional pharmaceutical agent is a selective inhibitor of CDK18. In certain embodiments, the additional pharmaceutical agent is a non-selective inhibitor of CDK14. In certain embodiments, the additional pharmaceutical agent is a non-selective inhibitor of CDK15. In certain embodiments, the additional pharmaceutical agent is a non-selective inhibitor of CDK16. In certain embodiments, the additional pharmaceutical agent is a non-selective inhibitor of CDK17. In certain embodiments, the additional pharmaceutical agent is a non-selective inhibitor of CDK18. In certain embodiments, the additional pharmaceutical agent includes an anti-cancer agent (e.g., chemotherapeutics), anti-inflammatory agent, steroids, immunosuppressant, radiation therapy, or other agents. In certain embodiments, the additional pharmaceutical agent is an anti-proliferative agent. In certain embodiments, the additional pharmaceutical agent is an inhibitor of a kinase. In certain embodiments, the additional pharmaceutical agent is a non-selective inhibitor of a kinase. In certain embodiments, the additional pharmaceutical agent is an immunotherapy agent (e.g., PD1 inhibitor, PDL1 inhibitor). In certain embodiments, the additional pharmaceutical agent is an immune checkpoint inhibitor.

In some embodiments, the additional pharmaceutical agent is a topoisomerase inhibitor, a MCL1 inhibitor, a BCL-2 inhibitor, a BCL-xL inhibitor, a BRD4 inhibitor, a BRCA1 inhibitor, BRCA2 inhibitor, HER1 inhibitor, HER2 inhibitor, a CDK9 inhibitor, a Jumonji histone demethylase inhibitor, or a DNA damage inducer. In some embodiments, the additional pharmaceutical agent is etoposide, obatoclax, navitoclax, JQ1, 4-(((5'-chloro-2'-(((1R,4R)-4-(((R)-1-methoxypropan-2-yl)amino)cyclohexyl)amino)-[2,4'-bipyridin]-6-yl)amino)methyl)tetrahydro-2H-pyran-4-carbonitrile, JIB04, or cisplatin. Exemplary chemotherapeutic agents include alkylating agents such as nitrogen mustards, ethylenimines, methylmelamines, alkyl sulfonates, nitrosoureas, and triazenes; antimetabolites such as folic acid analogs, pyrimidine analogs, in particular fluorouracil and cytosine arabinoside, and purine analogs; natural products such as vinca alkaloids epi-podophyllotoxins, antibiotics, enzymes, and biological response modifiers; and miscellaneous products such as platinum coordination complexes, anthracenedione, substituted urea such as hydroxyurea, methyl hydrazine derivatives, and adrenocorticoid suppressant. Exemplary chemotherapeutic agents also include anthracycline antibiotics, actinomycin D, plicamycin, puromycin, gramicidin D, paclitaxel, colchicine, cytochalasin B, emetine, maytansine, amsacrine, cisplatin, carboplatin, mitomycin, altretamine, cyclophosphamide, lomustine, and carmustine. In certain embodiments, a pharmaceutical composition described herein further comprises a combination of the additional pharmaceutical agents described herein.

The inventive compounds or compositions may synergistically augment inhibition of CDK induced by the additional pharmaceutical agent(s) in the biological sample or subject. Thus, the combination of the inventive compounds or compositions and the additional pharmaceutical agent(s) may be useful in treating proliferative diseases resistant to a treatment using the additional pharmaceutical agent(s) without the inventive compounds or compositions.

In some embodiments, the activity of a protein kinase is non-selectively inhibited by the compounds or pharmaceutical compositions described herein. In some embodiments, the activity of the protein kinase being inhibited is selectively inhibited by the compounds or pharmaceutical compositions described herein, compared to the activity of a different protein (e.g., a different protein kinase). In certain embodiments, the activity of a CDK (e.g., CDK14, CDK15, CDK16, CDK17, CDK18) is selectively inhibited by a compound or pharmaceutical composition described herein, compared to the activity of a different protein. In certain embodiments, the activity of CDK14 is selectively inhibited by a compound or pharmaceutical composition described herein, compared to the activity of another CDK (e.g., CDK15, CDK16, CDK17, or CDK18). In certain embodiments, the activity of CDK14 is selectively inhibited by a compound or pharmaceutical composition described herein, compared to the activity of another CDK (e.g., CDK16).

The selectivity of a compound or pharmaceutical composition described herein in inhibiting the activity of a protein kinase over a different protein (e.g., a different protein kinase) may be measured by the quotient of the $IC_{50}$ value of the compound or pharmaceutical composition in inhibiting the activity of the different protein over the $IC_{50}$ value of the compound or pharmaceutical composition in inhibiting the activity of the protein kinase. The selectivity of a compound or pharmaceutical composition described herein for a protein kinase over a different protein may also be measured by the quotient of the $K_d$ value of an adduct of the compound or pharmaceutical composition and the different protein over the $K_d$ value of an adduct of the compound or pharmaceutical composition and the protein kinase. In certain embodiments, the selectivity is at least 2-fold, at least 3-fold, at least 5-fold, at least 10-fold, at least 30-fold, at least 100-fold, at least 300-fold, at least 1,000-fold, at least 3,000-fold, at least 10,000-fold, at least 30,000-fold, or at least 100,000-fold. In certain embodiments, the selectivity is not more than 100,000-fold, not more than 10,000-fold, not more than 1,000-fold, not more than 100-fold, not more than 10-fold, or not more than 2-fold. Combinations of the above-referenced ranges (e.g., at least 2-fold and not more than 10,000-fold) are also within the scope of the disclosure.

In certain embodiments, a kit described herein includes a first container comprising a compound or pharmaceutical composition described herein. In certain embodiments, a kit described herein is useful in treating and/or preventing a disease, such as a proliferative disease (e.g., cancers (e.g., carcinoma); lung cancer, breast cancer, liver cancer, pancreatic cancer, gastric cancer, ovarian cancer, colon cancer, colorectal cancer)), metabolic disorder (e.g., diabetes), autoimmune disease, or neurological disease (e.g., Alzheimer's disease, gliosis, spinal cord injury); in treating and/or preventing a metabolic disorder (e.g., diabetes), autoimmune disease, neurological disease (e.g., Alzheimer's disease, gliosis, spinal cord injury), in a subject in need thereof, inhibiting the activity of a protein kinase (e.g., a CDK (e.g., CDK14, CDK15, CDK16, CDK17, CDK18)) in a subject, biological sample, tissue, or cell, and/or inducing apoptosis in a cell.

In certain embodiments, a kit described herein further includes instructions for using the compound or pharmaceutical composition included in the kit. A kit described herein may also include information as required by a regulatory agency such as the U.S. Food and Drug Administration (FDA). In certain embodiments, the information included in the kits is prescribing information. In certain embodiments, the kits and instructions provide for treating a proliferative disease in a subject in need thereof, preventing a disease, such as a proliferative disease, metabolic disorder, autoimmune disease, or neurological disease in a subject in need thereof, inhibiting the activity of a protein kinase (e.g., a CDK (e.g., CDK14, CDK15, CDK16, CDK17, CDK18)) in a subject, biological sample, tissue, or cell, and/or inducing apoptosis in a cell. A kit described herein may include one or more additional pharmaceutical agents described herein as a separate composition.

EXAMPLES

In order that the present disclosure may be more fully understood, the following examples are set forth. The synthetic and biological examples described in this application are offered to illustrate the compounds, pharmaceutical compositions, and methods provided herein and are not to be construed in any way as limiting their scope.

Example 1. Cdk14 Biology Assays

Pull Down/Cellular Pull Down Protocol

Figure 4A:
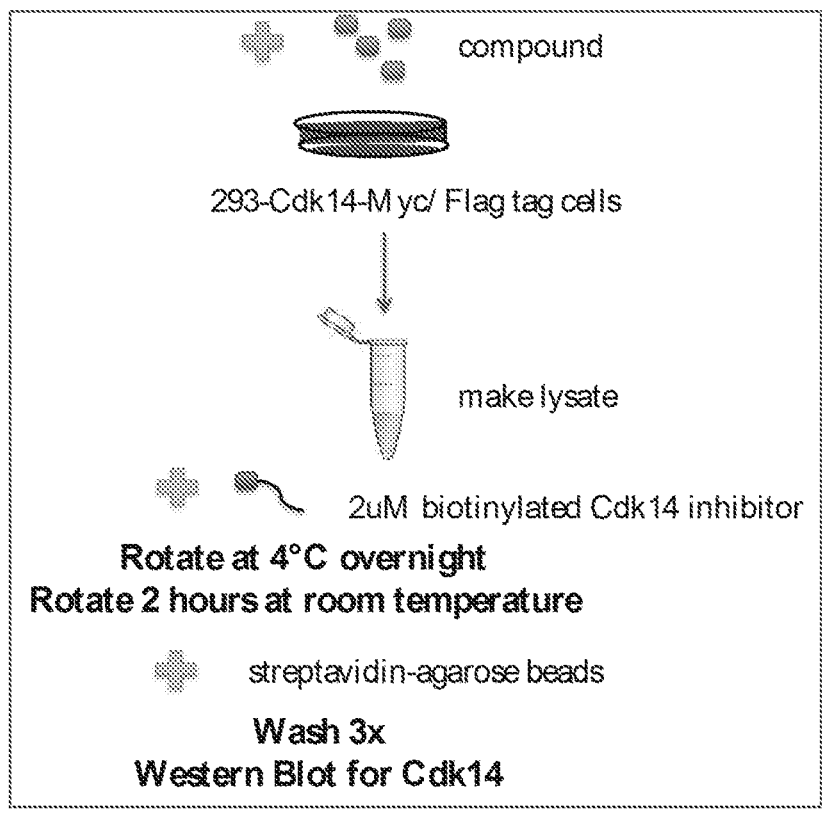
FIGS. 4A and 4B show dose dependent CDK14 inhibition by exemplary compounds in cellular pull-down assay.
Figure 4B:
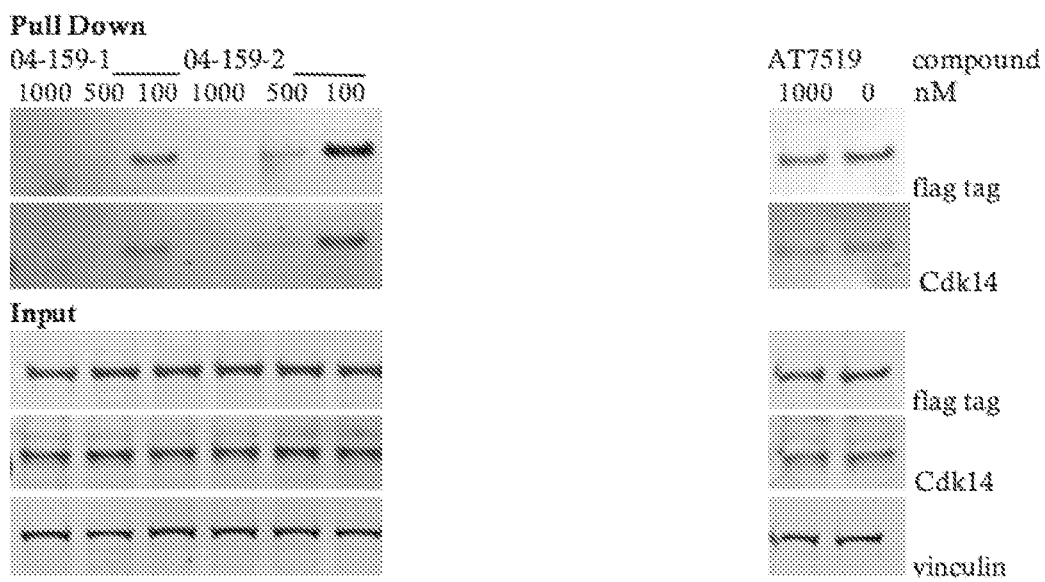
Figure 5:
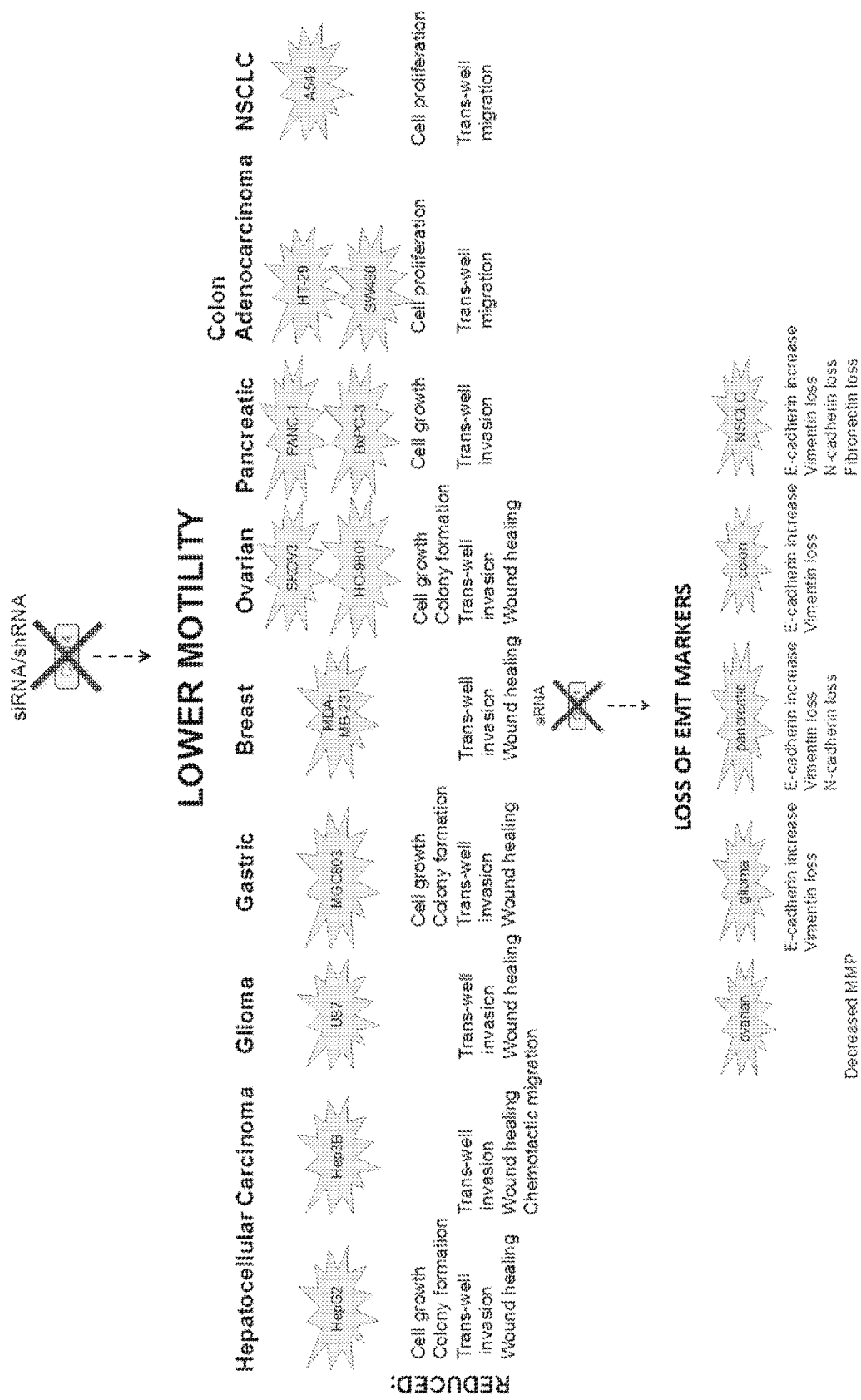
FIG. 5 shows a literature summary of the reported role of CDK14 in promoting cell motility and epithelial-mesenchymal transition (EMT) in cancer.

HEK293 cells overexpressing a Cdk14-flag fusion protein were treated with candidate compounds for 4 hours. Cells were washed with PBS, harvested and lysed in Pierce IP buffer with protease and phosphatase inhibitors (Roche). Lysates were clarified by centrifugation, then incubated with 1 µM biotin-FMF-03-198 (or 1 µM biotin-ATP mimetic) overnight at 4° C. To enhance pulldown, lysates were incubated at room temperature for an additional 2 hours. Lysates were then incubated with streptavidin agarose (Thermo scientific, cat. #20349) for 2 hours at 4° C. Beads were then washed 3 times with Pierce IP buffer, then boiled at 95° C. for 5 minutes in 2× LDS+10% β-mercaptoethanol. Proteins of interest engaged by the biotinylated compound were then assessed using western blotting. The results of the dose dependent CDK14 inhibition by exemplary compounds in cellular pulldown assay are provided in FIG. 4B. The results of the cellular pulldown protocol are provided in Tables 1 and and 2A, 2B, 2C, and 2D below (Columns titled "CDK2 pulldown," "CDK9 pulldown," "CDK12 pulldown blocked," "CDK14 pulldown blocked," and "Cellular Potency Pulldown.")

Figure 3A:
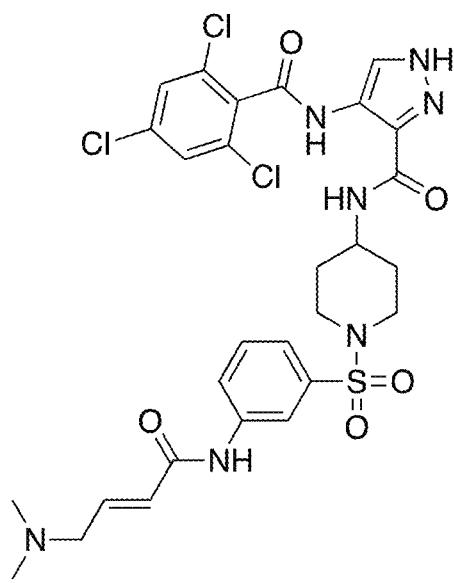
Figure 3C:
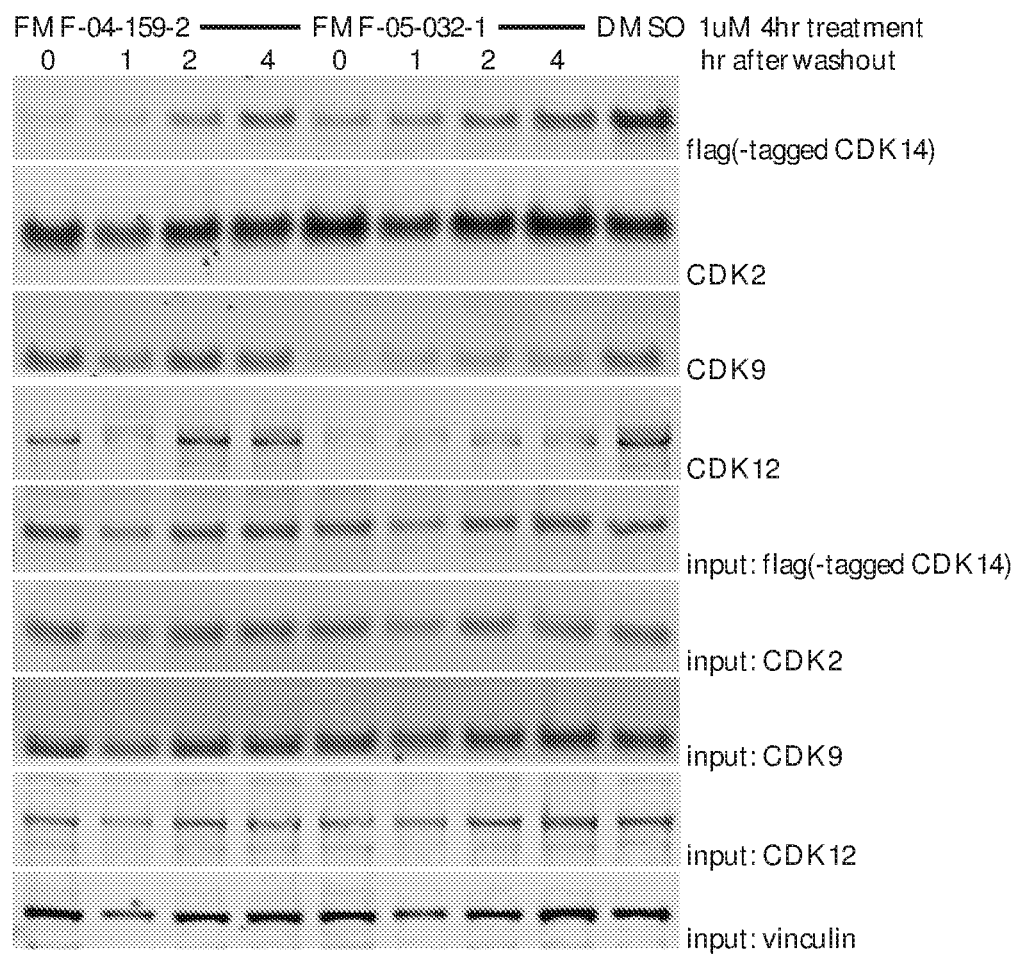

For washout pull downs, after 4 hour compound treatment cells were washed 1× with PBS, 1× with media (DMEM+10% FBS+1% Penn/Strep), then fresh media was replaced. Cells were incubated at 37° C. 5% $CO_2$. Cells were harvested at indicated times after washout for lysis and subsequent pull down, as described above. The results are provided in FIG. 3C.

Antiproliferation Assay Protocol

HCT116 cells were plated in 384-well plates at 750 cells/well in 50 ul fresh media (McCoy's 5A+10% FBS+1% Penn/Strep) and treated with 0.1 µl candidate compounds in four-fold dilution series using the Janus pinner. Cells were incubated with compounds for 72 hours in 37° C. 5% $CO_2$. Anti-proliferative effects of these compounds were assessed 72 hours after compound addition using Cell Titer Glo (Promega cat #G7571) as described in product manual by luminescence measurements using an Envision platereader. All proliferation assays were performed in biological quadruplicate. $IC_{50}$ values were determined using a non-linear regression curve fit in GraphPad Prism 6. The results of the assay are provided in Tables 1 and 2A, 2B, 2C, and 2D below, in the column "HCT116 $IC_{50}$.":

TABLE 1

| | IC$_{50}$ assay with exemplary compounds | | | | | | | | |
|---|---|---|---|---|---|---|---|---|---|
| Compound | CDK14 IC$_{50}$ (nM) LanthaScreen | CDK2 pulldown | CDK9 pulldown | CDK12 pulldown blocked | CDK2 IC$_{50}$ (nM) | CDK16 IC$_{50}$ (nM) | CDK14 pulldown blocked (nM) | HCT116 IC$_{50}$ (nM) | MS labeling of CDK14* |
| FMF-04-159-2 | 46.6 | N | N | slight | 8.2 | 10.1 | 500 | 450.2 | 100% |
| FMF-05-032-1 | 2.9 | N | Y | Y | 36 | 8.2 | 1000 | 115 | 67% |
| FMF-04-107-2 | 14 | N | N | N | 4.5 | 2.3 | 50 | 523.7 | 100% |
| FMF-05-118-1 | assay interference | N | N | N | 2.9 | 2.9 | 1000 | 102 | 50% |

In vitro Kinase Assays

Lanthascreen Eu kinase binding assays were conducted for Cdk14/CycY largely as performed in the commercial assay service by Life Technologies, but included a 30 minute pre-incubation step of the kinase with candidate compounds to facilitate covalent bond formation. The results of the assays are provided in Table 1 above and Tables 2A, 2B, 2C, and 2D below, in the column "CDK14 IC$_{50}$."

Lanthascreen Eu kinase binding assays were conducted for CDK16/CycY at Life Technologies. The results of the assays are provided in Table 1 above and Tables 2A, 2B, 2C, and 2D below, in the columns "CDK2 IC$_{50}$" and CDK16 IC$_{50}$." Z'LYTE kinase assays were conducted for CDK2/CycA at Life Technologies using Km ATP concentrations. Cdk14 $^{33}$P kinase assays were performed by Reaction Biology Corp. The results of the assays are provided in Tables 2A, 2B, 2C, and 2D below, in the column "IC$_{50}$ CDK14 $^{33}$P kinase assay."

Kinativ Live Cell Profiling Protocol

HCT116 cells were plated in fresh media (McCoy's 5A+10% FBS+1% Penn/Strep) in 15 cm plates and treated for 4 hours with candidate compounds. For washout conditions, compound-containing media was removed from cells, and cells were washed 1× with PBS and 1× with media before fresh media was replaced. Cells were incubated for an additional 2 hours after washout. To harvest cells, plates were washed 1× with cold PBS, then collected by scraping and centrifugation. Cell pellets were snap-frozen in liquid nitrogen.

The remainder of the Kinativ profiling experiment was performed by ActivX Biosciences (La Jolla, CA) as described below. The cell pellets were lysed by sonication in lysis buffer (50 mM HEPES, pH 7.5, 150 mM NaCl, 0.1% Triton X-100, phosphatase inhibitors [Cocktail II AG Scientific #P-1518]). After lysis, the samples were cleared by centrifugation, and the supernatant collected for probe-labeling. 50 µl of a 10× aqueous solution of the desthiobiotin-ATP-acylphosphate probe (ATP probe), synthesized as described previously[1], was added to each sample for a final probe concentration of 20 µM, and samples were incubated with probe for 10 min.

Samples were prepared for MS analysis as described previously[2]. Briefly, probe-labeled lysates were denatured and reduced (6 M urea, 10 mM DTT, 65° C., 15 min), alkylated (40 mM iodoacetamide, 37° C., 30 min), and gel filtered (Biorad Econo-Pac 10G) into 10 mM ammonium bicarbonate, 2 M urea, 5 mM methionine. The desalted protein mixture was digested with trypsin (0.015 mg/ml) for 1 hour at 37° C., and desthiobiotinylated peptides captured using 12.5 µl high-capacity streptavidin resin (Thermo Scientific). Captured peptides were then washed extensively, and probe-labeled peptides eluted from the streptavidin beads using two 35 µl washes of a 50% CH$_3$CN/water mixture containing 0.1% TFA at 20-25° C.

Figures 2A, 2B:
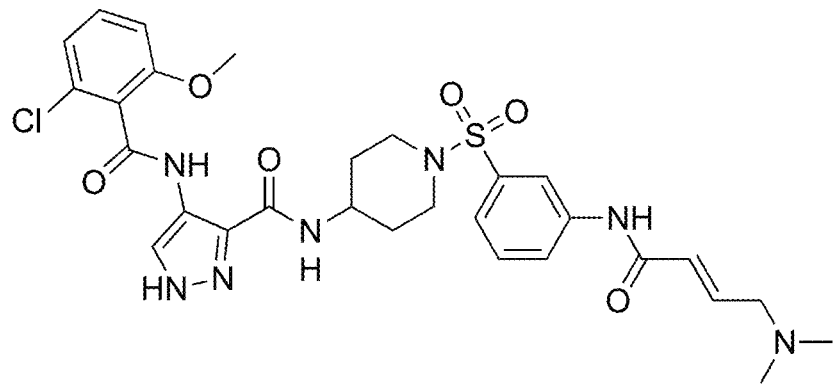
FIGS. 2A to 2E show the chemical structure of exemplary CDK inhibitor FMF-04-107-2 (FIG. 2A), KiNativ profiling +/− washout (FIG. 2B), identification of labeled peptides in CDK14 (FIG. 2C), Mass Spectrometry (MS) labeling of recombinant CDK14 (FIG. 2D), and competition MS labeling of recombinant CDK14/CDK16 (FIG. 2E).
Figure 2C:
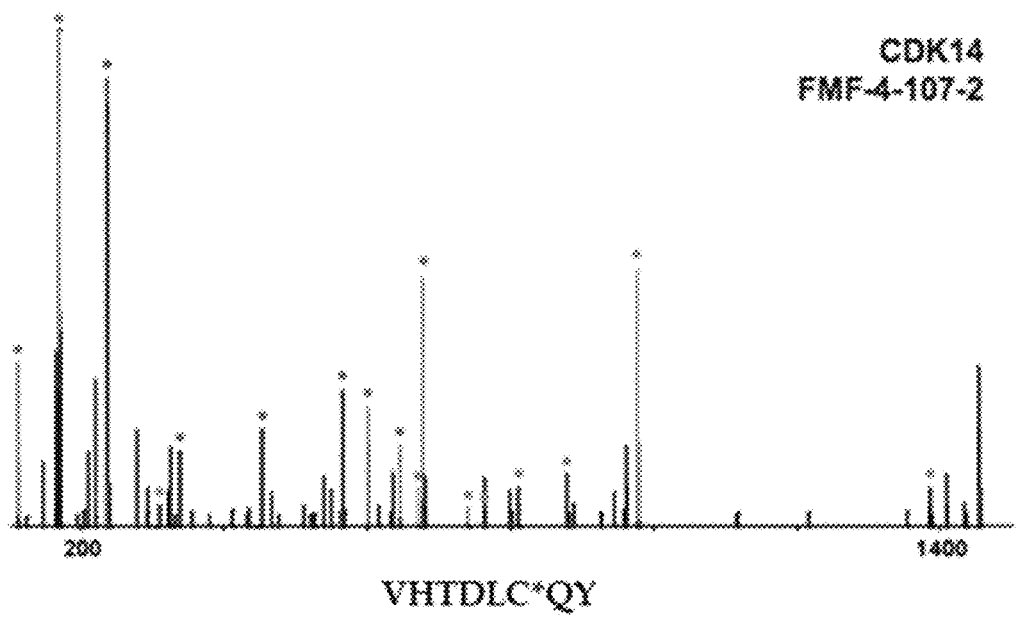
Figure 2D:
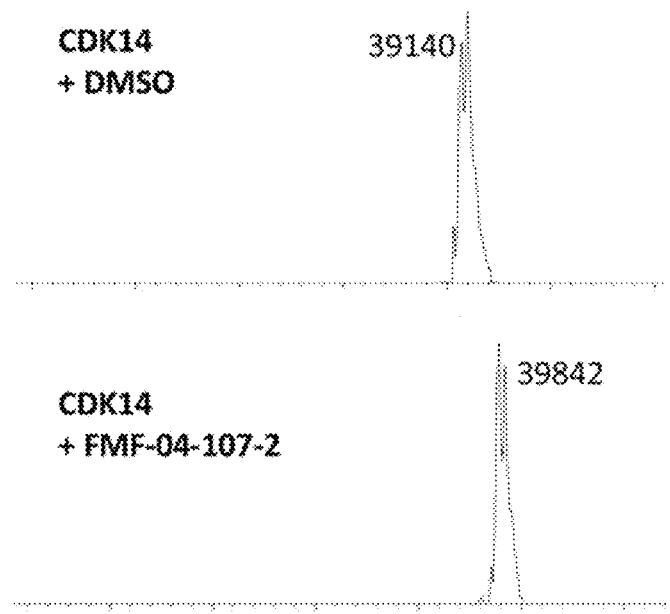
Figure 2E:
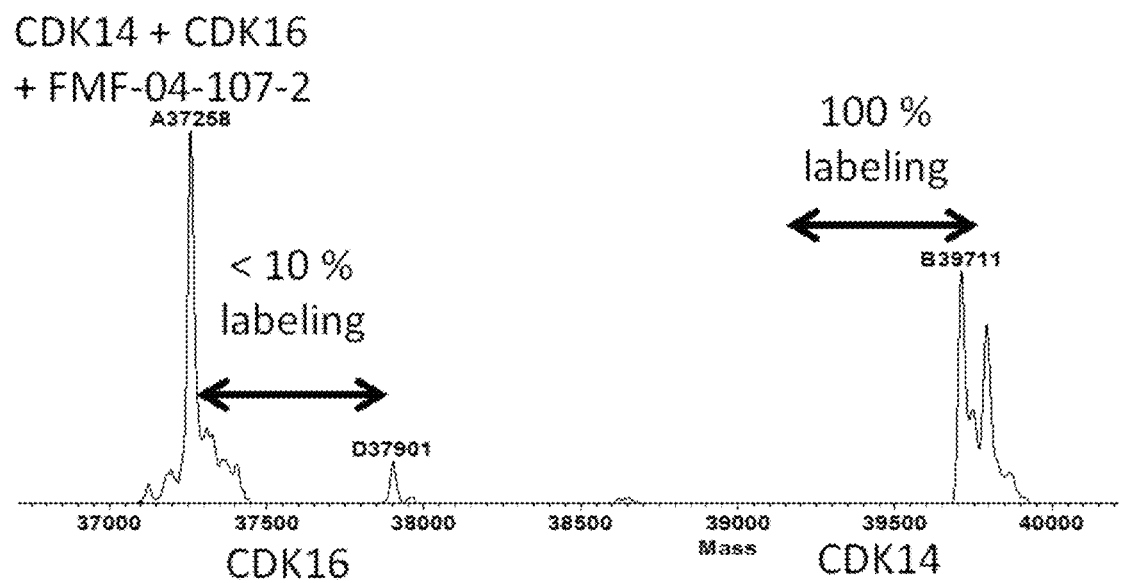

Samples were analyzed by LC-MS/MS as described previously[3]. Samples were analyzed on Thermo LTQ ion trap mass spectrometers coupled with Agilent 1100 series micro-HPLC systems with autosamplers, essentially as described, using a custom target list comprising 352 unique kinase peptides that had been previously identified during the characterization of various in data dependent mode[3,4]. The results are provided in FIG. 2B and FIG. 3B.

For signal extraction/quantitation, typically up to four ions were selected for based on their presence, intensity, and correlation to the reference MS/MS spectrum. The resulting chromatographic peaks from each run were then integrated and the integrated peak areas used to determine % inhibition values relative to control runs. For each peptide quantitated, the MS signal for the compound-treated sample relative to the MS signal for the DMSO-treated control was expressed as fold-change. All data points were visually verified, as were all data points showing variability outside of normal limits. Significance of data points changing more than two-fold were determined according to the Student t test using Excel 2010.

Protein Labeling and Mass Spectrometry Analysis

Recombinant Cdk14 was incubated with 10-fold molar excess of compound for 2 hours at room temperature and analyzed by LC/ESI-MS as described[5]. For each analysis, 5 µg protein was injected onto a self-packed reversed phase column (1/32" O.D.×500 um I.D., 5 cm of POROS 50R2 resin). After desalting for four minutes, protein was eluted with an HPLC gradient (0-100% B in 4 minutes, A=0.2M acetic acid in water, B=0.2 M acetic acid in acetonitrile, flow rate=10 µL/min) into an LTQ ion trap mass spectrometer (ThermoFisher). Mass spectra were deconvoluted using MagTran 1.03b2 software.[6] To determine the site of modification, proteins were reduced with DTT (10 mM final concentration), alkylated with iodoacetamide (22.5 mM final concentration), digested with chymotrypsin (37° C., overnight), desalted using SOLA-C$_{18}$ plates (ThermoFisher Scientific, Madison, WI) and dried by vacuum centrifugation. After reconstituting in 50% acetonitrile, 1% formic acid, 100 mM ammonium acetate, peptides were analyzed by CE-MS using a ZipChip CE system and autosampler interfaced to a QExactive HF mass spectrometer.[7] (ThermoFisher Scientific, San Jose, CA). Peptide solution was loaded for 30 seconds and separation performed at 500 V/cm on an HR chip for 10 minutes with a background electrolyte consisting of 1% formic acid in 50% acetonitrile. Pressure assist was utilized and started at 1 minute. The mass spectrometer was operated in data dependent mode and subjected the 5 most abundant ions in each MS scan (60 k resolution, 1E6 target, lock mass enabled) to MS/MS (15 k resolution, 2E5 target, 100 ms max inject time). Dynamic exclusion was enabled with a repeat count of 1 and an exclusion time of 6 seconds. MS/MS data was extracted to .mgf using mulitplierz scripts[8,9] and searched against a forward-reverse human NCBI refseq database using Mascot version 2.2. Search parameters specified fixed carbamidomethylation of cysteine, and variable oxidation (methionine) and FMF-4-107-2 or FMF-3-198-2 modification (cysteine). Precursor mass tolerance was set to 10 ppm and product ion tolerance was 25 mmu. The results of the assays are provided in Table 1 above, in the column "MS labeling of CDK14*."

Example 2. Exemplary Compounds

TABLE 2A

Exemplary Compounds and Assay Data

| Compound Name | $R_1$ | $R_3$ (as part of $R_1$) | $IC_{50}$ CDK14 binding by Lanthascreen (nM) | HCT116 $IC_{50}$ (nM) | $IC_{50}$ CDK14 $^{33}P$ kinase assay (nM) | Cellular Potency by Pulldown (nM) | $IC_{50}$ CDK16 Lanthascreen binding (nM) | $IC_{50}$ CDK2 Z'LYTE kinase assay (nM) |
|---|---|---|---|---|---|---|---|---|
| AT7519 | (4-piperidinyl-NH) | — | 2.2 | 132 | 110 | 1000 | 3.9 | 27.4 |
| FMF-03-177-1 | (piperidine-N-acryloyl-$R_3$) | H | 401 | 341 | | | | |
| FMF-03-177-2 | (piperidine-N-acryloyl-$R_3$) | —CH$_2$NMe$_2$ | 208 | 1063 | | | | |
| FMF-03-183-1 | (3-piperidine-N-acryloyl-$R_3$) | H | 569 | 39 | | | | |
| FMF-03-183-2 | (3-piperidine-N-acryloyl-$R_3$) | —CH$_2$NMe$_2$ | 148 | 157 | | | | |

TABLE 2A-continued

Exemplary Compounds and Assay Data

| Compound Name | R₁ | R₃ (as part of R₁) | IC$_{50}$ CDK14 binding by Lanthascreen (nM) | HCT116 IC$_{50}$ (nM) | IC$_{50}$ CDK 14 $^{33}$P kinase assay (nM) | Cellular Potency by Pulldown (nM) | IC$_{50}$ CDK16 Lanthascreen binding (nM) | IC$_{50}$ CDK2 Z'LYTE kinase assay (nM) |
|---|---|---|---|---|---|---|---|---|
| FMF-03-184-1 | (3-piperidinyl with N-acryloyl R₃) | H | 479 | 737 | | | | |
| FMF-03-184-2 | (3-piperidinyl with N-acryloyl R₃) | —CH₂NMe₂ | 976 | 1341 | | | | |
| FMF-03-188-1 | (3-phenyl-NH-C(O)-CH=CH-R₃) | H | >1000 | 169 | | | | |
| FMF-03-188-2 | (3-phenyl-NH-C(O)-CH=CH-R₃) | —CH₂NMe₂ | 88 | 723 | | | | |
| FMF-03-182-1 | (4-phenyl-NH-C(O)-CH=CH-R₃) | H | >1000 | 17 | | | | |

TABLE 2A-continued
Exemplary Compounds and Assay Data
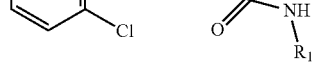
| Compound Name | R$_1$ | R$_3$ (as part of R$_1$) | IC$_{50}$ CDK14 binding by Lanth-ascreen (nM) | HCT116 IC$_{50}$ (nM) | IC$_{50}$ CDK14 $^{33}$P kinase assay (nM) | Cellular Potency by Pull-down (nM) | IC$_{50}$ CDK16 Lanth-ascreen binding (nM) | IC$_{50}$ CDK2 Z'LYTE kinase assay (nM) |
|---|---|---|---|---|---|---|---|---|
| FMF-03-182-2 |  | —CH$_2$NMe$_2$ | 82 | 395 | | | | |
| FMF-03-186-1 | 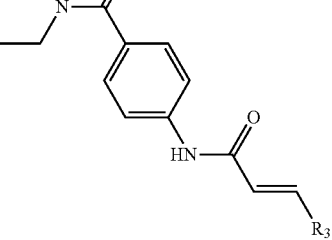 | H | 126 | 42 | | | | |
| FMF-03-187-1 | 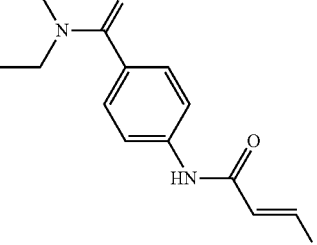 | —CH$_2$NMe$_2$ | 82 | 71 | | | | |
| FMF-03-196-1 | 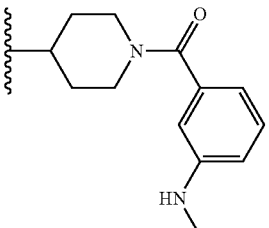 | H | 45 | 32 | 36.5 | 1000 | 11.4 | 3.4 |

TABLE 2A-continued
Exemplary Compounds and Assay Data
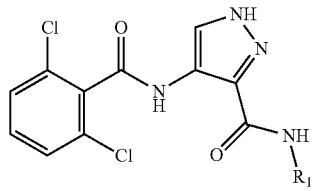
| Compound Name | R₁ | R₃ (as part of R₁) | IC$_{50}$ CDK14 binding by Lanthascreen (nM) | HCT116 IC$_{50}$ (nM) | IC$_{50}$ CDK 14 $^{33}$P kinase assay (nM) | Cellular Potency by Pulldown (nM) | IC$_{50}$ CDK16 Lanthascreen binding (nM) | IC$_{50}$ CDK2 Z'LYTE kinase assay (nM) |
|---|---|---|---|---|---|---|---|---|
| FMF-03-196-2 | | —CH$_2$NMe$_2$ | 77 | 485 | | | | |
| FMF-03-199-1 | | H | 10 | <0.1 | | | | |
| FMF-03-199-2 | | —CH$_2$NMe$_2$ | 14 | 2.6 | 786 | N | 18.2 | 24 |

TABLE 2A-continued

Exemplary Compounds and Assay Data

| Compound Name | R₁ | R₃ (as part of R₁) | IC$_{50}$ CDK14 binding by Lanthascreen (nM) | HCT116 IC$_{50}$ (nM) | IC$_{50}$ CDK 14 $^{33}$P kinase assay (nM) | Cellular Potency by Pulldown (nM) | IC$_{50}$ CDK16 Lanthascreen binding (nM) | IC$_{50}$ CDK2 Z'LYTE kinase assay (nM) |
|---|---|---|---|---|---|---|---|---|
| FMF-03-200-1 | *(piperidine-CH₂-phenyl-NH-C(O)-CH=CH-R₃)* | H | <0.1 | 0.9 | | | | |
| FMF-03-200-2 | *(piperidine-CH₂-phenyl-NH-C(O)-CH=CH-R₃)* | —CH₂NMe₂ | <1 | 2.2 | 76.6 | 250 | 10.2 | 26 |
| FMF-04-172-2 [FMF-03-200-R] | *(piperidine-CH₂-phenyl-NH-C(O)-CH₂-CH₂-R₃)* | H | 82 | 123 | 692 | N | | |

TABLE 2A-continued

Exemplary Compounds and Assay Data

[Core structure: 2,6-dichloro-N-(3-(R₁-carbamoyl)-1H-pyrazol-4-yl)benzamide]

| Compound Name | R₁ | R₃ (as part of R₁) | IC$_{50}$ CDK14 binding by Lanthascreen (nM) | HCT116 IC$_{50}$ (nM) | IC$_{50}$ CDK 14 $^{33}$P kinase assay (nM) | Cellular Potency by Pulldown (nM) | IC$_{50}$ CDK16 Lanthascreen binding (nM) | IC$_{50}$ CDK2 Z'LYTE kinase assay (nM) |
|---|---|---|---|---|---|---|---|---|
| FMF-04-147-1 [FMF-03-200-degron1] | piperidine-CH₂-phenyl-NHC(O)CH₂CH₂-R₃ | PEG₃–pomalidomide | 63 | 271 | | | | |
| FMF-04-131-1 [FMF-03-200-2-biotin] | piperidine-CH₂-phenyl-NHC(O)CH=CH-R₃ | —CH₂NMe₂—PEG₃—Biotin | 49 | — | | Y | | |
| FMF-03-197-1 | piperidine-N-SO₂-phenyl-NHC(O)CH=CH-R₃ | H | 62 | 31 | | | | |

TABLE 2A-continued

Exemplary Compounds and Assay Data

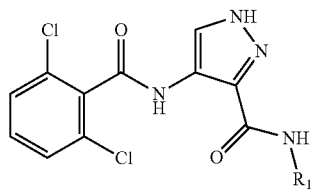

| Compound Name | $R_1$ | $R_3$ (as part of $R_1$) | $IC_{50}$ CDK14 binding by Lanthascreen (nM) | HCT116 $IC_{50}$ (nM) | $IC_{50}$ CDK 14 $^{33}P$ kinase assay (nM) | Cellular Potency Pulldown (nM) | $IC_{50}$ CDK16 Lanthascreen binding (nM) | $IC_{50}$ CDK2 Z'LYTE kinase assay (nM) |
|---|---|---|---|---|---|---|---|---|
| FMF-03-197-2 | (piperidine-N-sulfonyl-phenyl-NHC(O)CH=CH-R3, para) | —CH$_2$NMe$_2$ | 2.6 | 23 | 42.8 | N | 1.2 | 2.8 |
| FMF-03-198-1 | (piperidine-N-sulfonyl-phenyl-NHC(O)CH=CH-R3, meta) | H | 0.9 | >0.1 | | | | |
| FMF-03-198-2 | (piperidine-N-sulfonyl-phenyl-NHC(O)CH=CH-R3, meta) | —CH$_2$NMe$_2$ | 1.8 | 5 | 43.7 | 50 | 0.9 | 0.9 |

TABLE 2A-continued

Exemplary Compounds and Assay Data

| Compound Name | R₁ | R₃ (as part of R₁) | IC₅₀ CDK14 binding by Lanth-ascreen (nM) | HCT116 IC₅₀ (nM) | IC₅₀ CDK14 $^{33}$P kinase assay (nM) | Cellular Potency by Pull-down (nM) | IC₅₀ CDK16 Lanth-ascreen binding (nM) | IC₅₀ CDK2 Z'LYTE kinase assay (nM) |
|---|---|---|---|---|---|---|---|---|
| FMF-04-060-1 [FMF-03-198-R] | *piperidine-N-SO₂-phenyl-NHC(O)-CH₂CH₂-R₃* | H | 11 | 76 | 181 | | 2.3 | 3 |
| FMF-04-153-1 [FMF-03-198-2-biotin] | *piperidine-N-SO₂-phenyl-NHC(O)-CH=CH-R₃* | —CH₂NMe₂— PEG₃—Biotin | 8 | — | | Y | | |
| FMF-04-058-1 | *3-piperidine-N-C(O)-phenyl-NHC(O)-CH=CH-R₃* | H | >1000 | >10000 | | | | |

TABLE 2A-continued
Exemplary Compounds and Assay Data
| Compound Name | R$_1$ | R$_3$ (as part of R$_1$) | IC$_{50}$ CDK14 binding by Lanth-ascreen (nM) | HCT116 IC$_{50}$ (nM) | IC$_{50}$ CDK 14 $^{33}$P kinase assay (nM) | Cellular Potency by Pull-down (nM) | IC$_{50}$ CDK16 Lanth-ascreen binding (nM) | IC$_{50}$ CDK2 Z'LYTE kinase assay (nM) |
|---|---|---|---|---|---|---|---|---|
| FMF-04-058-2 | 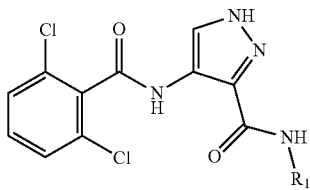 | —CH$_2$NMe$_2$ | >1000 | 726 | | | | |
| FMF-04-059-1 | 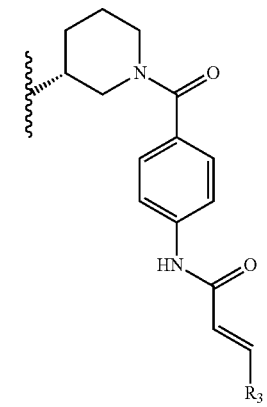 | H | >1000 | 4041 | | | | |
| FMF-04-059-2 | 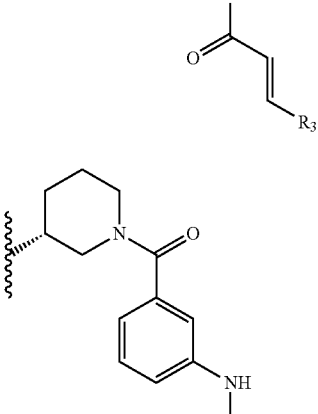 | —CH$_2$NMe$_2$ | >1000 | >10000 | | | | |

TABLE 2A-continued

Exemplary Compounds and Assay Data

| Compound Name | R₁ | R₃ (as part of R₁) | IC$_{50}$ CDK14 binding by Lanth-ascreen (nM) | HCT116 IC$_{50}$ (nM) | IC$_{50}$ CDK14 $^{33}$P kinase assay (nM) | Cellular Potency by Pull-down (nM) | IC$_{50}$ CDK16 Lanth-ascreen binding (nM) | IC$_{50}$ CDK2 Z'LYTE kinase assay (nM) |
|---|---|---|---|---|---|---|---|---|
| FMF-04-056-1 | | H | >1000 | >10000 | | | | |
| FMF-04-056-2 | | —CH₂NMe₂ | ND | >10000 | | | | |
| FMF-04-057-1 | | H | 836 | >10000 | | | | |

211
212
TABLE 2A-continued
Exemplary Compounds and Assay Data
| Compound Name | R₁ | R₃ (as part of R₁) | IC₅₀ CDK14 binding by Lanth-ascreen (nM) | HCT116 IC₅₀ (nM) | IC₅₀ CDK 14 $^{33}$P kinase assay (nM) | Cellular Potency by Pull-down (nM) | IC₅₀ CDK16 Lanth-ascreen binding (nM) | IC₅₀ CDK2 Z'LYTE kinase assay (nM) |
|---|---|---|---|---|---|---|---|---|
| FMF-04-057-2 | 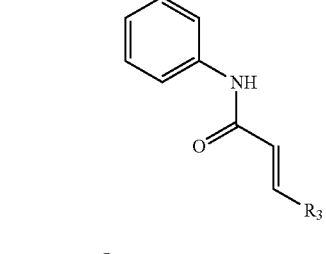 | —CH₂NMe₂ | >1000 | 9840 | | | | |
| FMF-04-012-1 | 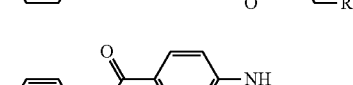 | H | 169 | 8 | | | | |
| FMF-04-012-2 | 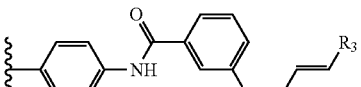 | —CH₂NMe₂ | 68 | 14 | 560 | N | 111 | 52.8 |
| FMF-03-205-1 | 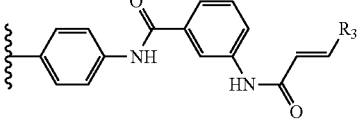 | H | 1010 | 6 | | 500 | | |
| FMF-03-206-1 | 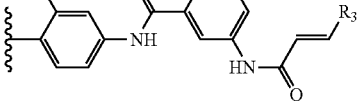 | —CH₂NMe₂ | 17 | 37 | 342 | 1000 | 56.8 | 22.4 |
| FMF-04-085-1 | 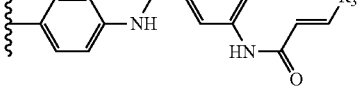 | H | >1000 | — | | | | |
| FMF-04-085-2 |  | —CH₂NMe₂ | 1161 | 320 | | | | |

TABLE 2A-continued

Exemplary Compounds and Assay Data

| Compound Name | R₁ | R₃ (as part of R₁) | IC$_{50}$ CDK14 binding by Lanth-ascreen (nM) | HCT116 IC$_{50}$ (nM) | IC$_{50}$ CDK14 $^{33}$P kinase assay (nM) | Cellular Potency by Pull-down (nM) | IC$_{50}$ CDK16 Lanth-ascreen binding (nM) | IC$_{50}$ CDK2 Z'LYTE kinase assay (nM) |
|---|---|---|---|---|---|---|---|---|
| FMF-03-203-1 | | H | 609 | 6 | | | | |
| FMF-03-204-1 | | —CH$_2$NMe$_2$ | 72 | 24 | | | | |
| FMF-04-011-1 | | H | 308 | 31 | | | | |

TABLE 2A-continued

Exemplary Compounds and Assay Data

[Structure: 2,6-dichlorobenzamide linked via NH to pyrazole bearing C(O)NH-R₁]

| Compound Name | R₁ | R₃ (as part of R₁) | IC$_{50}$ CDK14 binding by Lanth-ascreen (nM) | IC$_{50}$ HCT116 (nM) | CDK 14 $^{33}$P kinase assay (nM) | Cellular Potency (nM) | IC$_{50}$ CDK16 by Pull-down Lanth-ascreen binding (nM) | IC$_{50}$ CDK2 Z'LYTE kinase assay (nM) |
|---|---|---|---|---|---|---|---|---|
| FMF-04-196-1 | [3-(acrylamido)phenyl-NHC(O)-phenyl-] | —CH₂NMe₂ | 41 | 366 | | | | |
| FMF-05-064-1 | [4-(acrylamido)benzyl-] | H | 1700 | 117 | | | 478 | 15 |
| FMF-05-064-2 | [4-(acrylamido)benzyl-] | —CH₂NMe₂ | 108 | 4700 | | LOW (>1 μM) | | |

TABLE 2A-continued

Exemplary Compounds and Assay Data

[Structure: 2,6-dichlorobenzamide linked to 1H-pyrazole with carboxamide NH-R₁]

| Compound Name | R₁ | R₃ (as part of R₁) | IC₅₀ CDK14 binding by Lanthascreen (nM) | HCT116 IC₅₀ (nM) | IC₅₀ CDK14 $^{33}P$ kinase assay (nM) | Cellular Potency by Pulldown (nM) | IC₅₀ CDK16 Lanthascreen binding (nM) | IC₅₀ CDK2 Z'LYTE kinase assay (nM) |
|---|---|---|---|---|---|---|---|---|
| FMF-05-067-1 | [3-(acrylamido)benzyl group with R₃] | H | ND | 8500 | >1000 | | | |
| FMF-05-067-2 | [3-(acrylamido)benzyl group with R₃] | —CH₂NMe₂ | 183 | >10000 | | | | |
| FMF-05-073-1 | [4-(4-acrylamidophenyl)piperidinyl with R₃] | H | 154 | 30 | | | | |
| FMF-05-073-2 | [4-(4-acrylamidophenyl)piperidinyl with R₃] | —CH₂NMe₂ | 45 | 541 | | 27.7 | 17 | |
| FMF-05-085-1 | [4-(3-acrylamidophenyl)piperidinyl with R₃] | H | ND | 93 | | | | |

TABLE 2A-continued

Exemplary Compounds and Assay Data

| Compound Name | R₁ | R₃ (as part of R₁) | IC$_{50}$ CDK14 binding by Lanth-ascreen (nM) | HCT116 IC$_{50}$ (nM) | IC$_{50}$ CDK14 $^{33}$P kinase assay (nM) | Cellular Potency by Pull-down (nM) | IC$_{50}$ CDK16 Lanth-ascreen binding (nM) | IC$_{50}$ CDK2 Z'LYTE kinase assay (nM) |
|---|---|---|---|---|---|---|---|---|
| FMF-05-085-2 | | —CH$_2$NMe$_2$ | 27 | 427 | | Y | 74.4 | 20 |
| FMF-05-074-1 | | H | 1200 | 2900 | | | | |
| FMF-05-074-2 | | —CH$_2$NMe$_2$ | 116 | >10000 | | | | |
| FMF-05-086-1 | | H | 1100 | 826 | | | | |

TABLE 2A-continued

Exemplary Compounds and Assay Data

[Structure: 2,6-dichlorobenzamide linked via NH to a 1H-pyrazole bearing a C(O)NH-R$_1$ group]

| Compound Name | R$_1$ | R$_3$ (as part of R$_1$) | IC$_{50}$ CDK14 binding by Lanthascreen (nM) | HCT116 IC$_{50}$ (nM) | IC$_{50}$ CDK 14 $^{33}$P kinase assay (nM) | Cellular Potency by Pulldown (nM) | IC$_{50}$ CDK16 Lanthascreen binding (nM) | IC$_{50}$ CDK2 Z'LYTE kinase assay (nM) |
|---|---|---|---|---|---|---|---|---|
| FMF-05-086-2 | [3-(pyrrolidin-3-yl)-N-phenyl acrylamide] | —CH$_2$NMe$_2$ | 218 | >10000 | | | | |
| FMF-05-075-1 | [4-(pyrrolidin-3-yl)-N-phenyl acrylamide] | H | 267 | 64 | | | | |
| FMF-05-075-2 | [4-(pyrrolidin-3-yl)-N-phenyl acrylamide] | —CH$_2$NMe$_2$ | 738 | 714 | | | | |

TABLE 2A-continued

Exemplary Compounds and Assay Data

| Compound Name | R₁ | R₃ (as part of R₁) | IC$_{50}$ CDK14 binding by Lanthascreen (nM) | HCT116 IC$_{50}$ (nM) | IC$_{50}$ CDK14 $^{33}$P kinase assay (nM) | Cellular Potency by Pulldown (nM) | IC$_{50}$ CDK16 Lanthascreen binding (nM) | IC$_{50}$ CDK2 Z'LYTE kinase assay (nM) |
|---|---|---|---|---|---|---|---|---|
| FMF-05-087-1 | (pyrrolidine-N-phenyl-NHC(O)CH=CH-R₃) | H | 1100 | 22 | | | | |
| FMF-05-087-2 | (pyrrolidine-N-phenyl-NHC(O)CH=CH-R₃) | —CH₂NMe₂ | 1300 | 123 | | | | |
| FMF-05-066-1 | (pyrrolidine-N-SO₂-phenyl-NHC(O)CH=CH-R₃) | H | >10000 | 3000 | | | | |

TABLE 2A-continued
Exemplary Compounds and Assay Data
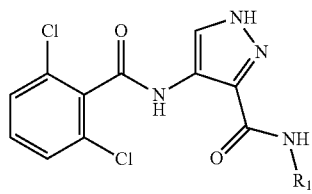
| Compound Name | R₁ | R₃ (as part of R₁) | IC$_{50}$ CDK14 binding by Lanthascreen (nM) | HCT116 IC$_{50}$ (nM) | IC$_{50}$ CDK 14 $^{33}$P kinase assay (nM) | Cellular Potency by Pull-down (nM) | IC$_{50}$ CDK16 Lanthascreen binding (nM) | IC$_{50}$ CDK2 Z'LYTE kinase assay (nM) |
|---|---|---|---|---|---|---|---|---|
| FMF-05-065-1 | (structure) | H | >10000 | 467 | | | | |
| FMF-05-084-2 | (structure) | —CH₂NMe₂ | 41 | >10000 | | N | | |
| FMF-05-068-1 | (structure) | H | 450 | 6200 | | | | |

TABLE 2A-continued
Exemplary Compounds and Assay Data
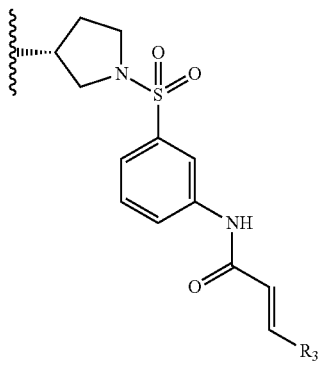
| Compound Name | R₁ | R₃ (as part of R₁) | IC$_{50}$ CDK14 binding by Lanthascreen (nM) | HCT116 IC$_{50}$ (nM) | IC$_{50}$ CDK 14 $^{33}$P kinase assay (nM) | Cellular Potency by Pulldown (nM) | IC$_{50}$ CDK16 Lanthascreen binding (nM) | IC$_{50}$ CDK2 Z'LYTE kinase assay (nM) |
|---|---|---|---|---|---|---|---|---|
| FMF-05-068-2 | 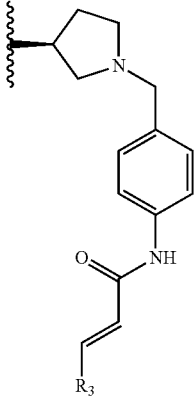 | —CH$_2$NMe$_2$ | 308 | >10000 | | | | |
| FMF-05-072-1 | 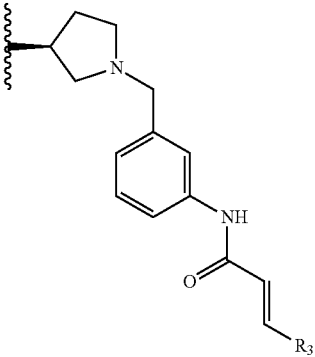 | H | 257 | <1 | | | | |
| FMF-05-071-1 | 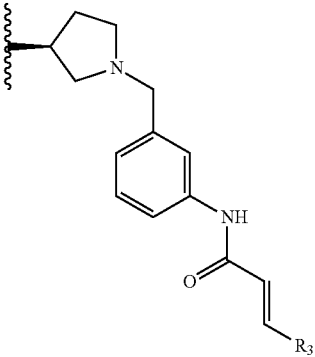 | H | 282 | <1 | | | | |

TABLE 2A-continued

Exemplary Compounds and Assay Data

| Compound Name | R₁ | R₃ (as part of R₁) | IC₅₀ CDK14 binding by Lanthascreen (nM) | HCT116 IC₅₀ (nM) | IC₅₀ CDK14 $^{33}$P kinase assay (nM) | Cellular Potency by Pulldown (nM) | IC₅₀ CDK16 Lanthascreen binding (nM) | IC₅₀ CDK2 Z'LYTE kinase assay (nM) |
|---|---|---|---|---|---|---|---|---|
| FMF-05-070-1 | | H | 572 | 31 | | | | |
| FMF-05-069-1 | | H | 150 | 27 | | | | |

TABLE 2B
Exemplary Compounds and Assay Data
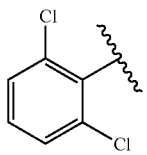
| Compound Name | R₂ | R₃ | IC$_{50}$ CDK14 binding by Lanthascreen (nM) | HCT116 IC$_{50}$ (nM) | IC$_{50}$ CDK14 $^{33}$P kinase assay (nM) | Cellular Potency by Pulldown (nM) | IC$_{50}$ CDK16 Lanthascreen binding (nM) | IC$_{50}$ CDK2 Z'LYTE kinase assay (nM) |
|---|---|---|---|---|---|---|---|---|
| FMF-03-198-1 | 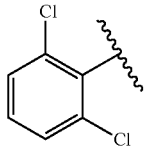 | H | 0.9 | >0.1 | | 50 | | |
| FMF-03-198-2 | 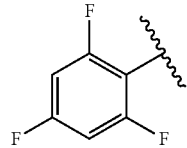 | —CH$_2$NMe$_2$ | 1.7 | 5 | 43.7 | 50 | 0.9 | 0.9 |
| FMF-04-095-1 | 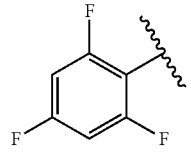 | H | 122 | 7 | >1000 | | ? | 7.5 |
| FMF-04-095-2 | 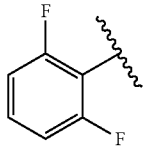 [SMILES: *c1c(F)cccc1F] | —CH$_2$NMe$_2$ | 10.2 | 90 | 380 | 500 | 5.2 | 3.7 |
| FMF-04-096-1 | 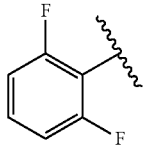 [SMILES: *c1c(F)cccc1F] | H | >1000 | 114 | 284 | | | |
| FMF-04-096-2 | 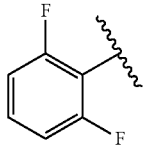 [SMILES: *c1c(F)cccc1F] | —CH$_2$NMe$_2$ | 3.4 | 157 | 268 | 250 | 2.6 | 2.6 |

TABLE 2B-continued

Exemplary Compounds and Assay Data

| Compound Name | R₂ | R₃ | IC$_{50}$ CDK14 binding by Lantha-screen (nM) | HCT116 IC$_{50}$ (nM) | IC$_{50}$ CDK14 $^{33}$P kinase assay (nM) | Cellular Potency by Pull-down (nM) | IC$_{50}$ CDK16 Lantha-screen binding (nM) | IC$_{50}$ CDK2 Z'LYTE kinase assay (nM) |
|---|---|---|---|---|---|---|---|---|
| FMF-04-097-1 | 2-F, 6-OMe phenyl | H | 1.6 | 9 | 88 | | | |
| FMF-04-097-2 | 2-F, 6-OMe phenyl | —CH₂NMe₂ | >1000 (assay interferance?) | 174 | 238 | 250 | 2.8 | 3.7 |
| FMF-04-107-1 | 2-Cl, 6-OMe phenyl | H | 2.2 | 115 | 386 | | | |
| FMF-04-107-2 | 3-Cl, 2-Me, 6-OMe phenyl | —CH₂NMe₂ | 2.9 | 524 | 202 | 50 | 2.3 | 4.5 |
| FMF-04-159-1 | 2,4,6-triCl phenyl | H | 49 | 25 | 1052 | 500 | 46.6 | 20.6 |
| FMF-04-159-2 | 2,4,6-triCl phenyl | —CH₂NMe₂ | 47 | 450 | 718 | 500 | 8.2 | 10.1 |

TABLE 2B-continued
Exemplary Compounds and Assay Data
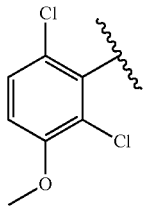 [SMILES: *c1c(Cl)ccc(OC)c1Cl]
| Compound Name | R$_2$ | R$_3$ | IC$_{50}$ CDK14 binding by Lanthascreen (nM) | HCT116 IC$_{50}$ (nM) | IC$_{50}$ CDK14 $^{33}$P kinase assay (nM) | Cellular Potency by Pulldown (nM) | IC$_{50}$ CDK16 Lanthascreen binding (nM) | IC$_{50}$ CDK2 Z'LYTE kinase assay (nM) |
|---|---|---|---|---|---|---|---|---|
| FMF-04-184-1 | 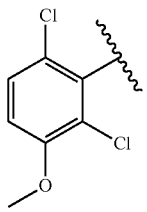 | H | 0.4 | <1 | | 100 | | |
| FMF-04-184-2 | 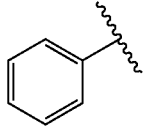 [SMILES: *c1ccccc1] | —CH$_2$NMe$_2$ | 6.4 | 23 | | 100 | 1.8 | 3.5 |
| FMF-05-027-1 | 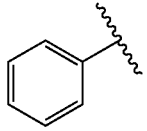 [SMILES: *c1ccccc1] | H | 315 | 382 | | | | |
| FMF-05-027-2 | 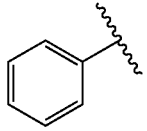 [SMILES: *c1ccccc1] | CH$_2$NMe$_2$ | 3 | 440 | | Y | 9.8 | 2.8 |
| FMF-05-028-1 | 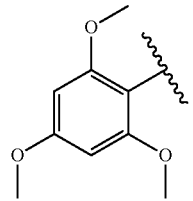 [SMILES: *c1c(OC)cc(OC)cc1OC] | H | 48 | >10000 | | LOW (>1 uM) | | |

TABLE 2B-continued

Exemplary Compounds and Assay Data

| Compound Name | R$_2$ | R$_3$ | IC$_{50}$ CDK14 binding by Lantha-screen (nM) | HCT116 IC$_{50}$ (nM) | IC$_{50}$ CDK14 $^{33}$P kinase assay (nM) | Cellular Poten-cy by Pull-down (nM) | IC$_{50}$ CDK16 Lantha-screen binding (nM) | IC$_{50}$ CDK2 Z'LYTE kinase assay (nM) |
|---|---|---|---|---|---|---|---|---|
| FMF-05-028-2 | 2,4,6-trimethoxyphenyl | —CH$_2$NMe$_2$ | 221 | >10000 | | | | |
| FMF-05-033-1 (FMF-04-107-R) | 2-chloro-6-methoxyphenyl | -propyl | 0.8 | 172 | 135 | | 3.4 | 3 |
| FMF-05-035-1 (FMF-04-107-2-desthiobiotin) | 2-chloro-6-methoxyphenyl | CH$_2$NMe$_2$—PEG3-desthiobiotin | 46 | | | | | |
| FMF-05-116-1 | 4,4-difluorocyclohexyl | —CH$_2$NMe$_2$ | 332.2 | 8204 | N | | 140 | 51.5 |

TABLE 2B-continued
Exemplary Compounds and Assay Data
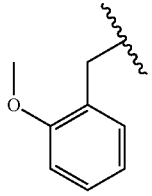 [SMILES: *Cc1ccccc1OC]
| Compound Name | R$_2$ | R$_3$ | IC$_{50}$ CDK14 binding by Lantha-screen (nM) | HCT116 IC$_{50}$ (nM) | IC$_{50}$ CDK14 $^{33}$P kinase assay (nM) | Cellular Poten-cy by Pull-down (nM) | IC$_{50}$ CDK16 Lantha-screen binding (nM) | IC$_{50}$ CDK2 Z'LYTE kinase assay (nM) |
|---|---|---|---|---|---|---|---|---|
| FMF-05-117-1 | 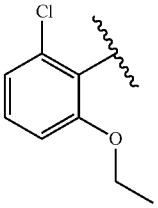 [SMILES: *c1c(Cl)cccc1OCC] | —CH$_2$NMe$_2$ | 14 | 395 | | N | 17 | 5.71 |
| FMF-05-118-1 | 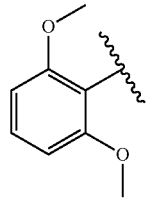 [SMILES: *c1c(OC)cccc1OC] | —CH$_2$NMe$_2$ | | 102 | 1000 | | 2.91 | 2.95 |
| FMF-05-119-1 | 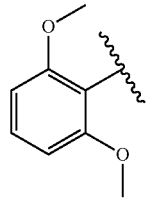 [SMILES: *c1c(OC)cccc1OC] | —CH$_2$NMe$_2$ | 49.5 | 4112 | | N | 11.3 | 24.6 |

TABLE 2C

Exemplary Compounds and Assay Data

[Chemical structure: pyrazole core with R2-C(=O)-NH- substituent, and carboxamide linked to piperidine-N-CH2-phenyl-NH-C(=O)-CH=CH-R3]

| Compound Name | R$_2$ | R$_3$ | IC$_{50}$ CDK14 binding by Lantha-screen (nM) | HCT116 IC$_{50}$ (nM) | IC$_{50}$ CDK14 $^{33}$P kinase assay (nM) | Cellular Potency by Pulldown (nM) | IC$_{50}$ CDK16 Lantha-screen binding (nM) | IC$_{50}$ CDK2 Z'LYTE kinase assay (nM) |
|---|---|---|---|---|---|---|---|---|
| FMF-03-200-1 | 2,6-diCl-phenyl | H | <0.1 | 0.9 | | 500 | | |
| FMF-03-200-2 | 2,6-diCl-phenyl | —CH$_2$NMe$_2$ | <0.1 | 2.1 | 76.6 | 500 | 10.2 | 26 |
| FMF-04-172-2 (FMF-03-200-R) | 2,6-diCl-phenyl | PROPYL | 0.8 | 173 | | | 29.4 | 19.6 |
| FMF-04-161-1 | 2-Cl-6-OMe-phenyl | H | 11 | 9 | 557 | 100 | 12.8 | 50.2 |
| FMF-05-032-1 | 2-Cl-6-OMe-phenyl | —CH$_2$NMe$_2$ | 2.9 | 115 | | 500 | 8.2 | 36 |

TABLE 2C-continued
Exemplary Compounds and Assay Data
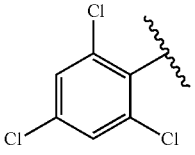
| Compound Name | R$_2$ | R$_3$ | IC$_{50}$ CDK14 binding by Lantha-screen (nM) | HCT116 IC$_{50}$ (nM) | IC$_{50}$ CDK14 $^{33}$P kinase assay (nM) | Cellular Potency by Pulldown (nM) | IC$_{50}$ CDK16 Lantha-screen binding (nM) | IC$_{50}$ CDK2 Z'LYTE kinase assay (nM) |
|---|---|---|---|---|---|---|---|---|
| FMF-04-158-1 | 2,4,6-trichlorophenyl | H | 198 | 11 | | | | |
| FMF-04-158-2 | 2,4,6-trichlorophenyl | —CH$_2$NMe$_2$ | 339 | 156 | | | | |
| FMF-04-160-1 | 2,6-difluorophenyl | H | 64 | 7 | 1474 | 500 | 120 | 165 |
| FMF-04-160-2 | 2,6-difluorophenyl | —CH$_2$NMe$_2$ | 223 | 437 | | | | |

TABLE 2C-continued
Exemplary Compounds and Assay Data
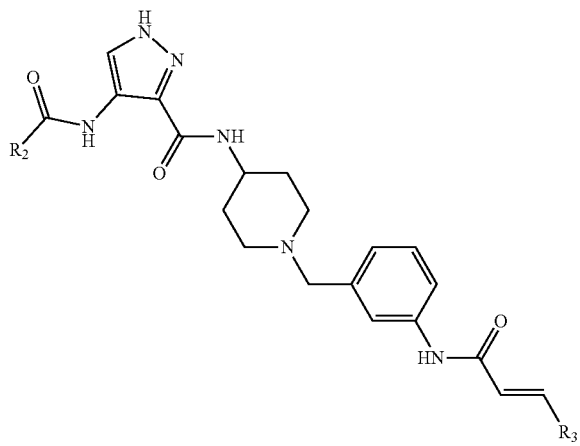
| Compound Name | R$_2$ | R$_3$ | IC$_{50}$ CDK14 binding by Lanthascreen (nM) | HCT116 IC$_{50}$ (nM) | IC$_{50}$ CDK14 $^{33}$P kinase assay (nM) | Cellular Potency by Pulldown (nM) | IC$_{50}$ CDK16 Lanthascreen binding (nM) | IC$_{50}$ CDK2 Z'LYTE kinase assay (nM) |
|---|---|---|---|---|---|---|---|---|
| n/a | 2-F-6-OMe-phenyl | H | | | | | | |
| IHK-01-013-2 | 2-F-6-OMe-phenyl | —CH$_2$NMe$_2$ | 4.2 | 77 | | | 7.4 | 53 |
| FMF-04-200-1 | 2,4,6-triF-phenyl | H | 31 | 1.9 | | | | |
| FMF-04-200-2 | 2,4,6-triF-phenyl | —CH$_2$NMe$_2$ | 17 | 293 | N | | 110 | 508 |

TABLE 2D
Exemplary Compounds and Assay Data
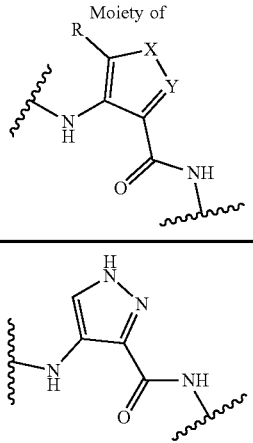
| Compound Name | Moiety of R group | R₃ | IC$_{50}$ CDK14 binding by Lantha-screen (nM) | HCT116 IC$_{50}$ (nM) | IC$_{50}$ CDK14 $^{33}$P kinase assay (nM) | Cellular Potency by Pull-down (nM) | IC$_{50}$ CDK16 Lantha-screen binding (nM) | IC$_{50}$ CDK2 Z'LYTE kinase assay (nM) |
|---|---|---|---|---|---|---|---|---|
| FMF-03-198-1 | 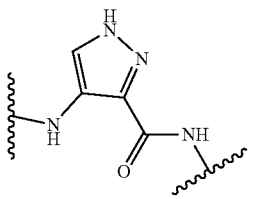 [SMILES: *NC(=O)c1n[nH]cc1N*] | H | 0.9 | >0.1 | | 50 | | |
| FMF-03-198-2 | 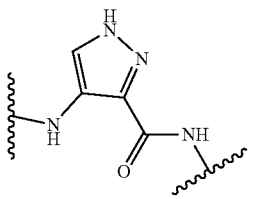 [SMILES: *NC(=O)c1n[nH]cc1N*] | —CH$_2$NMe$_2$ | 1.7 | 5 | 43.7 | 50 | 0.9 | 0.9 |
| FMF-04-089-1 | 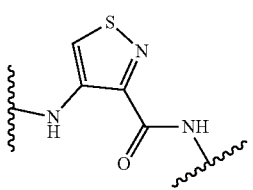 | H | >1000 | 563 | | N | | |
| FMF-04-089-2 | 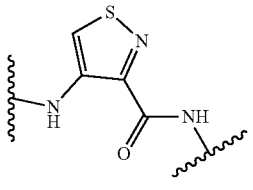 [SMILES: *NC(=O)c1nscc1N*] | —CH$_2$NMe$_2$ | >1000 | 3045 | | N | 404 | 439 |
| FMF-04-180-1 | 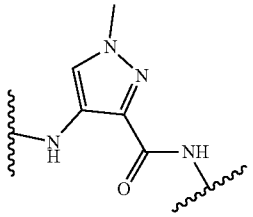 [SMILES: *NC(=O)c1nn(C)cc1N*] | H | >1000 | 9000 | | N | | |

US 12,187,701 B2
TABLE 2D-continued
Exemplary Compounds and Assay Data
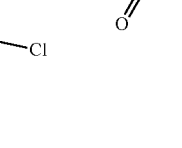
| Compound Name | Moiety of <br> 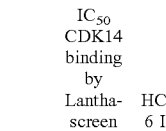 | R$_3$ | IC$_{50}$ CDK14 binding by Lantha-screen (nM) | HCT116 IC$_{50}$ (nM) | IC$_{50}$ CDK14 $^{33}$P kinase assay (nM) | Cellular Potency by Pull-down (nM) | IC$_{50}$ CDK16 Lantha-screen binding (nM) | IC$_{50}$ CDK2 Z'LYTE kinase assay (nM) |
|---|---|---|---|---|---|---|---|---|
| FMF-04-180-2 | 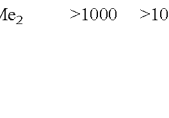 | —CH$_2$NMe$_2$ | >1000 | >10000 | | N | >10000 | >10000 |
| FMF-04-120-1 | 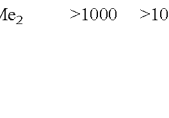 | H | >1000 | 2415 | | | | |
| FMF-04-121-1 | 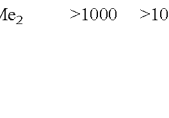 | —CH$_2$NMe$_2$ | 486 | 2862 | | | 6700 | >10000 |
| FMF-04-086-1 |  | H | >1000 | >10000 | | | | |
| FMF-04-086-2 |  | —CH$_2$NMe$_2$ | >1000 | >10000 | | | 894 | 664 |

TABLE 2D-continued

Exemplary Compounds and Assay Data

| Compound Name | Moiety of [structure] | R₃ | IC₅₀ CDK14 binding by Lantha-screen (nM) | HCT116 IC₅₀ (nM) | IC₅₀ CDK14 ³³P kinase assay (nM) | Cellular Potency by Pull-down (nM) | IC₅₀ CDK16 Lantha-screen binding (nM) | IC₅₀ CDK2 Z'LYTE kinase assay (nM) |
|---|---|---|---|---|---|---|---|---|
| FMF-04-181-1 | | H | >1000 | >10000 | | N | | |
| FMF-04-181-2 | | —CH₂NMe₂ | >1000 | >10000 | | N | 124 | 125 |
| FMF-04-199-1 | | —CH₂NMe₂ | 1000 | >10000 | | | 8900 | >10000 |
| FMF-04-197-1 | | —CH₂NMe₂ | 28 | >10000 | | | 5900 | 5900 |

Example 3. Exemplary Synthesis of Cdk14 Inhibitors
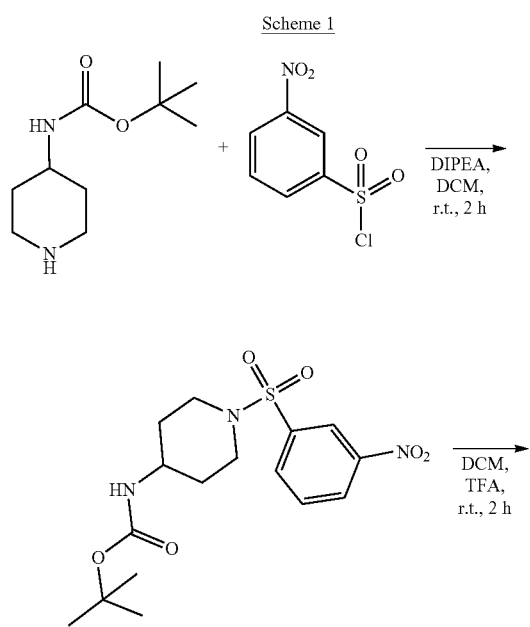
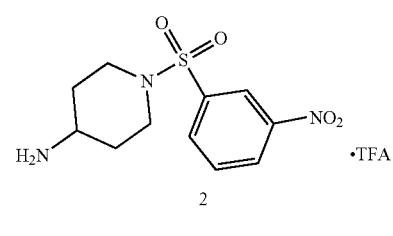
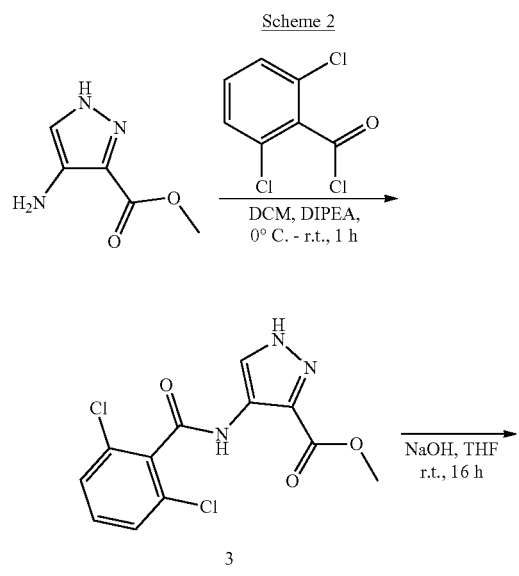
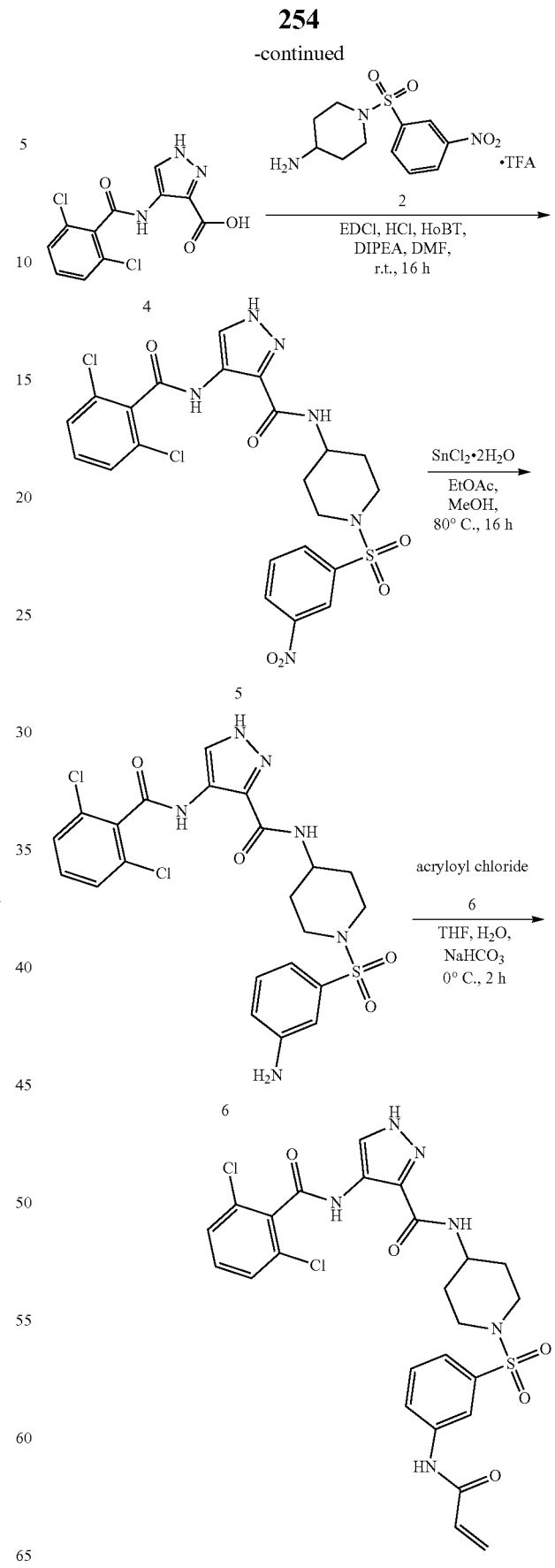

Scheme 3
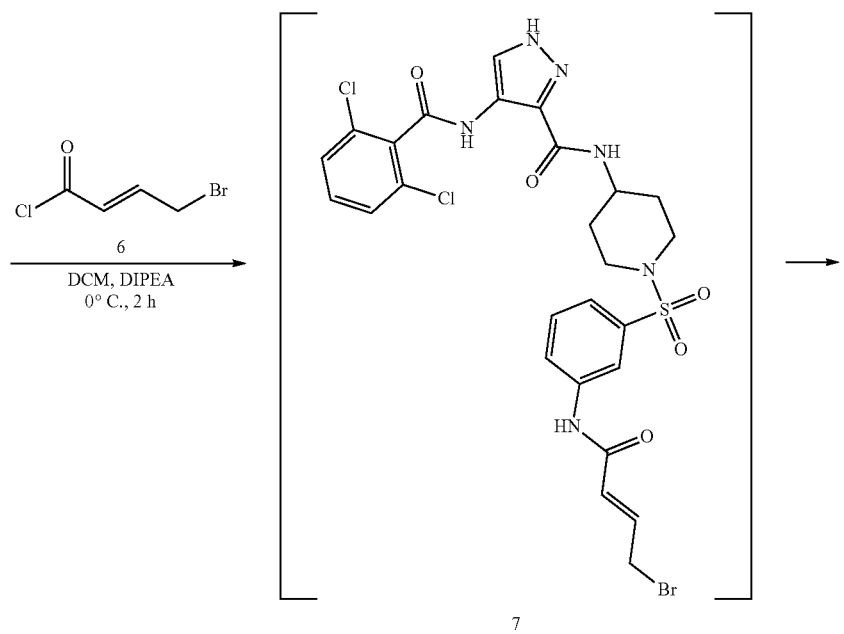
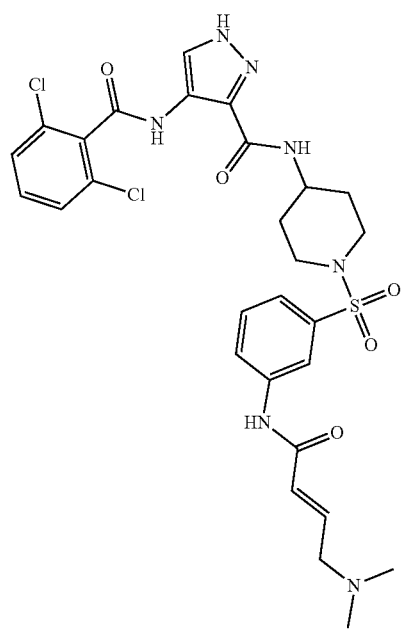
FMF-03-198-2

Method 1

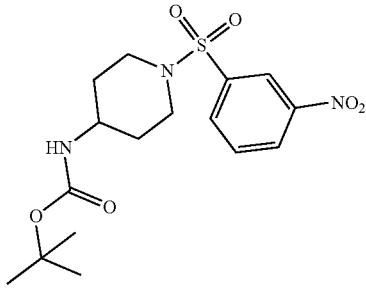

tert-butyl (1-((3-nitrophenyl)sulfonyl)piperidin-4-yl) carbamate tert-butyl piperidin-4-ylcarbamate (1.0 g, 5.0 mmol), 3-nitrobenzenesulfonyl chloride (1.22 g, 5.5 mmol), triethylamine (1.1 mL, 7.5 mmol) were stirred at room temperature ("r.t.") in DCM (20 mL) for 2 h. The reaction mixture was concentrated in vacuo, and diluted with sat. aq sodium bicarbonate (50 mL) and extacted with 100 mL DCM three times. The organics were combined, dried over sodium sulfate, filtered, and concentrated in vacuo. The product was used without further purification. Off-white solid (1.8 g, 4.7 mmol). MS (ESI) m/z 386 (M+H)$^+$. Expected mass from chemical formula $C_{16}H_{23}N_3O_6$: 385.44 Da.

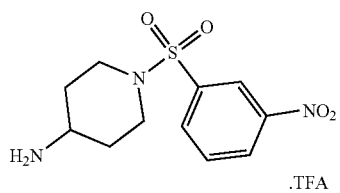

1-((3-nitrophenyl)sulfonyl)piperidin-4-amine

Intermediate 1 (1.8 g, 4.7 mmol) and TFA (2 mL) were stirred in DCM (20 mL) at r.t. for 16 h. The reaction mixture was concentrated in vacuo to afford the product as a white solid (1.87 g, 4.7 mmol). $^1$H NMR (500 MHz, DMSO-$d_6$) δ 9.09 (s, 2H), 8.56 (dd, J=8.2, 2.2 Hz, 1H), 8.39 (t, J=2.0 Hz, 1H), 8.19 (dt, J=7.8, 1.2 Hz, 1H), 7.97 (t, J=8.0 Hz, 1H), 3.72 (d, J=9.1 Hz, 1H), 3.61 (ddt, J=10.5, 6.6, 3.9 Hz, 2H), 3.13 (dd, J=7.4, 4.2 Hz, 3H), 1.98 (dd, J=13.5, 3.8 Hz, 2H), 1.58 (qd, J=11.9, 4.2 Hz, 2H). MS (ESI) m/z 286 (M+H)$^+$. Expected mass from chemical formula $C_{16}H_{23}N_3O_6$: 285.32 Da.

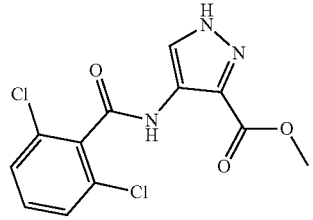

methyl 4-(2,6-dichlorobenzamido)-1H-pyrazole-3-carboxylate methyl 4-amino-1H-pyrazole-3-carboxylate (1.0 g, 7.09 mmol) and triethylamine (1.5 mL, 8.5 mmol) were stirred in dioxane (10 mL) at 0° C. A solution of 2,6-dichlorobenzoyl chloride (1.5 g, 7.17 mmol) in THF (5 mL) was added dropwise until the starting material was consumed. The reaction was filtered, and the resultant solid washed with dioxane (3×20 mL). The filtrates were combined and used directly in the next reaction.

MS (ESI) m/z 315 (M+H)$^+$. Expected mass from chemical formula $C_{12}H_9N_3O_3$: 314.12 Da.

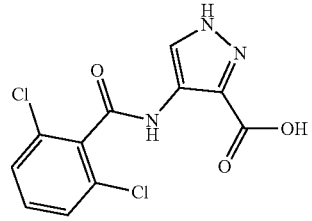

4-(2,6-dichlorobenzamido)-1H-pyrazole-3-carboxylic acid

Intermediate 3 in dioxane (15 mL) was added to 2N aq. NaOH (15 mL). The solution was stirred at r.t. for 6 h. The reaction mixture was concentrated in vacuo and dissolved in water (30 mL). The solution was cooled to 0° C. and conc. HCl added dropwise to pH 1. The precipitate was filtered and washed with water (3×5 mL). The precipitate was azeotroped with toluene, to afford the title compound as a pale gray solid (1.58 g, 0.52 mmol). $^1$H NMR (500 MHz, DMSO-$d_6$) δ 9.86 (s, 1H), 8.28 (s, 1H), 7.57-7.44 (m, 5H). MS (ESI) m/z 301 (M+H)$^+$. Expected mass from chemical formula $C_{11}H_7N_3O_3$: 300.10 Da.

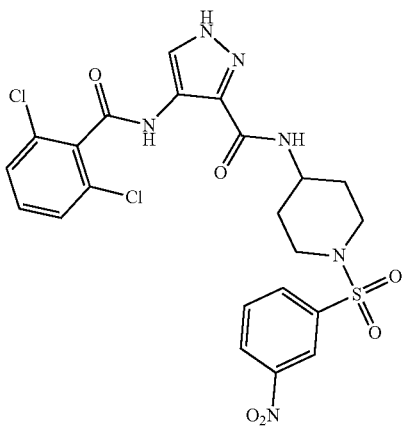

4-(2,6-dichlorobenzamido)-N-(1-((3-nitrophenyl)
sulfonyl)piperidin-4-yl)-1H-pyrazole-3-carboxamide Intermediate 2 (144 mg, 0.36 mmol), intermediate 4 (100 mg, 0.33 mmol), HoBt (60 mg, 0.44 mmol), EDCI.HCl (80 mg, 0.42 mmol) were dissolved in DMF (2 mL) and stirred at r.t. for 16 h. The reaction was diluted with sat. aq sodium bicarbonate (25 mL) and extracted with EtOAc (3×50 mL). The organics were combined, dried over sodium sulfate, filtered, and concentrated in vacuo. The residue was purified by flash chromatography (50-100% EtOAc in Hexanes) to afford the title compound as a yellow solid (150 mg, 0.26 mmol).

MS (ESI) m/z 568 (M+H)$^+$. Expected mass from chemical formula $C_{22}H_{20}N_6O_6S$: 567.40 Da.

6

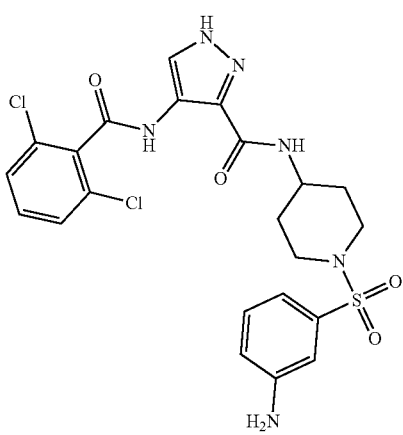

N-(1-((3-aminophenyl)sulfonyl)piperidin-4-yl)-4-(2,6-dichlorobenzamido)-1H-pyrazole-3-carboxamide Intermediate 5 (155 mg, 0.26 mmol), SnCl$_2$·2H$_2$O (146 mg, 0.65 mmol) and HCl (cat.) were dissolved in EtOAc (4 mL) and MeOH (1 mL). The reaction was stirred at 80° C. for 16 h. The reaction mixture was cooled to r.t. and quenched with sat. aq sodium bicarbonate (5 mL). The reaction was diluted with sat. aq sodium bicarbonate (25 mL) and extracted with EtOAc (3×50 mL). The organics were combined, dried over sodium sulfate, filtered, and concentrated in vacuo to afford the title compound as a yellow powder. (122 mg, 0.22 mmol). $^1$H NMR (500 MHz, DMSO-d$_6$) δ 10.13 (s, 1H), 8.43 (dd, J=8.2, 3.7 Hz, 1H), 8.39-8.31 (m, 1H), 7.59-7.54 (m, 2H), 7.54-7.46 (m, 2H), 7.24 (td, J=7.8, 3.4 Hz, 1H), 6.92 (dt, J=9.1, 2.1 Hz, 1H), 6.85-6.77 (m, 2H), 5.63 (d, J=3.1 Hz, 2H), 3.71 (dtd, J=11.2, 7.5, 4.1 Hz, 1H), 3.66-3.54 (m, 2H), 2.67-2.55 (m, 2H), 2.31 (td, J=12.0, 2.7 Hz, 1H), 1.80 (dd, J=12.9, 3.5 Hz, 2H), 1.70 (pd, J=12.4, 11.1, 3.0 Hz, 2H). MS (ESI) m/z 538 (M+H)$^+$. Expected mass from chemical formula $C_{22}H_{22}N_6O_4S$: 537.42 Da.

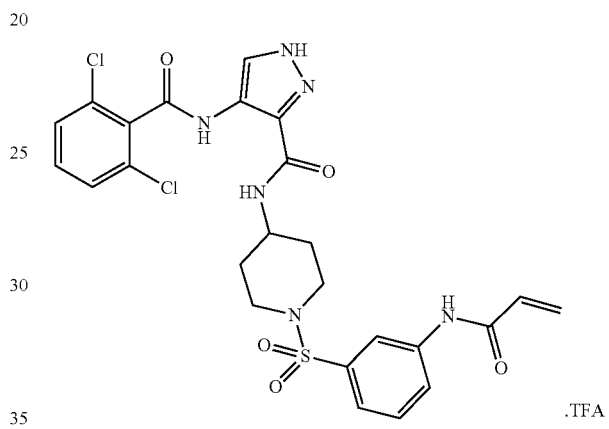

FMF-03-198-1

N-(1-((3-acrylamidophenyl)sulfonyl)piperidin-4-yl)-4-(2,6-dichlorobenzamido)-1H-pyrazole-3-carboxamide Intermediate 6 (50 mg, 0.09 mmol) was dissolved in THF (5 mL) and with sat. aq sodium bicarbonate (5 mL). The reaction was cooled to 0° C. and acryloyl chloride (12 mg, 0.14 mmol) in THF (1 mL) was added dropwise until the starting material was consumed. The reaction was diluted with sat. aq sodium bicarbonate (25 mL) and extracted with iPrOH:CHCl$_3$ (1:4, 3×50 mL). The organics were combined, dried over sodium sulfate, filtered, and concentrated in vacuo. The residue was purified by HPLC to afford the title compound (10 mg, 0.02 mmol) as a white powder. $^1$H NMR (500 MHz, DMSO-d$_6$) δ 13.42 (s, 1H), 10.52 (s, 1H), 10.11 (s, 1H), 8.44 (d, J=8.2 Hz, 1H), 8.35 (s, 1H), 8.15 (t, J=2.0 Hz, 1H), 7.94 (ddd, J=8.2, 2.1, 1.0 Hz, 1H), 7.63-7.54 (m, 3H), 7.51 (dd, J=9.2, 6.9 Hz, 1H), 7.42 (dt, J=8.1, 1.2 Hz, 1H), 6.43 (dd, J=17.0, 10.1 Hz, 1H), 6.31 (dd, J=17.0, 2.0 Hz, 1H), 5.82 (dd, J=10.1, 2.0 Hz, 1H), 3.77-3.67 (m, 1H), 3.62 (d, J=11.7 Hz, 2H), 2.41-2.32 (m, 2H), 1.80 (d, J=12.7 Hz, 2H), 1.75-1.64 (m, 2H). MS (ESI) m/z 592 (M+H)$^+$. Expected mass from chemical formula $C_{25}H_{24}Cl_2N_6O_5S$: 591.46

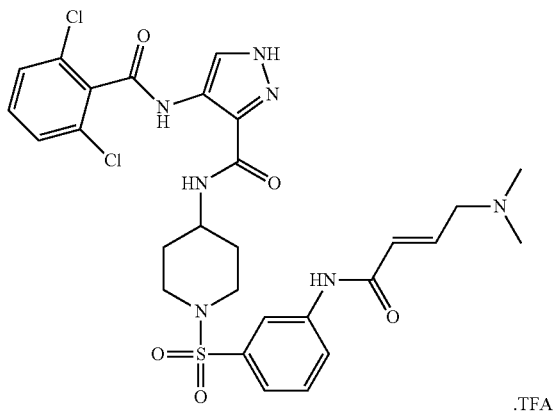 [SMILES: CN(C)C/C=C/C(=O)Nc1cccc(S(=O)(=O)N2CCC(NC(=O)c3n[nH]cc3NC(=O)c3c(Cl)cccc3Cl)CC2)c1]

FMF-03-198-2

(E)-4-(2,6-dichlorobenzamido)-N-(1-((3-(4-(dimethylamino)but-2-enamido)phenyl)sulfonyl)piperidin-4-yl)-1H-pyrazole-3-carboxamide Intermediate 6 (50 mg, 0.09 mmol) and DIPEA (100 μL, 1.1 mmol) were dissolved in DCM (10 mL). The reaction was cooled to 0° C. and (E)-4-bromobut-2-enoyl chloride (26 mg, 0.14 mmol) in DCM (1 mL) was added dropwise until the starting material was consumed. The reaction mixture was concentrated in vacuo. The residue was purified by HPLC to afford the title compound (2 mg, 0.004 mmol) as a white powder. $^1$H NMR (500 MHz, DMSO-$d_6$) δ 13.44 (s, 1H), 10.73 (s, 1H), 10.11 (s, 1H), 10.01 (s, 1H), 8.45 (d, J=8.4 Hz, 1H), 8.35 (s, 1H), 8.18 (t, J=2.0 Hz, 1H), 7.95-7.88 (m, 1H), 7.66-7.48 (m, 4H), 7.45 (dt, J=7.8, 1.3 Hz, 1H), 6.79 (dt, J=14.8, 7.2 Hz, 1H), 6.51-6.40 (m, 1H), 3.97 (d, J=7.1 Hz, 2H), 3.77-3.67 (m, 1H), 3.63 (d, J=11.5 Hz, 2H), 2.81 (s, 6H), 2.34 (d, J=11.9 Hz, 2H), 1.80 (d, J=12.3 Hz, 2H), 1.70 (d, J=12.7 Hz, 2H). MS (ESI) m/z 649 (M+H)$^+$. Expected mass from chemical formula $C_{28}H_{31}Cl_2N_7O_5S$: 648.56

Final Compounds

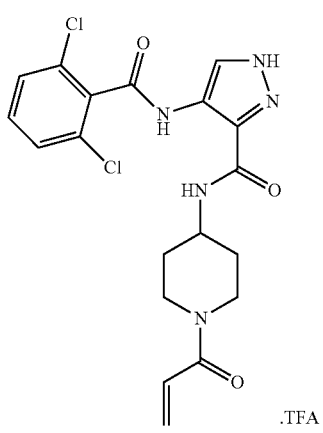 [SMILES: C=CC(=O)N1CCC(NC(=O)c2n[nH]cc2NC(=O)c2c(Cl)cccc2Cl)CC1]

FMF-03-177-1

N-(1-acryloylpiperidin-4-yl)-4-(2,6-dichlorobenzamido)-1H-pyrazole-3-carboxamide The compound was prepared according to method 1 (4 mg, 0.009 mmol) as a white powder. $^1$H NMR (500 MHz, DMSO-$d_6$) δ 13.42 (s, 1H), 10.17 (s, 1H), 8.42 (d, J=8.3 Hz, 1H), 8.36 (s, 1H), 7.65-7.46 (m, 3H), 6.82 (dd, J=16.7, 10.5 Hz, 1H), 6.09 (dd, J=16.7, 2.5 Hz, 1H), 5.67 (dd, J=10.4, 2.5 Hz, 1H), 4.41 (d, J=13.2 Hz, 1H), 4.12-3.91 (m, 3H), 3.09 (t, J=13.2 Hz, 1H), 2.75-2.62 (m, 1H), 1.78 (s, 2H), 1.49 (d, J=14.7 Hz, 3H). MS (ESI) m/z 437 (M+H)$^+$. Expected mass from chemical formula $C_{19}H_{19}Cl_2N_5O_3$: 436.29 Da.

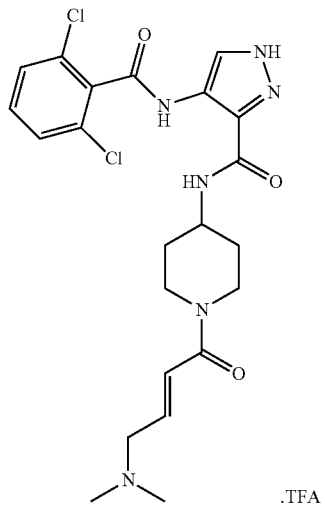 [SMILES: CN(C)C/C=C/C(=O)N1CCC(NC(=O)c2n[nH]cc2NC(=O)c2c(Cl)cccc2Cl)CC1]

FMF-03-177-2

(E)-4-(2,6-dichlorobenzamido)-N-(1-(4-(dimethylamino)but-2-enoyl)piperidin-4-yl)-1H-pyrazole-3-carboxamide The compound was prepared according to method 1 (5 mg, 0.01 mmol) as a white powder. $^1$H NMR (500 MHz, DMSO-$d_6$) δ 13.45 (s, 1H), 10.16 (s, 1H), 9.90 (s, 1H), 8.55-8.23 (m, 2H), 7.67-7.43 (m, 3H), 6.94 (dd, J=15.0, 1.4 Hz, 1H), 6.58 (dt, J=14.7, 7.1 Hz, 1H), 4.40 (d, J=13.1 Hz, 1H), 4.12-3.94 (m, 2H), 3.87 (d, J=7.2 Hz, 2H), 3.13 (t, J=13.0 Hz, 1H), 2.78 (s, 6H), 2.71 (d, J=12.5 Hz, 1H), 1.81 (t, J=14.2 Hz, 2H), 1.52 (t, J=12.6 Hz, 2H). MS (ESI) m/z 494 (M+H)$^+$. Expected mass from chemical formula $C_{22}H_{26}Cl_2N_6O_3$: 493 Da.

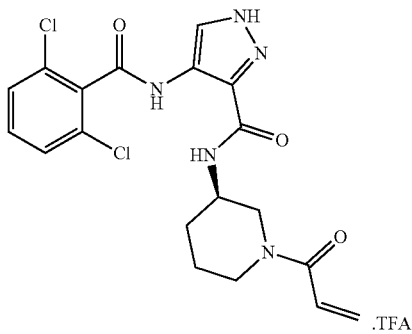 [SMILES: C=CC(=O)N1CCC[C@@H](NC(=O)c2n[nH]cc2NC(=O)c2c(Cl)cccc2Cl)C1]

FMF-03-183-1

(R)—N-(1-acryloylpiperidin-3-yl)-4-(2,6-dichlorobenzamido)-1H-pyrazole-3-carboxamide The compound was prepared according to method 1 (8 mg, 0.01 mmol) as a white powder. $^1$H NMR (500 MHz, DMSO-$d_6$) δ 13.44 (s, 1H), 10.19-10.06 (m, 1H), 8.36 (d, J=13.0 Hz, 2H), 7.65-7.46 (m, 3H), 6.76 (ddd, J=39.4, 16.6, 10.5 Hz, 1H), 6.07 (dd, J=16.7, 7.3 Hz, 1H), 5.64 (t, J=13.2 Hz, 1H), 4.23 (dd, J=81.1, 12.6 Hz, 1H), 3.92 (t, J=15.3 Hz, 1H), 3.76 (s, 1H), 3.09 (dt, J=86.6, 12.2 Hz, 1H), 2.77 (dt, J=22.6, 11.8 Hz, 1H), 1.86 (d, J=11.3 Hz, 1H), 1.73 (d, J=13.2 Hz, 2H), 1.38 (s, 1H). MS (ESI) m/z 437 (M+H)$^+$. Expected mass from chemical formula $C_{19}H_{19}Cl_2N_5O_3$: 436.29

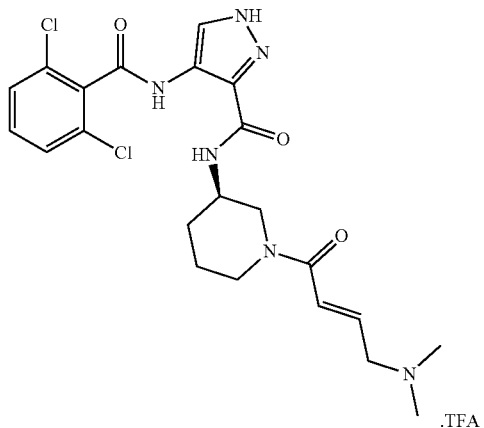 [SMILES: CN(C)C/C=C/C(=O)N1CCC[C@@H](NC(=O)c2n[nH]cc2NC(=O)c2c(Cl)cccc2Cl)C1]

FMF-03-183-2

(R,E)-4-(2,6-dichlorobenzamido)-N-(1-(4-(dimethylamino)but-2-enoyl)piperidin-3-yl)-1H-pyrazole-3-carboxamide The compound was prepared according to method 1 (3 mg, 0.006 mmol) as a white powder. $^1$H NMR (500 MHz, DMSO-$d_6$) δ 13.49 (d, J=12.6 Hz, 1H), 10.11 (d, J=16.2 Hz, 1H), 9.85 (s, 1H), 8.41 (d, J=34.1 Hz, 2H), 7.65-7.47 (m, 3H), 6.88 (dd, J=32.3, 15.1 Hz, 1H), 6.63-6.46 (m, 1H), 4.38-4.10 (m, 1H), 4.00-3.62 (m, 3H), 3.13 (dt, J=98.2, 12.1 Hz, 1H), 2.84-2.78 (m, 1H), 2.77 (s, 3H), 2.69 (s, 3H), 1.87 (d, J=11.9 Hz, 1H), 1.73 (s, 2H), 1.41 (d, J=15.5 Hz, 1H).

MS (ESI) m/z 494 (M+H)$^+$. Expected mass from chemical formula $C_{22}H_{26}Cl_2N_6O_3$: 493.39

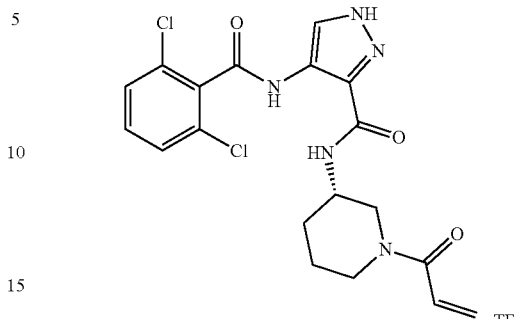

FMF-03-184-1

(S)—N-(1-acryloylpiperidin-3-yl)-4-(2,6-dichlorobenzamido)-1H-pyrazole-3-carboxamide The compound was prepared according to method 1 (4 mg, 0.005 mmol) as a white powder. $^1$H NMR (500 MHz, DMSO-$d_6$) δ 13.44 (s, 1H), 10.13 (d, J=14.1 Hz, 1H), 8.37 (s, 1H), 7.66-7.46 (m, 3H), 6.76 (ddd, J=40.3, 16.6, 10.4 Hz, 1H), 6.07 (dd, J=16.8, 7.9 Hz, 1H), 5.64 (dd, J=16.1, 10.2 Hz, 1H), 4.37-4.03 (m, 1H), 3.92 (t, J=15.3 Hz, 1H), 3.76 (s, 1H), 3.22-2.92 (m, 1H), 2.87-2.64 (m, 1H), 1.93-1.79 (m, 1H), 1.72 (s, 2H), 1.38 (s, 1H). MS (ESI) m/z 437 (M+H)$^+$. Expected mass from chemical formula $C_{19}H_{19}Cl_2N_5O_3$: 436.29

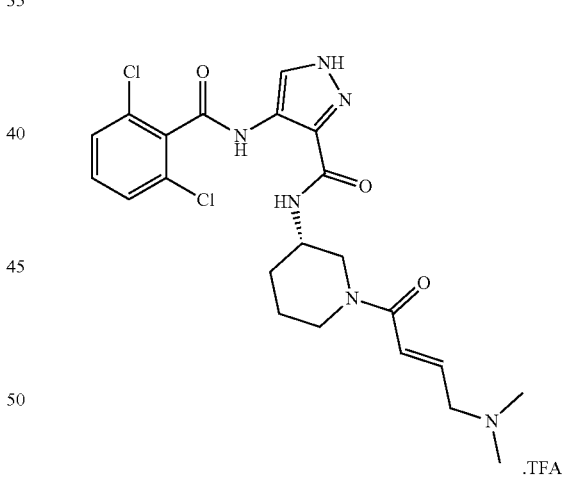

FMF-03-184-2

(S,E)-4-(2,6-dichlorobenzamido)-N-(1-(4-(dimethylamino)but-2-enoyl)piperidin-3-yl)-1H-pyrazole-3-carboxamide The compound was prepared according to method 1 (10 mg, 0.01 mmol) as a white powder. $^1$H NMR (500 MHz, DMSO-$d_6$) δ 13.48 (d, J=11.7 Hz, 1H), 10.11 (d, J=16.0 Hz, 1H), 9.77 (s, 1H), 8.41 (d, J=28.7 Hz, 2H), 7.65-7.44 (m, 3H), 6.88 (dd, J=32.4, 15.1 Hz, 1H), 6.55 (dq, J=20.2, 7.0 Hz, 1H), 4.24 (dd, J=88.3, 12.7 Hz, 1H), 3.85 (qd, J=24.7, 21.0, 14.7 Hz, 4H), 3.27-2.98 (m, 1H), 2.77 (s, 3H), 2.69 (s, 3H), 1.87 (d, J=12.0 Hz, 1H), 1.74 (d, J=13.1 Hz, 2H), 1.39 (s, 1H). MS (ESI) m/z 494 (M+H)$^+$. Expected mass from chemical formula $C_{22}H_{26}Cl_2N_6O_3$: 493.39

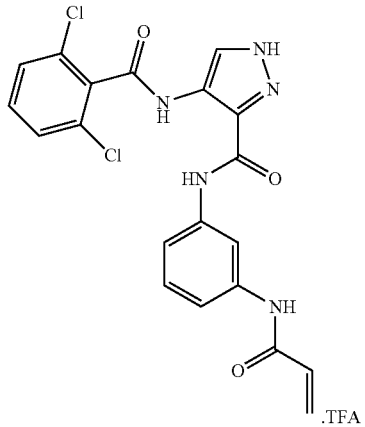 [SMILES: C=CC(=O)Nc1cccc(NC(=O)c2n[nH]cc2NC(=O)c2c(Cl)cccc2Cl)c1]

FMF-03-188-1

N-(3-acrylamidophenyl)-4-(2,6-dichlorobenzamido)-1H-pyrazole-3-carboxamide

The compound was prepared according to method 1 (2 mg, 0.005 mmol) as a white powder. $^1$H NMR (500 MHz, DMSO-d$_6$) δ 10.07 (s, 1H), 8.51 (s, 1H), 7.98-7.88 (m, 2H), 7.80-7.73 (m, 2H), 7.65 (dd, J=7.7, 1.7 Hz, 1H), 7.50 (ddd, J=8.7, 7.3, 1.8 Hz, 1H), 7.27 (d, J=8.3 Hz, 1H), 7.19 (d, J=7.4 Hz, 3H). MS (ESI) m/z 445 (M+H)$^+$. Expected mass from chemical formula $C_{20}H_{15}Cl_2N_5O_3$: 444.27

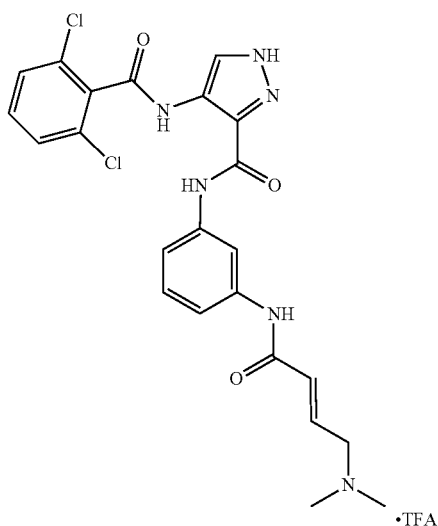 [SMILES: CN(C)C/C=C/C(=O)Nc1cccc(NC(=O)c2n[nH]cc2NC(=O)c2c(Cl)cccc2Cl)c1]

FMF-03-188-2

(E)-4-(2,6-dichlorobenzamido)-N-(3-(4-(dimethylamino)but-2-enamido)phenyl)-1H-pyrazole-3-carboxamide The compound was prepared according to method 1 (2 mg, 0.004 mmol) as a white powder. $^1$H NMR (500 MHz, DMSO-d$_6$) δ 13.65 (s, 1H), 10.35 (d, J=17.6 Hz, 2H), 10.10 (d, J=28.8 Hz, 2H), 8.44 (s, 1H), 8.23 (t, J=2.1 Hz, 1H), 7.63-7.43 (m, 4H), 7.39 (dt, J=8.2, 1.3 Hz, 1H), 7.27 (t, J=8.1 Hz, 1H), 6.74 (dt, J=14.7, 7.2 Hz, 1H), 6.46 (dd, J=15.3, 1.4 Hz, 1H), 3.99-3.84 (m, 2H), 2.80 (s, 6H). MS (ESI) m/z 502 (M+H)$^+$. Expected mass from chemical formula $C_{23}H_{22}Cl_2N_6O_3$: 501.37

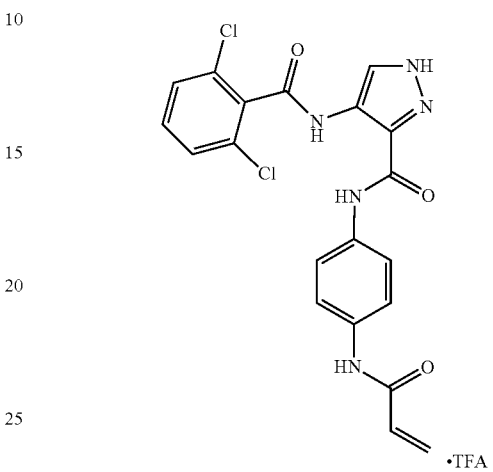

FMF-03-182-1

N-(4-acrylamidophenyl)-4-(2,6-dichlorobenzamido)-1H-pyrazole-3-carboxamide

The compound was prepared according to method 1 (10 mg, 0.02 mmol) as a white powder. $^1$H NMR (500 MHz, DMSO-d$_6$) δ 13.58 (s, 1H), 10.30 (s, 1H), 10.14 (d, J=16.4 Hz, 2H), 8.44 (d, J=1.5 Hz, 1H), 7.78-7.65 (m, 2H), 7.65-7.43 (m, 5H), 6.42 (dd, J=16.9, 10.1 Hz, 1H), 6.24 (dd, J=17.0, 2.1 Hz, 1H), 5.74 (dd, J=10.1, 2.1 Hz, 1H). MS (ESI) m/z 445 (M+H)$^+$. Expected mass from chemical formula $C_{20}H_{15}Cl_2N_5O_3$: 444.27

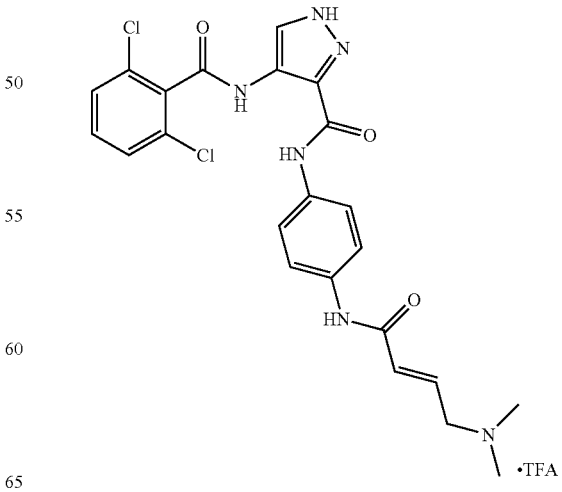

FMF-03-182-2

(E)-4-(2,6-dichlorobenzamido)-N-(4-(4-(dimethyl-amino)but-2-enamido)phenyl)-1H-pyrazole-3-carboxamide The compound was prepared according to method 1 (10 mg, 0.02 mmol) as a white powder.

$^1$H NMR (500 MHz, DMSO-$d_6$) δ 13.61 (s, 1H), 10.32 (d, J=12.6 Hz, 2H), 10.14 (s, 1H), 9.87 (s, 1H), 8.45 (s, 1H), 7.75 (d, J=9.0 Hz, 2H), 7.65-7.47 (m, 5H), 6.73 (dt, J=14.7, 7.2 Hz, 1H), 6.44 (dd, J=15.2, 1.5 Hz, 1H), 4.00-3.85 (m, 2H), 2.80 (s, 6H). MS (ESI) m/z 502 (M+H)$^+$. Expected mass from chemical formula $C_{23}H_{22}Cl_2N_6O_3$: 501.37

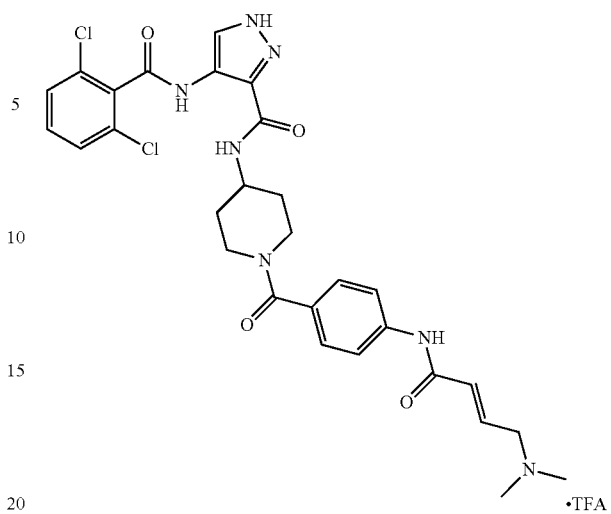

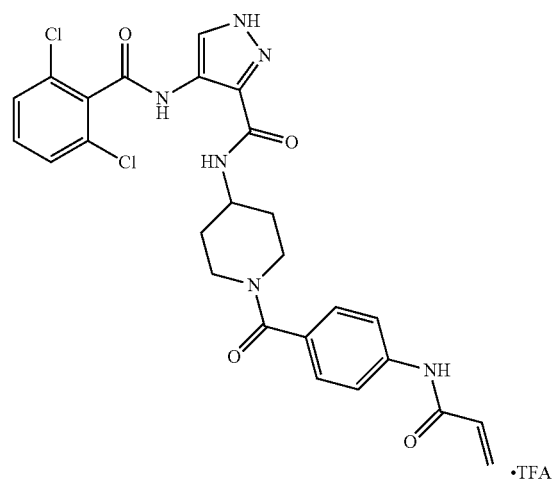 [SMILES: C=CC(=O)Nc1ccc(C(=O)N2CCC(NC(=O)c3n[nH]cc3NC(=O)c3c(Cl)cccc3Cl)CC2)cc1]

FMF-03-186-1

N-(1-(4-acrylamidobenzoyl)piperidin-4-yl)-4-(2,6-dichlorobenzamido)-1H-pyrazole-3-carboxamide The compound was prepared according to method 1 (3 mg, 0.006 mmol) as a white powder. $^1$H NMR (500 MHz, DMSO-$d_6$) δ 13.42 (s, 1H), 10.31 (s, 1H), 10.16 (s, 1H), 8.48-8.25 (m, 2H), 7.77-7.64 (m, 2H), 7.63-7.45 (m, 3H), 7.42-7.30 (m, 2H), 6.45 (dd, J=17.0, 10.2 Hz, 1H), 6.29 (dd, J=17.0, 2.0 Hz, 1H), 5.79 (dd, J=10.1, 2.0 Hz, 1H), 4.59-3.54 (m, 1H), 4.02 (ddp, J=11.8, 8.5, 4.3 Hz, 1H), 3.22-2.70 (m, 1H), 1.77 (s, 2H), 1.59 (d, J=12.6 Hz, 2H), 1.33-1.10 (m, 1H).

MS (ESI) m/z 556 (M+H)$^+$. Expected mass from chemical formula $C_{26}H_{24}Cl_2N_6O_4$: 555.42

FMF-03-187-1

(E)-4-(2,6-dichlorobenzamido)-N-(1-(4-(4-(dimethylamino)but-2-enamido)benzoyl)piperidin-4-yl)-1H-pyrazole-3-carboxamide The compound was prepared according to method 1 (4 mg, 0.005 mmol) as a white powder. $^1$H NMR (500 MHz, DMSO-$d_6$) δ 13.45 (s, 1H), 10.52 (s, 1H), 10.16 (s, 1H), 9.98 (d, J=37.2 Hz, 1H), 8.39 (d, J=8.2 Hz, 1H), 8.35 (s, 1H), 7.79-7.68 (m, 2H), 7.62-7.49 (m, 3H), 7.42-7.34 (m, 2H), 6.77 (dt, J=14.7, 7.2 Hz, 1H), 6.48 (dd, J=15.3, 1.5 Hz, 1H), 4.56-4.17 (m, 1H), 4.02 (tdd, J=11.4, 7.9, 4.1 Hz, 1H), 3.96 (d, J=7.2 Hz, 2H), 2.80 (d, J=15.8 Hz, 7H), 1.78 (s, 2H), 1.60 (s, 2H).

MS (ESI) m/z 613 (M+H)$^+$. Expected mass from chemical formula $C_{29}H_{31}Cl_2N_7O_4$: 612.51

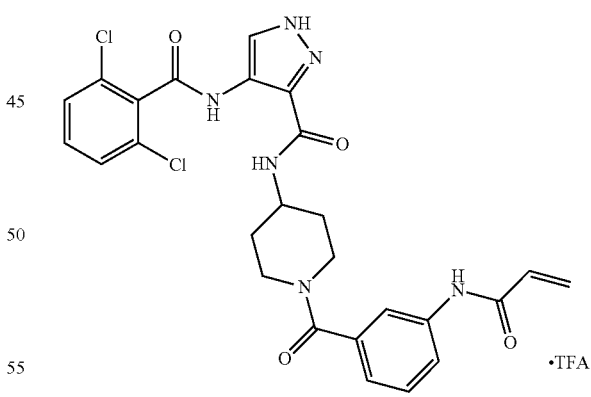

FMF-03-196-1

N-(1-(3-acrylamidobenzoyl)piperidin-4-yl)-4-(2,6-dichlorobenzamido)-1H-pyrazole-3-carboxamide The compound was prepared according to method 1 (2 mg, 0.003 mmol) as a white powder.
$^1$H NMR (500 MHz, DMSO-$d_6$) δ 13.43 (s, 1H), 10.29 (s, 1H), 10.17 (s, 1H), 8.44 (d, J=8.1 Hz, 1H), 8.35 (s, 1H), 7.82

(d, J=1.9 Hz, 1H), 7.67-7.46 (m, 4H), 7.40 (t, J=7.9 Hz, 1H), 7.06 (dt, J=7.6, 1.3 Hz, 1H), 6.44 (dd, J=17.0, 10.1 Hz, 1H), 6.28 (dd, J=17.0, 2.0 Hz, 1H), 5.78 (dd, J=10.1, 2.0 Hz, 1H), 4.46 (s, 1H), 4.03 (ddp, J=11.6, 8.3, 4.2 Hz, 1H), 3.89 (t, J=6.2 Hz, 1H), 3.63 (s, 1H), 3.14 (d, J=38.6 Hz, 1H), 2.97-2.77 (m, 1H), 1.78 (d, J=49.1 Hz, 3H), 1.61 (s, 3H). MS (ESI) m/z 556 (M+H)$^+$. Expected mass from chemical formula $C_{26}H_{24}Cl_2N_6O_4$: 555.42

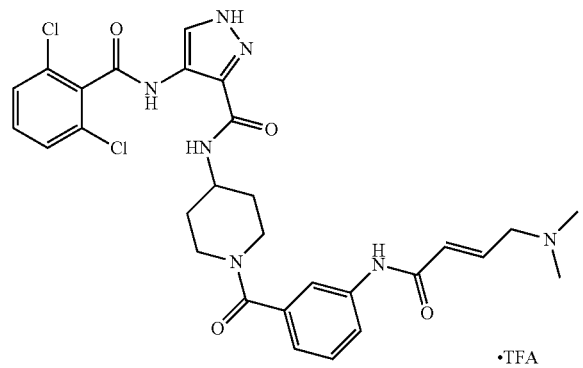 [SMILES: CN(C)C/C=C/C(=O)Nc1cccc(C(=O)N2CCC(NC(=O)c3n[nH]cc3NC(=O)c3c(Cl)cccc3Cl)CC2)c1]

FMF-03-196-2

(E)-4-(2,6-dichlorobenzamido)-N-(1-(3-(4-(dimethylamino)but-2-enamido)benzoyl)piperidin-4-yl)-1H-pyrazole-3-carboxamide The compound was prepared according to method 1 (10 mg, 0.01 mmol) as a white powder. $^1$H NMR (500 MHz, DMSO-d$_6$) δ 13.45 (s, 1H), 10.50 (s, 1H), 10.16 (s, 1H), 10.07 (s, 1H), 8.43 (d, J=8.4 Hz, 1H), 8.35 (s, 1H), 7.82 (d, J=1.9 Hz, 1H), 7.64 (dt, J=8.3, 1.4 Hz, 1H), 7.60 (d, J=1.6 Hz, 1H), 7.58 (s, 1H), 7.53 (dd, J=9.2, 6.8 Hz, 1H), 7.42 (t, J=7.9 Hz, 1H), 7.12-7.03 (m, 1H), 6.77 (dt, J=14.7, 7.2 Hz, 1H), 6.47 (d, J=15.5 Hz, 1H), 4.45 (s, 2H), 4.02 (dt, J=11.5, 5.7 Hz, 1H), 3.96 (d, J=7.2 Hz, 2H), 3.62 (s, 1H), 3.14-2.99 (m, 1H), 2.88 (s, 1H), 2.80 (s, 6H), 1.78 (d, J=47.5 Hz, 2H), 1.58 (s, 2H). MS (ESI) m/z 613 (M+H)$^+$. Expected mass from chemical formula $C_{29}H_{31}Cl_2N_7O_4$: 612.51

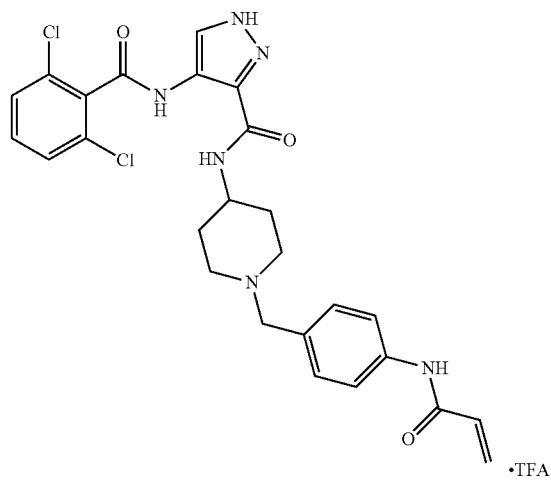 [SMILES: C=CC(=O)Nc1ccc(CN2CCC(NC(=O)c3n[nH]cc3NC(=O)c3c(Cl)cccc3Cl)CC2)cc1]

FMF-03-199-1

N-(1-(4-acrylamidobenzyl)piperidin-4-yl)-4-(2,6-dichlorobenzamido)-1H-pyrazole-3-carboxamide The compound was prepared according to method 1 (2 mg, 0.003 mmol) as a white powder.

$^1$H NMR (500 MHz, DMSO-d$_6$) δ 13.50 (d, J=22.8 Hz, 1H), 10.33 (s, 1H), 10.11 (d, J=8.4 Hz, 1H), 8.37 (s, 1H), 7.89 (s, 1H), 7.77-7.72 (m, 2H), 7.61-7.56 (m, 2H), 7.55-7.51 (m, 1H), 7.46-7.41 (m, 2H), 6.45 (dd, J=17.0, 10.1 Hz, 1H), 6.28 (dd, J=17.0, 1.9 Hz, 1H), 5.79 (dd, J=10.1, 2.0 Hz, 1H), 4.23 (d, J=5.0 Hz, 2H), 3.96 (dd, J=7.6, 4.0 Hz, 1H), 3.03 (q, J=11.8 Hz, 2H), 1.97 (d, J=13.3 Hz, 2H), 1.84 (q, J=12.8 Hz, 2H). MS (ESI) m/z 542 (M+H)$^+$. Expected mass from chemical formula $C_{26}H_{26}Cl_2N_6O_3$: 541.43.

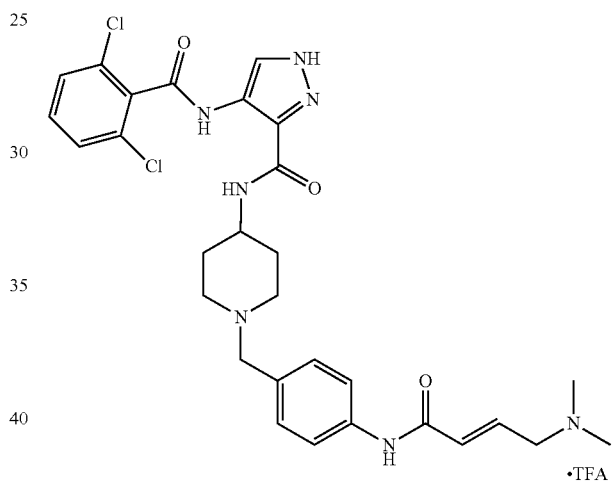

FMF-03-199-2

(E)-4-(2,6-dichlorobenzamido)-N-(1-(4-(4-(dimethylamino)but-2-enamido)benzyl)piperidin-4-yl)-1H-pyrazole-3-carboxamide The compound was prepared according to method 1 (2 mg, 0.003 mmol) as a white powder. $^1$H NMR (500 MHz, DMSO-d$_6$) δ 10.54 (s, 1H), 10.12 (s, 1H), 8.67 (d, J=7.9 Hz, 1H), 8.36 (s, 1H), 7.75 (d, J=8.3 Hz, 2H), 7.63-7.56 (m, 3H), 7.53 (dd, J=9.2, 6.8 Hz, 1H), 7.50-7.42 (m, 2H), 6.77 (dt, J=14.8, 7.2 Hz, 1H), 6.49 (d, J=15.3 Hz, 1H), 4.31 (s, 1H), 4.23 (s, 2H), 3.96 (d, J=7.0 Hz, 2H), 3.37 (d, J=12.6 Hz, 2H), 3.28-3.21 (m, 2H), 2.81 (s, 6H), 2.01-1.91 (m, 2H), 1.85 (q, J=12.9, 12.2 Hz, 2H). MS (ESI) m/z 599 (M+H)$^+$. Expected mass from chemical formula $C_{28}H_{33}Cl_2N_7O_3$: 598.53

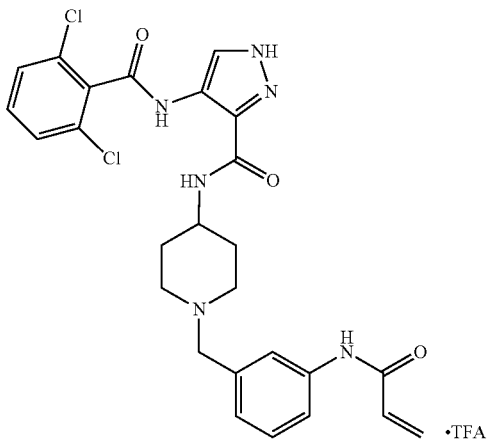 [SMILES: C=CC(=O)Nc1cccc(CN2CCC(NC(=O)c3n[nH]cc3NC(=O)c3c(Cl)cccc3Cl)CC2)c1]

FMF-03-200-1

N-(1-(3-acrylamidobenzyl)piperidin-4-yl)-4-(2,6-dichlorobenzamido)-1H-pyrazole-3-carboxamide The compound was prepared according to method 1 (2 mg, 0.003 mmol) as a white powder. $^1$H NMR (500 MHz, DMSO-$d_6$) δ 13.49 (s, 1H), 10.34 (d, J=4.7 Hz, 1H), 10.12 (d, J=8.3 Hz, 1H), 8.68 (d, J=7.9 Hz, 1H), 8.36 (s, 1H), 7.98 (s, 1H), 7.64-7.48 (m, 5H), 7.44 (q, J=7.8 Hz, 1H), 7.21 (t, J=8.8 Hz, 1H), 6.47 (dd, J=17.0, 10.1 Hz, 1H), 6.28 (dd, J=16.9, 2.0 Hz, 1H), 5.79 (dd, J=10.1, 2.0 Hz, 1H), 4.27 (d, J=5.0 Hz, 2H), 3.96 (dt, J=7.9, 3.9 Hz, 1H), 3.39 (d, J=12.3 Hz, 2H), 3.07 (q, J=11.8, 11.4 Hz, 2H), 1.97 (d, J=13.3 Hz, 2H), 1.86 (dd, J=18.5, 8.4 Hz, 2H). MS (ESI) m/z 542 (M+H)$^+$. Expected mass from chemical formula $C_{26}H_{26}Cl_2N_6O_3$: 541.43.

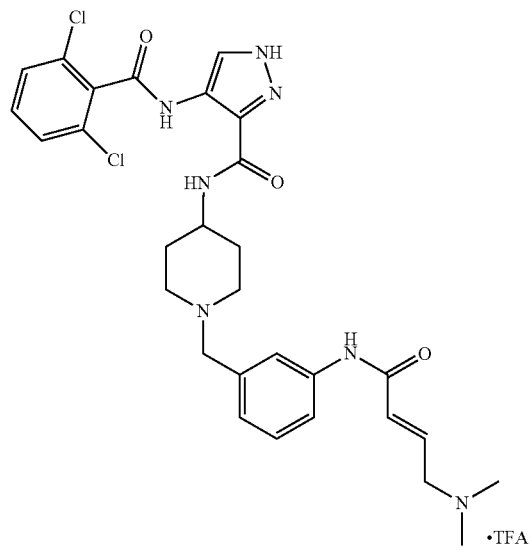 [SMILES: CN(C)C/C=C/C(=O)Nc1cccc(CN2CCC(NC(=O)c3n[nH]cc3NC(=O)c3c(Cl)cccc3Cl)CC2)c1]

FMF-03-200-2

The compound was prepared according to method 1 (4 mg, 0.005 mmol) as a white powder. $^1$H NMR (500 MHz, DMSO-$d_6$) δ 13.52 (s, 1H), 10.54 (s, 1H), 10.12 (s, 1H), 8.68 (d, J=7.8 Hz, 1H), 8.36 (s, 1H), 7.93 (s, 1H), 7.67-7.49 (m, 5H), 7.44 (t, J=7.8 Hz, 1H), 7.23 (d, J=7.7 Hz, 1H), 6.76 (dt, J=14.8, 7.1 Hz, 1H), 6.50 (dt, J=15.2, 1.3 Hz, 1H), 4.27 (s, 1H), 3.96 (d, J=7.3 Hz, 2H), 3.39 (d, J=12.0 Hz, 2H), 3.05 (d, J=12.6 Hz, 2H), 2.81 (s, 6H), 1.97 (d, J=13.2 Hz, 2H), 1.88 (d, J=13.6 Hz, 2H). MS (ESI) m/z 599 (M+H)$^+$. Expected mass from chemical formula $C_{28}H_{33}Cl_2N_7O_3$: 598.53

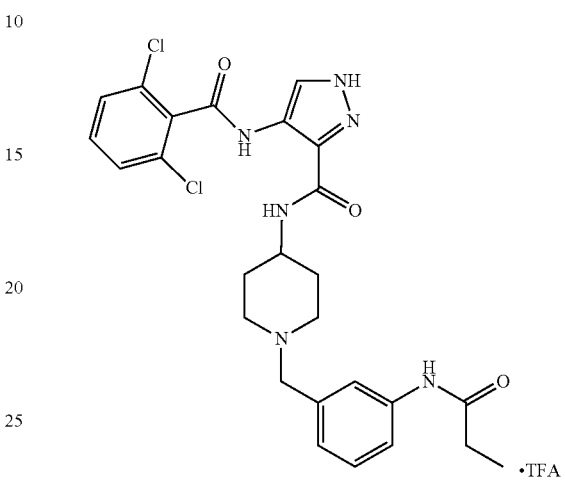

FMF-04-172-1 (FMF-03-200-R)

4-(2,6-dichlorobenzamido)-N-(1-(3-propionamido-benzyl)piperidin-4-yl)-1H-pyrazole-3-carboxamide The compound was prepared according to method 1 (20 mg, 0.036 mmol) as a white powder. $^1$H NMR (500 MHz, DMSO-$d_6$) δ 13.48 (s, 1H), 10.12 (d, J=8.9 Hz, 1H), 10.03 (d, J=4.8 Hz, 1H), 9.52 (s, 1H), 8.79-8.59 (m, 1H), 8.38 (d, J=16.9 Hz, 1H), 7.92 (t, J=1.9 Hz, 1H), 7.64-7.42 (m, 5H), 7.39 (t, J=7.9 Hz, 1H), 7.15 (dt, J=7.6, 1.3 Hz, 1H), 4.25 (d, J=5.2 Hz, 2H), 3.96 (dt, J=11.8, 4.0 Hz, 1H), 3.37 (d, J=11.8 Hz, 2H), 3.03 (dd, J=22.2, 10.7 Hz, 2H), 2.34 (q, J=7.5 Hz, 2H), 1.99-1.82 (m, 4H), 1.09 (t, J=7.5 Hz, 3H). MS (ESI) m/z 544 (M+H)$^+$. Expected mass from chemical formula $C_{28}H_{33}Cl_2N_7O_3$: 543.45

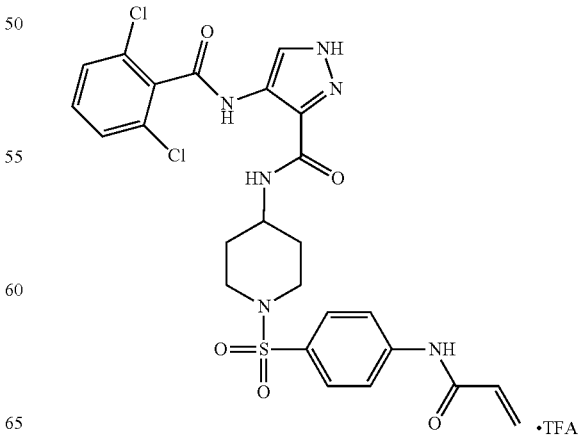

FMF-03-197-1

N-(1-((4-acrylamidophenyl)sulfonyl)piperidin-4-yl)-4-(2,6-dichlorobenzamido)-1H-pyrazole-3-carboxamide The compound was prepared according to method 1 (2 mg, 0.004 mmol) as a white powder. $^1$H NMR (500 MHz, DMSO-$d_6$) δ 13.41 (s, 1H), 10.57 (s, 1H), 10.12 (s, 1H), 8.34 (s, 1H), 7.94-7.89 (m, 2H), 7.73-7.68 (m, 2H), 7.59-7.54 (m, 2H), 7.51 (dd, J=9.2, 6.9 Hz, 1H), 6.46 (dd, J=17.0, 10.1 Hz, 1H), 6.32 (dd, J=17.0, 1.9 Hz, 1H), 5.83 (dd, J=10.1, 1.9 Hz, 1H), 3.74-3.67 (m, 1H), 3.61 (d, J=12.3 Hz, 2H), 2.31 (t, J=11.7 Hz, 2H), 1.79 (d, J=12.7 Hz, 2H), 1.68 (d, J=11.9 Hz, 2H). MS (ESI) m/z 592 (M+H)$^+$. Expected mass from chemical formula $C_{25}H_{24}Cl_2N_6O_5S$: 591.46

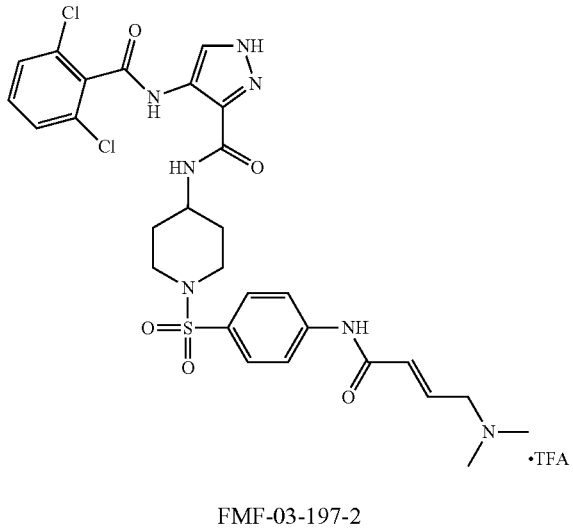

FMF-03-197-2

(E)-4-(2,6-dichlorobenzamido)-N-(1-((4-(4-(dimethylamino)but-2-enamido)phenyl)sulfonyl)piperidin-4-yl)-1H-pyrazole-3-carboxamide The compound was prepared according to method 1 (2 mg, 0.004 mmol) as a white powder. $^1$H NMR (500 MHz, DMSO-$d_6$) δ 13.44 (s, 1H), 10.77 (s, 1H), 10.12 (d, J=7.7 Hz, 1H), 10.00 (s, 1H), 8.44 (d, J=8.5 Hz, 1H), 8.35 (s, 1H), 7.96-7.87 (m, 2H), 7.77-7.67 (m, 2H), 7.60-7.47 (m, 4H), 6.80 (dt, J=14.7, 7.2 Hz, 1H), 6.49 (dt, J=15.3, 1.3 Hz, 1H), 3.97 (d, J=7.1 Hz, 2H), 3.75-3.65 (m, 1H), 3.62 (d, J=11.5 Hz, 2H), 2.81 (s, 6H), 2.29 (t, J=11.7 Hz, 2H), 1.78 (s, 2H), 1.69 (d, J=12.1 Hz, 2H). MS (ESI) m/z 649 (M+H)$^+$. Expected mass from chemical formula $C_{28}H_{31}Cl_2N_7O_5S$: 648.56

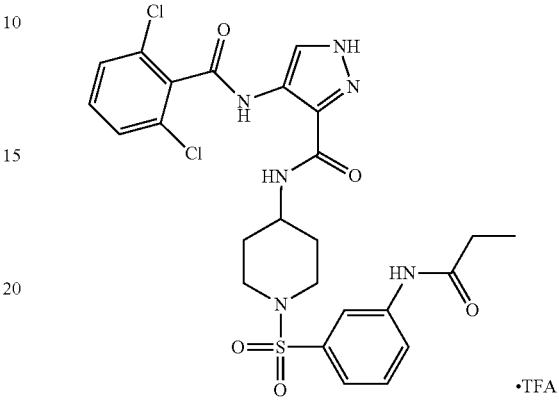

FMF-04-060-1 (FMF-03-198-R)

4-(2,6-dichlorobenzamido)-N-(1-((3-propionamidophenyl)sulfonyl)piperidin-4-yl)-1H-pyrazole-3-carboxamide The compound was prepared according to method 1 (12 mg, 0.02 mmol) as a white powder. $^1$H NMR (500 MHz, DMSO-$d_6$) δ 13.41 (d, J=1.5 Hz, 1H), 10.23 (s, 1H), 10.12 (s, 1H), 8.44 (d, J=8.2 Hz, 1H), 8.35 (d, J=1.4 Hz, 1H), 8.08 (t, J=2.0 Hz, 1H), 7.85 (ddd, J=8.2, 2.1, 1.0 Hz, 1H), 7.60-7.46 (m, 4H), 7.37 (dt, J=7.8, 1.3 Hz, 1H), 4.09 (s, 3H), 3.71 (ddp, J=11.5, 8.2, 4.3 Hz, 1H), 3.61 (d, J=11.8 Hz, 2H), 2.35 (q, J=7.5 Hz, 2H), 1.80 (dd, J=13.0, 3.8 Hz, 2H), 1.74-1.64 (m, 2H), 1.09 (t, J=7.5 Hz, 3H). MS (ESI) m/z 594 (M+H)$^+$. Expected mass from chemical formula $C_{25}H_{26}Cl_2N_6O_5S$: 593.48

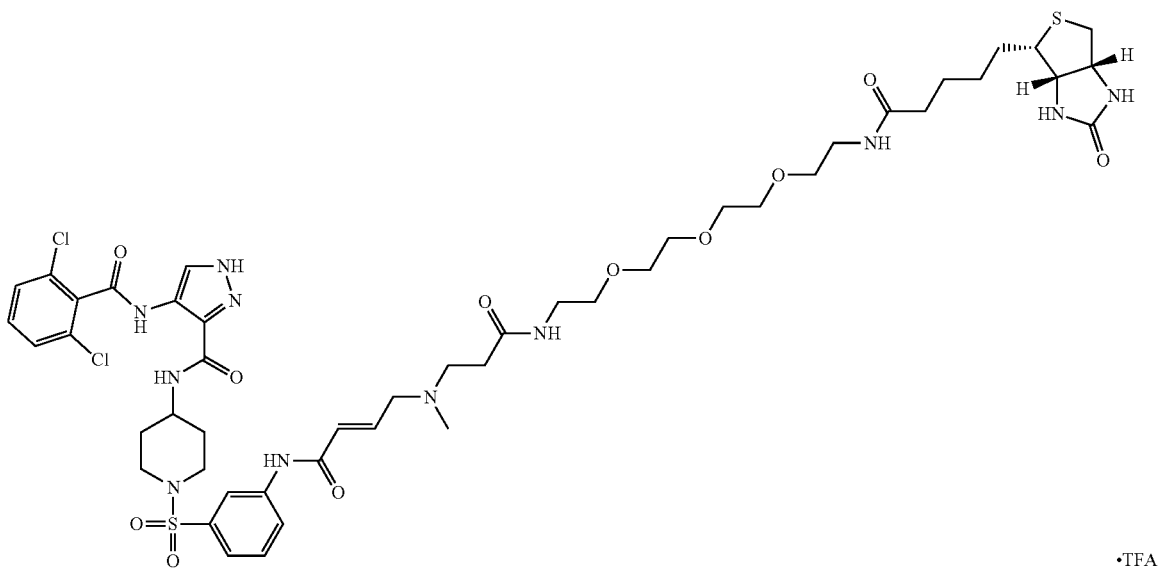 [SMILES: CN(C/C=C/C(=O)Nc1cccc(S(=O)(=O)N2CCC(NC(=O)c3n[nH]cc3NC(=O)c3c(Cl)cccc3Cl)CC2)c1)CCC(=O)NCCOCCOCCOCCNC(=O)CCCC[C@@H]1SC[C@@H]2NC(=O)N[C@@H]21]

FMF-04-153-1 (Biotin-FMF-03-198-2)

4-(2,6-dichlorobenzamido)-N-(1-((3-((E)-5-methyl-8,22-dioxo-26-((3aS,4S,6aR)-2-oxohexahydro-1H-thieno[3,4-d]imidazol-4-yl)-12,15,18-trioxa-5,9,21-triazahexacos-2-enamido)phenyl)sulfonyl)piperidin-4-yl)-1H-pyrazole-3-carboxamide The compound was prepared according to method 1 (4 mg, 0.003 mmol) as a white powder. MS (ESI) m/z 1108 (M+H)$^+$, 554 [(M+H)$^+$/2]. Expected mass from chemical formula $C_{48}H_{65}Cl_2N_{11}O_{11}S_2$: 1107.13

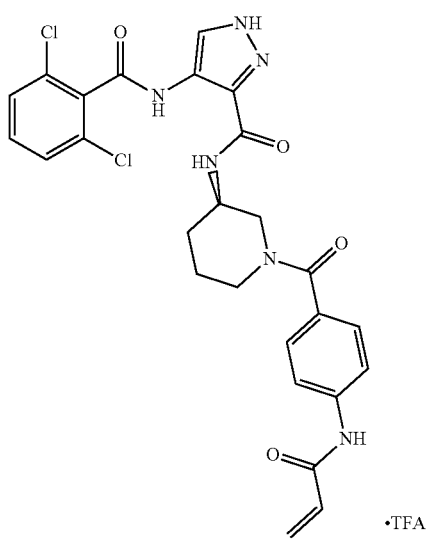 [SMILES: C=CC(=O)Nc1ccc(C(=O)N2CCC[C@@H](NC(=O)c3n[nH]cc3NC(=O)c3c(Cl)cccc3Cl)C2)cc1]

FMF-04-058-1

(R)—N-(1-(4-acrylamidobenzoyl)piperidin-3-yl)-4-(2,6-dichlorobenzamido)-1H-pyrazole-3-carboxamide The compound was prepared according to method 1 (8 mg, 0.014 mmol) as a white powder. $^1$H NMR (500 MHz, DMSO-d$_6$) δ 13.28 (s, 1H), 10.47 (d, J=40.2 Hz, 1H), 10.35 (s, 1H), 8.31 (s, 1H), 8.22 (s, 1H), 7.81 (d, J=8.4 Hz, 2H), 7.76-7.69 (m, 2H), 7.63-7.54 (m, 2H), 7.50 (dd, J=9.1, 7.0 Hz, 1H), 6.46 (dd, J=17.0, 10.1 Hz, 1H), 6.29 (dd, J=17.0, 1.9 Hz, 1H), 5.80 (dd, J=10.1, 2.0 Hz, 1H), 4.61 (d, J=90.4 Hz, 1H), 4.47-4.12 (m, 1H), 3.91 (d, J=17.2 Hz, 1H), 2.96 (s, OH), 2.89-2.75 (m, 1H), 2.00-1.73 (m, 2H), 1.73-1.44 (m, 2H). MS (ESI) m/z 556 (M+H)$^+$. Expected mass from chemical formula $C_{26}H_{24}Cl_2N_6O_4$: 555.42

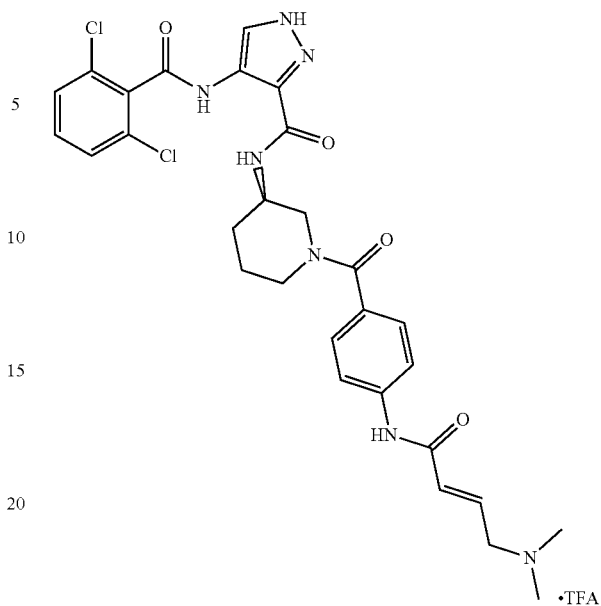

FMF-04-058-2

(R,E)-4-(2,6-dichlorobenzamido)-N-(1-(4-(4-(dimethylamino)but-2-enamido)benzoyl)piperidin-3-yl)-1H-pyrazole-3-carboxamide The compound was prepared according to method 1 (4 mg, 0.007 mmol) as a white powder. $^1$H NMR (500 MHz, DMSO-d$_6$) δ 13.28 (s, 1H), 10.47 (d, J=40.2 Hz, 1H), 10.35 (s, 1H), 8.31 (s, 1H), 8.22 (s, 1H), 7.81 (d, J=8.4 Hz, 2H), 7.76-7.69 (m, 2H), 7.60-7.54 (m, 2H), 7.50 (dd, J=9.1, 7.0 Hz, 1H), 6.46 (dd, J=17.0, 10.1 Hz, 1H), 6.29 (dd, J=17.0, 1.9 Hz, 1H), 5.80 (dd, J=10.1, 2.0 Hz, 1H), 4.61 (d, J=89.6 Hz, 1H), 4.42 (d, J=12.4 Hz, 1H), 4.18 (s, 1H), 3.99-3.88 (m, 2H), 3.18 (s, 6H), 2.96 (s, 1H), 2.90-2.77 (m, 1H), 2.00-1.91 (m, 1H), 1.79 (s, 1H), 1.63 (d, J=12.2 Hz, 1H), 1.51 (s, 1H). MS (ESI) m/z 613 (M+H)$^+$. Expected mass from chemical formula $C_{29}H_{31}Cl_2N_7O_4$: 612.51

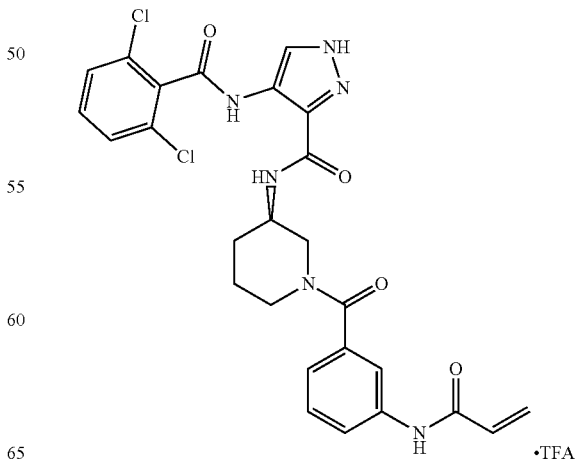

FMF-04-059-1

(R)—N-(1-(3-acrylamidobenzoyl)piperidin-3-yl)-4-(2,6-dichlorobenzamido)-1H-pyrazole-3-carboxamide The compound was prepared according to method 1 (10 mg, 0.018 mmol) as a white powder. $^1$H NMR (500 MHz, DMSO-$d_6$) δ 13.28 (s, 1H), 10.46 (d, J=38.9 Hz, 1H), 10.28 (s, 1H), 8.35 (d, J=8.0 Hz, 1H), 8.02 (s, 1H), 7.88 (d, J=8.0 Hz, 1H), 7.62-7.54 (m, 2H), 7.50 (dd, J=9.2, 6.8 Hz, 2H), 7.39 (d, J=7.5 Hz, 1H), 6.44 (dd, J=16.9, 10.1 Hz, 1H), 6.28 (dd, J=17.0, 2.0 Hz, 1H), 5.78 (dd, J=10.1, 2.0 Hz, 1H), 4.66 (d, J=118.3 Hz, 1H), 4.47-4.18 (m, 1H), 3.91 (d, J=21.1 Hz, 1H), 2.90 (d, J=8.2 Hz, 1H), 2.83 (dd, J=13.7, 8.7 Hz, 1H), 1.95 (s, 1H), 1.79 (s, 1H), 1.63 (d, J=11.7 Hz, 1H), 1.52 (s, 1H). MS (ESI) m/z 556 (M+H)$^+$. Expected mass from chemical formula $C_{26}H_{24}Cl_2N_6O_4$: 555.42

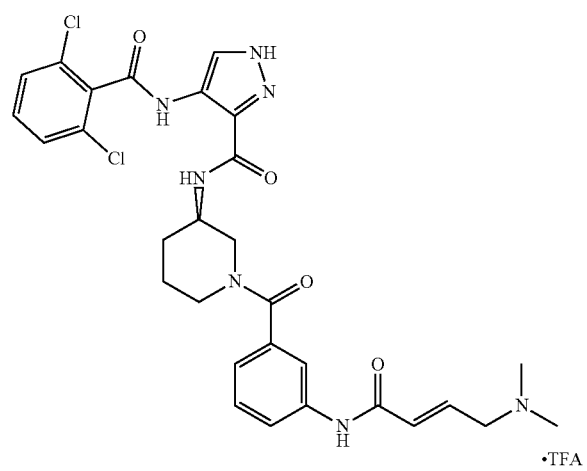 [SMILES: CN(C)C/C=C/C(=O)Nc1cccc(C(=O)N2CCC[C@@H](NC(=O)c3n[nH]cc3NC(=O)c3c(Cl)cccc3Cl)C2)c1]

FMF-04-059-2

(R,E)-4-(2,6-dichlorobenzamido)-N-(1-(3-(4-(dimethylamino)but-2-enamido)benzoyl)piperidin-3-yl)-1H-pyrazole-3-carboxamide The compound was prepared according to method 1 (10 mg, 0.016 mmol) as a white powder. $^1$H NMR (500 MHz, DMSO-$d_6$) δ 13.29 (s, 1H), 10.48 (s, 1H), 9.94 (s, 1H), 8.36 (d, J=7.9 Hz, 1H), 8.31 (s, 1H), 8.05 (s, 1H), 7.88 (d, J=8.1 Hz, 1H), 7.59-7.48 (m, 4H), 7.40 (d, J=7.3 Hz, 1H), 6.77 (dt, J=15.3, 7.2 Hz, 1H), 6.47 (dt, J=15.2, 1.2 Hz, 1H), 4.62 (d, J=109.9 Hz, 1H), 4.47-4.17 (m, 1H), 4.00-3.88 (m, 3H), 3.39-3.29 (m, 1H), 2.98-2.84 (m, 1H), 2.81 (s, 6H), 1.95 (d, J=12.1 Hz, 1H), 1.79 (s, 1H), 1.64 (d, J=11.3 Hz, 1H), 1.52 (s, 1H). MS (ESI) m/z 613 (M+H)$^+$. Expected mass from chemical formula $C_{29}H_{31}Cl_2N_7O_4$: 612.51

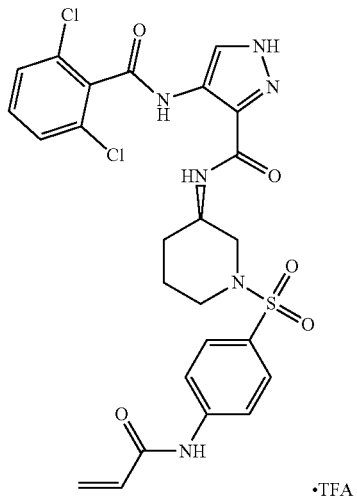 [SMILES: C=CC(=O)Nc1ccc(S(=O)(=O)N2CCC[C@@H](NC(=O)c3n[nH]cc3NC(=O)c3c(Cl)cccc3Cl)C2)cc1]

FMF-04-056-1

(R)—N-(1-((4-acrylamidophenyl)sulfonyl)piperidin-3-yl)-4-(2,6-dichlorobenzamido)-1H-pyrazole-3-carboxamide The compound was prepared according to method 1 (10 mg, 0.016 mmol) as a white powder. $^1$H NMR (500 MHz, DMSO-$d_6$) δ 13.26 (s, 1H), 10.49 (d, J=15.2 Hz, 1H), 10.39 (d, J=27.3 Hz, 1H), 8.29 (s, 1H), 7.94-7.75 (m, 1H), 7.71 (d, J=6.9 Hz, 1H), 7.61-7.53 (m, 2H), 7.50 (dd, J=9.2, 6.9 Hz, 1H), 6.47 (dd, J=16.9, 10.2 Hz, 1H), 6.32 (dd, J=17.0, 1.9 Hz, 1H), 5.83 (dd, J=10.1, 1.9 Hz, 1H), 4.40-4.00 (m, 1H), 3.09 (d, J=25.5 Hz, 2H), 2.93-2.60 (m, 1H), 2.57-2.53 (m, 1H), 1.64 (s, 2H), 1.34 (s, 2H). MS (ESI) m/z 592 (M+H)$^+$. Expected mass from chemical formula $C_{25}H_{24}Cl_2N_6O_5S$: 591.46

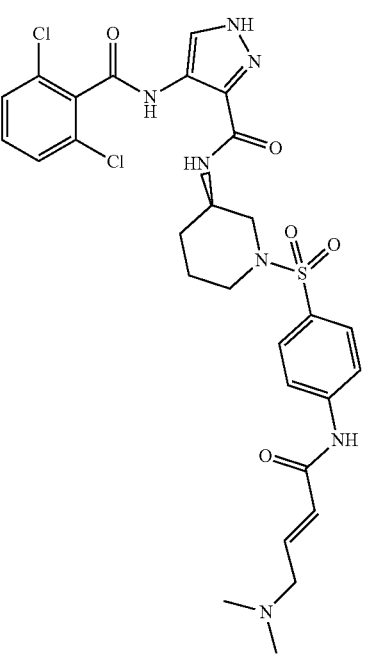

FMF-04-056-2

(R,E)-4-(2,6-dichlorobenzamido)-N-(1-((4-(4-(dimethylamino)but-2-enamido)phenyl)sulfonyl)piperidin-3-yl)-1H-pyrazole-3-carboxamide The compound was prepared according to method 1 (8 mg, 0.014 mmol) as a white powder. $^1$H NMR (500 MHz, DMSO-$d_6$) δ 13.26 (s, 1H), 10.68 (d, J=18.9 Hz, 1H), 10.38 (d, J=27.3 Hz, 1H), 9.98 (s, 1H), 8.29 (s, 1H), 7.82 (d, J=23.4 Hz, 4H), 7.72 (s, 1H), 7.58-7.54 (m, 2H), 7.50 (dd, J=9.2, 6.8 Hz, 1H), 6.80 (dt, J=15.4, 7.1 Hz, 1H), 6.49 (d, J=15.3 Hz, 1H), 4.17 (d, J=110.5 Hz, 2H), 3.97 (d, J=7.2 Hz, 2H), 3.15-2.98 (m, 2H), 2.81 (s, 6H), 2.76-2.61 (m, 1H), 1.64 (s, 2H), 1.34 (s, 2H). MS (ESI) m/z 649 (M+H)$^+$. Expected mass from chemical formula $C_{28}H_{31}Cl_2N_7O_5S$: 648.56

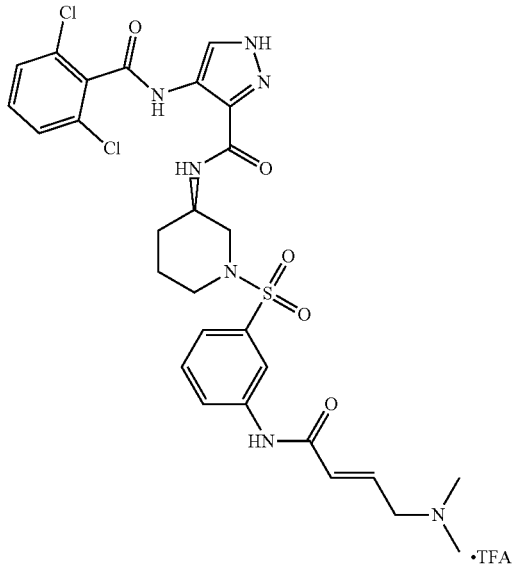

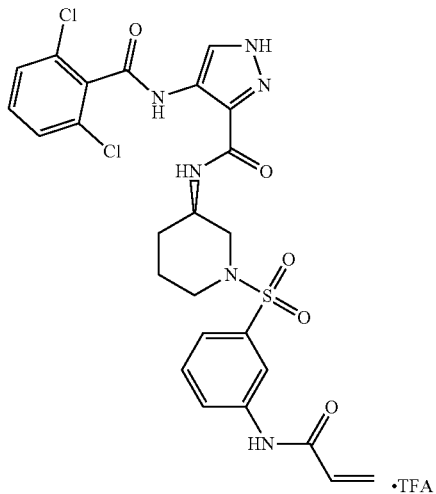 [SMILES: C=CC(=O)Nc1cccc(S(=O)(=O)N2CCC[C@@H](NC(=O)c3n[nH]cc3NC(=O)c3c(Cl)cccc3Cl)C2)c1]

FMF-04-057-1

(R)—N-(1-((3-acrylamidophenyl)sulfonyl)piperidin-3-yl)-4-(2,6-dichlorobenzamido)-1H-pyrazole-3-carboxamide The compound was prepared according to method 1 (7 mg, 0.012 mmol) as a white powder.

$^1$H NMR (500 MHz, DMSO-$d_6$) δ 13.24 (s, 1H), 10.41 (dd, J=26.9, 18.5 Hz, 2H), 8.32 (s, 1H), 8.22 (d, J=18.1 Hz, 1H), 7.86 (d, J=11.2 Hz, 1H), 7.60-7.46 (m, 6H), 6.43 (dd, J=17.0, 10.1 Hz, 1H), 6.30 (dd, J=17.0, 2.0 Hz, 1H), 5.81 (dd, J=10.0, 2.0 Hz, 1H), 4.34 (dd, J=27.1, 13.1 Hz, 1H), 3.09 (d, J=48.9 Hz, 3H), 2.89-2.61 (m, 1H), 1.65 (s, 2H), 1.34 (d, J=6.8 Hz, 2H). MS (ESI) m/z 592 (M+H)$^+$. Expected mass from chemical formula $C_{25}H_{24}Cl_2N_6O_5S$: 591.46

FMF-04-057-2

(R,E)-4-(2,6-dichlorobenzamido)-N-(1-((3-(4-(dimethylamino)but-2-enamido)phenyl)sulfonyl)piperidin-3-yl)-1H-pyrazole-3-carboxamide The compound was prepared according to method 1 (5 mg, 0.007 mmol) as a white powder.
$^1$H NMR (500 MHz, DMSO-$d_6$) δ 13.25 (s, 1H), 10.63 (d, J=19.8 Hz, 1H), 10.40 (s, 1H), 10.01 (s, 1H), 8.42-8.14 (m, 2H), 7.88 (d, J=32.5 Hz, 1H), 7.60-7.50 (m, 5H), 6.78 (dt, J=15.3, 7.1 Hz, 1H), 6.46 (dt, J=15.3, 1.3 Hz, 1H), 4.31-4.07 (m, 2H), 3.97 (d, J=7.1 Hz, 2H), 3.14-3.01 (m, 2H), 2.75-2.62 (m, OH), 1.65 (s, 2H), 1.36 (t, J=9.9 Hz, 2H). MS (ESI) m/z 649 (M+H)$^+$. Expected mass from chemical formula $C_{28}H_{31}Cl_2N_7O_5S$: 648.56

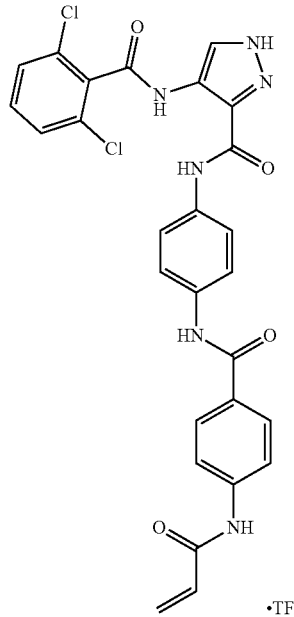

FMF-04-012-1

The compound was prepared according to method 1 (3 mg, 0.004 mmol) as an off-white solid. $^1$H NMR (500 MHz, DMSO-d$_6$) δ 13.59 (s, 1H), 10.42 (s, 1H), 10.31 (s, 1H), 10.14 (d, J=24.0 Hz, 2H), 8.45 (s, 1H), 8.01-7.93 (m, 2H), 7.85-7.67 (m, 6H), 7.64-7.50 (m, 3H), 6.48 (dd, J=16.9, 10.2 Hz, 1H), 6.31 (dd, J=17.0, 1.9 Hz, 1H), 5.81 (dd, J=10.1, 1.9 Hz, 1H). MS (ESI) m/z 564 (M+H)$^+$. Expected mass from chemical formula C$_{27}$H$_{20}$Cl$_2$N$_6$O$_4$: 563.40

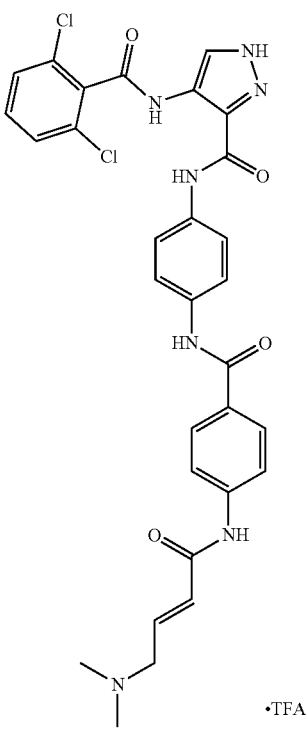 [SMILES: CN(C)C/C=C/C(=O)Nc1ccc(C(=O)Nc2ccc(NC(=O)c3n[nH]cc3NC(=O)c3c(Cl)cccc3Cl)cc2)cc1]

FMF-04-012-2

(E)-4-(2,6-dichlorobenzamido)-N-(4-(4-(4-(dimethylamino)but-2-enamido)benzamido)phenyl)-1H-pyrazole-3-carboxamide The compound was prepared according to method 1 (5 mg, 0.007 mmol) as an off-white solid. $^1$H NMR (500 MHz, DMSO-d$_6$) δ 13.60 (s, 1H), 10.61 (s, 1H), 10.32 (s, 1H), 10.15 (d, J=14.3 Hz, 2H), 8.45 (s, 1H), 8.03-7.89 (m, 2H), 7.87-7.63 (m, 7H), 7.63-7.49 (m, 3H), 6.79 (dt, J=15.2, 7.1 Hz, 1H), 6.50 (dt, J=15.2, 1.3 Hz, 1H), 3.97 (d, J=7.1 Hz, 2H), 2.82 (s, 6H). MS (ESI) m/z 621 (M+H)$^+$. Expected mass from chemical formula C$_{30}$H$_{27}$Cl$_2$N$_7$O$_4$: 620.49

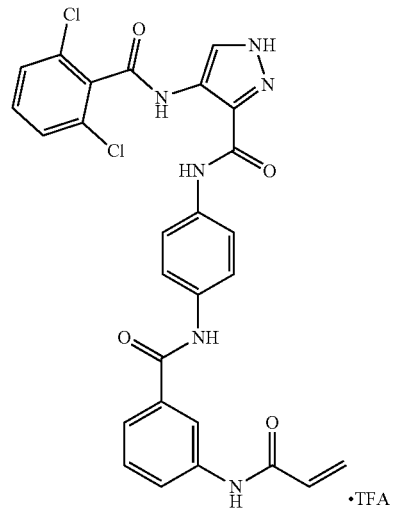 [SMILES: C=CC(=O)Nc1cccc(C(=O)Nc2ccc(NC(=O)c3n[nH]cc3NC(=O)c3c(Cl)cccc3Cl)cc2)c1]

FMF-03-205-1

N-(4-(3-acrylamidobenzamido)phenyl)-4-(2,6-dichlorobenzamido)-1H-pyrazole-3-carboxamide The compound was prepared according to method 1 (2 mg, 0.003 mmol) as an off-white solid. $^1$H NMR (500 MHz, DMSO-d$_6$) δ 13.59 (s, 1H), 10.34 (d, J=15.2 Hz, 2H), 10.25 (s, 1H), 10.17 (s, 1H), 8.45 (s, 1H), 8.16 (t, J=1.9 Hz, 1H), 7.93 (ddd, J=8.1, 2.2, 1.0 Hz, 1H), 7.79-7.67 (m, 4H), 7.68-7.57 (m, 3H), 7.56-7.45 (m, 2H), 6.47 (dd, J=16.9, 10.1 Hz, 1H), 6.30 (dd, J=17.0, 1.9 Hz, 1H), 5.79 (dd, J=10.1, 1.9 Hz, 1H). MS (ESI) m/z 564 (M+H)$^+$. Expected mass from chemical formula C$_{27}$H$_{20}$Cl$_2$N$_6$O$_4$: 563.40

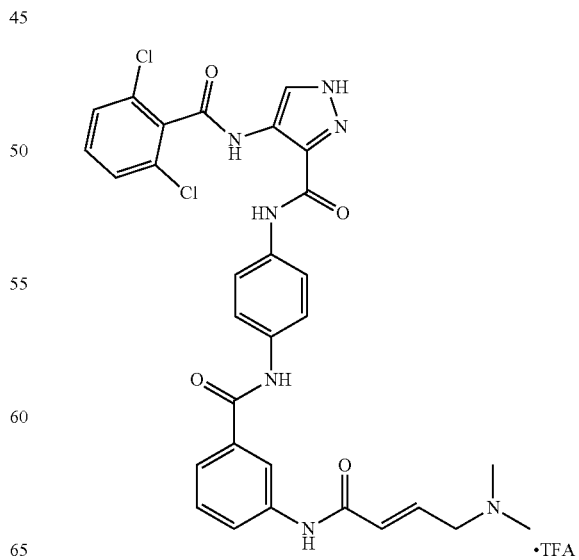

FMF-03-206-1

(E)-4-(2,6-dichlorobenzamido)-N-(4-(3-(4-(dimethylamino)but-2-enamido)benzamido)phenyl)-1H-pyrazole-3-carboxamide The compound was prepared according to method 1 (2 mg, 0.003 mmol) as an off-white solid. $^1$H NMR (500 MHz, DMSO-$d_6$) δ 13.63 (s, 1H), 10.56 (s, 1H), 10.27 (s, 1H), 10.16 (s, 1H), 8.45 (s, 1H), 8.18 (t, J=2.0 Hz, 1H), 7.81-7.64 (m, 6H), 7.64-7.43 (m, 5H), 6.79 (dt, J=15.4, 7.1 Hz, 1H), 6.55-6.43 (m, 1H), 4.01-3.92 (m, 2H), 2.81 (s, 6H). MS (ESI) m/z 621 (M+H)$^+$. Expected mass from chemical formula $C_{30}H_{27}Cl_2N_7O_4$: 620.49

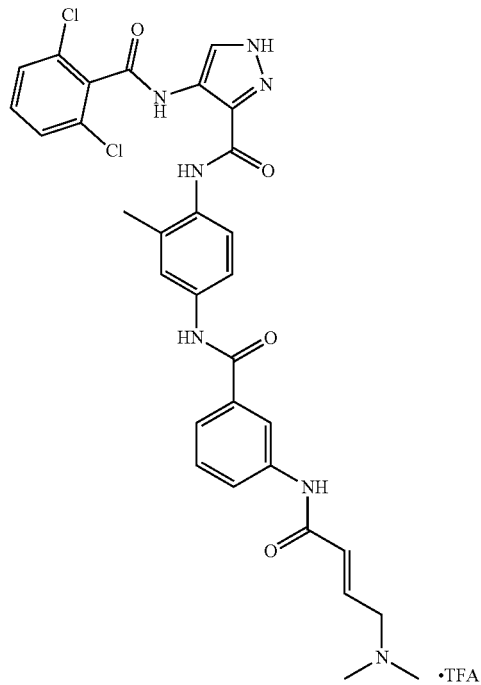 [SMILES: Cc1cc(NC(=O)c2cccc(NC(=O)/C=C/CN(C)C)c2)ccc1NC(=O)c1n[nH]cc1NC(=O)c1c(Cl)cccc1Cl]

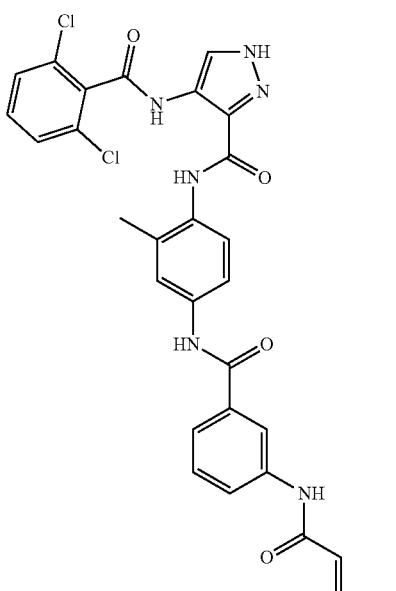

FMF-04-085-1

N-(4-(3-acrylamidobenzamido)-2-methylphenyl)-4-(2,6-dichlorobenzamido)-1H-pyrazole-3-carboxamide The compound was prepared according to method 1 (12 mg, 0.02 mmol) as an off-white solid. $^1$H NMR (500 MHz, DMSO-$d_6$) δ 10.37 (s, 1H), 10.23 (s, 1H), 10.13 (s, 1H), 9.78 (s, 1H), 8.44 (s, 1H), 8.17 (t, J=2.0 Hz, 1H), 7.93 (ddd, J=8.0, 2.1, 1.0 Hz, 1H), 7.70-7.62 (m, 2H), 7.60-7.55 (m, 3H), 7.54-7.46 (m, 2H), 7.42 (d, J=8.6 Hz, 1H), 6.47 (dd, J=17.0, 10.2 Hz, 1H), 6.30 (dd, J=17.0, 2.0 Hz, 1H), 5.79 (dd, J=10.1, 1.9 Hz, 1H), 2.25 (s, 3H). MS (ESI) m/z 578 (M+H)$^+$. Expected mass from chemical formula $C_{28}H_{22}Cl_2N_6O_4$: 577.42

FMF-04-085-2

(E)-4-(2,6-dichlorobenzamido)-N-(4-(3-(4-(dimethylamino)but-2-enamido)benzamido)-2-methylphenyl)-1H-pyrazole-3-carboxamide The compound was prepared according to method 1 (14 mg, 0.02 mmol) as an off-white solid. $^1$H NMR (500 MHz, DMSO-$d_6$) δ 10.55 (s, 1H), 10.24 (s, 1H), 10.12 (s, 1H), 9.79 (s, 1H), 8.44 (s, 1H), 8.18 (t, J=2.0 Hz, 1H), 7.92 (dd, J=8.1, 2.1 Hz, 1H), 7.71-7.64 (m, 2H), 7.61-7.47 (m, 5H), 7.42 (d, J=8.6 Hz, 1H), 6.78 (dt, J=15.3, 7.1 Hz, 1H), 6.48 (dt, J=15.4, 1.3 Hz, 1H), 3.93 (d, J=6.7 Hz, 2H), 2.79 (s, 6H), 2.25 (s, 3H). MS (ESI) m/z 645 (M+H)$^+$. Expected mass from chemical formula $C_{31}H_{29}Cl_2N_7O_4$: 634.5

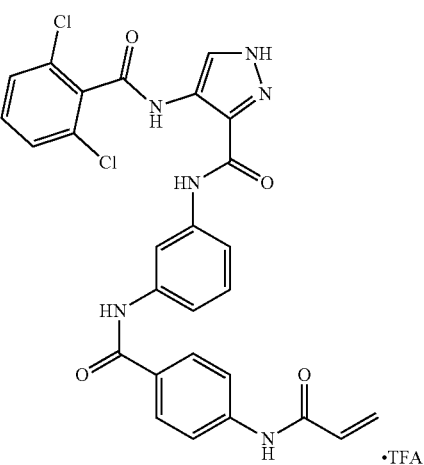 [SMILES: C=CC(=O)Nc1ccc(C(=O)Nc2cccc(NC(=O)c3n[nH]cc3NC(=O)c3c(Cl)cccc3Cl)c2)cc1]

FMF-03-203-1

N-(3-(4-acrylamidobenzamido)phenyl)-4-(2,6-dichlorobenzamido)-1H-pyrazole-3-carboxamide The compound was prepared according to method 1 (2 mg, 0.003 mmol) as an off-white solid. $^1$H NMR (500 MHz, DMSO-$d_6$) δ 13.61 (s, 1H), 10.43 (s, 1H), 10.33 (s, 1H), 10.15 (s, 2H), 8.45 (s, 1H), 8.34 (s, 1H), 7.99-7.93 (m, 2H), 7.83-7.77 (m, 2H), 7.61-7.52 (m, 4H), 7.40 (dt, J=8.2, 1.3 Hz, 1H), 7.27 (t, J=8.1 Hz, 1H), 6.48 (dd, J=17.0, 10.1 Hz, 1H), 6.31 (dd, J=17.0, 1.9 Hz, 1H), 5.81 (dd, J=10.1, 1.9 Hz, 1H). MS (ESI) m/z 564 (M+H)$^+$. Expected mass from chemical formula $C_{27}H_{20}Cl_2N_6O_4$: 563.40

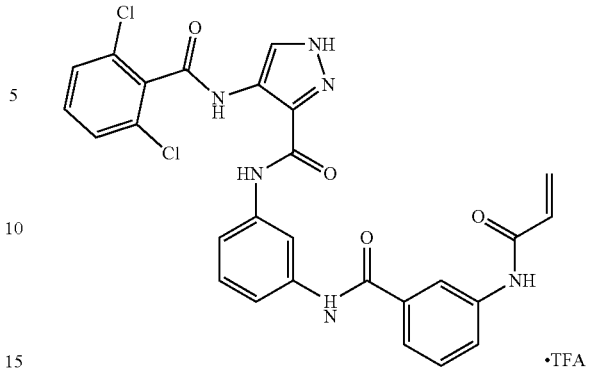

FMF-04-011-1

N-(3-(3-acrylamidobenzamido)phenyl)-4-(2,6-dichlorobenzamido)-1H-pyrazole-3-carboxamide The compound was prepared according to method 1 (2 mg, 0.003 mmol) as an off-white solid. $^1$H NMR (500 MHz, DMSO-$d_6$) δ 13.62 (s, 1H), 10.35 (d, J=8.6 Hz, 2H), 10.15 (s, 1H), 8.45 (s, 1H), 8.33 (q, J=4.2, 3.2 Hz, 1H), 8.15 (t, J=1.9 Hz, 1H), 7.98-7.87 (m, 1H), 7.65 (dt, J=7.9, 1.3 Hz, 1H), 7.62-7.44 (m, 5H), 7.42 (ddd, J=8.1, 2.1, 1.0 Hz, 1H), 7.28 (t, J=8.1 Hz, 1H), 6.47 (dd, J=17.0, 10.2 Hz, 1H), 6.29 (dd, J=17.0, 2.0 Hz, 1H), 5.79 (dd, J=10.1, 1.9 Hz, 1H). MS (ESI) m/z 564 (M+H)$^+$. Expected mass from chemical formula $C_{27}H_{20}Cl_2N_6O_4$: 563.40

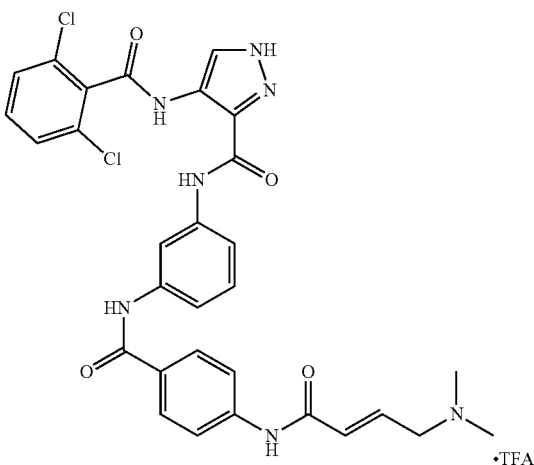 [SMILES: CN(C)C/C=C/C(=O)Nc1ccc(C(=O)Nc2cccc(NC(=O)c3n[nH]cc3NC(=O)c3c(Cl)cccc3Cl)c2)cc1]

FMF-03-204-1

(E)-4-(2,6-dichlorobenzamido)-N-(3-(4-(4-(dimethylamino)but-2-enamido)benzamido)phenyl)-1H-pyrazole-3-carboxamide The compound was prepared according to method 1 (2 mg, 0.003 mmol) as an off-white solid. $^1$H NMR (500 MHz, DMSO-$d_6$) δ 13.64 (s, 1H), 10.63 (s, 1H), 10.33 (s, 1H), 10.16 (d, J=10.6 Hz, 2H), 8.45 (s, 1H), 8.34 (d, J=2.1 Hz, 1H), 7.97 (d, 2H), 7.80 (d, 2H), 7.61-7.57 (m, 2H), 7.55-7.51 (m, 2H), 7.41 (dt, J=8.2, 1.2 Hz, 1H), 7.28 (t, J=8.1 Hz, 1H), 6.79 (dt, J=15.3, 7.1 Hz, 1H), 6.50 (dt, J=15.2, 1.4 Hz, 1H), 3.96 (d, 2H), 2.81 (s, 6H). MS (ESI) m/z 621 (M+H)$^+$. Expected mass from chemical formula $C_{30}H_{27}Cl_2N_7O_4$: 620.49

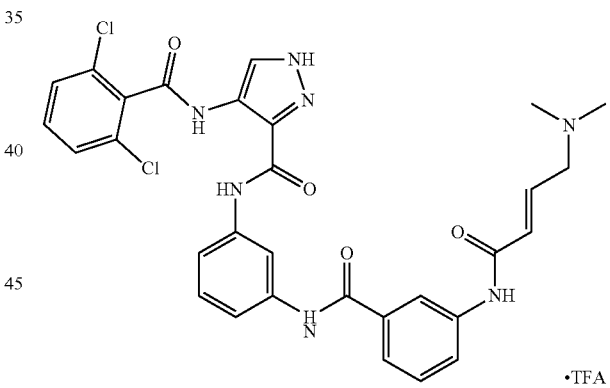

FMF-04-196-1

(E)-4-(2,6-dichlorobenzamido)-N-(3-(3-(4-(dimethylamino)but-2-enamido)benzamido)phenyl)-1H-pyrazole-3-carboxamide The compound was prepared according to method 1 (6 mg, 0.009 mmol) as an off-white solid. $^1$H NMR (500 MHz, DMSO-$d_6$) δ 13.60 (s, 1H), 10.52 (s, 1H), 10.33 (s, 1H), 10.25 (s, 1H), 10.16 (s, 1H), 8.45 (d, J=1.5 Hz, 1H), 8.21-8.11 (m, 1H), 7.95-7.89 (m, 1H), 7.82-7.74 (m, 2H), 7.70 (dd, J=9.0, 7.0 Hz, 3H), 7.64-7.57 (m, 2H), 7.57-7.44 (m, 2H), 7.06 (s, OH), 6.78 (dt, J=14.8, 7.1 Hz, 1H), 6.48 (d, J=15.4 Hz, 1H), 3.96 (s, 2H), 2.82 (s, 6H). MS (ESI) m/z 621 (M+H)$^+$. Expected mass from chemical formula $C_{30}H_{27}Cl_2N_7O_4$: 620.49

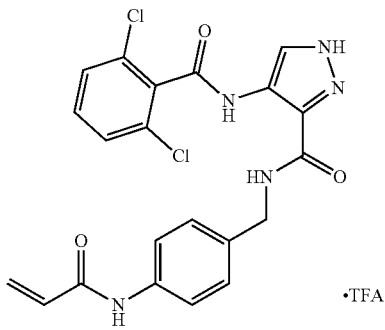 [SMILES: C=CC(=O)Nc1ccc(CNC(=O)c2n[nH]cc2NC(=O)c2c(Cl)cccc2Cl)cc1]

FMF-05-064-1

N-(4-acrylamidobenzyl)-4-(2,6-dichlorobenzamido)-1H-pyrazole-3-carboxamide

The compound was prepared according to method 1 (14 mg, 0.031 mmol) as an off-white solid $^1$H NMR (500 MHz, DMSO-$d_6$) δ 13.42 (s, 1H), 10.12 (d, J=10.5 Hz, 2H), 9.01 (t, J=6.3 Hz, 1H), 8.37 (s, 1H), 7.65-7.43 (m, 5H), 7.31-7.17 (m, 2H), 6.42 (dd, J=17.0, 10.1 Hz, 1H), 6.24 (dd, J=17.0, 2.0 Hz, 1H), 5.74 (dd, J=10.1, 2.0 Hz, 1H), 4.36 (d, J=6.4 Hz, 2H). MS (ESI) m/z 459 (M+H)$^+$. Expected mass from chemical formula $C_{21}H_{17}Cl_2N_5O_3$: 458.30

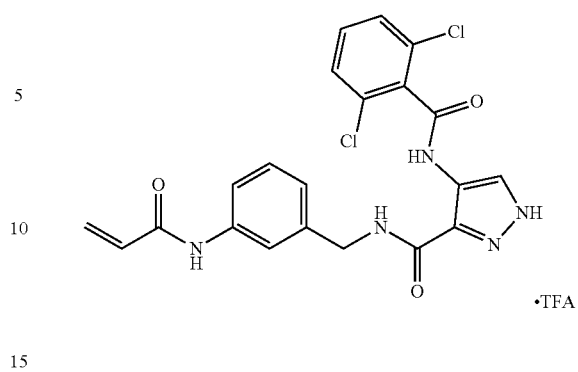

FMF-05-067-1

N-(3-acrylamidobenzyl)-4-(2,6-dichlorobenzamido)-1H-pyrazole-3-carboxamide

The compound was prepared according to method 1 (30 mg, 0.065 mmol) as an off-white solid. $^1$H NMR (500 MHz, DMSO-$d_6$) δ 13.44 (s, 1H), 10.11 (d, J=8.4 Hz, 2H), 9.05 (s, 1H), 8.38 (s, 1H), 7.96 (s, 1H), 7.65-7.46 (m, 5H), 7.25 (t, J=7.9 Hz, 1H), 7.06-6.93 (m, 1H), 6.42 (dd, J=17.0, 10.1 Hz, 1H), 6.23 (dd, J=17.0, 2.0 Hz, 1H), 5.73 (dd, J=10.1, 2.0 Hz, 1H), 4.39 (d, J=6.5 Hz, 2H). MS (ESI) m/z 459 (M+H)$^+$. Expected mass from chemical formula $C_{21}H_{17}Cl_2N_5O_3$: 458.30

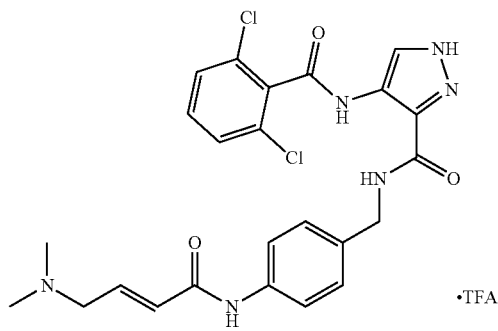 [SMILES: CN(C)C/C=C/C(=O)Nc1ccc(CNC(=O)c2n[nH]cc2NC(=O)c2c(Cl)cccc2Cl)cc1]

FMF-05-064-2

(E)-4-(2,6-dichlorobenzamido)-N-(4-(4-(dimethylamino)but-2-enamido)benzyl)-1H-pyrazole-3-carboxamide The compound was prepared according to method 1 (20 mg, 0.038 mmol) as an off-white solid. $^1$H NMR (500 MHz, DMSO-$d_6$) δ 13.44 (s, 1H), 10.29 (s, 1H), 10.12 (s, 1H), 9.77 (s, 1H), 9.03 (t, J=6.3 Hz, 1H), 8.38 (d, J=1.5 Hz, 1H), 7.63-7.45 (m, 5H), 7.27 (d, J=8.5 Hz, 2H), 6.72 (dt, J=14.7, 7.2 Hz, 1H), 6.44 (dd, J=15.3, 1.4 Hz, 1H), 4.36 (d, J=6.3 Hz, 2H), 3.93 (d, J=7.2 Hz, 2H), 2.80 (s, 6H). MS (ESI) m/z 516 (M+H)$^+$. Expected mass from chemical formula $C_{24}H_{24}Cl_2N_6O_3$: 515.40

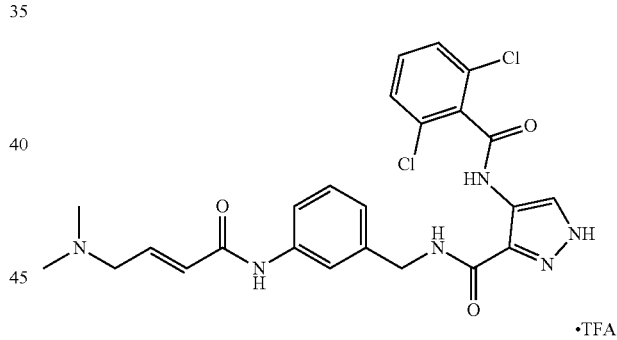

FMF-05-064-2

(E)-4-(2,6-dichlorobenzamido)-N-(3-(4-(dimethylamino)but-2-enamido)benzyl)-1H-pyrazole-3-carboxamide The compound was prepared according to method 1 (11 mg, 0.021 mmol) as an off-white solid. $^1$H NMR (500 MHz, DMSO-$d_6$) δ 13.45 (s, 1H), 10.26 (s, 1H), 10.11 (s, 1H), 9.06 (t, J=6.3 Hz, 1H), 8.39 (d, J=1.4 Hz, 1H), 7.66-7.46 (m, 5H), 7.27 (t, J=7.9 Hz, 1H), 7.03 (d, J=7.6 Hz, 1H), 6.76-6.64 (m, 1H), 6.41 (d, J=15.3 Hz, 1H), 4.40 (d, J=6.4 Hz, 2H), 2.74 (s, 6H). MS (ESI) m/z 516 (M+H)$^+$. Expected mass from chemical formula $C_{24}H_{24}Cl_2N_6O_3$: 515.40

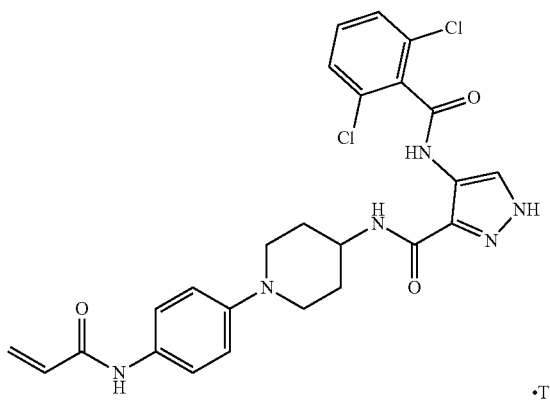

FMF-05-073-1

N-(1-(4-acrylamidophenyl)piperidin-4-yl)-4-(2,6-dichlorobenzamido)-1H-pyrazole-3-carboxamide The compound was prepared according to method 1 (39 mg, 0.074 mmol) as a white powder. $^1$H NMR (500 MHz, DMSO-d$_6$) δ 13.48 (s, 1H), 10.18 (s, 1H), 10.11 (s, 1H), 8.55 (s, 1H), 8.37 (s, 1H), 7.88-7.47 (m, 5H), 7.20 (s, 2H), 6.42 (dd, J=17.0, 10.1 Hz, 1H), 6.24 (dd, J=17.0, 2.1 Hz, 1H), 5.80-5.67 (m, 1H), 3.99 (d, J=17.4 Hz, 1H), 3.65 (d, J=12.0 Hz, 2H), 3.10 (d, J=71.6 Hz, 2H), 1.91 (s, 4H). MS (ESI) m/z 528 (M+H)$^+$. Expected mass from chemical formula C$_{25}$H$_{24}$Cl$_2$N$_6$O$_3$: 527.41

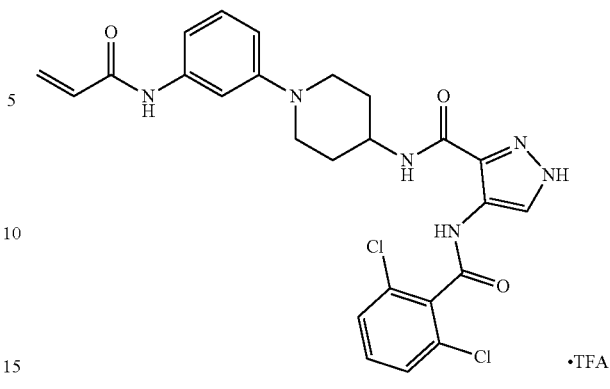

FMF-05-085-1

N-(1-(3-acrylamidophenyl)piperidin-4-yl)-4-(2,6-dichlorobenzamido)-1H-pyrazole-3-carboxamide The compound was prepared according to method 1 (30 mg, 0.057 mmol) as a white powder.
$^1$H NMR (500 MHz, DMSO-d$_6$) δ 13.39 (s, 1H), 10.19 (s, 1H), 10.03 (d, J=14.7 Hz, 1H), 8.46 (d, J=8.1 Hz, 1H), 8.35 (s, 1H), 7.66-7.49 (m, 3H), 7.46 (d, J=20.8 Hz, 1H), 7.26-7.07 (m, 2H), 6.78 (s, 1H), 6.43 (dd, J=16.9, 10.1 Hz, 1H), 6.24 (dd, J=17.0, 2.1 Hz, 1H), 5.74 (dd, J=10.1, 2.0 Hz, 1H), 4.03-3.94 (m, 1H), 3.67 (d, J=12.8 Hz, 2H), 2.87 (d, J=24.6 Hz, 2H), 1.92-1.74 (m, 4H). MS (ESI) m/z 528 (M+H)$^+$. Expected mass from chemical formula C$_{25}$H$_{24}$Cl$_2$N$_6$O$_3$: 527.41

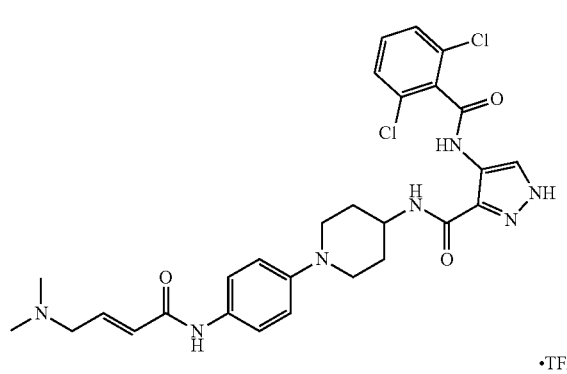

FMF-05-073-2

(E)-4-(2,6-dichlorobenzamido)-N-(1-(4-(4-(dimethylamino)but-2-enamido)phenyl)piperidin-4-yl)-1H-pyrazole-3-carboxamide The compound was prepared according to method 1 (35 mg, 0.060 mmol) as a white powder.
$^1$H NMR (500 MHz, DMSO-d$_6$) δ 13.47 (s, 1H), 10.22 (s, 1H), 9.90 (s, 1H), 8.48 (d, J=8.0 Hz, 1H), 8.36 (s, 1H), 7.63-7.54 (m, 4H), 7.08 (s, 2H), 6.71 (dt, J=14.8, 7.2 Hz, 1H), 6.43 (dd, J=15.0, 1.5 Hz, 1H), 3.99-3.90 (m, 3H), 3.65 (d, J=12.3 Hz, 2H), 2.88 (s, 2H), 2.83-2.77 (m, 7H), 1.93-1.82 (m, 4H). MS (ESI) m/z 585 (M+H)$^+$. Expected mass from chemical formula C$_{28}$H$_{31}$Cl$_2$N$_7$O$_3$: 584.50

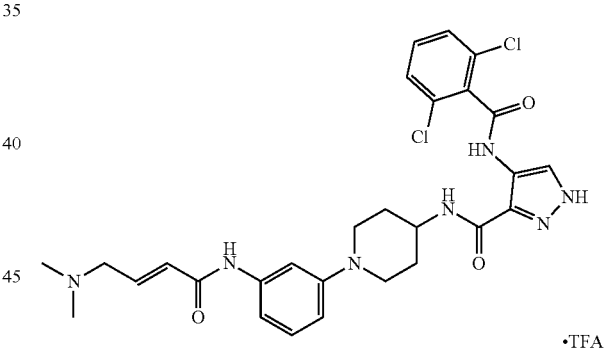

FMF-05-085-2

(E)-4-(2,6-dichlorobenzamido)-N-(1-(3-(4-(dimethylamino)but-2-enamido)phenyl)piperidin-4-yl)-1H-pyrazole-3-carboxamide The compound was prepared according to method 1 (40 mg, 0.068 mmol) as a white powder.
$^1$H NMR (500 MHz, DMSO-d$_6$) δ 13.48 (s, 1H), 10.20 (d, J=8.3 Hz, 2H), 9.93 (s, 1H), 8.44 (d, J=8.3 Hz, 1H), 8.35 (s, 1H), 7.64-7.57 (m, 2H), 7.54 (dd, J=9.2, 6.9 Hz, 1H), 7.37 (s, 1H), 7.17 (t, J=8.1 Hz, 1H), 7.11 (d, J=8.0 Hz, 1H), 6.76 (d, J=4.5 Hz, 1H), 6.72 (dd, J=15.1, 7.5 Hz, 1H), 6.45 (dd, J=15.3, 1.3 Hz, 1H), 4.03-3.87 (m, 4H), 3.67 (d, J=12.5 Hz, 2H), 2.80 (s, 6H), 2.55 (s, 1H), 1.85-1.73 (m, 4H). MS (ESI) m/z 585 (M+H)$^+$. Expected mass from chemical formula C$_{28}$H$_{31}$Cl$_2$N$_7$O$_3$: 584.50

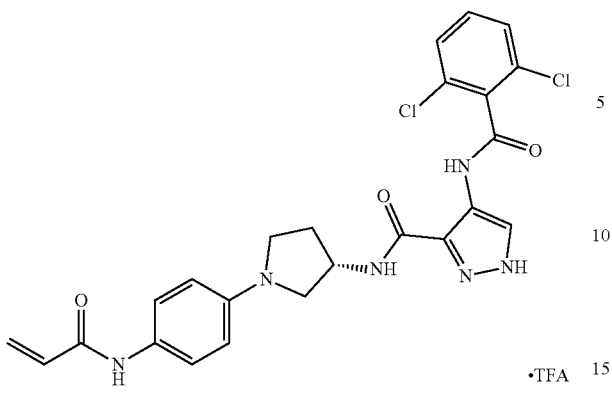

FMF-05-074-1

(S)—N-(1-(4-acrylamidophenyl)pyrrolidin-3-yl)-4-(2,6-dichlorobenzamido)-1H-pyrazole-3-carboxamide The compound was prepared according to method 1 (19 mg, 0.067 mmol) as a white powder.
$^1$H NMR (500 MHz, DMSO-d$_6$) δ 13.43 (s, 1H), 10.16 (s, 1H), 9.82 (s, 1H), 8.65 (d, J=7.3 Hz, 1H), 8.36 (s, 1H), 7.63-7.50 (m, 3H), 7.50-7.43 (m, 2H), 6.55-6.45 (m, 2H), 6.39 (dd, J=17.0, 10.2 Hz, 1H), 6.18 (dd, J=16.9, 2.1 Hz, 1H), 5.67 (dd, J=10.1, 2.2 Hz, 1H), 4.58 (h, J=6.9 Hz, 1H), 3.50 (dd, J=9.5, 7.0 Hz, 1H), 3.39 (td, J=8.7, 5.0 Hz, 1H), 3.30-3.18 (m, 2H), 2.27-2.08 (m, 2H). MS (ESI) m/z 514 (M+H)$^+$. Expected mass from chemical formula C$_{24}$H$_{22}$Cl$_2$N$_6$O$_3$: 513.38

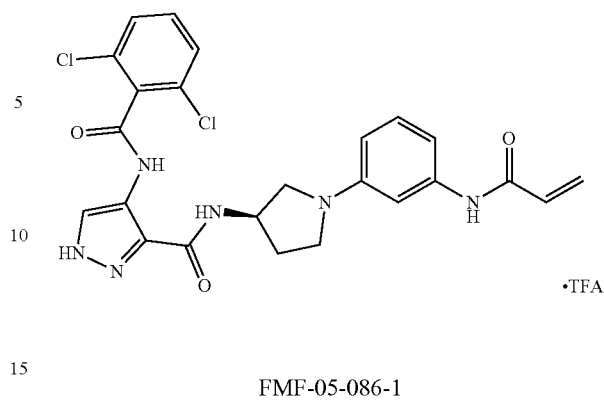

FMF-05-086-1

(S)—N-(1-(3-acrylamidophenyl)pyrrolidin-3-yl)-4-(2,6-dichlorobenzamido)-1H-pyrazole-3-carboxamide The compound was prepared according to method 1 (30 mg, 0.058 mmol) as a white powder. $^1$H NMR (500 MHz, DMSO-d$_6$) δ 10.16 (s, 1H), 9.93 (s, 1H), 8.68 (d, J=7.2 Hz, 1H), 8.36 (s, 1H), 7.63-7.57 (m, 2H), 7.53 (dd, J=9.1, 6.9 Hz, 1H), 7.09 (t, J=8.3 Hz, 1H), 6.98-6.90 (m, 2H), 6.43 (dd, J=17.0, 10.2 Hz, 1H), 6.29-6.25 (m, 1H), 6.24 (d, J=2.1 Hz, 1H), 5.72 (dd, J=10.1, 2.1 Hz, 1H), 4.57 (h, J=6.7 Hz, 1H), 3.50 (dd, J=9.5, 6.9 Hz, 1H), 3.39 (td, J=8.5, 5.1 Hz, 1H), 3.24 (ddd, J=15.2, 9.3, 6.5 Hz, 2H), 2.27-2.09 (m, 2H). MS (ESI) m/z 514 (M+H)$^+$. Expected mass from chemical formula C$_{24}$H$_{22}$Cl$_2$N$_6$O$_3$: 513.38

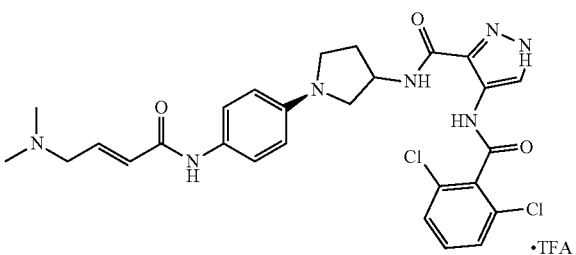

FMF-05-074-2

(S,E)-4-(2,6-dichlorobenzamido)-N-(1-(4-(4-(dimethylamino)but-2-enamido)phenyl)pyrrolidin-3-yl)-1H-pyrazole-3-carboxamide The compound was prepared according to method 1 (30 mg, 0.052 mmol) as a white powder. $^1$H NMR (500 MHz, DMSO-d$_6$) δ 13.45 (s, 1H), 10.16 (s, 1H), 10.00 (s, 1H), 9.75 (s, 1H), 8.66 (d, J=7.4 Hz, 1H), 8.37 (s, 1H), 7.64-7.43 (m, 5H), 6.66 (dt, J=14.8, 7.3 Hz, 1H), 6.57-6.47 (m, 2H), 6.41 (d, J=15.3 Hz, 1H), 4.57 (h, J=6.8 Hz, 1H), 3.92 (d, J=7.2 Hz, 2H), 3.50 (dd, J=9.5, 7.0 Hz, 1H), 3.39 (td, J=8.6, 4.9 Hz, 1H), 3.28-3.17 (m, 2H), 2.80 (d, J=2.6 Hz, 6H), 2.18 (dp, J=35.3, 7.0, 6.4 Hz, 2H). MS (ESI) m/z 571 (M+H)$^+$. Expected mass from chemical formula C$_{27}$H$_{29}$Cl$_2$N$_7$O$_3$: 570.48

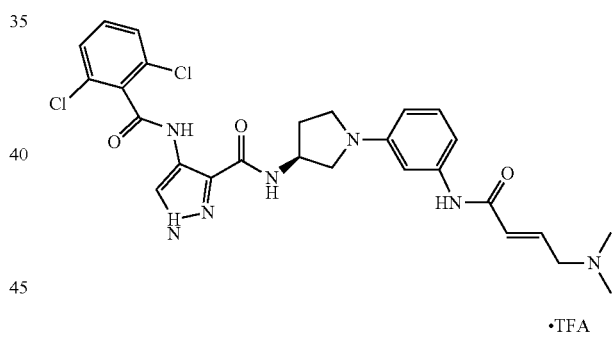

FMF-05-086-2

(S,E)-4-(2,6-dichlorobenzamido)-N-(1-(3-(4-(dimethylamino)but-2-enamido)phenyl)pyrrolidin-3-yl)-1H-pyrazole-3-carboxamide The compound was prepared according to method 1 (25 mg, 0.044 mmol) as a white powder. $^1$H NMR (500 MHz, DMSO-d$_6$) δ 13.46 (s, 1H), 10.14 (d, J=20.1 Hz, 2H), 9.92 (s, 1H), 8.69 (d, J=7.2 Hz, 1H), 8.37 (s, 1H), 7.62-7.50 (m, 3H), 7.10 (t, J=8.0 Hz, 1H), 6.94 (dd, J=8.4, 1.7 Hz, 2H), 6.71 (dt, J=14.8, 7.2 Hz, 1H), 6.45 (dd, J=15.2, 1.4 Hz, 1H), 6.34-6.23 (m, 1H), 4.57 (h, J=6.8 Hz, 1H), 3.94 (dd, J=7.0, 3.4 Hz, 2H), 3.50 (dd, J=9.5, 6.9 Hz, 1H), 3.39 (td, J=8.5, 5.0 Hz, 1H), 3.30-3.19 (m, 2H), 2.80 (d, J=3.3 Hz, 6H), 2.28-2.09 (m, 2H). MS (ESI) m/z 571 (M+H)$^+$. Expected mass from chemical formula C$_{27}$H$_{29}$Cl$_2$N$_7$O$_3$: 570.48

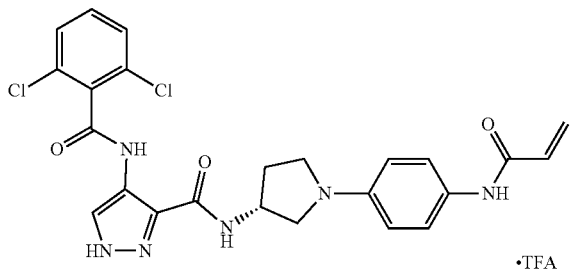 [SMILES: C=CC(=O)Nc1ccc(N2CC[C@@H](NC(=O)c3n[nH]cc3NC(=O)c3c(Cl)cccc3Cl)C2)cc1]

FMF-05-075-1

(R)—N-(1-(4-acrylamidophenyl)pyrrolidin-3-yl)-4-(2,6-dichlorobenzamido)-1H-pyrazole-3-carboxamide The compound was prepared according to method 1 (25 mg, 0.048 mmol) as a white powder. $^1$H NMR (500 MHz, DMSO-d$_6$) δ 10.16 (s, 1H), 9.82 (s, 1H), 8.65 (d, J=7.4 Hz, 1H), 8.36 (s, 1H), 7.62-7.56 (m, 2H), 7.56-7.52 (m, 1H), 7.50-7.45 (m, 2H), 6.54-6.47 (m, 2H), 6.39 (dd, J=16.9, 10.2 Hz, 1H), 6.18 (dd, J=17.0, 2.1 Hz, 1H), 5.67 (dd, J=10.1, 2.1 Hz, 1H), 4.58 (h, J=6.9 Hz, 1H), 3.50 (dd, J=9.5, 7.0 Hz, 1H), 3.39 (td, J=8.6, 5.0 Hz, 1H), 3.28-3.19 (m, 2H), 2.22 (dtd, J=12.3, 7.4, 5.1 Hz, 1H), 2.18-2.09 (m, 1H). MS (ESI) m/z 514 (M+H)$^+$. Expected mass from chemical formula $C_{24}H_{22}Cl_2N_6O_3$: 513.38

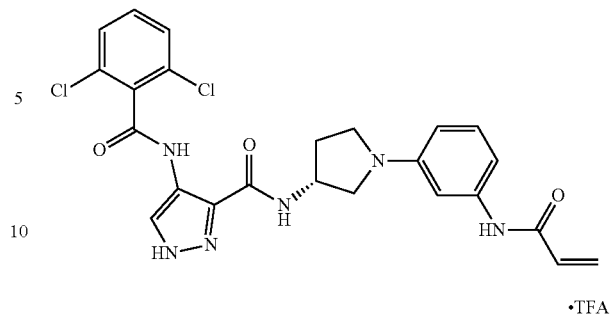

FMF-05-087-1

(R)—N-(1-(3-acrylamidophenyl)pyrrolidin-3-yl)-4-(2,6-dichlorobenzamido)-1H-pyrazole-3-carboxamide The compound was prepared according to method 1 (25 mg, 0.048 mmol) as a white powder. $^1$H NMR (500 MHz, DMSO-d$_6$) δ 10.16 (s, 1H), 9.92 (s, 1H), 8.68 (d, J=7.2 Hz, 1H), 8.36 (s, 1H), 7.63-7.57 (m, 2H), 7.53 (dd, J=9.1, 6.9 Hz, 1H), 7.09 (t, J=8.3 Hz, 1H), 6.99-6.89 (m, 2H), 6.43 (dd, J=17.0, 10.1 Hz, 1H), 6.21 (d, J=2.1 Hz, 1H), 5.72 (dd, J=10.1, 2.1 Hz, 1H), 4.57 (h, J=6.8 Hz, 1H), 3.51-3.48 (m, 1H), 3.39 (td, J=8.5, 5.1 Hz, 1H), 3.24 (ddd, J=15.2, 9.2, 6.5 Hz, 2H), 2.28-2.09 (m, 2H). MS (ESI) m/z 514 (M+H)$^+$. Expected mass from chemical formula $C_{24}H_{22}Cl_2N_6O_3$: 513.38

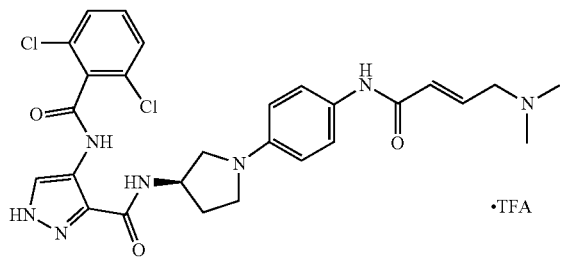 [SMILES: CN(C)C/C=C/C(=O)Nc1ccc(N2CC[C@@H](NC(=O)c3n[nH]cc3NC(=O)c3c(Cl)cccc3Cl)C2)cc1]

FMF-05-075-2

(R,E)-4-(2,6-dichlorobenzamido)-N-(1-(4-(4-(dimethylamino)but-2-enamido)phenyl)pyrrolidin-3-yl)-1H-pyrazole-3-carboxamide The compound was prepared according to method 1 (25 mg, 0.048 mmol) as a white powder. $^1$H NMR (500 MHz, DMSO-d$_6$) δ 13.45 (s, 1H), 10.16 (s, 1H), 10.00 (s, 1H), 9.77 (s, 1H), 8.66 (s, 1H), 8.37 (s, 1H), 7.62-7.51 (m, 3H), 7.51-7.46 (m, 2H), 6.66 (dt, J=14.8, 7.2 Hz, 1H), 6.56-6.47 (m, 2H), 6.41 (dd, J=15.2, 1.4 Hz, 1H), 4.57 (h, J=6.9 Hz, 1H), 3.92 (d, J=7.2 Hz, 2H), 3.50 (dd, J=9.5, 7.0 Hz, 1H), 3.39 (td, J=8.6, 5.0 Hz, 1H), 3.29-3.17 (m, 2H), 2.80 (s, 7H), 2.27-2.06 (m, 2H). MS (ESI) m/z 571 (M+H)$^+$. Expected mass from chemical formula $C_{27}H_{29}Cl_2N_7O_3$: 570.48

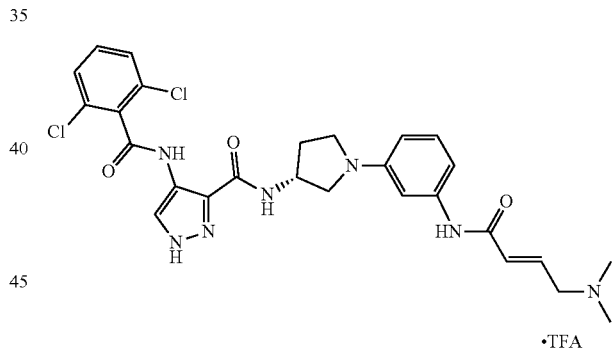

FMF-05-087-2

(R,E)-4-(2,6-dichlorobenzamido)-N-(1-(3-(4-(dimethylamino)but-2-enamido)phenyl)pyrrolidin-3-yl)-1H-pyrazole-3-carboxamide The compound was prepared according to method 1 (25 mg, 0.048 mmol) as a white powder. $^1$H NMR (500 MHz, DMSO-d$_6$) δ 13.46 (s, 1H), 10.14 (d, J=22.9 Hz, 2H), 9.85 (s, 1H), 8.69 (s, 1H), 8.38 (s, 1H), 7.64-7.45 (m, 3H), 7.10 (t, J=8.0 Hz, 1H), 6.99-6.84 (m, 2H), 6.71 (dt, J=14.7, 7.2 Hz, 1H), 6.49-6.35 (m, 1H), 6.33-6.22 (m, 1H), 4.57 (h, J=6.8 Hz, 1H), 3.99-3.87 (m, 2H), 3.45-3.31 (m, 2H), 3.24 (ddd, J=15.2, 12.0, 6.4 Hz, 2H), 2.80 (s, 6H), 2.19 (dp, J=33.3, 6.2 Hz, 2H). MS (ESI) m/z 571 (M+H)$^+$. Expected mass from chemical formula $C_{27}H_{29}Cl_2N_7O_3$: 570.48

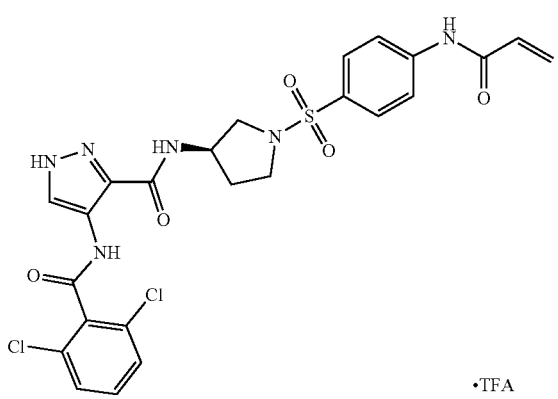 [SMILES: C=CC(=O)Nc1ccc(S(=O)(=O)N2CC[C@@H](NC(=O)c3n[nH]cc3NC(=O)c3c(Cl)cccc3Cl)C2)cc1]

FMF-05-066-1

(R)—N-(1-((4-acrylamidophenyl)sulfonyl)pyrrolidin-3-yl)-4-(2,6-dichlorobenzamido)-1H-pyrazole-3-carboxamide The compound was prepared according to method 1 (13 mg, 0.022 mmol) as a white powder. $^1$H NMR (500 MHz, DMSO-d$_6$) δ 13.42 (s, 1H), 10.55 (s, 1H), 10.06 (s, 1H), 8.63-8.53 (m, 1H), 8.35 (s, 1H), 7.93-7.82 (m, 2H), 7.80-7.69 (m, 2H), 7.61-7.48 (m, 3H), 6.47 (dd, J=17.0, 10.1 Hz, 1H), 6.32 (dd, J=17.0, 1.9 Hz, 1H), 5.83 (dd, J=10.1, 1.9 Hz, 1H), 4.23 (p, J=7.1 Hz, 1H), 3.41 (dd, J=10.0, 7.1 Hz, 1H), 3.20-3.11 (m, 1H), 3.07 (dd, J=10.0, 6.8 Hz, 1H), 2.03-1.94 (m, 1H), 1.88 (dd, J=12.6, 7.4 Hz, 1H). MS (ESI) m/z 578 (M+H)$^+$. Expected mass from chemical formula C$_{24}$H$_{22}$Cl$_2$N$_6$O$_5$S: 577.44

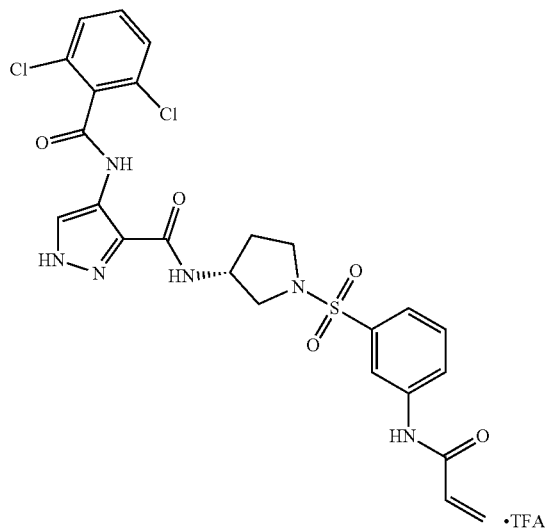 [SMILES: C=CC(=O)Nc1cccc(S(=O)(=O)N2CC[C@@H](NC(=O)c3n[nH]cc3NC(=O)c3c(Cl)cccc3Cl)C2)c1]

FMF-05-065-1

(R)-N-(1-((3-acrylamidophenyl)sulfonyl)pyrrolidin-3-yl)-4-(2,6-dichlorobenzamido)-1H-pyrazole-3-carboxamide The compound was prepared according to method 1 (30 mg, 0.051 mmol) as a white powder. $^1$H NMR (500 MHz, DMSO-d$_6$) δ 13.42 (s, 1H), 10.51 (s, 1H), 10.08-10.02 (m, 1H), 8.36 (dd, J=15.3, 1.4 Hz, 1H), 8.18 (t, J=2.0 Hz, 1H), 7.94 (dd, J=10.1, 8.2 Hz, 1H), 7.63-7.44 (m, 7H), 6.46-6.37 (m, 1H), 6.30 (dd, J=17.0, 2.0 Hz, 1H), 5.81 (dd, J=10.1, 2.0 Hz, 1H), 4.29-4.19 (m, 1H), 2.80-2.72 (m, 4H), 1.96 (ddt, J=43.2, 14.2, 7.0 Hz, 2H). MS (ESI) m/z 577 (M+H)$^+$. Expected mass from chemical formula C$_{24}$H$_{22}$Cl$_2$N$_6$O$_5$S: 577.44

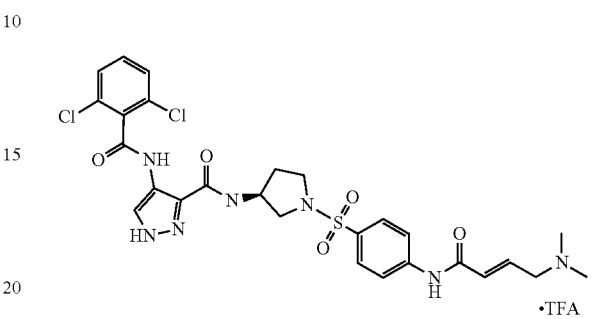

FMF-05-084-2

(S,E)-4-(2,6-dichlorobenzamido)-N-(1-((4-(4-(dimethylamino)but-2-enamido)phenyl)sulfonyl)pyrrolidin-3-yl)-1H-pyrazole-3-carboxamide The compound was prepared according to method 1 (18 mg, 0.028 mmol) as a white powder. $^1$H NMR (500 MHz, DMSO-d$_6$) δ 13.43 (s, 1H), 10.66 (s, 1H), 10.05 (s, 1H), 9.89 (s, 1H), 8.57 (s, 1H), 8.35 (s, 1H), 8.20 (t, J=2.0 Hz, 1H), 7.91 (dt, J=8.3, 1.3 Hz, 1H), 7.60-7.48 (m, 6H), 6.79 (dt, J=14.8, 7.2 Hz, 1H), 6.49-6.36 (m, 1H), 4.24 (h, J=6.8 Hz, 1H), 3.97 (d, J=7.1 Hz, 2H), 3.47-3.30 (m, 2H), 3.23-3.03 (m, 2H), 2.81 (s, 6H), 1.96 (dp, J=36.6, 6.8, 6.3 Hz, 2H). MS (ESI) m/z 635 (M+H)$^+$. Expected mass from chemical formula C$_{27}$H$_{29}$Cl$_2$N$_7$O$_5$S: 634.53

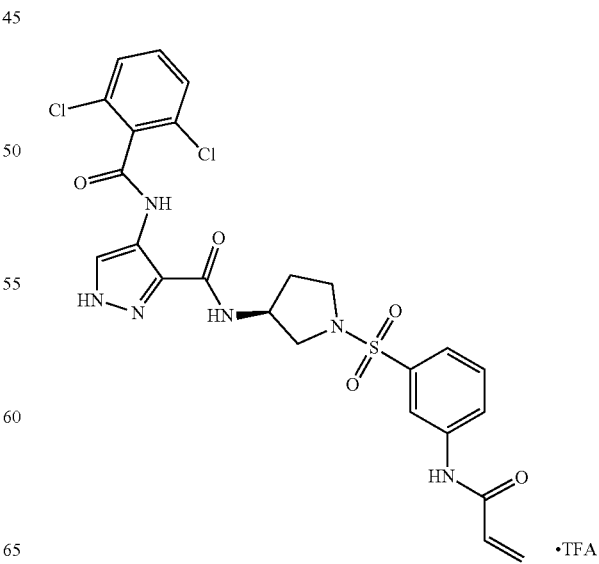

FMF-05-068-1

(S)—N-(1-((3-acrylamidophenyl)sulfonyl)pyrrolidin-3-yl)-4-(2,6-dichlorobenzamido)-1H-pyrazole-3-carboxamide The compound was prepared according to method 1 (17 mg, 0.028 mmol) as a white powder. ¹H NMR (500 MHz, DMSO-d₆) δ 13.41 (s, 1H), 10.53 (s, 1H), 10.06 (s, 1H), 8.60 (d, J=7.2 Hz, 1H), 8.35 (d, J=1.4 Hz, 1H), 7.94-7.83 (m, 2H), 7.83-7.68 (m, 2H), 7.66-7.45 (m, 3H), 6.55-6.35 (m, 1H), 6.32 (dd, J=17.0, 1.9 Hz, 1H), 5.84 (dd, J=10.1, 1.9 Hz, 1H), 4.24 (q, J=7.1 Hz, 1H), 3.41 (dd, J=9.9, 7.0 Hz, 1H), 3.20-3.11 (m, 1H), 3.07 (dd, J=10.0, 6.8 Hz, 1H), 2.03-1.94 (m, 1H), 1.88 (dd, J=12.5, 7.6 Hz, 1H). MS (ESI) m/z 577 (M+H)⁺. Expected mass from chemical formula C₂₄H₂₂Cl₂N₆O₅S: 577.44

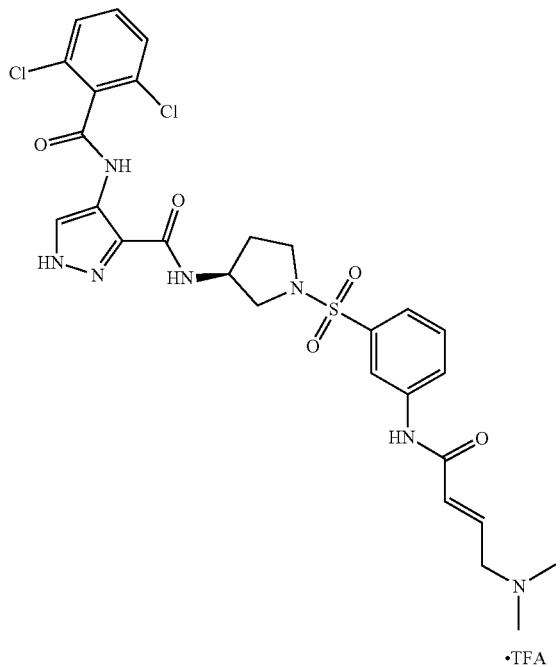 [SMILES: CN(C)C/C=C/C(=O)Nc1cccc(S(=O)(=O)N2CC[C@H](NC(=O)c3n[nH]cc3NC(=O)c3c(Cl)cccc3Cl)C2)c1]

FMF-05-068-2

(S,E)-4-(2,6-dichlorobenzamido)-N-(1-((3-(4-(dimethylamino)but-2-enamido)phenyl)sulfonyl)pyrrolidin-3-yl)-1H-pyrazole-3-carboxamide The compound was prepared according to method 1 (9 mg, 0.014 mmol) as a white powder. ¹H NMR (500 MHz, DMSO-d₆) δ 13.42 (s, 1H), 10.72 (d, J=20.4 Hz, 1H), 10.05 (s, 1H), 9.79 (s, 1H), 8.60 (d, J=7.1 Hz, 1H), 8.35 (s, 1H), 7.95-7.83 (m, 2H), 7.83-7.74 (m, 2H), 7.60-7.46 (m, 3H), 6.80 (dt, J=14.9, 7.1 Hz, 1H), 6.47 (d, J=15.4 Hz, 1H), 4.22 (q, J=6.7 Hz, 2H), 4.02-3.93 (m, 2H), 3.19-3.05 (m, 3H), 2.81 (s, 6H), 2.03-1.83 (m, 2H). MS (ESI) m/z 635 (M+H)⁺. Expected mass from chemical formula C₂₇H₂₉Cl₂N₇O₅S: 634.53

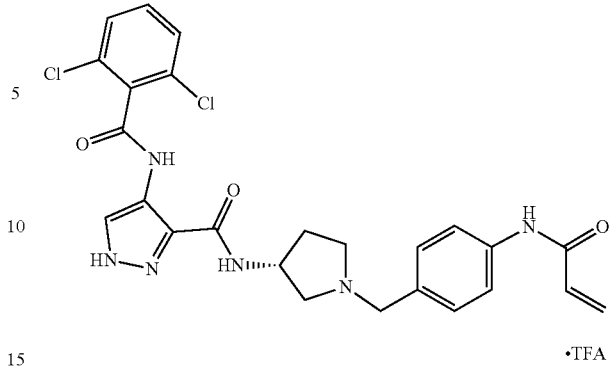

FMF-05-072-1

(R)—N-(1-(4-acrylamidobenzyl)pyrrolidin-3-yl)-4-(2,6-dichlorobenzamido)-1H-pyrazole-3-carboxamide The compound was prepared according to method 1 (11 mg, 0.021 mmol) as a white powder. ¹H NMR (500 MHz, DMSO-d₆) δ 13.53 (d, J=7.8 Hz, 1H), 10.31 (s, 1H), 10.04 (d, J=13.6 Hz, 1H), 8.40 (d, J=5.7 Hz, 1H), 7.76 (s, 1H), 7.74 (s, 1H), 7.62-7.56 (m, 3H), 7.53 (ddd, J=9.1, 6.8, 3.5 Hz, 2H), 7.47 (dd, J=8.6, 3.2 Hz, 2H), 6.45 (dd, J=17.0, 10.1 Hz, 1H), 6.28 (dd, J=17.0, 2.0 Hz, 1H), 5.79 (dd, J=10.1, 1.9 Hz, 1H), 4.60 (d, J=57.0 Hz, 2H), 4.40-4.31 (m, 2H), 3.60 (d, J=53.3 Hz, 2H), 3.18 (s, 1H), 2.13 (d, J=40.9 Hz, 2H). MS (ESI) m/z 528 (M+H)⁺. Expected mass from chemical formula C₂₅H₂₄Cl₂N₆O₃: 527.41

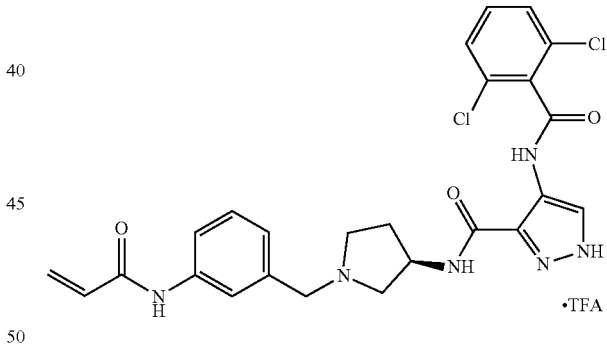

FMF-05-071-1

(R)—N-(1-(3-acrylamidobenzyl)pyrrolidin-3-yl)-4-(2,6-dichlorobenzamido)-1H-pyrazole-3-carboxamide The compound was prepared according to method 1 (17 mg, 0.032 mmol) as a white powder. ¹H NMR (500 MHz, DMSO-d₆) δ 13.54 (d, J=8.9 Hz, 1H), 10.31 (s, 1H), 10.04 (d, J=13.8 Hz, 1H), 8.85 (dd, J=170.2, 7.4 Hz, 1H), 8.40 (d, J=6.0 Hz, 1H), 8.03 (s, 1H), 7.64-7.49 (m, 5H), 7.43 (t, J=7.9 Hz, 1H), 7.28-7.16 (m, 1H), 6.46 (dd, J=17.0, 10.1 Hz, 1H), 6.28 (dd, J=17.0, 2.0 Hz, 1H), 5.79 (dd, J=10.1, 2.0 Hz, 1H), 4.68 (s, 1H), 4.56 (dd, J=13.6, 7.1 Hz, 1H), 4.39 (td, J=18.6, 17.6, 8.4 Hz, 2H), 3.74-3.56 (m, 1H), 3.20 (dd, J=16.6, 7.9

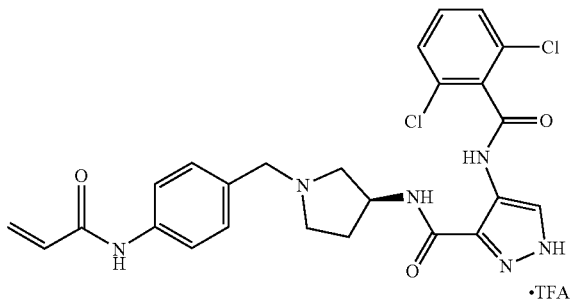 [SMILES: C=CC(=O)Nc1ccc(CN2CC[C@H](NC(=O)c3n[nH]cc3NC(=O)c3c(Cl)cccc3Cl)C2)cc1]

FMF-05-070-1

(S)—N-(1-(4-acrylamidobenzyl)pyrrolidin-3-yl)-4-(2,6-dichlorobenzamido)-1H-pyrazole-3-carboxamide The compound was prepared according to method 1 (14 mg, 0.026 mmol) as a white powder. $^1$H NMR (500 MHz, DMSO-$d_6$) δ 13.53 (d, J=7.8 Hz, 1H), 10.31 (s, 1H), 10.04 (d, J=13.5 Hz, 1H), 8.40 (d, J=5.7 Hz, 1H), 7.85-7.66 (m, 2H), 7.66-7.43 (m, 5H), 6.45 (dd, J=17.0, 10.2 Hz, 1H), 6.28 (dd, J=16.9, 2.0 Hz, 1H), 5.79 (dd, J=10.1, 2.0 Hz, 1H), 4.66 (s, 1H), 4.54 (t, J=7.1 Hz, OH), 4.41-4.28 (m, 2H), 3.76-3.55 (m, 1H), 3.18 (s, 1H), 2.27-2.08 (m, 1H). MS (ESI) m/z 528 (M+H)$^+$. Expected mass from chemical formula $C_{25}H_{24}Cl_2N_6O_3$: 527.41

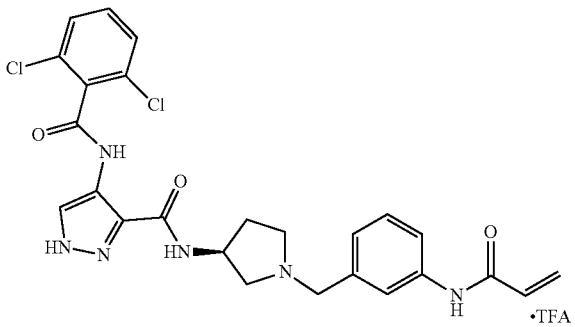 [SMILES: C=CC(=O)Nc1cccc(CN2CC[C@H](NC(=O)c3n[nH]cc3NC(=O)c3c(Cl)cccc3Cl)C2)c1]

FMF-05-069-1

(S)—N-(1-(3-acrylamidobenzyl)pyrrolidin-3-yl)-4-(2,6-dichlorobenzamido)-1H-pyrazole-3-carboxamide The compound was prepared according to method 1 (36 mg, 0.068 mmolS) as a white powder. $^1$H NMR (500 MHz, DMSO-$d_6$) δ 13.54 (d, J=8.8 Hz, 1H), 10.31 (d, J=6.5 Hz, 1H), 10.04 (d, J=13.7 Hz, 1H), 8.40 (d, J=6.0 Hz, 1H), 8.03 (s, 1H), 7.62-7.50 (m, 5H), 7.43 (t, J=7.9 Hz, 1H), 7.22 (s, 1H), 6.46 (dd, J=17.0, 10.1 Hz, 1H), 6.28 (dd, J=17.0, 2.0 Hz, 1H), 5.79 (dd, J=10.1, 2.0 Hz, 1H), 4.67 (s, 1H), 4.54 (s, 2H), 4.47-4.33 (m, 4H), 3.26-3.16 (m, 1H), 2.26-2.10 (m, 1H). MS (ESI) m/z 528 (M+H)$^+$. Expected mass from chemical formula $C_{25}H_{24}Cl_2N_6O_3$: 527.41

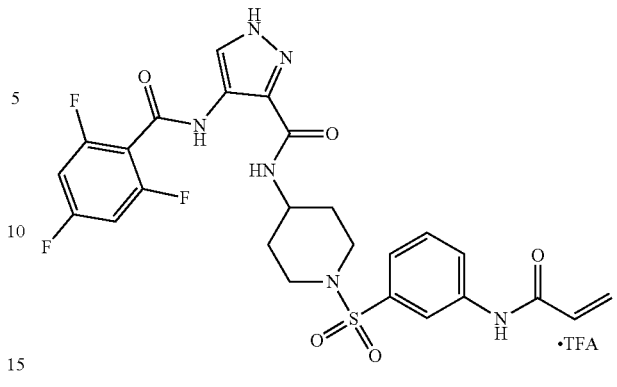

FMF-04-095-1

N-(1-((3-acrylamidophenyl)sulfonyl)piperidin-4-yl)-4-(2,4,6-trifluorobenzamido)-1H-pyrazole-3-carboxamide The compound was prepared according to method 1 (12 mg, 0.021 mmol) as a white powder. $^1$H NMR (500 MHz, DMSO-$d_6$) δ 13.41 (s, 1H), 10.55 (s, 1H), 10.37 (s, 1H), 8.43 (d, J=8.2 Hz, 1H), 8.32 (s, 1H), 8.17 (t, J=2.0 Hz, 1H), 7.94 (ddd, J=8.2, 2.2, 1.0 Hz, 1H), 7.61 (t, J=8.0 Hz, 1H), 7.47-7.40 (m, 1H), 7.38-7.34 (m, 1H), 6.44 (dd, J=17.0, 10.1 Hz, 1H), 6.31 (dd, J=16.9, 1.9 Hz, 1H), 5.82 (dd, J=10.0, 1.9 Hz, 1H), 3.81-3.71 (m, 1H), 3.63 (d, J=11.7 Hz, 2H), 2.46-2.32 (m, 2H), 1.81 (d, J=12.5 Hz, 2H), 1.71 (q, J=11.7 Hz, 2H). MS (ESI) m/z 577 (M+H)$^+$. Expected mass from chemical formula $C_{25}H_{23}F_3N_6O_5S$: 576.55

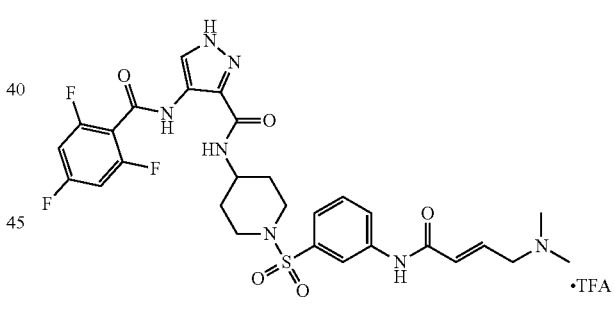

FMF-04-095-1

(E)-N-(1-((3-(4-(dimethylamino)but-2-enamido)phenyl)sulfonyl)piperidin-4-yl)-4-(2,4,6-trifluorobenzamido)-1H-pyrazole-3-carboxamide The compound was prepared according to method 1 (15 mg, 0.021 mmol) as a white powder. $^1$H NMR (500 MHz, DMSO-$d_6$) δ 13.42 (s, 1H), 10.74 (s, 1H), 10.36 (s, 1H), 8.44 (d, J=8.2 Hz, 1H), 8.32 (s, 1H), 8.19 (t, J=2.0 Hz, 1H), 7.96-7.89 (m, 1H), 7.62 (t, J=8.0 Hz, 1H), 7.45 (dt, J=7.9, 1.3 Hz, 1H), 7.38-7.33 (m, 2H), 6.80 (dt, J=15.3, 7.1 Hz, 1H), 6.46 (dd, J=15.3, 1.4 Hz, 1H), 3.96 (d, J=7.1 Hz, 2H), 3.81-3.69 (m, 1H), 3.64 (d, J=11.6 Hz, 2H), 2.80 (s, 6H), 2.44-2.30 (m, 2H), 1.81 (d, J=12.6 Hz, 2H), 1.76-1.64 (m, 2H). MS (ESI) m/z 635 (M+H)$^+$. Expected mass from chemical formula $C_{28}H_{30}F_3N_7O_5S$: 633.65

301

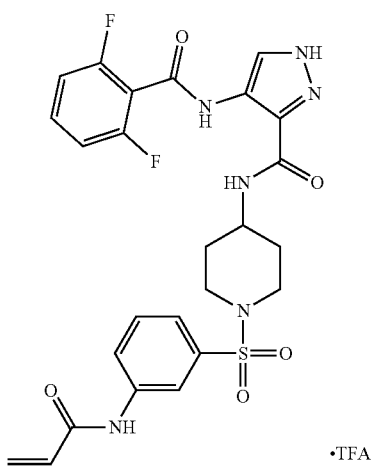 [SMILES: C=CC(=O)Nc1cccc(S(=O)(=O)N2CCC(NC(=O)c3n[nH]cc3NC(=O)c3c(F)cccc3F)CC2)c1]

FMF-04-096-1

N-(1-((3-acrylamidophenyl)sulfonyl)piperidin-4-yl)-4-(2,6-difluorobenzamido)-1H-pyrazole-3-carboxamide The compound was prepared according to method 1 (3 mg, 0.005 mmol) as a white powder. $^1$H NMR (500 MHz, DMSO-$d_6$) δ 13.41 (s, 1H), 10.58 (s, 1H), 10.35 (s, 1H), 8.44 (d, J=8.2 Hz, 1H), 8.33 (d, J=1.5 Hz, 1H), 8.17 (t, J=1.9 Hz, 1H), 7.95 (ddd, J=8.3, 2.2, 1.0 Hz, 1H), 7.65-7.55 (m, 2H), 7.43 (ddd, J=7.8, 1.9, 1.0 Hz, 1H), 7.29-7.18 (m, 2H), 6.45 (dd, J=17.0, 10.1 Hz, 1H), 6.31 (dd, J=17.0, 1.9 Hz, 1H), 5.82 (dd, J=10.1, 2.0 Hz, 1H), 3.76 (tdt, J=11.5, 8.3, 4.2 Hz, 1H), 3.63 (dt, J=12.3, 3.6 Hz, 2H), 2.44-2.33 (m, 2H), 1.84-1.76 (m, 2H), 1.71 (tt, J=12.8, 6.5 Hz, 2H). MS (ESI) m/z 559 (M+H)$^+$. Expected mass from chemical formula $C_{25}H_{24}F_2N_6O_5S$: 558.56

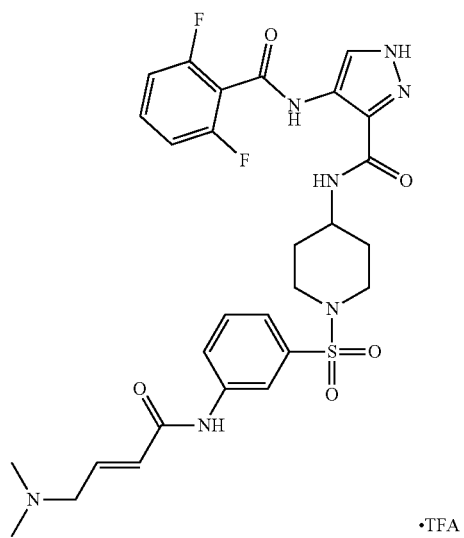 [SMILES: CN(C)C/C=C/C(=O)Nc1cccc(S(=O)(=O)N2CCC(NC(=O)c3n[nH]cc3NC(=O)c3c(F)cccc3F)CC2)c1]

·TFA

302

FMF-04-096-2

(E)-4-(2,6-difluorobenzamido)-N-(1-((3-(4-(dimethylamino)but-2-enamido)phenyl)sulfonyl)piperidin-4-yl)-1H-pyrazole-3-carboxamide The compound was prepared according to method 1 (19 mg, 0.031 mmol) as a white powder. $^1$H NMR (500 MHz, DMSO-$d_6$) δ 13.47 (s, 1H), 10.80 (s, 1H), 10.34 (s, 1H), 8.44 (d, J=8.1 Hz, 1H), 8.32 (s, 1H), 8.21 (dt, J=11.5, 2.0 Hz, 1H), 7.93 (ddd, J=8.6, 2.5, 1.4 Hz, 1H), 7.67-7.55 (m, 3H), 7.45 (ddt, J=7.8, 6.4, 1.3 Hz, 1H), 6.80 (dt, J=15.4, 7.1 Hz, 1H), 6.51-6.43 (m, 1H), 3.95 (d, J=7.1 Hz, 2H), 3.79-3.70 (m, 2H), 3.63 (d, J=11.5 Hz, 3H), 2.79 (s, 6H), 2.41-2.35 (m, 3H), 1.81 (d, J=12.3 Hz, 3H), 1.70 (d, J=12.6 Hz, 3H). MS (ESI) m/z 616 (M+H)$^+$. Expected mass from chemical formula $C_{28}H_{31}F_2N_7O_5S$: 615.66

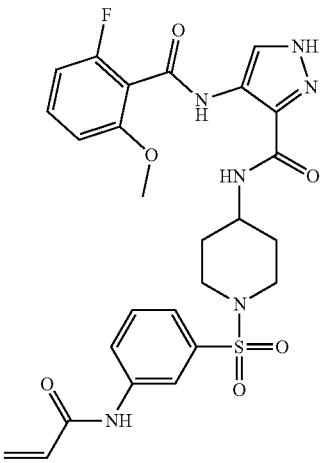

·TFA

FMF-04-097-1

N-(1-((3-acrylamidophenyl)sulfonyl)piperidin-4-yl)-4-(2-fluoro-6-methoxybenzamido)-1H-pyrazole-3-carboxamide The compound was prepared according to method 1 (4 mg, 0.007 mmol) as a white powder. $^1$H NMR (500 MHz, DMSO-$d_6$) δ 13.33 (s, 1H), 10.53 (s, 1H), 10.20 (s, 1H), 8.39 (d, J=8.2 Hz, 1H), 8.30 (d, J=1.4 Hz, 1H), 8.16 (t, J=2.0 Hz, 1H), 7.94 (ddd, J=8.1, 2.1, 1.0 Hz, 1H), 7.60 (t, J=8.0 Hz, 1H), 7.49 (td, J=8.5, 6.8 Hz, 1H), 7.43 (ddd, J=7.8, 1.8, 1.0 Hz, 1H), 7.00 (d, J=8.5 Hz, 1H), 6.91 (ddd, J=9.3, 8.4, 0.9 Hz, 1H), 6.44 (dd, J=17.0, 10.1 Hz, 1H), 6.31 (dd, J=17.0, 1.9 Hz, 1H), 5.82 (dd, J=10.1, 2.0 Hz, 1H), 3.84 (s, 3H), 3.79-3.68 (m, 1H), 3.63 (d, J=11.6 Hz, 2H), 3.09 (q, J=7.3 Hz, 1H), 2.42-2.31 (m, 2H), 1.81 (d, J=12.1 Hz, 2H), 1.76-1.65 (m, 2H). MS (ESI) m/z 571 (M+H)$^+$. Expected mass from chemical formula $C_{26}H_{27}FN_6O_6S$: 570.60

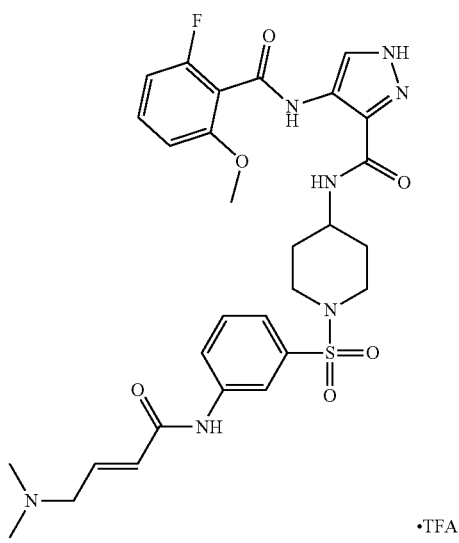

FMF-04-097-2

(E)-N-(1-((3-(4-(dimethylamino)but-2-enamido)phenyl)sulfonyl)piperidin-4-yl)-4-(2-fluoro-6-methoxybenzamido)-1H-pyrazole-3-carboxamide The compound was prepared according to method 1 (15 mg, 0.023 mmol) as a white powder. $^1$H NMR (500 MHz, DMSO-$d_6$) δ 13.39 (s, 1H), 10.83 (s, 1H), 10.18 (d, J=4.3 Hz, 1H), 8.40 (d, J=8.2 Hz, 1H), 8.30 (s, 1H), 8.20 (t, J=2.0 Hz, 1H), 7.97-7.91 (m, 1H), 7.61 (t, J=8.0 Hz, 1H), 7.49 (td, J=8.5, 6.8 Hz, 1H), 7.44 (dt, J=7.9, 1.3 Hz, 1H), 7.00 (d, J=8.5 Hz, 1H), 6.91 (dd, J=9.5, 8.3 Hz, 1H), 6.82 (dt, J=15.3, 7.1 Hz, 1H), 6.48 (dt, J=15.2, 1.3 Hz, 1H), 3.91 (d, J=7.1 Hz, 2H), 3.84 (s, 3H), 3.78-3.68 (m, 1H), 3.62 (d, J=11.5 Hz, 2H), 2.75 (s, 6H), 2.41-2.33 (m, 2H), 1.80 (d, J=12.6 Hz, 2H), 1.70 (d, J=12.3 Hz, 2H). MS (ESI) m/z 629 (M+H)$^+$. Expected mass from chemical formula $C_{29}H_{34}FN_7O_6S$: 627.69

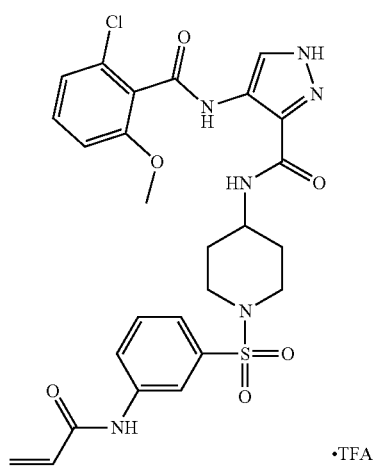 [SMILES: C=CC(=O)Nc1cccc(S(=O)(=O)N2CCC(NC(=O)c3n[nH]cc3NC(=O)c3c(Cl)cccc3OC)CC2)c1]

FMF-04-107-1

N-(1-((3-acrylamidophenyl)sulfonyl)piperidin-4-yl)-4-(2-chloro-6-methoxybenzamido)-1H-pyrazole-3-carboxamide The compound was prepared according to method 1 (6 mg, 0.010 mmol) as a white powder.

$^1$H NMR (500 MHz, DMSO-$d_6$) δ 13.39 (s, 1H), 10.56 (s, 1H), 9.87 (s, 1H), 8.42 (d, J=8.1 Hz, 1H), 8.30 (s, 1H), 8.16 (t, J=2.0 Hz, 1H), 7.93 (ddd, J=8.2, 2.2, 0.9 Hz, 1H), 7.60 (t, J=8.0 Hz, 1H), 7.48-7.40 (m, 2H), 7.14-7.10 (m, 2H), 6.44 (dd, J=17.0, 10.1 Hz, 1H), 6.31 (dd, J=17.0, 2.0 Hz, 1H), 5.81 (dd, J=10.1, 1.9 Hz, 1H), 3.79 (s, 3H), 3.75-3.67 (m, 1H), 3.64-3.60 (m, 2H), 2.42-2.30 (m, 2H), 1.79 (d, J=12.5 Hz, 2H), 1.69 (q, J=11.8, 11.3 Hz, 2H). MS (ESI) m/z 588 (M+H)$^+$. Expected mass from chemical formula $C_{26}H_{27}ClN_6O_6S$: 587.05

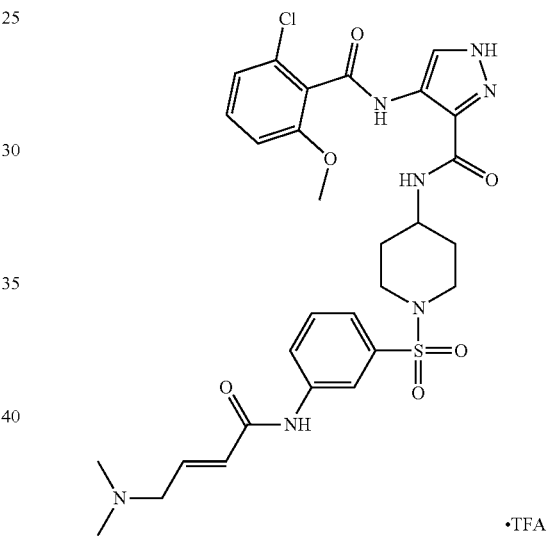

FMF-04-107-2

(E)-4-(2-chloro-6-methoxybenzamido)-N-(1-((3-(4-(dimethylamino)but-2-enamido)phenyl)sulfonyl)piperidin-4-yl)-1H-pyrazole-3-carboxamide The compound was prepared according to method 1 (3 mg, 0.004 mmol) as a white powder. $^1$H NMR (500 MHz, DMSO-$d_6$) δ 13.39 (s, 1H), 10.74 (s, 1H), 9.87 (s, 1H), 8.43 (d, J=8.2 Hz, 1H), 8.35-8.27 (m, 1H), 8.18 (t, J=2.0 Hz, 1H), 7.92 (ddd, J=8.3, 2.2, 1.0 Hz, 1H), 7.61 (t, J=8.0 Hz, 1H), 7.48-7.42 (m, 2H), 7.12 (dd, J=8.3, 5.6 Hz, 2H), 6.80 (dt, J=15.4, 7.1 Hz, 1H), 6.49-6.42 (m, 1H), 3.93 (d, J=7.0 Hz, 2H), 3.79 (s, 3H), 3.75-3.67 (m, 1H), 3.67-3.59 (m, 2H), 2.78 (s, 6H), 2.39-2.31 (m, 2H), 1.79 (d, J=12.6 Hz, 2H), 1.74-1.65 (m, 2H). MS (ESI) m/z 645 (M+H)$^+$. Expected mass from chemical formula $C_{29}H_{34}ClN_7O_6S$: 644.14

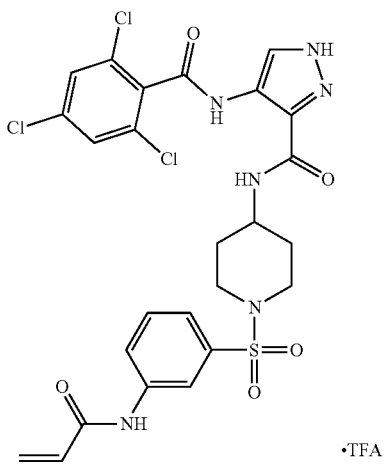 [SMILES: C=CC(=O)Nc1cccc(S(=O)(=O)N2CCC(NC(=O)c3n[nH]cc3NC(=O)c3c(Cl)cc(Cl)cc3Cl)CC2)c1]

FMF-04-159-1

N-(1-((3-acrylamidophenyl)sulfonyl)piperidin-4-yl)-4-(2,4,6-trichlorobenzamido)-1H-pyrazole-3-carboxamide The compound was prepared according to method 1 (6 mg, 0.009 mmol) as a white powder. $^1$H NMR (500 MHz, DMSO-d$_6$) δ 13.41 (s, 1H), 10.52 (s, 1H), 10.20 (d, J=10.0 Hz, 1H), 8.34 (s, 1H), 8.15 (t, J=2.0 Hz, 1H), 7.94 (ddd, J=8.2, 2.2, 1.0 Hz, 1H), 7.79 (d, J=1.8 Hz, 2H), 7.60 (t, J=8.0 Hz, 1H), 7.43 (ddd, J=7.8, 1.9, 1.0 Hz, 1H), 6.43 (dd, J=17.0, 10.1 Hz, 1H), 6.31 (dd, J=17.0, 1.9 Hz, 1H), 5.82 (dd, J=10.0, 2.0 Hz, 1H), 3.72 (dq, J=11.2, 7.3, 5.6 Hz, 1H), 3.61 (dd, J=7.6, 5.2 Hz, 2H), 2.38 (t, J=12.0 Hz, 2H), 1.81 (d, J=12.4 Hz, 2H), 1.69 (d, J=12.1 Hz, 3H). MS (ESI) m/z 627 (M+H)$^+$. Expected mass from chemical formula C$_{25}$H$_{23}$Cl$_3$N$_6$O$_5$S: 625.91

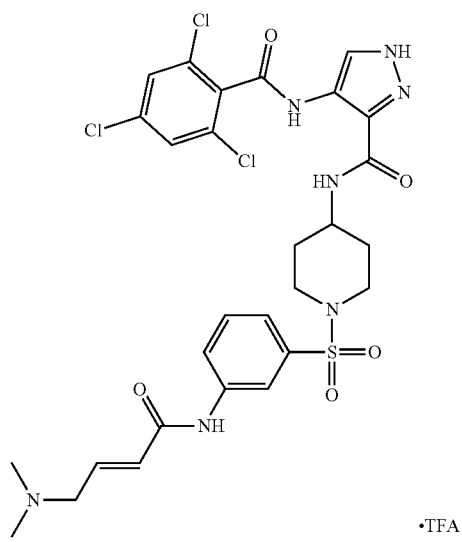 [SMILES: CN(C)C/C=C/C(=O)Nc1cccc(S(=O)(=O)N2CCC(NC(=O)c3n[nH]cc3NC(=O)c3c(Cl)cc(Cl)cc3Cl)CC2)c1]

FMF-04-159-2

(E)-N-(1-((3-(4-(dimethylamino)but-2-enamido)phenyl)sulfonyl)piperidin-4-yl)-4-(2,4,6-trichlorobenzamido)-1H-pyrazole-3-carboxamide The compound was prepared according to method 1 (17 mg, 0.024 mmol) as a white powder. $^1$H NMR (500 MHz, DMSO-d$_6$) δ 13.42 (s, 1H), 10.70 (s, 1H), 10.18 (s, 1H), 9.84 (s, 1H), 8.42 (d, J=8.2 Hz, 1H), 8.35 (d, J=1.5 Hz, 1H), 8.17 (t, J=2.0 Hz, 1H), 8.00-7.85 (m, 1H), 7.79 (s, 2H), 7.62 (t, J=8.0 Hz, 1H), 7.45 (dt, J=7.9, 1.3 Hz, 1H), 6.79 (dt, J=14.8, 7.1 Hz, 1H), 6.50-6.37 (m, 1H), 3.96 (d, J=7.2 Hz, 2H), 3.83-3.68 (m, OH), 3.63 (d, J=11.6 Hz, 2H), 2.81 (s, 6H), 2.41-2.29 (m, 2H), 1.87-1.64 (m, 4H). MS (ESI) m/z 689 (M+H)$^+$. Expected mass from chemical formula C$_{28}$H$_{30}$Cl$_3$N$_7$O$_5$S: 683.00

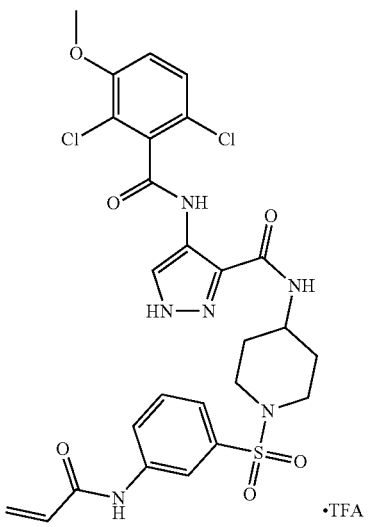 [SMILES: C=CC(=O)Nc1cccc(S(=O)(=O)N2CCC(NC(=O)c3n[nH]cc3NC(=O)c3c(Cl)ccc(OC)c3Cl)CC2)c1]

FMF-04-184-1

N-(1-((3-acrylamidophenyl)sulfonyl)piperidin-4-yl)-4-(2,6-dichloro-3-methoxybenzamido)-1H-pyrazole-3-carboxamide The compound was prepared according to method 1 (10 mg, 0.016 mmol) as a white powder. $^1$H NMR (500 MHz, DMSO-d$_6$) δ 13.42 (s, 1H), 10.52 (s, 1H), 10.05 (s, 1H), 8.43 (d, J=8.1 Hz, 1H), 8.32 (s, 1H), 8.15 (t, J=2.0 Hz, 1H), 7.94 (ddd, J=8.2, 2.2, 1.0 Hz, 1H), 7.60 (t, J=8.0 Hz, 1H), 7.52 (d, J=9.0 Hz, 1H), 7.42 (dt, J=7.9, 1.3 Hz, 1H), 7.28 (d, J=9.1 Hz, 1H), 6.43 (dd, J=17.0, 10.1 Hz, 1H), 6.31 (dd, J=16.9, 2.0 Hz, 1H), 5.82 (dd, J=10.1, 2.0 Hz, 1H), 3.90 (s, 3H), 3.72 (qd, J=11.5, 5.9 Hz, 1H), 3.62 (d, J=11.7 Hz, 2H), 2.43-2.31 (m, 2H), 1.90-1.63 (m, 5H). MS (ESI) m/z 622 (M+H)$^+$. Expected mass from chemical formula C$_{26}$H$_{26}$Cl$_2$N$_6$O$_6$S: 621.49

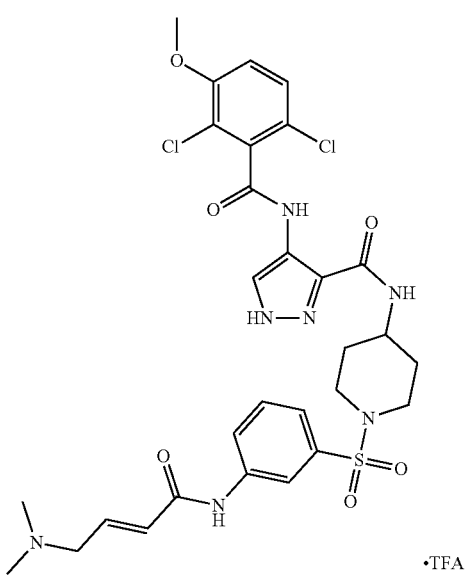 [SMILES: COc1ccc(Cl)c(C(=O)Nc2c[nH]nc2C(=O)NC2CCN(S(=O)(=O)c3cccc(NC(=O)/C=C/CN(C)C)c3)CC2)c1Cl]

FMF-04-184-2

(E)-4-(2,6-dichloro-3-methoxybenzamido)-N-(1-((3-(4-(dimethylamino)but-2-enamido)phenyl)sulfonyl)piperidin-4-yl)-1H-pyrazole-3-carboxamide The compound was prepared according to method 1 (21 mg, 0.031 mmol) as a white powder. $^1$H NMR (500 MHz, DMSO-$d_6$) δ 13.43 (s, 1H), 10.71 (s, 1H), 10.04 (s, 1H), 9.90 (s, 1H), 8.45 (t, J=6.5 Hz, 1H), 8.33 (s, 1H), 8.17 (t, J=2.0 Hz, 1H), 7.95-7.89 (m, 1H), 7.62 (t, J=8.0 Hz, 1H), 7.52 (d, J=9.0 Hz, 1H), 7.45 (dt, J=7.8, 1.3 Hz, 1H), 7.28 (d, J=9.0 Hz, 1H), 6.79 (dt, J=14.7, 7.2 Hz, 1H), 6.48-6.42 (m, 1H), 4.01-3.94 (m, 2H), 3.90 (s, 3H), 3.71 (tdt, J=11.6, 8.3, 4.0 Hz, 1H), 3.63 (d, J=11.7 Hz, 3H), 2.81 (s, 6H), 2.41-2.30 (m, 2H), 1.80 (dd, J=12.8, 3.9 Hz, 2H), 1.74-1.63 (m, 2H).

MS (ESI) m/z 679 (M+H)$^+$. Expected mass from chemical formula $C_{29}H_{33}Cl_2N_7O_6S$: 678.59

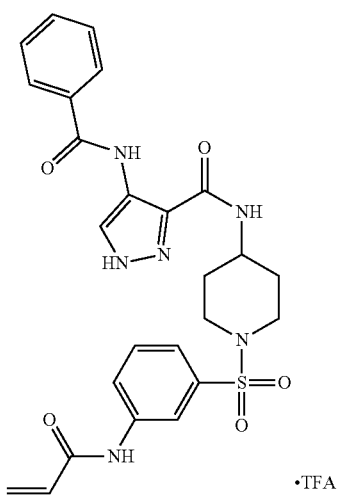 [SMILES: C=CC(=O)Nc1cccc(S(=O)(=O)N2CCC(NC(=O)c3n[nH]cc3NC(=O)c3ccccc3)CC2)c1]

FMF-05-027-1

N-(1-((3-acrylamidophenyl)sulfonyl)piperidin-4-yl)-4-benzamido-1H-pyrazole-3-carboxamide The compound was prepared according to method 1 (3 mg, 0.006 mmol) as a white powder. $^1$H NMR (500 MHz, DMSO-$d_6$) δ 13.35 (s, 1H), 10.74 (s, 1H), 10.56 (s, 1H), 8.51 (d, J=8.3 Hz, 1H), 8.31 (d, J=1.4 Hz, 1H), 8.19-8.16 (m, 1H), 7.96 (ddd, J=8.3, 2.2, 1.0 Hz, 1H), 7.88-7.78 (m, 2H), 7.68-7.52 (m, 4H), 7.44 (dt, J=7.9, 1.2 Hz, 1H), 6.45 (dd, J=17.0, 10.1 Hz, 1H), 6.32 (dd, J=16.9, 2.0 Hz, 1H), 5.83 (dd, J=10.1, 2.0 Hz, 1H), 3.92-3.77 (m, 1H), 3.65 (d, J=11.8 Hz, 2H), 2.47-2.34 (m, 2H), 1.84 (d, J=12.5 Hz, 2H), 1.74 (dt, J=13.1, 10.0 Hz, 2H). MS (ESI) m/z 523 (M+H)$^+$. Expected mass from chemical formula $C_{25}H_{26}N_6O_5S$: 522.58

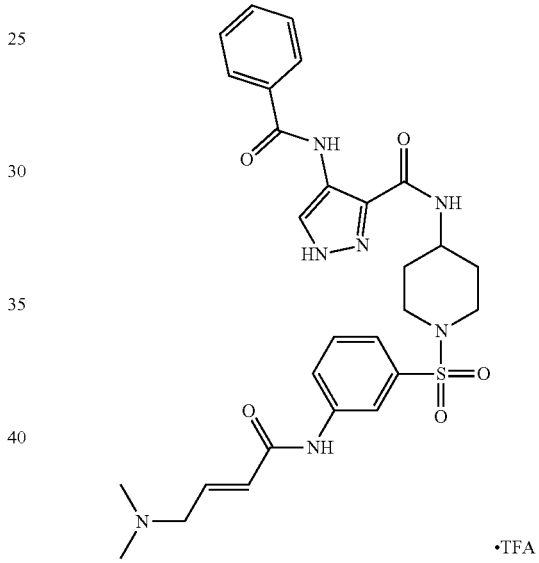

FMF-05-027-2

(E)-4-benzamido-N-(1-((3-(4-(dimethylamino)but-2-enamido)phenyl)sulfonyl)piperidin-4-yl)-1H-pyrazole-3-carboxamide The compound was prepared according to method 1 (8 mg, 0.013 mmol) as a white powder. $^1$H NMR (500 MHz, DMSO-$d_6$) δ 13.37 (s, 1H), 10.75 (s, 1H), 10.02 (s, 1H), 8.52 (d, J=8.3 Hz, 1H), 8.31 (s, 1H), 8.20 (t, J=2.0 Hz, 1H), 7.94 (dd, J=8.3, 2.1 Hz, 1H), 7.90-7.81 (m, 2H), 7.63 (dt, J=9.0, 7.6 Hz, 2H), 7.57 (dd, J=8.3, 6.7 Hz, 2H), 7.47 (d, J=7.7 Hz, 1H), 6.81 (dt, J=14.8, 7.2 Hz, 1H), 6.48 (d, J=15.3 Hz, 1H), 3.98 (d, J=7.1 Hz, 2H), 3.83 (tt, J=9.8, 6.3 Hz, 1H), 3.66 (d, J=11.7 Hz, 2H), 2.82 (s, 6H), 2.46-2.35 (m, 2H), 1.84 (d, J=12.5 Hz, 2H), 1.79-1.67 (m, 2H). MS (ESI) m/z 580 (M+H)$^+$. Expected mass from chemical formula $C_{28}H_{33}N_7O_5S$: 579.68

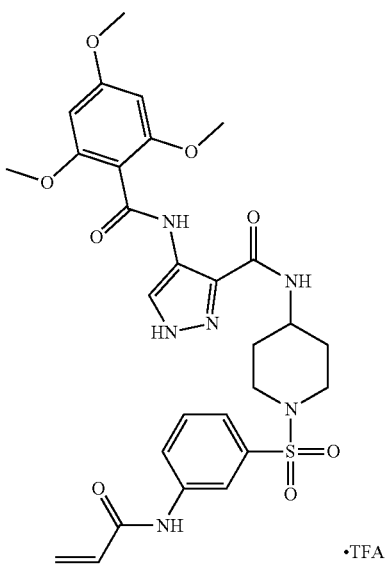 [SMILES: C=CC(=O)Nc1cccc(S(=O)(=O)N2CCC(NC(=O)c3n[nH]cc3NC(=O)c3c(OC)cc(OC)cc3OC)CC2)c1]

FMF-05-028-1

N-(1-((3-acrylamidophenyl)sulfonyl)piperidin-4-yl)-4-(2,4,6-trimethoxybenzamido)-1H-pyrazole-3-carboxamide The compound was prepared according to method 1 (3 mg, 0.004 mmol) as a white powder. $^1$H NMR (500 MHz, DMSO-$d_6$) δ 13.25 (s, 1H), 10.53 (s, 1H), 9.68 (s, 1H), 8.32 (d, J=8.3 Hz, 1H), 8.25 (s, 1H), 8.15 (t, J=2.0 Hz, 1H), 7.94 (ddd, J=8.2, 2.2, 1.0 Hz, 1H), 7.60 (t, J=8.0 Hz, 1H), 7.42 (dt, J=8.0, 1.2 Hz, 1H), 6.44 (dd, J=17.0, 10.1 Hz, 1H), 6.31 (dd, J=17.0, 1.9 Hz, 1H), 6.27 (s, 2H), 5.82 (dd, J=10.1, 2.0 Hz, 1H), 3.81 (s, 3H), 3.73 (s, 6H), 3.62 (d, J=11.9 Hz, 2H), 2.43-2.31 (m, 2H), 1.80 (d, J=12.5 Hz, 2H), 1.74-1.63 (m, 2H). MS (ESI) m/z 613 (M+H)$^+$. Expected mass from chemical formula $C_{28}H_{32}N_6O_8S$: 612.66

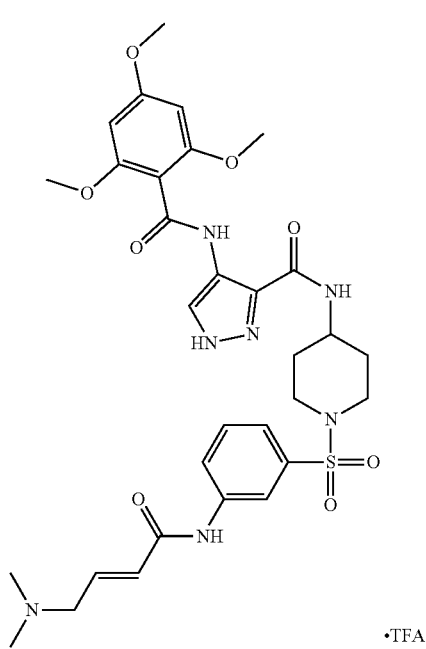 [SMILES: COc1cc(OC)c(C(=O)Nc2c[nH]nc2C(=O)NC2CCN(S(=O)(=O)c3cccc(NC(=O)/C=C/CN(C)C)c3)CC2)c(OC)c1]

FMF-05-028-2

(E)-N-(1-((3-(4-(dimethylamino)but-2-enamido)phenyl)sulfonyl)piperidin-4-yl)-4-(2,4,6-trimethoxybenzamido)-1H-pyrazole-3-carboxamide The compound was prepared according to method 1 (8 mg, 0.012 mmol) as a white powder. $^1$H NMR (500 MHz, DMSO-$d_6$) δ 13.26 (s, 1H), 10.73 (s, 1H), 10.02 (s, 1H), 9.67 (s, 1H), 8.34 (d, J=8.1 Hz, 1H), 8.25 (s, 1H), 8.18 (t, J=2.0 Hz, 1H), 7.96-7.89 (m, 1H), 7.62 (t, J=8.0 Hz, 1H), 7.45 (dt, J=7.9, 1.2 Hz, 1H), 6.80 (dt, J=14.8, 7.2 Hz, 1H), 6.50-6.41 (m, 1H), 6.28 (s, 2H), 3.97 (d, J=7.1 Hz, 2H), 3.81 (s, 3H), 3.73 (s, 6H), 3.62 (d, J=11.3 Hz, 2H), 3.08 (d, J=6.8 Hz, 1H), 2.81 (s, 5H), 2.43-2.27 (m, 2H), 1.80 (d, J=12.3 Hz, 2H), 1.70 (d, J=12.6 Hz, 2H). MS (ESI) m/z 671 (M+H)$^+$. Expected mass from chemical formula $C_{31}H_{39}N_7O_8S$: 669.75

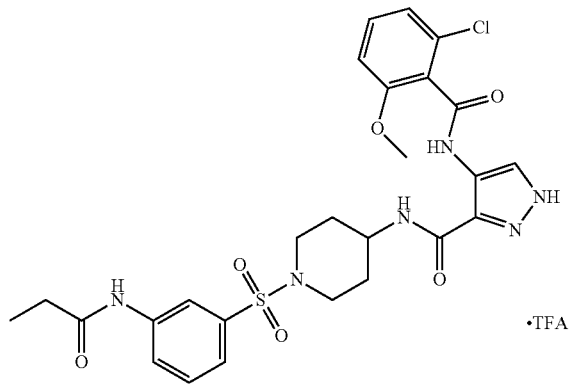 [SMILES: CCC(=O)Nc1cccc(S(=O)(=O)N2CCC(NC(=O)c3n[nH]cc3NC(=O)c3c(Cl)cccc3OC)CC2)c1]

FMF-05-033-1

4-(2-chloro-6-methoxybenzamido)-N-(1-((3-propionamidophenyl)sulfonyl)piperidin-4-yl)-1H-pyrazole-3-carboxamide The compound was prepared according to method 1 (7 mg, 0.012 mmol) as a white powder. $^1$H NMR (500 MHz, DMSO-$d_6$) δ 13.36 (s, 1H), 10.23 (s, 1H), 9.87 (s, 1H), 8.41 (d, J=8.2 Hz, 1H), 8.30 (s, 1H), 8.09 (t, J=2.0 Hz, 1H), 7.85 (ddd, J=8.2, 2.2, 1.0 Hz, 1H), 7.56 (t, J=8.0 Hz, 1H), 7.45 (td, J=8.3, 3.0 Hz, 1H), 7.39-7.34 (m, 1H), 7.17-7.07 (m, 2H), 3.79 (s, 3H), 3.76-3.65 (m, 1H), 3.61 (d, J=11.8 Hz, 2H), 2.38-2.34 (m, 2H), 2.35-2.31 (m, 1H), 1.89-1.76 (m, 3H), 1.68 (tt, J=12.0, 6.2 Hz, 2H), 1.09 (t, J=7.5 Hz, 3H). MS (ESI) m/z 590 (M+H)$^+$. Expected mass from chemical formula $C_{26}H_{29}Cl_1N_6O_6S$: 589.06

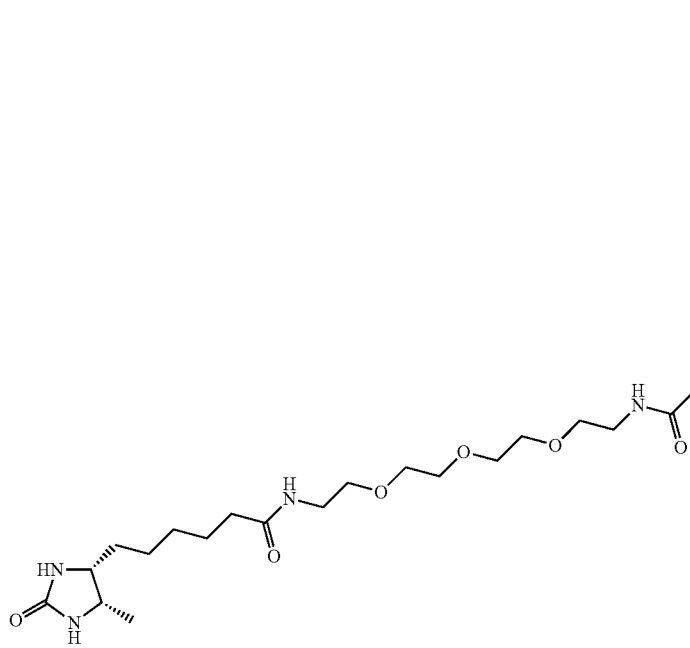

FMF-05-035-1

4-(2-chloro-6-methoxybenzamido)-N-(1-((3-((E)-5-methyl-27-((4R,5S)—5-methyl-2-oxoimidazolidin-4-yl)-8,22-dioxo-12,15,18-trioxa-5,9,21-triazaheptacos-2-enamido)phenyl)sulfonyl)piperidin-4-yl)-1H-pyrazole-3-carboxamide The compound was prepared according to method 1 (5 mg, 0.005 mmol) as a white powder. MS (ESI) m/z 1073, 537 (M+H)$^+$, [(M+H)$^+$/2]. Expected mass from chemical formula $C_{49}H_{70}Cl_1N_{11}O_{12}S$: 1072.67

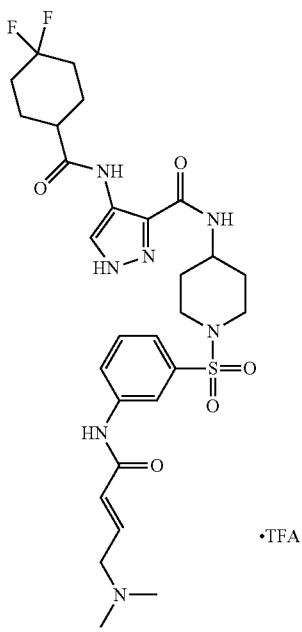 [SMILES: CN(C)C/C=C/C(=O)Nc1cccc(S(=O)(=O)N2CCC(NC(=O)c3n[nH]cc3NC(=O)C3CCC(F)(F)CC3)CC2)c1]

FMF-05-116-1

(E)-4-(4,4-difluorocyclohexane-1-carboxamido)-N-(1-((3-(4-(dimethylamino)but-2-enamido)phenyl)sulfonyl)piperidin-4-yl)-1H-pyrazole-3-carboxamide The compound was prepared according to method 1 (2 mg, 0.003 mmol) as a white powder. $^1$H NMR (500 MHz, DMSO-d$_6$) δ 13.27-13.16 (m, 1H), 10.73 (s, 1H), 9.99 (s, 1H), 9.79 (s, 1H), 8.37 (d, J=8.2 Hz, 1H), 8.25-8.09 (m, 2H), 7.94 (ddd, J=8.2, 2.3, 1.0 Hz, 1H), 7.64 (t, J=8.0 Hz, 1H), 7.46 (dt, J=7.9, 1.2 Hz, 1H), 6.81 (dt, J=14.6, 7.1 Hz, 1H), 6.47 (dd, J=15.3, 1.4 Hz, 1H), 3.96 (d, J=7.1 Hz, 2H), 3.83-3.70 (m, 1H), 3.65 (d, J=11.5 Hz, 2H), 3.10 (s, 1H), 2.80 (s, 6H), 2.44-2.34 (m, 2H), 2.10-1.54 (m, 10H), 1.28-1.14 (m, 2H). MS (ESI) m/z 623 (M+H)$^+$. Expected mass from chemical formula $C_{28}H_{37}F_2N_7O_5S$: 621.70

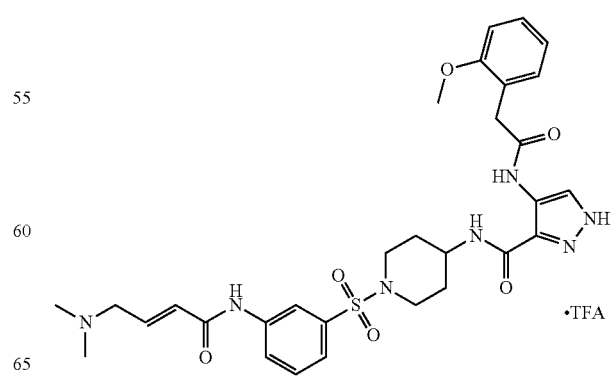

FMF-05-117-1

(E)-N-(1-((3-(4-(dimethylamino)but-2-enamido)phenyl)sulfonyl)piperidin-4-yl)-4-(2-(2-methoxyphenyl)acetamido)-1H-pyrazole-3-carboxamide The compound was prepared according to method 1 (5 mg, 0.008 mmol) as a white powder. $^1$H NMR (500 MHz, DMSO-$d_6$) δ 13.16 (s, 1H), 10.73 (s, 1H), 9.95 (s, 1H), 9.67 (s, 1H), 8.22 (d, J=8.3 Hz, 1H), 8.18 (d, J=2.0 Hz, 1H), 8.13 (s, 1H), 7.95 (ddd, J=8.2, 2.1, 1.0 Hz, 1H), 7.64 (t, J=8.0 Hz, 1H), 7.46 (dt, J=8.0, 1.2 Hz, 1H), 7.28-7.20 (m, 2H), 7.02-6.95 (m, 1H), 6.91 (td, J=7.4, 1.2 Hz, 1H), 6.81 (dt, J=14.8, 7.1 Hz, 1H), 6.47 (dt, J=15.5, 1.3 Hz, 1H), 3.98 (d, J=7.2 Hz, 2H), 3.79 (s, 3H), 3.76-3.68 (m, 1H), 3.62 (d, J=18.2 Hz, 4H), 2.82 (s, 6H), 2.44-2.32 (m, 2H), 1.80 (d, J=12.3 Hz, 2H), 1.71 (t, J=11.6 Hz, 2H). MS (ESI) m/z 625 (M+H)$^+$. Expected mass from chemical formula $C_{30}H_{37}N_7O_6S$: 623.70

FMF-05-118-1

(E)-4-(2-chloro-6-ethoxybenzamido)-N-(1-((3-(4-(dimethylamino)but-2-enamido)phenyl)sulfonyl)piperidin-4-yl)-1H-pyrazole-3-carboxamide The compound was prepared according to method 1 (5 mg, 0.007 mmol) as a white powder. $^1$H NMR (500 MHz, DMSO-$d_6$) δ 13.37 (s, 1H), 10.71 (s, 1H), 9.87 (d, J=7.5 Hz, 1H), 8.42 (d, J=8.3 Hz, 1H), 8.31 (s, 1H), 8.17 (t, J=2.0 Hz, 1H), 7.92 (ddd, J=8.2, 2.2, 1.0 Hz, 1H), 7.62 (t, J=8.0 Hz, 1H), 7.49-7.36 (m, 2H), 7.16-7.04 (m, 2H), 6.85-6.73 (m, 1H), 6.52-6.35 (m, 1H), 4.09 (q, J=7.0 Hz, 2H), 3.97 (d, J=7.2 Hz, 2H), 3.75-3.67 (m, 1H), 3.63 (d, J=11.6 Hz, 2H), 2.81 (s, 6H), 2.41-2.30 (m, 2H), 1.80 (d, J=12.4 Hz, 2H), 1.69 (d, J=10.6 Hz, 2H), 1.21 (t, J=7.0 Hz, 3H). MS (ESI) m/z 659 (M+H)$^+$. Expected mass from chemical formula $C_{30}H_{36}ClN_7O_6S$: 658.17

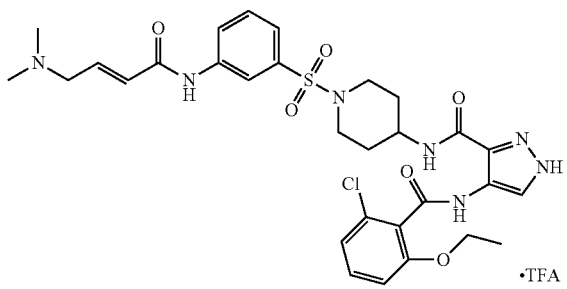 [SMILES: CCOc1cccc(Cl)c1C(=O)Nc1c[nH]nc1C(=O)NC1CCN(S(=O)(=O)c2cccc(NC(=O)/C=C/CN(C)C)c2)CC1]

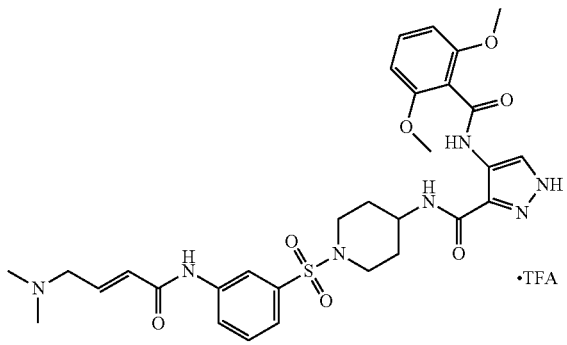 [SMILES: COc1cccc(OC)c1C(=O)Nc1c[nH]nc1C(=O)NC1CCN(S(=O)(=O)c2cccc(NC(=O)/C=C/CN(C)C)c2)CC1]

FMF-05-119-1

(E)-4-(2,6-dimethoxybenzamido)-N-(1-((3-(4-(dimethylamino)but-2-enamido)phenyl)sulfonyl)piperidin-4-yl)-1H-pyrazole-3-carboxamide The compound was prepared according to method 1 (3 mg, 0.004 mmol) as a white powder. $^1$H NMR (500 MHz, DMSO-$d_6$) δ 13.31 (s, 1H), 10.73 (s, 1H), 10.02 (s, 1H), 9.67 (s, 1H), 8.37 (d, J=8.2 Hz, 1H), 8.28 (s, 1H), 8.18 (t, J=2.0 Hz, 1H), 7.92 (ddd, J=8.3, 2.1, 1.0 Hz, 1H), 7.62 (t, J=8.0 Hz, 1H), 7.45 (dt, J=7.9, 1.2 Hz, 1H), 7.37 (t, J=8.4 Hz, 1H), 6.80 (dt, J=14.8, 7.2 Hz, 1H), 6.73 (d, J=8.5 Hz, 2H), 6.50-6.38 (m, 1H), 3.97 (d, J=7.2 Hz, 2H), 3.74 (s, 6H), 3.66-3.58 (m, 2H), 2.81 (s, 6H), 2.35 (t, J=11.6 Hz, 2H), 1.79 (t, J=7.5 Hz, 2H), 1.69 (q, J=11.7, 11.1 Hz, 2H), 1.30-1.18 (m, 1H). MS (ESI) m/z 640 (M+H)$^+$. Expected mass from chemical formula $C_{30}H_{37}N_7O_7S$: 639.73

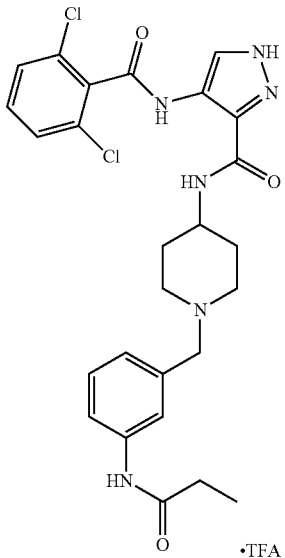 [SMILES: CCC(=O)Nc1cccc(CN2CCC(NC(=O)c3n[nH]cc3NC(=O)c3c(Cl)cccc3Cl)CC2)c1]

FMF-04-172-2

4-(2,6-dichlorobenzamido)-N-(1-(3-propionamidobenzyl)piperidin-4-yl)-1H-pyrazole-3-carboxamide The compound was prepared according to method 1 (20 mg, 0.026 mmol) as a white powder. $^1$H NMR (500 MHz, DMSO-$d_6$) δ 13.48 (s, 1H), 10.12 (d, J=8.9 Hz, 1H), 10.03 (d, J=4.8 Hz, 1H), 9.52 (s, 1H), 8.79-8.59 (m, 1H), 8.38 (d, J=16.9 Hz, 1H), 7.92 (t, J=1.9 Hz, 1H), 7.64-7.42 (m, 5H), 7.39 (t, J=7.9 Hz, 1H), 7.15 (dt, J=7.6, 1.3 Hz, 1H), 4.25 (d, J=5.2 Hz, 2H), 3.96 (dt, J=11.8, 4.0 Hz, 1H), 3.37 (d, J=11.8 Hz, 2H), 3.03 (dd, J=22.2, 10.7 Hz, 2H), 2.34 (q, J=7.5 Hz, 2H), 1.99-1.82 (m, 4H), 1.09 (t, J=7.5 Hz, 3H). MS (ESI) m/z 544 (M+H)$^+$. Expected mass from chemical formula $C_{26}H_{28}N_6O_3$: 543.45

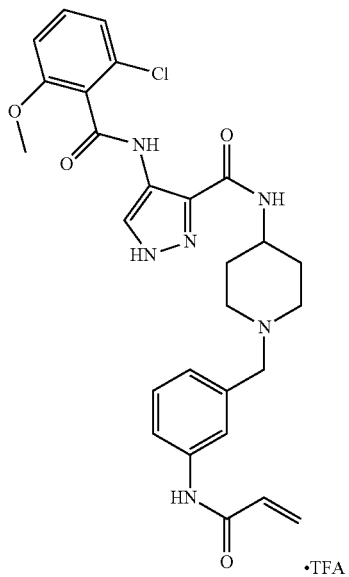 [SMILES: C=CC(=O)Nc1cccc(CN2CCC(NC(=O)c3n[nH]cc3NC(=O)c3c(Cl)cccc3OC)CC2)c1]

FMF-04-161-1

N-(1-(3-acrylamidobenzyl)piperidin-4-yl)-4-(2-chloro-6-methoxybenzamido)-1H-pyrazole-3-carboxamide The compound was prepared according to method 1 (14 mg, 0.026 mmol) as a white powder. $^1$H NMR (500 MHz, DMSO-$d_6$) δ 13.45 (d, J=26.9 Hz, 1H), 10.32 (d, J=5.1 Hz, 1H), 9.86 (d, J=14.9 Hz, 1H), 8.68 (d, J=7.7 Hz, 1H), 8.36 (d, J=16.7 Hz, 1H), 7.99 (d, J=1.9 Hz, 1H), 7.58 (dt, J=8.3, 1.3 Hz, 1H), 7.45 (dt, J=18.9, 8.1 Hz, 2H), 7.21 (dd, J=9.5, 7.8 Hz, 1H), 7.15 (t, J=7.7 Hz, 2H), 6.46 (dd, J=17.0, 10.1 Hz, 1H), 6.28 (dd, J=17.0, 2.0 Hz, 1H), 5.79 (dd, J=10.1, 2.0 Hz, 1H), 4.27 (d, J=5.2 Hz, 2H), 4.02-3.90 (m, 1H), 3.38 (d, J=12.1 Hz, 2H), 3.06 (q, J=11.7 Hz, 2H), 1.98 (d, J=20.0 Hz, 2H), 1.85 (q, J=12.5 Hz, 3H). MS (ESI) m/z 538 (M+H)$^+$. Expected mass from chemical formula $C_{27}H_{29}ClN_6O_4$: 537.02

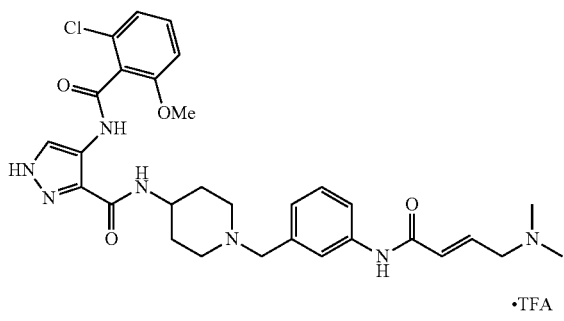 [SMILES: COc1cccc(Cl)c1C(=O)Nc1c[nH]nc1C(=O)NC1CCN(Cc2cccc(NC(=O)/C=C/CN(C)C)c2)CC1]

FMF-05-032-1

(E)-4-(2-chloro-6-methoxybenzamido)-N-(1-(3-(4-(dimethylamino)but-2-enamido)benzyl)piperidin-4-yl)-1H-pyrazole-3-carboxamide The compound was prepared according to method 1 (11 mg, 0.018 mmol) as a white powder. $^1$H NMR (500 MHz, DMSO-$d_6$) δ 13.44 (s, 1H), 10.52 (s, 1H), 10.15 (s, 1H), 9.86 (d, J=12.2 Hz, 1H), 8.68 (d, J=7.9 Hz, 1H), 8.33 (s, 1H), 7.92 (s, 1H), 7.46 (dt, J=12.6, 8.1 Hz, 2H), 7.14 (t, J=7.8 Hz, 3H), 6.76 (dt, J=14.9, 7.2 Hz, 1H), 6.49 (dd, J=15.3, 1.4 Hz, 1H), 4.27 (d, J=5.0 Hz, 2H), 3.96 (d, J=7.2 Hz, 3H), 3.81 (s, 4H), 3.63 (pt, J=6.6, 3.2 Hz, 1H), 3.39 (d, J=12.0 Hz, 2H), 3.15 (qd, J=7.4, 4.3 Hz, 1H), 3.06 (q, J=15.0 Hz, 3H), 2.81 (s, 7H), 2.02-1.93 (m, 2H), 1.86 (p, J=12.4 Hz, 3H). MS (ESI) m/z 595 (M+H)$^+$. Expected mass from chemical formula $C_{27}H_{29}ClN_6O_4$: 594.11

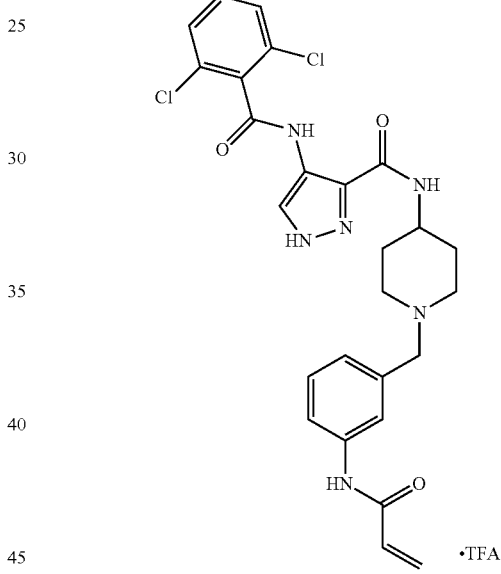

FMF-04-158-1

N-(1-(3-acrylamidobenzyl)piperidin-4-yl)-4-(2,4,6-trichlorobenzamido)-1H-pyrazole-3-carboxamide The compound was prepared according to method 1 (19 mg, 0.031 mmol) as a white powder. $^1$H NMR (500 MHz, DMSO-$d_6$) δ 13.46 (s, 1H), 10.32 (d, J=4.3 Hz, 1H), 10.20 (s, 1H), 8.66 (d, J=7.9 Hz, 1H), 8.38 (s, 1H), 7.99 (d, J=2.0 Hz, 1H), 7.81 (s, 2H), 7.58 (dt, J=8.3, 1.4 Hz, 1H), 7.45 (q, J=7.6 Hz, 1H), 7.21 (d, J=7.8 Hz, 1H), 6.47 (dd, J=17.0, 10.1 Hz, 1H), 6.29 (dd, J=17.0, 1.9 Hz, 1H), 5.80 (dd, J=10.1, 2.0 Hz, 1H), 4.27 (d, J=5.2 Hz, 2H), 3.39 (d, J=12.0 Hz, 2H), 3.08 (q, J=11.7 Hz, 2H), 2.05-1.73 (m, 4H). MS (ESI) m/z 577 (M+H)$^+$. Expected mass from chemical formula $C_{27}H_{29}ClN_6O_4$: 575.88

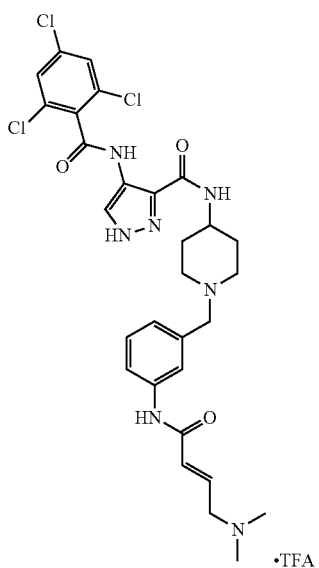 [SMILES: CN(C)C/C=C/C(=O)Nc1cccc(CN2CCC(NC(=O)c3n[nH]cc3NC(=O)c3c(Cl)cc(Cl)cc3Cl)CC2)c1]

FMF-04-158-2

(E)-N-(1-(3-(4-(dimethylamino)but-2-enamido)benzyl)piperidin-4-yl)-4-(2,4,6-trichlorobenzamido)-1H-pyrazole-3-carboxamide The compound was prepared according to method 1 (8 mg, 0.012 mmol) as a white powder. $^1$H NMR (500 MHz, DMSO-$d_6$) δ 13.49 (s, 1H), 10.52 (s, 1H), 10.20 (d, J=2.9 Hz, 1H), 9.62 (s, 1H), 8.65 (s, 1H), 8.37 (s, 1H), 7.93 (s, 1H), 7.81 (d, J=3.7 Hz, 2H), 7.45 (p, J=6.2, 5.5 Hz, 1H), 7.24 (d, J=7.6 Hz, 1H), 6.76 (dt, J=14.8, 7.2 Hz, 1H), 6.49 (dt, J=15.3, 1.3 Hz, 1H), 4.28 (d, J=5.0 Hz, 2H), 3.96 (d, J=7.8 Hz, 2H), 3.39 (d, J=12.3 Hz, 2H), 3.07 (d, J=15.3 Hz, 3H), 2.81 (s, 6H), 2.69 (s, 1H), 1.98 (d, J=13.1 Hz, 2H), 1.94-1.81 (m, 2H). MS (ESI) m/z 634 (M+H)$^+$. Expected mass from chemical formula $C_{29}H_{32}Cl_3N_7O_3$: 632.97

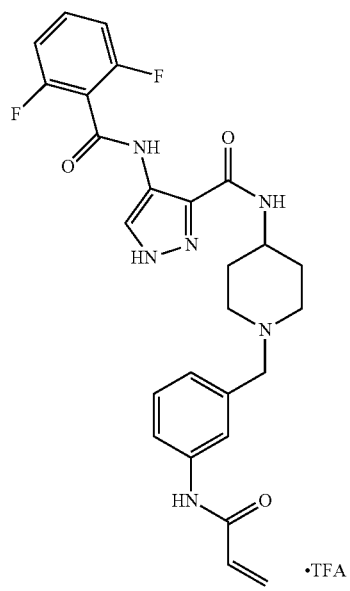 [SMILES: C=CC(=O)Nc1cccc(CN2CCC(NC(=O)c3n[nH]cc3NC(=O)c3c(F)cccc3F)CC2)c1]

FMF-04-160-1

N-(1-(3-acrylamidobenzyl)piperidin-4-yl)-4-(2,6-difluorobenzamido)-1H-pyrazole-3-carboxamide The compound was prepared according to method 1 (15 mg, 0.029 mmol) as a white powder. $^1$H NMR (500 MHz, DMSO-$d_6$) δ 13.48 (d, J=26.2 Hz, 1H), 10.42-10.29 (m, 2H), 8.69 (d, J=7.9 Hz, 1H), 8.37 (d, J=15.8 Hz, 1H), 7.99 (d, J=1.9 Hz, 1H), 7.70-7.55 (m, 2H), 7.45 (q, J=7.6 Hz, 1H), 7.33-7.18 (m, 3H), 6.47 (dd, J=17.0, 10.1 Hz, 1H), 6.29 (dd, J=17.0, 2.0 Hz, 1H), 5.80 (dd, J=10.1, 2.0 Hz, 1H), 4.27 (d, J=5.2 Hz, 2H), 3.99 (dt, J=11.6, 4.0 Hz, 1H), 3.40 (d, J=12.1 Hz, 2H), 3.09 (q, J=11.5 Hz, 2H), 1.98 (d, J=13.3 Hz, 2H), 1.86 (q, J=12.7 Hz, 3H). MS (ESI) m/z 509 (M+H)$^+$. Expected mass from chemical formula $C_{29}H_{32}Cl_3N_7O_3$: 508.53

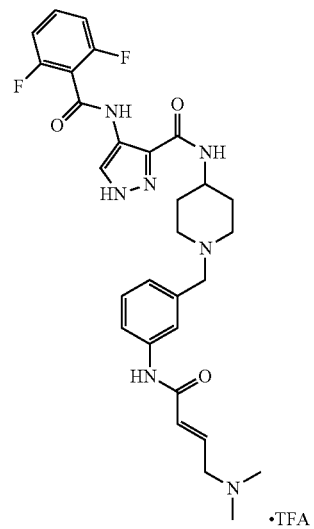 [SMILES: CN(C)C/C=C/C(=O)Nc1cccc(CN2CCC(NC(=O)c3n[nH]cc3NC(=O)c3c(F)cccc3F)CC2)c1]

FMF-04-160-2

(E)-4-(2,6-difluorobenzamido)-N-(1-(3-(4-(dimethylamino)but-2-enamido)benzyl)piperidin-4-yl)-1H-pyrazole-3-carboxamide The compound was prepared according to method 1 (18 mg, 0.029 mmol) as a white powder. $^1$H NMR (500 MHz, DMSO-$d_6$) δ 13.46 (s, 1H), 10.51 (s, 1H), 10.34 (d, J=8.7 Hz, 1H), 8.69 (d, J=7.5 Hz, 1H), 8.36 (s, 1H), 7.93 (s, 1H), 7.70-7.56 (m, 2H), 7.46 (q, J=7.9, 7.3 Hz, 1H), 7.32-7.18 (m, 4H), 6.76 (dt, J=14.7, 7.2 Hz, 1H), 6.49 (dd, J=15.3, 1.5 Hz, 1H), 4.28 (d, J=5.1 Hz, 2H), 3.96 (d, J=7.4 Hz, 2H), 3.40 (d, J=12.1 Hz, 2H), 3.13-3.02 (m, 2H), 2.81 (d, J=2.8 Hz, 6H), 1.98 (d, J=13.3 Hz, 2H), 1.89-1.82 (m, 2H). MS (ESI) m/z 566 (M+H)$^+$. Expected mass from chemical formula $C_{29}H_{33}F_2N_7O_3$: 565.63

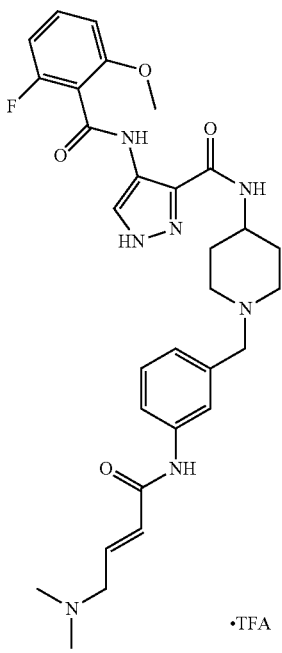 [SMILES: COc1cccc(F)c1C(=O)Nc1c[nH]nc1C(=O)NC1CCN(Cc2cccc(NC(=O)/C=C/CN(C)C)c2)CC1]

IHK-01-013-2

(E)-N-(1-(3-(4-(dimethylamino)but-2-enamido)benzyl)piperidin-4-yl)-4-(2-fluoro-6-methoxybenzamido)-1H-pyrazole-3-carboxamide The compound was prepared according to method 1 (9 mg, 0.015 mmol) as a white powder. $^1$H NMR (500 MHz, DMSO-$d_6$) δ 13.40 (s, 1H), 10.51 (s, 1H), 10.19 (d, J=3.2 Hz, 1H), 9.62 (s, 1H), 8.65 (d, J=7.8 Hz, 1H), 8.33 (s, 1H), 7.92 (s, 1H), 7.65-7.61 (m, 1H), 7.56-7.42 (m, 3H), 7.24 (t, J=7.5 Hz, 1H), 7.03 (d, J=8.5 Hz, 1H), 6.93 (t, J=8.9 Hz, 2H), 6.75 (dd, J=15.1, 7.4 Hz, 1H), 6.52-6.45 (m, 1H), 3.96 (d, J=7.3 Hz, 3H), 3.87 (s, 4H), 3.39 (d, J=12.0 Hz, 2H), 3.27 (s, 1H), 3.09 (s, 2H), 2.81 (s, 6H), 2.02-1.81 (m, 6H). MS (ESI) m/z 578 (M+H)$^+$. Expected mass from chemical formula $C_{30}H_{36}FN_7O_4$: 577.66

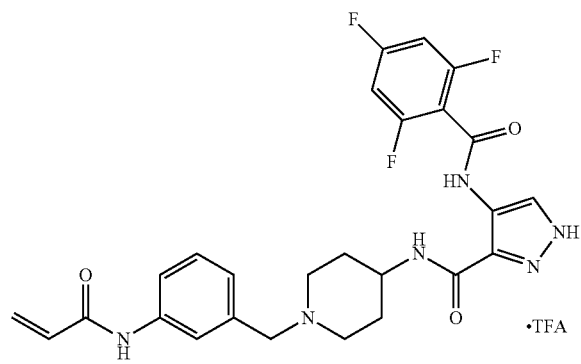 [SMILES: C=CC(=O)Nc1cccc(CN2CCC(NC(=O)c3n[nH]cc3NC(=O)c3c(F)cc(F)cc3F)CC2)c1]

FMF-04-200-1

N-(1-(3-acrylamidobenzyl)piperidin-4-yl)-4-(2,4,6-trifluorobenzamido)-1H-pyrazole-3-carboxamide The compound was prepared according to method 1 (3 mg, 0.005 mmol) as a white powder. $^1$H NMR (500 MHz, DMSO-$d_6$) δ 13.45 (s, 1H), 10.35 (d, J=22.2 Hz, 2H), 8.68 (d, J=8.0 Hz, 1H), 8.35 (s, 1H), 7.99 (s, 1H), 7.59 (dd, J=7.7, 2.0 Hz, 1H), 7.49-7.34 (m, 3H), 7.22 (d, J=7.8 Hz, 1H), 6.55 (s, 1H), 6.47 (dd, J=17.0, 10.1 Hz, 1H), 6.29 (dd, J=17.0, 2.0 Hz, 1H), 5.79 (dd, J=10.1, 2.0 Hz, 1H), 4.51-4.34 (m, 1H), 4.27 (d, J=5.1 Hz, 2H), 4.10 (s, 1H), 3.89 (s, OH), 3.09 (d, J=11.7 Hz, 2H), 2.04-1.80 (m, 4H). MS (ESI) m/z 527 (M+H)$^+$. Expected mass from chemical formula $C_{26}H_{25}F_3N_6O_3$: 526.52

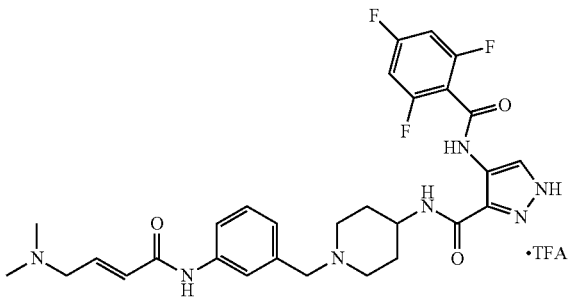 [SMILES: CN(C)C/C=C/C(=O)Nc1cccc(CN2CCC(NC(=O)c3n[nH]cc3NC(=O)c3c(F)cc(F)cc3F)CC2)c1]

FMF-04-200-2

(E)-N-(1-(3-(4-(dimethylamino)but-2-enamido)benzyl)piperidin-4-yl)-4-(2,4,6-trifluorobenzamido)-1H-pyrazole-3-carboxamide The compound was prepared according to method 1 (15 mg, 0.025 mmol) as a white powder. $^1$H NMR (500 MHz, DMSO-$d_6$) δ 13.56 (d, J=37.6 Hz, 1H), 10.62 (s, 1H), 10.37 (s, 1H), 8.67 (d, J=7.5 Hz, 1H), 8.36 (d, J=27.5 Hz, 1H), 7.94 (d, J=10.2 Hz, 1H), 7.65 (d, J=8.3 Hz, 1H), 7.53-7.31 (m, 2H), 7.25 (d, J=7.2 Hz, 1H), 6.77 (dq, J=15.8, 8.5, 7.8 Hz, 1H), 6.57-6.48 (m, 1H), 4.25 (d, J=23.6 Hz, 2H), 3.95 (d, J=7.2 Hz, 2H), 3.08 (ddt, J=13.3, 7.4, 4.8 Hz, 1H), 2.90-2.82 (m, 2H), 2.80 (d, J=3.5 Hz, 6H), 1.95 (t, J=21.1 Hz, 4H), 1.24 (s, 2H). MS (ESI) m/z 584 (M+H)$^+$. Expected mass from chemical formula $C_{29}H_{32}F_3N_7O_3$: 583.62

321

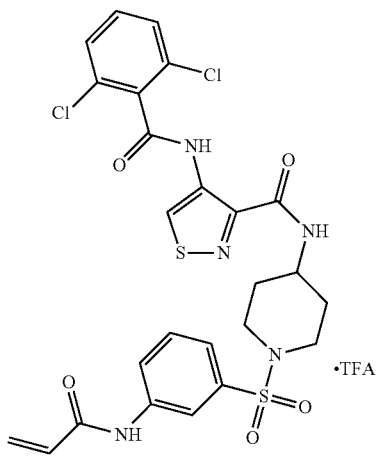 [SMILES: C=CC(=O)Nc1cccc(S(=O)(=O)N2CCC(NC(=O)c3nscc3NC(=O)c3c(Cl)cccc3Cl)CC2)c1]

FMF-04-089-1]

N-(1-((3-acrylamidophenyl)sulfonyl)piperidin-4-yl)-4-(2,6-dichlorobenzamido)isothiazole-3-carboxamide The compound was prepared according to method 1 (12 mg, 0.019 mmol) as a white powder. $^1$H NMR (500 MHz, DMSO-d$_6$) δ 11.15 (s, 1H), 10.55 (s, 1H), 9.48 (s, 1H), 9.08 (d, J=8.2 Hz, 1H), 8.16 (t, J=2.0 Hz, 1H), 7.93 (ddd, J=8.2, 2.1, 1.0 Hz, 1H), 7.64-7.51 (m, 4H), 7.42 (ddd, J=7.8, 1.8, 1.0 Hz, 1H), 6.44 (dd, J=17.0, 10.1 Hz, 1H), 6.31 (dd, J=17.0, 1.9 Hz, 1H), 5.81 (dd, J=10.0, 1.9 Hz, 1H), 3.80-3.68 (m, 1H), 3.63 (d, J=11.9 Hz, 3H), 2.42-2.33 (m, 2H), 1.81 (d, J=12.7 Hz, 2H), 1.71 (qd, J=12.1, 4.1 Hz, 2H). MS (ESI) m/z 609 (M+H)$^+$. Expected mass from chemical formula C$_{25}$H$_{23}$Cl$_2$N$_5$O$_5$S$_2$: 608.51

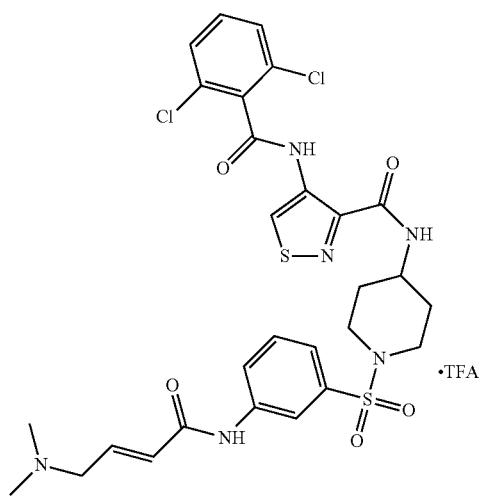 [SMILES: CN(C)C/C=C/C(=O)Nc1cccc(S(=O)(=O)N2CCC(NC(=O)c3nscc3NC(=O)c3c(Cl)cccc3Cl)CC2)c1]

FMF-04-089-2

(E)-4-(2,6-dichlorobenzamido)-N-(1-((3-(4-(dimethylamino)but-2-enamido)phenyl)sulfonyl)piperidin-4-yl)isothiazole-3-carboxamide The compound was prepared according to method 1 (12 mg, 0.019 mmol) as a white powder. $^1$H NMR (500 MHz, DMSO-d$_6$) δ 11.14 (s, 1H), 10.75 (s, 1H), 9.48 (s, 1H), 9.09 (dd, J=8.2, 4.5 Hz, 1H), 8.22-8.15 (m, 1H), 7.95-7.88 (m, 1H), 7.65-7.57 (m, 3H), 7.55 (dd, J=9.2, 6.8 Hz, 1H), 7.44 (dt, J=7.9, 1.2 Hz, 1H), 6.79 (dt, J=15.3, 7.1 Hz, 1H), 6.50-6.41 (m, 1H), 3.94 (d, J=7.1 Hz, 2H), 3.78-3.69 (m, 1H), 3.63 (d, J=11.5 Hz, 2H), 2.79 (s, 5H), 2.37 (td, J=12.0, 2.7 Hz, 2H), 1.81 (dd, J=12.8, 3.9 Hz, 2H), 1.76-1.65 (m, 2H). MS (ESI) m/z 666 (M+H)$^+$. Expected mass from chemical formula C$_{28}$H$_{30}$Cl$_2$N$_6$O$_5$S$_2$: 665.61

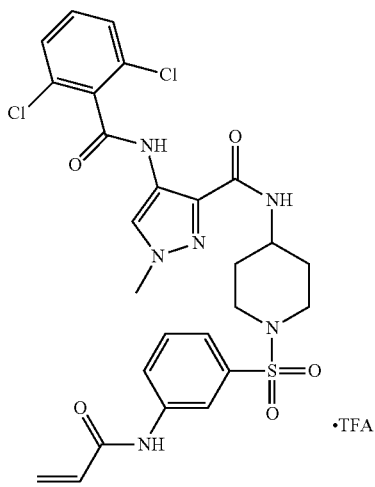 [SMILES: C=CC(=O)Nc1cccc(S(=O)(=O)N2CCC(NC(=O)c3nn(C)cc3NC(=O)c3c(Cl)cccc3Cl)CC2)c1]

FMF-04-180-1

N-(1-((3-acrylamidophenyl)sulfonyl)piperidin-4-yl)-4-(2,6-dichlorobenzamido)-1-methyl-1H-pyrazole-3-carboxamide The compound was prepared according to method 1 (14 mg, 0.023 mmol) as a white powder. $^1$H NMR (500 MHz, DMSO-d$_6$) δ 10.51 (s, 1H), 10.13 (s, 1H), 8.41 (d, J=8.6 Hz, 2H), 8.15 (t, J=2.0 Hz, 1H), 7.93 (ddd, J=8.2, 2.1, 0.9 Hz, 1H), 7.64-7.54 (m, 3H), 7.51 (dd, J=9.2, 6.8 Hz, 1H), 7.42 (ddd, J=7.8, 1.9, 1.0 Hz, 1H), 6.43 (dd, J=17.0, 10.1 Hz, 1H), 6.31 (dd, J=17.0, 2.0 Hz, 1H), 5.82 (dd, J=10.1, 2.0 Hz, 1H), 3.93 (s, 3H), 3.71 (dtt, J=11.6, 8.4, 4.4 Hz, 1H), 3.62 (d, J=11.8 Hz, 2H), 2.36 (td, J=12.1, 2.7 Hz, 2H), 1.85-1.62 (m, 4H). MS (ESI) m/z 606 (M+H)$^+$. Expected mass from chemical formula C$_{26}$H$_{26}$Cl$_2$N$_6$O$_5$S 605.49

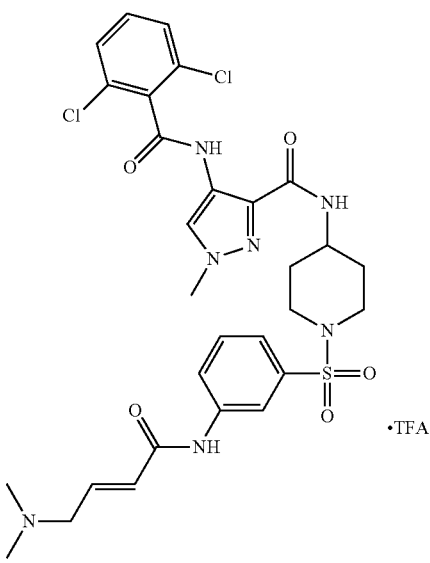 [SMILES: CN(C)C/C=C/C(=O)Nc1cccc(S(=O)(=O)N2CCC(NC(=O)c3nn(C)cc3NC(=O)c3c(Cl)cccc3Cl)CC2)c1]

FMF-04-180-2

(E)-4-(2,6-dichlorobenzamido)-N-(1-((3-(4-(dimethylamino)but-2-enamido)phenyl)sulfonyl)piperidin-4-yl)-1-methyl-1H-pyrazole-3-carboxamide The compound was prepared according to method 1 (26 mg, 0.039 mmol) as a white powder. $^1$H NMR (500 MHz, DMSO-$d_6$) δ 10.71 (s, 1H), 10.12 (s, 1H), 9.92 (s, 1H), 8.46-8.36 (m, 2H), 8.17 (t, J=2.0 Hz, 1H), 7.92 (ddd, J=8.2, 2.1, 1.0 Hz, 1H), 7.62 (t, J 8.0 Hz, 1H), 7.58-7.55 (m, 2H), 7.51 (dd, J=9.2, 6.8 Hz, 1H), 7.47-7.43 (m, 1H), 6.79 (dt, J=15.4, 7.1 Hz, 1H), 6.45 (dt, J=15.4, 1.3 Hz, 1H), 4.01-3.95 (m, 2H), 3.93 (s, 3H), 3.76-3.67 (m, 1H), 3.62 (d, J=11.4 Hz, 2H), 2.81 (s, 6H), 2.35 (td, J=12.0, 2.7 Hz, 2H), 1.81-1.65 (m, 5H). MS (ESI) m/z 663 (M+H)$^+$. Expected mass from chemical formula $C_{29}H_{33}Cl_2N_7O_5S$: 662.59

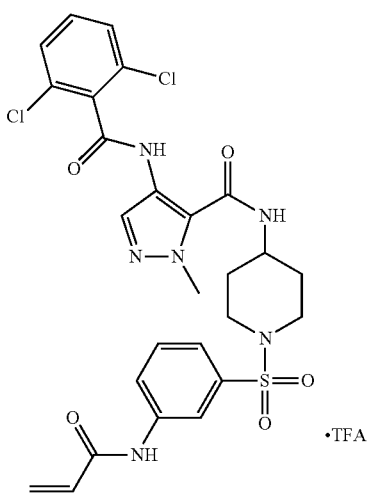 [SMILES: C=CC(=O)Nc1cccc(S(=O)(=O)N2CCC(NC(=O)c3c(NC(=O)c4c(Cl)cccc4Cl)cnn3C)CC2)c1]

FMF-04-120-1

N-(1-((3-acrylamidophenyl)sulfonyl)piperidin-4-yl)-4-(2,6-dichlorobenzamido)-1-methyl-1H-pyrazole-5-carboxamide The compound was prepared according to method 1 (5 mg, 0.008 mmol) as a white powder. $^1$H NMR (500 MHz, DMSO-$d_6$) δ 10.53 (s, 1H), 10.29 (s, 1H), 8.16 (t, J=1.9 Hz, 1H), 8.10 (d, J=7.3 Hz, 1H), 7.94 (ddd, J=8.2, 2.2, 1.0 Hz, 1H), 7.63 (s, 1H), 7.60-7.55 (m, 3H), 7.50 (dd, J=9.0, 7.1 Hz, 1H), 7.46-7.40 (m, 1H), 6.44 (dd, J=17.0, 10.1 Hz, 1H), 6.31 (dd, J=17.0, 2.0 Hz, 1H), 5.82 (dd, J=10.1, 2.0 Hz, 1H), 3.84 (s, 3H), 3.54 (d, J=12.1 Hz, 1H), 2.55 (s, 2H), 2.00-1.89 (m, 2H), 1.59-1.47 (m, 2H). MS (ESI) m/z 606 (M+H)$^+$. Expected mass from chemical formula $C_{26}H_{26}Cl_2N_6O_5S$: 605.49

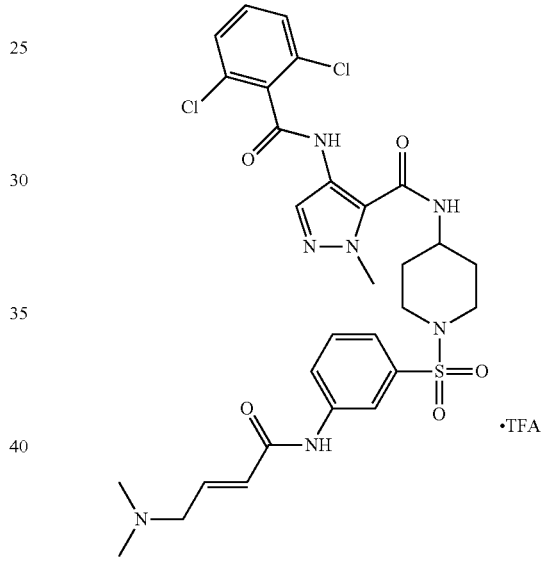

FMF-04-121-1

(E)-4-(2,6-dichlorobenzamido)-N-(1-((3-(4-(dimethylamino)but-2-enamido)phenyl)sulfonyl)piperidin-4-yl)-1-methyl-1H-pyrazole-5-carboxamide The compound was prepared according to method 1 (14 mg, 0.021 mmol) as a white powder. $^1$H NMR (500 MHz, DMSO-$d_6$) δ 10.70 (s, 1H), 10.30 (s, 1H), 8.18 (t, J=2.0 Hz, 1H), 8.10 (d, J=7.3 Hz, 1H), 7.92 (ddd, J=8.2, 2.2, 1.0 Hz, 1H), 7.66-7.61 (m, 2H), 7.59-7.55 (m, 2H), 7.50 (dd, J=9.0, 7.0 Hz, 1H), 7.45 (dt, J=8.0, 1.2 Hz, 1H), 6.80 (dt, J=15.4, 7.2 Hz, 1H), 6.45 (dt, J=15.3, 1.4 Hz, 1H), 4.01-3.92 (m, 2H), 3.85 (s, 3H), 3.55 (d, J=11.9 Hz, 2H), 2.81 (s, 6H), 2.55 (s, 2H), 1.94 (d, J=12.7 Hz, 2H), 1.53 (q, J=9.6 Hz, 2H). MS (ESI) m/z 663 (M+H)$^+$. Expected mass from chemical formula $C_{29}H_{33}Cl_2N_7O_5S$: 662.59

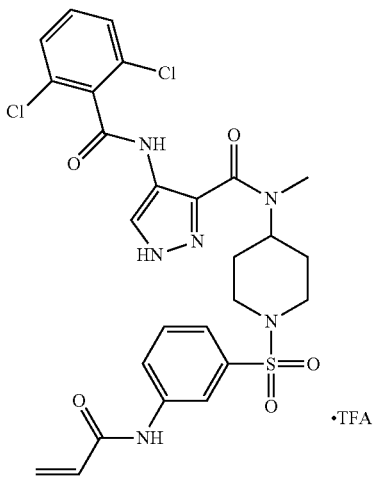 [SMILES: C=CC(=O)Nc1cccc(S(=O)(=O)N2CCC(N(C)C(=O)c3n[nH]cc3NC(=O)c3c(Cl)cccc3Cl)CC2)c1]

FMF-04-086-1

N-(1-((3-acrylamidophenyl)sulfonyl)piperidin-4-yl)-4-(2,6-dichlorobenzamido)-N-methyl-1H-pyrazole-3-carboxamide The compound was prepared according to method 1 (11 mg, 0.018 mmol) as a white powder. $^1$H NMR (500 MHz, DMSO-d$_6$) δ 13.23 (d, J=77.7 Hz, 1H), 10.53 (d, J=7.5 Hz, 1H), 10.39 (d, J=9.1 Hz, 1H), 8.28 (d, J=25.1 Hz, 1H), 8.18 (d, J=9.0 Hz, 1H), 7.92 (t, J=7.1 Hz, 1H), 7.61 (q, J=7.6 Hz, 1H), 7.55 (d, J=1.7 Hz, 1H), 7.54 (s, OH), 7.49 (dd, J=9.2, 6.8 Hz, 1H), 7.46-7.41 (m, 1H), 6.43 (dd, J=16.6, 10.0 Hz, 1H), 6.31 (dd, J=17.1, 4.4 Hz, 1H), 5.82 (dd, J=9.9, 4.8 Hz, 1H), 4.38 (d, J=111.5 Hz, 1H), 3.75 (d, J=11.6 Hz, 2H), 2.98 (d, J=164.0 Hz, 3H), 2.45-2.35 (m, 1H), 2.21 (t, J=11.8 Hz, 1H), 1.91-1.61 (m, 5H). MS (ESI) m/z 606 (M+H)$^+$. Expected mass from chemical formula C$_{26}$H$_{26}$Cl$_2$N$_6$O$_5$S: 605.49

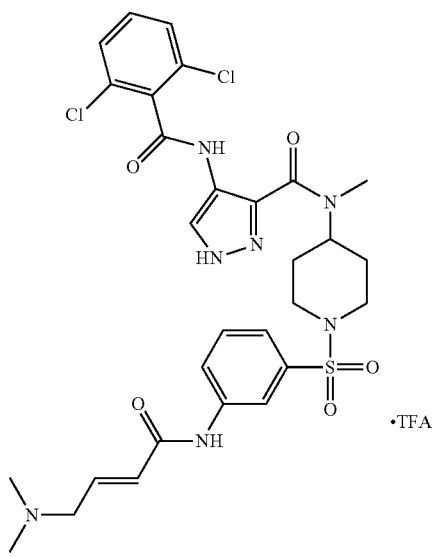 [SMILES: CN(C)C/C=C/C(=O)Nc1cccc(S(=O)(=O)N2CCC(N(C)C(=O)c3n[nH]cc3NC(=O)c3c(Cl)cccc3Cl)CC2)c1]

FMF-04-086-2

(E)-4-(2,6-dichlorobenzamido)-N-(1-((3-(4-(dimethylamino)but-2-enamido)phenyl)sulfonyl)piperidin-4-yl)-N-methyl-1H-pyrazole-3-carboxamide The compound was prepared according to method 1 (11 mg, 0.018 mmol) as a white powder. $^1$H NMR (500 MHz, DMSO-d$_6$) δ 13.25 (d, J=80.4 Hz, 1H), 10.72 (d, J=5.6 Hz, 1H), 10.39 (s, 1H), 8.32-8.15 (m, 2H), 7.91 (s, 1H), 7.62 (q, J=7.5 Hz, 1H), 7.57-7.42 (m, 4H), 6.84-6.73 (m, 1H), 6.44 (d, J=15.3 Hz, 1H), 4.54-4.14 (m, 2H), 3.88 (s, 2H), 3.76 (d, J=11.4 Hz, 2H), 3.20-3.04 (m, 3H), 2.81 (s, 2H), 2.74 (s, 6H), 2.44-2.35 (m, 1H), 2.21 (t, J=11.7 Hz, 1H), 1.91-1.63 (m, 5H). MS (ESI) m/z 663 (M+H)$^+$. Expected mass from chemical formula C$_{29}$H$_{33}$Cl$_2$N$_7$O$_5$S: 662.59

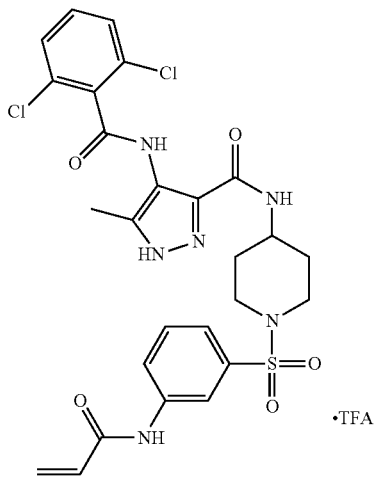 [SMILES: C=CC(=O)Nc1cccc(S(=O)(=O)N2CCC(NC(=O)c3n[nH]c(C)c3NC(=O)c3c(Cl)cccc3Cl)CC2)c1]

FMF-04-181-1

N-(1-((3-acrylamidophenyl)sulfonyl)piperidin-4-yl)-4-(2,6-dichlorobenzamido)-5-methyl-1H-pyrazole-3-carboxamide The compound was prepared according to method 1 (22 mg, 0.036 mmol) as a white powder. $^1$H NMR (500 MHz, DMSO-d$_6$) δ 10.52 (s, 1H), 10.00 (s, 1H), 8.15 (t, J=2.0 Hz, 1H), 7.98-7.93 (m, 1H), 7.85 (s, 1H), 7.60 (t, J=8.0 Hz, 1H), 7.56-7.51 (m, 2H), 7.47 (dd, J=9.1, 7.0 Hz, 1H), 7.43 (dt, J=7.9, 1.3 Hz, 1H), 6.44 (dd, J=17.0, 10.1 Hz, 1H), 6.32 (dd, J=17.0, 2.0 Hz, 1H), 5.82 (dd, J=10.0, 1.9 Hz, 1H), 3.78-3.67 (m, 1H), 3.61 (d, J=11.8 Hz, 2H), 2.43 (td, J=12.0, 2.6

Hz, 2H), 2.24 (s, 3H), 1.84 (d, J=12.2 Hz, 2H), 1.60 (dd, J=12.3, 8.8 Hz, 2H). MS (ESI) m/z 606 (M+H)⁺. Expected mass from chemical formula $C_{26}H_{26}Cl_2N_6O_5S$: 605.49

2H), 3.78-3.67 (m, 1H), 3.66-3.57 (m, 2H), 2.81 (s, 6H), 2.47-2.35 (m, 2H), 2.24 (s, 3H), 1.84 (d, J=12.4 Hz, 2H), 1.62 (d, J=12.5 Hz, 2H). MS (ESI) m/z 663 (M+H)⁺. Expected mass from chemical formula $C_{29}H_{33}Cl_2N_7O_5S$: 662.59

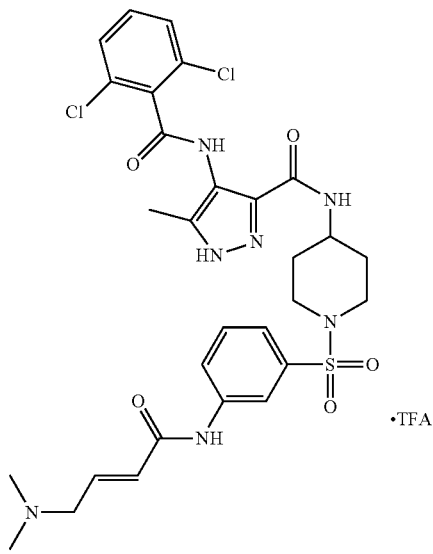 [SMILES: Cc1[nH]nc(C(=O)NC2CCN(S(=O)(=O)c3cccc(NC(=O)/C=C/CN(C)C)c3)CC2)c1NC(=O)c1c(Cl)cccc1Cl]

FMF-04-181-2

(E)-4-(2,6-dichlorobenzamido)-N-(1-((3-(4-(dimethylamino)but-2-enamido)phenyl)sulfonyl)piperidin-4-yl)-5-methyl-1H-pyrazole-3-carboxamide The compound was prepared according to method 1 (24 mg, 0.036 mmol) as a white powder. ¹H NMR (500 MHz, DMSO-d₆) δ 10.71 (s, 1H), 9.94 (d, J=42.1 Hz, 2H), 8.18 (t, J=2.0 Hz, 1H), 7.98-7.91 (m, 1H), 7.86 (s, 1H), 7.62 (t, J=8.0 Hz, 1H), 7.53 (d, J=7.3 Hz, 2H), 7.49 (s, 1H), 6.80 (dt, J=15.3, 7.2 Hz, 1H), 6.50-6.43 (m, 1H), 3.98 (d, J=7.0 Hz,

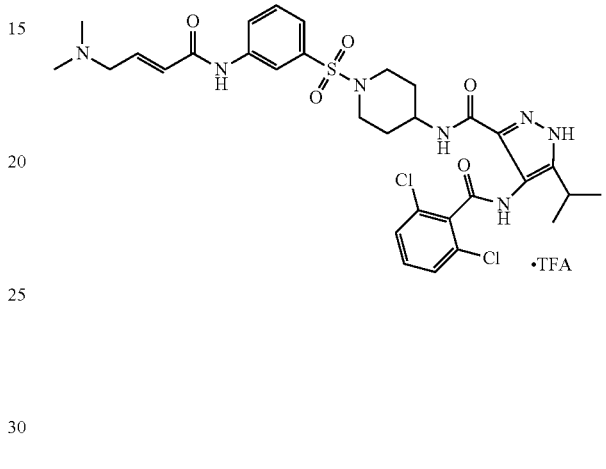

FMF-04-199-1

(E)-4-(2,6-dichlorobenzamido)-N-(1-((3-(4-(dimethylamino)but-2-enamido)phenyl)sulfonyl)piperidin-4-yl)-5-isopropyl-1H-pyrazole-3-carboxamide The compound was prepared according to method 1 (15 mg, 0.021 mmol) as a white powder. ¹H NMR (500 MHz, DMSO-d₆) δ 10.73 (s, 1H), 9.96 (d, J=43.3 Hz, 2H), 8.18 (t, J=2.0 Hz, 1H), 7.94 (dd, J=8.3, 2.1 Hz, 1H), 7.62 (t, J=8.0 Hz, 1H), 7.56-7.38 (m, 4H), 6.80 (dt, J=14.7, 7.2 Hz, 1H), 6.47 (dd, J=15.3, 1.5 Hz, 1H), 3.98 (d, J=7.1 Hz, 2H), 3.76-3.67 (m, 1H), 3.61 (dt, J=12.8, 3.8 Hz, 3H), 2.81 (s, 7H), 1.85 (d, J=12.4 Hz, 2H), 1.61 (d, J=12.4 Hz, 2H), 1.23 (d, J=7.1 Hz, 6H), 1.04 (d, J=6.1 Hz, 1H). MS (ESI) m/z 691 (M+H)⁺. Expected mass from chemical formula $C_{31}H_{37}Cl_2N_7O_5S$: 690.64

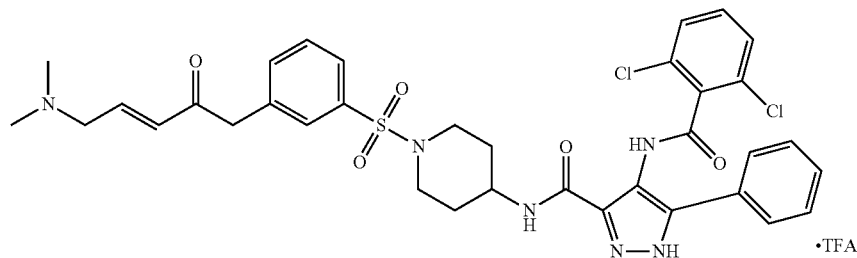 [SMILES: CN(C)C/C=C/C(=O)Cc1cccc(S(=O)(=O)N2CCC(NC(=O)c3n[nH]c(-c4ccccc4)c3NC(=O)c3c(Cl)cccc3Cl)CC2)c1]

FMF-04-197-1

(E)-4-(2,6-dichlorobenzamido)-N-(1-((3-(4-(dimethylamino)but-2-enamido)phenyl)sulfonyl)piperidin-4-yl)-5-phenyl-1H-pyrazole-3-carboxamide The compound was prepared according to method 1 (4 mg, 0.005 mmol) as a white powder. $^1$H NMR (500 MHz, DMSO-$d_6$) δ 10.74 (s, 1H), 8.19 (t, J=2.0 Hz, 1H), 7.94 (dd, J=8.2, 2.2 Hz, 1H), 7.73 (d, J=7.5 Hz, 2H), 7.62 (t, J=7.7 Hz, 1H), 7.50-7.42 (m, 7H), 6.81 (dt, J=14.8, 7.2 Hz, 1H), 6.49-6.42 (m, 1H), 3.98 (d, J=7.0 Hz, 1H), 3.74 (s, 2H), 3.61 (d, J=11.5 Hz, 2H), 2.81 (s, 6H), 1.89 (d, J=21.7 Hz, 2H), 1.64 (s, 2H). MS (ESI) m/z 725 (M+H)$^+$. Expected mass from chemical formula $C_{34}H_{35}Cl_2N_7O_5S$: 724.66

REFERENCES

1. Patricelli, M. P. et al. Functional interrogation of the kinome using nucleotide acyl phosphates. *Biochemistry* 46, 350-358 (2007).
2. Dorde, M. & Galas, S. The cyclin-dependent protein kinases and the control of cell division. *FASEB J.* 8, 1114-1121 (1994).
3. Patricelli, M. P. et al. In situ kinase profiling reveals functionally relevant properties of native kinases. *Chem. Biol.* 18, 699-710 (2011).
4. Nomanbhoy, T. K. et al. Chemoproteomic evaluation of target engagement by the cyclin-dependent kinase 4 and 6 inhibitor Palbociclib correlates with cancer cell response. *Biochemistry* 55, 5434-5441 (2016).
5. Zhang T, et al. Discovery of potent and selective covalent inhibitors of JNK. *Chemistry & biology* 19, 140-154 (2012).
6. Zhang Z, Marshall AGA. Universal algorithm for fast and automated charge state deconvolution of electrospray mass-to-charge ratio spectra. *Journal of the American Society for Mass Spectrometry* 9, 225-233 (1998).
7. Gao Y, Zhang T, Terai H, Ficarro S B, Kwiatkowski N, Hao M F, Sharma B, Christensen C L, Chipumuro E, Wong K K, Marto J A, Hammerman P S, Gray N S, George R E. Overcoming Resistance to the THZ Series of Covalent Transcriptional CDK Inhibitors. *Cell Chem Biol* (2017).
8. Askenazi M, Parikh J R, Marto J A. mzAPI: a new strategy for efficiently sharing mass spectrometry data. *Nature methods* 6, 240-241 (2009).
9. Parikh J R, Askenazi M, Ficarro S B, Cashorali T, Webber J T, Blank N C, Zhang Y, Marto J A. multiplierz: an extensible API based desktop environment for proteomics data analysis. *BMC Bioinformatics* (2009).
10. Zheng, L., Zhou, Z. & He, Z. Knockdown of PFTK1 inhibits tumor cell proliferation, invasion and epithelial-to-mesenchymal transition in pancreatic cancer. *Int J Clin Exp Pathol* 8, 14005-12 (2015).
11. Pang E Y, Bai A H, To K-F F, et al. Identification of PFTAIRE protein kinase 1, a novel cell division cycle-2 related gene, in the motile phenotype of hepatocellular carcinoma cells. Hepatology. 2007; 46(2):436-45.
12. Sun, T., Co, N. N. & Wong, N. PFTK1 interacts with cyclin Y to activate non-canonical Wnt signaling in hepatocellular carcinoma. *Biochem. Biophys. Res. Commun.* 449, 163-8 (2014).
13. Yang, L. et al. PFTK1 Promotes Gastric Cancer Progression by Regulating Proliferation, Migration and Invasion. *PLoS ONE* 10, e0140451 (2015).
14. Zhu, J., Liu, C., Liu, F., Wang, Y. & Zhu, M. Knockdown of PFTAIRE Protein Kinase 1 (PFTK1) Inhibits Proliferation, Invasion, and EMT in Colon Cancer Cells. *Oncol. Res.* 24, 137-44 (2016).
15. Mao Y, Jia Y, Zhu H, et al. High expression of PFTK1 in cancer cells predicts poor prognosis in colorectal cancer. Mol Med Rep. 2017.
16. Liu, M.-H. H., Shi, S.-M. M., Li, K. & Chen, E.-Q. Q. Knockdown of PFTK1 Expression by RNAi Inhibits the Proliferation and Invasion of Human Non-Small Lung Adenocarcinoma Cells. *Oncol. Res.* 24, 181-7 (2016).
17. Fan, S. et al. Knockdown of PFTK1 Inhibits the Migration of Glioma Cells. *J. Mol. Neurosci.* 57, 257-64 (2015).
18. Gu, X. et al. Upregulated PFTK1 promotes tumor cell proliferation, migration, and invasion in breast cancer. *Med. Oncol.* 32, 195 (2015).
19. Ou-Yang, J., Huang, L.-H. H. & Sun, X.-X. X. Cyclin-Dependent Kinase 14 Promotes Cell Proliferation, Migration and Invasion in Ovarian Cancer by Inhibiting Wnt Signaling Pathway. Gynecol. Obstet. Invest. (2016)
20. Zhang W, Liu R, Tang C, et al. PFTK1 regulates cell proliferation, migration and invasion in epithelial ovarian cancer. Int J Biol Macromol. 2016; 85:405-416.
21. Liu H, Shi H, Fan Q, Sun X. Cyclin Y regulates the proliferation, migration, and invasion of ovarian cancer cells via Wnt signaling pathway. Tumour Biol. 2016.
22. Liu M-H H, Shi S-M M, Li K, Chen E-Q Q. Knockdown of PFTK1 Expression by RNAi Inhibits the Proliferation and Invasion of Human Non-Small Lung Adenocarcinoma Cells. Oncol Res. 2016; 24(3):181-7. doi:10.3727/096504016X14635761799038.
23. Leung W K, Ching A K K, Chan A W, et al. A novel interplay between oncogenic PFTK1 protein kinase and tumor suppressor TAGLN2 in the control of liver cancer cell motility. Oncogene. 2011; 30(44):4464-75
24. Chaput et al., Potential role of PCTAIRE-2, PCTAIRE-3 and P-Histone $H_4$ in amyloid precursor protein-dependent Alzheimer pathology. Oncotarget. 2016
25. Zi Z et al. CCNYL1, but Not CCNY, Cooperates with CDK16 to Regulate Spermatogenesis in Mouse. pLoS Genet. 2015.
26. Park et al., ALS2CR7 (CDK15) attenuates TRAIL induced apoptosis by inducing phosphorylation of survivin Thr34. Biochemical and Biophysical Research Communications. 2014.
27. Duan C, Liu Y, Lu L, et al. CDK14 Contributes to Reactive Gliosis via Interaction with Cyclin Y in Rat Model of Spinal Cord Injury. J Mol Neurosci. 2015. doi:10.1007/s12031-015-0639-x.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or all of the group members are present in, employed in, or otherwise relevant to a given product or process.

Furthermore, the disclosure encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the disclosure, or aspects described herein, is/are referred to as comprising particular elements and/or features, certain embodiments described herein or aspects described herein consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments described herein, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present disclosure that falls within the prior art may be explicitly excluded from any one or more of the claims. Because such embodiments are deemed to be known to one of ordinary skill in the art, they may be excluded even if the exclusion is not set forth explicitly herein. Any particular embodiment described herein can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present disclosure, as defined in the following claims.

What is claimed is:

1. A compound of Formula (I):

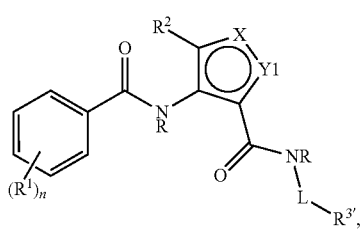

or a pharmaceutically acceptable salt, tautomer, stereoisomer, or isotopically labeled compound thereof, wherein:

each instance of $R^1$ is independently selected from the group consisting of is halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, $-OR^{D1}$, $-N(R^{D1a})_2$, and $-SR^{D1}$, wherein each instance of $R^{D1}$ is independently selected from hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, and a sulfur protecting group when attached to a sulfur atom;

each occurrence of $R^{D1a}$ is independently selected from the group consisting of hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, and a nitrogen protecting group; or two instances of $R^{D1}$a are taken together with their intervening atoms to form a substituted or unsubstituted heterocyclic or substituted or unsubstituted heteroaryl ring;

$R^2$ is hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, or optionally substituted heteroaryl;

each instance of R is independently selected from the group consisting of hydrogen, optionally substituted alkyl, and a nitrogen protecting group;

$R^x$ is selected from the group consisting of hydrogen, optionally substituted alkyl, and a nitrogen protecting group;

n is 0, 1, 2, 3, 4, or 5;

X is N, $-NR^x$, S, or O, as valency permits;

Y1 is N, $-NR^x$, S, or O, as valency permits;

L is an optionally substituted $C_{1-6}$ hydrocarbon chain, optionally wherein one or more carbon units of the hydrocarbon chain are independently replaced with $-C(=O)-$, $-O-$, $-S-$, $-S(=O)O-$, $-NR(C=O)-$, $-NR-$, optionally substituted carbocyclylene, optionally substituted heterocyclylene, optionally substituted arylene, or optionally substituted heteroarylene; or L is of the formula:

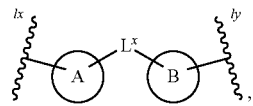

wherein:
Ring A is optionally substituted heterocyclylene, optionally substituted arylene, or optionally substituted heteroarylene;

Ring B is optionally substituted heterocyclylene or optionally substituted arylene;

L$^x$ is a bond, —CH$_2$—, —C(=O)—, —S(=O)$_2$, or —NH(C=O)—; and lx indicates the point of attachment to —NR—, and ly indicates the point of attachment to R$^3$;

R$^3$ is of formula:

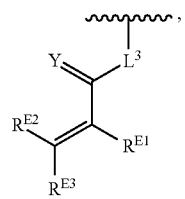

(i-1)

wherein:

L$^3$ is a bond or an optionally substituted C$_{1-4}$ hydrocarbon chain, optionally wherein one or more carbon units of the hydrocarbon chain are independently replaced with —C(=O)—, —S—, —NR$^{L3a}$—, —NR$^{L3a}$C(=O)—, —C(=O)NR$^{L3a}$—, SC(=O)—, —C(=O)S—, —OC(=O)—, —C(=O)O—, —NR$^{L3a}$C(=S)—, —C(=S)NR$^{L3a}$—, trans-CR$^{L3b}$=CR$^{L3b}$—, cis-CR$^{L3b}$=CR$^{L3b}$—, —S(=O)—, —S(=O)O—, —OS(=O)—, —S(=O)NR$^{L3a}$—, —NR$^{L3a}$S(=O)—, —S(=O)$_2$—, —S(=O)$_2$O—, —OS(=O)$_2$—, —S(=O)$_2$NR$^{L3a}$—, or —NR$^{L3a}$S(=O)$_2$—, wherein each instance of R$^{L3a}$ is independently hydrogen, substituted or unsubstituted C$_{1-6}$ alkyl, or a nitrogen protecting group, and wherein each occurrence of R$^{L3b}$ is independently hydrogen, halogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two R$^{L3b}$ groups are joined to form an optionally substituted carbocyclic or optionally substituted heterocyclic ring;

each of R$^{E1}$, R$^{E2}$, and R$^{E3}$ is independently hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —CH$_2$OR$^{EE}$, —CH$_2$N(R$^{EE}$)$_2$, —CH$_2$SR$^{EE}$, —OR$^{EE}$—N(R$^{EE}$)$_2$, —Si(R$^{EE}$)$_3$, or —SR$^{EE}$, wherein each instance of R$^E$E is independently hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, or optionally substituted heteroaryl, or two R$^{EE}$ groups are joined to form an optionally substituted heterocyclic ring; or R$^{E1}$ and R$^{E3}$, or R$^{E2}$ and R$^{E3}$, or R$^{E1}$ and R$^{E2}$ are joined to form an optionally substituted carbocyclic or optionally substituted heterocyclic ring; and each instance of Y is independently O, S, or NR$^{E7}$, wherein R$^{E7}$ is hydrogen, substituted or unsubstituted C$_{1-6}$ alkyl, or a nitrogen protecting group.

2. The compound of claim 1, or a pharmaceutically acceptable salt, tautomer, stereoisomer, or isotopically labeled compound thereof, wherein L is optionally substituted 6-membered heterocyclylene or optionally substituted arylene.

3. The compound of claim 1, or a pharmaceutically acceptable salt, tautomer, stereoisomer, or isotopically labeled compound thereof, wherein L is of the formula:

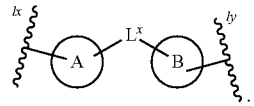

4. The compound of claim 1, or a pharmaceutically acceptable salt, tautomer, stereoisomer, or isotopically labeled compound thereof, wherein L is of the formula:

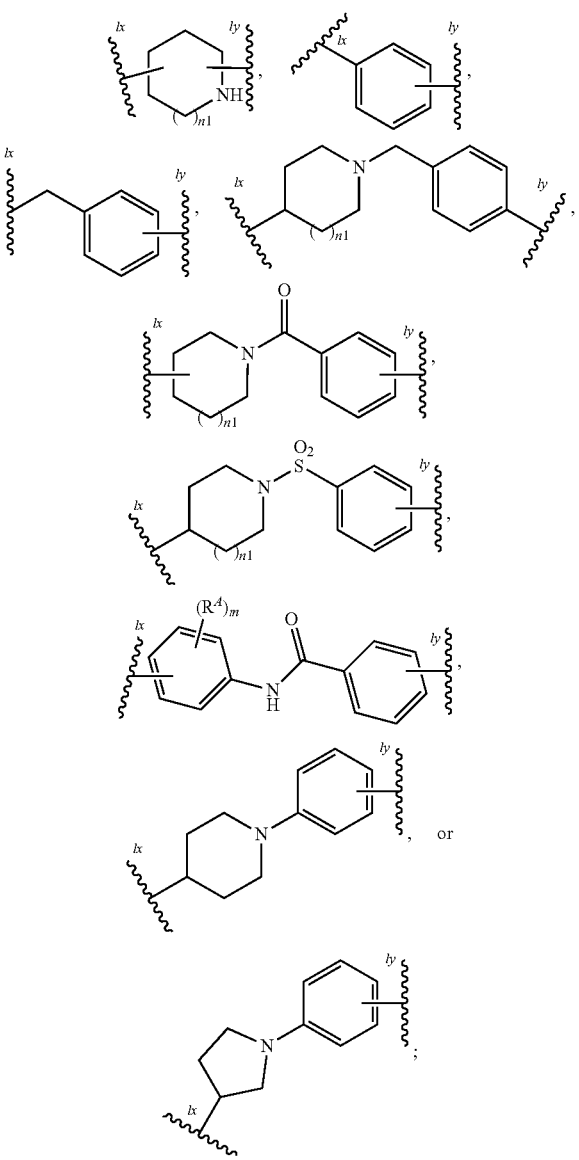

each instance of R$^A$ is independently halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^{D1}$, —N(R$^{D1a}$)$_2$, or —SR$^{D1}$;

n1 is 0 or 1;

m is 0, 1, 2, 3, or 4;

1× indicates the point of attachment to —NR—; and ly indicates the point of attachment to R$^3$.

5. The compound of claim 1, or a pharmaceutically acceptable salt, tautomer, stereoisomer, or isotopically labeled compound thereof, wherein L is of the formula:

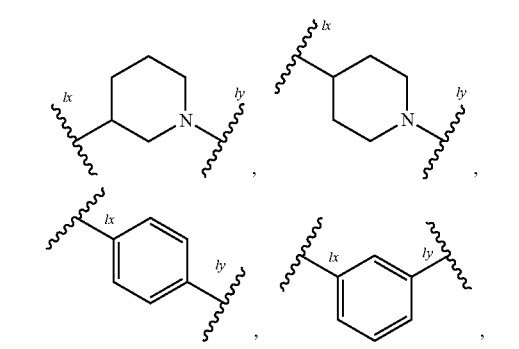

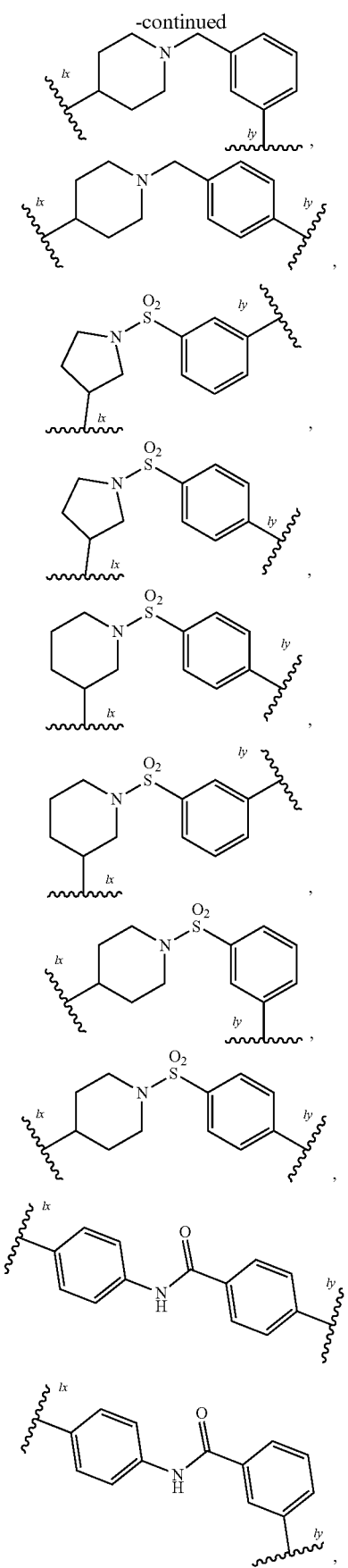

-continued

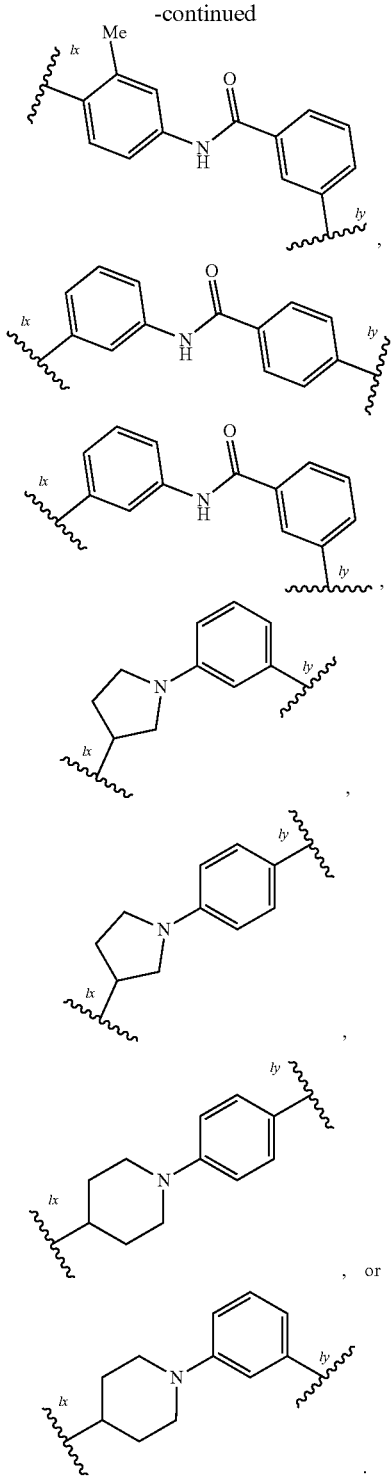

1x indicates the point of attachment to —NR—; and 1y indicates the point of attachment to $R^3$.

6. The compound of claim 1, or a pharmaceutically acceptable salt, tautomer, stereoisomer, or isotopically labeled compound thereof, wherein at least one instance of $R^1$ is halogen or —$OR^{D1}$; and each instance of $R^{D1}$ is independently selected from hydrogen or optionally substituted alkyl.

7. The compound of claim 1, or a pharmaceutically acceptable salt, tautomer, stereoisomer, or isotopically labeled compound thereof, wherein at least one instance of R is hydrogen.

8. The compound of claim 1, or a pharmaceutically acceptable salt, tautomer, stereoisomer, or isotopically labeled compound thereof, wherein n is 2 and both instances of R are hydrogen.

9. The compound of claim 1, or a pharmaceutically acceptable salt, tautomer, stereoisomer, or isotopically labeled compound thereof, wherein $R^2$ is hydrogen.

10. The compound of claim 1, or a pharmaceutically acceptable salt, tautomer, stereoisomer, or isotopically labeled compound thereof, wherein $R^2$ is optionally substituted $C_{1-6}$ alkyl or optionally substituted aryl.

11. The compound of claim 1, or a pharmaceutically acceptable salt, tautomer, stereoisomer, or isotopically labeled compound thereof, wherein:

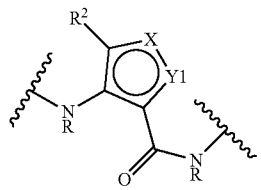

is of the formula:

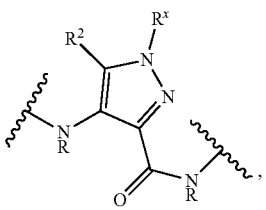

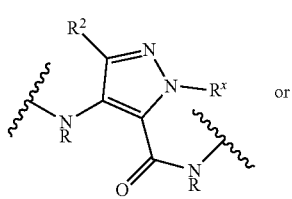
or

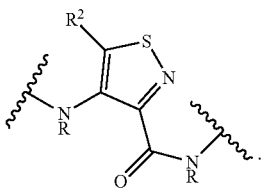

12. The compound of claim 1, or a pharmaceutically acceptable salt, tautomer, stereoisomer, or isotopically labeled compound thereof, wherein:

is of the formula:

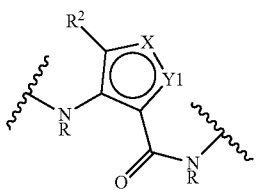

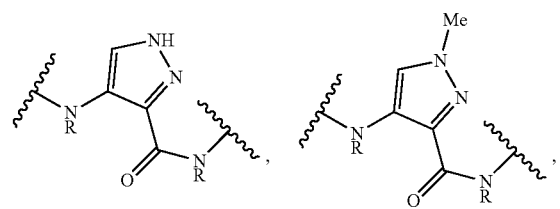

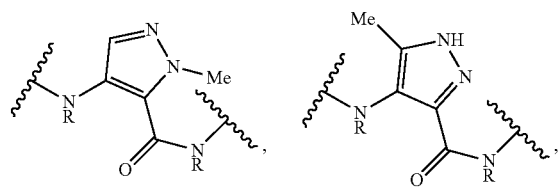

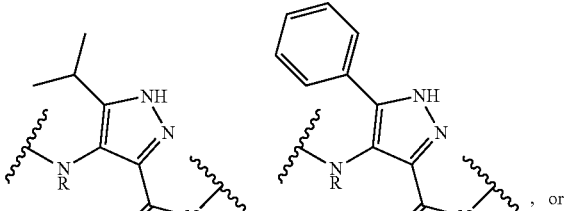

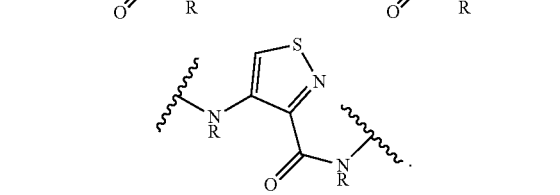

13. The compound of claim 1, or a pharmaceutically acceptable salt, tautomer, stereoisomer, or isotopically labeled compound thereof, wherein R³ is of formula:

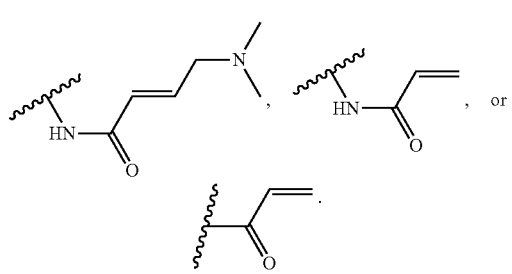

14. The compound of claim 1, or a pharmaceutically acceptable salt, tautomer, stereoisomer, or isotopically labeled compound thereof, wherein:

is of the formula:

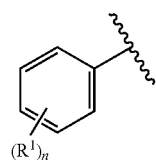

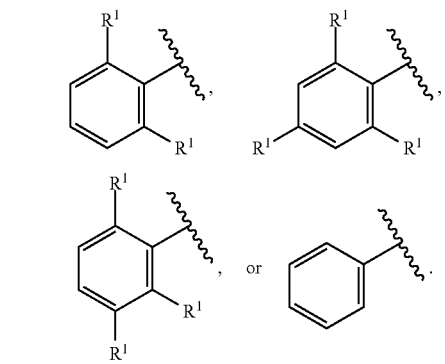

15. The compound of claim 1, wherein the compound is of formula:

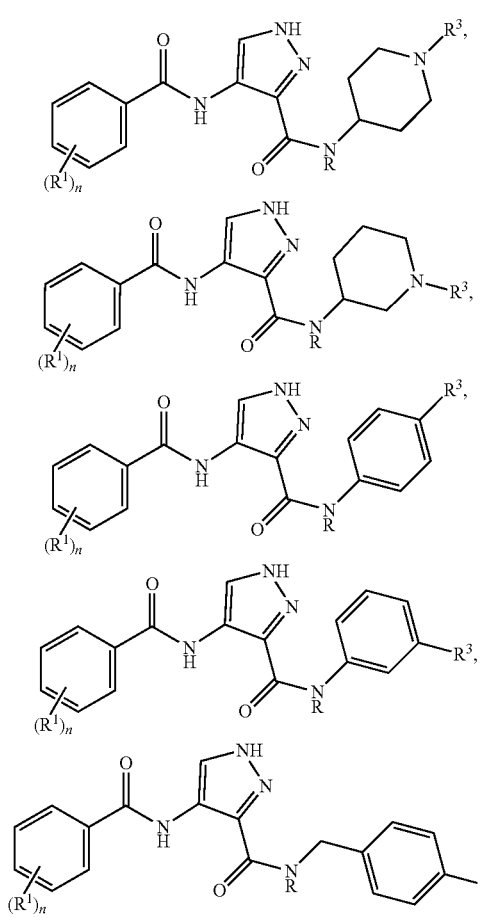

-continued
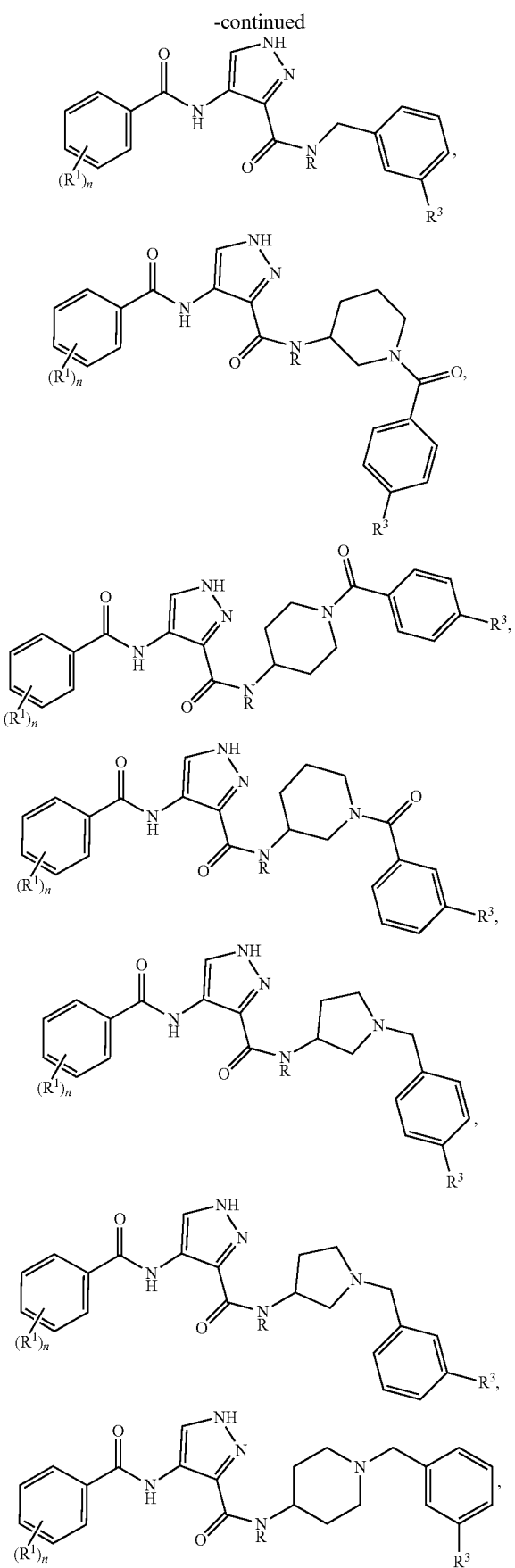
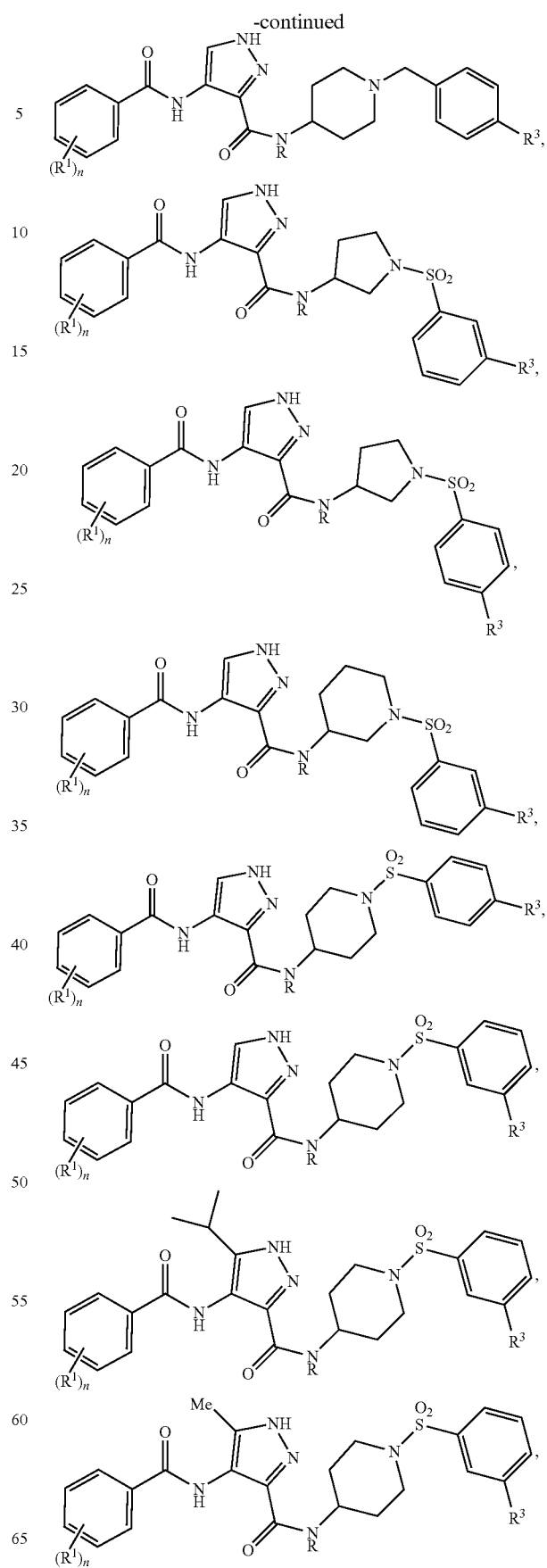

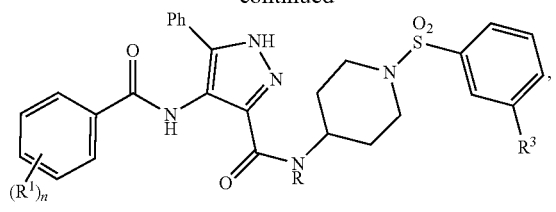
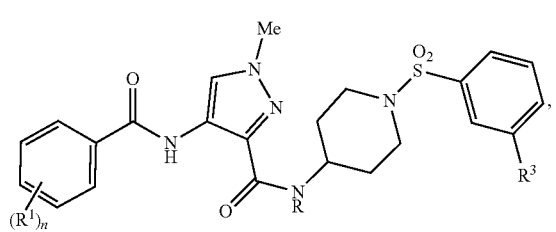
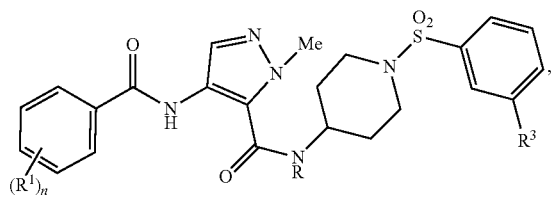
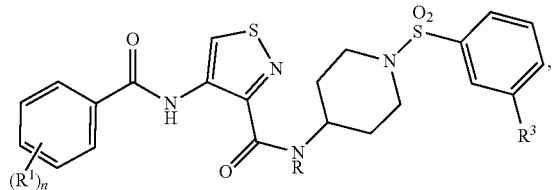
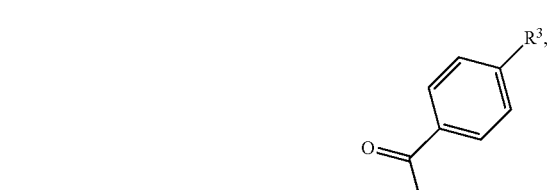
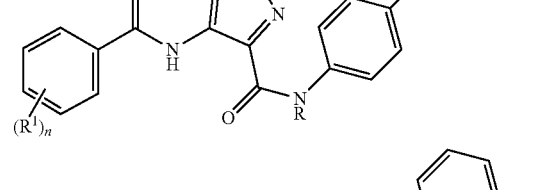
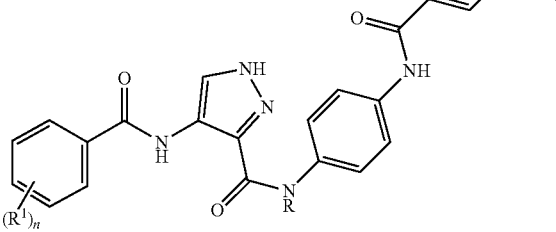
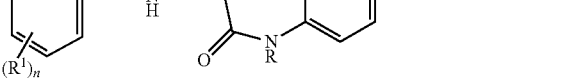
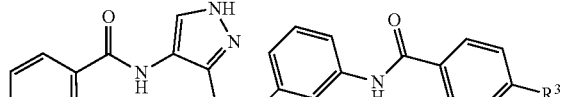
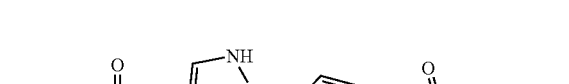
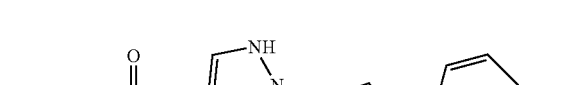
or a pharmaceutically acceptable salt, tautomer, stereoisomer, or isotopically labeled compound thereof.
16. The compound of claim 1, wherein the compound is of formula:

345 346
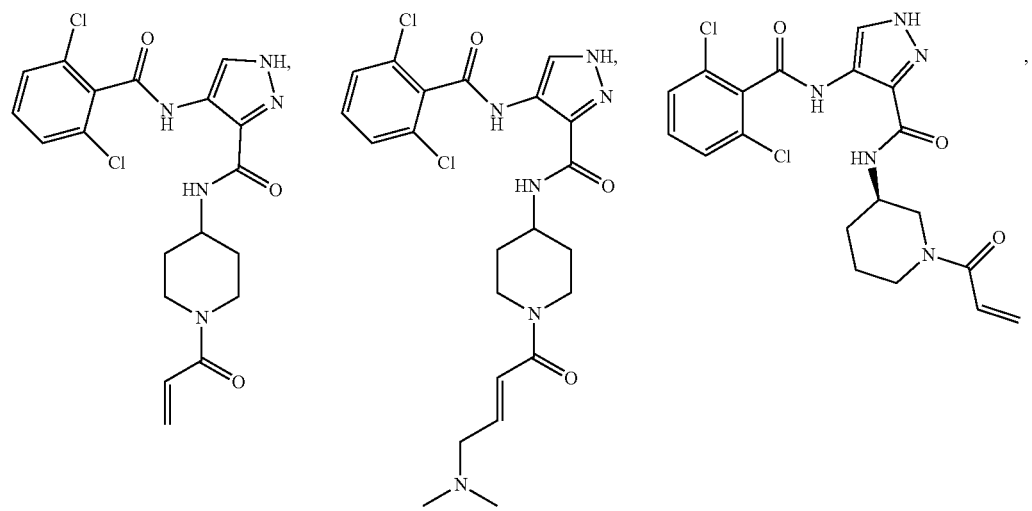
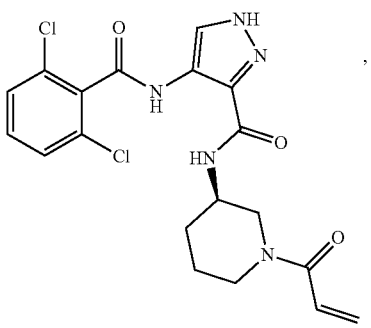
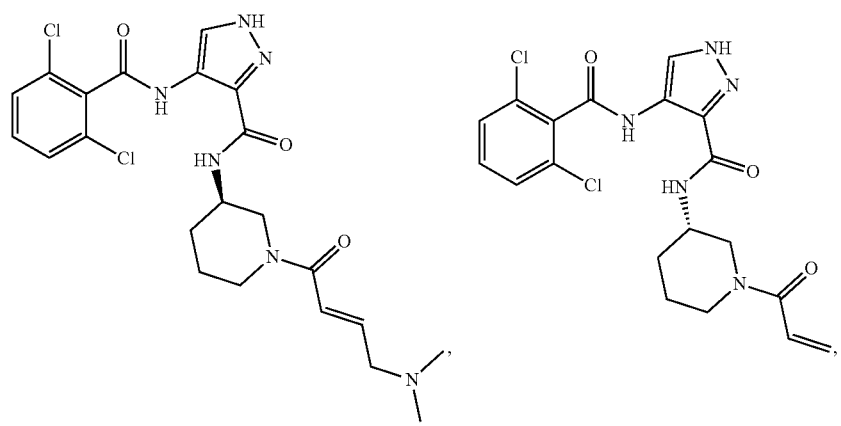
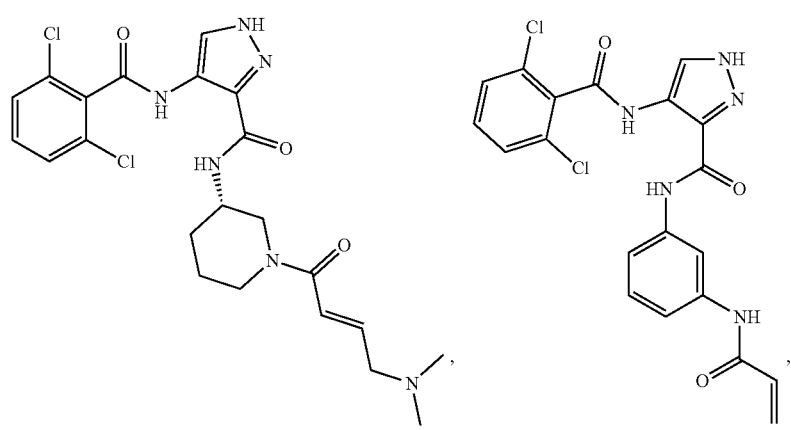

347
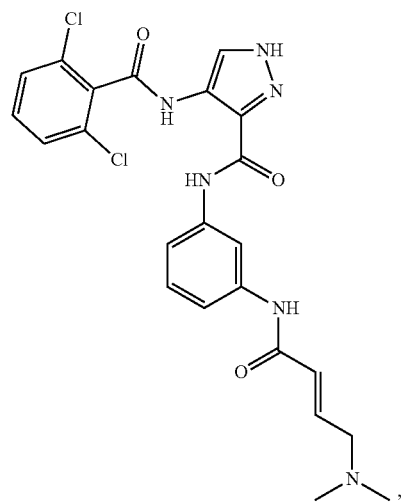
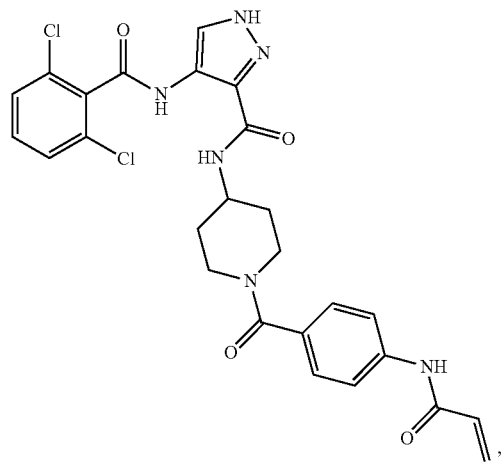
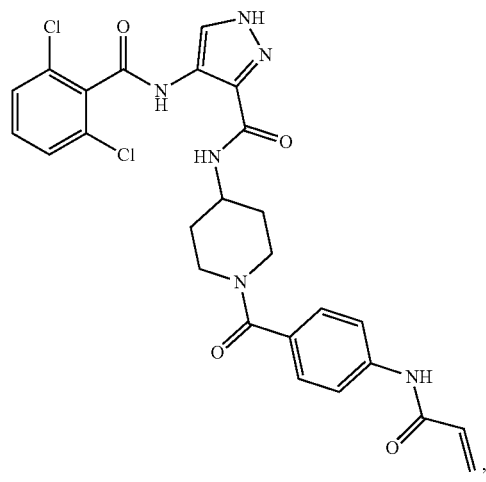
-continued
348
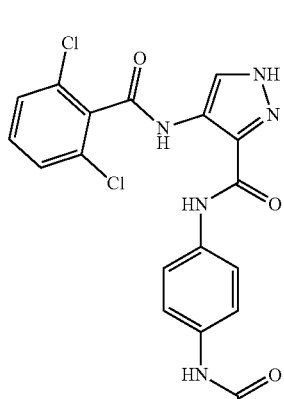
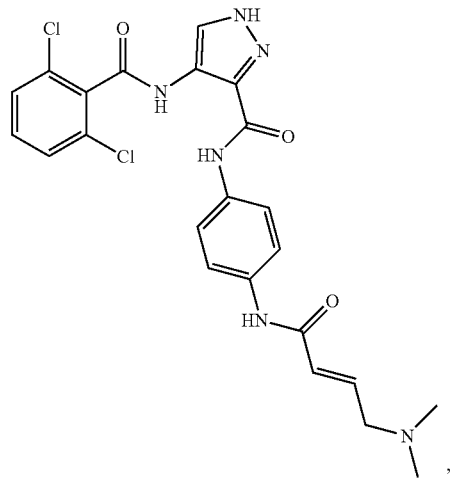
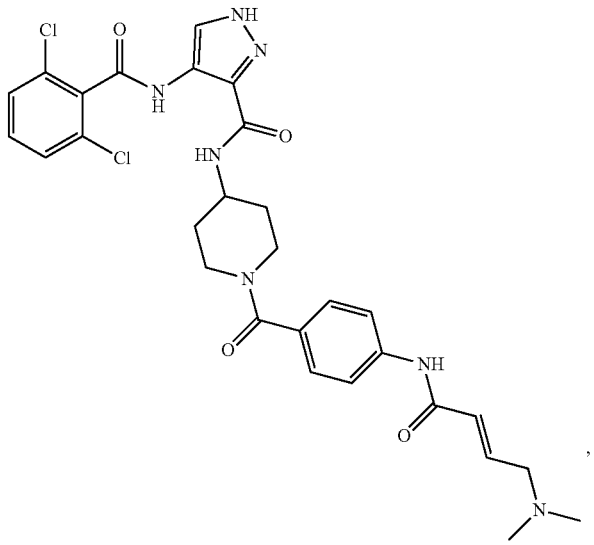
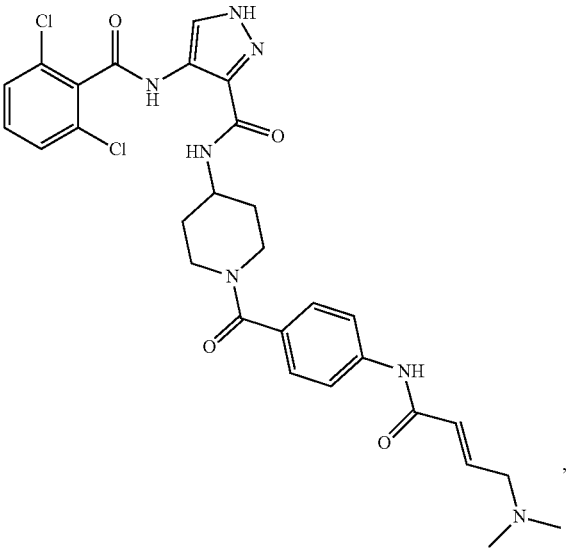

349
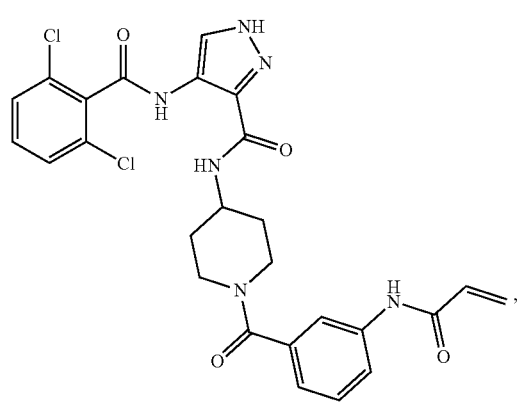
350
-continued
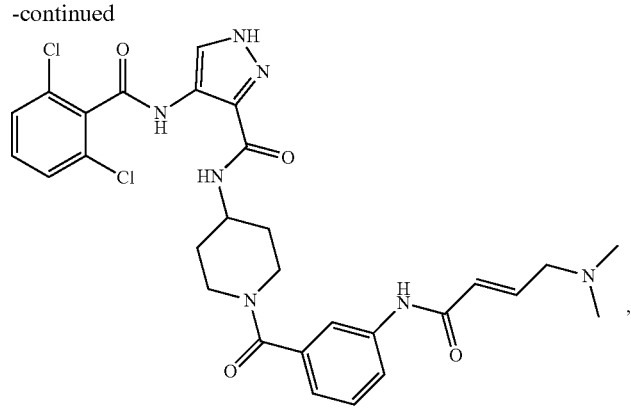
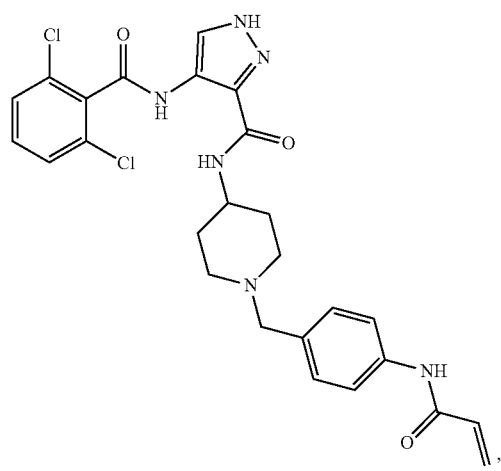
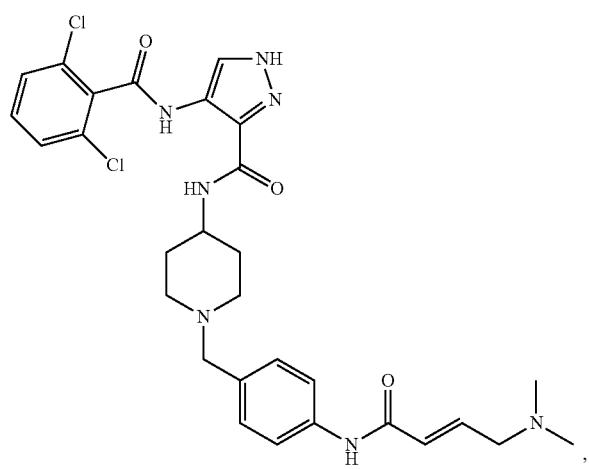
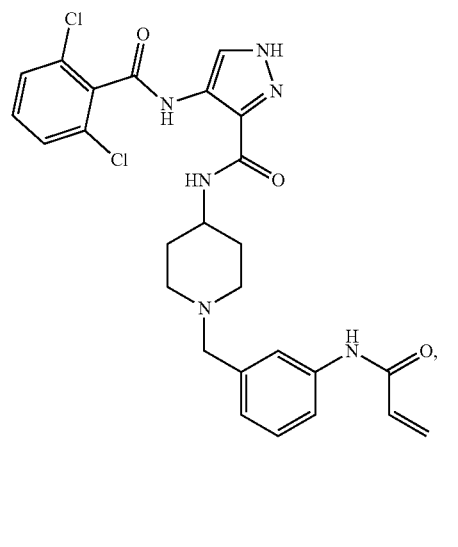
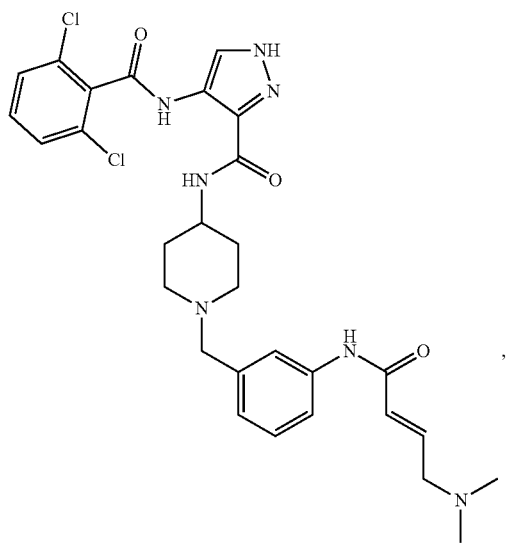

351
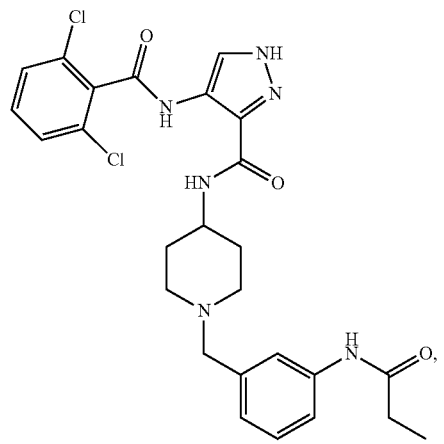
352
-continued
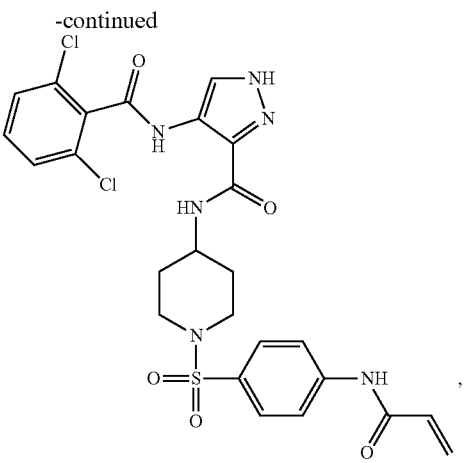
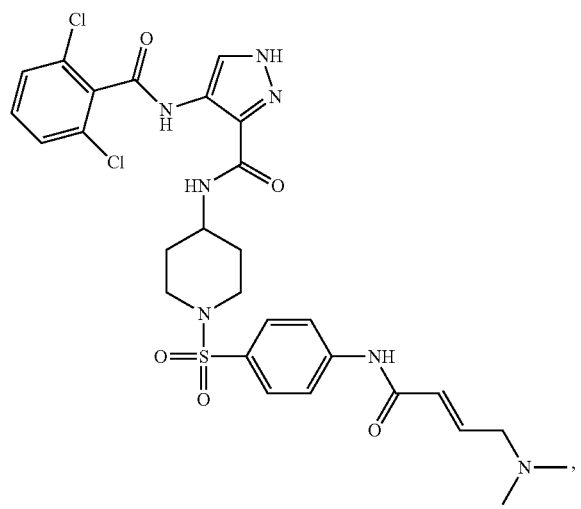
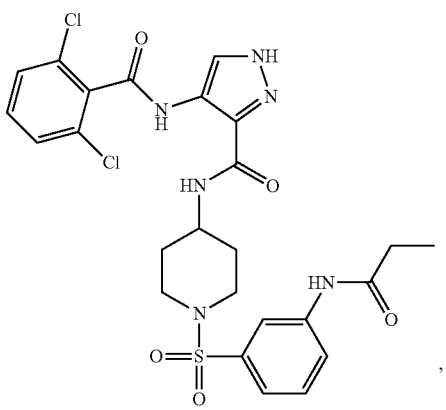
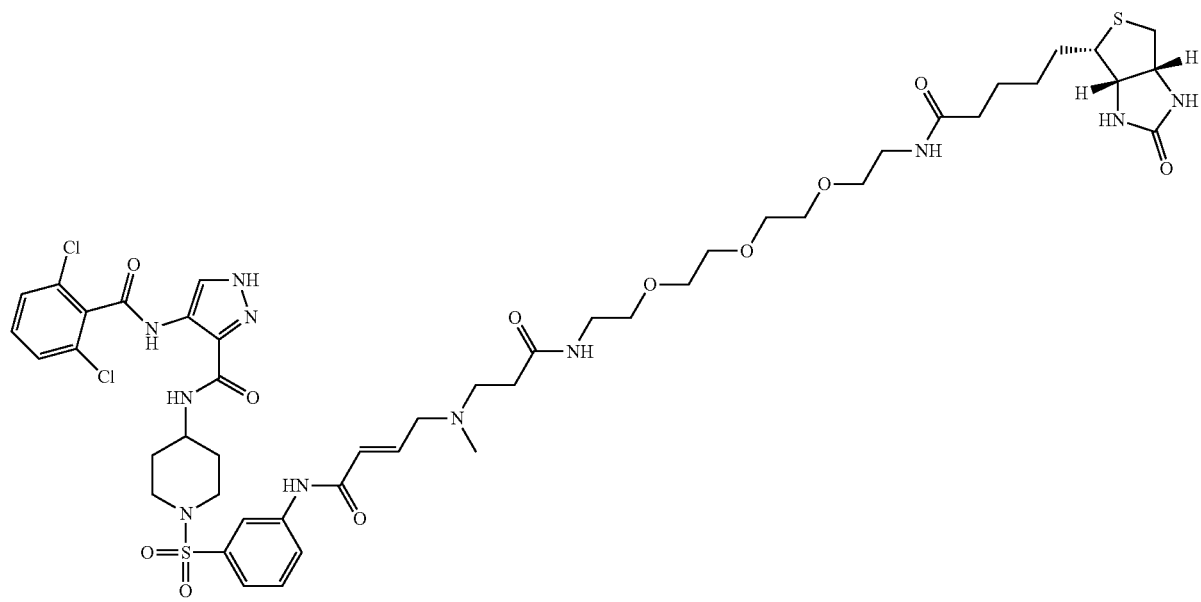

353
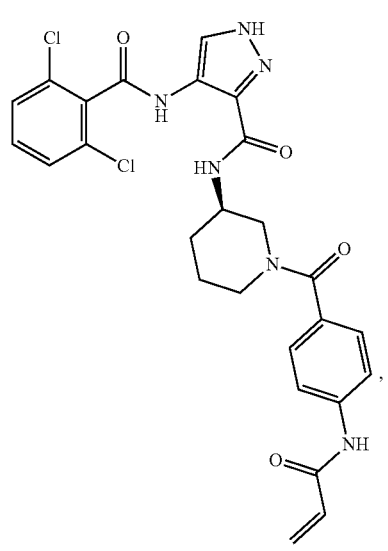
354
-continued
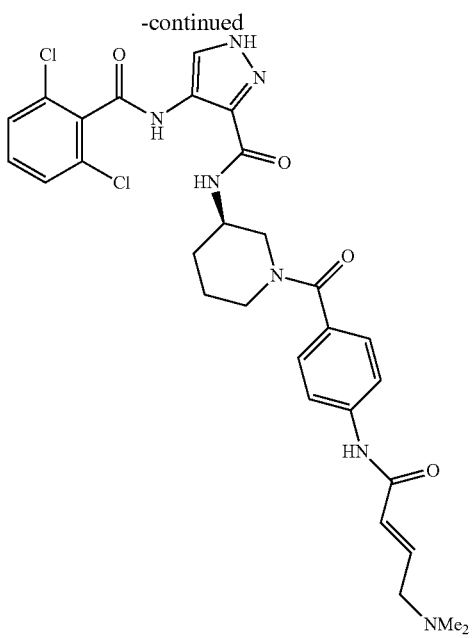
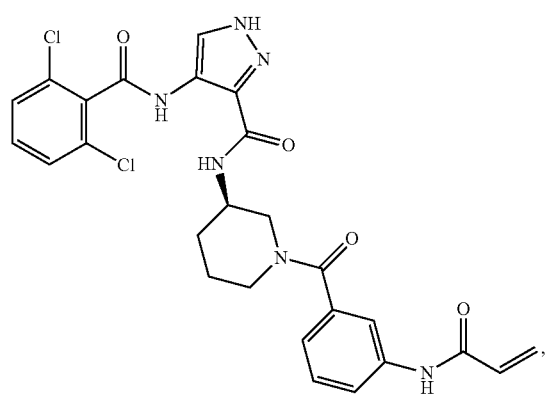
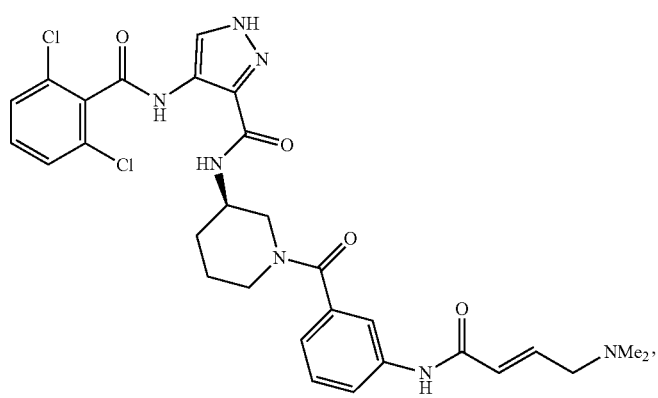
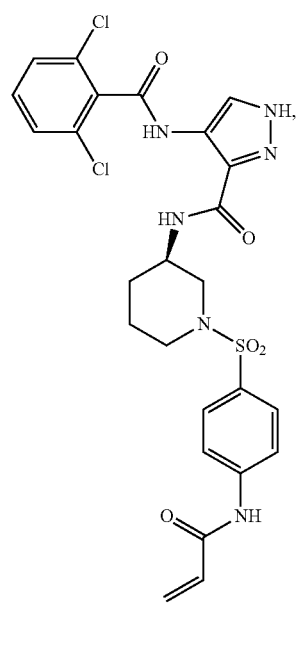
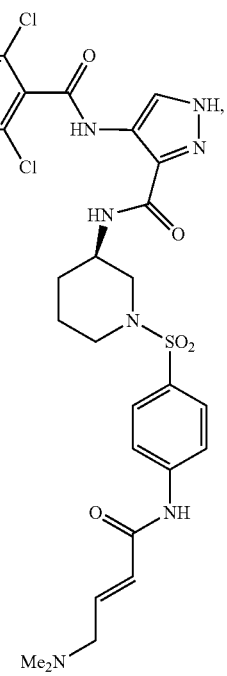
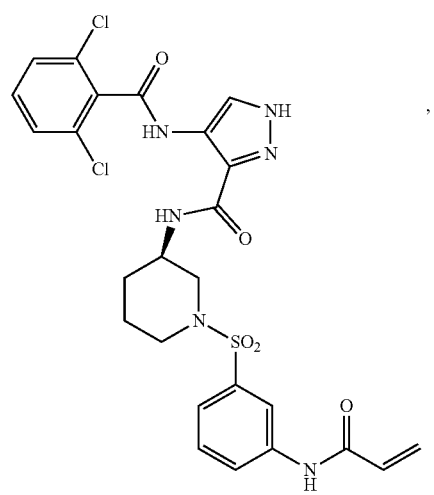

355
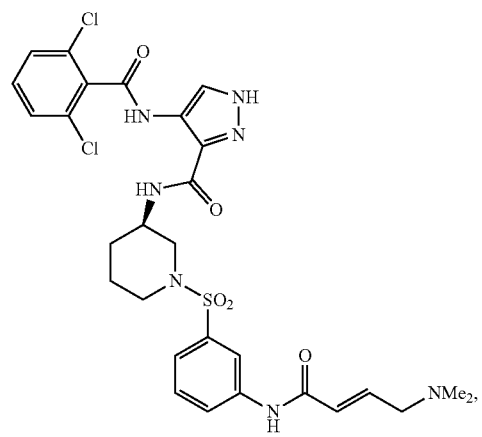
-continued
356
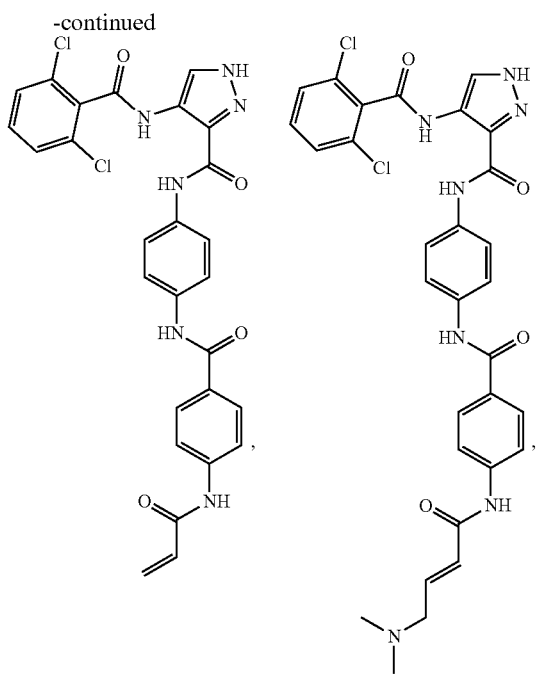
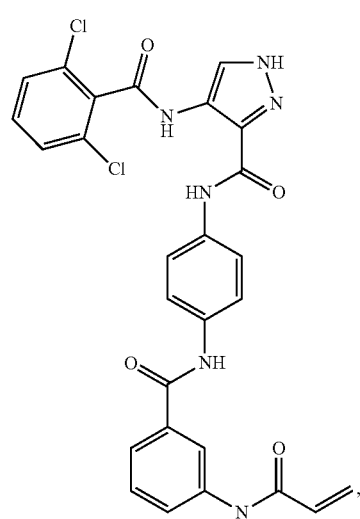
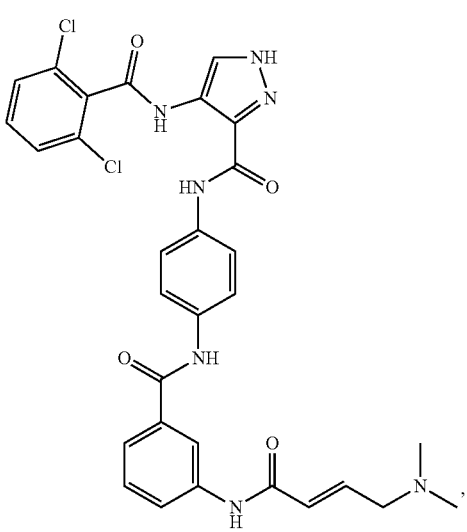
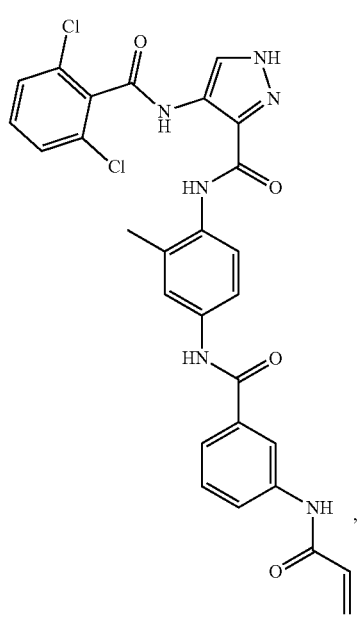

-continued
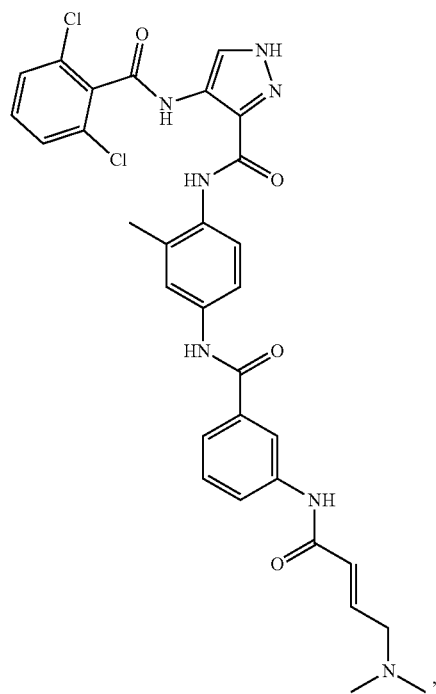
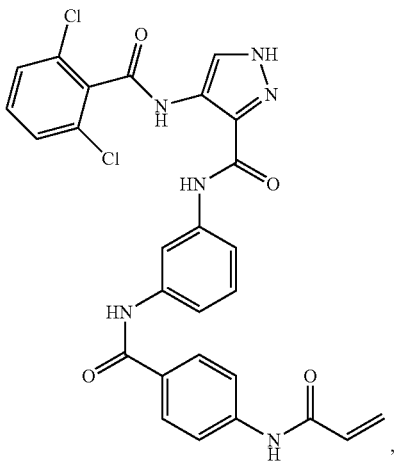
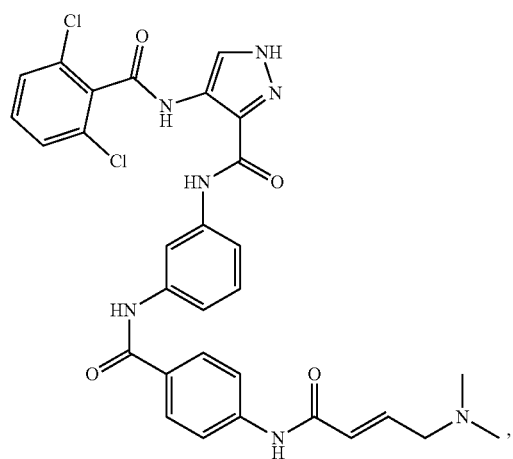
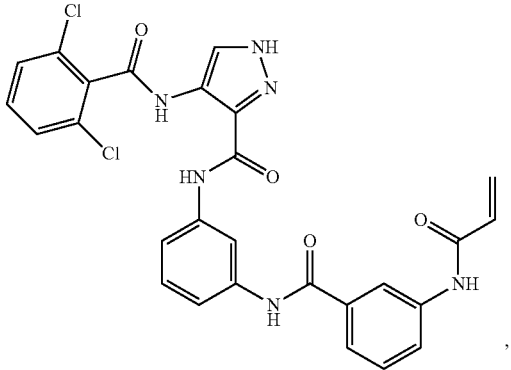
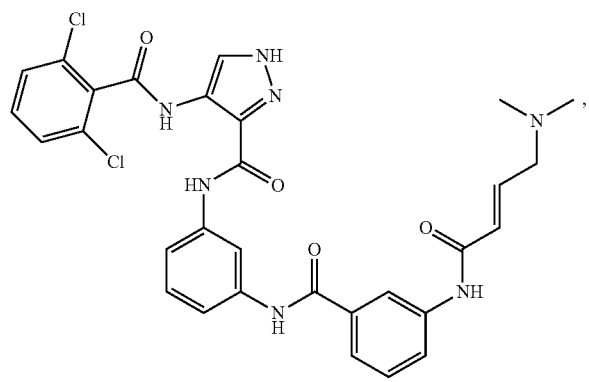
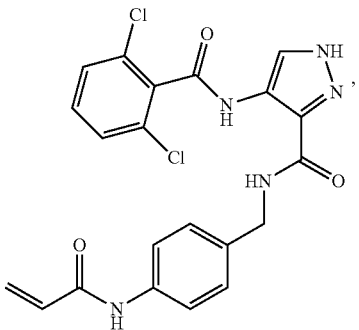

-continued
359
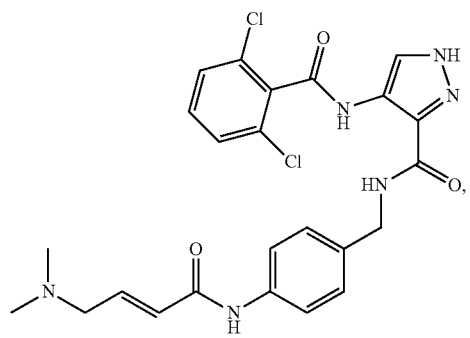
360
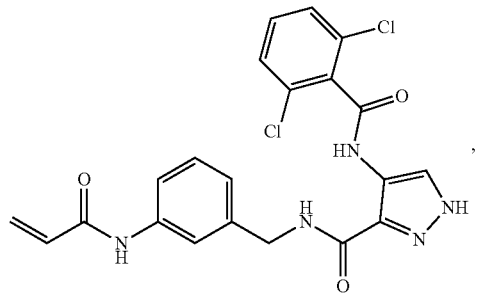
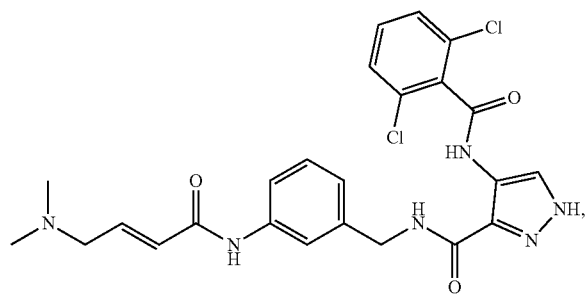
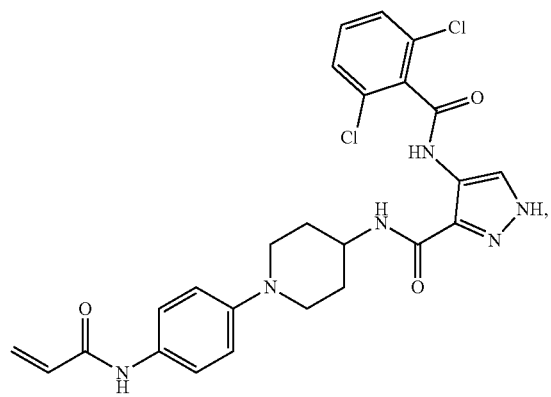
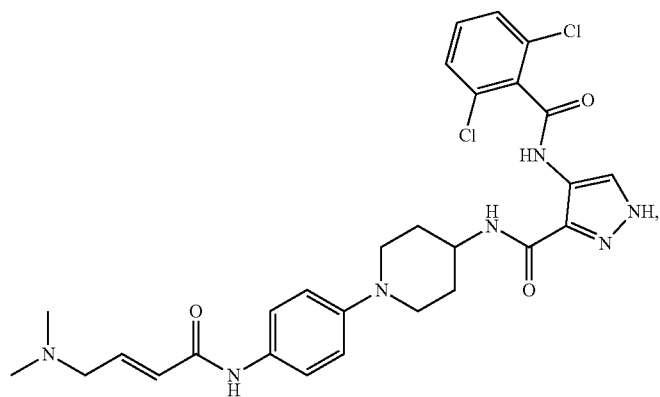
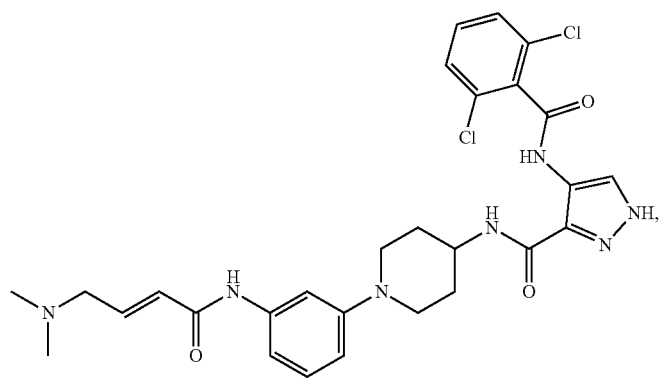

-continued
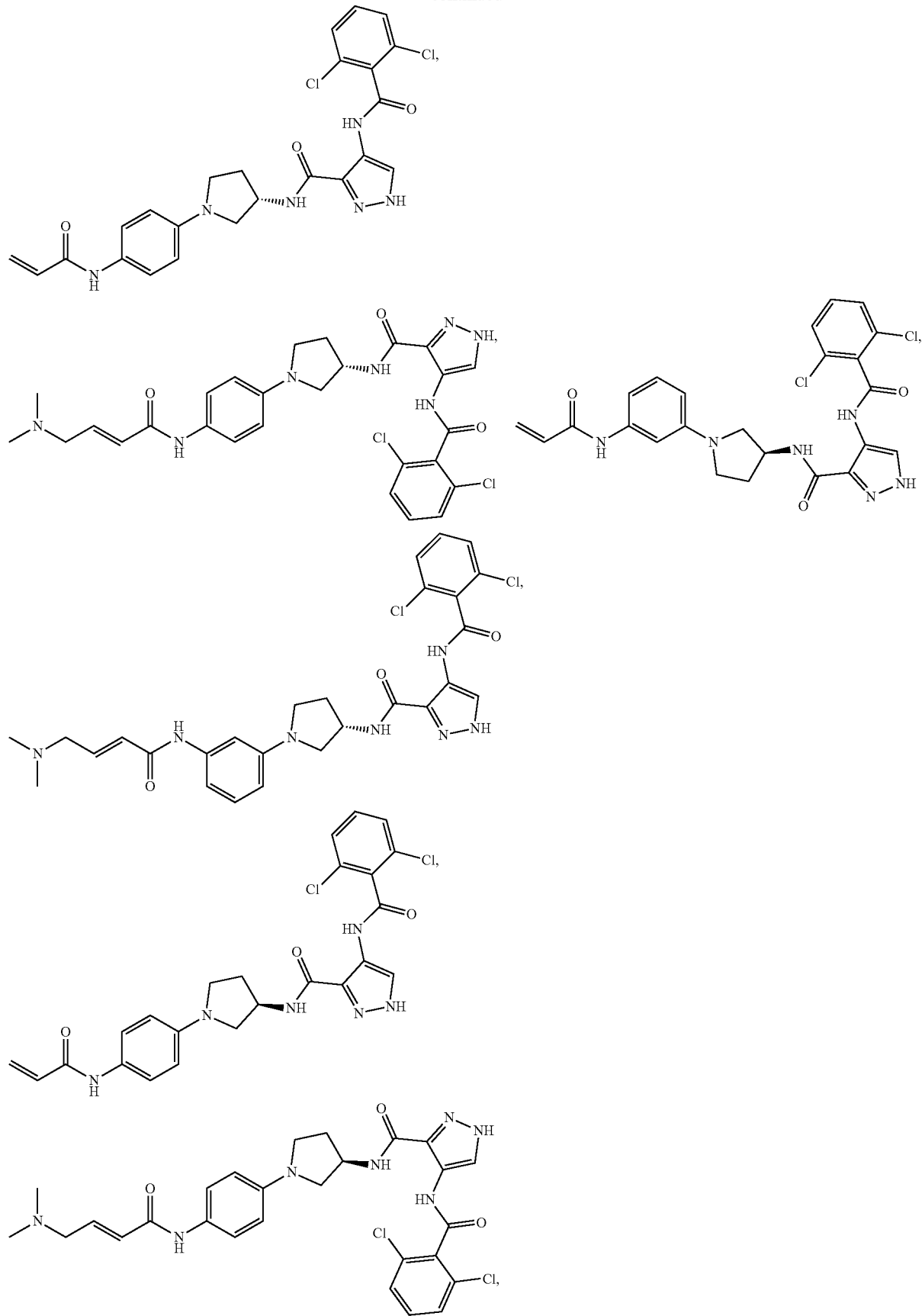

-continued
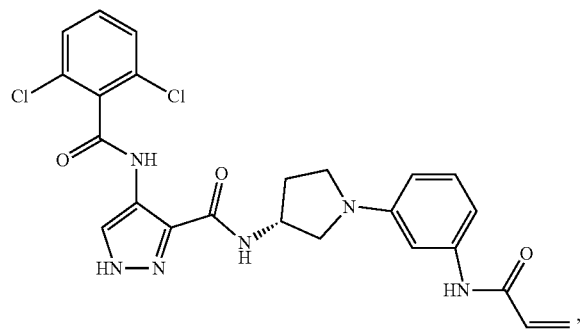
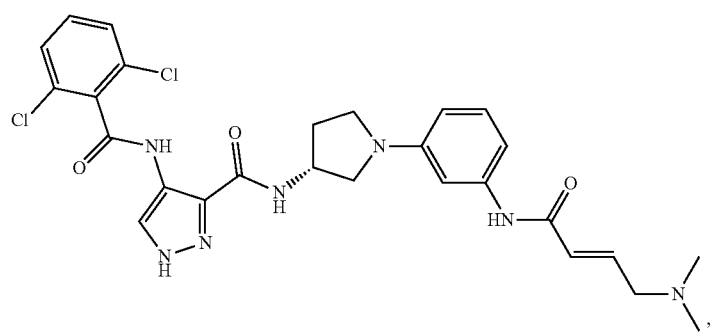
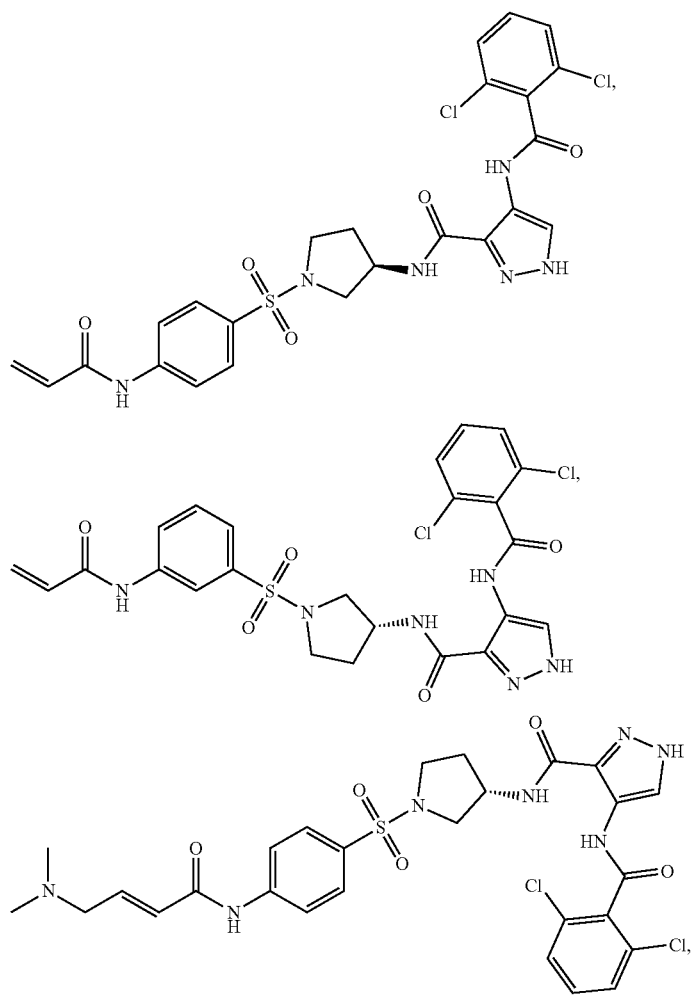

-continued
365
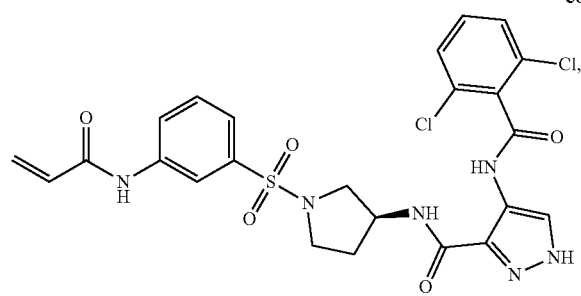
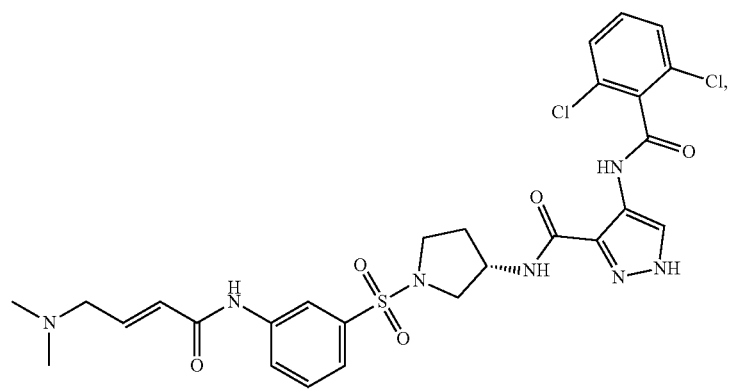
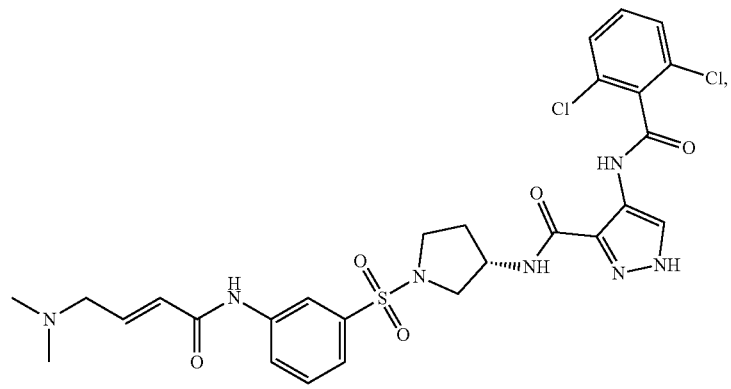
366
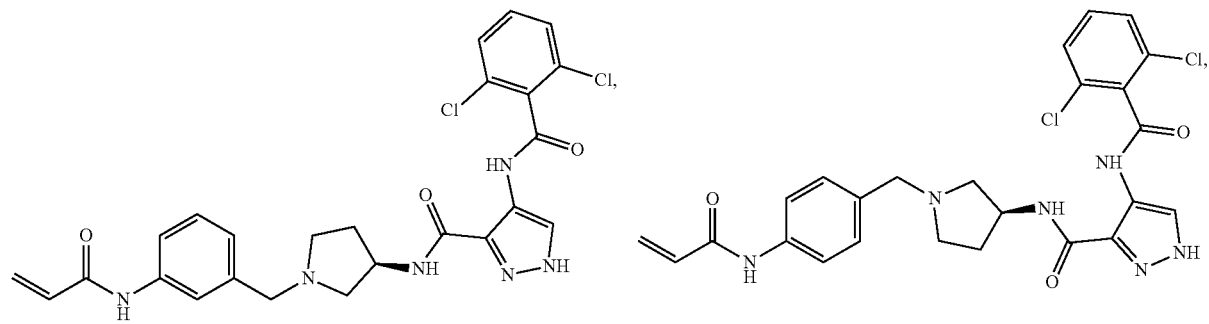

367 368
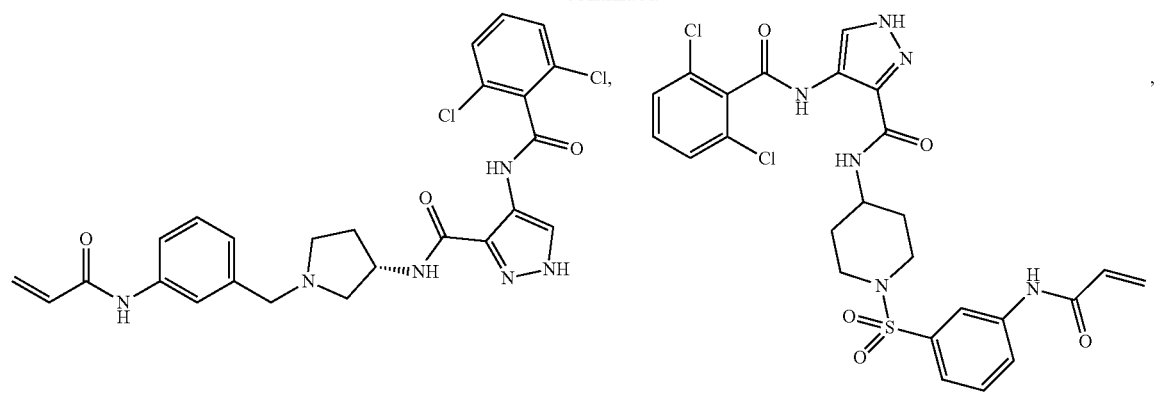
-continued
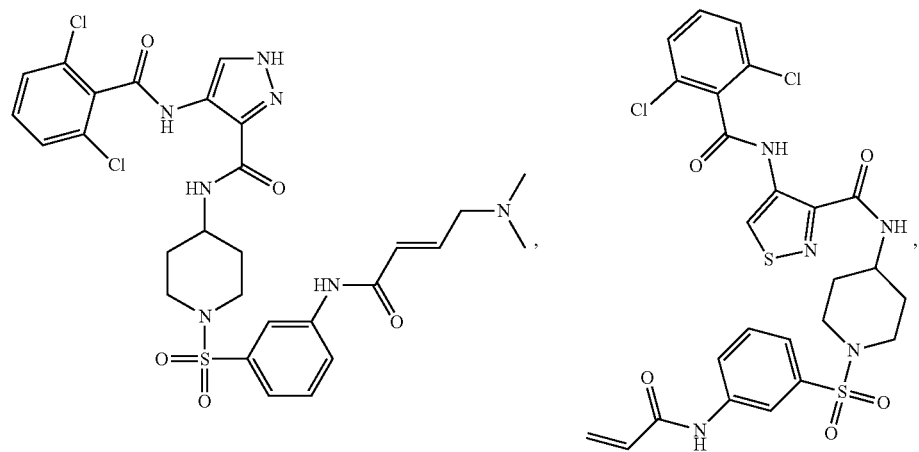
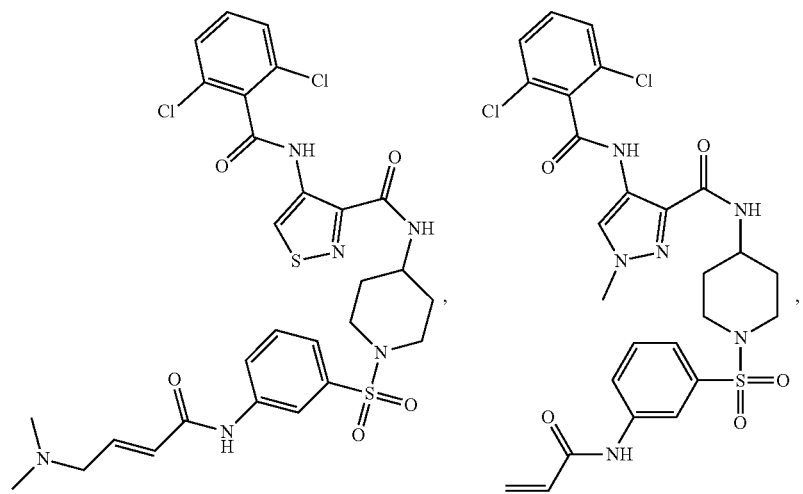

369
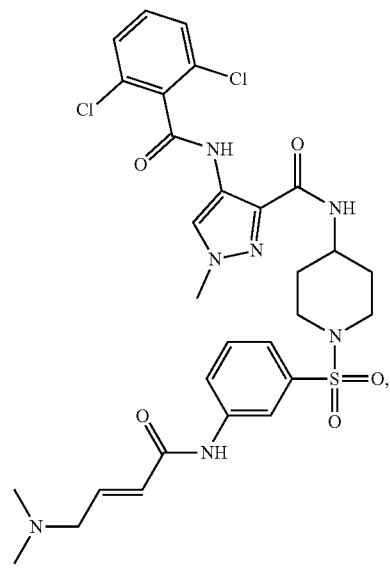
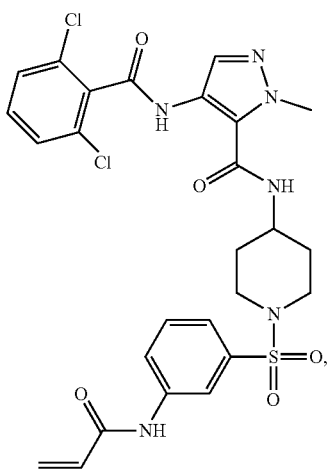
-continued
370
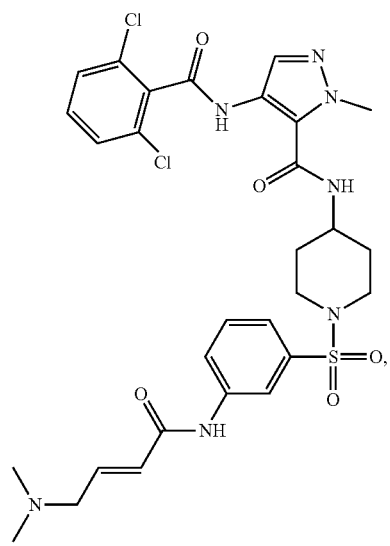
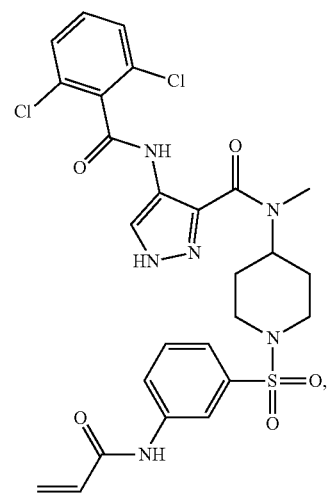
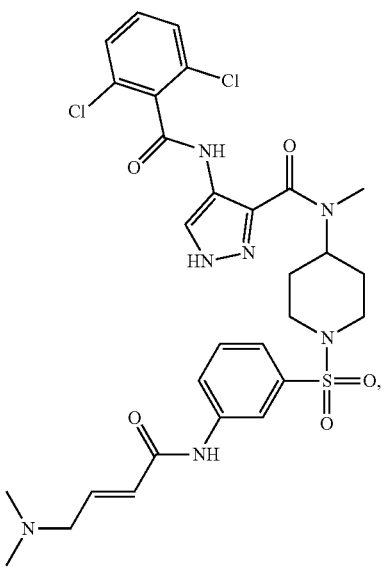
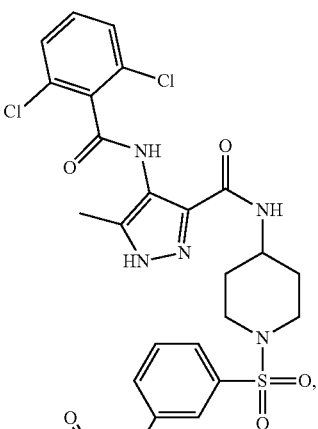
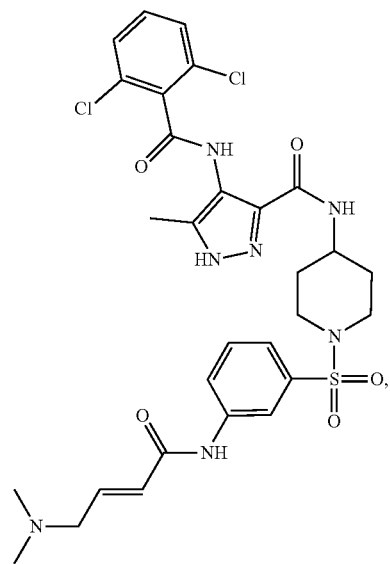
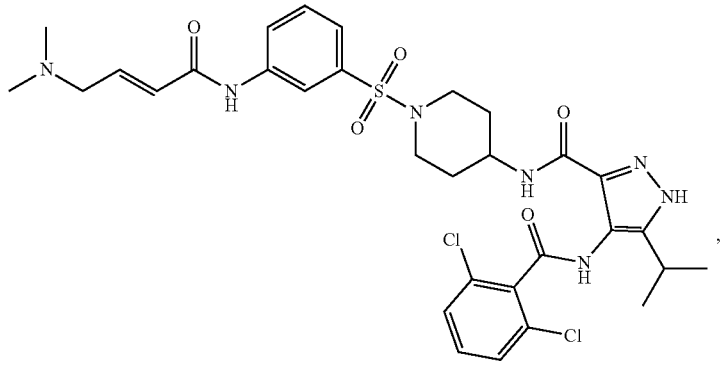

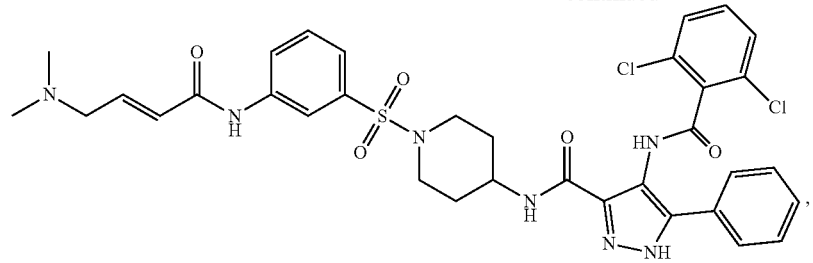
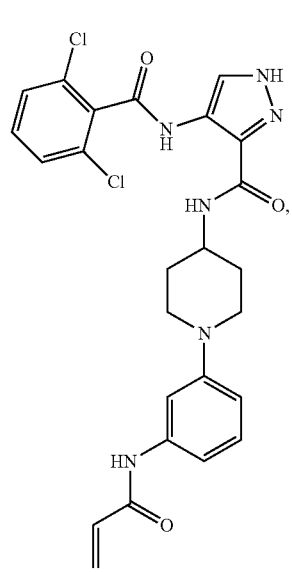
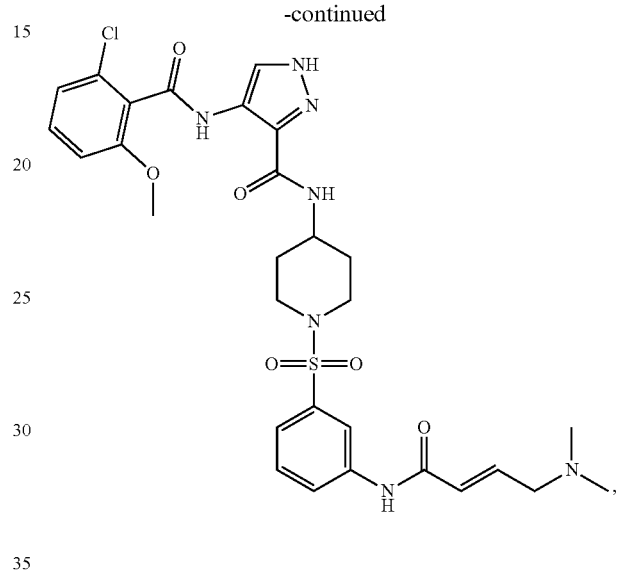
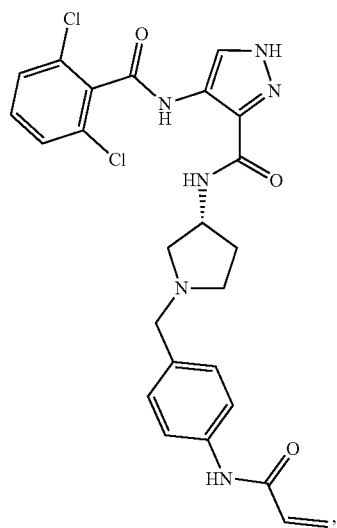
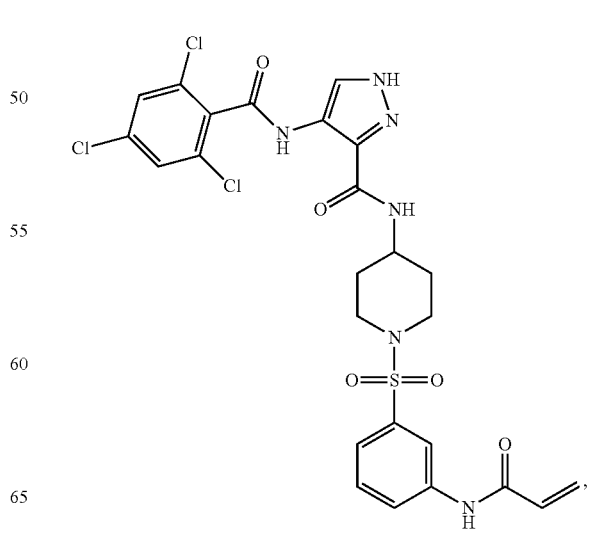

373
-continued
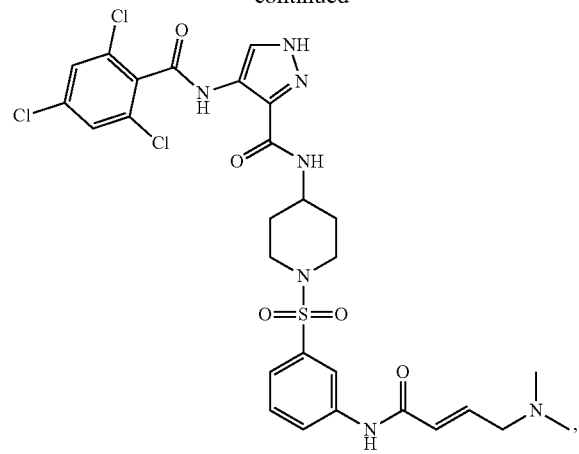
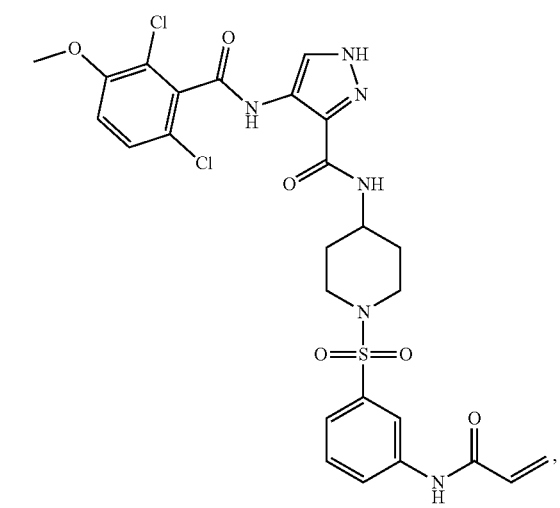
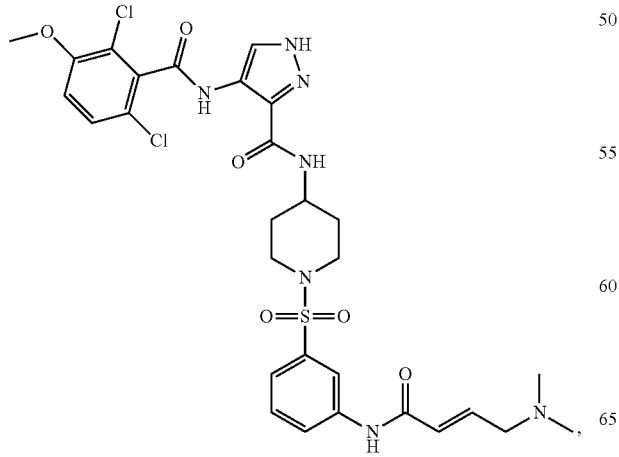
374
-continued
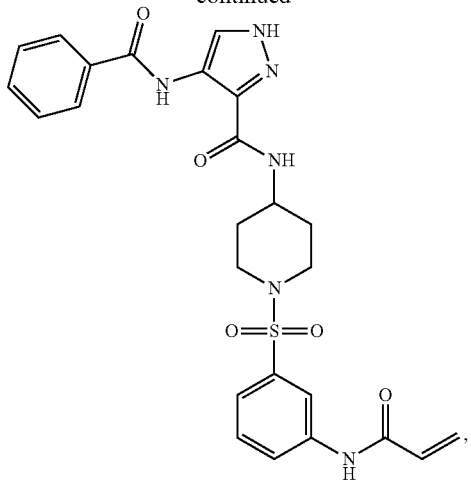
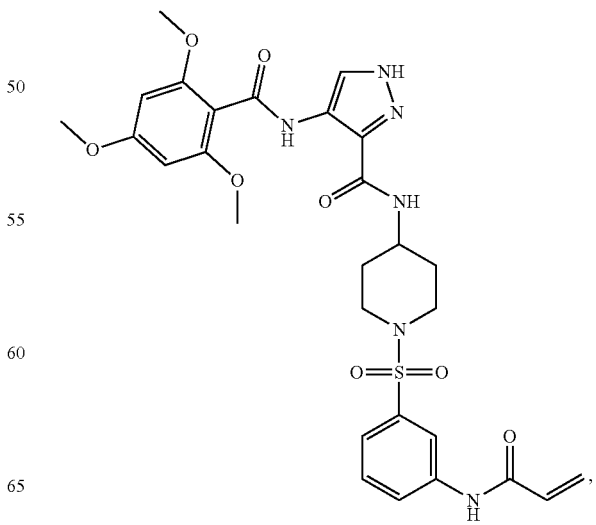

375
-continued
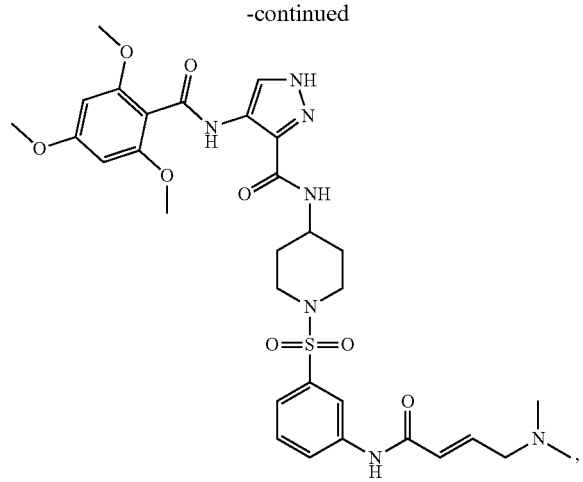
376
-continued
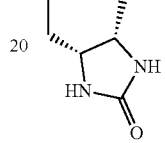
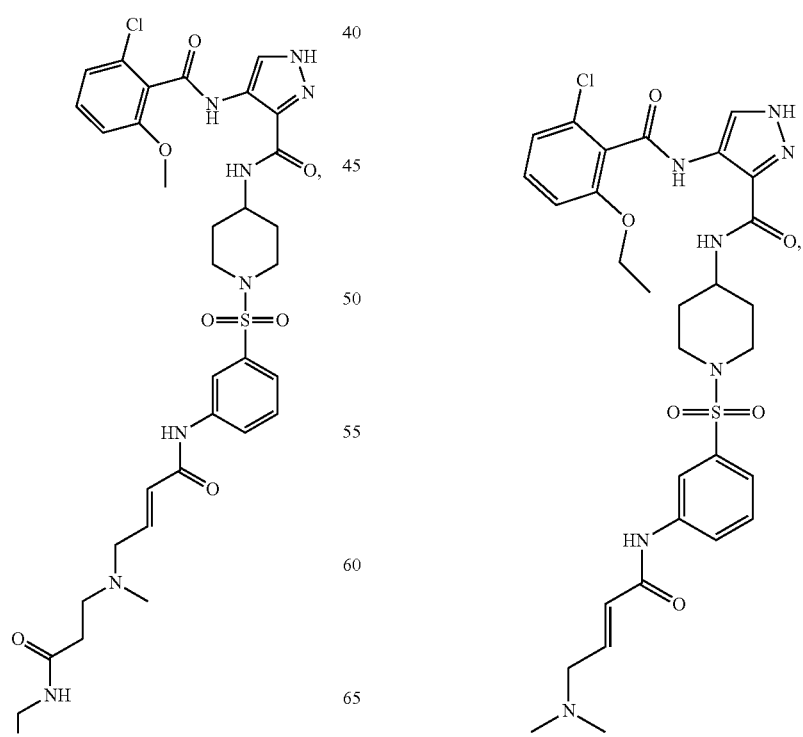

377
-continued
378
-continued
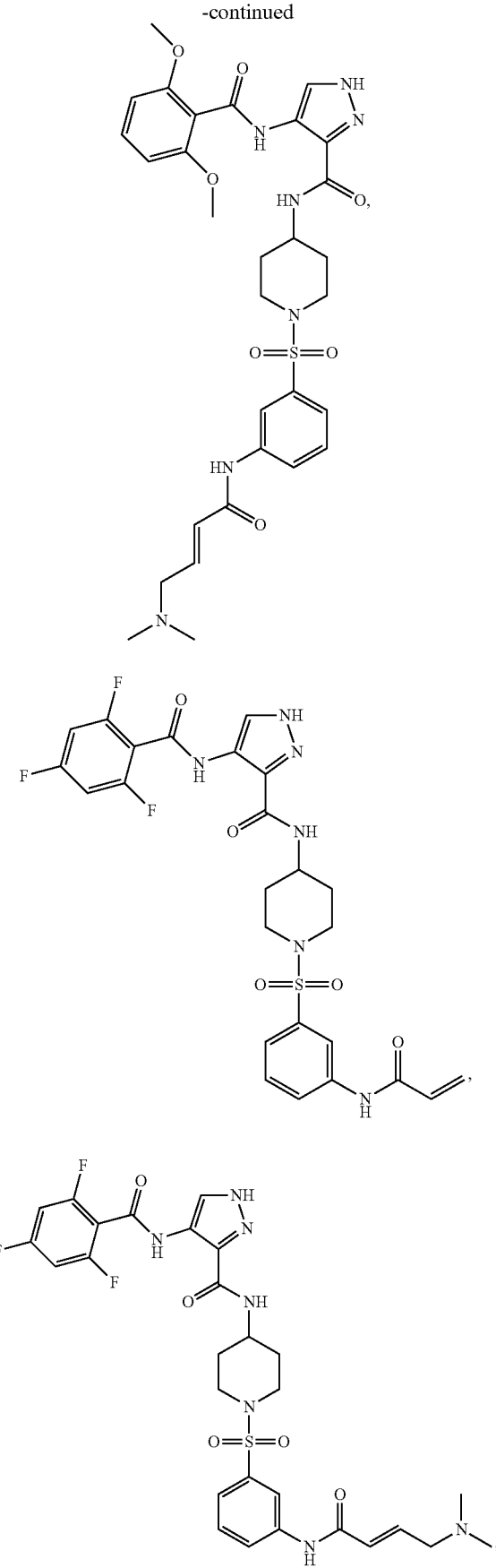
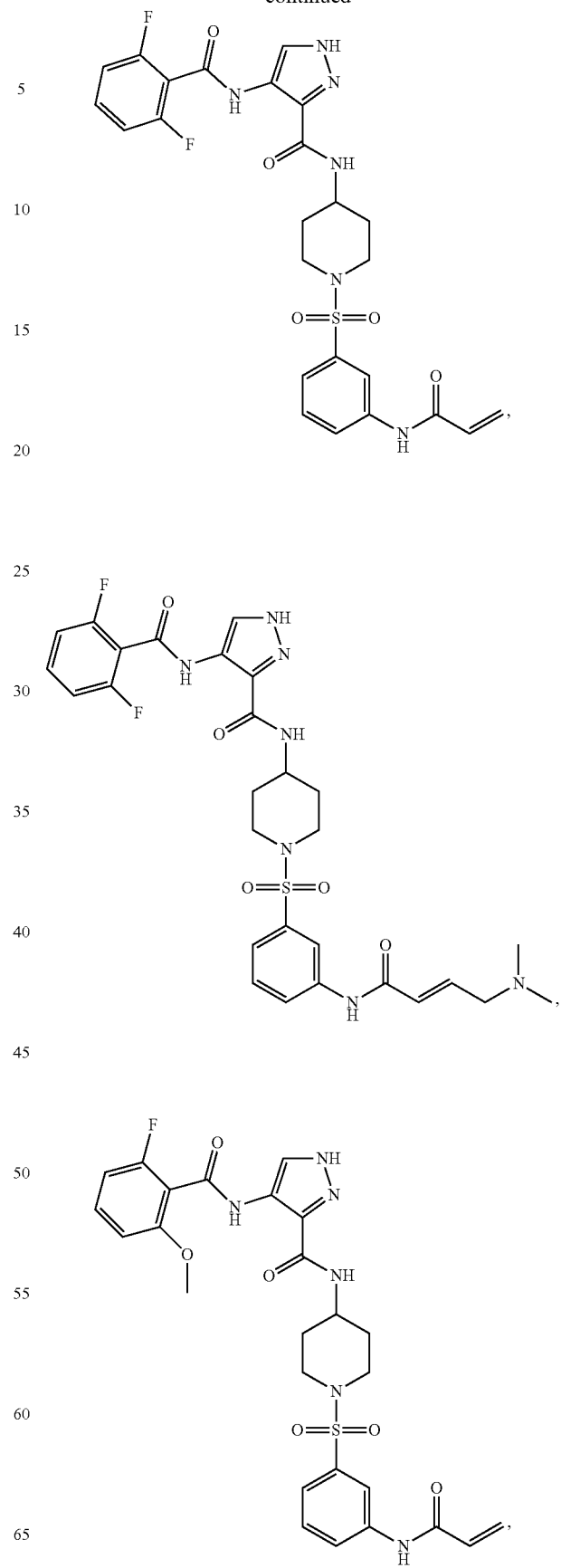

379
-continued
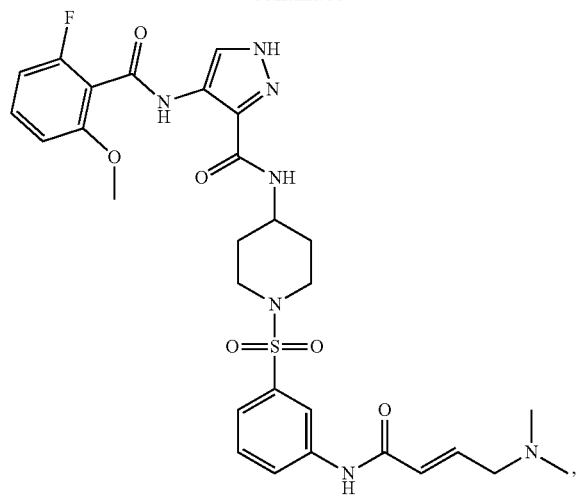
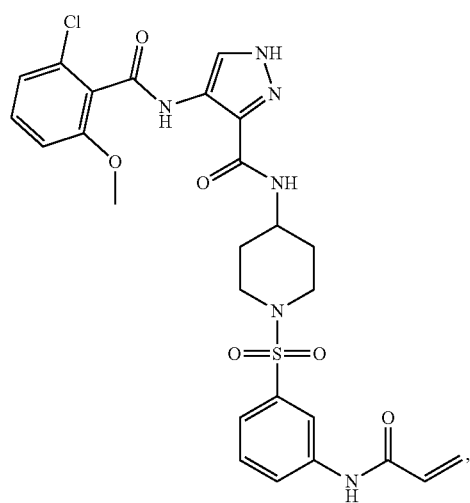
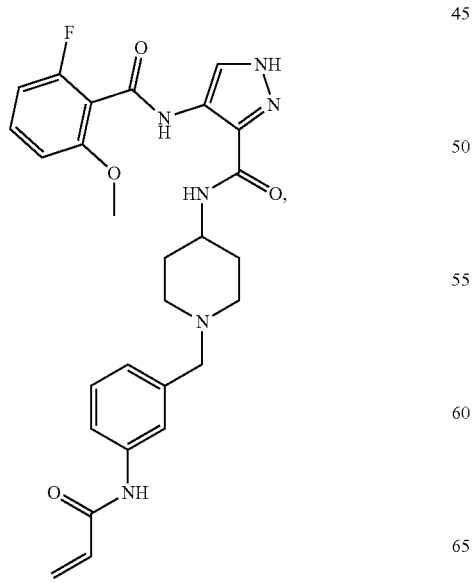
380
-continued
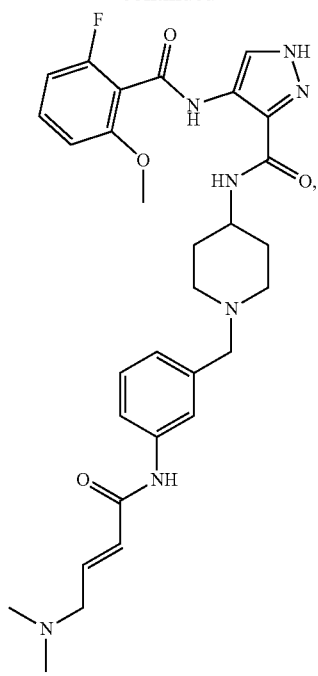
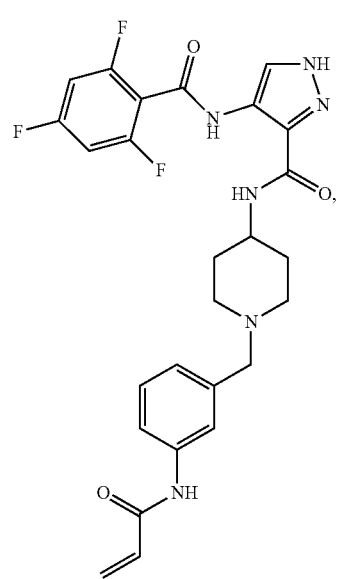

381
-continued
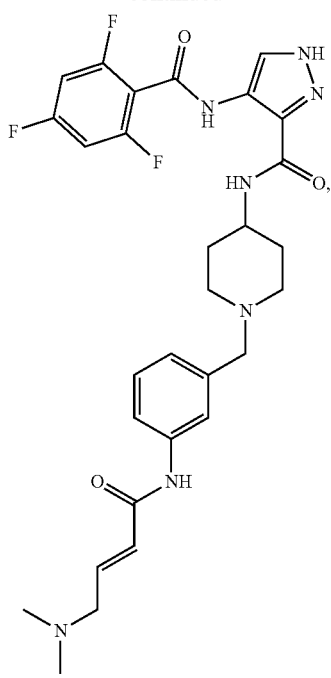
382
-continued
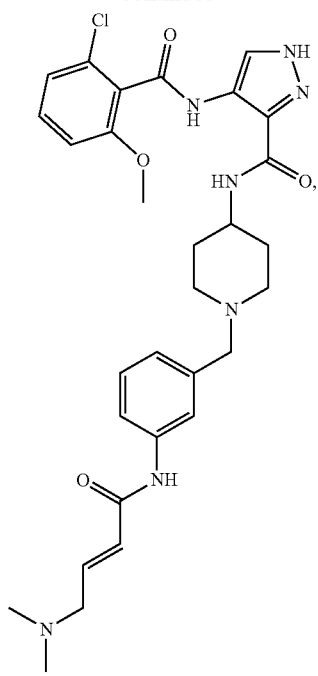
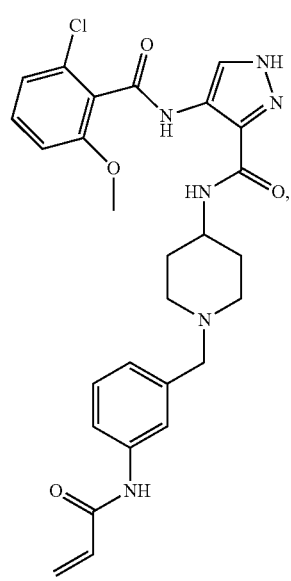
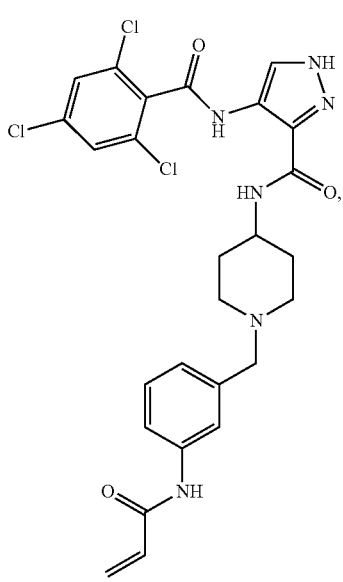

383
-continued

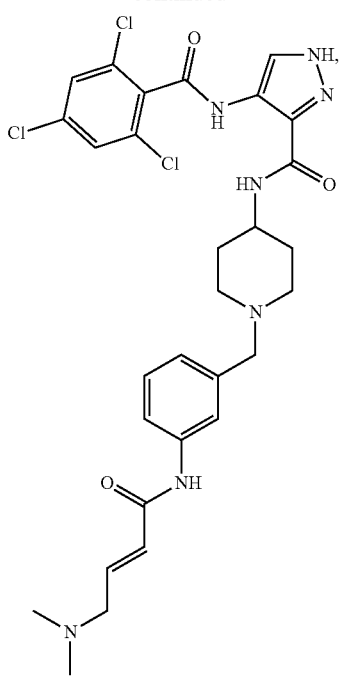

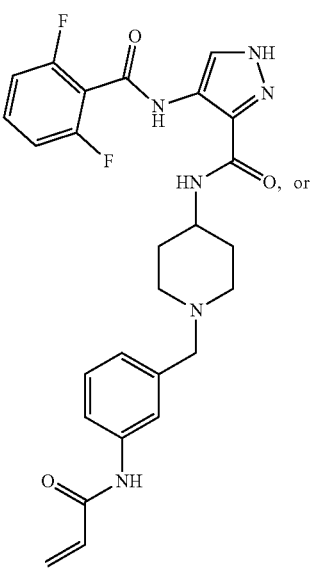

384
-continued

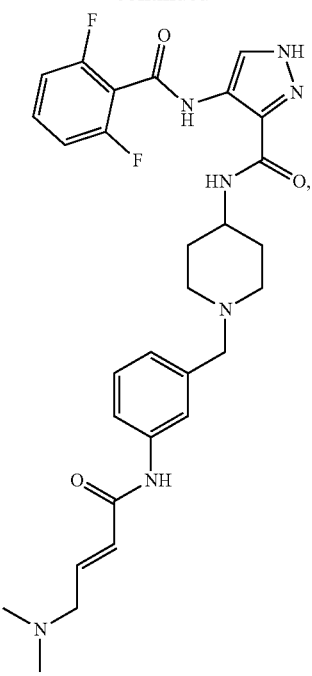 [SMILES: CN(C)C/C=C/C(=O)Nc1cccc(CN2CCC(NC(=O)c3n[nH]cc3NC(=O)c3c(F)cccc3F)CC2)c1]

or a pharmaceutically acceptable salt, tautomer, stereoisomer, or isotopically labeled compound thereof.

17. A pharmaceutical composition comprising a compound of claim 1, or a pharmaceutically acceptable salt, tautomer, stereoisomer, or isotopically labeled compound thereof, and optionally a pharmaceutically acceptable excipient.

18. A method of treating a disease in a subject in need thereof, the method comprising administering to the subject a therapeutically effective amount of a compound of claim 1, or a pharmaceutically acceptable salt, tautomer, stereoisomer, or isotopically labeled compound thereof, wherein the disease is a carcinoma, lung cancer, breast cancer, liver cancer, pancreatic cancer, gastric cancer, ovarian cancer, colon cancer, colorectal cancer, diabetes, Alzheimer's disease, gliosis, or spinal cord injury.

19. A method of male contraception in a subject in need thereof, the method comprising administering to the subject an effective amount of a compound of claim 1, or a pharmaceutically acceptable salt, tautomer, stereoisomer, or isotopically labeled compound thereof.

20. A method of inhibiting the activity of a cyclin-dependent kinase (CDK) in a biological sample, tissue, cell, or subject, the method comprising administering to the subject or contacting the biological sample, tissue, or cell with an effective amount of a compound of claim 1, or a pharmaceutically acceptable salt, tautomer, stereoisomer, or isotopically labeled compound thereof.

21. A kit comprising:
  a compound of claim 1, or a pharmaceutically acceptable salt, tautomer, stereoisomer, or isotopically labeled compound thereof; and
  instructions for using the compound, or the pharmaceutically acceptable salt, tautomer, stereoisomer, or isotopically labeled compound thereof.

22. A compound of the formula:
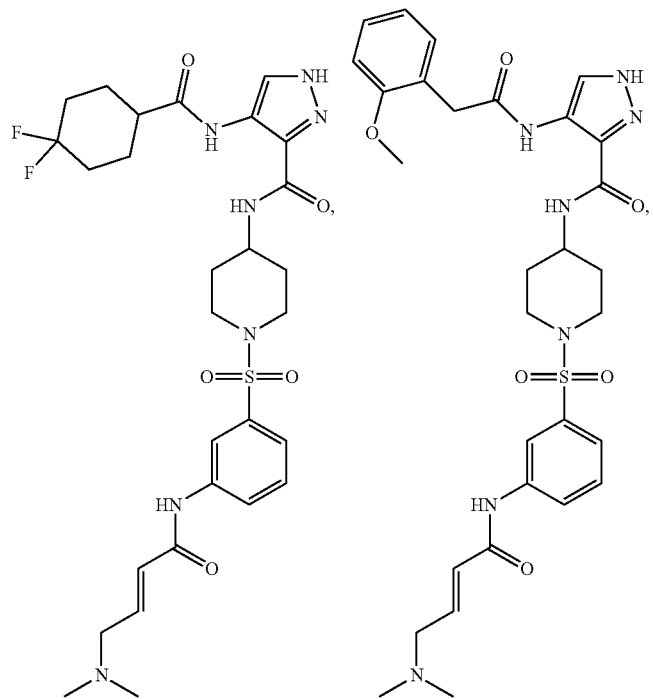
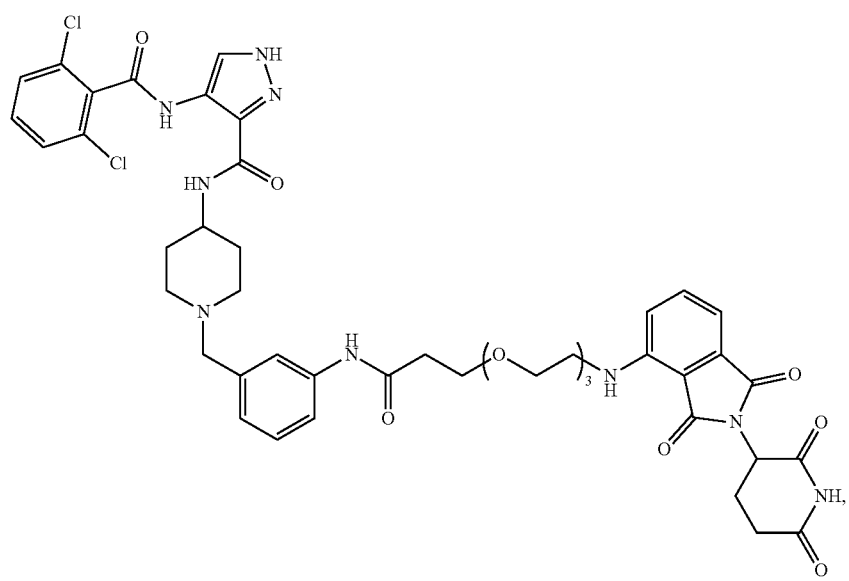

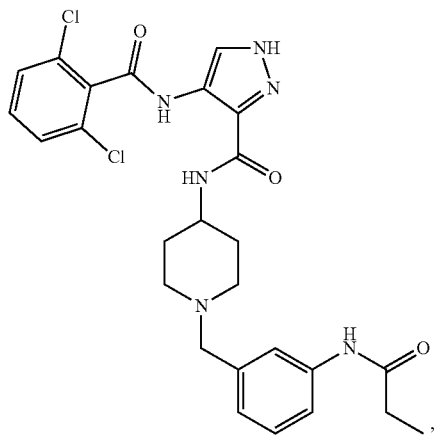 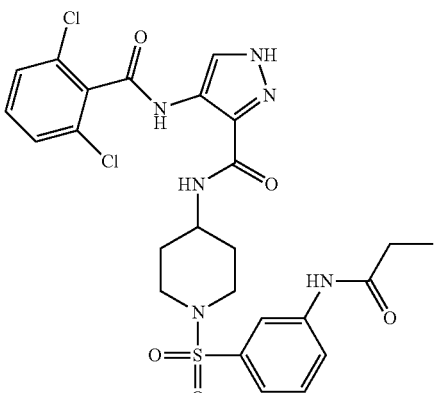 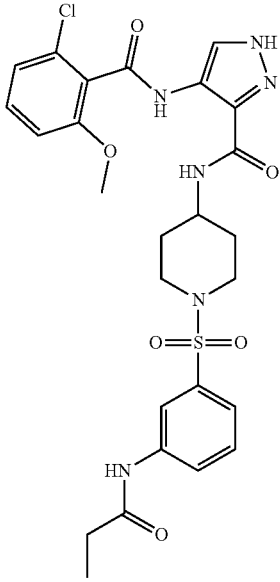

, or , or , or a pharmaceutically acceptable salt, tautomer, stereoisomer, or isotopically labeled compound thereof.

23. A pharmaceutical composition comprising a compound of claim 22, or a pharmaceutically acceptable salt, tautomer, stereoisomer, or isotopically labeled compound thereof, and optionally a pharmaceutically acceptable excipient.

24. A kit comprising:
a compound of claim 22, or a pharmaceutically acceptable salt, tautomer, stereoisomer, or isotopically labeled compound thereof; and
instructions for using the compound, or the pharmaceutically acceptable salt, tautomer, stereoisomer, or isotopically labeled compound thereof.

25. A method of treating a disease in a subject in need thereof, the method comprising administering to the subject a therapeutically effective amount of a compound of claim 22, or a pharmaceutically acceptable salt, tautomer, stereoisomer, or isotopically labeled compound thereof, wherein the disease is a carcinoma, lung cancer, breast cancer, liver cancer, pancreatic cancer, gastric cancer, ovarian cancer, colon cancer, colorectal cancer, diabetes, Alzheimer's disease, gliosis, or spinal cord injury.

26. A method of male contraception in a subject in need thereof, the method comprising administering to the subject an effective amount of a compound of claim 22, or a pharmaceutically acceptable salt, tautomer, stereoisomer, or isotopically labeled compound thereof.

27. A method of inhibiting the activity of a cyclin-dependent kinase (CDK) in a biological sample, tissue, cell, or subject, the method comprising administering to the subject or contacting the biological sample, tissue, or cell with an effective amount of a compound of claim 22, or a pharmaceutically acceptable salt, tautomer, stereoisomer, or isotopically labeled compound thereof.

28. A method of inducing apoptosis in a cell in a biological sample or subject, the method comprising administering to the biological sample or subject a therapeutically effective amount of a compound of claim 1, or a pharmaceutically acceptable salt, tautomer, stereoisomer, or isotopically labeled compound thereof.

29. A method of inducing apoptosis in a cell in a biological sample or subject, the method comprising administering to the biological sample or subject a therapeutically effective amount of a compound of claim 22, or a pharmaceutically acceptable salt, tautomer, stereoisomer, or isotopically labeled compound thereof.

30. The compound of claim 1, or a pharmaceutically acceptable salt, tautomer, stereoisomer, or isotopically labeled compound thereof, wherein:
Y is O.

31. The compound of claim 30, or a pharmaceutically acceptable salt, tautomer, stereoisomer, or isotopically labeled compound thereof, wherein $R^{E1}$ and $R^{E2}$ are hydrogen.

32. The compound of claim 31, or a pharmaceutically acceptable salt, tautomer, stereoisomer, or isotopically labeled compound thereof, wherein $R^{E3}$ is hydrogen or optionally substituted alkyl.

33. The compound of claim 31, or a pharmaceutically acceptable salt, tautomer, stereoisomer, or isotopically labeled compound thereof, wherein:
$R^{E3}$ is —$CH_2N(R^{EF})_2$; and
each instance of $R^{EF}$ is independently hydrogen, optionally substituted alkyl, optionally substituted alkoxy, optionally substituted alkenyl, optionally substituted alkynyl, optionally substituted carbocyclyl, optionally substituted heterocyclyl, optionally substituted aryl, or optionally substituted heteroaryl; or two $R^{EF}$ groups are joined to form an optionally substituted heterocyclic ring.

34. The compound of claim 31, or a pharmaceutically acceptable salt, tautomer, stereoisomer, or isotopically labeled compound thereof, wherein $R^3$ is of formula:

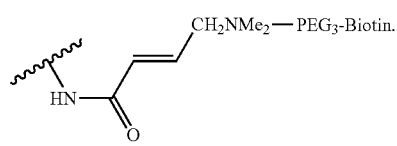

35. The compound of claim 1, wherein the compound is of formula:

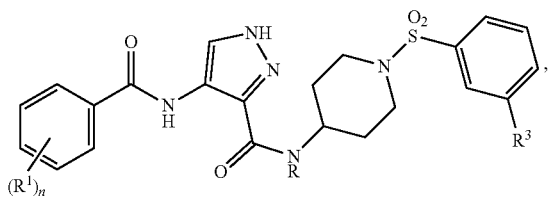

or a pharmaceutically acceptable salt, tautomer, stereoisomer, or isotopically labeled compound thereof.

36. The compound of claim 1, wherein the compound is of formula:

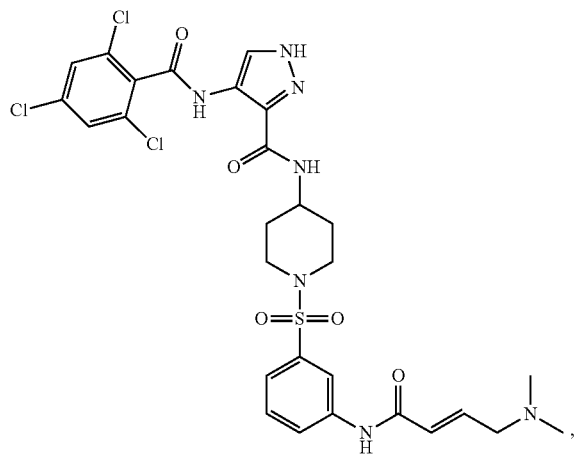 [SMILES: CN(C)C/C=C/C(=O)Nc1cccc(S(=O)(=O)N2CCC(NC(=O)c3n[nH]cc3NC(=O)c3c(Cl)cc(Cl)cc3Cl)CC2)c1]

or a pharmaceutically acceptable salt, tautomer, or isotopically labeled compound thereof.

37. The compound of claim 16, or a pharmaceutically acceptable salt thereof.

38. The compound of claim 22, or a pharmaceutically acceptable salt thereof.

39. The method of claim 18, wherein the disease is a carcinoma.

40. The method of claim 18, wherein the disease is lung cancer.

41. The method of claim 18, wherein the disease is non-small-cell lung cancer.

42. The method of claim 18, wherein the disease is breast cancer.

43. The method of claim 18, wherein the disease is liver cancer.

44. The method of claim 18, wherein the disease is pancreatic cancer.

45. The method of claim 18, wherein the disease is gastric cancer.

46. The method of claim 18, wherein the disease is ovarian cancer.

47. The method of claim 18, wherein the disease is colon cancer or colorectal cancer.

48. The method of claim 18, wherein the disease is diabetes.

49. The method of claim 18, wherein the disease is Alzheimer's disease.

50. The method of claim 18, wherein the disease is gliosis.

51. The method of claim 18, wherein the disease is spinal cord injury.

52. The method of claim 18, wherein the subject is a human.

53. The method of claim 25, wherein the disease is, lung cancer, breast cancer, liver cancer, pancreatic cancer, gastric cancer, ovarian cancer, colon cancer, or colorectal cancer.

* * * * *